(12) United States Patent
Cummings et al.

(10) Patent No.: US 11,027,015 B2
(45) Date of Patent: Jun. 8, 2021

(54) ANTIBODIES SPECIFICALLY BINDING TO MASP-3 FOR THE TREATMENT OF VARIOUS DISEASES AND DISORDERS

(71) Applicant: Omeros Corporation, Seattle, WA (US)

(72) Inventors: W. Jason Cummings, Bellevue, WA (US); Gregory A. Demopulos, Mercer Island, WA (US); Thomas Dudler, Bellevue, WA (US); Larry W. Tjoelker, Kirkland, WA (US); Christi L. Wood, Snohomish, WA (US); Munehisa Yabuki, Seattle, WA (US)

(73) Assignee: Omeros Corporation, Seattle, WA (US)

(*) Notice: Subject to any disclaimer, the term of this patent is extended or adjusted under 35 U.S.C. 154(b) by 0 days.

(21) Appl. No.: 16/909,578

(22) Filed: Jun. 23, 2020

(65) Prior Publication Data
US 2020/0317510 A1 Oct. 8, 2020

Related U.S. Application Data

(62) Division of application No. 16/837,600, filed on Apr. 1, 2020, now Pat. No. 10,745,274, which is a division of application No. 15/665,030, filed on Jul. 31, 2017, now Pat. No. 10,639,369.

(60) Provisional application No. 62/478,336, filed on Mar. 29, 2017, provisional application No. 62/419,420, filed on Nov. 8, 2016, provisional application No. 62/369,674, filed on Aug. 1, 2016.

(51) Int. Cl.
| | | |
|---|---|---|
| *A61K 39/395* | (2006.01) |
| *C07K 16/40* | (2006.01) |
| *C01F 17/206* | (2020.01) |
| *B82Y 25/00* | (2011.01) |
| *C09K 11/77* | (2006.01) |
| *H01F 1/00* | (2006.01) |
| *C12N 9/64* | (2006.01) |
| *A61K 39/00* | (2006.01) |

(52) U.S. Cl.
CPC .......... *A61K 39/3955* (2013.01); *B82Y 25/00* (2013.01); *C01F 17/206* (2020.01); *C07K 16/40* (2013.01); *C09K 11/77* (2013.01); *C09K 11/7728* (2013.01); *C12N 9/6424* (2013.01); *C12Y 304/21104* (2013.01); *H01F 1/0054* (2013.01); *A61K 39/00* (2013.01); *A61K 2039/505* (2013.01); *A61K 2039/54* (2013.01); *A61K 2039/545* (2013.01); *C01P 2002/54* (2013.01); *C01P 2002/84* (2013.01); *C01P 2004/64* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/734* (2013.01); *C07K 2317/76* (2013.01); *C07K 2317/90* (2013.01); *C07K 2317/92* (2013.01)

(58) Field of Classification Search
CPC .............. A61K 39/3955; C12N 9/6424; C12Y 304/21104; C07K 16/40
See application file for complete search history.

(56) References Cited

U.S. PATENT DOCUMENTS

| | | |
|---|---|---|
| 4,331,647 A | 5/1982 | Goldenberg |
| 4,816,567 A | 3/1989 | Cabilly et al. |
| 4,946,778 A | 8/1990 | Ladner et al. |
| 5,211,657 A | 5/1993 | Yamada et al. |
| 5,223,409 A | 6/1993 | Ladner et al. |
| 5,403,484 A | 4/1995 | Ladner et al. |
| 5,552,157 A | 9/1996 | Yagi et al. |
| 5,565,213 A | 10/1996 | Nakamori |
| 5,567,434 A | 10/1996 | Szoka, Jr. |
| 5,571,698 A | 11/1996 | Ladner et al. |
| 5,693,762 A | 12/1997 | Queen et al. |
| 5,738,868 A | 4/1998 | Shinkarenko |
| 5,741,516 A | 4/1998 | Webb et al. |
| 5,795,587 A | 8/1998 | Gao et al. |
| 6,355,245 B1 | 3/2002 | Evans et al. |
| 7,919,094 B2 | 4/2011 | Schwaeble et al. |
| 2002/0019369 A1 | 2/2002 | Li et al. |
| 2003/0186419 A1 | 10/2003 | Jensenius |
| 2004/0115194 A1 | 6/2004 | Wang |
| 2004/0259771 A1 | 12/2004 | Stahl et al. |
| 2009/0017031 A1 | 1/2009 | Fung |
| 2009/0093033 A1 | 4/2009 | Luy et al. |
| 2012/0122107 A1 | 5/2012 | Thiel et al. |
| 2012/0282285 A1 | 11/2012 | Garred et al. |

FOREIGN PATENT DOCUMENTS

| | | |
|---|---|---|
| WO | WO 94/13804 | 6/1994 |
| WO | WO 95/23161 | 8/1995 |
| WO | WO 96/27011 | 9/1996 |
| WO | WO 2004/009664 A2 | 1/2004 |
| WO | WO 2007/024715 | 3/2007 |
| WO | WO 2008/024188 | 2/2008 |

(Continued)

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*

(Continued)

*Primary Examiner* — Sharon X Wen
(74) *Attorney, Agent, or Firm* — Tineka J. Quinton

(57) ABSTRACT

The present invention relates to MASP-3 inhibitory antibodies and compositions comprising such antibodies for use in inhibiting the adverse effects of MASP-3 dependent complement activation.

19 Claims, 93 Drawing Sheets

Specification includes a Sequence Listing.

(56) References Cited

FOREIGN PATENT DOCUMENTS

| WO | WO 2009/029315 A2 | 3/2009 |
|---|---|---|
| WO | WO 2013/192240 A2 | 12/2013 |

OTHER PUBLICATIONS

Wu et al. (J. Mol. Biol. (1999) 294, 151-162).*
Padlan et al. (PNAS 1989, 86:5938-5942).*
Lamminmaki et al. (JBC 2001, 276:36687-36694).*
Chen, C., et al., "Stoichiometry of Complexes between Mannose—Binding Protein and its Associated Serine Proteases," *The Journal of Biological Chemistry* 276(28):25894-25902 (2001).
Ji, H., et al., "Arthritis Critically Dependent on Innate Immune System Players," *Immunity* 16:157-168 (2002).
Lynch, N.J., et al., "L-Ficolin Specifically Binds to Lipoteichoic Acid, a Cell Wall Constituent of Gram-Positive Bacteria, and Activates the Lectin Pathway of Complement," *The Journal of Immunology* 172:1198-1202 (2004).
Stover, C.M., et al., "Two Constituents of the Initiation Complex of the Mannan-Binding Lectin Activation Pathway of Complement Are Encoded by a Single Structural Gene," *The Journal of Immunology* 162:3481-3490 (1999).
Stover, C.M., et al., "The rat and mouse homologues of MASP-2 and Map19, components of the lectin activation pathway of complement," *J Immunol* 163(12):6848-6859 (1999).
Thiel, S., et al., "A Second Serine Protease Associated with Mannan-Binding Lectin that Activates Complement," *Nature* 386:506-510 (1997).
Thiel, S., et al., "Interaction of C1q and Mannan-Binding Lectin (MBL) with C1r, C1s, MBL-Associated Serine Proteases 1 and 2, and the MBL-Associated Protein MAp19," *The Journal of Immunology* 165:878-887 (2000).
Vorup-Jensen, T., et al., "Distinct Pathways of Mannan-Binding Lectin (MBL)- and C1 Complex Autoactivation Revealed by Reconstitution of MBL with Recombinant MBL-Associated Serine Protease-2," *The Journal of Immunology* 165:2093-2100 (2000).
Zundel, S., et al., "Characterization of Recombinant Mannan-Building Lectin-Associated Serine Protease (MASP)-3 Suggests an Activation Mechanism Different from that of MASP-1 and Masp-$2^{1,2}$," *The Journal of Immunology* 172:4342-4350 (2004).
Matsushita, M., et al., "Cutting Edge: Complement-Activatting Complex of Ficolin and Mannose-Binding Lectin-Associated Serine Protease," *The Journal of Immunology* 164:2281-2284 (2000).
Rodrigues, M.L., et al., "Engineering Fab' Fragments for Efficient F(ab)$_2$ Formation in *Escherichia coli* and for Improved In Vivo Stability," *The Journal of Immunology* 151(12):6954-6961 (1993).
Wang, Y., et al., "Anti-C5 monoclonal antbody therapy prevents collagen-induced arthritis and ameliorates established disease," *Proc. Natl. Acad. Sci. USA* 92:8955-8959 (1995).
Lachmann, P.J., et al., "Initiation of Complement Activation," *Springer Seminars Immunopathology* 7:143-162 (1984).
Riedemann, N.C., et al., "Complement in Ischemia Reperfusion Injury," *American Journal of Pathology* 162(2):363-367 (2003).
Matsushita, M. et al., "Activation of the Lectin Complement Pathway by H-Ficolin (Hakata Antigen)," *The Journal of Immunology* 168:3502-3506 (2002).
Stengaard-Pedersen, K., et al., "Inherited Deficiency of Mannan-Binding Lectin-Associated Serine Protease 2," *The New England Journal of Medicine* 349(6):554-560 (2003).
Takahashi, M., et al., "A Truncated Form of Mannose-Binding Lectin-Associated Serine Protease (MASP)-2 Expressed by Alternative Polyadenylation is a Component of the Lectin Complement Pathway," *International Immunology* 11(5):859-863 (1999).
Ambrus, G., et al., "Natural Substrates and Inhibitors of Mannan-Binding Lectin-Associated Serine Protease-1 and -2: A Study on Recombinant Catalytic Fragments," *The Journal of Immunology* 170:1374-1382 (2003).
Moller-Kristensen, M., et al., "Levels of Mannan-Binding Lectin-Associated Serine Protease-2 in Healthy Individuals," *Journal of Immunological Methods* 282:159-167 (2003).
Dahl, M.R., et al., "MASP-3 and its Association with Distinct Complexes of the Mannan-Binding Lectin Complement Activation Pathway," *Immunity* 15:127-135 (2001).
Liszewski, M., et al., "The Complement System," *Fundamental Immunology, Third Edition*:918-937 (1993).
Collard, C.D., et al., "Complement Activation after Oxidative Stress: Role of the Lectin Complement Pathway," *American Journal of Pathology* 156(5):1549-1556 (2000).
Lu, J., et al., "Collectins and Ficolins: Sugar Pattern Recognition Molecules of the Mammalian Innate Immune System," *Biochimica et Biophysica Acta* 1572:387-400 (2002).
Jordan, J.E., et al., "Inhibition of Mannose-Binding Lectin Reduces Postischemic Myocardial Reperfusion Injury," *Circulation* 104:1413-1418 (2001).
Maynard, Y., et al., "Characterization of a Mannose and N-Acetylglucosamine-Specific Lectin Present in Rat Hepatocytes," *The Journal of Biological Chemistry* 257(7):3788-3794 (1982).
Stahl, G.L., et al., "Role for the alternative complement pathway in ischemia/reperfusion injury," *Am J Pathol* 162(2):449-455 (2003).
Lee, R.T., et al., "Multivalent Ligand Binding by Serum Mannose-Binding Protein," *Archives of Biochemistry and Biophysics* 299(1): 129-136 (1992).
Collard, C.D., et al., "Endothelial Oxidative Stress Activates the Lectin Complement Pathway," *American Journal of Pathology* 159(3): 1045-1054 (2001).
Ji, Y.H., et al., "Activation of the C4 and C3 Components of Complement by a Proteinase in Serum Bactericidal Factor, Ra Reactive Factor," *The Journal of Immunology* 150(2):571-578 (1993).
Kilpatrick, D.C., "Mannan-Binding Lectin: Clinical Significance and Applications," *Biochimica et Biophysica Acta* 1572:401-413 (2002).
Weis, W.I., et al., "Structure of a C-Type Mannose-Binding Protein Complexed with an Oligosaccharide," *Nature* 360:127-134 (1992).
Kalli, K., et al., "Therapeutic Uses of Recombinant Complement Protein Inhibitors," *Springer Seminars in Immunopathology* 15(4):417-431 (1994).
Brodeur, J., et al., "Synovial Fluid Levels of Complement SC5b-9 and Fragment Bb are Elevated in Patients with Rheumatoid Arthritis," *Arthritis and Rheumatism* 34(12):1531-1537 (1991).
El-Ghobarey, A.F., et al., "Alternative pathway complement activation in rheumatoid arthritis," *J Rheumatology* 7(4):453-460 (1980).
Pangburn, M.K., et al., "Formation of the Initial C3 Convertase of the Alternative Complement Pathway: Acquisition of C3b-like Activities by Spontaneous Hydrolysis of the Putative Thioester in Native C3," *J. Exp. Med.* 154:856-867 (1981).
Wallis, R., et al., "Localization of the Serine Protease-binding Sites in the Collagen-like Domain of Mannose-binding Protein," *The Journal of Biological Chemistry* 279(14):14065-14073 (2004).
Presanis, J., et al., "Differential Substrate and Inhibitor Profiles for Human MASP-1 and MASP-2," *Molecular Immunology* 40:921-929 (2003).
Sim, R.B., et al., "Innate Immunity: Serine Proteseases of the Complement System," *Biochemical Society Transcripts* 25(5):545-550 (2000).
Clackson, T., et al., "Making Antibody Fragments Using Phage Display Libraries," *Nature* 352:624-628 (1991).
Bird, R.E., et al., "Single-Chain Antigen-Binding Proteins," *Science* 242:423-426 (1988).
Carter, P., et al., "Humanization of an Anti-p185HER2 Antibody for Human Cancer Therapy," *Proc. Natl. Acad. Sci.* 89:4285-4289 (1992).
Aggarwal, A., et al., "Evidence for Activation of the Alternate Complement Pathway in Patients with Juvenile Rheumatoid Arthritis," *Rheumatology* 39:189-192 (2000).
Makino, K., et al., "A Microcapsule Self-Regulating Delivery System for Insulin," *Journal of Controlled Release* 12:235-239 (1990).
Lee, V.H.L., "Protease Inhibitors and Penetration Enhancers as Approaches to Modify Peptide Absorption," *Journal of Controlled Release* 13:213-223 (1990).
Jolliffe, L.K., et al., "Humanized Antibodies: Enhancing Therapeutic Utility Through Antibody Engineering," *Intern. Rev. Immunology* 10:241-250 (1993).

(56) References Cited

OTHER PUBLICATIONS

Hori, R., et al., "Enhanced Bioavailability of Subcutaneously Injected Insulin Coadministered with Collagen in Rats and Humans," *Pharmaceutical Research* 6(9):813-816 (1989).
Flugelman, M.Y., et al., "Low Level In Vivo Gene Transfer into the Arterial Wall Through a Perforated Balloon Catheter," *Circulation* 85:1110-1117 (1992).
De Boer, A.G., et al., "Rectal Absorption Enhancement of Peptide Drugs," *Journal of Controlled Release* 13:241-246 (1990).
Fuertges, R., et al., "The Clinical Efficacy of Poly(ethylene glycol)-Modified Proteins," *The Journal of Controlled Release* 11:139-148 (1990).
Riechmann, L., et al., "Reshaping human antibodies for therapy," *Nature* 332:323-327 (1988).
Singer, I.I., et al., "Optimal Humanization of 1B4, an Anti-CD18 Murine Monoclonal Antibody, is Achieved by Correct Choice of Human V-Region Framework Sequences," *The Journal of Immunology* 150(7):2844-2857 (1993).
Schwaeble, W., et al., "The Mannan-Binding Lectin-Associated Serine Proteases (MASPs) and MAp19: Four Components of the Lectin Pathway Activation Complex Encoded by Two Genes," *Immunobiology* 205:455-466 (2002).
Sandhu, J.S., et al., "Protein Engineering of Antibodies," *Critical Reviews in Biotechnology* 12(5/6):437-462 (1992).
Ravetch, J.V., et al., "Fc Receptors," *Annu. Rev. Immunology.* 9:457-92 (1991).
Rosenblatt, J., et al., "The Effect of Collagen Fiber Size Distribution on the Release Rate of Proteins from Collagen Matrices by Diffusion," *Journal of Controlled Release* 9:195-203 (1989).
Porter, R.R., "The Hydrolysis of Rabbit γ-Globulin and Antibodies with Crystalline Papain," *Biochem. J.* 73:119-126 (1959).
Presta, L.G., "Antibody Engineering," *Current Opinion in Structural Biology* 2:593-596 (1992).
Lee, V.H.L., "Enzymatic Barriers to Peptide and Protein Absorption," *CRC Critical Reviews in Therapeutic Drug Carrier Systems* 5(2):69-97 (1988).
Yamakawa, I., et al., "Sustained Release of Insulin by Double-Layered Implant Using Poly(D,L-Lactic Acid)," *Journal of Pharmaceutical Sciences* 79(6):505-509 (1990).
Pack, P., et al., "Improved Bivalent Miniantibodies, with Identical Avidity as Whole Antibodies, Produced by High Cell Density Fermentation of *Escherichia coli*," *Bio/Technology* 11:1271-1277 (1993).
Taylor, L.D., et al., "Human Immunoglobulin Transgenes Undergo Rearrangement, Somatic Mutation and Class Switching in Mice that Lack Endogenous IgM," *International Immunology* 6(4):579-591 (1994).
Takakura, Y. et al., "Control of Pharmaceutical Properties of Soybean Trypsin Inhibitor by Conjugation with Dextran I: Synthesis and Characterization," *Journal of Pharmaceutical Sciences* 78(2):117-121 (1989).
Takakura, Y., et al., "Control of Pharmaceutical Properties of Soybean Trypsin Inhibitor by Conjugation with Dextran II: Biopharmaceutical and Pharmacological Properties," *Journal of Pharmaceutical Sciences* 78(3):219-222 (1989).
Van de Winkel, J.G.J., et al., "Human IgG Fc receptor heterogeneity: molecular aspects and clinical implications," *Immunology Today* 14(5):215-221 (1993).
Vaughan, T.J., et al., "Human Antibodies by Design," *Nature Biotechnology* 16:535-539 (1998).
Scatchard, G., "The Attractions of Proteins for Small Molecules and Ions," *Annals New York Academy of Sciences* 51:660-672 (1949).
Green, L.L., et al., "Antigen-specific Human Monoclonal Antibodies from Mice Engineered with Human Ig Heavy and Light Chain YACs," *Nature Genetics* 7:13-21 (1994).
Duncan, A.R., et al., "The Binding Site for C1q and IgG," *Nature* 332:738-740 (1988).

Hogaboam, C., et al., "Mannose-Binding Lectin Deficiency Alters the Development of Fungal Asthma: Effects on Airway Response, Inflammation, and Cytokine Profile," *Journal of Leukocyte Biology* 75:805-814 (2004).
Matsushita, M., et al., "Activation of the Classical Complement Pathway by Mannose-Binding Protein in Association with a Novel C1s-like Serine Protease," *J. Exp. Med.* 176:1497-1502 (1992).
Morgan, B.P., et al., "Clinical Complementology: Recent Progress and Future Trends," *Eur J Clin Invest* 24:219-228 (1994).
Holmskov, U., et al., "Collectins and Ficolins: Humoral Lectins of the Innate Immune Defense," *Annu Rev Immunology* 21:547-78 (2003).
Ikeda, K., et al., "Complement Activation and Inhibition in Experimental Models of Arthritis," *Molecular Immunology* 36:905-914 (1999).
Bae, Y.H., et al., "Insulin Permeation Through Thermo-Sensitive Hydrogels," *Journal of Controlled Release* 9:271-279 (1989).
Asano, M. et al., "In Vivo Characteristics of Low Molecular Weight Copoly($_L$-Lactic Acid/Glycolic Acid) Formulations with Controlled Release of Luteinizing Hormone-Releasing Hormone Agonist," *Journal of Controlled Release* 9:111-122 (1989).
Köhler, G., et al., "Continuous Cultures of Fused Cells Secreting Antibody of Predefined Specificity," *Nature* 256:495-497 (1975).
Kuhlman, M., et al., "The Human Mannose-Binding Protein Functions as an Opsonin," *The Journal of Experimental Medicine* 169:1733-1745 (1989).
Lonberg, N., et al., "Antigen-Specific Human Antibodies from Mice Comprising Four Distinct Genetic Modifications," *Nature* 368:856-859 (1994).
Marks, J.D., et al., "By-Passing Immunization: Human Antibodies from V-Gene Libraries Displayed on Phage," *Journal of Molecular Biology* 222:581-597 (1991).
Matsushita, M., et al., "A Novel Human Serum Lectin with Collagen- and Fibrinogen-Like Domains that Functions as an Opsonin," *The Journal of Biological Chemistry* 271(5):2448-2454 (1996).
Mariani, M., et al., "A New Enzymatic Method to Obtain High-Yield F(ab)$_2$ Suitable for Clinical Use from Mouse IgG1," *Molecular Immunology* 28(1/2):69-77 (1991).
Mollnes, T., et al., "Complement Activation in Synovial Fluid and Tissue from Patients with Juvenile Rheumatoid Arthritis," *Arthritis and Rheumatism* 29(11):1359-1364 (1986).
Morrison, S.L., et al., "Chimeric Human Antibody Molecules: Mouse Antigen-binding Domains with Human Constant Region Domains," *Proc. Natl. Acad. Sci. USA* 81:6851-6855 (1984).
Nisonoff, A., et al., "Separation of Univalent Fragments from the Bivalent Rabbit Antibody Molecule by Reduction of Disulfide Bonds," *Archives of Biochemistry and Biophysics* 89:230-244 (1960).
Pickering, M.C., et al., "Uncontrolled C3 Activation Causes Membranoproliferative Glomerulonephritis in Mice Deficient in Complement Factor H," *Nature Genetics* 31:424-428 (2002).
Isaacs, J.D., et al., "Therapy with Monoclonal Antibodies: An In Vivo Model for the Assessment of Therapeutic Potential," *The Journal of Immunology* 148(10):3062-3071 (1992).
Whitlow, M., et al., "Single-Chain Fv Proteins and their Fusion Proteins," *Methods: A Companion to Methods in Enzymology* 2(2):97-105 (1991).
Larrick, J.W., et al., "PCR Amplification of Antibody Genes," *Methods: A Companion to Methods in Enzymology* 2(2):106-110 (1991).
Jones, P.T., et al., "Replacing the Complementarity-Determining Regions in a Human Antibody with those from a Mouse," *Nature* 321:522-525 (1986).
Ward, E.S., et al., "Genetic Manipulation and Expression of Antibodies," *Monoclonal Antibodies: Principles and Applications* pp. 137-185 (Wiley-Liss, Inc.) (1995).
Courtenay-Luck, N.S., "Genetic Manipulation of Monoclonal Antibodies," *Monoclonal Antibodies: Production, Engineering and Clinical Application*, Ritter and Ladyman, eds., (Cambridge University Press) pp. 166-179 (1995).
Kelley, R.F., "Engineering Therapeutic Antibodies," *Protein Engineering: Principles and Practice*, Cleland and Craik, eds., (Wiley-Liss, Inc.) pp. 399-434 (1996).

(56) References Cited

OTHER PUBLICATIONS

Baines, M.G., et al., "Purification of Immunoglobulin G (IgG)," *Methods in Molecular Biology, vol. 10: Immunochemical Protocols*, Manson, ed., (The Humana Press, Inc.) pp. 79-104 (1992).

Matsushita, M., et al., "The Role of Ficolins in Innate Immunity," *Immunobiology* 205:490-497 (2002).

Lynch, N., et al., "Composition of the Lectin Pathway of Complement in *Gallus gallus*: Absence of Mannan-Binding Lectin-Associated Serine Protease-1 in Birds," *The Journal of Immunology* 174:4998-5006 (2005).

Hart, M., et al., "Gastrointestinal Ischemia-Reperfusion Injury is Lectin Complement Pathway Dependent without Involving C1q[1]," *The Journal of Immunology* 174:6373-6380 (2005).

Walsh, M., et al., "Mannose-Binding Lectin is a Regulator of Inflammation that Accompanies Myocardial Ischemia and Reperfusion Injury[1]," *The Journal of Immunology* 175:541-546 (2005).

Malhotra, R., et al., "Glycosylation Changes of IgG Associated with Rheumatoid Arthritis can Activate Complement via the Mannose-Binding Protein," *Nature Medicine* 1(3):237-243 (1995).

Cuchacovich, M., et al., "Potential Pathogenicity of Deglycosylated IgG Cross Reactive with Streptokinase and Fibronectin in the Serum of Patients with Rheumatoid Arthritis," *The Journal of Rheumatology* 23(1):44-51 (1996).

Taube, C., et al., "Inhibition of complement activation decreases airway inflammation and hyperresponsiveness," *Am J Respir Crit Care Med* 168:1333-1341 (2003).

Stover, C.M., et al., "Murine Serine Proteases MASP-1 and MASP-3, Components of the Lectin Pathway Activation Complex of Complement, are Encoded by a Single Structural Gene," *Genes and Immunity* 4:374-384 (2003).

Takahashi, M., et al., "Essential Role of Mannose-Binding Lectin-Associated Serine Protease-1 Activation of the Complement Factor D," *The Journal of Experimental Medicine* 207(1):29-37 (2009).

Trendelenburg, M., et al., "Influence of Functional Deficiency of Complement Mannose-Binding Lectin on Outcome of Patients with Acute ST-Elevation Myocardial Infarction Undergoing Primary Percutaneous Coronary Intervention," *European Heart Journal* 31(10):1181-1187 (2010).

Lindorfer, M., et al., "A Novel Approach to Preventing the Hemolysis of Paroxysmal Nocturnal Hemoglobinuria: Both Complement-Mediated Cytolysis and C3 Deposition are Blocked by a Monoclonal Antibody Specific for the Alternative Pathway of Complement," *Blood* 115(11):2283-2291 (2010).

Pickering, M.C., et al., "Spontaneous Hemolytic Uremic Syndrome Triggered by Complement Factor H Lacking Surface Recognition Domains," *J Exp Med* 204(6): 1249-1256 (2007).

Garred, P., et al., "Increased Frequency of Homozygosity of Abnormal Mannan-Binding-Protein Alleles in Patients with Suspected Immunodeficiency," *Lancet* 346:941-43 (1995).

Kawasaki, N., et al., "A Serum Lectin (Mannan-Binding Protein) Has Complement-Dependent Bactericidal Activity," *Journal of Biochemistry* 106:483-489 (1989).

Nielsen, S.L., et al., "The Level of Serum Opsonin, Mannan-Binding Protein in HIV-1 Antibody-Positive Patients," *Clinical and Experimental Immunology* 100:219-222 (1995).

Sato, T., et al., "Molecular Characterization of a Novel Serine Protease Involved in Activation of the Complement System by Mannose-Binding Protein," *International Immunology* 6(4):665-669 (1994).

Super, M., et al., "Association of Low Levels of Mannan-Binding Protein with a Common Defect of Opsonisation," *The Lancet*, 2(8674):1236-1239 (1989).

Takada, F., et al., "A New Member of the C1s Family of Complement Proteins Found in a Bactericidal Factor, Ra-Reactive Factor, in Human Serum," *Biochemical and Biophysical Research Communications*, 196(2):1003-1009 (1993).

Harlow, E., et al., "Antibodies: a Laboratory Manual," Cold Springs Harbor Laboratory, Cold Springs Harbor, New York, 1988. pp. 567-569.

Krarup, A., et al., "Simultaneous Activation of Complement and Coagulation by MBL-associated Serine Protease 2," *PLoS ONE* 7(e623):1-8 (2007).

Schwaeble, H-W., et al. "Targeting of Mannan-Binding Lectin-associated Serine Protease-2 Confers Protection from Myocardial and Gastrointestinal Ischemia/Reperfusion Injury," *PNAS* 108(18):7523-7528 (2011).

Skjoedt, M., et al., "MBL-Associated Serine Protease-3 Circulates in High Serum Concentrations Predominantly in Complex with Ficolin-3 and Regulates Ficolin-3 Mediated Complement Activation," *Immunobiology* 215:921-931 (2010).

Terai, I., et al. "Human Serum Mannose-Binding Lectin (MBL)-Associated Serine Protease-1 (MASP-1): Determination of Levels in Body Fluids and Identification of Two Forms in Serum," *Clinical and Experimental Immunology* 110:317-323 (1997).

Banda, N., et al., "Essential Role of Complement Mannose-Binding Lectin-Associated Serine Proteases-1/3 in the Murine Collagen Antibody-Induced Model of Inflammatory Arthritis," *The Journal of Immunology* 18:5598-5606 (2010).

Risitano, A.M., et al., "Achievements and Limitations of Complement Inhibition by Eculizumab in Paroxysmal Nocturnal Hemoglobinuria: the Role of Complement Component 3," *Minireviews in Medicinal Chemistry* 11:528-535 (2011).

Arumugam, T.V., et al., "Neuroprotection in Stroke by Complement Inhibition and Immunoglobulin Therapy," *Neuroscience* 158(3):1074-1089 (2009).

Morigi, M., et al., "Alternative Pathway Activation of Complement by Shiga Toxin Promotes Exuberant C3a Formation that Triggers Microvascular Thrombosis," *The Journal of Immunology* 187(1):172-80 (2011).

Loirat, C., et al. "Atypical Hemolytic Uremic Syndrome," *Orphanet Journal of Rare Diseases* 6:60 (2011).

Sprong, T., et al., "Mannose-Binding Lectin is a Critical Factor in Systemic Complement Activation During Meningococcal Septic Shock," *Clinical Infectious Diseases* 49:1380-1386 (2009).

Banda, N., et al., "Mechanisms of Mannose-Binding Lectin-Associated Serine Proteases-1/3 Activation of the Alternative Pathway of Complement," *Molecular Immunology* 49(1-2):281-289 (2011).

Rohrer, B., et al., "A Targeted Inhibitor of the Alternative Complement Pathway Reduces Angiogenesis in a Mouse Model of Age-Related Macular Degeneration" *Invest Ophthalmol Vis Sci* 50:3056-3064 (2009).

Pedersen, E.D., et al., "In Situ Disposition of Complement in Human Acute Brain Ischaemia," *Scandinavian Journal of Immunology* 69:555-562 (2009).

Lee, H., et al., "Early Complement Factors in the Local Tissue Immunocomplex Generated During Intestinal Ischemia/Reperfusion Injury" *Molecular Immunology* 47:972-981 (2010).

Thurman, J.M., et al., "Treatment with an Inhibitory Monoclonal Antibody to Mouse Factor B Protects Mice from Induction of Apoptosis and Renal Ischemia/Reperfusion Injury," *American Society of Nephrology* 17:707-715 (2006).

Castellano, G., et al. "Therapeutic Targeting of Classical and Lectin Pathways of Complement Protects from Ischemia-Reperfusion-Induced Renal Damage," *American Journal of Pathology* 176(4):1648-1659 (2010).

La Bonte, L.R., et al., "Mannose-Binding Lectin-Associated Serine Protease-1 is a Significant Contributor to Coagulation in a Murine Model of Occlusive Thrombosis," *The Journal of Immunology* 188:885-891 (2012).

Wang, Q., et al., "Identification of a Central Role for Complement in Osteoarthritis," *Nature Medicine* 17(12):1674-1679 (2011).

Van der Pol, P., et al., "Mannan-binding lecting mediates renal ischemia/reperfusion injury independent of complement activation," *Am J Transplant* 12:877-887 (2012).

Yongqing, T., et al., "Mannose-Binding Lectin Serine Proteases and Associated Proteins of the Lectin Pathway of Complement: Two Genes, Five Proteins and Many Functions?" *Biochimica et Biophysica Acta* 1824(1):253-262 (2012).

Eltzschig, H., et al., "Ischemia and Reperfusion—from Mechanism to Translation," *The Journal of Biological Chemistry* 287(24):20290-20300 (2012).

(56) References Cited

OTHER PUBLICATIONS

Deipenhorst, G.M.P., et al., "Complement-Mediated Ischemia-Reperfusion Injury," *Annals of Surgery* 249(6):889-899 (2009).
Sethi, S., et al., "Proliferative Glomerulonephritis Secondary to Dysfunction of the Alternative Pathway of Complement," *Clinical Journal of the American Society of Nephrology* 6:1009-1017 (2011).
Takeda, K., et al., "The Critical Role of Complement Alternative Pathway Regulator Factor H in Allergen-Induced Airway Hyper-responsiveness and Inflammation," *The Journal of Immunology* 188:661-667 (2012).
Thurman, J.M., et al., "Lack of a Functional Alternate Complement Pathway Ameliorates Ischemic Acute Renal Failure in Mice[1]," *The Journal of Immunology* 170:1517-1523 (2003).
Xiao, H., et al., "Alternative Complement Pathway in the Pathogenesis of Disease Mediated by Anti-Neutrophil Cytoplasmic Autoantibodies," *American Journal of Pathology* 170:52-64 (2007).
Xing, G., et al., "Complement Activation is Involved in Renal Damage in Human Antineutrophil Cytoplasmic Autoantibody Associated Pauci-Immune Vasculitis," *Journal of Clinical Immunology* 29:282-291 (2009).
Atkinson, C., et al., "Targeted Complement Inhibitors Protect Against Posttransplant Cardiac Ischemia and Reperfusion Injury and Reveal an Important Role for the Alternative Pathway of Complement Activation," *The Journal of Immunology* 185:7007-7013 (2010).
Banda, N.K., et al., "Complement Activation Pathways in Murine Immune Complex-Induced Arthritis and in C3a and C5a Generation In Vitro," *Clinical and Experimental Immunology* 159:100-108 (2009).
Rohrer, B., et al., "Eliminating Complement Factor D Reduces Photoreceptor Susceptibility to Light-Induced Damage," *Investigative Ophthalmology & Visual Science* 48(11):5282-5289 (2007).
Undar, A., et al., "Novel Anti-Factor D Monoclonal Antibody Inhibits Complement and Leukocyte Activation in a Baboon Model of Cardiopulmonary Bypass," *The Annals of Thoracic Surgery* 74:355-362 (2002).
Robbins, Richard A., et al., "Complement Activation by Cigarette Smoke," *American Journal of Physiology* 260(4 Part 1):L254-L259 (1991).
Hietala, M.A., et al., "Complement Activation by Both Classical and Alternative Pathways is Critical for the Effector Phase of Arthritis," *European Journal of Immunology* 34:1208-1215 (2004).
Moller-Kristensen, M., et al., "Mannan-binding Lectin Recognizes Structures on Ischaemic Reperfused Mouse Kidneys and is Implicated in Tissue Injury," *J Immunology* 61:426-434 (2005).
Taban, M., et al., "Acute Endophthalmitis Following Cataract Surgery," *Archives of Ophthalmology* 123:613-620 (2005).
Rutland-Brown, W., et al., "Incidence of Traumatic Brain Injury in the United States, 2003," *Journal of Head Trauma Rehabilitation* 21(6):544-548 (2006).
Smith, R.J.H., et al., "Dense Deposit Disease," *Molecular Immunology* 48:1604-1610 (2011).
Langlois, J.A., et al., "The Epidemiology and Impact of Traumatic Brain Injury," *Journal of Head Trauma Rehabilitation* 21(5):375-378 (2006).
Rohrer, B., et al., "Systemic Human CR2-Targeted Complement Alternative Pathway Inhibitor Ameliorates Mouse Laser-Induced Choroidal Neovascularization," *Journal of Ocular Pharmacology and Therapeutics* 28(4):402-409 (2012).
McInnes, I.B., et al., "The Pathogenesis of Rheumatoid Arthritis," *The New England Journal of Medicine* 365:2205-2219 (2011).
Khandhadia, S., et al., "Age-Related Macular Degeneration and the Complement System," *Immunobiology* 217:127-146 (2012).
Xing, G., et al., "Differential Deposition of C4d and MBL in Glomeruli," *The Journal of Clinical Immunology* 30:144-156 (2010).
Chow, S.P., et al., "Mannose-Binding Lectin as Part of the Complement Pathway: Characterisation of Non-Inflamed and Inflamed Human Eyes," *Clinical and Experimental Ophthalmology* 39(9):871-877 (2011).

Weiser, M.R., et al., "Experimental Murine Acid Aspiration Injury is Mediated by Neutrophils and the Alternative Complement Pathway," *Journal of Applied Physiology* 83:1090-1095 (1997).
Cervera, A., et al., "Genetically-Defined Deficiency of Mannose-Binding Lectin is Associated with Protection after Experimental Stroke in Mice and Outcome in Human Stroke," *PLoS One* 5(2):e8433 (2010). (Abstract only).
Leinhase, I., et al., "Inhibition of the Alternative Complement Activation Pathway in Traumatic Brain Injury by a Monoclonal Anti-Factor B Antibody: a Randomized Placebo-Controlled Study in Mice," *Journal of Neuroinflammation* 4:13 (2007).
Leinhase, I., et al., "Reduced Neuronal Cell Death After Experimental Brain Injury in Mice Lacking a Functional Alternative Pathway of Complement Activation," *BMC Neuroscience* 7:55 (2006).
Elliott, M. K., et al., "Effects of complement factor D deficiency on the renal disease of MRL/lpr mice." *Kidney Int* 65(1): 129-138 (2004).
Osthoff, M., et al., "Mannose-Binding Lectin Deficiency is Associated with Smaller Infarction Size and Favorable Outcome in Ischemic Stroke Patients," *PloS ONE* 6(6):e21338 (2011).
Lhotta, K., et al., "Glomerular Disposition of Mannose-Binding Lectin in Human Glomerulonephritis," *Nephrology Dialysis Transplantation* 14:881-886 (1999).
Iwaki, D., et al., "The Role of Mannose-Binding Lectin-Associated Serine Protease-3 in Activation of the Alternative Complement Pathway," *The Journal of Immunology* 187:3751-3758 (2011).
Hillmen, P., et al., "Effect of Eculizumab on Hemolysis and Transfusion Requirements in Patients with Paroxysmal Nocturnal Hemoglobinuria," *New England Journal of Medicine* 350:552-9 (2004).
Risitano, A.M., et al., "Complement Fraction 3 Binding on Erythrocytes as Additional Mechanism of Disease in Paroxysmal Nocturnal Hemoglobinuria Patients Treated by Eculizumab," *Blood* 113:4094-4100 (2009).
Teh, C., et al., "M-Ficolin is Expressed on Monocytes and is a Lectin Binding to N-acetyl-D-glucosamine and Mediates Monocyte Adhesion and Phagocytosis of *Escherichia coli*," *Immunology* 101:225-232 (2000).
Hansen, S., et al., "Collectin 11 (CL-11, CL-K1) is a MASP-1/3-Associated Plasma Collectin with Microbial-Binding Activity," *J Immunology* 185:6096-6104 (2010).
Jack, D.L., et al., "Mannose-binding Lectin Enhances Phagocytosis and Killing of *Neisseria meningitidis* by Human Macrophages," *J Leukoc Biol* 77:328-336 (2005).
Aoyagi, Y., et al., "Role of L-Ficolin Mannose-binding Lectin-associated Serine Protease Complexes in the Opsonophagocytosis of Type III Group B Streptococci," *J Immunology* 174:418-425 (2005).
Degn. S.E., et al., "Map19, the Alternative Splice Product of the MASP2 Gene," *J Immunological Methods* 373(1-2):89-101 (2011).
Schwaeble, W.J., et al., "Does Properdin Crosslink the Cellular and the Humoral Immune Response?" *Immunology Today* 20(1):17-21 (1999).
Risitano, A.M., et al., "Paroxysmal Nocturnal Hemoglobinuria: Pathophysiology, Natural History and Treatment Options in the Era of Biological Agents," *Biologics* 2:205-222 (2008).
Sullivan, M., et al., "Epidemiological Approach to Identifying Genetic Predispositions for Atypical Hemolytic Uremic Syndrome," *Ann Human Genetics* 74(1):17-26 (2010).
Lee, C-S., et al., "Invasive Pneumococcal Pneumonia is the Major Cause of Paediatric Haemolytic-Uraemic Syndrome in Taiwan," *Nephrology* 17:48-52 (2012).
Banerjee, R., et al., "*Streptococcus Pneumoniae*-Associated Hemolytic Uremic Syndrome Among Children in North America," *Pediatric Infectious Disease Journal* 30:736-739 (2011).
George, J. N., "Thrombotic Thrombocytopenic Purpura," *New England Journal of Medicine* 354:1927-35 (2006).
Tsai, H.-M., "Advances in the Pathogenesis, Diagnosis, and Treatment of Thrombotic Thrombocytopenic Purpura," *Journal of American Society of Nephrology* 14:1072-1081 (2003).

(56) References Cited

OTHER PUBLICATIONS

George, J.N., "The Association of Pregnancy with Thrombotic Thrombocytopenic Purpura-Hemolytic Uremic Syndrome," *Current Opinions in Hematology* 10(5):339-344 (2003).
Hamasaki, K., et al., "Systemic Lupus Erythematosus and Thrombotic Thrombocytopenic Purpura: a Case Report and Literature Review," *Clin Rheumatol* 22:355-358 (2003).
Azarm, T., et al., "Thrombotic Thrombocytopenic Purpura Associated with Clopidogrel: a Case Report and Review of the Literature," *J Res Med Sci* 16(3):353-357 (2011).
Moake, J.L., "Thrombotic Microangiopathies," *N Eng J Med* 347(8):589-600 (2002).
Pelras, S., et al., "Severe Transient ADAMTS13 Deficiency in Pneumococcal-associated Hemolytic Uremic Syndrome," *Pediatr Nephrol* 26:631-635 (2011).
Rock, G.A., et al., "Comparison of Plasma Exchange with Plasma Infusion in the Treatment of Thrombotic Thrombocytopenic Purpura," *N Engl J Med* 325(6):393-397 (1991).
Tsai, H.-M., "Thrombotic Thrombocytopenic Purpura: A Thrombotic Disorder Caused by ADAMTS13 Deficiency," *Hematol Oncol Clin North Am* 21(4):609-v (2007).
Galbusera, M., et al. "Inherited Thrombotic Thrombocytopenic Purpura," *Haematologica* 94(2):166-170 (2009).
Ruiz-Torres, M.P., et al., "Complement Activation: the Missing Link Between ADAMTS-13 Deficiency and Microvascular Thrombosis of Thrombotic Microangiopathies," *Thromb Haemost* 93:443-52 (2005).
Reti, M., et al., "Complement Activation in Thrombotic Thrombocytopenic Purpura," *J Thrombosis Haemostatsis* 10:791-798 (2012).
Peerschke, E.I., et al., "Complement Activation on Platelets: Implications for Vascular Inflammation and Thrombosis," *Mol Immunology* 47(13):2170-2175 (2010).
George, J.N., et al., "Systemic Malignancies as a Cause of Unexpected Microangiopathic Hemolytic Anemia and Thrombocytopenia," *Oncology* 25(10):908-14 (2011).
Mullins, R.F., et al., "Drusen Associated with Aging and Age-related Macular Degeneration Contain Proteins Common to Extracellular Deposits Associated with Atherosclerosis, Elastosis, Amyloidosis, and Dense Deposit Disease," *FASEB J* 14(7):835-846 (2000).
Johnson, L.V., et al., "A Potential for Immune Complex Pathogenesis in Drusen Formation," *Exp Eye Res* 70:441-449 (2000).
Wagner, E., et al., "Therapeutic Potential of Complement Modulation," *Nature Reviews* 9:43-56 (2010).
Coligan, J.E., et al. (Eds.). 1991. Production of Monoclonal Antibodies. *Current Protocols in Immunology*, pp. 2.5.1-2.6.7. vol. 1. John E. Wiley & Sons.
Gal, P., et al., "A True Autoactivating Enzyme: Structural Insight into Mannose-binding Lectin-associated Serine Protease Activations," *J Biol Chem* 280(9):33435-33444 (2005).
Takahashi, M., et al., "Mannose-binding Lectin (MBL)-associated Serine Protease (MASP)-1 Contributes to Activation of the Lectin Complement Pathway," *J Immunology* 180(9):6132-6138 (2008).
Knappik, A., et al., "Fully Synthetic Human Combinatorial Antibody Libraries (HuCAL) Based on Modular Consensus Frameworks and CDRs Randomized with Trinucleotides," *J MoL Biol* 296:57-86 (2000).
Gulla, K.C., et al., "Activation of Mannan-Binding Lectin-Associated Serine Proteases Leads to Generation of a Fibrin Clot," *Immunology* 129:482-495 (2009).
Degn, S., et al., "Map44, a Human Protein Associated with Pattern Recognition Molecules of the Complement System and Regulating the Lectin Pathway of Complement Activation[1]," *Journal of Immunology* 183:7371-7378 (2009).
Skjoedt, M., et al., "A Novel Mannose-Binding Lectin/Ficolin-Associated Protein is Highly Expressed in Heart and Skeletal Muscle Tissues and Inhibits Complement Activation," *The Journal of Biological Chemistry* 285(11):8234-8243 (2010).
Teillet, F., et al., "Crystal structure of the CUB1-EGF-CUB2 domain of human MASP-1/3 and identification of its interaction sites with mannan-binding lectin and ficolins." *J. Biol. Chem* 283(37): 25715-25724 (2008).
Dobó, J., et al., "MASP-1, a Promiscuous Complement Protease: Structure of its Catalytic Region Reveals the Basis of its Broad Specificity," *The Journal of Immunology* 183:1207-1214 (2009).
Harmat, V., et al., "The Structure of MBL-Associated Serine Protease-2 Reveals that Identical Substrate Specificities of C1s and MASP-2 are Realized Through Different Sets of Enzyme-Substrate Interactions," *Journal of Molecular Biology* 342:1533-1546 (2004).
Garred, P., et al., "Two Edged Role of Mannose Binding Lectin in Rheumatoid Arthritis: a Cross Sectional Study," *The Journal of Rheumatology* 27:26-34 (2000).
Takayama, Y., et al., "A 100-kDA Protein in the C4-Activating Component of Ra-Reactive Factor is a New Serine Protease Having Module Organization Similar to C1r and C1s[1]," *The Journal of Immunology* 152:2308 (1994).
Triolo, G., et al., "Impaired Expression of Erythrocyte Glycosyl-Phosphatidylinositol-Anchored Membrane CD59 in Patients with Psoriatic Arthritis. Relation to Terminal Complement Pathway Activation," *Clinical and Experimental Rheumatology* 21:225-228 (2003).
Sekine, H., et al., "The Role of MASP-1/3 in Complement Activation." *Adv. Exp. Med. Biol* 734: 41-53 (2013).
Harboe, M., et al., "The Quantitative Role of Alternative Pathway Amplification in Classical Pathway Induced Terminal Complement Activation," *Clinical Experimental Immunology* 138:439-446 (2004).
Rooryck, C., et al., "Mutations in Lectin Complement Pathway Genes COLEC11 and MASP1 Cause 3MC Syndrome," *Nature Genetics* ePub ahead of print (2011).
Le, Y., et al., "Human $^L$-Ficolin: Plasma Levels, Sugar Specificity, and Assignment of its Lectin Activity to the Fibrinogen-Like (FBG) Domain," *FEBS Letters* 425:367-370 (1998).
Endo, Y., et al., "Two Lineages of Mannose-Binding Lectin-Associated Serine Protease (MASP) in Vertebrates[1,2]," *The Journal of Immunology* 161:4924-4930 (1998).
Megyeri, M., et al., "Quantitative Characterization of the Activation Steps of Mannan-Binding Lectin (MBL)-Associated Serine Proteases (MASPs) Points to the Central Role of MASP-1 in the Initiation of Complement Lectin Pathway," *The Journal of Biological Chemistry* 288(13):8922-8934 (2013).
Israëls, J., et al., "Mannose-Binding Lectin and Infection Risk in Newborns: A Systemic Review," *Arch Dis Child Fetal Neonatal Ed* 95:F452-F461 (2010).
Mathieson, P., et al., "Complement-Mediated Adipocyte Lysis by Nephritic Factor Sera," *The Journal of Experimental Medicine* 177:1827-1831 (1993).
Ali, Y.M., et al., "The lectin pathway of complement activation is a critical component of the innate immune response to pneumococcal infection," *PLoS Pathog* 8(7):e1002793, doi:10.1371/journal.ppat.1002793.
Selander, B., et al., "Mannan-Binding Lectin Activates C3 and the Alternative Complement Pathway Without Involvement of C2," *The Journal of Clinical Investigation* 116(5): 1425-1434 (2006).
Shalaby, M.R., et al., "Development of Humanized Bispecific Antibodies Reactive with Cytotoxic Lymphocytes and Tumor Cells Overexpressing the HER2 Protooncogene," *The Journal of Experimental Medicine* 175:217-225 (1992).
Holliger, P., et al., "'Diabodies': Small Bivalent and Bispecific Antibody Fragments," *Proceedings of the National Academy of Sciences* 90:6444-6448 (1993).
Wu, C., et al., "Simultaneous Targeting of Multiple Disease Mediators by a Dual-Variable-Domain Immunoglobulin," *Nature Biotechnology* 25(11): 1290-1297 (2007).
Yabuki, M., et al., "Antibody Discovery Ex Vivo Accelerated by the LacO/LacI Regulatory Network," *PLoS ONE* 7(4):1-9 (2012).
Seo, H., et al., "Rapid Generation of Specific Antibodies by Enhanced Homologous Recombination," *Nature Biotechnology* 23(6):731-735 (2005).
Buerstedde, J.M., et al., "Light Chain Gene Conversion Continues at a High Rate in an ALV-Induced Cell Line," *The EMBO Journal* 9(3):921-927 (1990).

(56) References Cited

OTHER PUBLICATIONS

Maizels, N., "Immunoglobulin Gene Diversification," *Annu.Rev. Genet.* 39:23-46 (2005).
Cummings, W.J., et al., "Chromatin Structure Regulates Gene Conversion," *PLoS Biology* 5(10):2145-2155 (2007).
Nakamura, N., et al., "Characterization of the Interaction Between Serum Mannan-Binding Protein and Nucleic Acid Ligands," *Journal of Leukocyte Biology* 86:737-748 (2009).
Thiel, S., "Mannnan-Binding Lectin (MBL)-Associated Serine Protease-1 (MASP-1), a Serine Protease Associated with Humoral Pattern-Recognition Molecules: Normal and Acute-Phase Levels in Serum and Stoichiometry of Lectin Pathway Components," *Clinical and Experimental Immunology* 169:38-48 (2012).
Cumbers, S., et al., "Generation and Interactive Affinity Maturation of Antibodies In Vitro Using Hypermutating B-Cell Lines," *Nature Biotechnology* 20(11):1129-1134 (2002).
Bitter-Suermann, D., et al., "Activation of the Alternative Pathway of Complement: Efficient Fluid-Phase Amplification by Blockade of the Regulatory Complement Protein β1H Through Sulfated Polyanions*," *European Journal of Immunology* 11:291-295 (1981).
Johne, B., "Epitope Mapping and Binding Kinetics of Monoclonal Antibodies Studied by Real Time Biospecific Interaction Analysis Using Surface Plasmon Resonance," *Journal of Immunological Methods* 160:191-198 (1993).
Brennan, M., et al., "Preparation for Bispecific Antibodies by Chemical Recombination of Monoclonal Immunoglobulin $G_1$ Fragments," *Science* 229:81-83 (1985).
Tutt, A., et al., "Trispecific F(ab')$_3$ Derivatives That Use Cooperative Signaling Via the TCR/CD3 Complex and CD2 to Activate and Redirect Resting Cytotoxic T Cells," *The Journal of Immunology* 147(1):60-69 (1991).
Csuka, D., et al., "The Role of Ficolins and MASPs in Hereditary Angioedema Due to C1-Inhibitor Deficiency," *Molecular Immunology* 54:271-277 (2013).
Takada, F., et al., "Localization of the Genes for the 100-kDa Complement-Activating Components of Ra-Reactive Factor (CRARF and Crarf) to Human 3q27-q28 and Mouse 16B2-B3," *Genomics* 25:757-759 (1995).
Ruskamp, J., "Polymorphisms in the Mannan-Binding Lectin Gene are Not Associated with Questionnaire-Reported Respiratory Tract Infections in Children," *Journal of Infectious Diseases* 198:1707-1713 (2008).
Kostelny, S., et al., "Formation of a Bispecific Antibody by the Use of Leucine Zippers," *The Journal of Immunology* 148(5):1547-1553 (1992).
Zapata, G., et al., "Engineering Linear F(ab')$_2$ Fragments for Efficient Production in *Escherichia coli* and Enhanced Antiproliferative Activity," *Protein Engineering* 8(10):1057-1062 (1995).
Palaniyar, N., et al., "Innate Immune Collectins Bind Nucleic Acids and Enhance DNA Clearance in Vitro," *Annual NY Academy of Sciences* 1010:467-470 (2003).
Milstein, C., "Hybrid Hybridomas and Their Use in Immunohistochemistry," *Nature* 305:537-540 (1983).
Suresh, M.R., et al., "Bispecific Monoclonal Antibodies from Hybrid Hybridomas," *Methods in Enzymology* 121:210-228 (1986).
Gruber, M., et al., "Efficient Tumor Cell Lysis Mediated by a Bispecific Single Chain Antibody Expressed in *Escherichia coli*[1]," *The Journal of Immunology* 152:5368-5374 (1994).
Degn, S., "Biological Variations of MASP-3 and MAp44, Two Splice Products of the MASP1 Gene Involved in Regulation of the Complement System," *Journal of Immunological Methods* 361:37-50 (2010).
Thomsen, T., et al., "Ficolins and FIBCD1: Soluble and Membrane Bound Pattern Recognition Molecules with Acetyl Group Selectivity," *Molecular Immunology* 48:369-381 (2011).
Stanton, C.M. et al., "Evidence that the HTRA1 Interactome Influences Susceptibility to Age-Related Macular Degeneration," presented at *The Association for Research in Vision and Ophthalmology 2011 Conference* May 11, 2011 (Abstract Only).

Cummings, W.J., et al., "Genetic variation stimulated by epigenetic modification," *PLoS One* 3(12):e4075 (2007).
Lee, W.A., "Permeation Enhancers for the Nasal Delivery of Protein and Peptide Therapeutics," *BioPharm* 3(10):22-25 (1990).
Sugomoto, R., et al., "Cloning and Characterization of the Hakata Antigen, a Member of the Ficolin/Opsonin p35 Lectin Family," *The Journal of Biological Chemistry* 273(33):20721-20727 (1998).
Friedman, D.S., et al., "Prevalence of Age-Related Macular Degeneration," *Archives of Ophthalmology* 122:564-572 (2004).
Issa, P.C., "The Significance of the Complement System for the Pathogenesis of Age-Related Macular Degeneration—Current Evidence and Translation into Clinical Application," *Graefe's Archive for Clinical and Experimental Ophthalmology* 249:163-174 (2011).
Thurman, J.M., et al., "Oxidative Stress Renders Retinal Pigment Epithelial Cells Susceptible to Complement-Mediated Injury," *The Journal of Biological Chemistry* 284(25):16939-16947 (2009).
Collard, C.D., et al., "Complement Activation Following Oxidative Stress," *Molecular Immunology* 36:941-948 (1999).
Cai, X., et al., "Oxidative Stress: The Achilles Heel of Neurodegenerative Diseases of the Retina," *Frontiers in Bioscience* 17:1976-1995 (2012).
Rohrer, B., et al., "The Alternative Pathway is Required, but not alone Sufficient, for Retinal Pathology in Mouse Laser-Induced Choroidal Neovascularization," *Molecular Immunology* 48(6-7):e1-e8 (2011).
Ryan, S.J., "The Development of an Experimental Model of Subretinal Neovascularization in Disciform Macular Degeneration," *Transactions of the American Ophthalmological Society* 77:707-745 (1979).
Haahr-Pedersen, S., et al., "Level of Complement Activity Predicts Cardiac Dysfunction after Acute Myocardial Infarction Treated with Primary Percutaneous Coronary Intervention," *Journal of Invasive Cardiology* 21(1):13-19 (2009).
Rudd, P.M., et al., "Sugar-Mediated Ligand-Receptor Interactions in the Immune System," *Trends in Biotechnology* 22(10):524-530 (2004).
Chimenti, M.S., et al., "Complement System in Psoriatic Arthritis: a Useful Marker in Response Prediction and Monitoring of Anti-TNF Treatment," *Clinical and Experimental Rheumatology* 30:23-30 (2012).
Ballanti, E., et al., "Role of the Complement System in Rheumatoid Arthritis and Psoriatic Arthritis: Relationship with Anti-TNF Inhibitors," *Autoimmunity Reviews* 10:617-623 (2011).
Morrison, T.E. et al., "Complement Contributes to Inflammatory Tissue Destruction in a Mouse Model of Ross River Virus-Induced Disease," *The Journal of Virology* 81(10):5132-5143 (2007).
Gunn, B.M., et al., "Mannose Binding Lectin is Required for Alphavirus-Induced Arthritis/Myositis," *PloS Pathogens* 8(3):e1002586 (2012).
Levi, M. et al., "Coagulation Abnormalities in Critically Ill Patients" *Critical Care* 10(4):222 (2006).
Zheng, X.L., et al., "Pathogenesis of Thrombotic Microangiopathies," *Annual Review of Pathology* 3:249-277 (2008).
Thurman, J.M., et al., "Alternative Pathway of Complement in Children with Diarrhea-Associated Hemolytic Uremic Syndrome," *Clinical Journal of the American Society of Nephrology* 4:1920-1924 (2009).
Orth, D., et al., "Shiga Toxin Activates Complement and Binds Factor H: Evidence for an Active Role of Complement in Hemolytic Uremic Syndrome[1]," *The Journal of Immunology* 182:6394-6400 (2009).
Atkinson, J.P., "Complement Factor H and the Hemolytic Uremic Syndrome," *Journal of Experimental Medicine* 204(6):1245-1248 (2007).
Zhang, X., et al., "A Complex Role for Complement in Allergic Asthma," *Expert Reviews of Clinical Immunology* 6(2):269-277 (2010).
Varga, L., et al., "Studies on the Mechanisms of Allergen-Induced Activation of the Classical and Lectin Pathways of Complement," *Molecular Immunology* 39:839-846 (2003).
Kanemitsu, H., et al., "Complement Activation by Diesel Exhaust Particles (DEP)," *Biological & Pharmaceutical Bulletin* 21(2):129-132 (1998).

(56) References Cited

OTHER PUBLICATIONS

Taube, C., et al., "Factor B of the Alternative Complement Pathway Regulates Development of Airway Hyperresponsiveness and Inflammation," *PNAS* 103(21):8084-8089 (2006).
Alchi, B., "Membranoproliferative Glomerulonephritis," *Pediatric Nephrology* 25:1409-1418 (2010).
Daina, E., et al., "Eculizumab in a Patient with Dense-Deposit Disease," *New England Journal of Medicine* 366(12):1161-1163 (2012).
Vivarelli, M., et al., "Eculizumab for the Treatment of Dense-Deposit Disease," *The New England Journal of Medicine* 366(12):1163-1165 (2012).
Hedger, N., "Incidence and Outcome of Pauci-Immune Rapidly Progressive Glomerulonephritis in Wessex, UK: a 10-Year Retrospective Study," *Nephrology Dialysis Transplant* 15:1593-1599 (2000).
Chen, M., et al., "ANCA-Associated Vasculitides—Advances in Pathogenesis and Treatment," *Nature Reviews Rheumatology* 6:653-664 (2010).
Xiao, H., et al., "Antineutrophil Cytoplasmic Autoantibodies Specific for Myeloperoxidase Cause Glomerulonephritis and Vasculitis in Mice," *Journal of Clinical Investigation* 110:955-963 (2002).
Chen, M. et al., "Antineutrophil Cytoplasmic Autoantibody-Negative Pauci-immune Crescentic Glomerulonephritis," *Journal of the American Society of Nephrology* 18:599-605 (2007).
Chen, M., et al., "ANCA-Negative Pauci-immune Crescentic Glomerulonephritis," *Nature Reviews Nephrology* 5:313-318 (2009).
McAllister, T.W., "Neurobiological Consequences of Traumatic Brain Injury," *Dialogues of Clinical Neuroscience* 13:287-300 (2011).
Kuraya, M., et al., "Expression of H-Ficolin/Hakata Antigen, Mannose-Binding Lectin-Associated Serine Protease (MASP)-1 and MASP-3 by Human Glioma Cell Line T98G," *International Immunology* 15(1):109-117 (2003).
Søborg, C., et al., "Mannose-Binding Lectin Polymorphisms in Clinical Tuberculosis," *The Journal of Infectious Diseases* 188:777-782 (2003).
Valentin, D., "Evidence for Association Between Multiple Complement Pathway Genes and AMD," *Genetic Epidemiology* 31:224-237 (2007).
Wang, Y., et al., "Gene Profiling in Murine Corneas Challenged with *Aspergillus fumigatis*," *Molecular Vision* 13:1226-1233 (2007).
Papadopoulos, M., et al., "Aquaporin 4 and Neuromyelitis Optica," *The Lancet Neurology* 11:535-544 (2012).
Misu, T., et al., "Presence of Six Different Lesion Types Suggests Diverse Mechanisms of Tissue Injury in Neuromyelitis Optica," *Acta Neuropathologica* 125:815-827 (2013).
Jarius, S., et al., "Mechanisms of Disease: Aquaporin-4 Antibodies in Neuromyelitis Optica," *Nature Clinical Practice Neurology* 4(4):202-214 (2008).
Kuroda, H., "Increase of Complement Fragment C5A in Cerebrospinal Fluid During Exacerbation of Neuromyelitis Optica," *Journal of Neuroimmunology* 254:178-182 (2013).
Saadoun, S., et al., "Intra-Cerebral Injection of Neuromyelitis Optica Immunoglobulin G and Human Complement Produces Neuromyelitis Optica Lesions in Mice," *Brain* 133:349-361 (2010).
Tüzün, E., et al., "Enhanced Complement Consumption in Neuromyelitis Optica and Behçet's Disease Patients," *The Journal of Neuroimmunology* 233:211-215 (2011).
Al-Araji, A., et al., "Neuro-Behçet's Disease: Epidemiology, Clinical Characteristics, and Management," *The Lancet Neurology* 8:192-204 (2009).
Kirino, Y., et al., "Genome-Wide Association Analysis Identifies New Susceptibility Loci for Behçet's Disease and Epistasis Between HLA-B*51 and ERAP1," *Nature Genetics* 45(2):202-207 (2013).
Stevens, B., et al., "The Classical Complement Cascade Mediates CNS Synapse Elimination," *Cell* 131:1164-1178 (2007).
Marik, P.E., "Aspiration Pneumonitis and Aspiration Pneumonia," *The New England Journal of Medicine* 344(9):665-671 (2001).
Phuan, P.W., et al., "C1q-Targeted Monoclonal Antibody Prevents Complement-Dependent Cytotoxicity and Neuropathology in In Vitro and Mouse Models of Neuromyelitis Optica," *Acta Neuropathologica* 125:829-840 (2013).
Bardak, Y. et al., "The Demonstration of Serum Interleukin 6-8, Tumor Necrosis Factor-Alpha, Complement and Immunoglobulin Levels in Behçet's Disease with Other Ocular Involvement" *Ocular Immunology and Inflammation* 12(1):53-58 (2004).
Jongen, P.J.H., et al., "Humoral and Cellular Immunologic Study of Cerebrospinal Fluid in a Patient with Behcet Encephalitis," *Archives of Neurology* 49:1075-1078 (1992).
Epstein, J., et al., "The Collectins in Innate Immunity," *Current Opinions in Immunology* 8:29-35 (1996).
Ito, Y., et al., "An insulin-releasing system that is responsive to glucose," *J Controlled Release* 10:195-203 (1989).
Cortesio, C.L., et al., "Mannan-binding lectin-associated serine proease 3 cleaves synthetic peptides and insulin-like growth factor-binding protein 5," *Archives of Biochemistry and Biophysics* 449:164-170 (2006).
Harlow, E., Antibodies, A Laboratory Manual. 1988, pp. 37-59.
Møllet-Kristensen, M., et al., "Cooperation between MASP-1 and MASP-2 in the generation of C3 convertase through the MBL pathway," *International Immunology* 19(2):141-149 (2006).
Nandakumar, K.S., et al., "Collagen type II-specific monoclonal antibody-induced arthritis in mice," *Am J Pathol* 163(5):1827-1837 (2003).
Huugen, D., et al., "Inhibition of complement factor C5 protects against anti-myeloperoxidase antibody-mediated glomerulonephritis in mice," *Kidney International* 71:646-654 (2007).
Jarius, S., et al., :AQP4 antibodies in neuromyelitis optica: diagnostic and pathogenetic relevance, *Nature Reviews* 6:383-392 (2010).
Montes, T., et al., "Functional basis of protection against age-related macular degeneration conferred by a common polymorphism in complement factor B," *PNAS* 106(11):4366-4371 (2009).
Yaspan, B.L., et al., "Targeting factor D of the alternative complement pathway reduces geographic atrophy progression ssecondary to age-related macular degeration," *Sci. Transl. Med.* 9:1-13 (2017).
Timmerman, P., et al., "Functional reconstruction and synthetic mimicry of a conformational epitope using CLIPS™ technology," *J Molecular Recognition* 20:283-299 (2007).
Rycyzyn, M.A., et al., "The use of an anti-CD40 agonist monoclonal antibody during immunizations enhances hybridoma generation," *Hybridoma* 27(1):25-30 (2008).
Langedijk, J.P.M., et al., "Helical peptide arrays for lead identification and interaction site mapping," *Analytical Biochemistry* 417:149-155 (2011).
Hu, X., et al., "therapeutic inhibition of the alternative complement pathway attenuates chronic EAE," *Mol Immunol* 54(3-4):302-308 (2013).
Thiel, S. et al., "Clinical manifestations of mannan-binding lectin deficiency," *Mol Immunol* 43:86-96 (2006).
Degn, S. E., et al. "Mannan-Binding Lectin-Associated Serine Protease (MASP)-1 Is Crucial for Lectin Pathway Activation in Human Serum, whereas neither MASP-1 nor MASP-3 Is Required for Alternative Pathway Function." *J. Immunol* 189(8): 3957-3969 (2012).
Oroszlan, G., et al., "MASP-1 and MASP-2 Do Not Activate Pro-Factor D in Resting Human Blood, whereas MASP-3 Is a Potential Activator: Kinetic Analysis Involving Specific MASP-1 and MASP-2 Inhibitors." *J Immunol* 196(2): 857-865 (2016).
Atik, T., et al. "Novel MASP1 mutations are associated with an expanded phenotype in 3MC1 syndrome." *Orphanet J Rare Dis* 10: 128 (2015).
Gaboriaud, C., et al., "The serine protease domain of MASP-3: enzymatic properties and crystal structure in complex with ecotin." *PLoS One* 8(7): e67962 (2013).
Degn, S. E., et al., "The pro-factor D cleaving activity of MASP-1/-3 is not required for alternative pathway function." *J Immunol* 192(12):5447-5448 (2014).
Takahashi, M., et al., "Comment on "The pro-factor D cleaving activity of MASP-1/-3 is not required for alternative pathway function"." *J Immunol* 192(12): 5448-5449 (2014).

(56) References Cited

OTHER PUBLICATIONS

Ricklin, D., et al. "New milestones ahead in complement-targeted therapy." *Semin Immunol* 28(3): 208-222 (2016).

Machida, T. S., et al., "MASP-1/3 deficient MLR/Lpr mice lack the alternative complement pathway activation and are protected from development of lupus-like glomerulonephritis." *ACM/ARHP meeting.* (2013).

* cited by examiner

FIG. 3

Human MASP-3 (SEQ ID NO:2)

MRWLLLYYALCFSLSKASAHTVELNNMFGQIQSPGYPDSYPSDSEVTWNITVPDGFRIKLYFMHFNLESSYLCEYD
YVKVETEDQVLATFCGRETTDTEQTPGQEVVLSPGSFMSITFRSDFSNEERFTGFDAHYMAVDVDECKEREDEELS
CDHYCHNYIGGYYCSCRFGYILHTDNRTCRVECSDNLFTQRTGVITSPDFPNPYPKSSECLYTELEEGFMVNLQF } CUB1-EGF-CUB2
EDIFDIEDHPEVPCPYDYIKIKVGPKVLGPFCGEKAPEPISTQSHSVLILFHSDNSGENRGWRLSYRAAG
NECPELQPPVHGKIEPSQAKYFFKDQVLVSCDTGYKVLKDNVEMDTFQIECLKDTWSNKIPTCKIVDCRAPGELE
HGLITFSTRNNLTTYKSEIKYSCQEPYYKMLNNNTGIYTCSAQGVWMNKVLGRSLPTCLPECGQPSRSLPSLVKRI
IGGRNAEPGLFPWQALIVEDTSRVPNDKWFGSGALLSASWILTAAHVLRSQRRDTTVIPVSKEHVTVYLGLHDVR } CCP1-CCP2-SP
DKSGAVNSSAARVVLHPDFNIQNYNHDIALVQLQEPVPLGPHVMPVCLPRLEPEGPAPHMLGLVAGWGISNPNVTV
DEIISSGTRTLSDVLQYVKLPVVPHAECKTSYESRSGNYSVTENMFCAGYYEGGKDTCLGDSGGAFVIFDDLSQRW
VVQGLVSWGGPEECGSKQVYGVYTKVSNYVDWVWEQMGLPQSVVEPQVER

MASP-3 protein: multi-species alignment

MASP-3 SP domain: multispecies alignment

FIG. 46 RBC Survival in Treated Mice

High Affinity MASP-3 mAbs: Heavy Chain Variable Regions

High Affinity MASP-3 mAbs: Light Chain Variable Regions

Dendrogram of the VH regions of High Affinity MASP-3 mAbs

Dendrogram of the VL regions of High Affinity MASP-3 mAbs

Binding of purified recombinant MASP-3 mAbs to human MASP-3

Binding of MASP-3 mAbs to full-length mouse MASP-3

High Affinity MASP-3 mAbs inhibit CFD Cleavage by rMASP-3

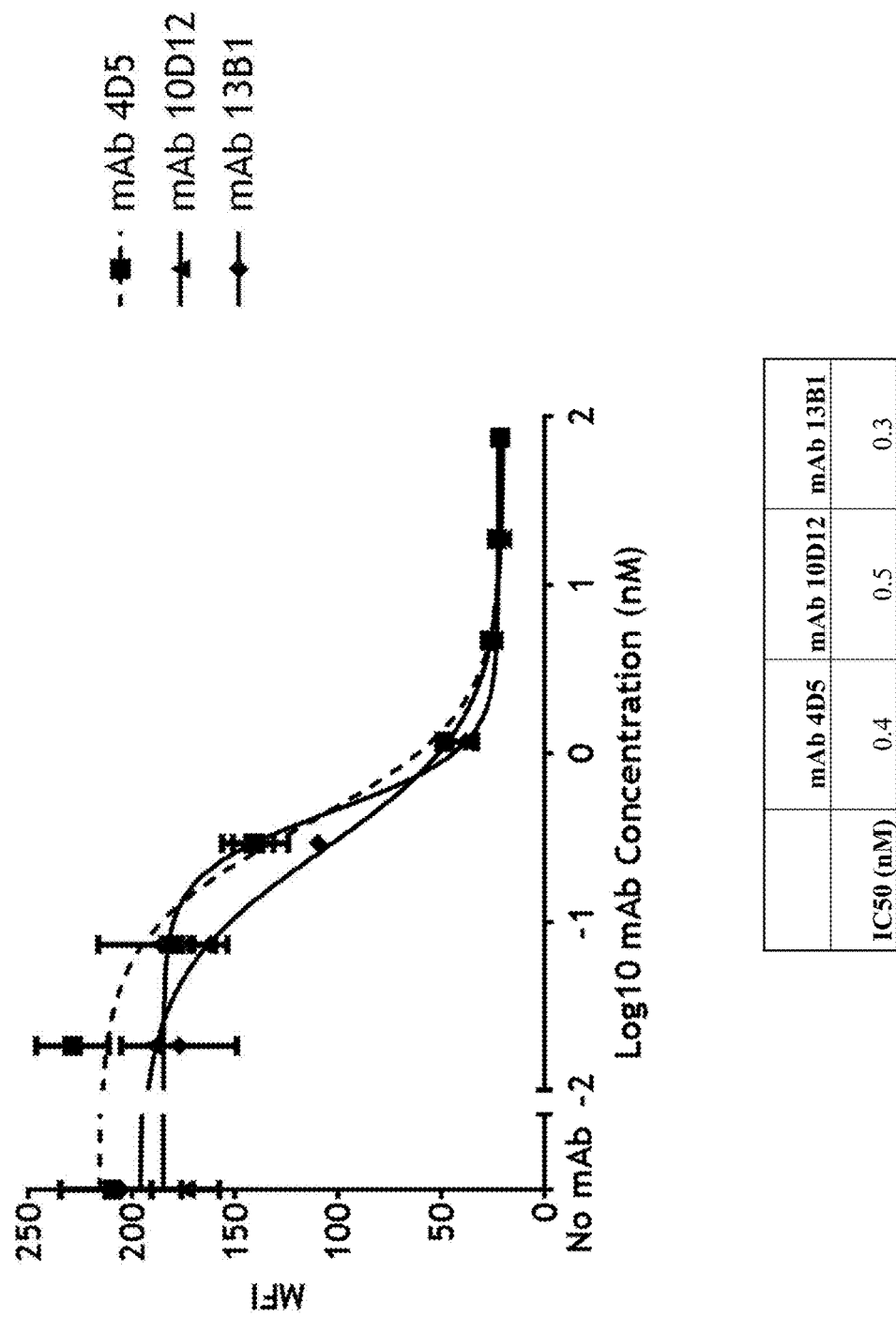

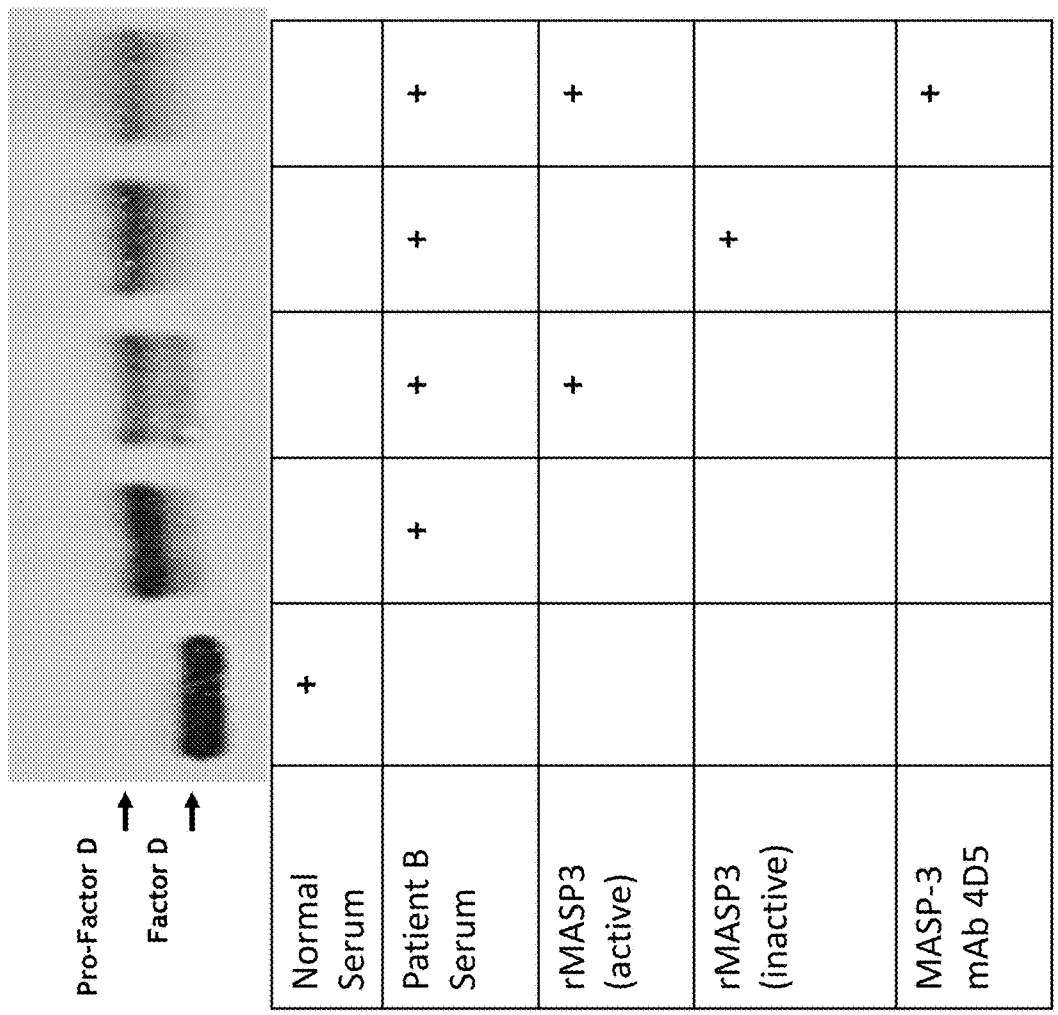

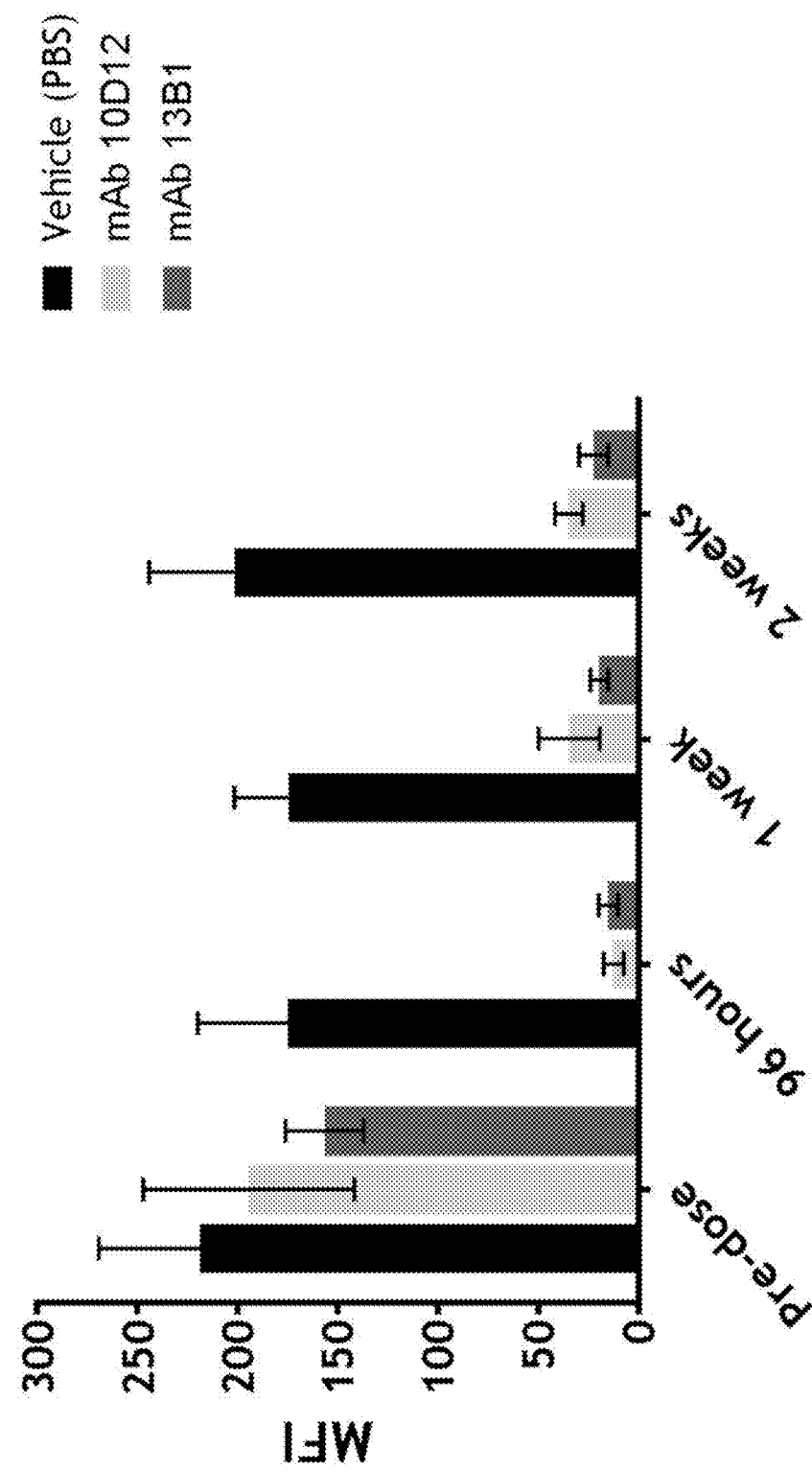

Status of the Ba fragment of Factor B in Mice treated with mAb 10D12

Serum from mice treated with mAb 10D12 shows inhibition of hemolysis

Competition binding analysis identifies MASP-3 mAbs (IgG4) that block the interaction between mAb 4D5 (IgG1) and MASP-3

Competition binding analysis identifies MASP-3 mAbs (IgG4) that block the interaction between mAb 10D12 (IgG1) and MASP-3

Competition binding analysis identifies MASP-3 mAbs (IgG4) that block the interaction between mAb 13B1 (IgG1) and MASP-3

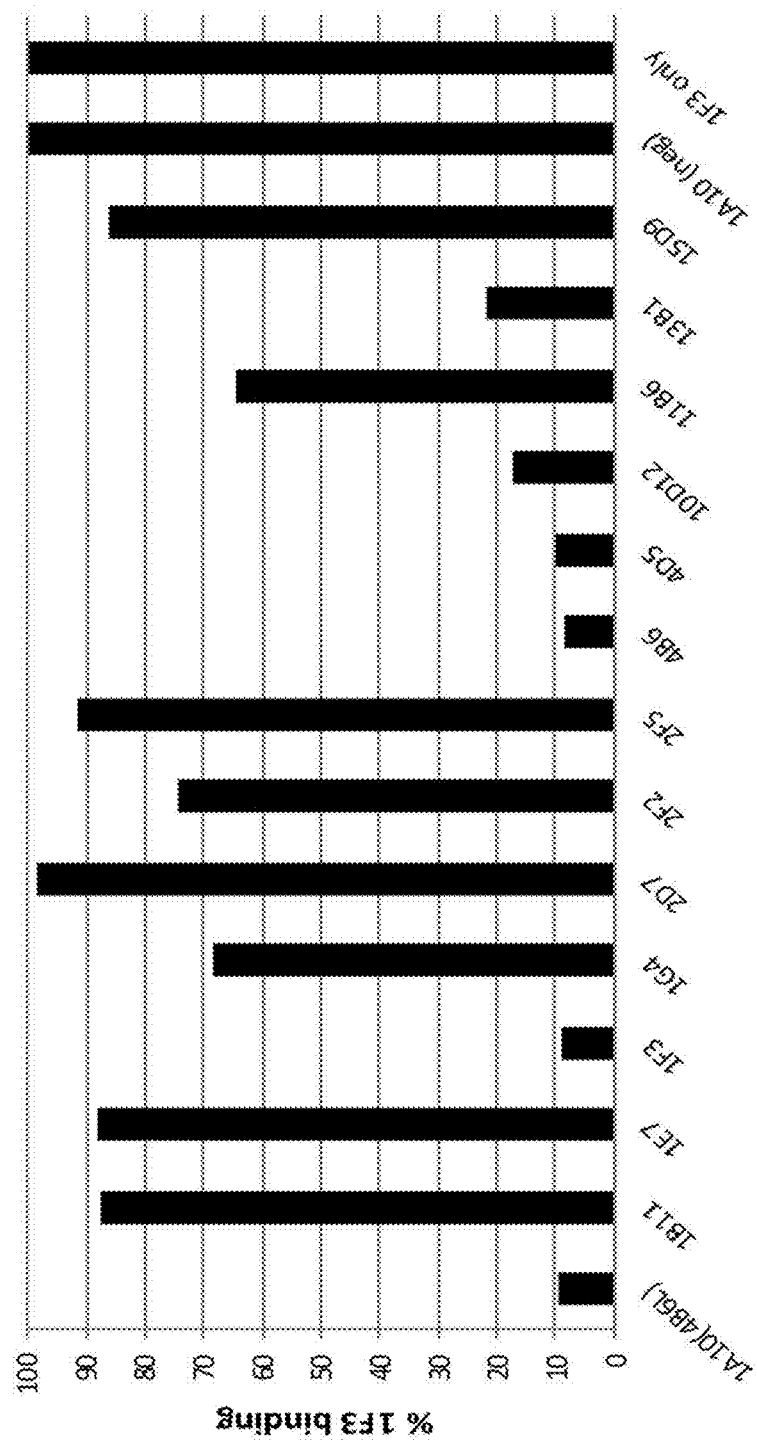
FIG. 61D Competition binding analysis identifies MASP-3 mAbs (IgG4) that block the interaction between mAb 1F3 (IgG4) and MASP-3

Competition binding analysis identifies MASP-3 mAbs (IgG4) that block the interaction between mAb 1G4 (IgG1

Regions of contact on MASP-3 by the MASP-3 mAbs

Regions of contact on human MASP-3 for mAbs 1F3, 4B6, 4D5 and 1A10

SEQ ID NO:9 = aa residues 498-509 of MASP-3
SEQ ID NO:11= aa residues 544-558 of MASP-3
SEQ ID NO:13= aa residues 639-649 of MASP-3
SEQ ID NO:14= aa residues 704-713 of MASP-3

Regions of contact on human MASP-3 for mAb 10D12

SEQ ID NO:9 = aa residues 498-509 of MASP-3

Regions of contact on human MASP-3 for mAb 13B1

SEQ ID NO:10 = aa residues 494 to 508 of MASP-3
SEQ ID NO:12 = aa residues 626 to 638 of MASP-3

Regions of contact on human MASP-3 for mAb 1B11

SEQ ID NO:16 = aa residues 435-447 of MASP-3
SEQ ID NO:17 = aa residues 454-464 of MASP-3
SEQ ID NO:21 = aa residues 583-589 of MASP-3
SEQ ID NO:22 = aa residues 614-623 of MASP-3

Regions of contact on human MASP-3 for mAb 1E7, 1G4 and 2D7

SEQ ID NO:17= aa residues 454 to 464 of MASP-3
SEQ ID NO:19= aa residues 514 to 523 of MASP-3
SEQ ID NO:23= aa residues 667 to 678 of MASP-3

Regions of contact on human MASP-3 for mAb 15D9 and 2F5

SEQ ID NO:17= aa residues 454 to 464 of MASP-3
SEQ ID NO:18= aa residues 479 to 493 of MASP-3
SEQ ID NO:20= aa residues 562 to 571 of MASP-3
SEQ ID NO:23= aa residues 667 to 678 of MASP-3

Analysis of Pro-Df/Mature Df in Serum from Monkey Treated with 13B1X

ANTIBODIES SPECIFICALLY BINDING TO MASP-3 FOR THE TREATMENT OF VARIOUS DISEASES AND DISORDERS

CROSS-REFERENCE TO RELATED APPLICATIONS

This application is a divisional of prior application Ser. No. 16/837,600, filed Apr. 1, 2020, which is a divisional of U.S. application Ser. No. 15/665,030, filed Jul. 31, 2017, now U.S. Pat. No. 10,639,369, which claims the benefit of U.S. Provisional Application No. 62/369,674, filed Aug. 1, 2016, and claims the benefit of U.S. Provisional Application No. 62/419,420, filed Nov. 8, 2016, and claims the benefit of U.S. Provisional Application No. 62/478,336, filed Mar. 29, 2017, all three of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0254_US3_Sequence_Listing_20200623_ST25; the file is 191 KB; was created on Jun. 23, 2020 and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York), in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has also been implicated in the pathogenesis of numerous acute and chronic disease states, including: myocardial infarction, stroke, ARDS, reperfusion injury, septic shock, capillary leakage following thermal burns, postcardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states. The growing recognition of the importance of complement-mediated tissue injury in a variety of disease states underscores the need for effective complement inhibitory drugs. To date, Eculizumab (Solaris®), an antibody against C5, is the only complement-targeting drug that has been approved for human use. Yet, C5 is one of several effector molecules located "downstream" in the complement system, and blockade of C5 does not inhibit activation of the complement system. Therefore, an inhibitor of the initiation steps of complement activation would have significant advantages over a "downstream" complement inhibitor.

Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and thus requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

The activation of the complement system results in the sequential activation of serine protease zymogens. The first step in activation of the classical pathway is the binding of a specific recognition molecule, C1q, to antigen-bound IgG and IgM molecules. C1q is associated with the C1r and C1s serine protease proenzymes as a complex called C1. Upon binding of C1q to an immune complex, autoproteolytic cleavage of the Arg-Ile site of C1r is followed by C1r-mediated cleavage and activation of C1s, which thereby acquires the ability to cleave C4 and C2. C4 is cleaved into two fragments, designated C4a and C4b, and, similarly, C2 is cleaved into C2a and C2b. C4b fragments are able to form covalent bonds with adjacent hydroxyl or amino groups and generate the C3 convertase (C4b2a) through noncovalent interaction with the C2a fragment of activated C2. C3 convertase (C4b2a) activates C3 by proteolytic cleavage into C3a and C3b subcomponents leading to generation of the C5 convertase (C4b2a3b), which, by cleaving C5 leads to the formation of the membrane attack complex (C5b combined with C6, C7, C8 and C-9, also referred to as "MAC") that can disrupt cellular membranes resulting in cell lysis. The activated forms of C3 and C4 (C3b and C4b) are covalently deposited on the foreign target surfaces, which are recognized by complement receptors on multiple phagocytes.

Independently, the first step in activation of the complement system through the lectin pathway is also the binding of specific recognition molecules, which is followed by the activation of associated serine protease proenzymes. However, rather than the binding of immune complexes by C1q, the recognition molecules in the lectin pathway comprise a group of carbohydrate-binding proteins (mannan-binding lectin (MBL), H-ficolin, M-ficolin, L-ficolin and C-type lectin CL-11), collectively referred to as lectins. See J. Lu et al., *Biochim. Biophys. Acta* 1572:387-400, (2002); Holmskov et al., *Annu. Rev. Immunol.* 21:547-578 (2003); Teh et al., *Immunology* 101:225-232 (2000)). See also J. Luet et al., *Biochim Biophys Acta* 1572:387-400 (2002); Holmskov et al, *Annu Rev Immunol* 21:547-578 (2003); Teh et al., *Immunology* 101:225-232 (2000); Hansen et al, *J. Immunol* 185(10):6096-6104 (2010).

Ikeda et al. first demonstrated that, like C1q, MBL could activate the complement system upon binding to yeast mannan-coated erythrocytes in a C4-dependent manner (Ikeda et al., *J. Biol. Chem.* 262:7451-7454, (1987)). MBL, a member of the collectin protein family, is a calcium-dependent lectin that binds carbohydrates with 3- and 4-hydroxy groups oriented in the equatorial plane of the pyranose ring. Prominent ligands for MBL are thus D-mannose and N-acetyl-D-glucosamine, while carbohydrates not fitting this steric requirement have undetectable affinity for MBL (Weis et al., *Nature* 360:127-134, (1992)). The interaction between MBL and monovalent sugars is extremely weak, with dissociation constants typically in the single-digit millimolar range. MBL achieves tight, specific binding to glycan ligands by avidity, i.e., by interacting simultaneously with multiple monosaccharide residues located in close proximity to each other (Lee et al., *Archiv. Biochem. Biophys.* 299:129-136, (1992)). MBL recognizes the carbohydrate patterns that commonly decorate microorganisms such as bacteria, yeast, parasites and certain viruses. In contrast, MBL does not recognize D-galactose and sialic acid, the penultimate and ultimate sugars that usually decorate "mature" complex glycoconjugates present on mammalian plasma and cell surface glycoproteins. This binding specificity is thought to promote recognition of "foreign" surfaces and help protect from "self-activation." However, MBL does bind with high affinity to clusters of high-mannose "precursor" glycans on N-linked glycoproteins and glycolipids sequestered in the endoplasmic reticulum and Golgi of mammalian cells (Maynard et al., *J. Biol. Chem.* 257:3788-3794, (1982)). In addition, it has been shown that MBL can bind the polynucleotides, DNA and RNA, which may be exposed on necrotic and apoptotic cells (Palaniyar et al., *Ann. N.Y. Acad. Sci.*, 1010:467-470 (2003); Nakamura et al., *J. Leuk. Biol.* 86:737-748 (2009)). Therefore, damaged cells are potential targets for lectin pathway activation via MBL binding.

The ficolins possess a different type of lectin domain than MBL, called the fibrinogen-like domain. Ficolins bind sugar residues in a $Ca^{++}$-independent manner. In humans, three kinds of ficolins (L-ficolin, M-ficolin and H-ficolin) have been identified. The two serum ficolins, L-ficolin and H-ficolin, have in common a specificity for N-acetyl-D-glucosamine; however, H-ficolin also binds N-acetyl-D-galactosamine. The difference in sugar specificity of L-ficolin, H-ficolin, CL-11, and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch et al., *J. Immunol.* 172:1198-1202, (2004)). In addition to acetylated sugar moieties, the ficolins can also bind acetylated amino acids and polypeptides (Thomsen et al., *Mol. Immunol.* 48(4):369-81 (2011)). The collectins (i.e., MBL) and the ficolins bear no significant similarity in amino acid sequence. However, the two groups of proteins have similar domain organizations and, like C1q, assemble into oligomeric structures, which maximize the possibility of multisite binding.

The serum concentrations of MBL are highly variable in healthy populations and this is genetically controlled by polymorphisms/mutations in both the promoter and coding regions of the MBL gene. As an acute phase protein, the expression of MBL is further upregulated during inflammation. L-ficolin is present in serum at concentrations similar to those of MBL. Therefore, the L-ficolin branch of the lectin pathway is potentially comparable to the MBL arm in strength. MBL and ficolins can also function as opsonins, which allow phagocytes to target MBL- and ficolin-decorated surfaces (see Jack et al., *J Leukoc Biol.*, 77(3):328-36 (2004), Matsushita and Fujita, *Immunobiology*, 205(4-5): 490-7 (2002), Aoyagi et al., *J Immunol*, 174(1):418-25 (2005). This opsonization requires the interaction of these proteins with phagocyte receptors (Kuhlman et al., *J. Exp. Med.* 169:1733, (1989); Matsushita et al., *J. Biol. Chem.* 271:2448-54, (1996)), the identity of which has not been established.

Human MBL forms a specific and high-affinity interaction through its collagen-like domain with unique C1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Matsushita et al., *J Exp Med* 176(6):1497-1502 (1992); Ji et al., *J. Immunol.* 150:571-578, (1993)). It was subsequently determined that the MASP activity was, in fact, a mixture of two proteases: MASP-1 and MASP-2 (Thiel et al., *Nature* 386:506-510, (1997)). However, it was demonstrated that the MBL-MASP-2 complex alone is sufficient for complement activation (Vorup-Jensen et al., *J. Immunol.* 165:2093-2100, (2000)). Furthermore, only MASP-2 cleaved C2 and C4 at high rates (Ambrus et al., *J. Immunol.* 170:1374-1382, (2003)). Therefore, MASP-2 is the protease responsible for activating C4 and C2 to generate the C3 convertase, C4b2a. This is a significant difference from the C1 complex of the classical pathway, where the coordinated action of two specific serine proteases (C1r and C1s) leads to the activation of the complement system. In addition, a third novel protease, MASP-3, has been isolated (Dahl, M. R., et al., *Immunity* 15:127-35, 2001). MASP-1 and MASP-3 are alternatively spliced products of the same gene.

MASPs share identical domain organizations with those of C1r and C1s, the enzymatic components of the C1 complex (Sim et al., *Biochem. Soc. Trans.* 28:545, (2000)). These domains include an N-terminal C1r/C1s/sea urchin VEGF/ bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain.

MBL can also associate with an alternatively spliced form of MASP-2, known as MBL-associated protein of 19 kDa (MAp19) or small MBL-associated protein (sMAP), which lacks the catalytic activity of MASP-2. (Stover, *J. Immunol.* 162:3481-90, (1999); Takahashi et al., *Int. Immunol.* 11:859-863, (1999)). MAp19 comprises the first two domains of MASP-2, followed by an extra sequence of four unique amino acids. The function of Map19 is unclear (Degn et al., *J Immunol. Methods*, 2011). The MASP-1 and MASP-2 genes are located on human chromosomes 3 and 1, respectively (Schwaeble et al., *Immunobiology* 205:455-466, (2002)).

Several lines of evidence suggest that there are different MBL-MASP complexes and a large fraction of the MASPs in serum is not complexed with MBL (Thiel, et al., *J. Immunol.* 165:878-887, (2000)). Both H- and L-ficolin bind to all MASPs and activate the lectin complement pathway, as does MBL (Dahl et al., *Immunity* 15:127-35, (2001); Matsushita et al., *J. Immunol.* 168:3502-3506, (2002)). Both the lectin and classical pathways form a common C3 convertase (C4b2a) and the two pathways converge at this step.

The lectin pathway is widely thought to have a major role in host defense against infection in the naïve host. Strong evidence for the involvement of MBL in host defense comes from analysis of patients with decreased serum levels of functional MBL (Kilpatrick, *Biochim. Biophys. Acta* 1572: 401-413, (2002)). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

In contrast to the classical and lectin pathways, no initiators of the alternative pathway have previously been found to fulfill the recognition functions that C1q and lectins perform in the other two pathways. Currently it is widely accepted that the alternative pathway spontaneously undergoes a low level of turnover activation, which can be readily amplified on foreign or other abnormal surfaces (bacteria, yeast, virally infected cells, or damaged tissue) that lack the proper molecular elements that keep spontaneous complement activation in check. There are four plasma proteins directly involved in the activation of the alternative pathway: C3, factors B and D, and properdin.

Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard et al., *Am. J. Pathol.* 156:1549-1556, (2000)). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan et al., *Circulation* 104:1413-1418, (2001)). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard et al., *Am. J. Pathol.* 159:1045-1054, (2001)). Other studies have implicated the classical and alternative pathways in the pathogenesis of ischemia/reperfusion injury and the role of the lectin pathway in this disease remains controversial (Riedermann, N.C., et al., *Am. J. Pathol.* 162:363-367, 2003).

Recent studies have shown that MASP-1 and MASP-3 convert the alternative pathway activation enzyme factor D from its zymogen form into its enzymatically active form (see Takahashi M. et al., *J Exp Med* 207(1):29-37 (2010); Iwaki et al., *J. Immunol.* 187:3751-58 (2011)). The physiological importance of this process is underlined by the absence of alternative pathway functional activity in plasma of MASP-1/3-deficient mice. Proteolytic generation of C3b from native C3 is required for the alternative pathway to function. Since the alternative pathway C3 convertase (C3bBb) contains C3b as an essential subunit, the question regarding the origin of the first C3b via the alternative pathway has presented a puzzling problem and has stimulated considerable research.

C3 belongs to a family of proteins (along with C4 and α-2 macroglobulin) that contain a rare posttranslational modification known as a thioester bond. The thioester group is composed of a glutamine whose terminal carbonyl group forms a covalent thioester linkage with the sulfhydryl group of a cysteine three amino acids away. This bond is unstable and the electrophilic glutamyl-thioester can react with nucleophilic moieties such as hydroxyl or amino groups and thus form a covalent bond with other molecules. The thioester bond is reasonably stable when sequestered within a hydrophobic pocket of intact C3. However, proteolytic cleavage of C3 to C3a and C3b results in exposure of the highly reactive thioester bond on C3b and, following nucleophilic attack by adjacent moieties comprising hydroxyl or amino groups, C3b becomes covalently linked to a target. In addition to its well-documented role in covalent attachment of C3b to complement targets, the C3 thioester is also thought to have a pivotal role in triggering the alternative pathway. According to the widely accepted "tick-over theory", the alternative pathway is initiated by the generation of a fluid-phase convertase, iC3Bb, which is formed from C3 with hydrolyzed thioester (iC3; $C3(H_2O)$) and factor B (Lachmann, P. J., et al., *Springer Semin. Immunopathol.* 7:143-162, (1984)). The C3b-like $C3(H_2O)$ is generated from native C3 by a slow spontaneous hydrolysis of the internal thioester in the protein (Pangburn, M. K., et al., *J. Exp. Med.* 154:856-867, 1981). Through the activity of the $C3(H_2O)Bb$ convertase, C3b molecules are deposited on the target surface thereby initiating the alternative pathway.

Prior to the instant discovery described herein, very little was known about the initiators of activation of the alternative pathway. Activators were thought to include yeast cell walls (zymosan), many pure polysaccharides, rabbit erythrocytes, certain immunoglobulins, viruses, fungi, bacteria, animal tumor cells, parasites, and damaged cells. The only feature common to these activators is the presence of carbohydrate, but the complexity and variety of carbohydrate structures has made it difficult to establish the shared molecular determinants which are recognized. It has been widely accepted that alternative pathway activation is controlled through the fine balance between inhibitory regulatory components of this pathway, such as factor H, factor I, DAF, and CR1, and properdin, the latter of which is the only positive regulator of the alternative pathway (see Schwaeble W. J. and Reid K. B., *Immunol Today* 20(1):17-21 (1999)).

In addition to the apparently unregulated activation mechanism described above, the alternative pathway can also provide a powerful amplification loop for the lectin/classical pathway C3 convertase (C4b2a) since any C3b generated can participate with factor B in forming additional alternative pathway C3 convertase (C3bBb). The alternative pathway C3 convertase is stabilized by the binding of properdin. Properdin extends the alternative pathway C3 convertase half-life six to ten-fold. Addition of C3b to the alternative pathway C3 convertase leads to the formation of the alternative pathway C5 convertase.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites, and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

In addition to its essential role in immune defense, the complement system contributes to tissue damage in many clinical conditions. Thus, there is a pressing need to develop therapeutically effective complement inhibitors to prevent these adverse effects.

SUMMARY

In one aspect, the present invention provides an isolated monoclonal antibody or antigen-binding fragment thereof that specifically binds to the serine protease domain of human MASP-3 (amino acid residues 450 to 728 of SEQ ID NO:2) with high affinity (having a $K_D$ of less than 500 pM), wherein the antibody or antigen-binding fragment thereof inhibits alternative pathway complement activation. In some embodiments, antibody or antigen-binding fragment is characterized by at least one or more of the following properties: (a) inhibits pro-Factor D maturation; (b) does not bind to human MASP-1 (SEQ ID NO:8); (c) inhibits the alternative pathway at a molar ratio of from about 1:1 to about 2.5:1 (MASP-3 target to mAb) in a mammalian subject (d) does not inhibit the classical pathway (e) inhibits of hemolysis and/or opsonization; (f) inhibits of MASP-3 serine protease substrate-specific cleavage; (g) reduces hemolysis or the reduction of C3 cleavage and C3b surface deposition; (h) reduces of Factor B and/or Bb deposition on an activating surface; (i) reduces resting levels (in circulation, and without the experimental addition of an activating surface) of active Factor D relative to pro-Factor D; (j) reduces the level of active Factor D relative to pro-Factor D in response to an activating surface; (k) reduces the production of resting and surface-induced levels of fluid-phase Ba, Bb, C3b, or C3a; and/or (1) reduces factor P deposition. In some embodiments, the isolated antibody or antigen-binding fragment thereof of paragraph 1 or 2, wherein said antibody or antigen-binding fragment thereof specifically binds to an epitope located within the serine protease domain of human MASP-3, wherein said epitope is located within at least one or more of: VLRSQRRDTTVI (SEQ ID NO:9), TAAHVLRSQRRDTTV (SEQ ID NO:10), DFNIQNYNH-DIALVQ (SEQ ID NO:11), PHAECKTSYESRS (SEQ ID NO:12), GNYSVTENMFC (SEQ ID NO:13), VSNYVDWVWE (SEQ ID NO:14) and/or VLR-SQRRDTTV (SEQ ID NO:15). In some embodiments, the antibody or antigen-binding fragment thereof binds to an epitope within at least one of: ECGQPSRSLPSLV (SEQ ID NO:16), RNAEPGLFPWQ (SEQ ID NO:17); KWFGSGALLSASWIL (SEQ ID NO:18); EHVTVYLGLH (SEQ ID NO:19); PVPLGPHVMP (SEQ ID NO:20); APHMLGL (SEQ ID NO:21); SDVLQYVKLP (SEQ ID NO:22); and/or AFVIFDDLSQRW (SEQ ID NO:23).

In another aspect, the present invention provides an isolated antibody, or antigen-binding fragment thereof, that binds to MASP-3 comprising: (a) a heavy chain variable region comprising a HC-CDR1 set forth as SEQ ID NO:209 (XXDIN, wherein X at position 1 is S or T and wherein X at position 2 is N or D); a HC-CDR2 set forth as SEQ ID NO:210 (WIYPRDXXXKYNXXFXD, wherein X at position 7 is G or D; X at position 8 is S, T or R; X at position 9 is I or T; X at position 13 is E or D; X at position 14 is K or E; and X at position 16 is T or K); and a HC-CDR3 set forth as SEQ ID NO:211 (XEDXY, wherein X at position 1 is L or V, and wherein X at position 4 is T or S); and (b) a light chain variable region comprising a LC-CDR1 set forth as SEQ ID NO:212 (KSSQSLLXXRTRKNYLX, wherein X at position 8 is N, I, Q or A; wherein X at position 9 is S or T; and wherein X at position 17 is A or S); a LC-CDR2 set forth as SEQ ID NO:144 (WASTRES) and a LC-CDR3 set forth as SEQ ID NO:146 (KQSYNLYT).

In another aspect, the present invention provides an isolated antibody, or antigen-binding fragment thereof, that binds to MASP-3 comprising: (a) a heavy chain variable region comprising a HC-CDR1 set forth as SEQ ID NO:213 (SYGXX, wherein X at position 4 is M or I and wherein X at position 5 is S or T); a HC-CDR2 set forth as SEQ ID NO:74; and a HC-CDR3 set forth as SEQ ID NO:214 (GGXAXDY, wherein X at position 3 is E or D and wherein X at position 5 is M or L); and (b) a light chain variable region comprising a LC-CDR1 set forth as SEQ ID NO:215 (KSSQSLLDSXXKTYLX, wherein X at position 10 is D, E or A; wherein X at position 11 is G or A; and wherein X at position 16 is N or S); a LC-CDR2 set forth as SEQ ID NO:155; and a LC-CDR3 set forth as SEQ ID NO:216 (WQGTHFPXT, wherein X at position 8 is W or Y).

In another aspect, the present invention provides an isolated antibody, or antigen-binding fragment thereof, that binds to MASP-3 comprising: (a) a heavy chain variable region comprising a HC-CDR1 set forth as SEQ ID NO:84 (GKWIE); a HC-CDR2 set forth as SEQ ID NO:86 (EIL-PGTGSTNYNEKFKG) or SEQ ID NO:275 (EILPGTGSTNYAQKFQG); and a HC-CDR3 set forth as SEQ ID NO:88 (SEDV); and (b) a light chain variable region comprising a LC-CDR1 set forth as SEQ ID NO:142 (KSSQSLLNSRTRKNYLA), SEQ ID NO:257 (KSSQSLLQSTRKNYLA); SEQ ID NO:258 (KSSQSLLASRTRKNYLA); or SEQ ID NO:259 (KSSQSLLNTRTRKNYLA), a LC-CDR2 set forth as SEQ ID NO:144 (WASTRES); and a LC-CDR3 set forth as SEQ ID NO:161 (KQSYNIPT).

In another aspect, the present invention provides an isolated antibody, or antigen-binding fragment thereof, that binds to MASP-3 comprising: (a) a heavy chain variable region comprising a HC-CDR1 set forth as SEQ ID NO:91 (GYWIE); a HC-CDR2 set forth as SEQ ID NO:93 (EMLPGSGSTHYNEKFKG), and a HC-CDR3 set forth as SEQ ID NO:95 (SIDY); and (b) a light chain variable region comprising a LC-CDR1 set forth as SEQ ID NO:163 (RSSQSLVQSNGNTYLH), a LC-CDR2 set forth as SEQ ID NO:165 (KVSNRFS) and a LC-CDR3 set forth as SEQ ID NO:167 (SQSTHVPPT).

In another aspect, the present invention provides an isolated antibody, or antigen-binding fragment thereof, that binds to MASP-3 comprising:
  (a) a heavy chain variable region comprising a HC-CDR1 set forth as SEQ ID NO:109 (RVHFAIRDTNYWMQ), a HC-CDR2 set forth as SEQ ID NO:110 (AIYPGNGDTSYNQKFKG), a HC-CDR3 set forth as SEQ ID NO:112 (GSHYFDY); and a light chain variable region comprising a LC-CDR1 set forth as SEQ ID NO:182 (RASQSIGTSIH), a LC-CDR2 set forth as SEQ ID NO:184 (YASESIS) and a LC-CDR3 set forth as SEQ ID NO:186 (QQSNSWPYT); or
  (b) a heavy chain variable region comprising a HC-CDR1 set forth as SEQ ID NO:125 (DYYMN), a HC-CDR2 set forth as SEQ ID NO:127 (DVNPNNDGTTYNQKFKG), a HC-CDR3 set forth as SEQ ID NO:129 (CPFYYLGKGTHFDY); and a light chain variable region comprising a LC-CDR1 set forth as SEQ ID NO:196 (RASQDISNFLN), a LC-CDR2 set forth as SEQ ID NO:198 (YTSRLHS) and a LC-CDR3 set forth as SEQ ID NO:200 (QQGFTLPWT); or (c) a heavy chain variable region comprising a HC-CDR1 set forth as SEQ ID NO:137 a HC-CDR2 set forth as SEQ ID NO:138, a HC-CDR3 set forth as SEQ ID NO:140; and a light chain variable region comprising a LC-CDR1 set forth as SEQ ID NO:206, a LC-CDR2 set forth as SEQ ID NO:207 and a LC-CDR3 set forth as SEQ ID NO:208; or (d) a heavy chain variable region comprising a HC-CDR1 set forth as SEQ ID NO:98, a HC-CDR2 set forth as SEQ ID NO:99, a HC-CDR3 set forth as SEQ ID NO:101; and a light chain variable region comprising a LC-CDR1 set forth as SEQ ID NO:169, a LC-CDR2 set forth as SEQ ID NO:171 and a LC-CDR3 set forth as SEQ ID NO:173; or (e) a heavy chain variable region comprising a HC-CDR1 set forth as SEQ ID NO:103, a HC-CDR2 set forth as SEQ ID NO:105, a HC-CDR3 set forth as SEQ ID NO:107; and a light chain variable region comprising a LC-CDR1 set forth as SEQ ID NO:176, a LC-CDR2 set forth as SEQ ID NO:178 and a LC-CDR3 set forth as SEQ ID NO:193; or (f) a heavy chain variable region comprising a HC-CDR1 set forth as SEQ ID NO:114, a HC-CDR2 set forth as SEQ ID NO:116, a HC-CDR3 set forth as SEQ ID NO:118; and a light chain variable region comprising a LC-CDR1 set forth as SEQ ID NO:188, a LC-CDR2 set forth as SEQ ID NO:178 and a LC-CDR3 set forth as SEQ ID NO:190; or (g) a heavy chain variable region comprising a HC-CDR1 set forth as SEQ ID NO:114, a HC-CDR2 set forth as SEQ ID NO:121, a HC-CDR3 set forth as SEQ ID NO:123; and a light chain variable region comprising a LC-CDR1 set forth as SEQ ID NO:191, a LC-CDR2 set forth as SEQ ID NO:178 and a LC-CDR3 set forth as SEQ ID NO:193.

In another aspect, the present invention provides a method of inhibiting alternative pathway complement activation in a mammal, the method comprising administering to a mammal subject in need thereof an amount of a composition comprising a high affinity MASP-3 inhibitory antibody or antigen-binding fragment thereof sufficient to inhibit alternative pathway complement pathway activation in the mammal. In one embodiment of the method, the antibody, or antigen binding fragment thereof binds to MASP-3 with an affinity of less than 500 pM. In one embodiment of the method, as a result of administering the composition comprising the antibody or antigen-binding fragment one or more of the following is present in the mammalian subject: (a) inhibition of Factor D maturation; (b) inhibition of the alternative pathway when administered to the subject at a molar ratio of from about 1:1 to about 2.5:1 (MASP-3 target to mAb); (c) the classical pathway is not inhibited; (d) inhibition of hemolysis and/or opsonization; (e) a reduction of hemolysis or the reduction of C3 cleavage and C3b surface deposition; (f) a reduction of Factor B and Bb deposition on an activating surface; (g) a reduction of resting levels (in circulation, and without the experimental addition of an activating surface) of active Factor D relative to pro-Factor D; (h) a reduction of levels of active Factor D relative to pro-Factor D in response to an activating surface; and/or (i) a reduction of the production of resting and surface-induced levels of fluid-phase Ba, Bb, C3b, or C3a. In one embodiment of the method, the composition comprises an MASP-3 inhibitory antibody that inhibits the alternative pathway at a molar ratio of from about 1:1 to about 2.5:1 (MASP-3 target to mAb).

In another aspect, the present invention provides a method of inhibiting MASP-3-dependent complement activation in a subject suffering from paroxysmal nocturnal hemoglobinuria (PNH), age-related macular degeneration (AMD), ischemia-reperfusion injury, arthritis, disseminated intravascular coagulation, thrombotic microangiopathy, asthma, dense deposit disease, pauci-immune necrotizing crescentic glomerulonephritis, traumatic brain injury, aspiration pneumonia, endophthalmitis, neuromyelitis optica or Behcet's disease. The method includes the step of administering to the subject a composition comprising an amount of a high affinity MASP-3 inhibitory agent effective to inhibit MASP-3-dependent complement activation. In some embodiments, the method further comprises administering to the subject a composition comprising a MASP-2 inhibitory agent.

In another aspect, the present invention provides a method of manufacturing a medicament for use in inhibiting the effects of MASP-3-dependent complement activation in living subjects in need thereof, comprising combining a therapeutically effective amount of a MASP-3 inhibitory agent in a pharmaceutical carrier. In some embodiments, the MASP-3 inhibitory agent is a high affinity MASP-3 inhibitory antibody. In some embodiments, the method in accordance with this aspect of the invention comprises manufacturing a medicament for use in inhibiting the effects of MASP-3-dependent complement activation in a subject suffering from, or at risk for developing a disease or disorder selected from the group consisting of paroxysmal nocturnal hemoglobinuria (PNH), age-related macular degeneration (AMD), ischemia-reperfusion injury, arthritis, disseminated intravascular coagulation, thrombotic microangiopathy, asthma, dense deposit disease, pauci-immune necrotizing crescentic glomerulonephritis, traumatic brain injury, aspiration pneumonia, endophthalmitis, neuromyelitis optica or Behcet's disease. In some embodiments, the method further comprises combining a therapeutically effective amount of a MASP-2 inhibitory agent into or with the medicament comprising the MASP-3 inhibitor.

In another aspect, the present invention provides a pharmaceutical composition comprising a physiologically acceptable carrier and a high affinity MASP-3 inhibitory monoclonal antibody or antigen binding fragment thereof that binds to human MASP-3 and inhibits alternative pathway complement activation. In one embodiment, said high affinity MASP-3 antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258, or SEQ ID NO:259 (ii) VLCDR2 comprising SEQ ID NO:144 and (iii) VLCDR3 comprising SEQ ID NO:161.

In another aspect, the present invention provides a method for treating a subject suffering from, or at risk for developing paroxysmal nocturnal hemoglobinuria (PNH), comprising administering to the subject a pharmaceutical composition comprising an effective amount of a high affinity monoclonal antibody or antigen binding fragment thereof that binds to human MASP-3 and inhibits alternative pathway complement activation to treat or reduce the risk of PNH in the subject. In one embodiment antibody or antigen binding fragment thereof comprises (a) a heavy chain variable region comprising (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258, or SEQ ID NO:259 (ii) VLCDR2 comprising SEQ ID NO:144 and (iii) VLCDR3 comprising SEQ ID NO:161. In some embodiments, the pharmaceutical composition increases the survival of red blood cells in the subject suffering from PNH. In some embodiments, wherein the subject suffering from or at risk for developing PNH exhibits one or more symptoms selected from the group consisting of (i) below normal levels of hemoglobin, (ii) below normal levels of platelets; (iii) above normal levels of reticulocytes, and (iv) above normal levels of bilirubin. In some embodiments, the pharmaceutical composition is administered systemically (e.g., subcutaneously, intra-muscularly, intravenously, intra-arterially or as an inhalant) to a subject suffering from, or at risk for developing PNH. In some embodiments, the subject suffering from or at risk for PNH has previously undergone, or is currently undergoing treatment with a terminal complement inhibitor that inhibits cleavage of complement protein C5. In some embodiments, the method further comprises administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In another aspect, the present invention provides a method for treating a subject suffering from, or at risk for developing arthritis (inflammatory and non-inflammatory arthritides) comprising administering to the subject a pharmaceutical composition comprising an effective amount of a high affinity monoclonal antibody or antigen binding fragment thereof that binds to human MASP-3 and inhibits alternative pathway complement activation to treat or reduce the risk of arthritis in the subject. In one embodiment, said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161. In some embodiments, the subject is suffering from arthritis selected from the group consisting of osteoarthritis, rheumatoid arthritis, juvenile rheumatoid arthritis, ankylosing spondylitis, Behcet's disease, infection-related arthritis and psoriatic arthritis. In some embodiments, the pharmaceutical composition is administered systemically (i.e., subcutaneously, intra-muscularly, intravenously, intra-arterially or as an inhalant). In some embodiments, the pharmaceutical composition is administered locally to a joint.

As described herein, the various embodiments of the high affinity MASP-3 inhibitory antibodies, optionally in combination with the various embodiments of the MASP-2 inhibitory agents can be used in the pharmaceutical compositions of the invention.

As described herein, the pharmaceutical compositions of the invention can be used in accordance with the methods of the invention.

These and other aspects and embodiments of the herein described invention will be evident upon reference to the following detailed description and drawings. All of the U.S. patents, U.S. patent application publications, U.S. patent applications, foreign patents, foreign patent applications and non-patent publications referred to in this specification are incorporated herein by reference in their entirety, as if each was incorporated individually.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 depicts the human MASP-3 amino acid sequence (SEQ ID NO:2) with the leader sequence shown in underline;

FIG. 26A is an amino acid sequence alignment of the VH regions of M3J5, M3M1, D14 and 1E10 to the chicken DT40 VH sequence, wherein dots represent amino acid identity with the DT40 sequence and dashes indicate spaces introduced to maximize the alignment, as described in Example 7;

FIG. 26B is an amino acid sequence alignment of the VL regions of M3J5, M3M1, D14 and 1E10 to the chicken DT40 VL sequence, wherein dots represent amino acid identity with the DT40 sequence and dashes indicate spaces introduced to maximize the alignment, as described in Example 7;

FIG. 55B graphically illustrates the level of complement factor Bb deposition on zymosan particles (determined by flow cytometric detection measured in MFI units) in the presence of varying concentrations of high affinity MASP-3 mAbs 4D5, 10D12 and 13B1 in factor D-depleted human serum, as described in Example 16;

FIG. 57 shows a Western blot analyzing the level of pro-Factor D) and Factor D in 3MC patient serum (Patient B) in the presence of active recombinant MASP-3 (rMASP-3), inactive rMASP-3, and active rMASP-3 plus high affinity MASP-3 mAb 4D5, as described in Example 16;

FIG. 58 graphically illustrates the level of C3/C3b/iC3b deposition on zymosan particles at various time points after a single dose of high affinity MASP-3 mAbs M3-1 (13B1, 10 mg/kg) or 10D12 (10 mg/kg) in wild-type mice, as described in Example 17;

FIG. 61D graphically illustrates the results of competition binding analysis to identify high affinity MASP-3 mAbs that block the interaction between high affinity MASP-3 mAb 1F3 and human MASP-3, as described in Example 18;

DESCRIPTION OF SEQUENCE LISTING

Figure 1:
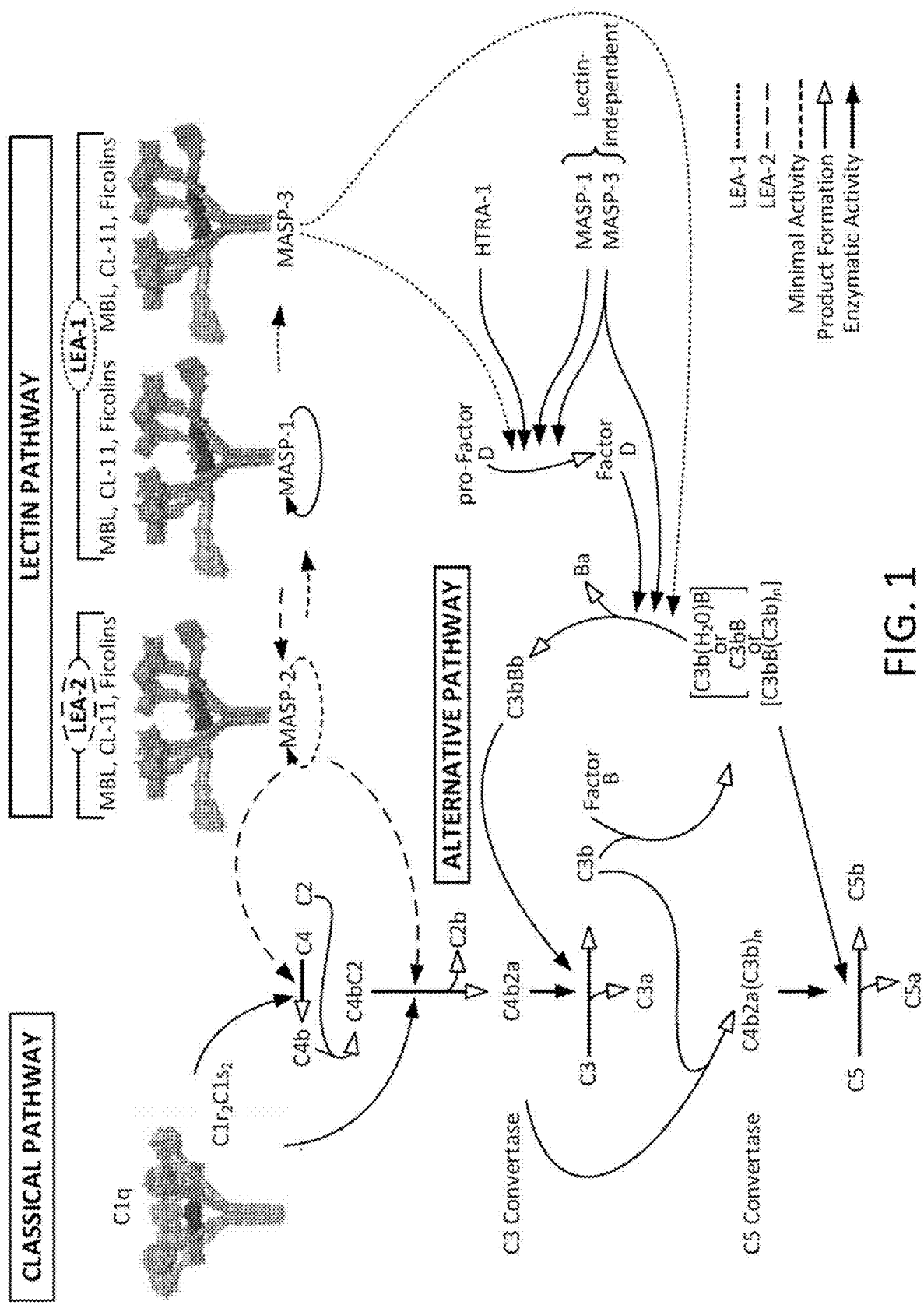
FIG. 1 illustrates a new understanding of the lectin and alternative pathways.

SEQ ID NO:1 human MASP-3 cDNA
SEQ ID NO:2 human MASP-3 protein (with leader)
SEQ ID NO:3 mouse MASP-3 protein (with leader)
SEQ ID NO:4 rat MASP-3 protein
SEQ ID NO:5 chicken MASP-3 protein
SEQ ID NO:6 rabbit MASP-3 protein
SEQ ID NO:7 Cynomolgus monkey MASP-3 protein
SEQ ID NO:8 human MASP-1 protein (with leader)
Human MASP-3 SP domain peptide fragments:
SEQ ID NO:9 (aa 498-509 of human MASP-3 w/leader)
SEQ ID NO:10 (aa 494-508 of human MASP-3 w/leader)
SEQ ID NO:11 (aa 544-558 of human MASP-3 w/leader)
SEQ ID NO:12 (aa 626-638 of human MASP-3 w/leader)
SEQ ID NO:13 (aa 639-649 of human MASP-3 w/leader)
SEQ ID NO:14 (aa 704-713 of human MASP-3 w/leader)
SEQ ID NO:15 (aa 498-508 of human MASP-3 w/leader)
SEQ ID NO:16 (aa 435-447 of human MASP-3 w/leader)
SEQ ID NO:17 (aa 454-464 of human MASP-3 w/leader)
SEQ ID NO:18 (aa 479-493 of human MASP-3 w/leader)
SEQ ID NO:19 (aa 514-523 of human MASP-3 w/leader)
SEQ ID NO:20 (aa 562-571 of human MASP-3 w/leader)
SEQ ID NO:21 (aa 583-589 of human MASP-3 w/leader)
SEQ ID NO:22 (aa 614-623 of human MASP-3 w/leader)
SEQ ID NO:23 (aa 667-678 of human MASP-3 w/leader)
SEQ ID NO:24-39: Heavy chain variable regions—mouse parental
SEQ ID NO:24 4D5_VH
SEQ ID NO:25 1F3_VH
SEQ ID NO:26 4B6_VH
SEQ ID NO:27 1A10_VH
SEQ ID NO:28 10D12_VH
SEQ ID NO:29 35C1_VH
SEQ ID NO:30 13B1_VH
SEQ ID NO:31 1G4_VH
SEQ ID NO:32 1E7_VH
SEQ ID NO:33 2D7_VH
SEQ ID NO:34 49C11_VH
SEQ ID NO:35 15D9_VH
SEQ ID NO:36 2F5_VH
SEQ ID NO:37 1B11_VH
SEQ ID NO:38 2F2_VH
SEQ ID NO:39 11B6_VH
SEQ ID NO:40-54: Light chain variable regions—mouse parental
SEQ ID NO:40 4D5_VL
SEQ ID NO:41 1F3_VL
SEQ ID NO:42 4B6/1A10_VL
SEQ ID NO:43 10D12_VL
SEQ ID NO:44 35C1_VL
SEQ ID NO:45 13B1_VL
SEQ ID NO:46 1G4_VL
SEQ ID NO:47 1E7_VL
SEQ ID NO:48 2D7_VL
SEQ ID NO:49 49C11_VL
SEQ ID NO:50 15D9_VL
SEQ ID NO:51 2F5_VL
SEQ ID NO: 52 1B11_VL
SEQ ID NO:53 2F2_VL
SEQ ID NO:54 11B6_VL
SEQ ID NO:55-140: heavy chain framework regions (FR) and complementarity-determining regions (CDRs) from mouse parental MASP-3 mAbs
SEQ ID NO:141-208: light chain FR and CDRs from mouse parental MASP-3 mAbs
SEQ ID NO:209-216: CDR consensus sequences
SEQ ID NO:217-232: DNA encoding heavy chain variable regions (mouse parental)
SEQ ID NO:233-247: DNA encoding light chain variable regions (mouse parental)
SEQ ID NO:248: humanized 4D5_VH-14 (h4D5_VH-14) heavy chain variable region
SEQ ID NO:249: humanized 4D5_VH-19 (h4D5_VH-19) heavy chain variable region
SEQ ID NO:250: humanized 4D5_VL-1 (h4D5_VL-1) light chain variable region
SEQ ID NO:251: humanized 10D12_VH-45 (h10D12_VH-45) heavy chain variable region
SEQ ID NO:252: humanized 10D12_VH-49 (h10D12_VH-49) heavy chain variable region
SEQ ID NO:253: humanized 10D12_VL-21 (h10D12-VL-21) light chain variable region
SEQ ID NO:254: humanized 13B1_VH-9 (h13B1-VH-9) heavy chain variable region
SEQ ID NO:255: humanized 13B1_VH-10 (h13B1-VH-10) heavy chain variable region
SEQ ID NO:256: humanized 13B1-VL-1 (h13B1-VL-1) light chain variable region
SEQ ID NO:257: 4D5 and 13B1 LC-CDR1-NQ
SEQ ID NO:258: 4D5 and 13B1 LC-CDR1-NA
SEQ ID NO:259: 4D5 and 13B1 LC-CDR1-ST
SEQ ID NO:260: consensus LC-CDR1 for 4D5, 13B1 parental and variants
SEQ ID NO:261: 10D12 LC-CDR1-DE
SEQ ID NO:262: 10D12 LC-CDR1-DA
SEQ ID NO:263: 10D12 LC-CDR1-GA
SEQ ID NO:264-277: HC FR and CDRs for humanized 4D5, 10D12 and 13B1
SEQ ID NO:278: h4D5_VL-1-NA
SEQ ID NO:279: h10D12_VL-21-GA
SEQ ID NO:280: h13B1_VL-1-NA
SEQ ID NO:281-287 LC FR and CDRs for humanized 4D5, 10D12 and 13B1
SEQ ID NO:288-293: DNA encoding humanized 4D5, 10D12, 13B1 heavy chain variable region and variants
SEQ ID NO:294-299: DNA encoding humanized 4D5, 10D12, 13B1 light chain variable region and variants
SEQ ID NO:300: parent DTLacO heavy chain variable region (VH) polypeptide
SEQ ID NO:301: MASP-3 specific clone M3J5 heavy chain variable region (VH) polypeptide
SEQ ID NO:302: MASP-3 specific clone M3M1 heavy chain variable region (VH) polypeptide
SEQ ID NO:303: parent DTLacO light chain variable region (VL) polypeptide
SEQ ID NO:304: MASP-3 specific clone M3J5 light chain variable region (VL) polypeptide
SEQ ID NO:305: MASP-3 specific clone M3M1 light chain variable region (VL) polypeptide
SEQ ID NO:306: MASP-3 clone D14 heavy chain variable region (VH) polypeptide
SEQ ID NO:307: MASP-3 clone D14 light chain variable region (VL) polypeptide
SEQ ID NO:308: MASP-1 clone 1E10 heavy chain variable region (VH) polypeptide
SEQ ID NO:309: MASP-1 clone 1E10 light chain variable region (VL) polypeptide SEQ ID NO:310: human IgG4 constant region
SEQ ID NO:311: human IgG4 constant region with S228P mutation
SEQ ID NO:312: human IgG4 constant region with S228P mutation_X
SEQ ID NO:313: human IgK constant region

DETAILED DESCRIPTION

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the lectin pathway effector arm 1 ("LEA-1") refers to lectin-dependent activation of factor B and factor D by MASP-3.

As used herein, the lectin pathway effector arm 2 ("LEA-2") refers to MASP-2-dependent complement activation.

As used herein, the term "MASP-3-dependent complement activation" comprises two components: (i) lectin MASP-3-dependent activation of factor B and factor D, encompassed in LEA-1-mediated complement activation, occurs in the presence of $Ca^{++}$, commonly leading to the conversion of C3bB to C3bBb and of pro-factor D to factor D; and (ii) lectin-independent conversion of factor B and factor D, which can occur in the absence of $Ca^{++}$, commonly leading to the conversion of C3bB to C3bBb and of pro-factor D to factor D. LEA-1-mediated complement activation and lectin-independent conversion of factor B and factor D have been determined to cause opsonization and/or lysis. While not wishing to be bound by any particular theory, it is believed that only when multiple C3b molecules associate and bind in close proximity, the C3bBb C3 convertase changes its substrate specificity and cleaves C5 as the alternative pathway C5 convertase termed C3bBb(C3b)n.

As used herein, the term "MASP-2-dependent complement activation", also referred to herein as LEA-2-mediated complement activation, comprises MASP-2 lectin-dependent activation, which occurs in the presence of $Ca^{++}$, leading to the formation of the lectin pathway C3 convertase C4b2a and upon accumulation of the C3 cleavage product C3b subsequently to the C5 convertase C4b2a(C3b)n, which has been determined to cause opsonization and/or lysis.

As used herein, the term "traditional understanding of the alternative pathway" also referred to as the "traditional alternative pathway" refers to the alternative pathway prior to the instant discovery described herein, i.e., complement activation that is triggered, for example, by zymosan from fungal and yeast cell walls, lipopolysaccharide (LPS) from Gram negative outer membranes, and rabbit erythrocytes, as well as from many pure polysaccharides, viruses, bacteria, animal tumor cells, parasites and damaged cells, and which has traditionally been thought to arise from spontaneous proteolytic generation of C3b from complement factor C3. As used herein, activation of the "traditional alternative pathway", also referred to herein as the "alternative pathway", is measured in $Mg^{++}$/EGTA buffer (i.e., in the absence of $Ca^{++}$).

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin). As described herein, the inventors have discovered that the lectin pathway is driven by the two effector arms, lectin pathway effector arm 1 (LEA-1), which is now known to be MASP-3-dependent, and lectin pathway effector arm 2 (LEA-2), which is MASP-2-dependent. As used herein, activation of the lectin pathways are assessed using $Ca^{++}$ containing buffers.

As used herein, the term "classical pathway" refers to complement activation that is triggered by antibody bound to a foreign particle and requires binding of the recognition molecule C1q.

As used herein, the term "HTRA-1" refers to the serine peptidase High-temperature requirement serine protease A1.

As used herein, the term "MASP-3 inhibitory agent" refers to any agent that directly inhibits MASP-3-dependent complement activation, including agents that bind to or directly interact with MASP-3, including MASP-3 antibodies and MASP-3 binding fragments thereof, natural and synthetic peptides, competitive substrates, small-molecules, expression inhibitors and isolated natural inhibitors, and also encompasses peptides that compete with MASP-3 for binding to another recognition molecule (e.g., MBL, CL-11, H-ficolin, M-ficolin, or L-ficolin) in the lectin pathway. In one embodiment, the MASP-3 inhibitory agent is specific to MASP-3, and does not bind to MASP-1 or MASP-2. An inhibitory agent that directly inhibits MASP-3 can be referred to as a direct MASP-3 inhibitory agent (e.g., a MASP-3 antibody), while an inhibitory agent that indirectly inhibits MASP-3 can be referred to as an indirect MASP-3 inhibitory agent (e.g., a MASP-1 antibody that inhibits MASP-3 activation). An example of a direct MASP-3 inhibitory agent is a MASP-3 specific inhibitory agent, such as a MASP-3 inhibitory agent that specifically binds to a portion of human MASP-3 (SEQ ID NO:2) with a binding affinity of at least 10 times greater than to other components in the complement system. Another example of a direct MASP-3 inhibitory agent is a high affinity MASP-3 antibody that specifically binds to the serine protease domain of human MASP-3 (SEQ ID NO:2), with an affinity of less than 500 pM and does not bind to human MASP-1 (SEQ ID NO:8). In one embodiment, a MASP-3 inhibitory agent indirectly inhibits MASP-3 activity, such as, for example, an inhibitor of MASP-3 activation, including an inhibitor of MASP-1-mediated MASP-3 activation (e.g., a MASP-1 antibody or MASP-1 binding fragments thereof, natural and synthetic peptides, small-molecules, expression inhibitors and isolated natural inhibitors, and also encompasses peptides that compete with MASP-1 for binding to MASP-3). In a preferred embodiment, a MASP-3 inhibitory agent, such as an antibody or antigen-binding fragment thereof or antigen binding peptide inhibits MASP-3-mediated maturation of factor D. In another embodiment, a MASP-3 inhibitory agent inhibits MASP-3-mediated activation of factor B. MASP-3 inhibitory agents useful in the method of the invention may reduce MASP-3-dependent complement activation by greater than 10%, such as greater than 20%, greater than 50%, or greater than 90%. In one embodiment, the MASP-3 inhibitory agent reduces MASP-3-dependent complement activation by greater than 90% (i.e., resulting in MASP-3 complement activation of only 10% or less). It is expected that MASP-3 inhibition will block, in full or in part, both LEA-1-related lysis and opsonization and lectin-independent conversion of factor B and factor D-related lysis and opsonization.

In one embodiment, a high affinity MASP-3 inhibitory antibody binds to the serine protease domain of MASP-3 (amino acid residues 450 to 728 of SEQ ID NO:2) with an affinity of less than 500 pM (e.g., less than 250 pM, less than 100 pM, less than 50 pM, or less than 10 pM) and inhibit the alternative pathway of complement activation in the blood of a mammalian subject by at least 50% (e.g., at least 60%, or at least 70%, or at least 80%, or at least 90%, or at least 95% or greater).

An "antibody" is an immunoglobulin molecule capable of specific binding to a target, such as a polypeptide, through at least one epitope recognition site located in the variable region (also referred to herein as the variable domain) of the immunoglobulin molecule.

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments"), that specifically bind to a target polypeptide, such as, for example, MASP-1, MASP-2 or MASP-3 polypeptides or portions thereof. It is not intended that the term "antibody" is limited as regards to the source of the antibody or the manner in which it is made (e.g., by hybridoma, phage selection, recombinant expression, transgenic animal, peptide synthesis, etc). Exemplary antibodies include polyclonal, monoclonal and recombinant antibodies; pan-specific, multispecific antibodies (e.g., bispecific antibodies, trispecific antibodies); humanized antibodies; murine antibodies; chimeric, mouse-human, mouse-primate, primate-human monoclonal antibodies; and anti-idiotype antibodies, and may be any intact antibody or fragment thereof. As used herein, the term "antibody" encompasses not only intact polyclonal or monoclonal antibodies, but also fragments thereof, such as a single variable region antibody (dAb), or other known antibody fragments such as Fab, Fab', F(ab')$_2$, Fv and the like, single chain (ScFv), synthetic variants thereof, naturally occurring variants, fusion proteins comprising an antibody portion with an antigen-binding fragment of the required specificity, humanized antibodies, chimeric antibodies, bi-specific antibodies, and any other modified configuration of the immunoglobulin molecule that comprises an antigen-binding site or fragment (epitope recognition site) of the required specificity.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific for the target antigen. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

As used herein, the term "antibody fragment" refers to a portion derived from or related to a full-length antibody, such as, for example, a MASP-1, MASP-2 or MASP-3 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

In certain embodiments, antibodies and antigen-binding fragments thereof as described herein include a heavy chain (VH) and a light chain (VL) complementarity-determining region ("CDR") set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino acid residues and certain structural features are very highly conserved. In this regard, all V region sequences contain an internal disulfide loop of around 90 amino acid residues. With the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence.

The structures and locations of immunoglobulin variable regions may be determined by reference to Kabat, E. A., et al., Sequences of Proteins of Immunological Interest, 4$^{th}$ Edition, US Department of Health and Human Services, 1987, and updates thereof, now available on the Internet (immuno.bme.nwu.edu.).

As used herein, a "single-chain Fv" or "scFv" antibody fragment comprises the V$_H$ and V$_L$ domains of an antibody, wherein these domains are present in a single polypeptide chain. Generally, the Fv polypeptide further comprises a polypeptide linker between the V$_H$ and V$_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody. In some embodiments, a chimeric antibody is comprised of an antigen-binding fragment of a MASP-3 inhibitory antibody operably linked or otherwise fused to a heterologous Fc portion of a different antibody. In some embodiments, the heterologous Fc domain may be from a different Ig class from the parent antibody, including IgA (including subclasses IgA1 and IgA2), IgD, IgE, IgG (including subclasses IgG1, IgG2, IgG3 and IgG4) and IgM.

As used herein, a "humanized antibody" is a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable regions fused onto constant domains or only the CDRs grafted onto appropriate framework regions in the variable domains. Epitope binding sites may be wild type or may be modified by one or more amino acid substitutions. Another approach focuses not only on providing human-derived constant regions, but also on modifying the variable regions as well so as to reshape them as closely as possible to human form. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

An antibody "specifically binds" to a target if it binds with greater affinity and/or avidity that it binds to other substances. In one embodiment, the antibody, or antigen-binding fragment thereof, specifically binds to the serine protease domain of human MASP-3 (amino acid residues 450 to 728 of SEQ ID NO:2). In one embodiment, the antibody, or antigen-binding fragment thereof, specifically binds to one or more of the epitopes described in TABLE 4, TABLE 28 or shown in FIG. 62.

As used herein, the term "mannan-binding lectin" ("MBL") is equivalent to mannan-binding protein ("MBP").

As used herein, the "membrane attack complex" ("MAC") refers to a complex of the terminal five complement components (C5b combined with C6, C7, C8 and C9) that inserts into and disrupts membranes (also referred to as C5b-9).

As used herein, "a subject" includes all mammals, including without limitation humans, non-human primates, dogs, cats, horses, sheep, goats, cows, rabbits, pigs and rodents.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "oligonucleotide" as used herein refers to an oligomer or polymer of ribonucleic acid (RNA) or deoxyribonucleic acid (DNA) or mimetics thereof. This term also covers those oligonucleobases composed of naturally-occurring nucleotides, sugars and covalent internucleoside (backbone) linkages as well as oligonucleotides having non-naturally-occurring modifications.

As used herein, an "epitope" refers to the site on a protein (e.g., a human MASP-3 protein) that is bound by an antibody. "Overlapping epitopes" include at least one (e.g., two, three, four, five, or six) common amino acid residue(s), including linear and non-linear epitopes.

As used herein, the terms "polypeptide," "peptide," and "protein" are used interchangeably and mean any peptide-linked chain of amino acids, regardless of length or post-translational modification. The MASP-3 proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments, the human MASP-3 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human MASP-3 protein having the amino acid sequence set forth in SEQ ID NO: 2.

In some embodiments, peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or 600 or more) amino acid residues in length (e.g., at least 6 contiguous amino acid residues in SEQ ID NO:2). In some embodiments, an antigenic peptide fragment of a human MASP-3 protein is fewer than 500 (e.g., fewer than 450, 400, 350, 325, 300, 275, 250, 225, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6) amino acid residues in length (e.g., fewer than 500 contiguous amino acid residues in SEQ ID NO:2.

In some embodiments, in the context of generating an antibody that binds MASP-3, the peptide fragments are antigenic and retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal (see below under "Methods for Producing an Antibody").

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

In representative embodiments, the human MASP-3 protein (SEQ ID NO:2) is encoded by the cDNA sequence set forth as SEQ ID NO:1. Those skilled in the art will recognize that the cDNA sequence disclosed in SEQ ID NO:1 represents a single allele of human MASP-3, and that allelic variation and alternative splicing are expected to occur. Allelic variants of the nucleotide sequences shown in SEQ ID NO:1, including those containing silent mutations and those in which mutations result in amino acid sequence changes, are within the scope of the present invention. Allelic variants of the MASP-3 sequence can be cloned by probing cDNA or genomic libraries from different individuals according to standard procedures, or may be identified by homology comparison search (e.g., BLAST searching) of databases containing such information.

As used herein, an "isolated nucleic acid molecule" is a nucleic acid molecule (e.g., a polynucleotide) that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein, a "nucleic acid molecule construct" is a nucleic acid molecule, either single- or double-stranded, that has been modified through human intervention to contain segments of nucleic acid combined and juxtaposed in an arrangement not existing in nature.

As used herein, an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the term "about" as used herein is meant to specify that the specific value provided may vary to a certain extent, such as a variation in the range of ±10%, preferably ±5%, most preferably ±2% are included in the given value. Where ranges are stated, the endpoints Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "an excipient" includes a plurality of such excipients and equivalents thereof known to those skilled in the art, reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

Each embodiment in this specification is to be applied mutatis mutandis to every other embodiment unless expressly stated otherwise. It is contemplated that any embodiment discussed in this specification can be implemented with respect to any method, kit, reagent, or composition of the invention, and vice versa. Furthermore, compositions of the invention can be used to achieve methods of the invention.

II. The Lectin Pathway: A New Understanding i. Overview: The Lectin Pathway has been Redefined As described herein, the inventors have made the surprising discovery that the lectin pathway of complement has two effector arms to activate complement, both driven by lectin pathway activation complexes formed of carbohydrate recognition components (MBL, CL-11 and ficolins): i) the effector arm formed by the lectin pathway-associated serine proteases MASP-1 and MASP-3, referred to herein as "lectin pathway effector arm 1" or "LEA-1"; and (ii) the MASP-2 driven activation effector arm, referred to herein as "lectin pathway effector arm 2", or "LEA-2". Both LEA-1 and LEA-2 can effect lysis and/or opsonization.

It has also been determined that lectin-independent conversion of factor B by MASP-3 and lectin-independent conversion of factor D by HTRA-1, MASP-1 and MASP-3, which both can occur in the absence of $Ca^{++}$, commonly lead to the conversion of C3bB to C3bBb and of pro-factor D to factor D. Therefore, inhibiting MASP-3 can inhibit both LEA-1 and the lectin-independent activation of factor B and/or factor D, which can result in the inhibition of lysis and/or opsonization.

FIG. 1 illustrates this new understanding of the pathways of complement activation. As shown in FIG. 1, LEA-1 is driven by lectin-bound MASP-3, which can activate the zymogen of factor D to its active form and/or cleave the C3b- or C3b($H_2O$)-bound factor B, leading to conversion of the C3bB zymogen complex into its enzymatically active form C3bBb. Activated factor D, generated by MASP-3, can also convert the C3bB or C3b($H_2O$) zymogen complexes into their enzymatically active form. MASP-1 is capable of rapid self-activation, whereas MASP-3 is not. In many cases, MASP-1 is the activator of MASP-3.

While in many examples lectins (i.e., MBL, CL-11 or ficolins) can direct activity to cellular surfaces, FIG. 1 also outlines the lectin-independent functions of MASP-3, MASP-1, and HTRA-1 in factor B activation and/or factor D maturation. As with the lectin-associated form of MASP-3 in LEA-1, the lectin-independent form of MASP-3 is capable of mediating conversion of C3bB or C3b($H_2O$) to C3bBb (see also FIGS. 29 and 30) and pro-factor D to factor D (see FIG. 32). MASP-1 (see also FIG. 32) and the non-MASP-related protein HTRA-1 can also activate factor D (Stanton et al., *Evidence That the HTRA1 Interactome Influences Susceptibility to Age-Related Macular Degeneration*, presented at The Association for Research in Vision and Ophthalmology 2011 conference on May 4, 2011) in a manner in which no lectin component is required.

Figure 28A:
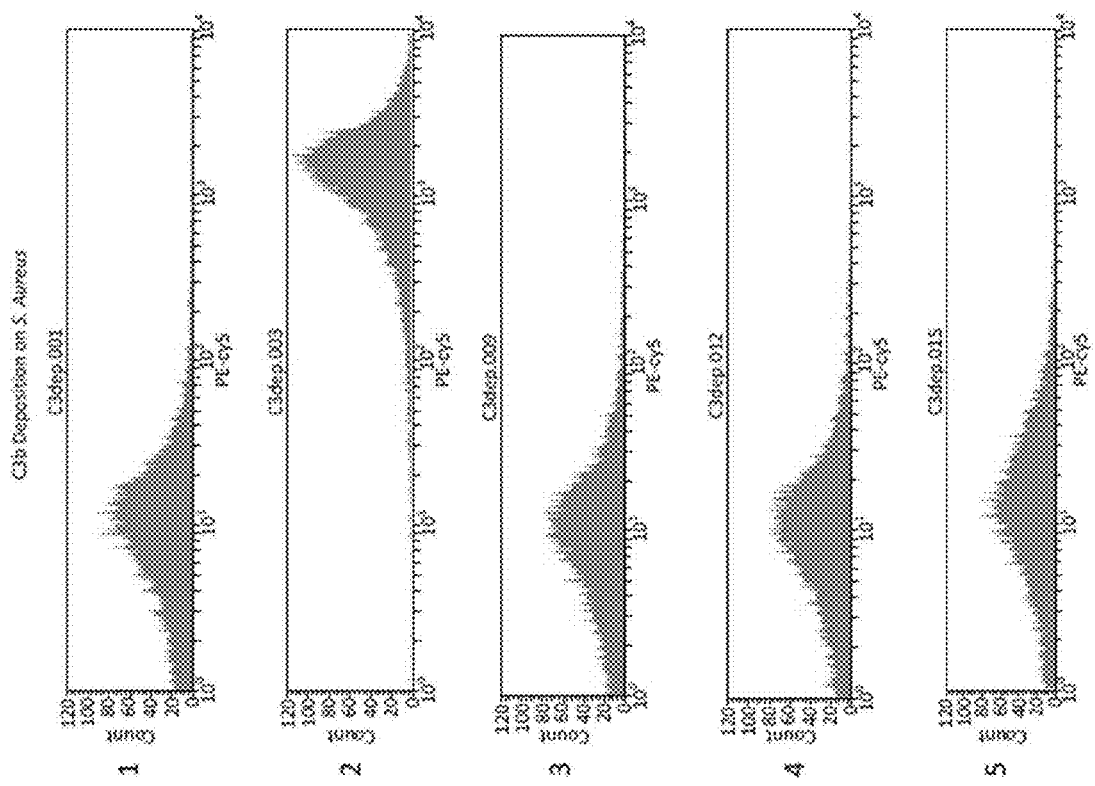
FIG. 28A provides the results of flow cytometry analysis for C3b deposition on heat-killed *Staphylococcus aureus*, demonstrating that in normal human serum in the presence of EDTA, which is known to inactivate the lectin and alternative pathways, no C3b deposition was observed (panel 1), in normal human serum treated with $Mg^{++}$/EGTA, alternative pathway-driven C3b deposition is observed (panel 2), and as shown in panel 3, 4 and 5, in factor B-depleted, factor D-depleted and properdin (factor P)-depleted serum, respectively, no alternative pathway driven C3b deposition is observed, as described in Example 8.
Figure 28B:
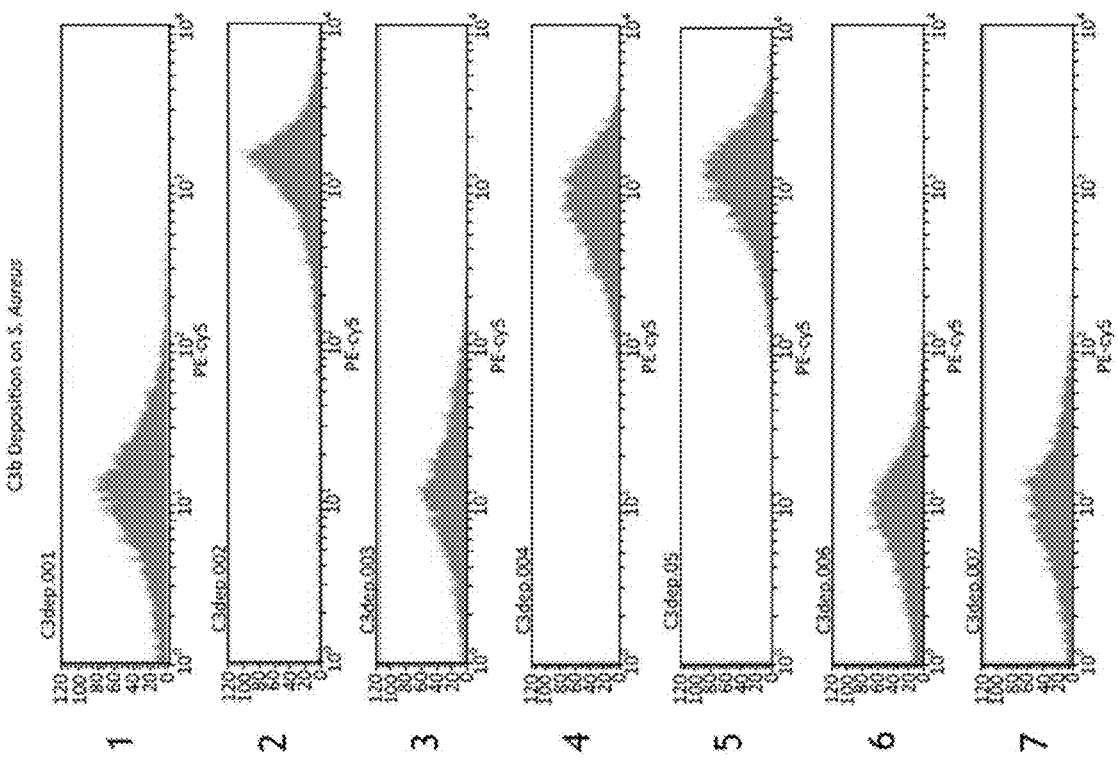
FIG. 28B provides the results of flow cytometry analysis for C3b deposition on heat-killed *S. aureus*, demonstrating that, as in EDTA-treated normal serum (panel 1), AP-driven C3b deposition is absent in 3MC serum in the presence of $Mg^{++}$/EGTA (panel 3), whereas panels 4 and 5 show that active full length rMASP-3 (panel 4) and active rMASP-3 (CCP1-CCP2-SP) (panel 5) both restore AP-driven C3b deposition in 3MC serum to levels observed in normal serum treated with $Mg^{++}$/EGTA (panel 2), neither inactive rMASP-3 (S679A) (panel 6) nor wild type rMASP-1 (panel 7) can restore AP-driven C3b deposition in 3MC serum, as described in Example 8.

Thus, MASP-1 (via LEA-1 and lectin-independent forms), MASP-3 (via LEA-1 and lectin-independent forms), and HTRA-1 (lectin-independent only) are capable of either direct or indirect activation at one or more points along a MASP-3-factor D-factor B axis. In doing so, they generate C3bBb, the C3 convertase of the alternative pathway, and they stimulate the production and deposition of C3b on microbial surfaces. C3b deposition plays a critical role in opsonization, labeling the surfaces of microbes for destruction by host phagocytic cells, such as macrophages. As an example herein (FIGS. 28A and 28B), MASP-3 is critical for opsonization of *S. aureus*. C3b deposition occurs rapidly on *S. aureus* exposed to human serum in a MASP-3-dependent fashion (FIGS. 28A and 28B).

The contributions of LEA-1 and the lectin-independent functions of MASP-3, MASP-1, or HTRA-1 are not limited to opsonization, however. As diagrammed in FIG. 1, these three components can also cause cell lysis by indirect or direct activation of factor B, and the production of C3b.

These components form complexes that generate the alternative pathway C5 convertase, C3bBb(C3b)$_n$. As described further herein, the requirement for MASP-3 and MBL, but not MASP-2 (and, therefore, not LEA-2 in this example), in the lysis of *N. meningitidis* (see FIGS. 11, 12 and 13) demonstrates a role for LEA-1 in lysis. In summary, the opsonization results obtained from the *S. aureus* studies and the lysis results observed in the *N. meningitidis* studies support the role of LEA-1 in both processes (as diagrammed in FIG. 1). Furthermore, these studies demonstrate that both opsonization and lysis can result from the conversion of C3bB or C3b(H$_2$0) and/or of pro-factor D to factor D; therefore, both processes can be outcomes of the lectin-independent roles of MASP-3, MASP-1, or HTRA-1. Thus, the model developed by the inventors in FIG. 1 supports the use of inhibitors of principally MASP-3, but also MASP-1 and/or HTRA-1, to block opsonization and/or lysis and to treat pathologies caused by dysregulation of these processes.

1. Lectin Pathway Effector Arm (LEA-1)

The first effector arm of the lectin pathway, LEA-1, is formed by the lectin pathway-associated serine proteases MASP-1 and MASP-3. As described herein, the inventors have now shown that, in the absence of MASP-3 and in the presence of MASP-1, the alternative pathway is not effectively activated on surface structures. These results demonstrate that MASP-3 plays a previously undisclosed role in initiating the alternative pathway, and this is confirmed using the MASP-3-deficient 3MC serum obtained from patients with the rare 3MC autosomal recessive disorder (Rooryck C, et al., Nat Genet. 43(3):197-203 (2011)) with mutations that render the serine protease domain of MASP-3 dysfunctional. Based on these novel findings, it is expected that complement activation involving the alternative pathway, as conventionally defined, is MASP-3-dependent. In fact, MASP-3, and its activation of LEA-1, may represent the hitherto elusive initiator of the alternative pathway.

As further described in Examples 1-4 herein, in MASP-2-deficient sera, the inventors observed a higher activity of lectin-dependent alternative pathway activation resulting in a higher bactericidal activity (i.e., lytic activity) against *N. meningitidis*. While not wishing to be bound by any particular theory, it is believed that in absence of MASP-2, MASP-1-bearing carbohydrate recognition complexes are more likely to bind close to MASP-3-bearing carbohydrate recognition complexes to activate MASP-3. It is known that, in many instances, activation of MASP-3 is dependent on MASP-1 activity, as MASP-3 is not an auto-activating enzyme and very often requires the activity of MASP-1 to be converted from its zymogen form into its enzymatically active form. MASP-1 (like MASP-2) is an auto-activating enzyme, while MASP-3 does not auto-activate and, in many instances, needs the enzymatic activity of MASP-1 to be converted into its enzymatically active form. See, Zundel S, et al., *J Immunol.*, 172(7):4342-50 (2004). In absence of MASP-2, all lectin pathway recognition complexes are either loaded with MASP-1 or MASP-3. Therefore, the absence of MASP-2 facilitates the MASP-1-mediated conversion of MASP-3 into its enzymatically active form. Once MASP-3 is activated, activated MASP-3 initiates alternative pathway activation, now referred to as "LEA-1" activation, through a MASP-3-mediated conversion of C3bB to C3bBb and/or conversion of pro-factor D to factor D. C3bBb, also referred to as the alternative pathway C3 convertase, cleaves additional C3 molecules yielding deposition of opsonic C3b molecules. If several C3b fragments bind in close proximity to the C3bBb convertase complex, this results in the formation of the alternative pathway C5 convertase C3bBb(C3b)n, which promotes formation of MAC. Additionally, C3b molecules deposited on the surface form new sites for factor B binding, which can now be cleaved by factor D and/or MASP-3 to form additional sites where alternative pathway C3 and C5 convertase complexes can be formed. This latter process is needed for effective lysis and does not require lectins once the initial C3b deposition has occurred. A recent publication (Iwaki D. et al., *J Immunol* 187(7):3751-8 (2011)) as well as data generated from the inventors (FIG. 30) demonstrate that the alternative pathway C3 convertase zymogen complex C3bB is converted into its enzymatically active form by activated MASP-3. The inventors now have discovered that the MASP-3-mediated cleavage of factor B represents a subcomponent of the newly described LEA-1, which promotes lectin-dependent formation of the alternative pathway C3 convertase C3bBb.

2. Lectin Pathway Effector Arm (LEA-2)

The second effector arm of the lectin pathway, LEA-2, is formed by the lectin pathway-associated serine protease MASP-2. MASP-2 is activated upon binding of the recognition components to their respective pattern, and may also be activated by MASP-1, and subsequently cleaves the complement component C4 into C4a and C4b. After the binding of the cleavage product C4b to plasma C2, C4b-bound C2 becomes substrate of a second MASP-2-mediated cleavage step which converts C4b-bound C2 into the enzymatically active complex C4bC2a and a small C2b cleavage fragment. C4b2a is the C3-converting C3 convertase of the lectin pathway, converting the abundant plasma component C3 into C3a and C3b. C3b binds to any surface in close proximity via a thioester bond. If several C3b fragments bind in close proximity to the C3 convertase complex C4b2a, this convertase alters its specificity to convert C5 into C5b and C5a, forming the C5 convertase complex C4b2a(C3b)n. While this C5 convertase can initiate formation of MAC, this process is thought to be insufficiently effective to promote lysis on its own. Rather, the initial C3b opsonins produced by LEA-2 form the nucleus for the formation of new alternative pathway C3 convertase and C5 convertase sites, which ultimately lead to abundant MAC formation and lysis. This latter event is mediated by factor D activation of factor B associated with LEA-2-formed C3b, and hence is dependent on LEA-1 by virtue of the essential role for MASP-1 in the maturation of factor D. There is also a MASP-2-dependent C4-bypass activation route to activate C3 in the absence of C4, which plays an important role in the pathophysiology of ischemia-reperfusion injury, since C4-deficient mice are not protected from ischemia-reperfusion injury while MASP-2-deficient mice are (Schwaeble et al., *PNAS,* 2011 supra). LEA-2 is also tied to the coagulation pathway, involving the cleavage of prothrombin to thrombin (common pathway) and also the cleavage of factor XII (Hageman factor) to convert into its enzymatically active form XIIa. Factor XIIa in turn cleaves factor XI to XIa (intrinsic pathway). The intrinsic pathway activation of the clotting cascade leads to fibrin formation, which is of critical importance for thrombus formation.

FIG. 1 illustrates the new understanding of the lectin pathway and alternative pathway based on the results provided herein. FIG. 1 delineates the role of LEA-2 in both opsonization and lysis. While MASP-2 is the initiator of "downstream" C3b deposition (and resultant opsonization) in multiple lectin-dependent settings physiologically (FIGS. 18A, 18B, 18C), it also plays a role in lysis of serum-sensitive bacteria. As illustrated in FIG. 1, the proposed molecular mechanism responsible for the increased bactericidal activity of MASP-2-deficient or MASP-2-depleted serum/plasma for serum-sensitive pathogens such as *N. meningitidis* is that, for the lysis of bacteria, lectin pathway recognition complexes associated with MASP-1 and MASP-3 have to bind in close proximity to each other on the bacterial surface, thereby allowing MASP-1 to cleave MASP-3. In contrast to MASP-1 and MASP-2, MASP-3 is not an auto-activating enzyme, but, in many instances, requires activation/cleavage by MASP-1 to be converted into its enzymatically active form.

As further shown in FIG. 1, activated MASP-3 can then cleave C3b-bound factor B on the pathogen surface to initiate the alternative activation cascade by formation of the enzymatically active alternative pathway C3 and C5 convertases C3bBb and C3bBb(C3b)n, respectively. MASP-2-bearing lectin-pathway activation complexes have no part in the activation of MASP-3 and, in the absence of or after depletion of MASP-2, all-lectin pathway activation complexes will either be loaded with MASP-1 or MASP-3. Therefore, in the absence of MASP-2, the likelihood is markedly increased that on the microbial surface MASP-1- and MASP-3-bearing lectin-pathway activation complexes will come to sit in close proximity to each other, leading to more MASP-3 being activated and thereby leading to a higher rate of MASP-3-mediated cleavage of C3b-bound factor B to form the alternative pathway C3 and C5 convertases C3bBb and C3bBb(C3b)n on the microbial surface. This leads to the activation of the terminal activation cascades C5b-C9 that forms the Membrane Attack Complex, composed of surface-bound C5b associated with C6, C5bC6 associated with C7, C5bC6C7 associated with C8, and C5bC6C7C8, leading to the polymerization of C9 that inserts into the bacterial surface structure and forms a pore in the bacterial wall, which will lead to osmolytic killing of the complement-targeted bacterium.

The core of this novel concept is that the data provided herein clearly show that the lectin pathway activation complexes drive the following two distinct activation routes, as illustrated in FIG. 1:

i) LEA-1: A MASP-3-dependent activation route that initiates and drives activation of complement by generating the alternative pathway convertase C3bBb through initial cleavage and activation of factor B on activator surfaces, which will then catalyze C3b deposition and formation of the alternative pathway convertase C3bBb. The MASP-3-driven activation route plays an essential role in the opsonization and lysis of microbes and drives the alternative pathway on the surface of bacteria, leading to optimal rates of activation to generate membrane attack complexes; and ii) LEA-2: A MASP-2-dependent activation route leading to the formation of the lectin pathway C3 convertase C4b2a and, upon accumulation of the C3 cleavage product C3b, subsequently to the C5 convertase C4b2a(C3b)n. In the absence of complement C4, MASP-2 can form an alternative C3 convertase complex which involves C2 and clotting factor XI.

In addition to its role in lysis, the MASP-2-driven activation route plays an important role in bacterial opsonization leading to microbes being coated with covalently bound C3b and cleavage products thereof (i.e., iC3b and C3dg), which will be targeted for the uptake and killing by C3 receptor-bearing phagocytes, such as granulocytes, macrophages, monocytes, microglia cells and the reticuloendothelial system. This is the most effective route of clearance of bacteria and microorganisms that are resistant to complement lysis. These include most of the gram-positive bacteria.

In addition to LEA-1 and LEA-2, there is the potential for lectin-independent activation of factor D by MASP-3, MASP-1 and/or HTRA-1, and there is also the potential for lectin-independent activation of factor B by MASP-3.

While not wishing to be bound by any particular theory, it is believed that each of (i) LEA-1, (ii) LEA-2 and (iii) lectin-independent activation of factor B and/or factor D lead to opsonization and/or the formation of MAC with resultant lysis.

ii. Background of MASP-1, MASP-2 and MASP-3

Three mannan-binding lectin-associated serine proteases (MASP-1, MASP-2 and MASP-3) are presently known to be associated in human serum with the mannan-binding lectin (MBL). Mannan-binding lectin is also called 'mannose-binding protein' or 'mannose-binding lectin' in the recent literature. The MBL-MASP complex plays an important role in innate immunity by virtue of the binding of MBL to carbohydrate structures present on a wide variety of microorganisms. The interaction of MBL with specific arrays of carbohydrate structures brings about the activation of the MASP proenzymes which, in turn, activate complement by cleaving the complement components C4 and C2 to form the C3 convertase C4b2b (Kawasaki et al., *J. Biochem* 106:483-489 (1989); Matsushita & Fujita, *J. Exp Med.* 176:1497-1502 (1992); Ji et al., *J. Immunol* 150:571-578 (1993)).

The MBL-MASP proenzyme complex was, until recently, considered to contain only one type of protease (MASP-1), but it is now clear that there are two other distinct proteases (i.e., MASP-2 and MASP-3) associated with MBL (Thiel et al., *Nature* 386:506-510 (1997); Dahl et al., *Immunity* 15:127-135 (2001)), as well as an additional serum protein of 19 kDa, referred to as "MAp19" or "sMAP" (Stover et al., *J. Immunol* 162:3481-3490 (1999); Stover et al., *J. Immunol* 163:6848-6859 (1999); Takahashi et al., *Int. Immunol* 11:859-63 (1999)).

MAp19 is an alternatively spliced gene product of the structural gene for MASP-2 and lacks the four C-terminal domains of MASP-2, including the serine endopeptidase domain. The abundantly expressed truncated mRNA transcript encoding MAp19 is generated by an alternative splicing/polyadenylation event of the MASP-2 gene. By a similar mechanism, the MASP-1/3 gene gives rise to three major gene products, the two serine proteases MASP-1 and MASP-3 and a truncated gene product of 44 kDa referred to as "MAp44" (Degn et al., *J. Immunol* 183(11):7371-8 (2009); Skjoedt et al., *J Biol Chem* 285:8234-43 (2010)).

MASP-1 was first described as the P-100 protease component of the serum Ra-reactive factor, which is now recognized as being a complex composed of MBL plus MASP (Matsushita et al., *Collectins and Innate Immunity*, (1996); Ji et al., *J Immunol* 150:571-578 (1993). The ability of an MBL-associated endopeptidase within the MBL-MASPs complex to act on the complement components C4 and C2 in a manner apparently identical to that of the C1s enzyme within the C1q-(C1r)$_2$-(C1s)$_2$ complex of the classical pathway of complement suggests that there is a MBL-MASPs complex which is functionally analogous to the C1q-(C1r)$_2$-(C1s)$_2$ complex. The C1q-(C1r)$_2$-(C1s)$_2$ complex is activated by the interaction of C1q with the Fc regions of antibody IgG or IgM present in immune complexes. This brings about the autoactivation of the C1r proenzyme which, in turn, activates the C1s proenzyme which then acts on complement components C4 and C2.

The stoichiometry of the MBL-MASPs complex differs from the one found for the C1q-(C1r)$_2$-(C1s)$_2$ complex in that different MBL oligomers appear to associate with different proportions of MASP-1/MAp19 or MASP-2/

MASP-3 (Dahl et al., Immunity 15:127-135 (2001). The majority of MASPs and MAp19 found in serum are not complexed with MBL (Thiel et al., *J Immunol* 165:878-887 (2000)) and may associate in part with ficolins, a recently described group of lectins having a fibrinogen-like domain able to bind to N-acetylglucosamine residues on microbial surfaces (Le et al., *FEBS Lett* 425:367 (1998); Sugimoto et al., *J. Biol Chem* 273:20721 (1998)). Among these, human L-ficolin, H-ficolin and M-ficolin associate with MASPs as well as with MAp19 and may activate the lectin pathway upon binding to the specific carbohydrate structures recognized by ficolins (Matsushita et al., *J Immunol* 164:2281-2284 (2000); Matsushita et al., *J Immunol* 168:3502-3506 (2002)). In addition to the ficolins and MBL, an MBL-like lectin collectin, called CL-11, has been identified as a lectin pathway recognition molecule (Hansen et al. *J Immunol* 185:6096-6104 (2010); Schwaeble et al. *PNAS* 108:7523-7528 (2011)). There is overwhelming evidence underlining the physiological importance of these alternative carbohydrate recognition molecules and it is therefore important to understand that MBL is not the only recognition component of the lectin activation pathway and that MBL deficiency is not to be mistaken for lectin-pathway deficiency. The existence of possibly an array of alternative carbohydrate-recognition complexes structurally related to MBL may broaden the spectrum of microbial structures that initiate a direct response of the innate immune system via activation of complement.

All lectin pathway recognition molecules are characterized by a specific MASPs-binding motif within their collagen-homologous stalk region (Wallis et al. *J. Biol Chem* 279:14065-14073 (2004)). The MASP-binding site in MBLs, CL-11 and ficolins is characterized by a distinct motif within this domain: Hyp-Gly-Lys-Xaa-Gly-Pro, where Hyp is hydroxyproline and Xaa is generally an aliphatic residue. Point mutations in this sequence disrupt MASP binding.

1. Respective Structures, Sequences, Chromosomal Localization and Splice Variants of MASP-1 and MASP-3

Figure 2:
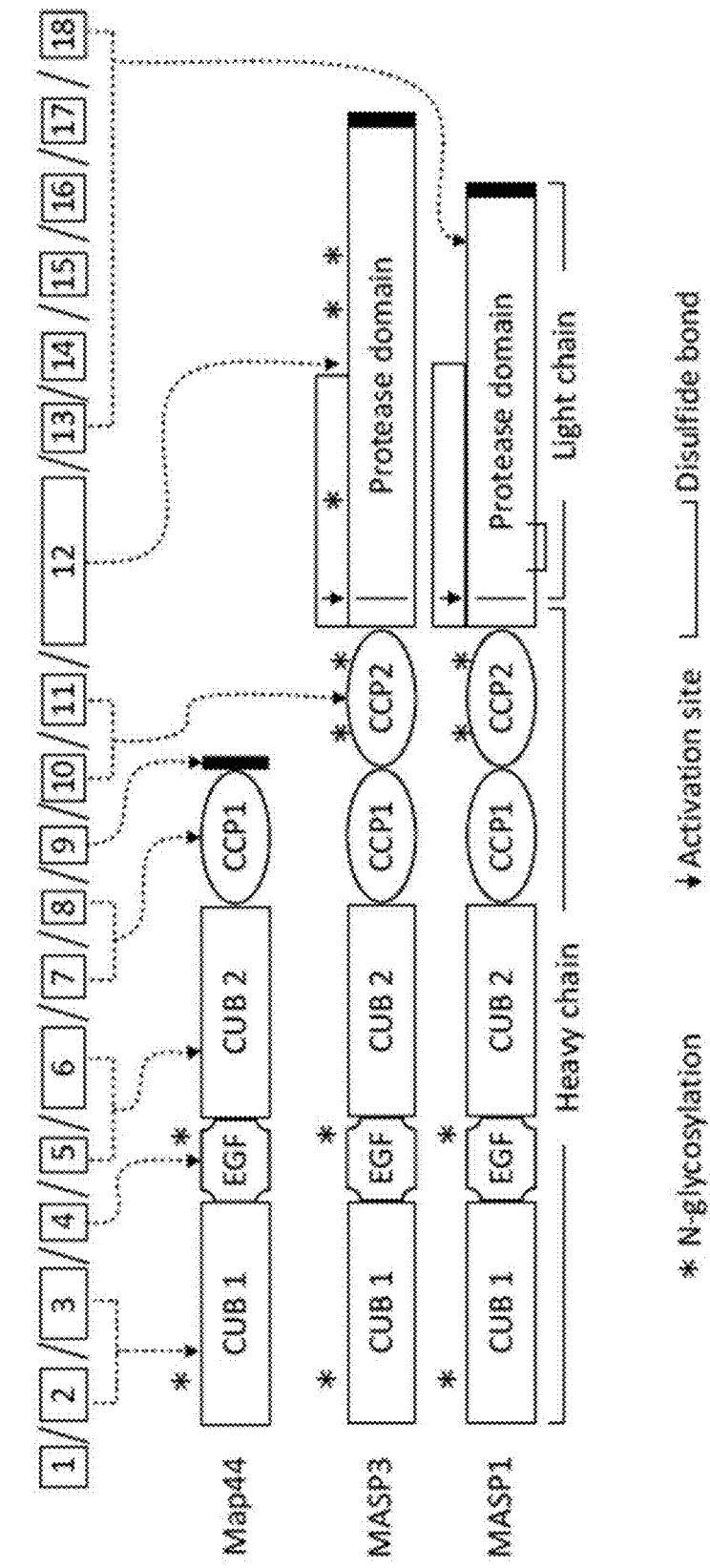
FIG. 2 is a schematic diagram adapted from Schwaeble et al., *Immunobiol* 205:455-466 (2002), as modified by Yongqing et al., *BBA* 1824:253 (2012), illustrating the MASP-1, MASP-3 and MAp44 protein domains and the exons encoding the same.

FIG. 2 is a schematic diagram illustrating the domain structure of the human MASP-1 polypeptide (SEQ ID NO:8), human MASP-3 polypeptide (SEQ ID NO:2) and human MAp44 polypeptide and the exons encoding the same. As shown in FIG. 2, the serine proteases MASP-1 and MASP-3 consist of six distinct domains arranged as found in C1r and C1s; i.e., (I) an N-terminal C1r/C1s/sea urchin VEGF/bone morphogenic protein (or CUBI) domain; (II) an epidermal growth factor (EGF)-like domain; (III) a second CUB domain (CUBII); (IV and V) two complement control protein (CCP1 and CCP2) domains; and (VI) a serine protease (SP) domain.

The cDNA-derived amino acid sequences of human and mouse MASP-1 (Sato et al., *Int Immunol* 6:665-669 (1994); Takada et al., *Biochem Biophys Res Commun* 196:1003-1009 (1993); Takayama et al., *J. Immunol* 152:2308-2316 (1994)), human, mouse, and rat MASP-2 (Thiel et al., *Nature* 386:506-510 (1997); Endo et al., *J Immunol* 161: 4924-30 (1998); Stover et al., *J. Immunol* 162:3481-3490 (1999); Stover et al., *J. Immunol* 163:6848-6859 (1999)), as well as human MASP-3 (Dahl et al., *Immunity* 15:127-135 (2001)) indicate that these proteases are serine peptidases having the characteristic triad of His, Asp and Ser residues within their putative catalytic domains (Genbank Accession numbers: human MASP-1: BAA04477.1 (SEQ ID NO:8); mouse MASP-1: BAA03944; rat MASP-1: AJ457084; Human MASP-3:AAK84071 (SEQ ID NO:2); mouse MASP-3: AB049755, as accessed on Genbank on Feb. 15, 2012 (SEQ ID NO:3); rat MASP-3 (SEQ ID NO:4); chicken MASP-3 (SEQ ID NO:5); rabbit MASP-3 (SEQ ID NO:6); and Cynomolgus monkey (SEQ ID NO:7).

As further shown in FIG. 2, upon conversion of the zymogen to the active form, the heavy chain (alpha, or A chain) and light chain (beta, or B chain) are split to yield a disulphide-linked A-chain and a smaller B-chain representing the serine protease domain. The single-chain proenzyme MASP-1 is activated (like proenzyme C1r and C1s) by cleavage of an Arg-Ile bond located between the second CCP domain (domain V) and the serine protease domain (domain VI). Proenzymes MASP-2 and MASP-3 are considered to be activated in a similar fashion to that of MASP-1. Each MASP protein forms homodimers and is individually associated with MBL and the ficolins in a $Ca^{++}$-dependent manner.

The human MASP-1 polypeptide (SEQ ID NO:8) and MASP-3 polypeptide (SEQ ID NO:2) arise from one structural gene (Dahl et al., *Immunity* 15:127-135 (2001), which has been mapped to the 3q27-28 region of the long arm of chromosome 3 (Takada et al., *Genomics* 25:757-759 (1995)). The MASP-3 and MASP-1 mRNA transcripts are generated from the primary transcript by an alternative splicing/polyadenylation process. The MASP-3 translation product is composed of an alpha chain, which is common to both MASP-1 and MASP-3, and a beta chain (the serine protease domain), which is unique to MASP-3. As shown in FIG. 2, the human MASP-1 gene encompasses 18 exons. The human MASP-1 cDNA is encoded by exons 2, 3, 4, 5, 6, 7, 8, 10, 11, 13, 14, 15, 16, 17 and 18. As further shown in FIG. 2, the human MASP 3 gene encompasses twelve exons. The human MASP-3 cDNA (set forth as SEQ ID NO:1) is encoded by exons 2, 3, 4, 5, 6, 7, 8, 10, 11 and 12. An alternative splice results in a protein termed MBL-associated protein 44 ("MAp44"), arising from exons 2, 3, 4, 5, 6, 7, 8 and 9.

The human MASP-1 polypeptide (SEQ ID NO: 8 from Genbank BAA04477.1) has 699 amino acid residues, which includes a leader peptide of 19 residues. When the leader peptide is omitted, the calculated molecular mass of MASP-1 is 76,976 Da. As shown in FIG. 2, the MASP-1 amino acid sequence contains four N-linked glycosylation sites. The domains of the human MASP-1 protein (with reference to SEQ ID NO:8) are shown in FIG. 2 and include an N-terminal C1r/C1s/sea urchin VEFG/bone morphogenic protein (CUBI) domain (aa 25-137 of SEQ ID NO:8), an epidermal growth factor-like domain (aa 139-181 of SEQ ID NO:8), a second CUB domain (CUBII) (aa 185-296 of SEQ ID NO:8), as well as a tandem of complement control protein (CCP1 aa 301-363 and CCP2 aa 367-432 of SEQ ID NO:8) domains and a serine protease domain (aa 449-694 of SEQ ID NO:8).

The human MASP-3 polypeptide (SEQ ID NO:2, from Genbank AAK84071) has 728 amino acid residues (as shown in FIG. 3), which includes a leader peptide of 19 residues (shown as the underlined amino acid residues in FIG. 3).

When the leader peptides are omitted, the calculated molecular mass of MASP-3 is 81,873 Da. As shown in FIG. 2, there are seven N-linked glycosylation sites in MASP-3. The domains of the human MASP-3 protein (with reference to SEQ ID NO:2) are shown in FIG. 2 and include an N-terminal C1r/C1s/sea urchin VEGF/bone morphogenic protein (CUBI) domain (aa 25-137 of SEQ ID NO:2), an epidermal growth factor-like domain (aa 139-181 of SEQ ID NO:2), a second CUB domain (CUBII) (aa 185-296 of SEQ ID NO:2), as well as a tandem of complement control protein (CCP1 aa 299-363 and CCP2 aa 367-432 of SEQ ID NO:2) domains and a serine protease domain (aa 450-728 of SEQ ID NO:2).

The MASP-3 translation product is composed of an alpha chain (heavy chain), containing the CUB-1-EGF-CUB-2-CCP-1-CCP-2 domains (alpha chain: aa 1-448 of SEQ ID NO:2) which is common to both MASP-1 and MASP-3, and a light chain (beta chain: aa 449-728 of SEQ ID NO:2), containing the serine protease domain, which is unique to MASP-3.

2. Comparison of MASP-3 Amino Acid Sequences from Various Species

Figure 4:
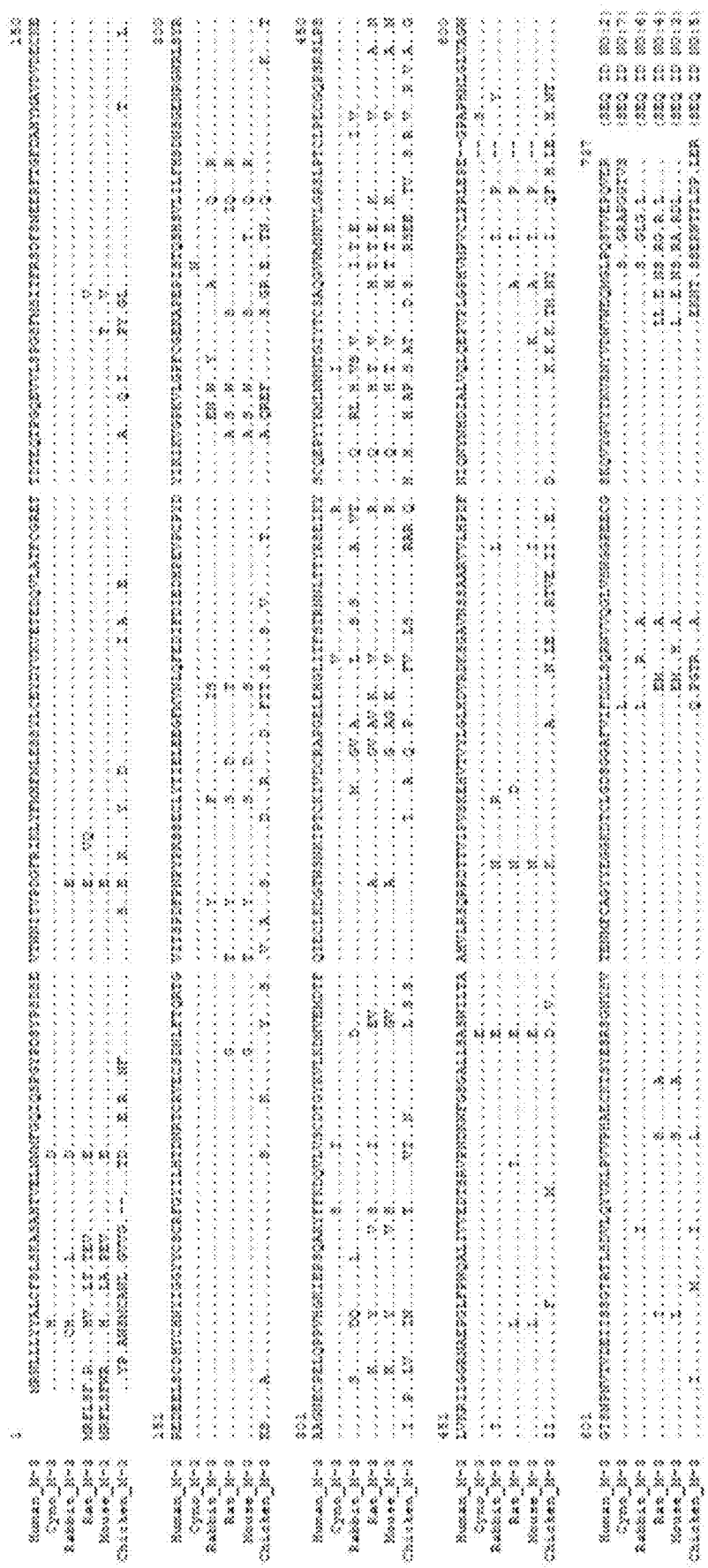
FIG. 4 shows an alignment of full length MASP-3 protein from multiple species.
Figure 5:
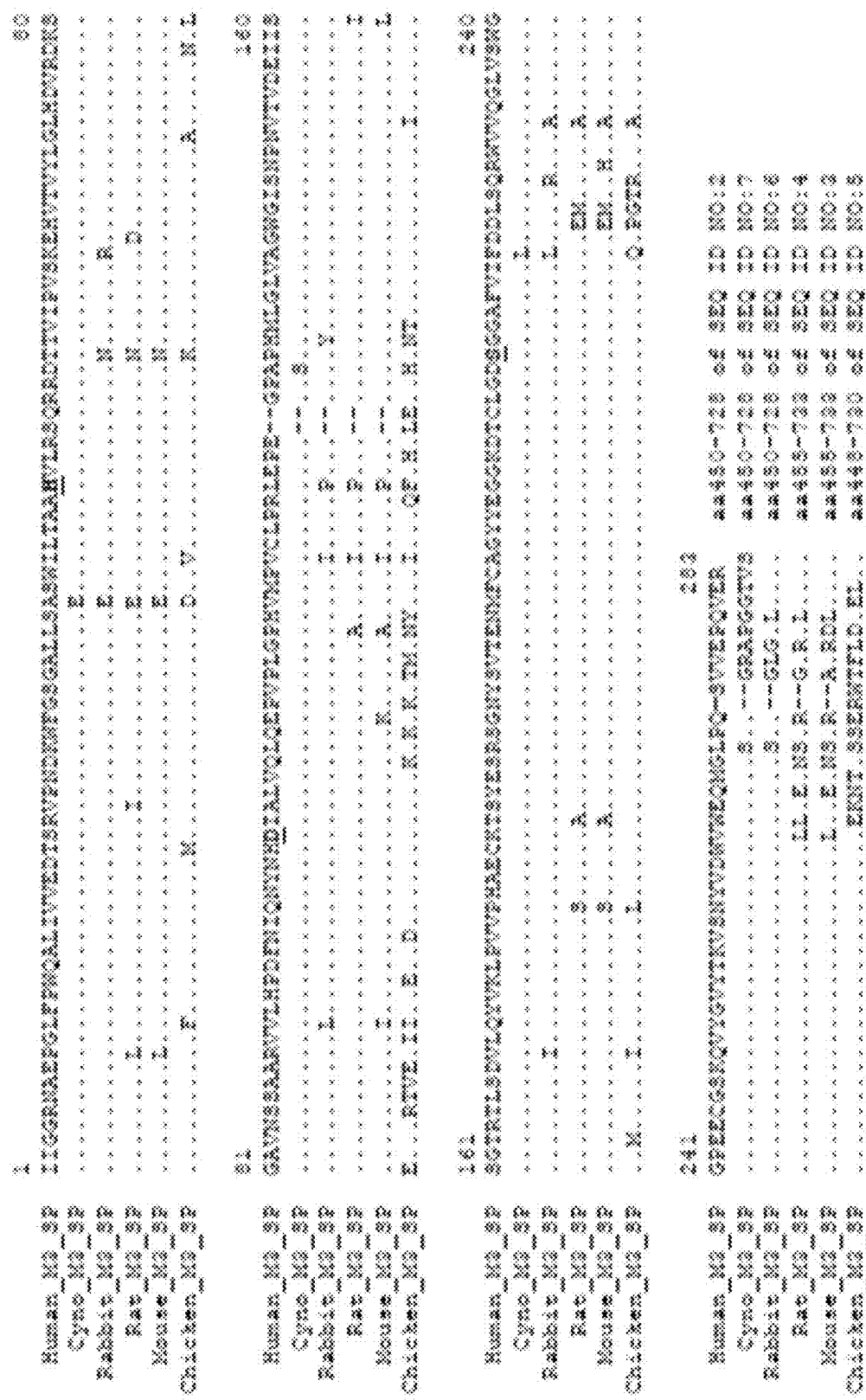
FIG. 5 shows an alignment of the SP domain of MASP-3 protein from multiple species.

FIG. 4 provides a multi-species alignment of MASP-3 showing a comparison of full-length MASP-3 protein from human (SEQ ID NO:2), cynomolgus monkey (SEQ ID NO:7), rat (SEQ ID NO:4), murine (SEQ ID NO:3), chicken (SEQ ID NO:5) and rabbit (SEQ ID NO:6). FIG. 5 provides a multi-species alignment of the serine protease (SP) domain from human (aa 450-728 of SEQ ID NO:2); rabbit (aa 450-728 of SEQ ID NO:6); murine (aa aa455-733 of SEQ ID NO:3); rat (aa 455-733 of SEQ ID NO:4) and chicken (aa aa448-730 of SEQ ID NO:5).

As shown in FIG. 4, there is a high level of amino acid sequence conservation of MASP-3 polypeptide amongst different species, particularly in the SP domain (FIG. 5). As further shown in FIG. 5, the catalytic triad (H at residue 497; D at residue 553 and S at residue 664 with reference to full length human MASP-3 (SEQ ID NO:2) is conserved across species. TABLE 1 summarizes the percent identity of the MASP-3 SP domain across species.

TABLE 1

Percent Identity of the MASP-3 SP domain Across Species

| | Cyno | Rabbit | Rat | Mouse | chicken |
|---|---|---|---|---|---|
| Human | 95% | 94% | 92% | 91% | 79% |
| Cyno | | 94% | 90% | 90% | 79% |
| Rabbit | | | 92% | 92% | 81% |
| Rat | | | | 97% | 78% |
| mouse | | | | | 78% |

MASP-3 has no proteolytic activity towards C4, C2 or C3 substrates. Conversely, MASP-3 was initially reported to act as an inhibitor of the lectin pathway (Dahl et al., *Immunity* 15:127-135 (2001)). This conclusion may have come about because in contrast to MASP-1 and MASP-2, MASP-3 is not an autoactivating enzyme (Zundel S. et al., *J Immunol* 172:4342-4350 (2004); Megyeri et al., *J. Biol. Chem.* 288: 8922-8934 (2013).

Recently, evidence for possible physiological functions of MASP-1 and MASP-3 emerged from transgenic mouse studies using a mouse strain with a combined MASP-1 and MASP-3 deficiency. While MASP-1/3-knockout mice have a functional lectin pathway (Schwaeble et al., *PNAS* 108: 7523-7528 (2011)), they appear to lack alternative pathway activity (Takahashi et al., *JEM* 207(1):29-37 (2010)). Lack of alternative pathway activity appears to be due to a processing defect of complement factor D, which is necessary for alternative pathway activity. In MASP-1/3 knockout mice, all factor D is circulating as a proteolytically inactive pro-form, whereas in the serum of normal mice, substantially all of factor D is in the active form. Biochemical analysis suggested that MASP-1 may be able to convert complement factor D from its zymogen form into its enzymatically active form (FIG. 32; Takahashi et al., *JEM* 207(1):29-37 (2010)). MASP-3 also cleaves pro-factor D zymogen and produce active factor D in vitro (FIG. 32; Takahashi et al., *JEM* 207(1):29-37 (2010)). Factor D is present as an active enzyme in circulation in normal individuals, and MASP-1 and MASP-3, as well as HTRA-1, may be responsible for this activation. Furthermore, mice with combined MBL and ficolin deficiencies still produce normal levels of factor D and have a fully functional alternative pathway. Thus, these physiological functions of MASP-1 and MASP-3 do not necessarily involve lectins, and are thus unrelated to the lectin pathway. Recombinant mouse and human MASP-3 also appear to cleave factor B and support C3 deposition on *S. aureus* in vitro (FIG. 29; Iwaki D. et al., *J Immunol* 187(7):3751-8 (2011)).

An unexpected physiological role for MASP-3 has emerged from recent studies of patients with 3MC syndrome (previously designated the Carnevale, Mingarelli, Malpuech, and Michels syndrome; OMIM #257920). These patients display severe developmental abnormalities, including cleft palate, cleft lip, cranial malformations and mental retardation. Genetic analysis identified 3MC patients that were homozygous for a dysfunctional MASP-3 gene (Rooryck et al., *Nat Genet.* 43(3):197-203 (2011)). Another group of 3MC patients was found to be homozygous for a mutation in the MASP-1 gene that leads to the absence of functional MASP-1 and MASP-3 proteins. Yet another group of 3MC patients lacked a functional CL-11 gene. (Rooryck et al., *Nat Genet.* 43(3):197-203 (2011)). Thus, the CL-11 MASP-3 axis appears to play a role during embryonic development. The molecular mechanisms of this developmental pathway are unclear. It is unlikely, however, to be mediated by a conventional complement-driven process since individuals with deficiencies of common complement components C3 do not develop this syndrome. Thus, prior to the discovery of the instant inventors, as described herein, a functional role for MASP-3 in lectin-dependent complement activation was previously not established.

The structures of the catalytic fragment of MASP-1 and MASP-2 have been determined by X-ray crystallography. Structural comparison of MASP-1 protease domain with those of other complement proteases revealed the basis of its relaxed substrate specificity (Dobó et al., *J. Immunol* 183: 1207-1214 (2009)). While the accessibility of the substrate binding groove of MASP-2 is restricted by surface loops (Harmat et al., *J Mol Biol* 342:1533-1546 (2004)), MASP-1 has an open substrate binding pocket which resembles that of trypsin rather than other complement proteases. A thrombin-like property of the MASP-1 structure is the unusually large 60 amino acid loop (loop B) which may interact with substrates. Another interesting feature of the MASP-1 structure is the internal salt bridge between the S1 Asp189 and Arg224. A similar salt bridge can be found in the substrate binding pocket of factor D, which can regulate its protease activity. C1s and MASP-2 have almost identical substrate specificities. Surprisingly, some of the eight surface loops of MASP-2, which determine the substrate specificities, have quite different conformations compared to those of C1s. This means that the two functionally related enzymes interact with the same substrates in a different manner. The structure of zymogen MASP-2 shows an inactive protease domain with disrupted oxyanion hole and substrate binding pocket (Gál et al., *J Biol Chem* 280:33435-33444 (2005)). Surprisingly, zymogen MASP-2 shows considerable activity on a large protein substrate, C4. It is likely that the structure of zymogen MASP-2 is quite flexible, enabling the transition between the inactive and the active forms. This flexibility, which is reflected in the structure, may play a role in the autoactivation process.

Northern blot analysis indicates that liver is the major source of MASP-1 and MASP-2 mRNA. Using a 5' specific cDNA probe for MASP-1, major MASP-1 transcript was seen at 4.8 kb and a minor one at approximately 3.4 kb, both present in human and mouse liver (Stover et al., *Genes Immunity* 4:374-84 (2003)). MASP-2 mRNA (2.6 kb) and MAp19 mRNA (1.0 kb) are abundantly expressed in liver tissue. MASP-3 is expressed in the liver, and also in many other tissues, including neuronal tissue (Lynch N. J. et al., *J Immunol* 174:4998-5006 (2005)).

A patient with a history of infections and chronic inflammatory disease was found to have a mutated form of MASP-2 that fails to form an active MBL-MASP complex (Stengaard-Pedersen et al., *N Engl J Med* 349:554-560 (2003)). Some investigators have determined that deficiency of MBL leads to a tendency to frequent infections in childhood (Super et al., *Lancet* 2:1236-1239 (1989); Garred et al., *Lancet* 346:941-943 (1995) and a decreased resistance to HIV infection (Nielsen et al., *Clin Exp Immunol* 100:219-222 (1995); Garred et al., *Mol Immunol* 33 (suppl 1):8 (1996)). However, other studies have not demonstrated a significant correlation of low MBL levels with increased infections (Egli et al., PLoS One. 8(1):e51983 (2013); Ruskamp et al., J Infect Dis. 198(11):1707-13 (2008); Israëls et al., Arch Dis Child Fetal Neonatal Ed. 95(6):F452-61 (2010)). While the literature is mixed, deficiency, or non-utilization, of MASP may have an adverse effect on an individual's ability to mount immediate, non-antibody-dependent defense against certain pathogens.

Supporting Data for the New Understanding, Underscoring Traditional Assay Conditions that are Devoid of $Ca^{++}$ and Results Obtained Using a More Physiological Set of Conditions that Include $Ca^{++}$.

Several independent lines of strong experimental evidence are provided herein pointing to the conclusion that the lectin pathway activation route of complement activates complement via two independent effector mechanisms: i) LEA-2: a MASP-2-driven path that mediates complement-driven opsonisation, chemotaxis (Schwaeble et al., *PNAS* 108:7523-7528 (2011)), and cell lysis, and ii) LEA-1: a novel MASP-3-dependent activation route that initiates complement activation by generating the alternative pathway convertase C3bBb through cleavage and activation of factor B on activator surfaces, which will then catalyze C3b deposition and formation of the alternative pathway convertase C3bBb, which can result in cell lysis as well as microbial opsonization. In addition, as described herein, separate lectin-independent activation of factor B and/or factor D by MASP-1, MASP-3, or HTRA-1, or a combination of any the three, can also lead to complement activation via the alternative pathway.

Figure 12:
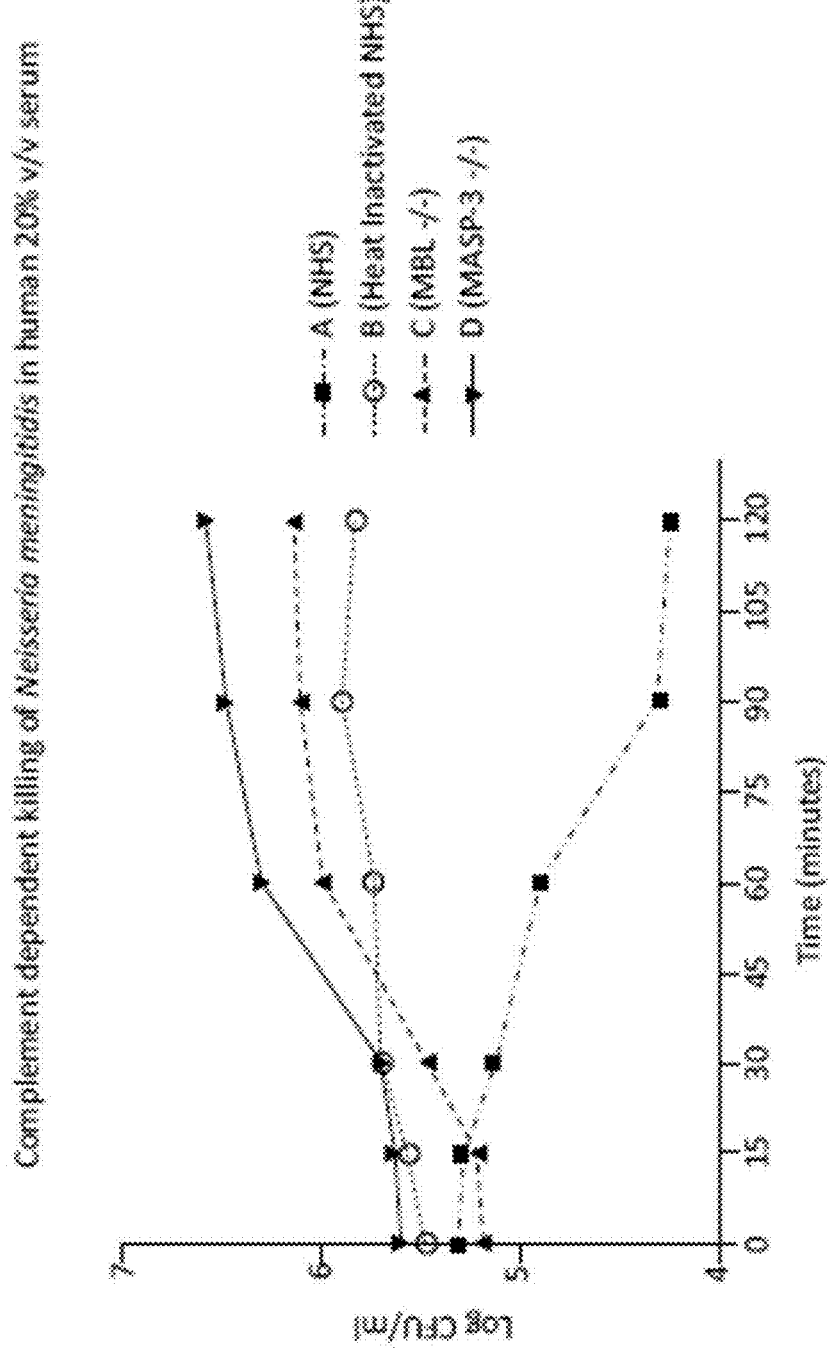
FIG. 12 graphically illustrates the log cfu/mL of viable counts of *N. meningitidis* serogroup B-MC58 recovered at different time points in the human sera samples shown in TABLE 8, showing that complement-dependent killing of *N. meningitidis* in human 20% (v/v) serum is MASP-3 and MBL-dependent, as described in Example 3.
Figure 13:
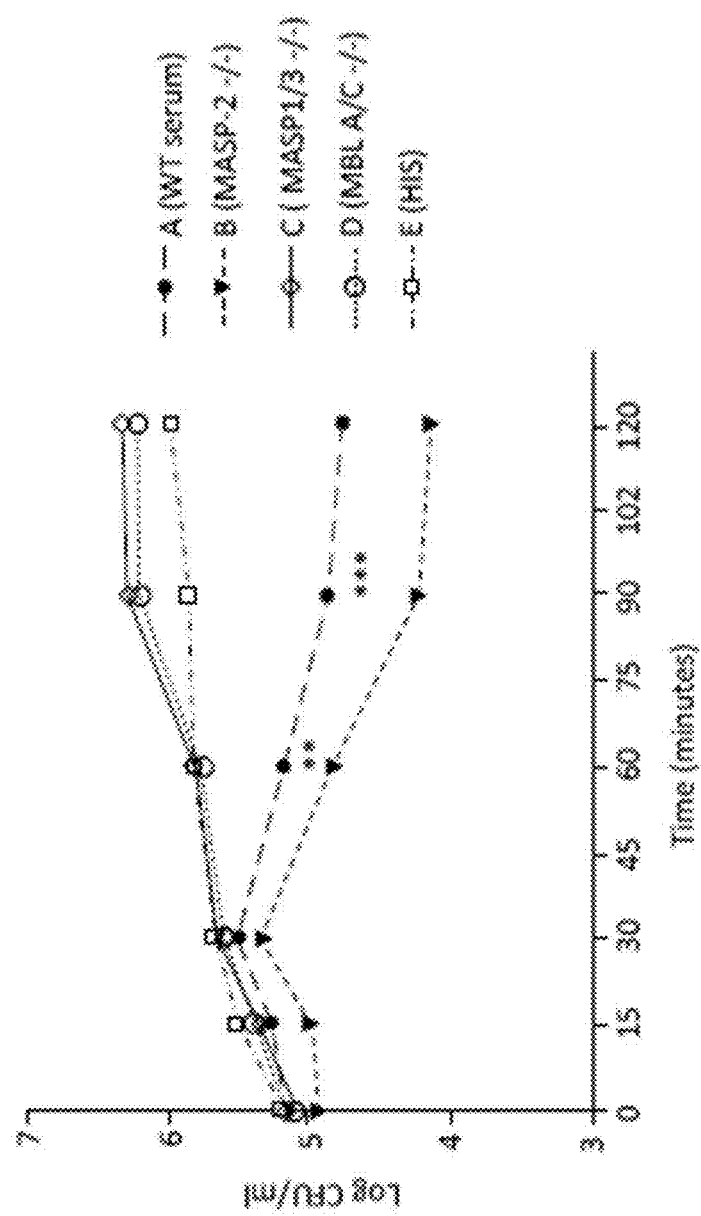
FIG. 13 graphically illustrates the log cfu/mL of viable counts of *N. meningitidis* serogroup B-MC58 recovered at different time points in the mouse sera samples shown in TABLE 10, showing that the MASP-2-/- knockout mouse (referred to as "MASP-2-/-") serum has a higher level of bactericidal activity for *N. meningitidis* than WT mouse serum, whereas in contrast, the MASP-1/3-/- mouse serum does not have any bactericidal activity, as described in Example 3.

A lectin pathway-dependent MASP-3-driven activation of the alternative pathway appears to contribute to the well-established factor D-mediated cleavage of C3b-bound factor B to achieve optimal activation rates for complement-dependent lysis through the terminal activation cascade to lyse bacterial cells through the formation of C5b-9 membrane attack complexes (MAC) on the cellular surface (FIGS. 12-13). This rate-limited event appears to require optimal coordination as it is defective in the absence of MASP-3 functional activity as well as in the absence of factor D functional activity. As described in Examples 1-4 herein, the inventors discovered this MASP-3-dependent lectin pathway function when studying the phenotype of MASP-2 deficiency and MASP-2 inhibition in experimental mouse models of *N. menigitidis* infection. Gene-targeted, MASP-2-deficient mice and wild-type mice treated with antibody-based MASP-2 inhibitors were highly resistant to experimental *N. meningitidis* infection (see FIGS. 6-10). When the infectious dose was adjusted to give approximately 60% mortality in the wild-type littermates, all of the MASP-2-deficient or MASP-2-depleted mice cleared the infection and survived (see FIG. 6 and FIG. 10). This extremely high degree of resistance was reflected in a significant increase of serum bactericidal activity in MASP-2-deficient or MASP-2-depleted mouse serum. Further experiments showed that this bactericidal activity was dependent on alternative pathway-driven bacterial lysis. Mouse sera deficient of factor B, or factor D, or C3 showed no bactericidal activity towards *N. meningitidis*, indicating that the alternative pathway is essential for driving the terminal activation cascade. A surprising result was that mouse sera deficient of MBL-A and MBL-C (both being the lectin-pathway recognition molecules that recognize *N. meningitidis*) as well as mouse sera deficient of the lectin pathway-associated serine proteases MASP-1 and MASP-3 had lost all bacteriolytic activity towards *N. meningitidis* (FIG. 13). A recent paper (Takahashi M. et al., *JEM* 207: 29-37 (2010)) and work presented herein (FIG. 32) demonstrate that MASP-1 can convert the zymogen form of factor D into its enzymatically active form and may in part explain the loss of lytic activity through the absence of enzymatically active factor D in these sera. This does not explain the lack of bactericidal activity in MBL-deficient mice since these mice have normal enzymatically active factor D (Banda et al., *Mol Imunol* 49(1-2):281-9 (2011)). Remarkably, when testing human sera from patients with the rare 3MC autosomal recessive disorder (Rooryck C, et al., *Nat Genet.* 43(3):197-203) with mutations that render the serine protease domain of MASP-3 dysfunctional, no bactericidal activity against *N. meningitidis* was detectable (n.b.: these sera have MASP-1 and factor D, but no MASP-3).

Figure 11:
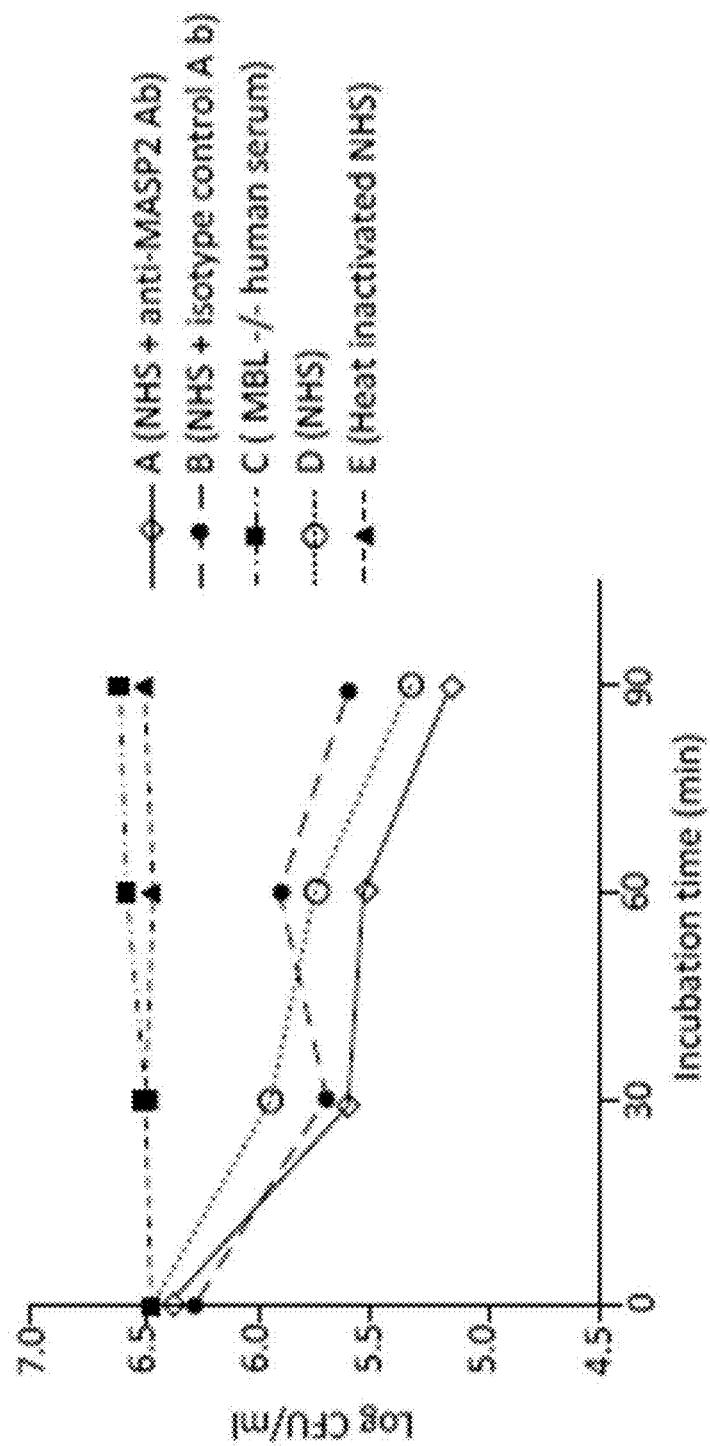
FIG. 11 graphically illustrates the log cfu/mL of viable counts of *N. meningitidis* serogroup B strain MC58 recovered at different time points in the human sera samples shown in TABLE 6 taken at various time points after incubation with *N. meningitidis* serogroup B strain MC58, as described in Example 3.

The hypothesis that human serum requires lectin pathway-mediated MASP-3-dependent activity to develop bactericidal activity is further supported by the observation that MBL-deficient human sera also fail to lyse *N. meningitidis* (FIGS. 11-12). MBL is the only human lectin-pathway recognition molecule that binds to this pathogen. Since MASP-3 does not auto-activate, the inventors hypothesize that the higher bacteriolytic activity in MASP-2-deficient sera could be explained by a favored activation of MASP-3 through MASP-1 since, in the absence of MASP-2, all lectin-pathway activation complexes that bind to the bacterial surface will be loaded with either MASP-1 or MASP-3. Since activated MASP-3 cleaves both factor D (FIG. 32) and factor B to generate their respective enzymatically active forms in vitro (FIG. 30 and Iwaki D., et al., *J. Immunol.* 187(7):3751-3758 (2011)), the most likely function of MASP-3 is to facilitate the formation of the alternative pathway C3 convertase (i.e., C3bBb).

While the data for the lectin-dependent role are compelling, multiple experiments suggest that MASP-3 and MASP-1 are not necessarily obligated to function in a complex with lectin molecules. Experiments such as that shown in FIG. 28B demonstrate the ability of MASP-3 to activate the alternative pathway (as demonstrated by C3b deposition on *S. aureus*) under conditions (i.e., the presence of EGTA) in which complexes with lectin would not be present. FIG. 28A demonstrates that deposition under these conditions is dependent upon factor B, factor D, and factor P, all critical components of the alternative pathway. Additionally, factor D activation by MASP-3 and MASP-1 (FIG. 32), and factor B activation by MASP-3 (FIG. 30) can occur in vitro in the absence of lectin. Finally, hemolysis studies of mouse erythrocytes in the presence of human serum demonstrate a clear role for both MBL and MASP-3 for cell lysis. However, the deficiency of MBL does not completely reproduce the severity of the deficiency of MASP-3, in contrast to what would be expected if all functional MASP-3 were complexed with MBL. Thus, the inventors do not wish to be constrained by the notion that all of the roles for MASP-3 (and MASP-1) demonstrated herein can be attributed solely to function associated with lectin.

The identification of the two effector arms of the lectin pathway, as well as the possible lectin-independent functions of MASP-1, MASP-3, and HTRA-1, represent novel opportunities for therapeutic interventions to effectively treat defined human pathologies caused by excessive complement activation in the presence of microbial pathogens or altered host cells or metabolic deposits. As described herein, the inventors have now discovered that in the absence of MASP-3 and in the presence of MASP-1, the alternative pathway is not activated on surface structures (see FIGS. 15-16, 28B, 34-35A,B, 38-39). Since the alternative pathway is important in driving the rate-limiting events leading to bacterial lysis as well as cell lysis (Mathieson P W, et al., *J Exp Med* 177(6):1827-3 (1993)), our results demonstrate that activated MASP-3 plays an important role in the lytic activity of complement. As shown in FIGS. 12-13, 19-21, 36-37, and 39-40, in serum of 3MC patients lacking MASP-3 but not MASP-1, the lytic terminal activation cascade of complement is defective. The data shown in FIGS. 12 and 13 demonstrate a loss of bacteriolytic activity in absence of MASP-3 and/or MASP-1/MASP-3 functional activity. Likewise, the loss of hemolytic activity in MASP-3-deficient human serum (FIGS. 19-21, 36-37 and 39-40), coupled with the ability to reconstitute hemolysis by adding recombinant MASP-3 (FIGS. 39-40), strongly supports the conclusion that activation of the alternative pathway on target surfaces (which is essential to drive complement-mediated lysis) depends on the presence of activated MASP-3. Based on the new understanding of the lectin pathway detailed above, alternative pathway activation of target surfaces is thus dependent upon LEA-1, and/or lectin-independent activation of factor B and/or factor D, which is also mediated by MASP-3, and therefore, agents that block MASP-3-dependent complement activation will prevent alternative pathway activation on target surfaces.

The disclosure of the essential role of MASP-3-dependent initiation of alternative pathway activation implies that the alternative pathway is not an independent, stand-alone pathway of complement activation as described in essentially all current medical textbooks and recent review articles on complement. The current and widely held scientific view is that the alternative pathway is activated on the surface of certain particulate targets (microbes, zymosan, and rabbit erythrocytes) through the amplification of spontaneous "tick-over" C3 activation. However, the absence of any alternative pathway activation in sera of MASP-1 and MASP-3 double-deficient mice and human 3MC patient serum on both zymosan-coated plates and two different bacteria (*N. meningitidis* and *S. aureus*), and the reduction of hemolysis of erythrocytes in MASP-3-deficient sera from human and mouse indicate that initiation of alternative pathway activation on these surfaces requires functional MASP-3. The required role for MASP-3 may be either lectin-dependent or -independent, and leads to formation of the alternative pathway C3 convertase and C5 convertase complexes, i.e. C3bBb and C3bBb(C3b)n, respectively. Thus, the inventors here disclose the existence of a previously elusive initiation routes for the alternative pathway. This initiation route is dependent upon (i) LEA-1, a newly discovered activation arm of the lectin pathway, and/or (ii) lectin-independent roles of the proteins MASP-3, MASP-1, and HTRA-1.

3. The Use of MASP-3 Inhibitory Agents for the Treatment of Alternative Pathway-Related Diseases and Conditions.

As described herein, high affinity MASP-3 inhibitory antibodies (e.g., with a binding affinity of less than 500 pM) which have been shown to completely inhibit the alternative pathway in mammalian subjects such as rodents and non-primates at molar concentrations less than the concentration of the MASP-3 target (e.g., at a molar ratio of from about 1:1 to about 2.5:1 (MASP-3 target to mAb) (see in Examples 11-21). As described in Example 11, a single dose administration of a high affinity MASP-3 inhibitory antibody, mAb 13B1, to mice led to near-complete ablation of systemic alternative pathway complement activity for at least 14 days. As further described in Example 12, in a study conducted in a well-established animal model associated with PNH it was demonstrated that mAb 13B1 significantly improved the survival of PNH-like red blood cells and protected PNH-like red blood cells significantly better than did C5 inhibition. As described in Example 13, it was further demonstrated that mAb 13B1 reduced the incidence and severity of disease in a mouse model of arthritis. The results in this example demonstrate that representative high affinity MASP-3 inhibitory mAbs 13B1, 10D12 and 4D5 are highly effective at blocking the alternative pathway in primates. Single dose administration of mAb 13B1, 10D12 or 4D5 to cynomolgus monkeys resulted in sustained ablation of systemic alternative pathway activity lasting for approximately 16 days. The extent of alternative pathway ablation in cynomolgus monkeys treated with high affinity MASP-3 inhibitory antibodies was comparable to that achieved by factor D blockade in vitro and in vivo, indicating complete blockade of factor D conversion by the MASP-3 inhibitory antibodies. Therefore, high affinity MASP-3 inhibitory mAbs have therapeutic utility in the treatment of patients suffering from diseases related to alternative pathway hyperactivity Accordingly, in one aspect the invention provides methods of inhibiting the alternative pathway in a mammalian subject in need thereof comprising administering to the subject a composition comprising an isolated monoclonal antibody or antigen-binding fragment thereof that specifically binds to the serine protease domain of human MASP-3 (amino acid residues 450 to 728 of SEQ ID NO:2) with high affinity (having a $K_D$ of less than 500 pM), in an amount effective to inhibits alternative pathway complement activation in the subject. In some embodiments, the subject is suffering from an alternative pathway-related disease or disorder, (i.e., a disease or disorder related to alternative pathway hyperactivity), such as for example, paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenic purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis, as further described below.

A. The Role of MASP-3 in Paroxysmal Nocturnal Hemoglobinuria and Therapeutic Methods Using MASP-3 Inhibitory Antibodies, Optionally in Combination with MASP-2 Inhibitory Agents Overview of PNH Paroxysmal nocturnal hemoglobinuria (PNH), sometimes also referred to as Marchiafava-Micheli syndrome, is an acquired, potentially life-threatening disease of the blood. PNH may develop on its own, referred to as "primary PNH" or in the context of other bone marrow disorders such as aplastic anemia, referred to as "secondary PNH." The majority of cases are primary PNH. PNH is characterized by complement-induced destruction of red blood cells (hemolysis), low red blood cell counts (anemia), thrombosis and bone marrow failure. Laboratory findings in PNH show changes consistent with intravascular hemolytic anemia: low hemoglobin, raised lactate dehydrogenase, raised reticulocyte counts (immature red cells released by the bone marrow to replace the destroyed cells), raised bilirubin (a breakdown product of hemoglobin), in the absence of autoreactive RBC-binding antibodies as a possible cause.

The hallmark of PNH is the chronic complement-mediated hemolysis caused by the unregulated activation of terminal complement components, including the membrane attack complex, on the surface of circulating RBCs. PNH RBCs are subject to uncontrolled complement activation and hemolysis due to the absence of the complement regulators CD55 and CD59 on their surface (Lindorfer, M. A., et al., *Blood* 115(11):2283-91 (2010), Risitano, et al., Mini-Reviews in Medicinal Chemistry, 11:528-535 (2011)). CD55 and CD59 are abundantly expressed on normal RBCs and control complement activation. CD55 acts as a negative regulator of the alternative pathway, inhibiting the assembly of the alternative pathway C3 convertase (C3bBb) complex and accelerating the decay of preformed convertase, thus blocking the formation of the membrane attack complex (MAC). CD59 inhibits the complement membrane attack complex directly by binding the C5b678 complex and preventing C9 from binding and polymerizing.

While hemolysis and anemia are the dominant clinical features of PNH, the disease is a complex hematologic disorder that further includes thrombosis and bone marrow failure as part of the clinical findings (Risitano et al, Mini Reviews in Med Chem, 11:528-535 (2011)). At the molecular level, PNH is caused by the abnormal clonal expansion of hematopoietic stem cells lacking a functional PIG A gene. PIG A is an X-linked gene encoding a glycosyl-phosphatidyl inositol transferase required for the stable surface expression of GPI-anchored class A glycoproteins, including CD55 and CD59. For reasons that are presently under investigation, hematopoietic stem cells with a dysfunctional PIG A gene that arise as the result of spontaneous somatic mutations can undergo clonal expansion to the point where their progeny constitute a significant portion of the peripheral hematopoietic cell pool. While both erythrocyte and lymphocyte progeny of the mutant stem cell clone lack CD55 and CD59, only the RBCs undergo overt lysis after they enter the circulation.

Current treatment for PNH includes blood transfusion for anemia, anticoagulation for thrombosis and the use of the monoclonal antibody eculizumab (Soliris®), which protects blood cells against immune destruction by inhibiting the complement system (Hillmen P. et al., *N. Engl. J. Med.* 350(6):552-559 (2004)). Eculizumab (Soliris®) is a humanized monoclonal antibody that targets the complement component C5, blocking its cleavage by C5 convertases, thereby preventing the production of C5a and the assembly of MAC. Treatment of PNH patients with eculizumab has resulted in a reduction of intravascular hemolysis, as measured by lactate dehydrogenase (LDH), leading to hemoglobin stabilization and transfusion independence in about half of the patients (Risitano et al, Mini-Reviews in Medicinal Chemistry, 11(6) (2011)). While nearly all patients undergoing therapy with eculizumab achieve normal or almost normal LDH levels (due to control of intravascular hemolysis), only about one third of the patients reach a hemoglobin value about 11 gr/dL, and the remaining patients on eculizumab continue to exhibit moderate to severe (i.e., transfusion-dependent) anemia, in about equal proportions (Risitano A. M. et al., *Blood* 113:4094-100 (2009)). As described in Risitano et al., Mini-Reviews in Medicinal Chemistry 11:528-535 (2011), it was demonstrated that PNH patients on eculizumab contained large amounts of C3 fragments bound to their PNH erythrocytes (while untreated patients did not). This finding lead to the recognition that in Soliris treated PNH patients, PNH RBCs that are no longer hemolyzed due to C5 blockade now can accumulate copious amounts of membrane-bound C3 fragments, which operate as opsonins, resulting in their entrapment in the reticuloendothelial cells through specific C3 receptors and subsequent extravascular hemolysis. Thus, while preventing intravascular hemolysis and the resulting sequelae, eculizumab therapy simply diverts the disposition of these RBCs from intravascular to extravascular hemolysis, resulting in substantial residual untreated anemia in many patients (Risitano A. M. et al., *Blood* 113:4094-100 (2009)). Therefore, therapeutic strategies in addition to the use of eculizumab are needed for those patients developing C3-fragment-mediated extravascular hemolysis, because they continue to require red cell transfusions. Such C3 fragment targeting approaches have demonstrated utility in experimental systems (Lindorfer et al., *Blood* 115:2283-91, 2010).

Complement-Initiating Mechanisms in PNH

The causal link between defective surface expression of the negative complement regulators CD55 and CD59 in PNH, combined with the effectiveness of eculizumab in preventing intravascular hemolysis, clearly define PNH as a condition mediated by the complement system. While this paradigm is widely accepted, the nature of the events initiating complement activation, and the complement activation pathway(s) involved remain unresolved. Because CD55 and CD59 negatively regulate the terminal amplification steps in the complement cascade common to all complement initiation pathways, deficiency of these molecules will lead to exaggerated formation and membrane integration of membrane attack complexes, regardless of whether complement activation is initiated by the lectin pathway, by the classical pathway or by spontaneous turnover of the alternative pathway. Thus, in PNH patients, any complement activation events that lead to C3b deposition on the RBC surface can trigger subsequent amplification and pathological hemolysis (intravascular and/or extravascular) and precipitate a hemolytic crisis. A clear mechanistic understanding of the molecular events triggering hemolytic crisis in PNH patients has remained elusive. Because no complement initiating event is overtly evident in PNH patients undergoing a hemolytic crisis, the prevailing view is that complement activation in PNH may occur spontaneously owing to low level "tick-over" activation of the alternative pathway, which is subsequently magnified by inappropriate control of terminal complement activation due to lack of CD55 and CD59.

However, it is important to note that in its natural history, PNH usually develops or is exacerbated after certain events, such as an infection or an injury (Risitano, *Biologics* 2:205-222 (2008)), which have been shown to trigger complement activation. This complement activation response is not dependent on prior immunity of the host towards the inciting pathogen, and hence likely does not involve the classical pathway. Rather, it appears that this complement activation response is initiated by lectin binding to foreign or "altered self" carbohydrate patterns expressed on the surface of microbial agents or damaged host tissue. Thus, the events precipitating hemolytic crisis in PNH are tightly linked to complement activation initiated via lectins. This makes it very likely that lectin activation pathways provide the initiating trigger that ultimately leads to hemolysis in PNH patients.

Using well-defined pathogens that activate complement via lectins as experimental models to dissect the activation cascades at the molecular level, we demonstrate that, depending on the inciting microbe, complement activation can be initiated by either LEA-2 or LEA-1, leading to opsonization and/or lysis. This same principle of dual responses (i.e., opsonization and/or lysis) to lectin initiation events will likely also apply to other types of infectious agents, or to complement activation by lectins following tissue injury to the host, or other lectin-driven complement activation events that may precipitate PNH. On the basis of this duality in the lectin pathway, we infer that LEA-2- and/or LEA-1-initiated complement activation in PNH patients promotes opsonization and/or lysis of RBCs with C3b and subsequent extravascular and intravascular hemolysis. Therefore, in the setting of PNH, inhibition of both LEA-1 and LEA-2 would be expected to address both intravascular and extravascular hemolysis, providing a significant advantage over the C5 inhibitor eculizumab.

It has been determined that exposure to *S. pneumoniae* preferentially triggers lectin-dependent activation of LEA-2, which leads to opsonization of this microbe with C3b. Since *S. pneumonia* is resistant to MAC-mediated lysis, its clearance from circulation occurs through opsonisation with C3b. This opsonization and subsequent removal from circulation is LEA-2-dependent, as indicated by compromised bacterial control in MASP-2-deficient mice and in mice treated with MASP-2 monoclonal antibodies (*PLOS Pathog.*, 8: e1002793. (2012)).

Figure 6:
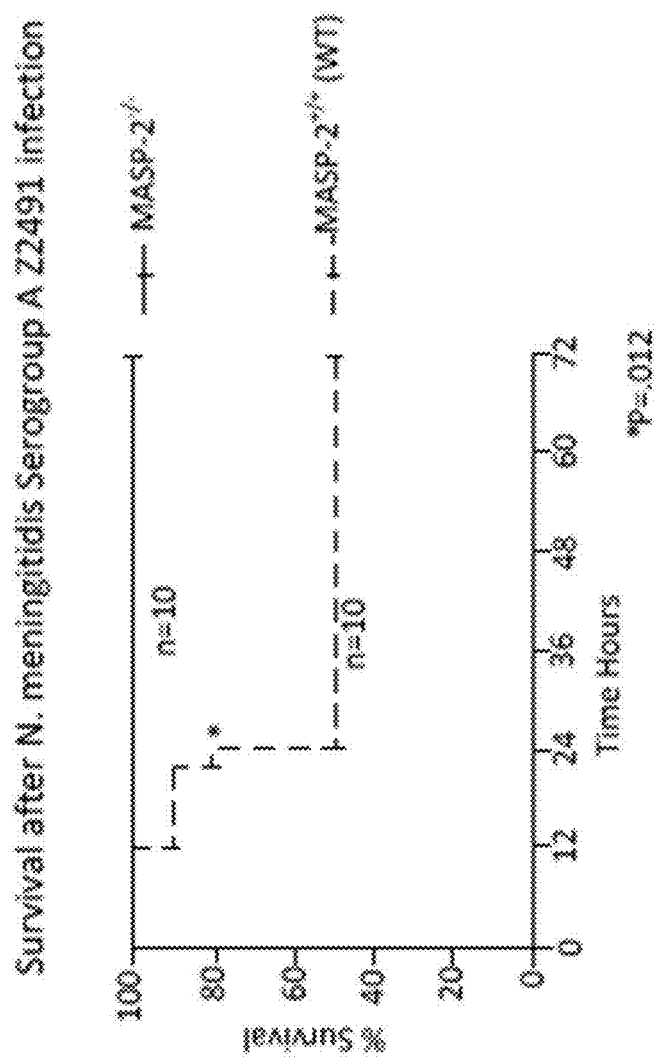
FIG. 6 is a Kaplan-Meyer plot graphically illustrating the percent survival of MASP-2 KO and WT mice after administration of an infective dose of $2.6 \times 10^7$ cfu of *N. meningitidis* serogroup A Z2491, demonstrating that MASP-2 deficient mice are protected from *N. meningitidis* induced mortality, as described in Example 1.
Figure 7:
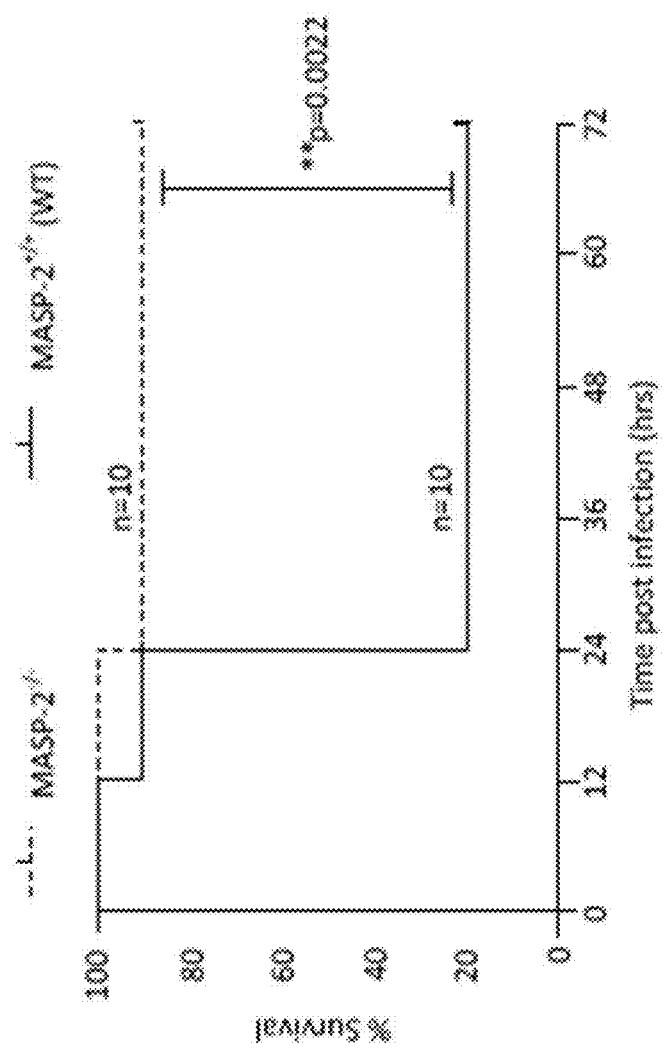
FIG. 7 is a Kaplan-Meyer plot graphically illustrating the percent survival of MASP-2 KO and WT mice after administration of an infective dose of $6 \times 10^6$ cfu of *N. meningitidis* serogroup B strain MC58, demonstrating that MASP-2 deficient mice are protected from *N. meningitidis* induced mortality, as described in Example 1.
Figure 8:
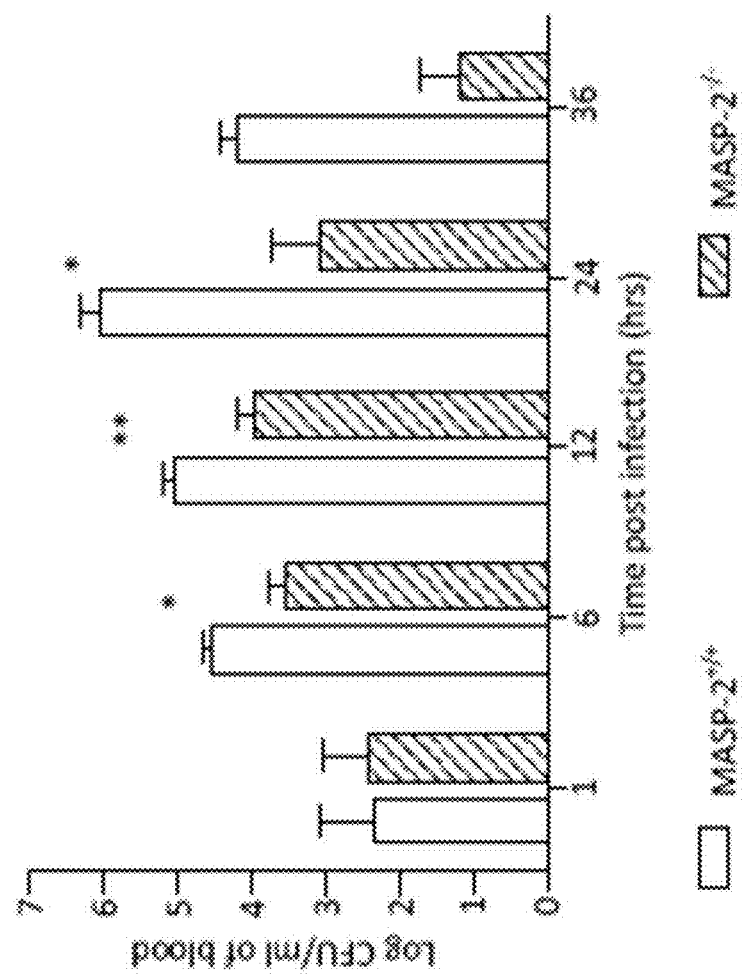
FIG. 8 graphically illustrates the log cfu/mL of *N. meningitidis* serogroup B strain MC58 per mL of blood recovered from MASP-2 KO and WT mice at different time points after i.p. infection with $6 \times 10^6$ cfu of *N. meningitidis* serogroup B strain MC58 (n=3 at different time points for both groups of mice), demonstrating that although the MASP-2 KO mice were infected with the same dose of *N. meningitidis* serogroup B strain MC58 as the WT mice, the MASP-2 KO mice have enhanced clearance of bacteremia as compared to WT, as described in Example 1.

In exploring the role of LEA-2 in the innate host responses to microbial agents, we tested additional pathogens. A dramatically different outcome was observed when *Neisseria meningitidis* was studied as a model organism. *N. meningitidis* also activates complement via lectins, and complement activation is required for containment of *N. meningitidis* infections in the naïve host. However, LEA-2 plays no host protective functional role in this response: As shown in FIGS. 6 and 7, blockade of LEA-2 through genetic ablation of MASP-2 does not reduce survival following infection with *N. meningitidis*. To the contrary, LEA-2 blockade by MASP-2 ablation significantly improved survival (FIGS. 6 and 7) as well as illness scores (FIG. 9) in these studies. LEA-2 blockade by administration of MASP-2 antibody yielded the same result (FIG. 10), eliminating secondary or compensatory effects in the knockout-mouse strain as a possible cause. These favorable outcomes in LEA-2-ablated animals were associated with a more rapid elimination of *N. meningitidis* from the blood (FIG. 8). Also, as described herein, incubation of *N. meningitidis* with normal human serum killed *N. meningitidis* (FIG. 11). Addition of a functional monoclonal antibody specific for human MASP-2 that blocks LEA-2, but not administration of an isotype control monoclonal antibody, may enhance this killing response. Yet, this process depends on lectins and at least a partially functional complement system, as MBL-deficient human serum or heat-inactivated human serum was unable to kill *N. meningitidis* (FIG. 11). Collectively, these novel findings suggest that *N. meningitidis* infections in the presence of a functional complement system are controlled by a lectin-dependent but LEA-2-independent pathway of complement activation.

The hypothesis that LEA-1 may be the complement pathway responsible for lectin-dependent killing of *N. meningitidis* was tested using a serum specimen from a 3MC patient. This patient was homozygous for a nonsense mutation in exon 12 of the MASP-1/3 gene. As a result, this patient lacked a functional MASP-3 protein, but was otherwise complement sufficient (exon 12 is specific for the MASP-3 transcript; the mutation has no effect on MASP-1 function or expression levels) (see *Nat Genet* 43(3):197-203 (2011)). Normal human serum efficiently kills *N. meningitidis*, but heat-inactivated serum deficient in MBL (one of the recognition molecules for the Lectin pathway) and MASP-3-deficient serum were unable to kill *N. meningitidis* (FIG. 12). Thus, LEA-1 appears to mediate *N. meningitidis* killing. This finding was confirmed using serum samples from knockout mouse strains. While complement containing normal mouse serum readily killed *N. meningitidis*, MBL-deficient or MASP-1/3-deficient mouse serum was as ineffective as heat-inactivated serum that lacks functional complement (FIG. 13). Conversely, MASP-2-deficient serum exhibited efficient killing of *N. meningitidis*.

These findings provide evidence for a hitherto unknown duality in the lectin pathway by revealing the existence of separate LEA-2 and LEA-1 pathways of lectin-dependent complement activation. In the examples detailed above, LEA-2 and LEA-1 are non-redundant and mediate distinct, functional outcomes. The data suggest that certain types of lectin pathway activators (including, but not limited to *S. pneumonia*) preferentially initiate complement activation via LEA-2 leading to opsonization, while others (exemplified by *N. meningitidis*) preferentially initiate complement activation via LEA-1 and promote cytolytic processes. The data do not, however, necessarily limit LEA-2 to opsonization and LEA-1 to cytolytic processes, as both pathways in other settings can mediate opsonization and/or lysis.

In the context of lectin-dependent complement activation by *N. meningitidis*, LEA-2 and LEA-1 arms appear to compete with each other, as blockade of LEA-2 enhanced LEA-1-dependent lytic destruction of the organism in vitro (FIG. 13). As detailed above, this finding can be explained by the increased likelihood of lectin MASP-1 complexes residing in close proximity to lectin MASP-3 complexes in the absence of MASP-2, which will enhance LEA-1 activation and thus promote more effective lysis of *N. meningitides*. Because lysis of *N. meningitidis* is the main protective mechanism in the naïve host, blockade of LEA-2 in vivo increases *N. meningitidis* clearance and leads to enhanced killing.

While the examples discussed above illustrate opposing effects of LEA-2 and LEA-1 with respect to outcomes following infection with *N. meningitidis*, there may be other settings where both LEA-2 and LEA-1 may synergize to produce a certain outcome. As detailed below, in other situations of pathological complement activation via lectins such as those present in PNH, LEA-2- and LEA-1-driven complement activation may cooperate in a synergistic manner to contribute to the overall pathology of PNH. In addition, as described herein, MASP-3 also contributes to the lectin-independent conversion of factor B and factor D, which can occur in the absence of Ca++, commonly leading to the conversion of C3bB to C3bBb and of pro-factor D to factor D, which may further contribute to the pathology of PNH.

Biology and Expected Functional Activity in PNH

This section describes the inhibitory effects of LEA-2 and LEA-1 blockade on hemolysis in an in vitro model of PNH. The findings support the utility of LEA-2-blocking agents (including, but not limited to, antibodies that bind to and block the function of MASP-2) and LEA-1-blocking agents (including, but not limited to, antibodies that bind to and block the function of MASP-1-mediated activation of MASP-3, MASP-3, or both) to treat subjects suffering from one or more aspects of PNH, and also the use of inhibitors of LEA-2 and/or LEA-1, and/or MASP-3-dependent, lectin-independent complement activation (including MASP-2 inhibitors, MASP-3 inhibitors, and dual- or bispecific MASP-2/MASP-3 or MASP-1/MASP-2 inhibitors, and pan-specific MASP-1/MASP-2/MASP-3 inhibitors) to ameliorate the effects of C3-fragment-mediated extravascular hemolysis in PNH patients undergoing therapy with a C5-inhibitor such as eculizumab.

MASP-2 Inhibitors to Block Opsonization and Extravascular Hemolysis of PNH RBCs Through the Reticuloendothelial System As detailed above, PNH patients become anemic owing to two distinct mechanisms of RBC clearance from circulation: intravascular hemolysis via activation of the membrane attack complex (MAC), and extravascular hemolysis following opsonization with C3b and subsequent clearance following complement receptor binding and uptake by the reticuloendothelial system. The intravascular hemolysis is largely prevented when a patient is treated with eculizumab. Because eculizumab blocks the terminal lytic effector mechanism that occurs downstream of both the complement-initiating activation event as well as the ensuing opsonization, eculizumab does not block extravascular hemolysis (Risitano A. M. et al., Blood 113:4094-100 (2009)). Instead, RBCs that would have undergone hemolysis in untreated PNH patients now can accumulate activated C3b proteins on their surface, which augments uptake by the reticuloendothelial system and enhances their extravascular hemolysis. Thus, eculizumab treatment effectively diverts RBC disposition from intravascular hemolysis to potential extravascular hemolysis. As a result, some eculizumab-treated PNH patients remain anemic. It follows that agents that block complement activation upstream and prevent the opsonization of PNH RBCs may be particularly suitable to block the extravascular hemolysis occasionally seen with eculizumab.

The microbial data presented here suggest that LEA-2 is often the dominant route for lectin-dependent opsonization. Furthermore, when lectin-dependent opsonization (measured as C3b deposition) was assessed on three prototypic lectin activation surfaces (mannan, FIG. 17A; zymosan, FIG. 17B, and S. pneumonia; FIG. 17C), LEA-2 appears to be the dominant route for lectin-dependent opsonization under physiologic conditions (i.e., in the presence of Ca++ wherein all complement pathways are operational). Under these experimental conditions, MASP-2-deficient serum (which lacks LEA-2) is substantially less effective in opsonizing the test surfaces than WT serum. MASP-1/3-deficient serum (which lacks LEA-1) is also compromised, though this effect is much less pronounced as compared to serum lacking LEA-2. The relative magnitude of the contributions of LEA-2 and LEA-1 to lectin-driven opsonization is further illustrated in FIGS. 18A-18C. While the alternative pathway of complement has been reported to support opsonization of lectin activating surfaces in the absence of lectin pathway or classical pathway (Selander et al., J Clin Invest 116(5):1425-1434 (2006)), the alternative pathway in isolation (measured under $Ca^{++}$-free assay conditions) appears substantially less effective than the LEA-2- and LEA-1-initiated processes described herein. By extrapolation, these data suggest that opsonization of PNH RBCs may also be preferentially initiated by LEA-2 and, to a lesser extent, by LEA-1 (possibly amplified by the alternative pathway amplification loop), rather than the result of lectin-independent alternative pathway activation. Therefore, LEA-2 inhibitors may be expected to be most effective at limiting opsonization and preventing extravascular hemolysis in PNH. However, recognition of the fact that lectins other than MBL, such as ficolins, bind to non-carbohydrate structures such as acetylated proteins, and that MASP-3 preferentially associates with H-ficolin (Skjoedt et al., Immunobiol. 215:921-931, 2010), leaves open the possibility of a significant role for LEA-1 in PNH-associated RBC opsonization as well. Therefore, LEA-1 inhibitors are expected to have additional anti-opsonization effects, and the combination of LEA-1 and LEA-2 inhibitors is expected to be optimal and mediate the most robust treatment benefit in limiting opsonization and extravascular hemolysis in PNH patients. Thus, LEA-2 and LEA-1 act additively or synergistically to promote opsonization, and a crossreactive or bispecific LEA-1/LEA-2 inhibitor is expected to be most effective at blocking opsonization and extravascular hemolysis in PNH.

Role of MASP-3 Inhibitors in PNH

Using an in vitro model of PNH, we demonstrated that complement activation and the resulting hemolysis in PNH are indeed initiated by LEA-2 and/or LEA-1 activation, and that it is not an independent function of the alternative pathway. These studies used mannan-sensitized RBCs of various mouse stains, including RBCs from Crry-deficient mice (an important negative regulator of the terminal complement pathway in mice) as well as RBCs from CD55/CD59-deficient mice, which lack the same complement regulators that are absent in PNH patients). When mannan-sensitized Crry-deficient RBCs were exposed to complement-sufficient human serum, the RBCs effectively hemolysed at a serum concentration of 3% (FIGS. 19 and 20) while complement-deficient serum (HI: heat-inactivated) was not hemolytic. Remarkably, complement-sufficient serum where LEA-2 was blocked by addition of MASP-2 antibody had reduced hemolytic activity, and 6% serum was needed for effective hemolysis. Similar observations were made when CD55/CD59-deficient RBCs were tested (FIG. 22). Complement-sufficient human serum supplemented with MASP-2 monoclonal antibody (i.e., serum where LEA-2 is suppressed) was about two-fold less effective than untreated serum in supporting hemolysis. Furthermore, higher concentrations of LEA-2-blocked serum (i.e., treated with antiMASP-2 monoclonal antibody) were needed to promote effective hemolysis of untreated WT RBCs compared to untreated serum (FIG. 21).

Figure 20:
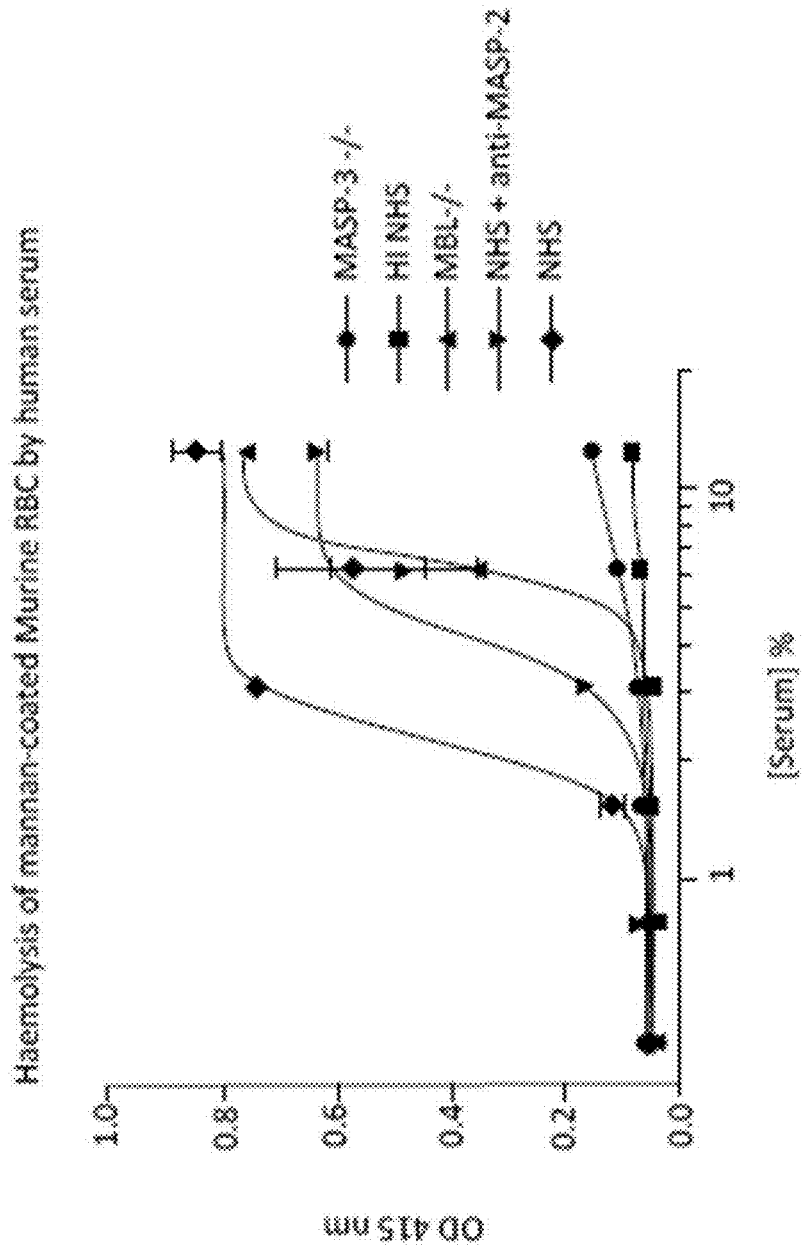
FIG. 20 graphically illustrates the level of hemolysis (as measured by hemoglobin release of lysed mouse erythrocytes (Crry/C3-/-) into the supernatant measured by photometry) of mannan-coated murine erythrocytes by human serum under physiological conditions (i.e., in the presence of $Ca^{++}$) over a range of serum concentration in serum from MASP-3-/-, heat inactivated (HI) NHS, MBL-/-, NHS+MASP-2 monoclonal antibody and NHS control, as described in Example 5.
Figure 21:
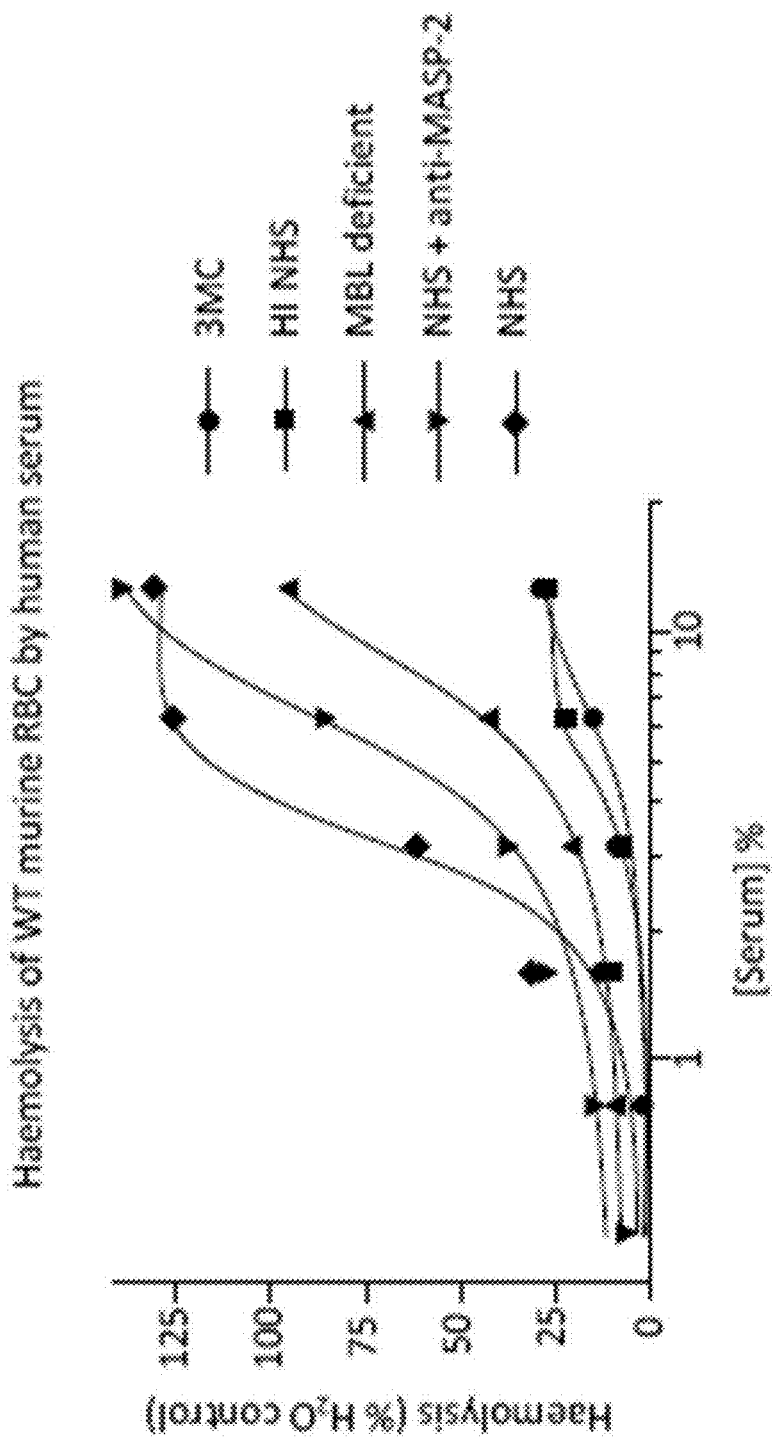
FIG. 21 graphically illustrates the level of hemolysis (as measured by hemoglobin release of lysed WT mouse erythrocytes into the supernatant measured by photometry) of non-coated murine erythrocytes by human serum under physiological conditions (i.e., in the presence of $Ca^{++}$) over a range of serum concentrations in serum from 3MC (MASP-3-/-), heat inactivated (HI) NHS, MBL-/-, NHS+MASP-2 monoclonal antibody and NHS control, as described in Example 5.
Figure 22:
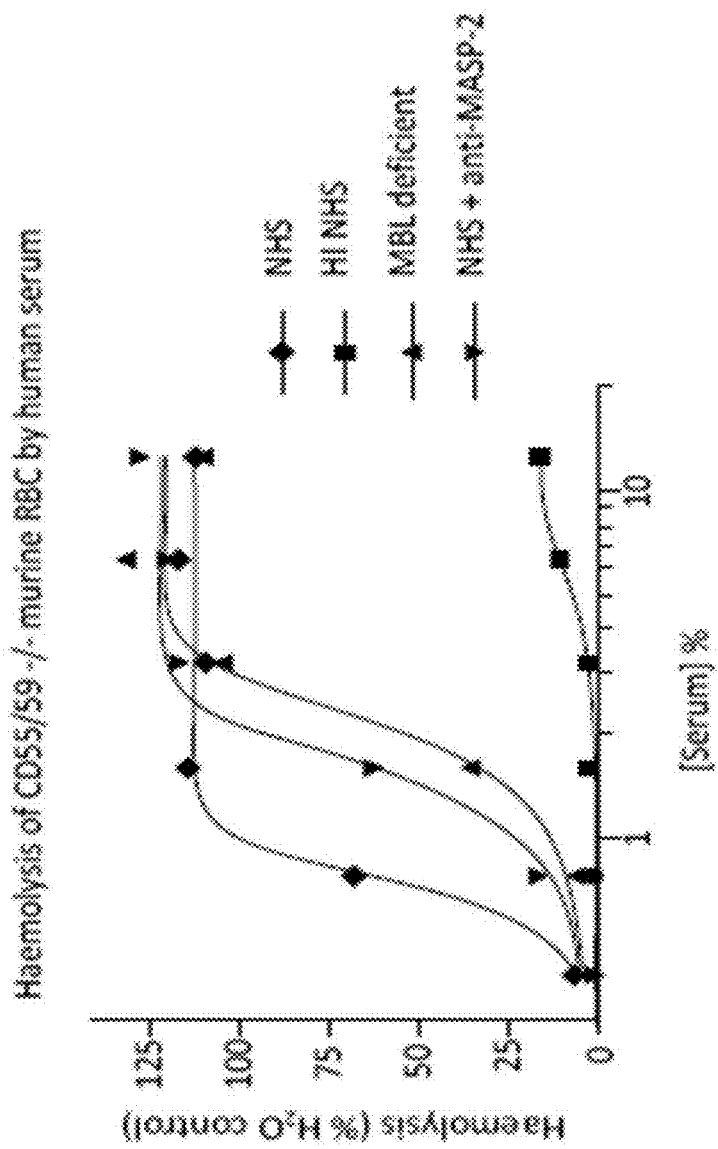
FIG. 22 graphically illustrates hemolysis (as measured by hemoglobin release of lysed mouse erythrocytes (CD55/59-/-) into the supernatant measured by photometry) of non-coated murine erythrocytes by human serum under physiological conditions (i.e., in the presence of $Ca^{++}$) over a range of serum concentrations in serum from heat inactivated (HI) NHS, MBL-/-, NHS+MASP-2 monoclonal antibody and NHS control, as described in Example 5.

Even more surprisingly, serum from a 3MC patient homozygous for a dysfunctional MASP-3 protein (and hence lacking LEA-1) was completely unable to hemolyze mannan-sensitized Crry-deficient RBCs (FIG. 20 and FIG. 21). A similar outcome was observed when unsensitized normal RBCs were used: As shown in FIG. 21, LEA-1-defective serum isolated from a 3MC patient was completely ineffective at mediating hemolysis. Collectively, these data indicate that whereas LEA-2 contributes significantly to the intravascular hemolysis response, LEA-1 is the predominant complement-initiating pathway leading to hemolysis. Thus, while LEA-2 blocking agents are expected to significantly reduce intravascular hemolysis of RBCs in PNH patients, LEA-1 blocking agents are expected to have a more profound effect and largely eliminate complement-driven hemolysis.

Figure 15:
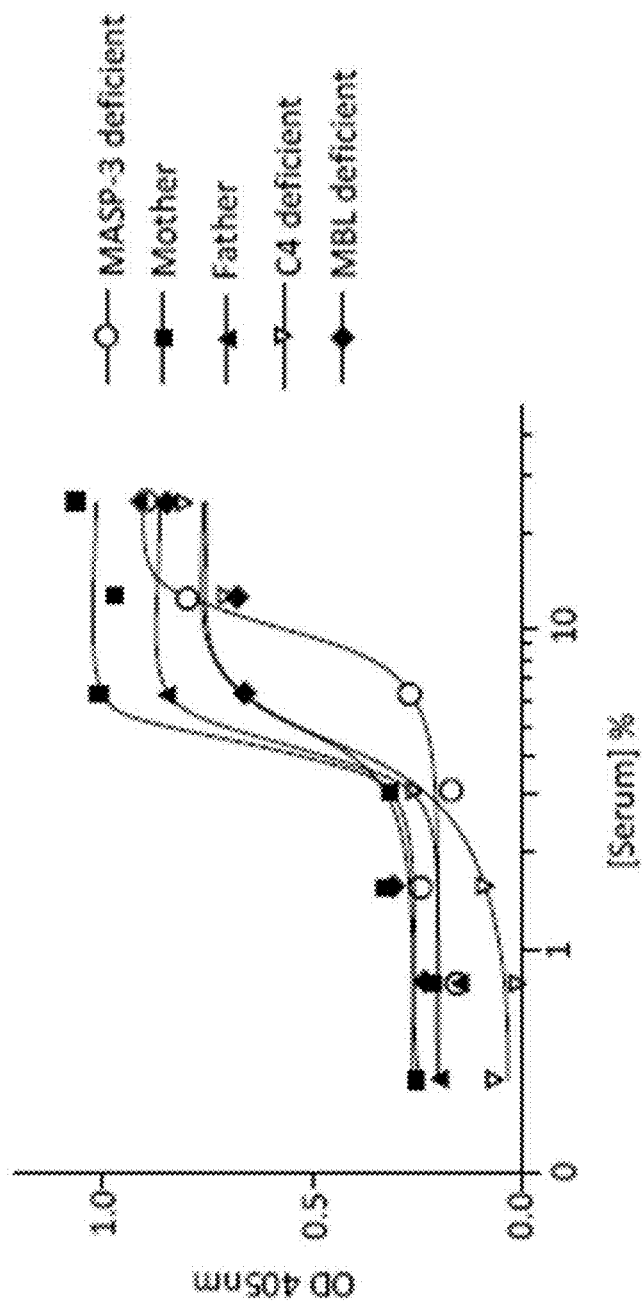
FIG. 15 graphically illustrates the level of alternative pathway-driven (AP-driven) C3b deposition on zymosan-coated microtiter plates under "traditional" alternative pathway-specific (AP-specific) conditions (i.e. BBS/EGTA/$Mg^{++}$ without $Ca^{++}$) as a function of serum concentration in serum samples obtained from MASP-3-deficient, C4-deficient and MBL-deficient human subjects, as described in Example 4.

It should be noted that the serum of the LEA-1-deficient 3MC patient used in this study possessed a diminished but functional alternative pathway when tested under conventional alternative pathway assay conditions (FIG. 15). This finding suggests that LEA-1 makes a greater contribution to hemolysis than alternative pathway activity as conventionally defined in this experimental setting of PNH. By inference, it is implied that LEA-1-blocking agents will be at least as effective as agents blocking other aspects of the alternative pathway in preventing or treating intravascular hemolysis in PNH patients.

Role of MASP-2 Inhibitors in PNH

The data presented herein suggest the following pathogenic mechanisms for anemia in PNH: intravascular hemolysis due to unregulated activation of terminal complement components and lysis of RBC by formation of MAC, which is initiated predominantly, though not exclusively, by LEA-1, and extravascular hemolysis caused by opsonization of RBCs by C3b, which appears to be initiated predominately by LEA-2. While a discernible role for LEA-2 in initiating complement activation and promoting MAC formation and hemolysis is apparent, this process appears substantially less effective than LEA-1-initiated complement activation leading to hemolysis. Thus, LEA-2-blocking agents are expected to significantly reduce intravascular hemolysis in PNH patients, though this therapeutic activity is expected to be only partial. By comparison, a more substantial reduction in intravascular hemolysis in PNH patients is expected for LEA-1-blocking agents.

Extravascular hemolysis, a less dramatic, yet equally important mechanism of RBC destruction that leads to anemia in PNH, is primarily the result of opsonization by C3b, which appears to be predominantly mediated by LEA-2. Thus, LEA-2-blocking agents may be expected to preferentially block RBC opsonization and the ensuing extravascular hemolysis in PNH. This unique therapeutic activity of LEA-2-blocking agents is expected to provide a significant treatment benefit to all PNH patients as no treatment currently exists for those PNH patients who experience this pathogenic process.

LEA-2 Inhibitors as Adjunct Treatment to LEA-1 Inhibitors or Terminal Complement Blocking Agents The data presented herein detail two pathogenic mechanisms for RBC clearance and anemia in PNH which can be targeted, separately or in combination, by distinct classes of therapeutic agents: the intravascular hemolysis initiated predominantly, though not exclusively, by LEA-1 and thus expected to be effectively prevented by a LEA-1-blocking agent, and extravascular hemolysis due to C3b opsonization driven predominantly by LEA-2, and thus effectively prevented by a LEA-2-blocking agent.

It is well documented that both intravascular and extravascular mechanisms of hemolysis lead to anemia in PNH patients (Risitano et al., *Blood* 113:4094-4100 (2009)).

Therefore, it is expected that a LEA-1-blocking agent that prevents intravascular hemolysis in combination with a LEA-2 blocking agent that primarily prevents extravascular hemolysis will be more effective than either agent alone in preventing the anemia that develops in PNH patients. In fact, the combination of LEA-1- and LEA-2-blocking agents is expected to prevent all relevant mechanisms of complement initiation in PNH and thus block all symptoms of anemia in PNH.

It is also known that C5-blocking agents (such as eculizumab) effectively block intravascular hemolysis but do not interfere with opsonization. This leaves some anti-C5-treated PNH patients with substantial residual anemia due to extravascular hemolysis mediated by LEA-2 that remains untreated. Therefore, it is expected that a C5-blocking agent (such as eculizumab) that prevents intravascular hemolysis in combination with a LEA-2 blocking agent that reduces extravascular hemolysis will be more effective than either agent alone in preventing the anemia that develops in PNH patients.

Other agents that block the terminal amplification loop of the complement system leading to C5 activation and MAC deposition (including, but not limited to agents that block properdin, factor B or factor D or enhance the inhibitory activity of factor I, factor H or other complement inhibitory factors) are also expected to inhibit intravascular hemolysis. However, these agents are not expected to interfere with LEA-2-mediated opsonization in PNH patients. This leaves some PNH patients treated with such agents with substantial residual anemia due to extravascular hemolysis mediated by LEA-2 that remains untreated. Therefore, it is expected that treatment with such agents that prevent intravascular hemolysis in combination with a LEA-2-blocking agent that minimizes extravascular hemolysis will be more effective than either agent alone in preventing the anemia that develops in PNH patients. In fact, the combination of such agents and a LEA-2 blocking agent is expected to prevent all relevant mechanisms of RBC destruction in PNH and thus block all symptoms of anemia in PNH.

Use of LEA-1 and LEA-2 Multiple, Bispecific or Pan-Specific Antibodies to Treat PNH As detailed above, the use of a combination of pharmacologic agents that individually block LEA-1 and LEA-2, and thus in combination block all complement activation events that mediate the intravascular as well as the extravascular hemolysis, is expected to provide the best clinical outcome for PNH patients. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity will effectively block intravascular as well as the extravascular hemolysis and prevent anemia in PNH. Such an entity may comprise or consist of a bispecific antibody where one antigen-combining site specifically recognizes MASP-1 and blocks LEA-1 and diminishes LEA-2 and the second antigen-combining site specifically recognizes MASP-2 and further blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 and diminishes LEA-2 while the second antigen-combining site specifically recognized MASP-2 and further blocks LEA-2. Based on the similarities in the overall protein sequence and architecture, it can also be envisioned that a conventional antibody with two identical binding sites can be developed that specifically binds to MASP-1 and to MASP-2 and to MASP-3 in a functional manner, thus achieving functional blockade of LEA-1 and LEA-2. Such an antibody with pan-MASP inhibitory activity is expected to block both the intravascular as well as the extravascular hemolysis and thus effectively treat the anemia in PNH patients.

As described in Examples 11-21 herein, high affinity MASP-3 inhibitory antibodies have been generated which have therapeutic utility for inhibition of the alternative pathway in AP-related diseases or conditions, such as PNH.

Accordingly, in one embodiment, the present invention provides a method for treating a subject suffering from, or at risk for developing PNH comprising an effective amount of a high affinity monoclonal antibody or antigen binding fragment thereof as disclosed herein that binds to human MASP-3 and inhibits alternative pathway complement activation to treat or reduce the risk of PNH in the subject.

In one embodiment, the present invention provides a method for treating a subject suffering from, or at risk for developing paroxysmal nocturnal hemoglobinuria (PNH), comprising administering to the subject a pharmaceutical composition comprising an effective amount of a monoclonal antibody or antigen binding fragment thereof as disclosed herein that binds to human MASP-3 and inhibits alternative pathway complement activation to treat or reduce the risk of PNH in the subject, such as, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259, (ii) VLCDR2 comprising SEQ ID NO:144 and (iii) VLCDR3 comprising SEQ ID NO:161. In some embodiments, the pharmaceutical composition increases the survival of red blood cells in the subject suffering from PNH. In some embodiments, wherein the subject suffering from or at risk for developing PNH exhibits one or more symptoms selected from the group consisting of (i) below normal levels of hemoglobin, (ii) below normal levels of platelets; (iii) above normal levels of reticulocytes, and (iv) above normal levels of bilirubin. In some embodiments, the pharmaceutical composition is administered systemically (e.g., subcutaneously, intra-muscularly, intravenously, intra-arterially or as an inhalant) to a subject suffering from, or at risk for developing PNH. In some embodiments, the subject suffering from or at risk for PNH has previously undergone, or is currently undergoing treatment with a terminal complement inhibitor that inhibits cleavage of complement protein C5. In some embodiments, the method further comprises administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

B. The Role of MASP-3 in Age-Related Macular Degeneration and Therapeutic Methods Using MASP-3 Inhibitory Antibodies, Optionally in Combination with and MASP-2 Inhibitory Agents Age related macular degeneration (AMD) is the leading cause of visual impairment and blindness in the elderly and accounts for up to 50% of cases of blindness in developed countries. The prevalence of AMD is around 3% in adults and increases with age such that almost two-thirds of the population over 80 years of age will have some signs. It is estimated that over 1.75 million individuals in the United States have advanced AMD and the prevalence is increasing as the population ages and is expected to reach almost 3 million by 2020 (Friedman, D. S., et al., Arch. Ophthalmol. 122:564-572, 2004). AMD is an abnormality of the retinal pigment epithelium (RPE) that results in degeneration of the photoreceptors of the overlying central retina, or macula, and loss of central vision. Early and intermediate forms of AMD are characterized by progressive deposits of drusen, a yellowish material containing lipid, protein, lipoprotein, and cellular debris, in the subretinal space adjacent to the RPE, along with pigmentary irregularities in the retina. Advanced AMD consists of two clinical subtypes: non-neovascular geographic atrophic ('dry') AMD and neovascular exudative ('wet') AMD. Although dry AMD accounts for 80-90% of advanced AMD, the majority of sudden and severe vision loss occurs in patients with wet AMD. It is not known whether the two types of AMD represent differing phenotypes arising from similar pathologies or two distinct conditions. Currently no therapy has been approved by the United States Food and Drug Administration (FDA) to treat dry AMD. FDA-approved treatment options for wet AMD include intravitreal injections of anti-angiogenic drugs (ranibizumab, pegaptanib sodium, aflibercept), laser therapy, photodynamic laser therapy, and implantable telescope.

The etiology and pathophysiology of AMD are complex and incompletely understood. Several lines of evidence support the role of dysregulation of the complement system in the pathogenesis of AMD. Gene association studies have identified multiple genetic loci associated with AMD, including genes coding for a range of complement proteins, factors, and regulators. The strongest association is with polymorphisms in the complement factor H (CFH) gene, with the Y402H variant homozygotes having approximately 6-fold and heterozygotes approximately 2.5-fold increased risk for developing AMD compared to the non-risk genotype (Khandhadia, S., et al., Immunobiol. 217:127-146, 2012). Mutations in other complement pathway encoding genes have also been associated with increased or decreased risk of AMD, including complement factor B (CFB), C2, C3, factor I, and CFH-related proteins 1 and 3 (Khandhadia et al.). Immunohistochemical and proteomic studies in donor eyes from AMD patients showed that proteins of the complement cascade to be increased and localized in drusen (Issa, P. C., et al., Graefes. Arch. Clin. Exp. Ophthalmol. 249:163-174, 2011). Furthermore, AMD patients have increased systemic complement activation as measured in peripheral blood (Issa et al., 2011, supra).

The alternative pathway of complement appears to be more relevant than the classical pathway in the pathogenesis of AMD. C1q, the essential recognition component for activation of the classical pathway, was not detected in drusen by immunohistochemical analyses (Mullins et al., FASEB J. 14:835 846, 2000; Johnson et al., Exp. Eye Res. 70:441 449, 2000). Genetic association studies have implicated CFH and CFB genes. These proteins are involved in the alternative pathway amplification loop, with CFH being a fluid phase inhibitor and CFB being an activating protease component of the alternative pathway. The Y402H variant of CFH affects interaction with ligand binding, including binding with C-reactive protein, heparin, M protein, and glycosaminoglycans. This altered binding to ligands may reduce binding to cell surfaces, which in turn may lead to reduced factor I mediated degradation of C3b activation fragment and impaired regulation of the alternative C3 convertase, resulting in over activation of the alternative pathway (Khandhadia et al., 2012, supra). Variations in the CFB gene are associated with a protective effect for the development of AMD. A functional variant fB32Q had 4 times less binding affinity to C3b than the risk variant fB32R, resulting in a reduction in C3 convertase formation (Montes, T. et al., *Proc. Natl. Acad. Sci. U.S.A.* 106:4366-4371, 2009).

Complement-Initiating Mechanisms in AMD

The human genetic linkage studies discussed above suggest an important role for the complement system in AMD pathogenesis. Furthermore, complement activation products are abundantly present in drusen (Issa, P. C., et al., *Graefes. Arch. Clin. Exp. Ophthalmol.* 249:163-174, 2011), a hallmark pathologic lesion in both wet and dry AMD. However, the nature of the events initiating complement activation, and the complement activation pathway(s) involved remain incompletely understood.

It is important to note that drusen deposits are composed of cellular debris and oxidative waste products originating from the retina that accumulate beneath the RPE as the eye ages. In addition, oxidative stress appears to play an important role (Cai et al; *Front Biosci.,* 17:1976-95, 2012), and has been shown to cause complement activation in RPE (*J Biol Chem.*, 284(25):16939-47, 2009). It is widely appreciated that both oxidative stress and cellular or tissue injury activate the complement system lectins. For example, Collard et al. have demonstrated that endothelial cells exposed to oxidative stress trigger abundant complement deposition mediated by lectins (Collard C D et al., *Mol Immunol.,* 36(13-14):941-8, 1999; Collard C. D. et al., *Am J Pathol.,* 156(5):1549-56, 2000), and that blockade of lectin binding and lectin-dependent complement activation improves outcomes in experimental models of oxidative stress injury (Collard C. D. et al., *Am J Pathol.,* 156(5):1549-56, 2000). Thus, it appears likely that oxidative waste products present in drusen also activate complement via the lectins. By inference, lectin-dependent complement activation may play a pivotal role in AMD pathogenesis.

The role of the complement system has been evaluated in mouse models of AMD. In the light-damage mouse model, an experimental model for oxidative stress-mediated photoreceptor degeneration, knockout mice with an elimination of the classical pathway (C1qα−/− on a C57BL/6 background) had the same sensitivity to light damage compared to wild-type littermates, whereas elimination of complement factor D of the alternative pathway (CFD−/−) resulted in protection from light damage (Rohrer, B. et al., *Invest. Ophthalmol. Vis. Sci.* 48:5282-5289, 2007). In a mouse model of choroidal neovascularization (CNV) induced by laser photocoagulation of the Bruch membrane, knockout mice without complement Factor B (CFB−/−) were protected against CNV compared with wild-type mice (Rohrer, B. et al., *Invest. Ophthalmol. Vis. Sci.* 50:3056-3064, 2009). In the same model, intravenous administration of a recombinant form of complement Factor H targeted to sites of complement activation (CR2-fH) reduced the extent of CNV. This protective effect was observed whether CR2-fH was administered at the time of laser injury or therapeutically (after laser injury). A human therapeutic version of CR2-fH (TT30) was also efficacious in the murine CNV model (Rohrer, B. et al. *J. Ocul. Pharmacol. Ther.,* 28:402-409, 2012). Because fB is activated by LEA-1, and because MASP-1 and MASP-3 contribute to the maturation of factor D, these findings imply that LEA-1 inhibitors may have therapeutic benefit in AMD patients. In addition, recent results reported from a Phase 2 study have shown that monthly intravitreal injection with Lampalizumab (previously referred to as FCFD4514S and anti-factor D, which is an antigen-binding fragment of a humanized monoclonal antibody directed against Factor D) reduced geographic atrophy area progression in patients with geographic atrophy secondary to AMD (Yaspan B. L. et al., *Sci Transl. Med.* 9, Issue 395, Jun. 21, 2017).

Initial experimental studies in a rodent model of AMD using MBL-deficient mice did not support a critical role for the lectin pathway in pathogenic complement activation (Rohrer et al., *Mol Immunol.* 48:e1-8, 2011). However, MBL is only one of several lectins, and lectins other than MBL may trigger complement activation in AMD. Indeed, our previous work has shown that MASP-2, the rate-limiting serine protease that is critically required for lectin pathway function, plays a critical role in AMD. As described in U.S. Pat. No. 7,919,094 (assigned to Omeros Corporation), incorporated herein by reference, MASP-2-deficient mice and mice treated with MASP-2 antibody were protected in a mouse model of laser-induced CNV, a validated preclinical model of wet AMD (Ryan et al., *Tr Am Opth Soc LXXVII:* 707-745, 1979). Thus, inhibitors of LEA-2 are expected to effectively prevent CNV and improve outcomes in AMD patients.

Thus, in view of the above, LEA-1 and LEA-2 inhibitors are expected to have independent therapeutic benefit in AMD. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bispecific antibody composed of MASP-1/3 and a MASP-2-specific binding site, or a dual specificity antibody where each binding site can bind to and block MASP-1/3 or MASP-2.

In accordance with the foregoing, an aspect of the invention thus provides a method for inhibiting LEA-1 dependent complement activation to treat age-related macular degeneration (wet and dry forms) by administering a composition comprising a therapeutically effective amount of a MASP 1 inhibitory agent, a MASP 3 inhibitory agent, or a combination of a MASP 1/3 inhibitory agent, in a pharmaceutical carrier to a subject suffering from such a condition. The MASP 1, MASP 3, or MASP 1/3 inhibitory composition may be administered locally to the eye, such as by irrigation, intravitreal administration, or application of the composition in the form of a gel, salve or drops. Alternately, the MASP 1, MASP 3, or MASP 1/3 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In one embodiment, the method according to this aspect of the invention further comprises inhibiting LEA-2-dependent complement activation in a subject suffering from age-related macular degeneration, comprising administering a therapeutically effective amount of a MASP-2 inhibitory agent and a MASP-1, MASP-3 or MASP1/3 inhibitory agent to the subject in need thereof. As detailed above, the use of a combination of pharmacologic agents that individually block LEA-1 and LEA-2 is expected to provide an improved therapeutic outcome in AMD patients as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP 2 inhibitory composition may be administered locally to the eye, such as by irrigation, intravitreal injection or topical application of the composition in the form of a gel, salve or drops. Alternately, the MASP 2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and optional MASP 2 inhibitory compositions of the present invention may be carried out by a single administration of the composition (e.g., a single composition comprising MASP-2 and MASP-3 inhibitory agents, or bispecific or dual inhibitory agents, or co-administration of separate compositions), or a limited sequence of administrations, for treatment of AMD. Alternatively, the composition may be administered at periodic intervals such as daily, biweekly, weekly, every other week, monthly or bimonthly over an extended period of time for treatment of AMD.

As described in Examples 11-21 herein, high affinity MASP-3 inhibitory antibodies have been generated which have therapeutic utility for inhibition of the alternative pathway in AP-related diseases or conditions, such as AMD.

Accordingly, in one embodiment, the present invention provides a method for treating a subject suffering from, or at risk for developing AMD comprising an effective amount of a high affinity monoclonal antibody or antigen binding fragment thereof as disclosed herein that binds to human MASP-3 and inhibits alternative pathway complement activation to treat or reduce the risk of AMD in the subject. In one embodiment, the present invention provides a method for treating a subject suffering from, or at risk for developing AMD comprising administering to the subject a pharmaceutical composition comprising an effective amount of a monoclonal antibody or antigen binding fragment thereof as disclosed herein that binds to human MASP-3 and inhibits alternative pathway complement activation to treat or reduce the risk of AMD in the subject, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259, (ii) VLCDR2 comprising SEQ ID NO:144 and (iii) VLCDR3 comprising SEQ ID NO:161.

C. The Role of MASP-3 in Ischemia Reperfusion Injury and Therapeutic Methods Using MASP-3 Inhibitory Antibodies, Optionally in Combination with MASP-2 Inhibitory Agents Tissue ischemia is the basis for a wide spectrum of clinical disorders. Although timely restoration of blood flow is essential to preservation of ischemic tissue, it has long been recognized that reperfusion, which can occur either spontaneously or through therapeutic intervention, may lead to additional tissue injury, a phenomenon that has been termed ischemia reperfusion (I/R) injury (Eltzschig, H. K. and Tobias, E., *Nat. Med.* 17:1391-1401, 2011). I/R injury may affect single organs, such as the heart (acute coronary syndrome), kidney (acute kidney injury), intestine (intestinal I/R), and brain (stroke). I/R injury may also affect multiple organs, such as following major trauma and resuscitation (multiple organ failure), circulatory arrest (hypoxic brain injury, acute kidney injury), peripheral vascular disease, and sickle cell disease (acute chest syndrome, acute kidney injury). Major surgery may be associated with I/R injury, including cardiac surgery (acute heart failure after cardiopulmonary bypass), thoracic surgery (acute lung injury), peripheral vascular surgery (compartment syndrome), vascular surgery (acute kidney injury), and solid organ transplantation (acute graft failure). Currently there are no specific therapies that target I/R injury and there is a need for effective treatments in order to maximize the salvage of tissue in the ischemic zone and improve functional outcome in these common settings.

The pathophysiology of I/R injury is complex and characterized by a robust inflammatory response following reperfusion. Activation of the complement system has been implicated as an important component of I/R injury and inhibition of complement activity has been efficacious in a variety of animal models (Diepenhorst, G. M. P. et al., *Ann. Surg.* 249:889-899, 2009). The relative importance of the classical, lectin, and alternative pathways in I/R injury is largely unsettled and may differ depending on the organs affected. Recently the availability of knockout mice deficient in specific complement proteins and pathway-specific inhibitors has generated data that implicate the lectin and alternative pathways in I/R injury.

The role of the alternative pathway in gastrointestinal I/R injury was investigated using factor D-deficient(−/−) and heterozygotus(+/−) mice (Stahl, G. L., et al. *Am. J. Pathol.* 162:449-455, 2003). Following transient gastrointestinal ischemia, intestinal and pulmonary injury were reduced but not prevented in factor D-deficient mice compared with heterozygotus mice, and addition of human factor D to Factor D(−/−) mice restored I/R injury. The same model was evaluated in C1q-deficient and MBL-A/C-deficient mice and the results showed that gastrointestinal I/R injury was independent of C1q and classical pathway activation, but that MBL and lectin pathway activation was required for intestinal injury (Hart, M. L., et al. *J. Immunol.* 174:6373-6380, 2005). Conversely, the C1q recognition molecule of the classical pathway was responsible for pulmonary injury after intestinal I/R (Hart, M. L., et al. *J. Immunol.* 174:6373-6380, 2005). One hypothesis is that activation of complement during I/R injury occurs through natural IgM binding to self-antigens present on the surface of ischemic (but not normal) tissue, for example non-muscle myosin heavy chains type II. In a mouse gastrointestinal I/R injury model, immunocomplexes from gut tissue were evaluated for the presence of initiating factors in the classical (C1q), lectin (MBL), or alternative (Factor B) pathways (Lee, H., et al., *Mol. Immunol.* 47:972-981, 2010). The results showed that C1q and MBL were detected whereas Factor B was not detected in these immunocomplexes, indicating involvement of the classical and lectin pathways but not the alternative pathway. In the same model, Factor B-deficient mice were not protected from local tissue injury, providing additional support for the lack of involvement of the alternative pathway. The role of the lectin pathway in gastrointestinal I/R injury was directly evaluated in MASP-2-deficient mice and the results showed that gastrointestinal injury was reduced in these mice compared with wide-type controls; treatment with MASP-2 monoclonal antibody was similarly protective (Schwaeble, W. J., et al., *Proc. Natl. Acad. Sci.* 108:7523-7528, 2011). Taken together, these results provide support for the involvement of the lectin pathway in gastrointestinal I/R injury, with conflicting data regarding involvement of the alternative pathway.

In a mouse myocardial I/R injury model, a pathogenic role was demonstrated for the lectin pathway as MBL-deficient mice were protected from myocardial injury whereas C1q-deficient and C2/fB-deficient mice were not (Walsh, M. C. et al., *J. Immunol.* 175:541-546, 2005). Protection from myocardial I/R injury was also observed in MASP-2-deficient mice (Schwaeble, W. J., et al., *Proc. Natl. Acad. Sci.* 108:7523-7528, 2011). Treatment of rats in a myocardial I/R model with monoclonal antibodies against rat MBL resulted in reduced post-ischemic reperfusion injury (Jordan, J. E., et al., *Circulation* 104:1413 18, 2001). In a study of myocardial infarction patients treated with angioplasty, MBL deficiency was associated with reduced 90-day mortality compared to MBL-sufficient counterparts (M Trendelenburg et al., *Eur Heart J.* 31:1181, 2010). Furthermore, myocardial infarction patients that develop cardiac dysfunction after angioplasty have approximately~three-fold higher MBL levels compared to patients with functional recovery (Haahr-Pedersen S., et al., *J Inv Cardiology,* 21:13, 2009). MBL antibodies also reduced complement deposition on endothelial cells in vitro after oxidative stress indicating a role for the lectin pathway in myocardial I/R injury (Collard, C. D., et al., *Am. J. Pathol.* 156:1549 56, 2000). In a mouse heterotopic isograft heart transplant model of FR injury, the role of the alternative pathway was investigated using the pathway-specific fusion protein CR2-fH (Atkinson, C., et al., *J. Immunol.* 185:7007-7013, 2010). Systemic administration of CR2-fH immediately posttransplantation resulted in a reduction in myocardial I/R injury to an extent comparable to treatment with CR2-Crry, which inhibits all complement pathways, indicating that the alternative pathway is of key importance in this model.

In a mouse model of renal I/R injury, the alternative pathway was implicated as factor B-deficient mice were protected from a decline in renal function and tubular injury, compared with wild-type mice (Thurman, J. M., et al., *J. Immunol.* 170:1517-1523, 2003). Treatment with an inhibitory monoclonal antibody to factor B prevented complement activation and reduced murine renal I/R injury (Thurman, J. M., et al., *J. Am. Soc. Nephrol.* 17:707-715, 2006). In a bilateral renal I/R injury model, MBL-A/C-deficient mice were protected from kidney damage compared with wild-type mice and recombinant human MBL reversed the protective effect in MBL-A/C-deficient mice, implicating a role for MBL in this model (Moller-Kristensen, M., et al., *Scand. J. Immunol.* 61:426-434, 2005). In a rat unilateral renal I/R injury model, inhibition of MBL with a monoclonal antibody to MBL-A preserved renal function after I/R (van der Pol, P., et al., *Am. J. Transplant.* 12:877-887, 2010). Interestingly, the role of MBL in this model did not appear to involve activation of the terminal complement components, as treatment with a C5 antibody was ineffective in preventing renal injury. Rather, MBL appeared to have a direct toxic effect on tubular cells, as human proximal tubular cells incubated with MBL in vitro internalized MBL with subsequent cellular apoptosis. In a swine model of renal I/R, Castellano G. et al., (*Am J Pathol,* 176(4):1648-59, 2010), tested a C1 inhibitor, which irreversibly inactivates C1r and C1s proteases in the classical pathway and also MASP-1 and MASP-2 proteases in MBL complexes of the lectin pathway, and found that C1 inhibitor reduced complement deposition in peritubular capillaries and glomerulus and reduced tubular damage.

The alternative pathway appears to be involved in experimental traumatic brain injury as factor B-deficient mice had reduced systemic complement activation as measured by serum C5a levels and reduced posttraumatic neuronal cell death compared with wide-type mice (Leinhase, I., et al., *BMC Neurosci.* 7:55-67, 2006). In human stroke, complement components C1q, C3c, and C4d were detected by immunohistochemical staining in ischemic lesions, suggesting activation via the classical pathway (Pedersen, E. D., et al., *Scand. J. Immunol.* 69:555-562, 2009). Targeting of the classical pathway in animal models of cerebral ischemia has yielded mixed results, with some studies demonstrating protection while others showing no benefit (Arumugam, T. V., et al., *Neuroscience* 158:1074-1089, 2009). Experimental and clinical studies have provided strong evidence for lectin pathway involvement. In experimental stroke models, deficiency of either MBL or MASP-2 results in reduced infarct sizes compared to wild-type mice (Cervera A, et al.; *PLoS One* 3; 5(2):e8433, 2010; Osthoff M. et al., *PLoS One,* 6(6):e21338, 2011). Furthermore, stroke patients with low levels of MBL have a better prognosis compared to their MBL-sufficient counterpart (Osthoff M. et al., *PLoS One,* 6(6):e21338, 2011).

In a baboon model of cardiopulmonary bypass, treatment with a factor D monoclonal antibody inhibited systemic inflammation as measured by plasma levels of C3a, sC5b-9, and IL-6, and reduced myocardial tissue injury, indicating involvement of the alternative pathway in this model (Undar, A., et al., *Ann. Thorac. Surg.* 74:355-362, 2002).

Thus, depending on the organ affected by I/R, all three pathways of complement can contribute to pathogenesis and adverse outcomes. Based on the experimental and clinical findings detailed above, LEA-2 inhibitors are expected to be protective in most settings of FR. Lectin-dependent activation of LEA-1 may cause complement activation via the alternative pathway at least in some settings. In addition, LEA-2-initiated complement activation may be further amplified by the alternative pathway amplification loop and thus exacerbate I/R-related tissue injury. Thus, LEA-1 inhibitors are expected to provide additional or complementary treatment benefits in patients suffering from an ischemia-related condition.

In view of the above, LEA-1 and LEA-2 inhibitors are expected to have independent therapeutic benefits in treating, preventing or reducing the severity of ischemia-reperfusion related conditions. In addition, LEA-1 and LEA-2 inhibitors used together may achieve additional treatment benefits compared to either agent alone. An optimally effective treatment for an I/R-related condition therefore comprises active pharmaceutical ingredients that, alone or in combination, block both LEA-1 and LEA-2. Combined LEA-1 and LEA-2 inhibition may be accomplished by co-administration of a LEA-1 blocking agent and a LEA-2 blocking agent. Preferentially, LEA-1 and LEA-2 inhibitory function may be encompassed in a single molecular entity, such as a bispecific antibody composed of MASP-1/3 and a MASP-2-specific binding site, or a dual specificity antibody where each binding site can bind to and block MASP-1/3 or MASP-2.

In accordance with the foregoing, an aspect of the invention thus provides a method for inhibiting LEA-1 dependent complement activation for treating, preventing or reducing the severity of ischemia reperfusion injuries by administering a composition comprising a therapeutically effective amount of a LEA-1 inhibitory agent comprising a MASP 1 inhibitory agent, a MASP 3 inhibitory agent, or a combination of a MASP 1/3 inhibitory agent, in a pharmaceutical carrier to a subject experiencing ischemic reperfusion. The MASP 1, MASP 3, or MASP 1/3 inhibitory composition may be administered to the subject by intra arterial, intravenous, intracranial, intramuscular, subcutaneous, or other parenteral administration, and potentially orally for non peptidergic inhibitors, and most suitably by intra arterial or intravenous administration. Administration of the LEA-1 inhibitory compositions of the present invention suitably commences immediately after or as soon as possible after an ischemia reperfusion event. In instances where reperfusion occurs in a controlled environment (e.g., following an aortic aneurism repair, organ transplant or reattachment of severed or traumatized limbs or digits), the LEA-1 inhibitory agent may be administered prior to and/or during and/or after reperfusion. Administration may be repeated periodically as determined by a physician for optimal therapeutic effect.

In some embodiments, the methods are used to treat or prevent an ischemia-reperfusion injury associated with at least one of aortic aneurysm repair, cardiopulmonary bypass, vascular reanastomosis in connection with organ transplants and/or extremity/digit replantation, stroke, myocardial infarction, and hemodynamic resuscitation following shock and/or surgical procedures.

In some embodiments, the methods are used to treat or prevent an ischemia-reperfusion injury in a subject that is about to undergo, is undergoing, or has undergone an organ transplant. In some embodiments, the methods are used to treat or prevent an ischemica-reperfusion injury in a subject that is about to undergo, is undergoing, or has undergone an organ transplant, provided that the organ transplant is not a kidney transplant.

In one embodiment, the method according to this aspect of the invention further comprises inhibiting LEA-2-dependent complement activation in a subject experiencing ischemic reperfusion, comprising administering a therapeutically effective amount of a MASP-2 inhibitory agent and a MASP-1, MASP-3, or MASP-1/3 inhibitory agent to the subject. As detailed above, the use of a combination of pharmacologic agents that individually block LEA-1 and LEA-2, is expected to provide an improved therapeutic outcome in treating, preventing, or reducing the severity of ischemia reperfusion injuries as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP 2 inhibitory composition may be administered to a subject in need thereof by intra arterial, intravenous, intracranial, intramuscular, subcutaneous, or other parenteral administration, and potentially orally for non peptidergic inhibitors, and most suitably by intra arterial or intravenous administration. Administration of the MASP-2 inhibitory compositions of the present invention suitably commences immediately after or as soon as possible after an ischemia reperfusion event. In instances where reperfusion occurs in a controlled environment (e.g., following an aortic aneurism repair, organ transplant or reattachment of severed or traumatized limbs or digits), the MASP-2 inhibitory agent may be administered prior to and/or during and/or after reperfusion. Administration may be repeated periodically as determined by a physician for optimal therapeutic effect.

Application of the MASP-3 inhibitory compositions and optional MASP 2 inhibitory compositions of the present invention may be carried out by a single administration of the composition (e.g., a single composition comprising MASP-2 and MASP-3 inhibitory agents, or bispecific or dual inhibitory agents, or co-administration of separate compositions), or a limited sequence of administrations, for treatment or prevention of ischemia reperfusion injuries. Alternatively, the composition may be administered at periodic intervals such as daily, biweekly, weekly, every other week, monthly or bimonthly over an extended period of time for treatment of a subject experiencing ischemic reperfusion.

As described in Examples 11-21 herein, high affinity MASP-3 inhibitory antibodies have been generated which have therapeutic utility for inhibition of the alternative pathway in AP-related diseases or conditions, such in a subject experiencing ischemic reperfusion.

Accordingly, in one embodiment, the present invention provides a method for treating a subject suffering from, or at risk for developing ischemia-reperfusion comprising an effective amount of a high affinity monoclonal antibody or antigen binding fragment thereof as disclosed herein that binds to human MASP-3 and inhibits alternative pathway complement activation to treat or reduce the risk of tissue injury associated with ischemia-reperfusion in the subject.

D. The Role of MASP-3 in Inflammatory and Non-Inflammatory Arthritides and Therapeutic Methods Using MASP-3 Inhibitory Antibodies, Optionally in Combination with and MASP-2 Inhibitory Agents Rheumatoid arthritis (RA) is a chronic inflammatory disease of synovial joints that may also have systemic manifestations. RA affects approximately 1% of the world population, with women being two to three times more likely to be afflicted. Joint inflammation manifests in swelling, pain, and stiffness. As the disease progresses there may be joint erosion and destruction, resulting in impaired range of motion and deformities. Treatment goals in RA include prevention or control of joint damage, prevention of loss of joint function and disease progression, relief of symptoms and improvement in quality of life, and achievement of drug-free remission. Pharmacological treatment of RA includes disease-modifying anti-rheumatic drugs (DMARDs), analgesics, and anti-inflammatory agents (glucocorticoids and non-steroidal anti-inflammatory drugs). DMARDs are the most important treatment because they can induce durable remissions and delay or halt the progression of joint destruction, which is irreversible. Traditional DMARDs include small molecules such as methotrexate, sulfasalazine, hydroxychloroquine, gold salts, leflunomide, D-penicillamine, cyclosporine, and azathioprine. If traditional DMARDs are inadequate to control the disease then several biologic agents targeting inflammatory cells or mediators are available treatment options, such as tumor necrosis factor inhibitors (etanercept, infliximab, adalimumab, certolizumab pegol, and golimumab), cytokine antagonists (anakinra and tocilizumab), rituximab, and abatacept.

Although adaptive immunity is clearly central to RA pathogenesis as evidenced by genetic association with T-cell activation genes and the presence of autoantibodies, innate immune mechanisms have also been implicated (McInnes, I. B. and Schett, G. *New Engl. J. Med.* 365:2205-2219, 2011). In human RA, synovial fluid levels of the alternative pathway cleavage fragment Bb were several fold higher than samples from patients with crystal-induced arthritis or degenerative joint disease, implicating preferential activation of the alternative pathway in RA patients (Brodeur, J. P., et al., *Arthritis Rheum.* 34:1531-1537, 1991). In the experimental anti-type II collagen antibody-passive transfer model of arthritis, factor B-deficient mice had decreased inflammation and joint damage compared with wild-type mice, whereas C4-deficient mice had similar disease activity as wild-type mice, indicating the requirement for the alternative pathway and not the classical pathway in this model (Banda, N. K. et al., *J. Immunol.* 177:1904-1912, 2006). In the same experimental model of collagen antibody-induced arthritis (CAIA), mice with only classical pathway active or only lectin pathway active were not capable of developing arthritis (Banda, N. K. et al., *Clin. Exp. Immunol.* 159:100-108, 2010). Data from this study suggested that either the classical or lectin pathways were capable of activating low levels of C3 in vitro. However, in the absence of the alternative pathway amplification loop, the level of joint deposition of C3 was inadequate to produce clinical disease. A key step in the activation of the alternative pathway is conversion of the zymogen of factor D (pro-factor D) to mature factor D, which is mediated by MASP-1 and/or MASP-3 (Takahashi, M., et al., *J. Exp. Med.* 207:29-37, 2010) and/or HTRA1 (Stanton et al., Evidence That the HTRA1 Interactome Influences Susceptibility to Age-Related Macular Degeneration, presented at The Association for Research in Vision and Ophthalmology 2011 conference on May 4, 2011). The role of MASP-1/3 was evaluated in murine CAIA and the results showed that MASP-1/3 deficient mice were protected from arthritis compared with wild-type mice (Banda, N. K., et al., *J. Immunol.* 185:5598-5606, 2010). In MASP-1/3-deficient mice, pro-factor D but not mature factor D was detected in serum during the evolution of CAIA, and the addition of human factor D in vitro reconstituted C3 activation and C5a generation using sera from these mice. In contrast, in a murine model of the effector phase of arthritis, C3-deficient mice developed very mild arthritis compared to WT mice while factor B-deficient mice still developed arthritis, indicating independent contribution of both the classical/lectin and alternative pathways (Hietala, M. A. et al., *Eur. J. Immunol.* 34:1208-1216, 2004). In the K/BxN T cell receptor transgenic mouse model of inflammatory arthritis, mice lacking C4 or C1q developed arthritis similar to wild-type mice whereas mice lacking factor B either did not develop arthritis or had mild arthritis, demonstrating the requirement for the alternative pathway and not the classical pathway in this model (Ji H. et al., *Immunity* 16:157-168, 2002). In the K/BxN model, mice lacking MBL-A were not protected from serum-induced arthritis, but as the role of MBL-C was not investigated, a potential role for the lectin pathway could not be eliminated (Ji et al., 2002, supra).

Two research groups have independently proposed that lectin-dependent complement activation promotes inflammation in RA patients via interaction of MBL with specific IgG glycoforms (Malhotra et al., *Nat. Med.* 1:237 243, 1995; Cuchacovich et al., *J. Rheumatol.* 23:44 51, 1996). It is noted that rheumatoid conditions are associated with a marked increase in IgG glycoforms that lack galactose (referred to as IgG0 glycoforms) in the Fc region of the molecule (Rudd et al., *Trends Biotechnology* 22:524 30, 2004). The percentage of IgG0 glycoforms increases with disease progression of rheumatoid conditions, and returns to normal when patients go into remission. In vivo, IgG0 is deposited on synovial tissue and MBL is present at increased levels in synovial fluid in individuals with RA. Aggregated agalactosyl IgG (IgG0) associated with RA can bind MBL and therefore can initiate lectin-dependent complement activation via LEA-1 and/or LEA-2. Furthermore, results from a clinical study looking at allelic variants of MBL in RA patients suggest that MBL may have an inflammatory enhancing role in the disease (Garred et al., *J. Rheumatol.* 27:26 34, 2000). Therefore, the lectin-dependent complement activation via LEA-1 and/or LEA-2 may play an important role in the pathogenesis of RA.

Complement activation also plays in important role in juvenile rheumatoid arthritis (Mollnes, T. E., et al., *Arthritis Rheum.* 29:1359 64, 1986). Similar to adult RA, in juvenile rheumatoid arthritis, elevated serum and synovial fluid levels of alternative pathway complement activation product Bb compared to C4d (a marker for classical or LEA-2 activation), indicate that complement activation is mediated predominantly by LEA-1 (El Ghobarey, A. F. et al., *J. Rheumatology* 7:453 460, 1980; Agarwal, A., et al., *Rheumatology* 39:189 192, 2000).

Similarly, complement activation plays an important role in psoriatic arthritis. Patients with this condition have increased complement activation products in their circulation, and their red blood cells appear to have lower levels of the complement regulator CD59 (Triolo, *Clin Exp Rheumatol.*, 21(2):225-8, 2003). Complement levels are associated with disease activity, and have a high predictive value to determine treatment outcomes (Chimenti at al., *Clin Exp Rheumatol.*, 30(1):23-30, 2012). In fact, recent studies suggest that the effect of anti-TNF therapy for this condition is attributable to complement modulation (Ballanti et al., *Autoimmun Rev.*, 10(10):617-23, 2011). While the precise role of complement in psoriatic arthritis has not been determined, the presence of C4d and Bb complement activation products in the circulation of these patients suggests an important role in pathogenesis. On the basis of the products observed, it is believed that LEA-1, and possibly also LEA-2 are responsible for pathologic complement activation in these patients.

Osteoarthritis (OA) is the most common form of arthritis, affecting over 25 million people in the United States. OA is characterized by breakdown and eventual loss of joint cartilage, accompanied by new bone formation and synovial proliferation, leading to pain, stiffness, loss of joint function, and disability. Joints that are frequently affected by OA are hands, neck, lower back, knees and hips. The disease is progressive and current treatments are for symptomatic pain relief and do not alter the natural history of disease. The pathogenesis of OA is unclear, but a role for complement has been implicated. In a proteomic and transcriptomic analyses of synovial fluid from patients with OA, several components of complement were aberrantly expressed compared to samples from healthy individuals, including classical (C1s and C4A) and alternative (factor B) pathways, and also C3, C5, C7, and C9 (Wang, Q., et al., *Nat. Med.* 17:1674-1679, 2011). Moreover, in a mouse model of OA induced by medial meniscectomy, C5-deficient mice had less cartilage loss, osteophyte formation and synovitis than C5-positive mice, and treatment of wild-type mice with CR2-fH, a fusion protein that inhibits the alternative pathway, attenuated the development of OA (Wang et al., 2011 supra).

Ross River virus (RRV) and chikungunya virus (CHIKV) belong to a group of mosquito-borne viruses that can cause acute and persistent arthritis and myositis in humans. In addition to causing endemic disease, these viruses can cause epidemics that involve millions of infected individuals. The arthritis is believed to be initiated by viral replication and induction of host inflammatory response in the joint and the complement system has been invoked as a key component in this process. Synovial fluid from humans with RRV-induced polyarthritis contains higher levels of C3a than synovial fluid from humans with OA (Morrison, T. E., et al., *J. Virol.* 81:5132-5143, 2007). In a mouse model of RRV infection, C3-deficient mice developed less severe arthritis compared with wild-type mice, implicating the role of complement (Morrison et al., 2007, supra). The specific complement pathway involved was investigated and mice with inactivated lectin pathway (MBL-A−/− and MBL-C−/−) had attenuated arthritis compared with wide-type mice. In contrast, mice with inactivated classical pathway (C1q−/−) or alternative pathway (factor B−/−) developed severe arthritis, indicating that the lectin pathway initiated by MBL had an essential role in this model (Gunn, B. M., et al., *PLoS Pathog.* 8:e1002586, 2012). Because arthritides involve damage to the joints, the initial joint damage caused by various etiologies may trigger a secondary wave of complement activation via LEA-2. In support of this concept, our previous work has demonstrated that MASP-2 KO mice have reduced joint injury compared to WT mice in the collagen-induced model of RA.

In view of the body of evidence detailed above, LEA-1 and LEA-2 inhibitors, alone or in combination, are expected to be therapeutically useful for the treatment of arthritides. An optimally effective treatment for arthritides may therefore comprise active pharmaceutical ingredients that, alone or in combination, can block both LEA-1 and LEA-2. Combined LEA-1 and LEA-2 inhibition may be accomplished by co-administration of an LEA-1 blocking agent and a LEA2 blocking agent. Preferentially, LEA-1 and LEA-2 inhibitory function may be encompassed in a single molecular entity, such as a bispecific antibody composed of MASP-1/3 and a MASP-2-specific binding site, or a dual specificity antibody where each binding site can bind to and block MASP-1/3 or MASP-2. In accordance with the foregoing, an aspect of the invention thus provides a method for inhibiting LEA-1 dependent complement activation for treating, preventing, or reducing the severity of inflammatory or non-inflammatory arthritides, including osteoarthritis, rheumatoid arthritis, juvenile rheumatoid arthritis and psoriatic arthritis, by administering a composition comprising a therapeutically effective amount of a LEA-1 inhibitory agent comprising a MASP-1 inhibitory agent, a MASP-3 inhibitory agent, or a combination of a MASP 1/3 inhibitory agent, in a pharmaceutical carrier to a subject suffering from, or at risk for developing, inflammatory or non-inflammatory arthritides. The MASP-1, MASP-3, or MASP 1/3 inhibitory composition may be administered to the subject systemically, such as by intra arterial, intravenous, intramuscular, subcutaneous, or other parenteral administration, or by oral administration. Alternatively, administration may be by local delivery, such as by intra-articular injection. The LEA-1 inhibitory agent may be administered periodically over an extended period of time for treatment or control of a chronic condition, or may be by single or repeated administration in the period before, during and/or following acute trauma or injury, including surgical procedures performed on the joint.

In one embodiment, the method according to this aspect of the invention further comprises inhibiting LEA-2-dependent complement activation in a subject suffering from, or at risk for developing, inflammatory or non-inflammatory arthritides (including osteoarthritis, rheumatoid arthritis, juvenile rheumatoid arthritis and psoriatic arthritis), by administering a therapeutically effective amount of a MASP-2 inhibitory agent and a MASP-1, MASP-3, or MASP1/3 inhibitory agent to the subject. As detailed above, the use of a combination of pharmacologic agents that individually block LEA-1 and LEA-2, is expected to provide an improved therapeutic outcome in treating or preventing arthritides as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory composition may be administered to the subject in need thereof systemically, such as by intra arterial, intravenous, intramuscular, subcutaneous, or other parenteral administration, or potentially by oral administration for non peptidergic inhibitors. Alternatively, administration may be by local delivery, such as by intra-articular injection. The MASP-2 inhibitory agent may be administered periodically over an extended period of time for treatment or control of a chronic condition, or may be by single or repeated administration in the period before, during and/or following acute trauma or injury, including surgical procedures performed on the joint.

Application of the MASP-3 inhibitory compositions and optional MASP 2 inhibitory compositions of the present invention may be carried out by a single administration of the composition (e.g., a single composition comprising MASP-2 and MASP-3 inhibitory agents, or bispecific or dual-inhibitory agents, or co-administration of separate compositions), or a limited sequence of administrations, for treating, preventing or reducing the severity of inflammatory or non-inflammatory arthritides. Alternatively, the composition may be administered at periodic intervals such as daily, biweekly, weekly, every other week, monthly or bimonthly over an extended period of time for treatment of a subject suffering from inflammatory or non-inflammatory arthritides.

As described in Examples 11-21 herein, high affinity MASP-3 inhibitory antibodies have been generated which have therapeutic utility for inhibition of the alternative pathway in AP-related diseases or conditions, such as arthritis.

Accordingly, in one embodiment, the present invention provides a method for treating a subject suffering from, or at risk for developing arthritis (inflammatory and non-inflammatory arthritides) comprising administering to the subject a pharmaceutical composition comprising an effective amount of a high affinity monoclonal antibody or antigen binding fragment thereof as disclosed herein that binds to human MASP-3 and inhibits alternative pathway complement activation to treat or reduce the risk of arthritis in the subject, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161. In some embodiments, the subject is suffering from arthritis selected from the group consisting of osteoarthritis, rheumatoid arthritis, juvenile rheumatoid arthritis, ankylosing spondylitis, Behcet's disease, infection-related arthritis and psoriatic arthritis. In some embodiments, the pharmaceutical composition is administered systemically (i.e., subcutaneously, intra-muscularly, intravenously, intra-arterially or as an inhalant). In some embodiments, the pharmaceutical composition is administered locally to a joint.

E. The Role of MASP-3 in Disseminated Intravascular Coagulation (DIC) and Therapeutic Methods Using MASP-3 Inhibitory Antibodies, Optionally in Combination with and MASP-2 Inhibitory Agents Disseminated intravascular coagulation (DIC) is a syndrome of pathologic overstimulation of the coagulation system that can manifest clinically as hemorrhage and/or thrombosis. DIC does not occur as a primary condition but rather in association with a variety of disease processes, including tissue damage (trauma, burns, heat stroke, transfusion reaction, acute transplant rejection), neoplasia, infections, obstetric conditions (placenta previa, amniotic fluid embolism, toxemia of pregnancy), and miscellaneous conditions such as cardiogenic shock, near drowning, fat embolism, aortic aneurysm. Thrombocytopenia is a frequent abnormality in patients in the intensive care unit, with an incidence of 35% to 44%, and DIC is the etiology in about 25% of these cases, i.e., DIC occurs in approximately 10% of critically ill patients (Levi, M. and Opal, S. M. *Crit. Care* 10:222-231, 2006). The pathophysiology of DIC is that the underlying disease process initiates a physiological coagulation response. However, the prothrombotic substances overwhelm the normal counterbalancing mechanisms such that there is the inappropriate deposition of fibrin and platelets in the microcirculation, leading to organ ischemia, hypofibrinogenemia, and thrombocytopenia. The diagnosis of DIC is based on the clinical presentation in the appropriate underlying illness or process, along with abnormalities in laboratory parameters (prothrombin time, partial thromboplastin time, fibrin degradation products, D-dimer, or platelet count). The primary treatment of DIC is to address the underlying condition that is the responsible trigger. Blood product support in the form of red blood cells, platelets, fresh frozen plasma, and cryoprecipitate may be necessary to treat or prevent clinical complications.

The role of the complement pathways in DIC has been investigated in several studies. Complement activation was evaluated in pediatric patients with meningococcal infection comparing the clinical course in relation to MBL genotype (Sprong, T. et al., *Clin. Infect. Dis.* 49:1380-1386, 2009). At admission to the hospital, patients with MBL deficiency had lower circulating levels of C3bc, terminal complement complex, C4bc, and C3bBbP than MBL-sufficient patients, indicating lower extent of common complement, terminal complement, and alternative pathway activation. Furthermore, extent of systemic complement activation correlated with disease severity and parameters of DIC and the MBL-deficient patients had a milder clinical course than MBL-sufficient patients. Therefore, although MBL deficiency is a risk factor for susceptibility to infections, MBL deficiency during septic shock may be associated with lower disease severity.

As demonstrated in Examples 1-4 herein, experimental studies have highlighted the important contribution of MBL and MASP-1/3 in innate immune response to *Neisseria menigitidis*, the etiological agent of meningococcal infection. MBL-deficient sera from mice or humans, MASP-3 deficient human sera, or the MASP-1/3 knockout mouse are less effective at activating complement and lysing meningococci in vitro compared to wild-type sera. Similarly, naïve MASP-1/3 knockout mice are more susceptible to neisserial infection than their wild-type counterparts. Thus, in the absence of adaptive immunity, the LEA-1 pathway contributes to innate-host resistance to neisserial infection. Conversely, LEA-1 augments pathologic complement activation triggering a harmful host response, including DIC.

In a murine model of arterial thrombosis, MBL-null and MASP-1/-3 knockout mice had decreased FeCl3-induced thrombogenesis compared with wild-type or C2/factor B-null mice, and the defect was reconstituted with recombinant human MBL (La Bonte, L. R., et al., *J. Immunol.* 188:885-891, 2012). In vitro, MBL-null or MASP-1/-3 knockout mouse sera had decreased thrombin substrate cleavage compared with wild-type or C2/factor B-null mouse sera; addition of recombinant human MASP-1 restored thrombin substrate cleavage in MASP-1/-3 knockout mouse sera (La Bonte et al., 2012, supra). These results indicate that MBL/MASP complexes, in particular MASP-1, play a key role in thrombus formation. Thus, LEA-1 may play an important role in pathologic thrombosis, including DIC.

Experimental studies have established an equally important role for LEA-2 in pathologic thrombosis. In vitro studies further demonstrate that LEA-2 provides a molecular link between the complement system and the coagulation system. MASP-2 has factor Xa-like activity and activates prothrombin through cleavage to form thrombin, which can subsequently clear fibrinogen and promote fibrin clot formation (see also Krarup et al., *PLoS One*, 18:2(7):e623, 2007).

Separate studies have shown that lectin-MASP complexes can promote clot formation, fibrin deposition and fibrinopeptide release in a MASP-2 dependent process (Gulla et al., *Immunology*, 129(4):482-95, 2010). Thus, LEA-2 promotes simultaneous lectin-dependent activation of complement and the coagulation system.

In vitro studies have further shown that MASP-1 has thrombin-like activity (Presanis J. S., et al., *Mol Immunol*, 40(13):921-9, 2004), and cleaves fibrinogen and factor XIII (Gulla K. C. et al., *Immunology*, 129(4):482-95, 2010), suggesting that LEA-1 may activate coagulation pathways independently or in concert with LEA-2.

The data detailed above suggest that LEA-1 and LEA-2 provide independent links between lectin-dependent complement activation and coagulation. Thus, in view of the above, LEA-1 and LEA-2 inhibitors are expected to have independent therapeutic benefits in treating a subject suffering from disseminated intravascular coagulation. In some embodiments, the subject is suffering from disseminated intravascular coagulation secondary to sepsis, trauma, infection (bacterial, viral, fungal, parasitic), malignancy, transplant rejection, transfusion reaction, obstetric complication, vascular aneurysm, hepatic failure, heat stroke, burn, radiation exposure, shock, or severe toxic reaction (e.g., snake bite, insect bite, transfusion reaction). In some embodiments, the trauma is a neurological trauma. In some embodiments, the infection is a bacterial infection, such as a *Neisseria meningitidis* infection.

In addition, LEA-1 and LEA-2 inhibitors used together may achieve additional treatment benefits compared to either agent alone. As both LEA-1 and LEA-2 are known to be activated by conditions that lead to DIC (for example infection or trauma), LEA-1- and LEA-2-blocking agents, either separately or in combination, are expected to have therapeutic utility in the treatment of DIC. LEA-1 and LEA-2 blocking agents may prevent different cross-talk mechanisms between complement and coagulation. LEA-1- and LEA-2-blocking agents may thus have complementary, additive or synergistic effects in preventing DIC and other thrombotic disorders.

In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bispecific antibody composed of MASP-1/3 and a MASP-2-specific binding site, or a dual specificity antibody where each binding site and bind to and block MASP-1/3 or MASP-2.

In accordance with the foregoing, an aspect of the invention thus provides a method for inhibiting LEA-1 dependent complement activation for treating, preventing, or reducing the severity of disseminated intravascular coagulation in a subject in need thereof comprising administering a composition comprising a therapeutically effective amount of a LEA-1 inhibitory agent comprising a MASP-1 inhibitory agent, a MASP 3 inhibitory agent, or a combination of a MASP-1/3 inhibitory agent, in a pharmaceutical carrier to a subject experiencing, or at risk for developing, disseminated intravascular coagulation. The MASP-1, MASP-3, or MASP-1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled. For treatment or prevention of DIC secondary to trauma or other acute event, the LEA-1 inhibitory composition may be administered immediately following the traumatic injury or prophylactically prior to, during, immediately following, or within one to seven days or longer, such as within 24 hours to 72 hours, after trauma-inducing injury or situations such as surgery in patients deemed at risk of DIC. In some embodiments, the LEA-1 inhibitory composition may suitably be administered in a fast acting dosage form, such as by intravenous or intra arterial delivery of a bolus of a solution containing the LEA-1 inhibitory agent composition.

In one embodiment, the method according to this aspect of the invention further comprises inhibiting LEA-2-dependent complement activation for treating, preventing, or reducing the severity of disseminated intravascular coagulation in a subject in need thereof, comprising administering a therapeutically effective amount of a MASP-2 inhibitory agent and a MASP-1, MASP-3, or MASP-1/3 inhibitory agent to the subject. As detailed above, the use of a combination of pharmacologic agents that individually block LEA-1 and LEA-2 is expected to provide an improved therapeutic outcome in treating or preventing disseminated intravascular coagulation as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject in need thereof systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled. For DIC secondary to trauma or other acute event, the MASP-2 inhibitory composition may be administered immediately following the traumatic injury or prophylactically prior to, during, immediately following, or within one to seven days or longer, such as within 24 hours to 72 hours, after trauma-inducing injury or situations such as surgery in patients deemed at risk of DIC. In some embodiments, the MASP-2 inhibitory composition may suitably be administered in a fast acting dosage form, such as by intravenous or intra arterial delivery of a bolus of a solution containing the MASP-2 inhibitory agent composition.

Application of the MASP-3 inhibitory compositions and optional MASP-2 inhibitory compositions of the present invention may be carried out by a single administration of the composition (e.g., a single composition comprising MASP-2 and MASP-3 inhibitory agents, or bispecific or dual-inhibitory agents, or co-administration of separate compositions), or a limited sequence of administrations, for treating, preventing, or reducing the severity of disseminated intravascular coagulation in subject in need thereof. Alternatively, the composition may be administered at periodic intervals such as daily, biweekly, weekly, every other week, monthly or bimonthly over an extended period of time for treatment of a subject experiencing, or at risk for developing disseminated intravascular coagulation.

As described in Examples 11-21 herein, high affinity MASP-3 inhibitory antibodies have been generated which have therapeutic utility for inhibition of the alternative pathway in AP-related diseases or conditions, such as disseminated intravascular coagulation.

Accordingly, in one embodiment, the present invention provides a method for treating a subject suffering from, or at risk for developing disseminated intravascular coagulation comprising an effective amount of a high affinity monoclonal antibody or antigen binding fragment thereof as disclosed herein that binds to human MASP-3 and inhibits alternative pathway complement activation to treat or reduce the risk of developing disseminated intravascular coagulation, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

F. The Role of MASP-3 in Thrombotic Microangiopathy (TMA), Including Hemolytic Uremic Syndrome (HUS), Atypical Hemolytic Uremic Syndrome (AHUS) and Thrombotic Thrombocytopenic Purpura (TTP) and Therapeutic Methods Using MASP-3 Inhibitory Antibodies, Optionally in Combination with MASP-2 Inhibitory Agents Thrombotic microangiopathy (TMA) refers to a group of disorders characterized clinically by thrombocytopenia, microangiopathic hemolytic anemia, and variable organ ischemia. The characteristic pathological features of TMA are platelet activation and the formation of microthrombi in the small arterioles and venules. The classic TMAs are hemolytic uremic syndrome (HUS) and thrombotic thrombocytopenic purpura (TTP). HUS is distinguished from TTP by the presence of acute renal failure. HUS occurs in two forms: diarrhea-associated (D+) or typical HUS, and diarrhea negative (D−) or atypical HUS (aHUS).

HUS

D+HUS is associated with a prodromal diarrheal illness usually caused by *Escherichia coli* O157 or another Shiga-toxin-producing strain of bacteria, accounts for over 90% of the HUS cases in children, and is the most common cause of acute renal failure in children. Although human infection with *Escherichia coli* O157 is relatively frequent, the percentages of bloody diarrhea that progresses to D+HUS ranged from 3% to 7% in sporadic cases and 20% to 30% in some outbreaks (Zheng, X. L. and Sadler, J. E., Annu. Rev. Pathol. 3:249-277, 2008). HUS usually occurs 4 to 6 days after the onset of diarrhea and approximately two-third of children require dialysis in the acute phase of the disease. Treatment of D+HUS is supportive as no specific treatments have been shown to be effective. The prognosis of D+HUS is favorable, with the majority of patients regaining renal function.

The pathogenesis of D+HUS involves bacteria-produced Shiga toxins that bind to membranes on microvascular endothelial cells, monocytes, and platelets. The microvasculature of the kidney is most often affected. Following binding, the toxin is internalized, leading to release of proinflammatory mediators and eventual cell death. It is thought that endothelial cell damage triggers renal microvascular thrombosis by promoting the activation of the coagulation cascade. There is evidence for activation of the complement system in D+HUS. In children with D+HUS, plasma levels of Bb and SC5b-9 were increased at the time of hospitalization compared to normal controls and, at day 28 after hospital discharge, the plasma levels had normalized (Thurman, J. M. et al., *Clin. J. Am. Soc. Nephrol.* 4:1920-1924, 2009). Shiga toxin 2 (Stx2) was found to activate human complement in the fluid phase in vitro, predominantly via the alternative pathway as activation proceeded in the presence of ethylene glycol tetraacetic acid which blocks the classical pathway (Orth, D. et al., *J. Immunol.* 182:6394-6400, 2009). Furthermore, Stx2 bound factor H and not factor I, and delayed the cofactor activity of factor H on cell surfaces (Orth et al, 2009, supra). These results suggest that Shiga toxin may cause renal damage through multiple potential mechanisms, including a direct toxic effect, and indirectly through activation of complement or inhibition of complement regulators. Toxic effects on the vascular endothelium are expected to activate complement via LEA-2, as evidenced by the effectiveness of MASP-2 blockade in preventing complement-mediated reperfusion injury in various vascular beds as described in Schwaeble, W. J., et al., *Proc. Natl. Acad. Sci.* 108:7523-7528, 2011.

In a murine model of HUS induced by co-injection of Shiga toxin and lipopolysaccharide, factor B-deficient mice had less thrombocytopenia and were protected from renal impairment compared with wild-type mice, implicating LEA-1-dependent activation of the alternative pathway in microvascular thrombosis (Morigi, M. et al., *J. Immunol.* 187:172-180, 2011). As described herein, in the same model, administration of MASP-2 antibody was also effective and increased survival following STX challenge, implicating LEA-2-dependent complement pathway in microvascular thrombosis.

Based on the foregoing, LEA-1 and LEA-2 inhibitors are expected to have independent therapeutic benefit in the treatment or prevention of HUS. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bispecific antibody composed of MASP-1/3 and a MASP-2-specific binding site, or a dual-specificity antibody where each binding site can bind to and block MASP-1/3 or MASP-2.

aHUS

Atypical HUS is a rare disease, with an estimated incidence of 2 per million in the United States (Loirat, C. and Fremeaux-Bacchi, V. Orphanet *J. Rare Dis.* 6:60-90, 2011). Atypical HUS can develop at any age, although the majority of patients have an onset during childhood. Atypical HUS is heterogeneous: some cases are familial, some are recurring, and some are triggered by an infectious illness, typically upper respiratory tract or gastroenteritis. The onset of aHUS is usually sudden and most patients require dialysis at admission. Extra renal manifestations are present in about 20% of patients and may involve the central nervous system, myocardial infarction, distal ischemic gangrene, or multiorgan failure. Treatment of aHUS includes supportive care for organ dysfunction, plasma infusion or plasma exchange, and eculizumab, a humanized monoclonal antibody that targets C5 that was recently approved for use in the United States and European Union. The prognosis in aHUS is not as good as in D+HUS, with approximately 25% mortality during the acute stage and most survivors develop end-stage renal disease.

Atypical HUS has been characterized as a disease of complement dysregulation in that approximately 50% of patients have mutations in genes encoding complement regulatory proteins (Zheng and Sadler, 2008 supra). Most mutations are seen in factor H (FH); other mutations include membrane cofactor protein (MCP), factor I (FI), factor B, and C3. Functional studies showed that the mutations in FH, MCP, and FI lead to loss of function and therefore more complement activation, whereas mutations in factor B are gain of function. The effects of these mutations predominantly affect the alternative pathway. These genetic abnormalities are risk factors rather than the only cause of disease as approximately 50% of family members who carry the mutation do not present with the disease by age 45 (Loirat and Fremeaux-Bacchi, 2011 supra).

Factor H is a complement control protein that protects host tissue from alternative pathway complement attack. FH regulates the alternative pathway amplification loop in three ways: it is a cofactor for FI, which cleaves C3b, it inhibits the formation of the alternative pathway C3 convertase, C3bBb, and it binds to polyanions on cell surfaces and tissue matrices and blocks deposition of C3b (Atkinson, J. P. and Goodship, T. H. J., *J. Exp. Med.* 6:1245-1248, 2007). The majority of FH mutations in aHUS patients occur in the C-terminal short consensus repeat domains of the protein, which result in defective binding of FH to heparin, C3b, and endothelium, but do not alter plasma C3 regulation which resides among N-terminal domains (Pickering, M. C. et al., *J. Exp. Med.* 204:1249-1256, 2007). FH-deficient mice have uncontrolled plasma C3 activation and spontaneously develop membranoproliferative glomerulonephritis type II, but not aHUS. However, FH-deficient mice that transgenically expressed a mouse FH protein functionally equivalent to aHUS-associated human FH mutants spontaneously develop a HUS but not membranoproliferative glomerulonephritis type II, providing in vivo evidence that defective control of alternative pathway activation in renal endothelium is a key event in the pathogenesis of FH-associated aHUS (Pickering et al., 2007 supra). Another form of FH-associated aHUS occurs in patients who have anti-FH autoantibodies resulting in a loss of FH functional activity; most of these patients have deletions in genes encoding five FH-related proteins (Loirat and Fremeaux-Bacchi, 2011, supra).

Similar to FH, MCP inhibits complement activation by regulating C3b deposition on target cells. MCP mutations result in proteins with low C3b-binding and cofactor activity, thus allowing for dysregulated alternative pathway activation. FI is a serine protease that cleaves C3b and C4b in the presence of cofactors, such as FH and MCP, and thereby prevents the formation of C3 and C5 convertases and inhibits both the alternative and the classical complement pathways. Most of the FI-associated aHUS mutations result in reduced FI activity for the degradation of C3b and C4b (Zheng and Stadler, 2008, supra). FB is a zymogen that carries the catalytic sites of the alternative pathway convertase C3bBb. Functional analysis showed that the aHUS associated FB mutations result in increased alternative pathway activation (Loirat and Fremeaux-Bacchi, 2011, supra). Heterozygous mutations in C3 are associated with aHUS. Most C3 mutations induce a defect of C3 to bind MCP, leading to an increased capacity of FB to bind C3b and increased formation of C3 convertase (Loirat and Fremeaux-Bacchi, 2011, supra). Thus, aHUS is a disease closely associated with mutations in the complement genes that lead to inadequate control of the alternative pathway amplification loop. Since the alternative pathway amplification loop is dependent on factor B proteolytic activity, and since LEA-1 is required for factor B activation (either by MASP-3 dependent cleavage or by factor D-mediated cleavage wherein the MASP-1 contributes to the maturation of factor D), LEA-1-blocking agents are expected to prevent uncontrolled complement activation in susceptible individuals. As a result, it is expected that LEA-1 blocking agents will effectively treat aHUS.

While the central role of a deregulated alternative pathway amplification loop in aHUS is widely accepted, the triggers initiating complement activation and the molecular pathways involved are unresolved. Not all individuals carrying the above-described mutations develop aHUS. In fact, familial studies have suggested that the penetrance of aHUS is only ~50% (Sullivan M. et al., *Ann Hum Genet* 74:17-26 2010). The natural history of the disease suggests that aHUS most often develops after an initiating event such as an infectious episode or an injury. Infectious agents are well known to activate the complement system. In the absence of pre-existing adaptive immunity, complement activation by infectious agents may be primarily initiated via LEA-1 or LEA-2. Thus, lectin-dependent complement activation triggered by an infection may represent the initiating trigger for subsequent pathological amplification of complement activation in aHUS-predisposed individuals, which may ultimately lead to disease progression. Accordingly, another aspect of the present invention comprises treating a patient suffering with aHUS secondary to an infection by administering an effective amount of a LEA-1- or a LEA-2-inhibitory agent.

Other forms of injury to host tissue will activate complement via LEA-2, in particular injury to the vascular endothelium. Human vascular endothelial cells subject to oxidative stress, for example, respond by expressing surface moieties that bind lectins and activate the LEA-2 pathway of complement (Collard et al., *Am J. Pathol* 156(5):1549-56, 2000). Vascular injury following ischemia/reperfusion also activates complement via LEA-2 in vivo (Moller-Kristensen et al., *Scand J Immunol* 61(5):426-34, 2005). Lectin pathway activation in this setting has pathological consequences for the host, and as shown in Examples 22 and 23, inhibition of LEA-2 by blocking MASP-2 prevents further host tissue injury and adverse outcomes (see also Schwaeble PNAS, 2011, supra).

Thus, other processes that precipitate aHUS are also known to activate LEA-1 or LEA-2. It is therefore likely that the LEA-1 and/or LEA-2 pathway may represent the initial complement activating mechanism that is inappropriately amplified in a deregulated fashion in individuals genetically predisposed to aHUS, thus initiating aHUS pathogenesis. By inference, agents that block activation of complement via LEA-1 and/or LEA-2 are expected to prevent disease progression or reduce exacerbations in aHUS susceptible individuals.

In further support of this concept, recent studies have identified *Streptococcus-pneumoniae* as an important etiological agent in pediatric cases of aHUS. (Lee, C. S. et al, *Nephrology*, 17(1):48-52 (2012); Banerjee R. et al., *Pediatr Infect Dis J.*, 30(9):736-9 (2011)). This particular etiology appears to have an unfavorable prognosis, with significant mortality and long-term morbidity. Notably, these cases involved non-enteric infections leading to manifestations of microangiopathy, uremia and hemolysis without evidence of concurrent mutations in complement genes known to predispose to aHUS. It is important to note that *S. pneumoniae* is particularly effective at activating complement, and does so predominantly through LEA-2. Thus, in cases of non-enteric HUS associated with pneumococcal infection, manifestations of microangiopathy, uremia and hemolysis are expected to be driven predominantly by activation of LEA-2, and agents that block LEA-2, including MASP-2 antibodies, are expected to prevent progression of aHUS or reduce disease severity in these patients. Accordingly, another aspect of the present invention comprises treating a patient suffering with non-enteric aHUS that is associated with *S. pneumoniae* infection by administering an effective amount of a MASP-2 inhibitory agent.

TTP

Thrombotic thrombocytopenic purpura (TTP) is a life-threatening disorder of the blood-coagulation system caused by autoimmune or hereditary dysfunctions that activate the coagulation cascade or the complement system (George, J N, *N Engl J Med;* 354:1927-35, 2006). This results in numerous microscopic clots, or thromboses, in small blood vessels throughout the body, which is a characteristic feature of TMAs. Red blood cells are subjected to shear stress, which damages their membranes, leading to intravascular hemolysis. The resulting reduced blood flow and endothelial injury results in organ damage, including brain, heart, and kidneys. TTP is clinically characterized by thrombocytopenia, microangiopathic hemolytic anemia, neurological changes, renal failure and fever. In the era before plasma exchange, the fatality rate was 90% during acute episodes. Even with plasma exchange, survival at six months is about 80%.

TTP may arise from genetic or acquired inhibition of the enzyme ADAMTS-13, a metalloprotease responsible for cleaving large multimers of von Willebrand factor (vWF) into smaller units. ADAMTS-13 inhibition or deficiency ultimately results in increased coagulation (Tsai, H. *J Am Soc Nephrol* 14: 1072-1081, 2003). ADAMTS-13 regulates the activity of vWF; in the absence of ADAMTS-13, vWF forms large multimers that are more likely to bind platelets and predisposes patients to platelet aggregation and thrombosis in the microvasculature.

Numerous mutations in ADAMTS13 have been identified in individuals with TTP. The disease can also develop due to autoantibodies against ADAMTS-13. In addition, TTP can develop during breast, gastrointestinal tract, or prostate cancer (George J N., Oncology (Williston Park). 25:908-14, 2011), pregnancy (second trimester or postpartum), (George J N., *Curr Opin Hematol* 10:339-344, 2003), or is associated with diseases, such as HIV or autoimmune diseases like systemic lupus erythematosis (Hamasaki K, et al., *Clin Rheumatol.* 22:355-8, 2003). TTP can also be caused by certain drug therapies, including heparin, quinine, immune mediated ingredient, cancer chemotherapeutic agents (bleomycin, cisplatin, cytosine arabinoside, daunomycin gemcitabine, mitomycin C, and tamoxifen), cyclosporine A, oral contraceptives, penicillin, rifampin and anti-platelet drugs including ticlopidine and clopidogrel (Azarm, T. et al., *J Res Med Sci.,* 16: 353-357, 2011). Other factors or conditions associated with TTP are toxins such as bee venoms, sepsis, splenic sequestration, transplantation, vasculitis, vascular surgery, and infections like *Streptococcus pneumoniae* and cytomegalovirus (Moake J L., *N Engl J Med.,* 347:589-600, 2002). TTP due to transient functional ADAMTS-13 deficiency can occur as a consequence of endothelial cell injury associated with *S. pneumoniae* infection (*Pediatr Nephrol,* 26:631-5, 2011).

Plasma exchange is the standard treatment for TTP (Rock G A, et al., *N Engl J Med* 325:393-397, 1991). Plasma exchange replaces ADAMTS-13 activity in patients with genetic defects and removes ADAMTS-13 autoantibodies in those patients with acquired autoimmune TTP (Tsai, H-M, *Hematol Oncol Clin North Am.,* 21(4): 609-v, 2007). Additional agents such as immunosuppressive drugs are routinely added to therapy (George, J N, *N Engl J Med,* 354:1927-35, 2006). However, plasma exchange is not successful for about 20% of patients, relapse occurs in more than a third of patients, and plasmapheresis is costly and technically demanding. Furthermore, many patients are unable to tolerate plasma exchange. Consequently, there remains a critical need for additional and better treatments for TTP.

Because TTP is a disorder of the blood coagulation cascade, treatment with antagonists of the complement system may aid in stabilizing and correcting the disease. While pathological activation of the alternative complement pathway is linked to aHUS, the role of complement activation in TTP is less clear. The functional deficiency of ADAMTS13 is important for the susceptibility to TTP, however it is not sufficient to cause acute episodes. Environmental factors and/or other genetic variations may contribute to the manifestation of TTP. For example, genes encoding proteins involved in the regulation of the coagulation cascade, vWF, platelet function, components of the endothelial vessel surface, or the complement system may be implicated in the development of acute thrombotic microangiopathy (Galbusera, M. et al., *Haematologica,* 94: 166-170, 2009). In particular, complement activation has been shown to play a critical role; serum from thrombotic microangiopathy associated with ADAMTS-13 deficiency has been shown to cause C3 and MAC deposition and subsequent neutrophil activation which could be abrogated by complement inactivation (Ruiz-Torres M P, et al., *Thromb Haemost,* 93:443-52, 2005). In addition, it has recently been shown that during acute episodes of TTP there are increased levels of C4d, C3bBbP, and C3a (M. Réti et al., *J Thromb Haemost.* 10(5):791-798, 2012), consistent with activation of the classical, lectin and alternative pathways. This increased amount of complement activation in acute episodes may initiate the terminal pathway activation and be responsible for further exacerbation of TTP.

The role of ADAMTS-13 and vWF in TTP clearly is responsible for activation and aggregation of platelets and their subsequent role in shear stress and deposition in microangiopathies. Activated platelets interact with and trigger both the classical and alternative pathways of complement. Platelet-mediated complement activation increases the inflammatory mediators C3a and C5a (Peerschke E. et al., *Mol Immunol,* 47:2170-5 (2010)). Platelets may thus serve as targets of classical complement activation in inherited or autoimmune TTP.

As described above, the lectin-dependent activation of complement, by virtue of the thrombin-like activity of MASP-1 and the LEA-2-mediated prothombin activation, is the dominant molecular pathway linking endothelial injury to the coagulation and microvascular thrombosis that occurs in HUS. Similarly, activation of LEA-1 and LEA-2 may directly drive the coagulation system in TTP. LEA-1 and LEA-2 pathway activation may be initiated in response to the initial endothelium injury caused by ADAMTS-13 deficiency in TTP. It is therefore expected that LEA-1 and LEA-2 inhibitors, including but not limited to antibodies that block MASP-2 function, MASP-1 function, MASP-3 function, or MASP-1 and MASP-3 function will mitigate the microangiopathies associated with microvascular coagulation, thrombosis, and hemolysis in patients suffering from TTP.

Patients suffering from TTP typically present in the emergency room with one or more of the following: purpura, renal failure, low platelets, anemia and/or thrombosis, including stroke. The current standard of care for TTP involves intra-catheter delivery (e.g., intravenous or other form of catheter) of replacement plasmapheresis for a period of two weeks or longer, typically three times a week, but up to daily. If the subject tests positive for the presence of an inhibitor of ADAMTS13 (i.e., an endogenous antibody against ADAMTS13), then the plasmapheresis may be carried out in combination with immunosuppressive therapy (e.g., corticosteroids, rituxan, or cyclosporine). Subjects with refractory TTP (approximately 20% of TTP patients) do not respond to at least two weeks of plasmapheresis therapy.

In accordance with the foregoing, in one embodiment, in the setting of an initial diagnosis of TTP, or in a subject exhibiting one or more symptoms consistent with a diagnosis of TTP (e.g., central nervous system involvement, severe thrombocytopenia (a platelet count of less than or equal to 5000/μL if off aspirin, less than or equal to 20,000/μL if on aspirin), severe cardiac involvement, severe pulmonary involvement, gastro-intestinal infarction or gangrene), a method is provided for treating the subject with an effective amount of a LEA-2 inhibitory agent (e.g., a MASP-2 antibody) or a LEA-1 inhibitory agent (e.g., a MASP-1 or MASP-3 antibody) as a first line therapy in the absence of plasmapheresis, or in combination with plasmapheresis. As a first-line therapy, the LEA-1 and/or LEA-2 inhibitory agent may be administered to the subject systemically, such as by intra arterial, intravenous, intramuscular, inhalational, nasal, subcutaneous or other parenteral administration. In some embodiments, the LEA-1 and/or LEA-2 inhibitory agent is administered to a subject as a first-line therapy in the absence of plasmapheresis to avoid the potential complications of plasmapheresis, such as hemorrhage, infection, and exposure to disorders and/or allergies inherent in the plasma donor, or in a subject otherwise averse to plasmapheresis, or in a setting where plasmapheresis is unavailable. In some embodiments, the LEA-1 and/or LEA-2 inhibitory agent is administered to the subject suffering from TTP in combination (including co-administration) with an immunosuppressive agent (e.g., corticosteroids, rituxan or cyclosporine) and/or in combination with concentrated ADAMTS-13.

In some embodiments, the method comprises administering a LEA-1 and/or LEA-2 inhibitory agent to a subject suffering from TTP via a catheter (e.g., intravenously) for a first time period (e.g., an acute phase lasting at least one day to a week or two weeks) followed by administering a LEA-1 and/or LEA-2 inhibitory agent to the subject subcutaneously for a second time period (e.g., a chronic phase of at least two weeks or longer). In some embodiments, the administration in the first and/or second time period occurs in the absence of plasmapheresis. In some embodiments, the method is used to maintain the subject to prevent the subject from suffering one or more symptoms associated with TTP.

In another embodiment, a method is provided for treating a subject suffering from refractory TTP (i.e., a subject that has not responded to at least two weeks of plasmaphoresis therapy), by administering an amount of a LEA-1 and/or LEA-2 inhibitor effective to reduce one or more symptoms of TTP. In one embodiment, the LEA-1 and/or LEA-2 inhibitor is administered to a subject with refractory TTP on a chronic basis, over a time period of at least two weeks or longer via subcutaneous or other parenteral administration. Administration may be repeated as determined by a physician until the condition has been resolved or is controlled.

In some embodiments, the method further comprises determining the level of at least one complement factor (e.g., C3, C5) in the subject prior to treatment, and optionally during treatment, wherein the determination of a reduced level of the at least one complement factor in comparison to a standard value or healthy control subject is indicative of the need for continued treatment with the LEA-1 and/or LEA-2 inhibitory agent.

In some embodiments, the method comprises administering, either subcutaneously or intravenously, a LEA-1 and/or LEA-2 inhibitory agent to a subject suffering from, or at risk for developing, TTP. Treatment is preferably daily, but can be as infrequent as monthly. Treatment is continued until the subject's platelet count is greater than 150,000/ml for at least two consecutive days.

In summary, LEA-1 and LEA-2 inhibitors are expected to have independent therapeutic benefit in the treatment of TMAs, including HUS, aHUS and TTP. In addition, LEA-1 and LEA-2 inhibitors used together are expected to achieve additional treatment benefit compared to either agent alone, or may provide effective treatment for a wider spectrum of patient subsets suffering from variant forms of TMA. Combined LEA-1 and LEA-2 inhibition may be accomplished by co-administration of a LEA-1 blocking agent and a LEA2 blocking agent. Optimally, LEA-1 and LEA-2 inhibitory function may be encompassed in a single molecular entity, such as a bispecific antibody composed of MASP-1/3 and a MASP-2-specific binding site, or a dual specificity antibody where each binding site can bind to and block MASP-1/3 or MASP-2.

In accordance with the foregoing, an aspect of the invention thus provides a method for inhibiting LEA-1 dependent complement activation for treating, preventing, or reducing the severity of a thrombotic microangiopathy, such as hemolytic uremic syndrome (HUS), atypical hemolytic uremic syndrome (aHUS) or thrombotic thrombocytopenic purpura (TTP) comprising administering a composition comprising a therapeutically effective amount of a LEA-1 inhibitory agent comprising a MASP 1 inhibitory agent, a MASP 3 inhibitory agent, or a combination of a MASP 1/3 inhibitory agent, in a pharmaceutical carrier to a subject suffering from, or at risk for developing a thrombotic microangiopathy. The MASP 1, MASP 3, or MASP 1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In one embodiment, the method according to this aspect of the invention further comprises inhibiting LEA-2-dependent complement activation for treating, preventing, or reducing the severity of a thrombotic microangiopathy, such as hemolytic uremic syndrome (HUS), atypical hemolytic uremic syndrome (aHUS) or thrombotic thrombocytopenic purpura (TTP) comprising administering a therapeutically effective amount of a MASP-2 inhibitory agent and a MASP-1, MASP-3, or MASP-1/3 inhibitory agent to a subject suffering from, or at risk for developing a thrombotic microangiopathy. As detailed above, the use of a combination of pharmacologic agents that individually block LEA-1 and LEA-2, is expected to provide an improved therapeutic outcome in treating or preventing or reducing the severity of a thrombotic microangiopathy as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and optional MASP-2 inhibitory compositions of the present invention may be carried out by a single administration of the composition (e.g., a single composition comprising MASP-2 and MASP-3 inhibitory agents, or bispecific or dual inhibitory agents, or co-administration of separate compositions), or a limited sequence of administrations, for treating, preventing or reducing the severity of a thrombotic microangiopathy in a subject suffering from, or at risk for developing, a thrombotic microangiopathy. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as a thrombotic microangiopathy (e.g., hemolytic uremic syndrome (HUS), atypical hemolytic uremic syndrome (aHUS), or thrombotic thrombocytopenic purpura (TTP).

Accordingly, in one embodiment, the present invention provides a method for treating a subject suffering from, or at risk for developing a thrombotic microangiopathy (e.g., hemolytic uremic syndrome (HUS), atypical hemolytic uremic syndrome (aHUS), or thrombotic thrombocytopenic purpura (TTP), comprising an effective amount of a high affinity monoclonal antibody or antigen binding fragment thereof as disclosed herein that binds to human MASP-3 and inhibits alternative pathway complement activation to treat or reduce the risk of developing a thrombotic microangiopathy (e.g., hemolytic uremic syndrome (HUS), atypical hemolytic uremic syndrome (aHUS), thrombotic thrombocytopenic purpura (TTP), or transplant-related TMA (TA-TMA), such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

G. The Role of MASP-3 in Asthma and Therapeutic Methods Using MASP-3 Inhibitory Antibodies, Optionally in Combination with MASP-2 Inhibitory Agents Asthma is a common chronic inflammatory disease of the airways. Approximately 25 million people in the United States have asthma, including seven million children under the age of 18, with more than half experiencing at least one asthma attack each year, leading to more than 1.7 million emergency department visits and 450,000 hospitalizations annually (world-wide-web at gov/health/prof/lung/asthma/naci/asthma-info/index.htm., accessed on May 4, 2012). The disease is heterogeneous with multiple clinical phenotypes. The most common phenotype is allergic asthma. Other phenotypes include nonallergic asthma, aspirin-exacerbated respiratory disease, post-infectious asthma, occupational asthma, airborne irritant-induced asthma, and exercise-induced asthma. The cardinal features of allergic asthma include airway hyperresponsiveness (AHR) to a variety of specific and nonspecific stimuli, excessive airway mucus production, pulmonary eosinophilia, and elevated concentration of serum IgE. The symptoms of asthma include coughing, wheezing, chest tightness, and shortness of breath. The goal of asthma treatment is to control the disease and minimize exacerbations, daily symptoms, and allow patients to be physically active. Current treatment guidelines recommend stepwise treatments until asthma control is attained. The first treatment step is as needed rapid-acting inhaled β2-agonist, followed by addition of controller medications such as inhaled corticosteroids, long-acting inhaled β2-agonists, leukotriene modifier drugs, theophylline, oral glucocorticosteroids, and anti-IgE monoclonal antibody.

Although asthma is multifactorial in origin, it is generally accepted that it arises as a result of inappropriate immunological responses to common environmental antigens in genetically susceptible individuals. Asthma is associated with complement activation and the anaphylatoxins (AT) C3a and C5a have proinflammatory and immunoregulatory properties that are relevant to the development and modulation of the allergic response (Zhang, X. and Kohl, J. *Expert. Rev. Clin. Immunol.*, 6:269-277, 2010). However, the relative involvement of the classical, alternative, and lectin pathways of complement in asthma is not well understood. The alternative pathway may be activated on the surface of allergens and the lectin pathway may be activated through recognition of allergen polysaccharide structures, both processes leading to the generation of AT. Complement may be activated by different pathways depending on the causative allergen involved. Highly allergic grass pollen of the Parietaria family for example is very effective at promoting MBL-dependent activation of C4, implicating LEA-2. Conversely, house dust mite allergen does not require MBL for complement activation (Varga et al. *Mol Immunol.*, 39(14):839-46, 2003).

Environmental triggers of asthma may activate complement by the alternative pathway. For example, in vitro exposure of human serum to cigarette smoke or diesel exhaust particles resulted in activation of complement and the effect was unaffected by the presence of EDTA, suggesting activation was via the alternative rather than classical pathway (Robbins, R. A. et al, *Am. J. Physiol.* 260: L254-L259, 1991; Kanemitsu, H., et al., *Biol. Pharm. Bull.* 21:129-132, 1998). The role of complement pathways in allergic airway inflammation was evaluated in a mouse ovalbumin sensitization and challenge model. Wild-type mice developed AHR and airway inflammation in response to aeroallergen challenge. A Crry-Ig fusion protein which inhibits all pathways of complement activation, was effective in preventing AHR and lung inflammation when administered systemically or locally by inhalation in the mouse ovalbumine model of allergic lung inflammation (Taube et al., *Am J Respir Crit Care Med.,* 168(11):1333-41, 2003).

In comparison to wild-type mice, factor B-deficient mice demonstrated less AHR and airway inflammation whereas C4-deficient mice had similar effects as wild-type mice (Taube, C., et al., *Proc. Natl. Acad. Sci. USA* 103:8084-8089, 2006). These results support a role for alternative pathway and not classical pathway involvement in the murine aeroallergen challenge model. Further evidence for the importance of the alternative pathway was provided in a study of factor H (FH) using the same mouse model (Takeda, K., et al., *J. Immunol.* 188:661-667, 2012). FH is a negative regulator of the alternative pathway and acts to prevent autologous injury of self tissues. Endogenous FH was found to be present in airways during allergen challenge and inhibition of FH with a recombinant competitive antagonist increased the extent of AHR and airway inflammation (Takeda et al., 2012, supra). Therapeutic delivery of CR2-fH, a chimeric protein that links the iC3b/C3d binding region of CR2 to the complement-regulatory region of FH which targets the complement regulatory activity of fH to sites of existing complement activation, protected the development of AHR and eosinophil infiltration into the airways after allergen challenge (Takeda et al., 2012, supra). The protective effect was demonstrated with ovalbumin as well as ragweed allergen, which is a relevant allergen in humans.

The role of lectin-dependent complement activation in asthma was evaluated in a mouse model of fungal asthma (Hogaboam et al., *J. Leukocyte Biol.* 75:805 814, 2004). These studies used mice genetically deficient in mannan binding lectin A (MBL-A), a carbohydrate binding protein that functions as the recognition component for activation of the lectin complement pathways. MBL-A(+/+) and MBL-A (−/−) *Aspergillus. fumigatus* sensitized mice were examined at days 4 and 28 after an i.t. challenge with *A. fumigatus* conidia. AHR in sensitized MBL-A(−/−) mice was significantly attenuated at both times after conidia challenge compared with the sensitized MBL-A(+/+) group. Lung TH2 cytokine levels (IL-4, IL-5 and IL-13) were significantly lower in *A. fumigatus*-sensitized MBL-A(−/−) mice compared to the wild-type group at day 4 after conidia. These results indicate that MBL-A and the lectin pathway have a major role in the development and maintenance of AHR during chronic fungal asthma.

The findings detailed above suggest the involvement of lectin-dependent complement activation in the pathogenesis of asthma. Experimental data suggest that factor B activation plays a pivotal role. In light of the fundamental role for LEA-1 in the lectin-dependent activation of factor B and subsequent activation of the alternative pathway, it is expected that LEA-1 blocking agents will be beneficial for the treatment of certain forms of asthma mediated by the alternative pathway. Such a treatment may thus be particularly useful in house dust mite-induced asthma, or asthma caused by environmental triggers such as cigarette smoke or diesel exhaust. Asthmatic responses triggered by grass pollen on the other hand are likely to invoke LEA-2-dependent complement activation. Therefore, LEA-2-blocking agents are expected to be particularly useful in treating the asthmatic conditions in this subset of patients.

In view of the data detailed above, the inventors believe that LEA-1 and LEA-2 mediate pathologic complement activation in asthma. Depending on the inciting allergic agent, LEA-1 or LEA-2 may be preferentially involved. Thus, a LEA-1-blocking agent combined with a LEA-2-blocking agent may have utility in the treatment of multiple forms of asthma regardless of the underlying etiology. LEA-1 and LEA-2-blocking agents may have complementary, additive or synergistic effects in preventing, treating or reversing pulmonary inflammation and symptoms of asthma.

Combined LEA-1 and LEA-2 inhibition may be accomplished by co-administration of a LEA-1-blocking agent and a LEA2-blocking agent. Optimally, LEA-1 and LEA-2 inhibitory function may be encompassed in a single molecular entity, such as a bispecific antibody composed of MASP-1/3 and a MASP-2-specific binding site, or a dual specificity antibody where each binding site can bind to and block MASP-1/3 or MASP-2.

In accordance with the foregoing, an aspect of the invention thus provides a method for inhibiting LEA-1 dependent complement activation for treating, preventing, or reducing the severity of asthma, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing asthma. The MASP-1, MASP-3, or MASP-1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In one embodiment, the method according to this aspect of the invention further comprises inhibiting LEA-2-dependent complement activation for treating, preventing, or reducing the severity of asthma, comprising administering a therapeutically effective amount of a MASP-2 inhibitory agent and a MASP-1, MASP-3, or MASP-1/3 inhibitory agent to a subject suffering from, or at risk for developing asthma. As detailed above, the use of a combination of pharmacologic agents that individually block LEA-1 and LEA-2, is expected to provide an improved therapeutic outcome in treating or preventing or reducing the severity of asthma as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and optional MASP-2 inhibitory compositions of the present invention may be carried out by a single administration of the composition (e.g., a single composition comprising MASP-2 and MASP-3 inhibitory agents, or bispecific or dual inhibitory agents, or co-administration of separate compositions), or a limited sequence of administrations, for treating, preventing or reducing the severity of a asthma in a subject suffering from, or at risk for developing asthma. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as asthma.

Accordingly, in one embodiment, the present invention provides a method for treating a subject suffering from, or at risk for developing asthma comprising an effective amount of a high affinity monoclonal antibody or antigen binding fragment thereof as disclosed herein that binds to human MASP-3 and inhibits alternative pathway complement activation to treat or reduce the risk of developing asthma, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

H. The Role of MASP-3 in Dense Deposit Disease, and Therapeutic Methods Using MASP-3 Inhibitory Antibodies, Optionally in Combination with MASP-2 Inhibitory Agents Membranoproliferative glomerulonephritis (MPGN) is a kidney disorder characterized morphologically by mesangial cell proliferation and thickening of the glomerular capillary wall due to subendothelial extension of the mesangium. MPGN is classified as primary (also referred to as idiopathic) or secondary, with underlying diseases such as infectious diseases, systemic immune complex diseases, neoplasms, chronic liver disease, and others. Idiopathic MPGN includes three morphologic types. Type I, or classical MPGN, is characterized by subendothelial deposits of immune complexes and activation of the classical complement pathway. Type II, or dense deposit disease (DDD), is characterized by additional intra-membraneous dense deposits. Type III is characterized by additional subepithelial deposits. Idiopathic MPGN is rare, accounting for approximately 4 to 7% of primary renal causes of nephrotic syndrome (Alchi, B. and Jayne, D. *Pediatr. Nephrol.* 25:1409-1418, 2010). MPGN primarily affects children and young adults and may present as nephrotic syndrome, acute nephritic syndrome, asymptomatic proteinuria and hematuria, or recurrent gross hematuria. Renal dysfunction occurs in the majority of patients and the disease has a slowly progressive course, with approximately 40% of patients developing end-stage renal disease within 10 years of diagnosis (Alchi and Jayne, 2010, supra). Current treatment options include corticosteroids, immunosuppressives, antiplatelet regimens, and plasma exchange.

DDD is diagnosed by the absence of immunoglobulin and presence of C3 by immunofluorescence staining of renal biopsies, and electron microscopy shows characteristic dense osmiophilic deposits along the glomerular basement membranes. DDD is caused by dysregulation of the alternative pathway of complement (Sethi et al, *Clin J Am Soc Nephrol.* 6(5):1009-17, 2011), which can arise from a number of different mechanisms. The most common complement system abnormality in DDD is the presence of C3 nephritic factors which are autoantibodies to the alternative pathway C3 convertase (C3bBb) that increases its half-life and therefore activation of the pathway (Smith, R. J. H. et al., *Mol. Immunol.* 48:1604-1610, 2011). Other alternative pathway abnormalities include factor H autoantibody that blocks the function of factor H, gain of function C3 mutations, and genetic deficiency of factor H (Smith et al., 2011, supra). Recent case reports show that eclizumab (anti-C5 monoclonal antibody) treatment was associated with improvements in renal function in two patients with DDD (Daina, E. et al., *New Engl. J. Med.* 366:1161-1163, 2012; Vivarelli, M. et al., *New Engl. J. Med.* 366:1163-1165, 2012), suggesting a causative role for complement activation in renal outcomes.

Given the above genetic, functional and immunohistochemical and anecdotal clinical data, the central role for complement in the pathogenesis of DDD is well established. Thus, interventions that block the disease-causing mechanisms of complement activation, or the subsequent complement activation products, are expected to be therapeutically useful to treat this condition.

While the human genetic data suggest that inappropriate control or excessive activation of the alternative pathways amplification loop plays a key role, complement-initiating events have not been identified. Immunohistochemical studies in renal biopsies show evidence of MBL deposition in diseased tissue, suggesting involvement of the lectin pathways in the initiation of pathological complement activation in DDD (Lhotta et al, *Nephrol Dial Transplant.*, 14(4):881-6, 1999). The importance of the alternative pathway has been further corroborated in experimental models. Factor H-deficient mice develop progressive proteinuria and the renal pathological lesions characteristic of the human condition (Pickering et al., *Nat Genet.*, 31(4):424, 2002). Pickering et al. further demonstrated that ablation of factor B, which mediates LEA-1-dependent activation of the alternative pathway, fully protects factor H-deficient mice from DDD (Pickering et al., *Nat Genet.*, 31(4):424, 2002).

Thus it is expected that agents that block LEA-1 will effectively block lectin-dependent activation of the alternative pathway, and will thus provide an effective treatment for DDD. Given that the alternative pathway amplification loop is dysregulated in DDD patients, it can further be expected that agents that block the amplification loop will be effective. Since LEA-1-targeting agents that block MASP-1 or MASP-1 and MASP-3 inhibit the maturation of factor D, such agents are predicted to effectively block the alternative pathway amplification loop.

As detailed above, pronounced MBL deposition has been found in diseased renal specimens, highlighting the probable involvement of lectin-driven activation events in DDD pathogenesis. Once an initial tissue injury to the glomerular capillaries is established, it is likely that additional MBL binding to injured glomerular endothelium and underlying mesangial structures occurs. Such tissue injuries are well known to lead to activation of LEA-2, which can thus cause further complement activation. Therefore, LEA-2-blocking agents are also expected to have utility in preventing further complement activation on injured glomerular structures, and thus forestall further disease progression towards end stage renal failure.

The data detailed above suggest that LEA-1 and LEA-2 promote separate pathologic complement activation processes in DDD. Thus, a LEA-1-blocking agent and a LEA-2 blocking agent, either alone or in combination are expected to be useful for treating DDD.

When used in combination, LEA-1- and LEA-2-blocking agents are expected to be more efficacious than either agent alone, or useful for treating different stages of the disease. LEA-1- and LEA-2-blocking agents may thus have complementary, additive or synergistic effects in preventing, treating or reversing DDD-associated renal dysfunction.

Combined LEA-1 and LEA-2 inhibition may be accomplished by co-administration of a LEA-1 blocking agent and a LEA2 blocking agent. Optimally, LEA-1 and LEA-2 blocking agents with inhibitory function may be encompassed in a single molecular entity, such as a bispecific antibody composed of MASP-1/3 and a MASP-2-specific binding site, or a dual-specificity antibody where each binding site can bind to and block MASP-1/3 or MASP-2.

In accordance with the foregoing, an aspect of the invention thus provides a method for inhibiting LEA-1 dependent complement activation for treating, preventing, or reducing the severity of dense deposit disease, comprising administering a composition comprising a therapeutically effective amount of a LEA-1 inhibitory agent comprising a MASP 1 inhibitory agent, a MASP 3 inhibitory agent, or a combination of a MASP 1/3 inhibitory agent, in a pharmaceutical carrier to a subject suffering from, or at risk for developing dense deposit disease. The MASP-1, MASP-3, or MASP-1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing, or reducing the severity of dense deposit disease, comprising administering a therapeutically effective amount of a MASP-2 inhibitory agent to a subject suffering from, or at risk for developing dense deposit disease. In another aspect, a method is provided comprising inhibiting both LEA-1 and LEA-2-dependent complement activation for treating, preventing, or reducing the severity of dense deposit disease, comprising administering a therapeutically effective amount of a MASP-2 inhibitory agent and a MASP-1, MASP-3, or MASP-1/3-inhibitory agent to a subject suffering from, or at risk for developing dense deposit disease.

In some embodiments, the method comprises inhibiting both LEA-1-dependent complement activation and LEA-2-dependent complement activation. As detailed above, the use of a combination of pharmacologic agents that individually block LEA-1 and LEA-2, is expected to provide an improved therapeutic outcome in treating, preventing or reducing the severity of dense deposit disease as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The LEA-1 and/or LEA-2 inhibitory agents may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating, preventing or reducing the severity of dense deposit disease in a subject in need thereof. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as dense deposit disease.

Accordingly, in one embodiment, the present invention provides a method for treating a subject suffering from, or at risk for developing dense deposit disease comprising an effective amount of a high affinity monoclonal antibody or antigen binding fragment thereof as disclosed herein that binds to human MASP-3 and inhibits alternative pathway complement activation to treat or reduce the risk of developing dense deposit disease, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

I. The Role of MASP-3 in Pauci-Immune Necrotizing Crescentic Glomerulonephritis, and Therapeutic Methods Using MASP-3 Inhibitory Antibodies, Optionally in Combination with and MASP-2 Inhibitory Agents Pauci-immune necrotizing crescentic glomerulonephritis (NCGN) is a form of rapidly progressive glomerulonephritis in which glomerular capillary walls show signs of inflammation yet have a paucity of detectable immunocomplex deposition or antibodies against the glomerular basement membrane. The condition is associated with a rapid decline in renal function. Most patients with NCGN are found to have antineutrophil cytoplasmic autoantibodies (ANCA) and thus belong to a group of diseases termed ANCA-associated vasculitis. Vasculitis is a disorder of blood vessels characterized by inflammation and fibrinoid necrosis of the vessel wall. Systemic vasculitides are classified based on vessel size: large, medium, and small. Several forms of small-vessel vasculitis are associated with the presence of ANCA, namely Wegener granulomatosis, microscopic polyangiitis, Churg-Strauss syndrome, and renal-limited vasculitis (NCGN). They can also be a manifestation of underlying conditions such as systemic lupus erythematosus. The target antigens for ANCA include proteinase-3 (PR3) and myeloperoxidase (MPO). Pauci-immune NCGN is rare, with a reported incidence of approximately 4 per million in Wessex, United Kingdom (Hedger, N. et al., *Nephrol. Dial. Transplant.* 15:1593-1599, 2000). In the Wessex series of 128 patients with pauci-immune NCGN, 73% were ANCA-positive and initial dialysis was required by 59% of patients and 36% needed long-term dialysis. Treatments for pauci-immune NCGN include corticosteroids and immunosuppressive agents such as cyclophosphamide and azathioprine. Additional treatment options for ANCA-associated vasculitides include rituximab and plasma exchange (Chen, M. and Kallenberg, C. G. M. *Nat. Rev. Rheumatol.* 6:653-664, 2010).

Although NCGN is characterized by a paucity of complement deposition, the alternative pathway of complement has been implicated in its pathogenesis. A renal biopsy evaluation of 7 patients with MPO-ANCA-associated pauci-immune NCGN detected the presence of membrane attack complex, C3d, factor B, and factor P (which were not detected in biopsies from normal controls or patients with minimal change disease), whereas C4d and mannose binding lectin were not detected, suggesting selective activation of the alternative pathway (Xing, G. Q. et al. *J. Clin. Immunol.* 29:282-291, 2009). Experimental NCGN can be induced by transfer of anti-MPO IgG into wild-type mice or anti-MPO splenocytes into immune-deficient mice (Xiao, H. et al. *J. Clin. Invest.* 110:955-963, 2002). In this mouse model of NCGN, the role of specific complement activation pathways was investigated using knockout mice. After injection of anti-MPO IgG, C4−/− mice developed renal disease comparable to wild-type mice whereas C5−/− and factor B−/− mice did not develop renal disease, indicating that the alternative pathway was involved in this model and the classical and lectin pathways were not (Xiao, H. et al. *Am. J. Pathol.* 170:52-64, 2007). Moreover, incubation of MPO-ANCA or PR3-ANCA IgG from patients with TNF-primed human neutrophils caused release of factors that resulted in complement activation in normal human serum as detected by generation of C3a; this effect was not observed with IgG from healthy subjects, suggesting the potential pathogenic role of ANCA in neutrophil and complement activation (Xiao et al., 2007, supra).

Based on the role outlined above for the alternative pathway in this condition, it is expected that blocking the activation of the alternative pathway will have utility in the treatment of ANCA positive NCGN. Given the requirement for fB activation for pathogenesis, it is expected that inhibitors of LEA-1 will be particularly useful in treating this condition, and in preventing the further decline in renal function in these patients.

Yet another subset of patients develops progressive renal vasculitis with crescent formation accompanied by a rapid decline in renal function in the absence of ANCA. This form of the condition is termed ANCA-negative NCGN and constitutes about one third of all patients with pauci immune NCGN (Chen et al, *JASN* 18(2): 599-605, 2007). These patients tend to be younger, and renal outcomes tend to be particularly severe. (Chen et al., *Nat Rev Nephrol.*, 5(6): 313-8, 2009). A discriminating pathological feature of these patients is the deposition of MBL and C4d in renal lesions (Xing et al., *J Clin Immunol.* 30(1):144-56, 2010). MBL and C4d staining intensity in renal biopsies correlated negatively with renal function (Xing et al., 2010, supra). These findings suggest an important role for lectin-dependent complement activation in pathogenesis. The fact that C4d, but not factor B is commonly found in diseased tissue specimens indicates LEA-2 involvement.

Based on the role of lectin-dependent complement activation in ANCA negative NCGN described above, it is expected that blocking the activation of the LEA-2 pathway will have utility in the treatment of ANCA negative NCGN.

The data detailed above suggest that LEA-1 and LEA-2 mediate pathologic complement activation in ANCA-positive and ANCA-negative NCGN, respectively. Thus, a LEA-1-blocking agent combined with a LEA-2-blocking agent is expected to have utility in the treatment of all forms of pauci-immune NCGN, regardless of the underlying etiology. LEA-1- and LEA-2-blocking agents may thus have complementary, additive or synergistic effects in preventing, treating or reversing NCGN-associated renal dysfunction.

LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1 blocking agent and a LEA-2 blocking agent. Optimally, LEA-1 and LEA-2 inhibitory function may be encompassed in a single molecular entity, such as a bispecific antibody composed of MASP-1/3 and a MASP-2-specific binding site, or a dual-specificity antibody where each binding site can bind to and block MASP-1/3 or MASP-2.

In accordance with the foregoing, an aspect of the invention thus provides a method for inhibiting LEA-1 dependent complement activation for treating, preventing, or reducing the severity of pauci-immune necrotizing crescentic glomerulonephritis, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing pauci-immune necrotizing crescentic glomerulonephritis. The MASP-1, MASP-3, or MASP-1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing, or reducing the severity of pauci-immune necrotizing crescentic glomerulonephritis, comprising administering a therapeutically effective amount of a MASP-2 inhibitory agent to a subject suffering from, or at risk for developing pauci-immune necrotizing crescentic glomerulonephritis. In another aspect, a method is provided comprising inhibiting both LEA-1 and LEA-2-dependent complement activation for treating, preventing, or reducing the severity of pauci-immune necrotizing crescentic glomerulonephritis, comprising administering a therapeutically effective amount of a MASP-2 inhibitory agent and a MASP-1, MASP-3, or MASP-1/3 inhibitory agent to a subject in need thereof.

In some embodiments, the method comprises inhibiting both LEA-1-dependent complement activation and LEA-2-dependent complement activation. As detailed above, the use of a combination of pharmacologic agents that individually block LEA-1 and LEA-2, is expected to provide an improved therapeutic outcome in treating or preventing or reducing the severity of pauci-immune necrotizing crescentic glomerulonephritis as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating, preventing or reducing the severity of pauci-immune necrotizing crescentic glomerulonephritis. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as Pauci-immune necrotizing crescentic glomerulonephritis (NCGN).

Accordingly, in one embodiment, the present invention provides a method for treating a subject suffering from, or at risk for developing Pauci-immune necrotizing crescentic glomerulonephritis (NCGN) comprising an effective amount of a high affinity monoclonal antibody or antigen binding fragment thereof as disclosed herein that binds to human MASP-3 and inhibits alternative pathway complement activation to treat or reduce the risk of developing Pauci-immune necrotizing crescentic glomerulonephritis (NCGN), such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

J. The Role of MASP-3 in Traumatic Brain Injury, and Therapeutic Methods Using MASP-3 Inhibitory Antibodies, Optionally in Combination with and MASP-2 Inhibitory Agents Traumatic brain injury (TBI) is a major global health problem that leads to at least 10 million deaths or hospitalizations annually (Langlois, J. A. et al., *J. Head Trauma Rehabil.* 21:375-378, 2006). In 2003 there were an estimated 1.6 million TBIs in the United States, including 1.2 million emergency department visits, 290,000 hospitalizations, and 51,000 deaths (Rutland-Brown, W. et al., *J. Head Trauma Rehabil.* 21:544-548, 2006). The majority of TBIs in the United States are caused by falls and motor vehicle traffic. TBI can result in long-term or lifelong physical, cognitive, behavioral, and emotional consequences. Over 5 million Americans are living with long-term or lifelong disability associated with a TBI (Langlois et al., 2006, supra).

TBI may involve penetration of the brain substance ("penetrating" injuries) or injuries that do not penetrate the brain ("closed" injuries). The injury profiles and associated neurobehavioral sequelae can be quite different between penetrating and closed TBI. Although each injury is unique, certain brain regions are particularly vulnerable to trauma-induced damage, including the frontal cortex and subfrontal white matter, the basal ganglia and diencephalon, the rostral brain stem, and the temporal lobes including the hippocampi (McAllister, T. W. *Dialogues Clin. Neurosci.* 13:287-300, 2011). TBI can lead to changes in several neurotransmitter systems, including release of glutamate and other excitatory amino acids during the acute phase and chronic alterations in the catecholaminergic and cholinergic systems, which may be associated with neurobehavioral disability (McAllister, 2011, supra). Survivors of significant TBI often suffer from cognitive defects, personality changes, and increased psychiatric disorders, particularly depression, anxiety, and post-traumatic stress disorder. Despite intense research, no clinically effective treatment for TBI that can reduce mortality and morbidity and improve functional outcome has yet to be found.

Complement Factors and TBI

Numerous studies have identified a relationship of complement proteins and neurological disorders, including Alzheimer's disease, multiple sclerosis, myasthenia gravis, Guillain-Barré syndrome, cerebral lupus, and stroke (reviewed in Wagner, E., et al., *Nature Rev Drug Disc.* 9: 43-56, 2010). Recently a role for C1q and C3 in synapse elimination has been demonstrated, thus complement factors are likely involved in both normal CNS function and neurodegenerative disease (Stevens, B. et al., *Cell* 131: 1164-1178, 2007). The gene for MASP-1 and MASP-3 is extensively expressed in the brain and also in a glioma cell line, T98G (Kuraya, M. et al., *Int Immunol.,* 15:109-17, 2003), consistent with a role of the lectin pathway in the CNS.

MASP-1 and MASP-3 are key to immediate defense against pathogens and altered self-cells, but the lectin pathway also is responsible for severe tissue damage after stroke, heart attack, and other ischemia reperfusion injuries. Similarly, MASP-1 and MASP-3 are likely mediators in the tissue damage caused by TBI. Inhibition of Factor B in the alternative pathway has been shown to attenuate TBI in two mouse models. Factor B knockout mice are protected from complement-mediated neuroinflammation and neuropathology after TBI (Leinhase I, et al., *BMC Neurosci.* 7:55, 2006). In addition, anti-factor B antibody attenuated cerebral tissue damage and neuronal cell death in TBI induced mice (Leinhase I, et al., *J Neuroinflammation* 4:13, 2007). MASP-3 directly activates Factor B (Iwaki, D. et al., *J Immunol.* 187:3751-8, 2011) and therefore is also a likely mediator in TBI. Similar to inhibition of Factor B, LEA-1 inhibitors, such as antibodies against MASP-3 are expected to provide a promising strategy for treating tissue damage and subsequent sequelae in TBI.

Thus, LEA-1 and LEA-2 inhibitors may have independent therapeutic benefit in TBI. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA2-blocking agent. Optimally, LEA-1 and LEA-2 inhibitory function may be encompassed in a single molecular entity, such as a bispecific antibody composed of MASP-1/3 and a MASP-2-specific binding site, or a dual-specificity antibody where each binding site can bind to and block MASP-1/3 or MASP-2.

In accordance with the foregoing, an aspect of the invention thus provides a method for inhibiting LEA-1 dependent complement activation for treating, or reducing the severity of traumatic brain injury, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from a traumatic brain injury. The MASP-1, MASP-3, or MASP-1/3 inhibitory composition may be administered to the subject systemically, such as by intra arterial, intravenous, intramuscular, inhalational, nasal, intracranial, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, or reducing the severity of traumatic brain injury, comprising administering a therapeutically effective amount of a MASP-2 inhibitory agent to a subject suffering from a traumatic brain injury. In another aspect, a method is provided comprising inhibiting both LEA-1 and LEA-2-dependent complement activation for treating, or reducing the severity of traumatic brain injury, comprising administering a therapeutically effective amount of a MASP-2 inhibitory agent and a MASP-1, MASP-3, or MASP-1/3 inhibitory agent to a subject suffering from a traumatic brain injury.

In some embodiments, the method comprises inhibiting both LEA-1-dependent complement activation and LEA-2-dependent complement activation. As detailed above, the use of a combination of pharmacologic agents that individually block LEA-1 and LEA-2 is expected to provide an improved therapeutic outcome in treating or reducing the severity of traumatic brain injury as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject systemically, such as by intra arterial, intravenous, intramuscular, inhalational, nasal, subcutaneous, intracranial, or other parenteral administration, or potentially by oral administration for non peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating or reducing the severity of traumatic brain injury. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as traumatic brain injury.

Accordingly, in one embodiment, the present invention provides a method for treating a subject suffering from, or at risk for developing traumatic brain injury comprising an effective amount of a high affinity monoclonal antibody or antigen binding fragment thereof as disclosed herein that binds to human MASP-3 and inhibits alternative pathway complement activation to treat or reduce the risk of developing traumatic brain injury, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

K. The Role of MASP-3 in Aspiration Pneumonia, and Therapeutic Methods Using MASP-3 Inhibitory Antibodies, Optionally in Combination with MASP-2 Inhibitory Agents Aspiration is defined as the inhalation of either oropharyngeal or gastric contents into the lower airways. Aspiration may result in complications of aspiration (chemical) pneumonitis, primary bacterial aspiration pneumonia, or secondary bacterial infection of chemical pneumonitis. Risk factors for aspiration include decreased levels of consciousness (e.g., head trauma, alcohol or drug-induced alterations in sensorium, stroke), various gastrointestinal and esophageal abnormalities, and neuromuscular diseases. It is estimated that 5-15% of the 4.5 million cases of community-acquired pneumonia are due to aspiration pneumonia (Marik, P. E. New Engl. J. Med. 344:665-671, 2001). Treatment of chemical pneumonitis is mainly supportive and the use of empiric antibiotics is controversial. Treatment of bacterial aspiration pneumonia is with appropriate antibiotics, which is based on whether the aspiration occurred in the community or in the hospital as the likely causative organisms differ between these settings. Measures should be taken to prevent aspiration in high-risk patients, for example elderly patients in nursing homes who have impaired gag reflexes. Measures that have been shown to be effective prophylaxis include elevation of the head of the bed while feeding, dental prophylaxis, and good oral hygiene. Prophylactic antibiotics have not been shown to be effective and are discouraged as they may lead to the emergence of resistant organisms.

Modulation of complement components has been proposed for numerous clinical indications, including infectious disease—sepsis, viral, bacterial, and fungal infections—and pulmonary conditions—respiratory distress syndrome, chronic obstructive pulmonary disease, and cystic fibrosis (reviewed in Wagner, E., et al., Nature Rev Drug Disc. 9: 43-56, 2010). Support for this proposal is provided by numerous clinical and genetic studies. For example, there is a significantly decreased frequency of patients with low MBL levels with clinical tuberculosis (Soborg et al., Journal of Infectious Diseases 188:777-82, 2003), suggesting that low levels of MBL are associated with protection from disease.

In a murine model of acid aspiration injury, Weiser M R et al., J. Appl. Physiol. 83(4): 1090-1095, 1997, demonstrated that C3-knockout mice were protected from serious injury; whereas C4-knockout mice were not protected, indicating that complement activation is mediated by the alternative pathway. Consequently, blocking the alternative pathway with LEA-1 inhibitors is expected to provide a therapeutic benefit in aspiration pneumonia.

Thus, LEA-1 and LEA-2 inhibitors may have independent therapeutic benefit in aspiration pneumonia. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bi-specific antibody composed of MASP-1/3 and a MASP-2-specific binding site, or a dual-specificity antibody where each binding site binds to and blocks MASP-1/3 or MASP-2.

An aspect of the invention thus provides a method for inhibiting LEA-1 dependent complement activation to treat aspiration pneumonia by administering a composition comprising a therapeutically effective amount of a MASP-1 inhibitory agent, a MASP-3 inhibitory agent, or a combination of a MASP-1/3 inhibitory agent, in a pharmaceutical carrier to a subject suffering from such a condition or other complement mediated pneumonia. The MASP-1, MASP-3, or MASP-1/3 inhibitory composition may be administered locally to the lung, as by an inhaler. Alternately, the MASP-1, MASP-3, or MASP-1/3 inhibitory agent may be administered to the subject systemically, such as by intra arterial, intravenous, intramuscular, inhalational, nasal, subcutaneous or other parenteral administration, or potentially by oral administration. Administration may be repeated as determined by a physician until the condition has been resolved or is controlled.

In accordance with the foregoing, an aspect of the invention thus provides a method for inhibiting LEA-1 dependent complement activation for treating, preventing or reducing the severity of aspiration pneumonia, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing aspiration pneumonia. The MASP-1, MASP-3, or MASP-1/3 inhibitory composition may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing or reducing the severity of aspiration pneumonia, comprising administering a therapeutically effective amount of a MASP-2 inhibitory agent to a subject suffering from, or at risk for developing aspiration pneumonia. In another aspect, a method is provided comprising inhibiting both LEA-1 and LEA-2-dependent complement activation for treating, or reducing the severity of aspiration pneumonia, comprising administering a therapeutically effective amount of a MASP-2 inhibitory agent and a MASP-1, MASP-3, or MASP-1/3 inhibitory agent to a subject suffering from aspiration pneumonia. In some embodiments, the method comprises inhibiting both LEA-1-dependent complement activation and LEA-2-dependent complement activation. As detailed above, the use of a combination of pharmacologic agents that individually block LEA-1 and LEA-2, is expected to provide an improved therapeutic outcome in treating or reducing the severity of aspiration pneumonia as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered to the subject systemically, such as by intra arterial, intravenous, intramuscular, inhalational, nasal, subcutaneous, or other parenteral administration, or potentially by oral administration for non-peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual-inhibitory agents, or co-administration of separate compositions), or a limited sequence of administrations, for treating, preventing or reducing the severity of aspiration pneumonia in a subject in need thereof. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as aspiration pneumonia.

Accordingly, in one embodiment, the present invention provides a method for treating a subject suffering from, or at risk for developing aspiration pneumonia comprising an effective amount of a high affinity monoclonal antibody or antigen binding fragment thereof as disclosed herein that binds to human MASP-3 and inhibits alternative pathway complement activation to treat or reduce the risk of developing aspiration pneumonia, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

L. The Role of MASP-3 in Endophthalmitis, and Therapeutic Methods Using MASP-3 Inhibitory Antibodies, Optionally in Combination with and MASP-2 Inhibitory Agents Endophthalmitis is an inflammatory condition of the intraocular cavities and is usually caused by infection. Endophthalmitis may be endogenous, resulting from hematogenous spread of organisms from a distant source of infection (e.g., endocarditis), or exogeneous, from direct inoculation of an organism from the outside as a complication of ocular surgery, foreign bodies, and/or blunt or penetrating ocular trauma. Exogenous endophthalmitis is much more common than endogenous and most cases of exogeneous endophthalmitis occur following ocular surgery. In the United States, cataract surgery is the leading cause of endophthalmitis and occurs in 0.1-0.3% of this procedure, with an apparent increase in the incidence over the last decade (Taban, M. et al., *Arch. Ophthalmol.* 123:613-620, 2005). Post-surgical endophthalmitis may present either acutely, within 2 weeks of surgery, or delayed, months after surgery. Acute endophthalmitis typically presents with pain, redness, lid swelling, and decreased visual acuity. Delayed-onset endophthalmitis is less common than the acute form and patients may report only mild pain and photosensitivity. Treatment of endophthalmitis depends on the underlying cause and may include systemic and/or intravitreal antibiotics. Endophthalmitis may result in decreased or loss of vision.

As previously described for AMD, multiple complement pathway genes have been associated with ophthalmologic disorders, and these specifically include genes of the lectin pathway. For example, MBL2 has been identified with subtypes of AMD (Dinu V, et al., *Genet Epidemiol* 31: 224-37, 2007). The LEA-1 and LEA-2 pathways are likely to be involved in ocular inflammatory conditions such as endophthalmitis (Chow S P et al., *Clin Experiment Ophthalmol.* 39:871-7, 2011). Chow et al. examined MBL levels of patients with endophthalmitis and demonstrated that both MBL levels and functional lectin pathway activity are significantly elevated in inflamed human eyes but virtually undetectable in non-inflamed control eyes. This suggests a role for MBL and the lectin pathway in sight-threatening ocular inflammatory conditions, particularly endophthalmitis. Furthermore, in a murine model of corneal fungal keratitis, the MBL-A gene was one of five upregulated inflammatory pathway genes (Wang Y., et al., *Mol Vis* 13: 1226-33, 2007).

Thus, LEA-1 and LEA-2 inhibitors are expected to have independent therapeutic benefit in treating endophthalmitis. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bi-specific antibody composed of MASP-1/3 and a MASP-2-specific binding site, or a dual-specificity antibody where each binding site binds to and blocks MASP-1/3 or MASP-2

In accordance with the foregoing, an aspect of the invention thus provides a method for inhibiting LEA-1 dependent complement activation for treating, preventing, or reducing the severity of endophthalmitis, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing endophthalmitis. The MASP-1, MASP-3, or MASP-1/3 inhibitory composition may be administered locally to the eye, such as by irrigation or application of the composition in the form of a topical gel, salve or drops, or by intravitreal administration. Alternately, the MASP-1, MASP-3, or MASP-1/3 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing, or reducing the severity of endophthalmitis, comprising administering a therapeutically effective amount of a MASP-2 inhibitory agent to a subject suffering from, or at risk for developing endophthalmitis. In another aspect, a method is provided comprising inhibiting both LEA-1 and LEA-2-dependent complement activation for treating, or reducing the severity of endophthalmitis, comprising administering a therapeutically effective amount of a MASP-2 inhibitory agent and a MASP-1, MASP-3, or MASP-1/3 inhibitory agent to a subject suffering from endophthalmitis.

In some embodiments, the method comprises inhibiting both LEA-1-dependent complement activation and LEA-2-dependent complement activation. As detailed above, the use of a combination of pharmacologic agents that individually block LEA-1 and LEA-2 is expected to provide an improved therapeutic outcome in treating or preventing or reducing the severity of endophthalmitis, as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered locally to the eye, such as by irrigation or application of the composition in the form of a topical gel, salve or drops, or by intravitreal injection. Alternately, the MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating, preventing or reducing the severity of endophthalmitis in a subject in need thereof. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as endophthalmitis.

Accordingly, in one embodiment, the present invention provides a method for treating a subject suffering from, or at risk for developing endophthalmitis comprising an effective amount of a high affinity monoclonal antibody or antigen binding fragment thereof as disclosed herein that binds to human MASP-3 and inhibits alternative pathway complement activation to treat or reduce the risk of developing endophthalmitis, such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

M. The Role of MASP-3 in Neuromyelitis Optica, and Therapeutic Methods Using MASP-3 Inhibitory Antibodies, Optionally in Combination with MASP-2 Inhibitory Agents Neuromyelitis optica (NMO) is an autoimmune disease that targets the optic nerves and spinal cord. This results in inflammation of the optic nerve, known as optic neuritis, and the spinal cord, known as myelitis. Spinal cord lesions in NMO may lead to weakness or paralysis in the legs or arms, blindness, bladder and bowel dysfunction, and sensory dysfunction.

NMO shares several similarities to multiple sclerosis (MS), since both are due to immune attack of CNS targets and both result in demyelination (Papadopoulos and Verkman, Lancet Neurol., 11(6):535-44, 2013). However, the molecular targets, treatments, and lesions for NMO are distinct from those of MS. While MS is largely mediated by T cells, NMO patients typically have antibodies that target the water channel protein aquaporin 4 (AQP4), a protein found in astrocytes that surround the blood-brain barrier. Interferon beta is the most commonly used therapy for MS, but it is generally acknowledged to be harmful in NMO. The inflammatory lesions of NMO are found in the spinal cord and optic nerve and may progress to the brain, including white and gray matter. The demyelination that occurs in NMO lesions is mediated by complement (Papadopoulos and Verkman, Lancet Neurol., 11(6):535-44, 2013).

Complement-dependent cytotoxicity appears to be the major mechanism causing development of NMO. Over 90% of NMO patients have IgG antibodies against AQP4 (Jarius and Wildemann, Jarius S, Wildemann B., Nat Rev Neurol. 2010 July; 6(7):383-92). These antibodies initiate formation of a lesion at the blood brain barrier. The initial antigen-antibody complex—AQP4/AQP4-IgG—on the surface of astrocytes activates the classical pathway of complement. This results in formation of the membrane attack complex on the astrocyte surface, leading to granulocyte infiltration, demyelination, and ultimately necrosis of astrocytes, oligodendrocytes and neurons (Misu et al., Acta Neuropathol 125(6):815-27, 2013). These cellular events are reflected in tissue destruction and formation of cystic, necrotic lesions.

The classical pathway of complement clearly is critical for NMO pathogenesis. NMO lesions show a vasculocentric deposition of immunoglobulin and activated complement components (Jarius et al., Nat Clin Pract Neurol. 4(4):202-14, 2008). In addition, complement proteins such as C5a have been isolated from cerebrospinal fluid of NMO patients (Kuroda et al., J Neuroimmunol., 254(1-2):178-82, 2013). Furthermore, serum IgG obtained from NMO patients can cause complement-dependent cytotoxicity in a mouse NMO model (Saadoun et al., Brain, 133(Pt 2):349-61, 2010). A monoclonal antibody against C1q prevents the complement mediated destruction of astrocytes and lesions in a mouse model of NMO (Phuan et al., Acta Neuropathol, 125(6): 829-40, 2013).

The alternative pathway of complement serves to amplify overall complement activity. Harboe and colleagues (2004) demonstrated that selective blockade of the alternative pathway inhibited more than 80% of membrane attack complex formation induced by the classical pathway (Harboe et al., Clin Exp Immunol 138(3):439-46, 2004). Tüzün and colleagues (2013) examined both classical and alternative pathway products in NMO patients (Tüzün E, et al., J Neuroimmunol. 233(1-2): 211-5, 2011). C4d, the breakdown product of C4, was measured to evaluate classical pathway activity and was increased in NMO patient sera compared to controls (an elevation of 2.14-fold). In addition, an increase of Factor Bb, the breakdown product of the alternative pathway Factor B, was observed in NMO patients compared to MS patients or normal control individuals (an elevation of 1.33-fold). This suggests that alternative pathway function is also increased in NMO. This activation would be expected to increase overall complement activation, and in fact sC5b-9, the final product of the complement cascade, was significantly increased (a 4.14-fold elevation).

Specific inhibitors of MASP-3 are expected to provide benefit in treating patients suffering from NMO. As demonstrated herein, serum lacking MASP-3 is unable to activate Factor B, an essential component of C5 convertase, or Factor D, the central activator of the alternative pathway. Therefore, blocking MASP-3 activity with an inhibitory agent such as an antibody or small molecule would also be expected to inhibit activation of Factor B and Factor D. Inhibition of these two factors will arrest the amplification of the alternative pathway, resulting in diminished overall complement activity. MASP-3 inhibition should thus significantly improve therapeutic outcomes in NMO.

Thus, LEA-1 and/or LEA-2 inhibitors are expected to have independent therapeutic benefit in treating NMO. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bi-specific antibody composed of MASP-1/3 and a MASP-2-specific binding site, or a dual-specificity antibody where each binding site binds to and blocks MASP-1/3 or MASP-2

In accordance with the foregoing, an aspect of the invention thus provides a method for inhibiting LEA-1 dependent complement activation for treating, preventing, or reducing the severity of NMO, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing NMO. The MASP-1, MASP-3, or MASP-1/3 inhibitory composition may be administered locally to the eye, such as by irrigation or application of the composition in the form of a topical gel, salve or drops, or by intravitreal administration. Alternately, the MASP-1, MASP-3, or MASP-1/3 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing, or reducing the severity of NMO, comprising administering a therapeutically effective amount of a MASP-2 inhibitory agent to a subject suffering from, or at risk for developing NMO. In another aspect, a method is provided comprising inhibiting both LEA-1 and LEA-2-dependent complement activation for treating, or reducing the severity of NMO, comprising administering a therapeutically effective amount of a MASP-2 inhibitory agent and a MASP-1, MASP-3, or MASP-1/3 inhibitory agent to a subject suffering from NMO.

In some embodiments, the method comprises inhibiting both LEA-1-dependent complement activation and LEA-2-dependent complement activation. As detailed above, the use of a combination of pharmacologic agents that individually block LEA-1 and LEA-2 is expected to provide an improved therapeutic outcome in treating or preventing or reducing the severity of NMO, as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered locally to the eye, such as by irrigation or application of the composition in the form of a topical gel, salve or drops, or by intravitreal injection. Alternately, the MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and/or the MASP 2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating, preventing or reducing the severity of NMO in a subject in need thereof. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as neuromyelitis optica (NMO).

Accordingly, in one embodiment, the present invention provides a method for treating a subject suffering from, or at risk for developing neuromyelitis optica (NMO). comprising an effective amount of a high affinity monoclonal antibody or antigen binding fragment thereof as disclosed herein that binds to human MASP-3 and inhibits alternative pathway complement activation to treat or reduce the risk of developing neuromyelitis optica (NMO), such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

N. The Role of MASP-3 in Behcet's Disease, and Therapeutic Methods Using MASP-3 Inhibitory Antibodies, Optionally in Combination with MASP-2 Inhibitory Agents Behçet's disease, or Behçet's syndrome, is a rare, immune-mediated small-vessel systemic vasculitis that often presents with mucous membrane ulceration and ocular problems. Behçet's disease (BD) was named in 1937 after the Turkish dermatologist Hulusi Behçet, who first described the triple-symptom complex of recurrent oral ulcers, genital ulcers, and uveitis. BD is a systemic, relapsing inflammatory disorder of unknown cause. The inflammatory perivasculitis of BD may involve the gastrointestinal tract, pulmonary, musculoskeletal, cardiovascular, and neurological systems. BD can be fatal due to ruptured vascular aneurysms or severe neurological complications. Optic neuropathy and atrophy may result from vasculitis and occlusion of the vessels supplying the optic nerve. See Al-Araji A, et al., *Lancet Neurol.,* 8(2):192-204, 2009.

The highest incidence of BD is in the Middle East and Far East regions, but it is rare in Europe and North America. BD is often initially controlled with corticosteroids and immunosuppressants, but many cases are refractory with serious morbidity and mortality. Biologic agents, including interferon-alpha, IVIG, anti-TNF, anti-IL-6, and anti-CD20, have shown benefit in some cases, but there is no consensus on best treatment.

While BD is clearly an inflammatory disorder, its pathobiology is not clear. There are genetic associations with HLA antigens, and genome wide association studies have implicated numerous cytokine genes (Kirino et al., *Nat Genet,* 45(2):202-7, 2013). The hyperactivity of the immune system appears to be regulated by the complement system. Increased levels of C3 have been observed in BD patient sera (Bardak and Aridoğan, *Ocul Immunol Inflamm* 12(1): 53-8, 2004), and elevated C3 and C4 in the cerebrospinal fluid correlates with disease (Jongen et al., *Arch Neurol,* 49(10):1075-8, 1992).

Tüzün and colleagues (2013) examined both classical and alternative pathway products in sera of BD patients (Tüzün E, et al., *J Neuroimmunol,* 233(1-2):211-5, 2011). 4d, the breakdown product of C4, is generated upstream of the alternative pathway and was measured to evaluate initial classical pathway activity. C4d was increased in BD patient sera compared to controls (an elevation of 2.18-fold). Factor Bb is the breakdown product of Factor B, and was measured to determine activity of the alternative pathway. BD patients had an increase of factor Bb compared to normal control individuals (an elevation of 2.19-fold) consistent with an increase in BD alternative pathway function. Because the alternative pathway of complement serves to amplify overall complement activity, this activation would be expected to increase overall complement activation. Harboe and colleagues (2004) demonstrated that selective blockade of the alternative pathway inhibited more than 80% of membrane attack complex formation induced by the classical pathway (Harboe M, et al., *Clin Exp Immunol,* 138(3):439-46, 2004). In fact, sC5b-9, the final product of the complement cascade, was significantly increased in BD patients (a 5.46-fold elevation). Specific inhibitors of MASP-3 should provide benefit in BD. Blocking MASP-3 should inhibit activation of Factor B and Factor D. This will stop the amplification of the alternative pathway, resulting in a diminished response of overall complement activity. MASP-3 inhibition should thus significantly improve therapeutic outcomes in BD. Thus, LEA-1 and/or LEA-2 inhibitors are expected to have independent therapeutic benefit in treating BD. In addition, LEA-1 and LEA-2 inhibitors used together may achieve additional treatment benefit compared to either agent alone, or may provide effective treatment for a wider spectrum of patient subsets. Combined LEA-1 and LEA-2 inhibition may be accomplished by co-administration of a LEA-1-blocking agent and a LEA-2-blocking agent. Optimally, LEA-1 and LEA-2 inhibitory function may be encompassed in a single molecular entity, such as a bi-specific antibody composed of MASP-1/3 and a MASP-2-specific binding site, or a dual-specificity antibody where each binding site binds to and blocks MASP-1/3 or MASP-2.

In accordance with the foregoing, an aspect of the invention thus provides a method for inhibiting LEA-1 dependent complement activation for treating, preventing, or reducing the severity of BD, comprising administering a composition comprising a therapeutically effective amount of a LEA-1 inhibitory agent comprising a MASP-1 inhibitory agent, a MASP-3 inhibitory agent, or a combination of a MASP-1/3 inhibitory agent, in a pharmaceutical carrier to a subject suffering from, or at risk for developing BD. The MASP-1, MASP-3, or MASP-1/3 inhibitory composition may be administered locally to the eye, such as by irrigation or application of the composition in the form of a topical gel, salve or drops, or by intravitreal administration. Alternately, the MASP-1, MASP-3, or MASP-1/3 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

In another aspect, a method is provided for inhibiting LEA-2-dependent complement activation for treating, preventing, or reducing the severity of BD, comprising administering a therapeutically effective amount of a MASP-2 inhibitory agent to a subject suffering from, or at risk for developing BD. In another aspect, a method is provided comprising inhibiting both LEA-1 and LEA-2-dependent complement activation for treating, or reducing the severity of BD, comprising administering a therapeutically effective amount of a MASP-2 inhibitory agent and a MASP-1, MASP-3, or MASP-1/3 inhibitory agent to a subject suffering from BD.

In some embodiments, the method comprises inhibiting both LEA-1-dependent complement activation and LEA-2-dependent complement activation. As detailed above, the use of a combination of pharmacologic agents that individually block LEA-1 and LEA-2 is expected to provide an improved therapeutic outcome in treating or preventing or reducing the severity of BD, as compared to the inhibition of LEA-1 alone. This outcome can be achieved for example, by co-administration of an antibody that has LEA-1-blocking activity together with an antibody that has LEA-2-blocking activity. In some embodiments, LEA-1- and LEA-2-blocking activities are combined into a single molecular entity, and that such entity with combined LEA-1- and LEA-2-blocking activity. Such an entity may comprise or consist of a bispecific antibody where one antigen-combining site specifically recognizes MASP-1 and blocks LEA-1 and the second antigen-combining site specifically recognizes MASP-2 and blocks LEA-2. Alternatively, such an entity may consist of a bispecific monoclonal antibody where one antigen-combining site specifically recognizes MASP-3 and thus blocks LEA-1 and the second antigen-combining site specifically recognizes MASP-2 and blocks LEA-2. Such an entity may optimally consist of a bispecific monoclonal antibody where one antigen-combining site specifically recognizes both MASP-1 and MASP-3 and thus blocks LEA-1 while the second antigen-combining site specifically recognized MASP-2 and blocks LEA-2.

The MASP-2 inhibitory agent may be administered locally to the eye, such as by irrigation or application of the composition in the form of a topical gel, salve or drops, or by intravitreal injection. Alternately, the MASP-2 inhibitory agent may be administered to the subject systemically, such as by intra arterial, intravenous, intramuscular, inhalational, nasal, subcutaneous or other parenteral administration, or potentially by oral administration for non peptidergic agents. Administration may be repeated as determined by a physician until the condition has been resolved or is controlled.

Application of the MASP-3 inhibitory compositions and/or the MASP-2 inhibitory compositions of the present invention may be carried out by a single administration of the composition (e.g., a single composition comprising MASP-2 and/or MASP-3 inhibitory agents, or bispecific or dual inhibitory agents, or co-administration of separate compositions), or a limited sequence of administrations, for treating, preventing or reducing the severity of BD in a subject in need thereof. Alternatively, the composition may be administered at periodic intervals such as daily, biweekly, weekly, every other week, monthly or bimonthly over an extended period of time for treatment of a subject in need thereof.

As described in Examples 11-21 herein, high affinity MASP-3 inhibitory antibodies have been generated which have therapeutic utility for inhibition of the alternative pathway in AP-related diseases or conditions, such as Behçet's disease (BD).

Accordingly, in one embodiment, the present invention provides a method for treating a subject suffering from, or at risk for developing Behçet's disease (BD) comprising an effective amount of a high affinity monoclonal antibody or antigen binding fragment thereof as disclosed herein that binds to human MASP-3 and inhibits alternative pathway complement activation to treat or reduce the risk of developing Behçet's disease (BD), such as, for example, wherein said antibody or antigen binding fragment thereof comprises (a) a heavy chain variable region comprising (i) VHCDR1 comprising SEQ ID NO:84, (ii) VHCDR2 comprising SEQ ID NO:86 or SEQ ID NO:275 and (iii) VHCDR3 comprising SEQ ID NO:88; and (b) a light chain variable region comprising (i) VLCDR1 comprising SEQ ID NO:142, SEQ ID NO:257, SEQ ID NO:258 or SEQ ID NO:259 (ii) VLCDR2 comprising SEQ ID NO:144 and (iii) VLCDR3 comprising SEQ ID NO:161.

MASP-3 Inhibitory Agents

With the recognition that the lectin pathway of complement is composed of two major complement activation arms, LEA-1 and LEA-2, and that there also is a lectin-independent complement activation arm, comes the realization that it would be highly desirable to specifically inhibit one or more of these effector arms that cause a pathology associated with alternative pathway complement activation, such as at least one of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenic purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis (MS), Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis, without completely shutting down the immune defense capabilities of complement (i.e., leaving the classical pathway intact). This would leave the C1q-dependent complement activation system intact to handle immune complex processing and to aid in host defense against infection.

Compositions for Inhibiting LEA-1-Mediated Complement Activation

As described herein, the inventors have unexpectedly discovered that activation of LEA-1, leading to lysis, is MASP-3-dependent. As further described herein, under physiological conditions, MASP-3-dependent LEA-1 activation also contributes to opsonization, thereby providing an additive effect with LEA-2-mediated complement activation. As demonstrated herein, in the presence of $Ca^{++}$, factor D is not required, as MASP-3 can drive activation of LEA-1 in factor $D^{-/-}$ sera. MASP-3, MASP-1, and HTRA-1 are able to convert pro-factor D to active factor D. Likewise, MASP-3 activation appears, in many instances, to be dependent on MASP-1, since MASP-3 (in contrast to MASP-1 and MASP-2) is not an auto-activating enzyme and is incapable of converting into its active form without the help of MASP-1 (Zundel, S. et al., J. Immunol. 172: 4342-4350 (2004); Megyeri et al., J. Biol. Chem. 288:8922-8934 (2013). As MASP-3 does not autoactivate and, in many instances, requires the activity of MASP-1 to be converted into its enzymatically active form, the MASP-3-mediated activation of the alternative pathway C3 convertase C3Bb can either be inhibited by targeting the MASP-3 zymogen or already-activated MASP-3, or by targeting MASP-1-mediated activation of MASP-3, or both, since, in many instances, in the absence of MASP-1 functional activity, MASP-3 remains in its zymogen form and is not capable of driving LEA-1 through direct formation of the alternative pathway C3 convertase (C3bBb).

Therefore, in one aspect of the invention, the preferred protein component to target in the development of therapeutic agents to specifically inhibit LEA-1 is an inhibitor of MASP-3 (including inhibitors of MASP-1-mediated MASP-3 activation (e.g., a MASP-1 inhibitor that inhibits MASP-3 activation)).

In accordance with the foregoing, in one aspect, the invention provides methods of inhibiting the adverse effects of LEA-1 (i.e., hemolysis and opsonization) by administering a MASP-3 inhibitory agent, such as a MASP-3 inhibitory antibody in a subject suffering from, or at risk for developing, a disease or disorder selected from the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) and thrombotic thrombocytopenic purpura (TTP), asthma, dense deposit disease, pauci-immune necrotizing crescentic glomerulonephritis, traumatic brain injury, aspiration pneumonia, endophthalmitis, neuromyelitis optica Behçet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis, comprising administering to the subject a pharmaceutical composition comprising an amount of a MASP-3 inhibitory agent effective to inhibit MASP-3-dependent complement activation and a pharmaceutically acceptable carrier.

MASP-3 inhibitory agents are administered in an amount effective to inhibit MASP-3-dependent complement activation in a living subject suffering from, or at risk for developing, paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis. In the practice of this aspect of the invention, representative MASP-3 inhibitory agents include: molecules that inhibit the biological activity of MASP-3, including molecules that inhibit at least one or more of the following: lectin MASP-3-dependent activation of factor B, lectin MASP-3-dependent activation of pro-factor D, MASP-3-dependent, lectin-independent activation of factor B, and MASP-3-dependent, lectin-independent activation of pro-factor D (such as small-molecule inhibitors, MASP-3 antibodies and fragments thereof, or blocking peptides which interact with MASP-3 or interfere with a protein-protein interaction), and molecules that decrease the expression of MASP-3 (such as MASP-3 antisense nucleic acid molecules, MASP-3 specific RNAi molecules and MASP-3 ribozymes). A MASP-3 inhibitory agent may effectively block MASP-3 protein-to-protein interactions, interfere with MASP-3 dimerization or assembly, block $Ca^{++}$ binding, interfere with the MASP-3 serine protease active site, or reduce MASP-3 protein expression, thereby preventing MASP-3 from activating LEA-1-mediated, or lectin-independent, complement activation. The MASP-3 inhibitory agents can be used alone as a primary therapy or in combination with other therapeutics as an adjuvant therapy to enhance the therapeutic benefits of other medical treatments, as further described herein.

High Affinity Monoclonal MASP-3 Inhibitory Antibodies

Figure 49A:
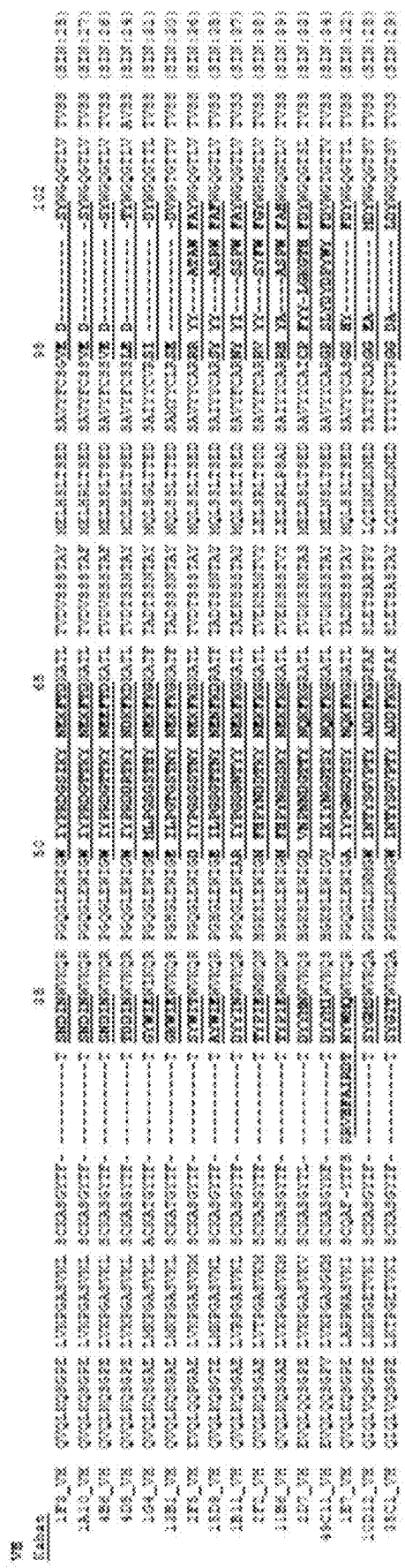
FIG. 49A shows the amino acid sequences of the VH regions of high affinity (≤500 pM) anti-human MASP-3 inhibitory mAbs, as described in Example 15.
Figure 49B:
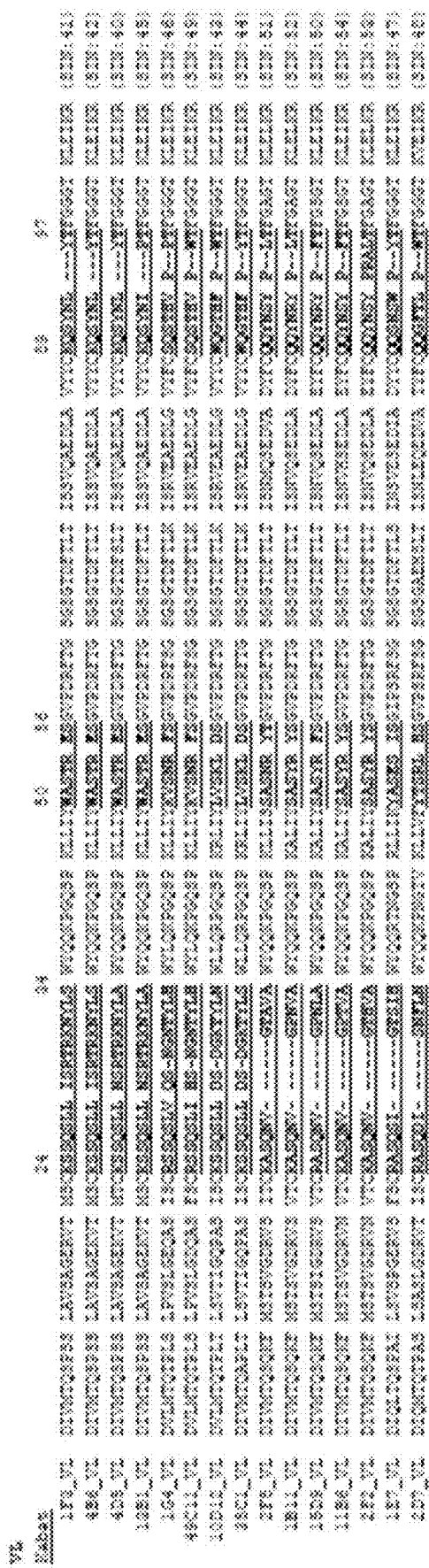
FIG. 49B shows the amino acid sequences of the VL regions of high affinity (≤500 pM) anti-human MASP-3 inhibitory mAbs, as described in Example 15.

As described in Examples 11-21 herein, and summarized in TABLES 2A, 2B and TABLE 3 below, the inventors have generated surprisingly high affinity (i.e. ≤500 pM) MASP-3 inhibitory antibodies that bind to an epitope in the serine protease domain of human MASP-3. As described herein, the inventors have demonstrated that these high affinity MASP-3 antibodies are capable of inhibiting alternative pathway complement activation in human serum, rodents and non-human primates. The variable light and heavy chain regions of these antibodies have been sequenced, isolated and analyzed in both a Fab format and in a full-length IgG format. As described in Example 15 and shown in dendrograms depicted in FIGS. 50A and 50B, the antibodies can be grouped according to sequence similarity. A summary of the heavy chain variable regions and the light chain variable regions of these antibodies is shown in FIGS. 49A and 49B and provided in TABLES 2A and 2B below. Humanized versions of representative high affinity MASP-3 inhibitory antibodies were generated as described in Example 19 and are summarized in TABLE 3.

TABLE 2A

MASP-3 high affinity inhibitory Antibody Sequences: mouse parental

| MASP-3 Antibody Reference No | Group | Heavy Chain Variable Region (amino acid) | Light Chain Variable Region (amino acid) | Heavy chain variable region (DNA) | Light chain variable region (DNA) |
|---|---|---|---|---|---|
| 4D5 | IA | SIN: 24 | SIN: 40 | SIN: 217 | SIN: 233 |
| 1F3 | IA | SIN: 25 | SIN: 41 | SIN: 218 | SIN: 234 |
| 4B6 | IA | SIN: 26 | SIN: 42 | SIN: 219 | SIN: 235 |
| 1A10 | IA | SIN: 27 | SIN: 42 | SIN: 220 | SIN: 235 |
| 10D12 | IB | SIN: 28 | SIN: 43 | SIN: 221 | SIN: 236 |
| 35C1 | IB | SIN: 29 | SIN: 44 | SIN: 222 | SIN: 237 |
| 13B1 | IC | SIN: 30 | SIN: 45 | SIN: 223 | SIN: 238 |
| 1G4 | II | SIN: 31 | SIN: 46 | SIN: 224 | SIN: 239 |
| 1E7 | IIIA | SIN: 32 | SIN: 47 | SIN: 225 | SIN: 240 |
| 2D7 | IIIA | SIN: 33 | SIN: 48 | SIN: 226 | SIN: 241 |
| 49C11 | IIIA | SIN: 34 | SIN: 49 | SIN: 227 | SIN: 242 |
| 15D9 | IIIB | SIN: 35 | SIN: 50 | SIN: 228 | SIN: 243 |
| 2F5 | IIIB | SIN: 36 | SIN: 51 | SIN: 229 | SIN: 244 |
| 1B11 | IIIC | SIN: 37 | SIN: 52 | SIN: 230 | SIN: 245 |
| 2F2 | IIID | SIN: 38 | SIN: 53 | SIN: 231 | SIN: 246 |
| 11B6 | IIID | SIN: 39 | SIN: 54 | SIN: 232 | SIN: 247 |

Note:
"SIN" refers to "SEQ ID NO: "

TABLE 2B

MASP-3 high affinity inhibitory antibodies: CDRs

| MASP-3 Antibody Reference No. | Heavy Chain Variable Region (amino acid) | Light Chain Variable Region (amino acid) | Heavy Chain: CDR1; CDR2; CDR3 (SEQ ID NOs) | Light Chain: CDR1; CDR2; CDR3 (SEQ ID NOs) |
|---|---|---|---|---|
| 4D5 | SIN: 24 | SIN: 40 | 56; 58; 60 | 142; 144; 146 |
| 1F3 | SIN: 25 | SIN: 41 | 62; 63; 65 | 149; 144; 146 |
| 4B6 | SIN: 26 | SIN: 42 | 62; 67; 65 | 149; 144; 146 |
| 1A10 | SIN: 27 | SIN: 42 | 62; 69; 65 | 149; 144; 146 |
| 10D12 | SIN: 28 | SIN: 43 | 72; 74; 76 | 153; 155; 157 |
| 35C1 | SIN: 29 | SIN: 44 | 79; 74; 82 | 159; 155; 160 |
| 13B1 | SIN: 30 | SIN: 45 | 84; 86; 88 | 142; 144; 161 |
| 1G4 | SIN: 31 | SIN: 46 | 91; 93; 95 | 163; 165; 167 |
| 1E7 | SIN: 32 | SIN: 47 | 109; 110; 112 | 182; 184; 186 |
| 2D7 | SIN: 33 | SIN: 48 | 125; 127; 129 | 196; 198; 200 |
| 49C11 | SIN: 34 | SIN: 49 | 132; 133; 135 | 203; 165; 204 |
| 15D9 | SIN: 35 | SIN: 50 | 137; 138; 140 | 206; 207; 208 |
| 2F5 | SIN: 36 | SIN: 51 | 98; 99; 101 | 169; 171; 173 |
| 1B11 | SIN: 37 | SIN: 52 | 103; 105; 107 | 176; 178; 180 |
| 2F2 | SIN: 38 | SIN: 53 | 114; 116; 118 | 188; 178; 190 |
| 11B6 | SIN: 39 | SIN: 54 | 114; 121; 123 | 191; 178; 193 |

TABLE 3

Representative high affinity MASP-3 inhibitory antibodies: humanized and modified to remove post-translational modification sites

| MASP-3 Antibody Reference No. | Heavy Chain Variable Region aa (SEQ ID NO) | Light Chain Variable Region aa (SEQ ID NO) | Heavy Chain: CDR1; CDR2; CDR3 (SEQ ID NOs) | Light Chain: CDR1; CDR2; CDR3 (SEQ ID NOs) |
|---|---|---|---|---|
| 4D5 parent | 24 | 40 | 56; 58; 60 | 142; 144; 146 |
| h4D5-14-1 | 248 | 250 | 56; 58; 60 | 142; 144; 146 |
| h4D5-19-1 | 249 | 250 | 56; 58; 60 | 142; 144; 146 |
| h4D5-14-1-NA | 248 | 278 | 56; 58; 60 | 258; 144; 146 |
| h4D5-19-1-NA | 249 | 278 | 56; 58; 60 | 258; 144; 146 |
| 10D12 parent | 28 | 43 | 72; 74; 76 | 153; 155; 157 |
| h10D12-45-21 | 251 | 253 | 72; 74; 76 | 153; 155; 157 |
| h10D12-49-21 | 252 | 253 | 72; 74; 76 | 153; 155; 157 |
| h10D12-45-21-GA | 251 | 279 | 72; 74; 76 | 263; 155; 157 |
| h10D12-49-21-GA | 252 | 279 | 72; 74; 76 | 263; 155; 157 |
| 13B1 parent | 30 | 45 | 84; 86; 88 | 142; 144; 161 |
| h13B1-9-1 | 254 | 256 | 84; 275; 88 | 142; 144; 161 |
| h13B1-10-1 | 255 | 256 | 84; 86; 88 | 142; 144; 161 |
| h13B1-9-1-NA | 254 | 280 | 84; 275; 88 | 258; 144; 161 |
| h13B1-10-1-NA | 255 | 280 | 84; 86; 88 | 258; 144; 161 |

Accordingly, in one aspect, the present invention provides an isolated monoclonal antibody or antigen-binding fragment thereof that specifically binds to the serine protease domain of human MASP-3 (amino acid residues 450 to 728 of SEQ ID NO:2) with high affinity (having a $K_D$ of less than 500 pM), wherein the antibody or antigen-binding fragment thereof inhibits alternative pathway complement activation. In some embodiments, the high affinity MASP-3 inhibitory antibody, or antigen-binding fragment thereof inhibits the alternative pathway at a molar ratio of from about 1:1 to about 2.5:1 target MASP-3 to mAb in a mammalian subject.

The inhibition of alternative pathway complement activation is characterized by at least one or more of the following changes in a component of the complement system that occurs as a result of administration of a high affinity MASP-3 inhibitory antibody in accordance with various embodiments of the invention: inhibition of hemolysis and/or opsonization; inhibition of lectin-independent conversion of factor B; inhibition of lectin-independent conversion of factor D, inhibition of MASP-3 serine protease substrate-specific cleavage; the reduction of hemolysis or the reduction of C3 cleavage and C3b surface deposition; the reduction of Factor B and Bb deposition on an activating surface; the reduction of resting levels (in circulation, and without the experimental addition of an activating surface) of active Factor D relative to pro-Factor D; the reduction of levels of active Factor D relative to pro-Factor D in response to an activating surface; and/or the production of resting and surface-induced levels of fluid-phase Ba, Bb, C3b, or C3a.

For example, as described herein the high affinity MASP-3 inhibitory antibodies, are antibodies or antigen-binding fragments thereof capable of inhibiting factor D maturation (i.e., cleavage of pro-factor D to factor D) in a mammalian subject. In some embodiments, the high affinity MASP-3 inhibitory antibodies are capable of inhibiting factor D maturation in full serum to a level less than 50% than that found in untreated control serum (such as less than 40%, for example less than 30%, such as less than 25%, for example less than 20%, such as less than 15%, for example less than 10%, such as less than 5% untreated control serum not contacted with a MASP-3 inhibitory antibody).

In preferred embodiments, the high affinity MASP-3 inhibitory antibodies selectively inhibit the alternative pathway, leaving the C1q-dependent complement activation system functionally intact.

In another aspect, the present disclosure features a nucleic acid molecule that encodes one or both of the heavy and light chain polypeptides of any of the MASP-3 inhibitory antibodies or antigen-binding fragments disclosed herein. Also featured is a vector (e.g., a cloning or expression vector) comprising the nucleic acid and a cell (e.g., an insect cell, bacterial cell, fungal cell, or mammalian cell) comprising the vector. The disclosure further provides a method for producing any of the MASP-3 inhibitory antibodies or antigen-binding fragments disclosed herein. The methods include, providing a cell containing an expression vector which contains a nucleic acid that encodes one or both of the heavy and light chain polypeptides of any of the antibodies or antigen-binding fragments disclosed herein. The cell or culture of cells is cultured under conditions and for a time sufficient to allow expression by the cell (or culture of cells) of the antibody or antigen-binding fragment thereof encoded by the nucleic acid. The method can also include isolating the antibody or antigen binding fragment thereof from the cell (or culture of cells) or from the media in which the cell or cells were cultured.

MASP-3 Epitopes and Peptides

As described in Example 18, illustrated in FIG. 62 and summarized in TABLE 4 below, the high affinity MASP-3 inhibitory antibodies and antigen-binding fragments thereof according to the present invention were found to specifically recognize one or more epitopes within the serine protease domain of human MASP-3 (amino acid residues 450 to 728 of SEQ ID NO:2). "Specifically recognises" means that the antibody binds to said epitope with significantly higher affinity than to any other molecule or part thereof.

TABLE 4

Representative High Affinity MASP-3 inhibitory antibodies: Epitope Binding Regions of MASP-3 (see also FIG. 62)

| Peptide Binding Fragments (Epitopes) with reference to human MASP-3 (w/leader) | MASP-3 mAb Ref No. |
|---|---|
| $_{498}$VLRSQRRDTTVI$_{509}$ (SIN: 9) | 1F3, 4B6, 4D5, 1A10, 10D12, |
| $_{494}$TAAHVLRSQRRDTTV$_{508}$ (SIN: 10) | 13B1 |
| $_{544}$DFNIQNYNHDIALVQ$_{558}$ (SIN: 11) | 1F3, 4B6, 4D5, 1A10 |
| $_{626}$PHAECKTSYESRS$_{638}$ (SIN: 12) | 13B1 |
| $_{639}$GNYSVTENMFC$_{649}$ (SIN: 13) | 1F3, 4B6, 4D5, 1A10 |
| $_{704}$VSNYVDWVWE$_{713}$ (SIN: 14) | 1F3, 4B6, 4D5, 1A10 |
| $_{498}$VLRSQRRDTTV$_{508}$ (SIN: 15) Core sequence of Group I | 1F3, 4B6, 4D5, 1A10, 10D12, 13B1 |
| $_{435}$ECGQPSRSLPSLV$_{447}$ (SIN: 16) | 1B11 |
| $_{454}$RNAEPGLFPWQ$_{464}$ (SIN: 17) Core sequence of Groups II and III | 1G4, 1E7, 2D7, 15D9, 2F5, 1B11 |
| $_{479}$KWFGSGALLSASWIL$_{493}$ (SIN 18) | 15D9, 2F5 |
| $_{514}$EHVTVYLGLH$_{523}$ (SIN: 19) | 1E7, 2D7, 1G4 |
| $_{562}$PVPLGPHVMP$_{571}$ (SIN: 20) | 15D9, 2F5 |

TABLE 4-continued

Representative High Affinity MASP-3 inhibitory antibodies: Epitope Binding Regions of MASP-3 (see also FIG. 62)

| Peptide Binding Fragments (Epitopes) with reference to human MASP-3 (w/leader) | MASP-3 mAb Ref No. |
|---|---|
| $_{583}$APHMLGL$_{589}$ (SIN: 21) | 1B11 |
| $_{614}$SDVLQYVKLP$_{623}$ (SIN: 22) | 1B11 |
| $_{667}$AFVIFDDLSQRW$_{678}$ (SIN: 23) | 1G4, 1E7, 2D7, 15D9, 2F5 |

Accordingly, in some embodiments, the high affinity MASP-3 inhibitory antibody or antigen-binding fragment thereof specifically binds to an epitope located within the serine protease domain of human MASP-3, wherein said epitope is located within at least one or more of: VLRSQRRDTTVI (SEQ ID NO:9), TAAHVLRSQRRDTTV (SEQ ID NO:10), DFNIQNYNHDIALVQ (SEQ ID NO:11), PHAECKTSYESRS (SEQ ID NO:12), GNYSVTENMFC (SEQ ID NO:13), VSNYVDWVWE (SEQ ID NO:14) and/or VLRSQRRDTTV (SEQ ID NO:15). In some embodiments, the antibody or antigen-binding fragment thereof binds to an epitope within SEQ ID NO:15. In some embodiments, the antibody or antigen-binding fragment binds to an epitope within SEQ ID NO:9. In some embodiments, the antibody or antigen-binding fragment thereof binds to an epitope within SEQ ID NO:10. In some embodiments, the antibody or antigen-binding fragment thereof binds to an epitope within SEQ ID NO:12. In some embodiments, the antibody or antigen-binding fragment thereof binds to an epitope within SEQ ID NO:10 and SEQ ID NO:12. In some embodiments, the antibody or antigen-binding fragment thereof binds to an epitope within at least one of SEQ ID NO:11, SEQ ID NO: 13 and/or SEQ ID NO:14.

In other embodiments, the high affinity MASP-3 inhibitory antibody or antigen-binding fragment thereof specifically binds to an epitope located within the serine protease domain of human MASP-3, wherein said epitope is located within at least one or more of: ECGQPSRSLPSLV (SEQ ID NO:16), RNAEPGLFPWQ (SEQ ID NO:17); KWFGSGALLSASWIL (SEQ ID NO:18); EHVTVYLGLH (SEQ ID NO:19); PVPLGPHVMP (SEQ ID NO:20); APHMLGL (SEQ ID NO:21); SDVLQYVKLP (SEQ ID NO:22); and/or AFVIFDDLSQRW (SEQ ID NO:23). In one embodiment, the antibody or antigen-binding fragment binds to an epitope within SEQ ID NO:17. In one embodiment, the antibody or antigen binding fragment binds to an epitope within EHVTVYLGLH (SEQ ID NO:19) and/or AFVIFDDLSQRW (SEQ ID NO:23). In one embodiment, the antibody or antigen-binding fragment binds to an epitope within SEQ ID NO:18, SEQ ID NO:20 and/or SEQ ID NO:23. In one embodiment, the antibody or antigen-binding fragment binds to an epitope within at least one of SEQ ID NO:16, SEQ ID NO: 21 and/or SEQ ID NO:22.

CDR Regions:

In one aspect of the present invention the antibody or functional equivalent thereof comprises specific hypervariable regions, designated CDRs. Preferably, the CDRs are CDRs according to the Kabat CDR definition. CDRs or hypervariable regions may for example be identified by sequence alignment to other antibodies. The CDR regions of the high affinity MASP-3 inhibitory antibodies are shown in TABLES 18-23.

Group IA mAbs

In one aspect, the invention provides an isolated antibody, or antigen-binding fragment thereof, that binds to MASP-3 comprising: (a) a heavy chain variable region comprising a HC-CDR1 set forth as SEQ ID NO:209 (XXDIN, wherein X at position 1 is S or T and wherein X at position 2 is N or D); a HC-CDR2 set forth as SEQ ID NO:210 (WIYPRDXXXKYNXXFXD, wherein X at position 7 is G or D; X at position 8 is S, T or R; X at position 9 is I or T; X at position 13 is E or D; X at position 14 is K or E; and X at position 16 is T or K); and a HC-CDR3 set forth as SEQ ID NO:211 (XEDXY, wherein X at position 1 is L or V, and wherein X at position 4 is T or S); and (b) a light chain variable region comprising a LC-CDR1 set forth as SEQ ID NO:212 (KSSQSLLXXRTRKNYLX, wherein X at position 8 is N, I, Q or A; wherein X at position 9 is S or T; and wherein X at position 17 is A or S); a LC-CDR2 set forth as SEQ ID NO:144 (WASTRES) and a LC-CDR3 set forth as SEQ ID NO:146 (KQSYNLYT). In one embodiment, the HC-CDR1 of the heavy chain variable region according to (a) comprises SEQ ID NO:56 (TDDIN). In one embodiment, the HC-CDR1 of the heavy chain variable region according to (a) comprises SEQ ID NO:62 (SNDIN). In one embodiment, the HC-CDR2 of the heavy chain variable region according to (a) comprises SEQ ID NO:58 (WIYPRDDRTKYNDKFKD). In one embodiment, the HC-CDR2 of the heavy chain variable region according to (a) comprises SEQ ID NO:63 (WIYPRDGSIKYNEKFTD). In one embodiment, the HC-CDR2 of the heavy chain variable region according to (a) comprises SEQ ID NO:67 (WIYPRDGTTKYNEEFTD). In one embodiment, the HC-CDR2 of the heavy chain variable region according to (a) comprises SEQ ID NO:69 (WIYPRDGTTKYNEKFTD). In one embodiment, the HC-CDR3 of the heavy chain variable region according to (a) comprises SEQ ID NO:60 (LEDTY). In one embodiment, the HC-CDR3 of the heavy chain variable region according to (a) comprises SEQ ID NO:65 (VEDSY). In one embodiment, the LC-CDR1 of the light chain variable region comprises SEQ ID NO:142 (KSSQSLLNSRTRKNYLA); SEQ ID NO:257 (KSSQSLLQSRTRKNYLA), SEQ ID NO:258 (KSSQSLLASRTRKNYLA); or SEQ ID NO:259 (KSSQSLLNTRTRKNYLA). In one embodiment, the LC-CDR1 comprises SEQ ID NO:258 (KSSQSLLASRTRKNYLA). In one embodiment, the LC-CDR1 comprises SEQ ID NO:149 (KSSQSLLISRTRKNYLS).

In one embodiment, the HC-CDR1 comprises SEQ ID NO:56, the HC-CDR2 comprises SEQ ID NO:58, the HC-CDR3 comprises SEQ ID NO:60 and the LC-CDR1 comprises SEQ ID NO:142, SEQ ID NO:257, SEQ ID NO:258 or SEQ ID NO:259; the LC-CDR2 comprises SEQ ID NO:144 and the LC-CDR3 comprises SEQ ID NO:146.

In one embodiment, the HC-CDR1 comprises SEQ ID NO:62, the HC-CDR2 comprises SEQ ID NO:63, SEQ ID NO:67 or SEQ ID NO:69, the HC-CDR3 comprises SEQ ID NO:65 and the LC-CDR1 comprises SEQ ID NO:149, the LC-CDR2 comprises SEQ ID NO:144 and the LC-CDR3 comprises SEQ ID NO:146.

Group IB mAbs

In another aspect, the invention provides an isolated antibody, or antigen-binding fragment thereof, that binds to MASP-3 comprising: (a) a heavy chain variable region comprising a HC-CDR1 set forth as SEQ ID NO:213 (SYGXX, wherein X at position 4 is M or I and wherein X at position 5 is S or T); a HC-CDR2 set forth as SEQ ID NO:74; and a HC-CDR3 set forth as SEQ ID NO:214 (GGXAXDY, wherein X at position 3 is E or D and wherein X at position 5 is M or L); and (b) a light chain variable region comprising a LC-CDR1 set forth as SEQ ID NO:215 (KSSQSLLDSXXKTYLX, wherein X at position 10 is D, E or A; wherein X at position 11 is G or A; and wherein X at position 16 is N or S); a LC-CDR2 set forth as SEQ ID NO:155; and a LC-CDR3 set forth as SEQ ID NO:216 (WQGTHFPXT, wherein X at position 8 is W or Y).

In one embodiment, the HC-CDR1 of the heavy chain variable region according to (a) comprises SEQ ID NO:72 (SYGMS). In one embodiment, the HC-CDR1 comprises SEQ ID NO:79 (SYGIT). In one embodiment, the HC-CDR3 comprises SEQ ID NO:76 (GGEAMDY). In one embodiment, the HC-CDR3 comprises SEQ ID NO:82 (GGDALDY). In one embodiment, the LC-CDR1 comprises SEQ ID NO:153 (KSSQSLLDSDGKTYLN); SEQ ID NO:261 (KSSQSLLDSEGKTYLN), SEQ ID NO:262 (KSSQSLLDSAGKTYLN) or SEQ ID NO:263 (KSSQSLLDSDAKTYLN). In one embodiment, the LC-CDR1 comprises SEQ ID NO:152. In one embodiment, the LC-CDR3 comprises SEQ ID NO:159 (KSSQSLLDSDGKTYLS).

In one embodiment, the LC-CDR3 comprises SEQ ID NO:160 (WQGTHFPYT). In one embodiment, the HC-CDR1 comprises SEQ ID NO:72, the HC-CDR2 comprises SEQ ID NO:74, the HC-CDR3 comprises SEQ ID NO:76, and the LC-CDR1 comprises SEQ ID NO:153, SEQ ID NO:261, SEQ ID NO:262 or SEQ ID NO:263; the LC-CDR2 comprises SEQ ID NO:155 and the LC-CDR3 comprises SEQ ID NO:157.

In one embodiment, the HC-CDR comprises SEQ ID NO:72, the HC-CDR2 comprises SEQ ID NO:74, the HC-CDR3 comprises SEQ ID NO:76, and the LC-CDR1 comprises SEQ ID NO:153 or SEQ ID NO:263, the LC-CDR2 comprises SEQ ID NO:155, and the LC-CDR3 comprises SEQ ID NO:157.

In one embodiment, the HC-CDR1 comprises SEQ ID NO:79, the HC-CDR2 comprises SEQ ID NO:74, the HC-CDR3 comprises SEQ ID NO:82, and the LC-CDR1 comprises SEQ ID NO:159, the LC-CDR2 comprises SEQ ID NO:155 and the LC-CDR3 comprises SEQ ID NO:160.

Group IC mAbs

In one aspect, the present invention provides an isolated antibody, or antigen-binding fragment thereof, that binds to MASP-3 comprising (a) a heavy chain variable region comprising a HC-CDR1 set forth as SEQ ID NO:84 (GKWIE); a HC-CDR2 set forth as SEQ ID NO:86 (EILPGTGSTNYNEKFKG) or SEQ ID NO:275 (EILPGTGSTNYAQKFQG); and a HC-CDR3 set forth as SEQ ID NO:88 (SEDV); and (b) a light chain variable region comprising a LC-CDR1 set forth as SEQ ID NO:142 (KSSQSLLNSRTRKNYLA), SEQ ID NO:257 (KSSQSLLQSRTRKNYLA); SEQ ID NO:258 (KSSQSLLASRTRKNYLA); or SEQ ID NO:259 (KSSQSLLNTRTRKNYLA), a LC-CDR2 set forth as SEQ ID NO:144 (WASTRES); and a LC-CDR3 set forth as SEQ ID NO:161 (KQSYNIPT). In one embodiment, the LC-CDR1 comprises SEQ ID NO:258.

Group II mAbs

In one aspect, the present invention provides an isolated antibody, or antigen-binding fragment thereof, that binds to MASP-3 comprising: (a) a heavy chain variable region comprising a HC-CDR1 set forth as SEQ ID NO:91 (GYWIE); a HC-CDR2 set forth as SEQ ID NO:93 (EMLPGSGSTHYNEKFKG), and a HC-CDR3 set forth as SEQ ID NO:95 (SIDY); and (b) a light chain variable region comprising a LC-CDR1 set forth as SEQ ID NO:163 (RSSQSLVQSNGNTYLH), a LC-CDR2 set forth as SEQ ID NO:165 (KVSNRFS) and a LC-CDR3 set forth as SEQ ID NO:167 (SQSTHVPPT).

Group III mAbs

In another aspect, the present invention provides an isolated antibody, or antigen-binding fragment thereof, that binds to MASP-3 comprising: (a) a heavy chain variable region comprising a HC-CDR1 set forth as SEQ ID NO:109 (RVHFAIRDTNYWMQ), a HC-CDR2 set forth as SEQ ID NO:110 (AIYPGNGDTSYNQKFKG), a HC-CDR3 set forth as SEQ ID NO:112 (GSHYFDY); and a light chain variable region comprising a LC-CDR1 set forth as SEQ ID NO:182 (RASQSIGTSIH), a LC-CDR2 set forth as SEQ ID NO:184 (YASESIS) and a LC-CDR3 set forth as SEQ ID NO:186 (QQSNSWPYT); or (b) a heavy chain variable region comprising a HC-CDR1 set forth as SEQ ID NO:125 (DYYMN), a HC-CDR2 set forth as SEQ ID NO:127 (DVNPNNDGTTYNQKFKG), a HC-CDR3 set forth as SEQ ID NO:129 (CPFYYLGKGTHFDY); and a light chain variable region comprising a LC-CDR1 set forth as SEQ ID NO:196 (RASQDISNFLN), a LC-CDR2 set forth as SEQ ID NO:198 (YTSRLHS) and a LC-CDR3 set forth as SEQ ID NO:200 (QQGFTLPWT); or (c) a heavy chain variable region comprising a HC-CDR1 set forth as SEQ ID NO:137 a HC-CDR2 set forth as SEQ ID NO:138, a HC-CDR3 set forth as SEQ ID NO:140; and a light chain variable region comprising a LC-CDR1 set forth as SEQ ID NO:206, a LC-CDR2 set forth as SEQ ID NO:207 and a LC-CDR3 set forth as SEQ ID NO:208; or (d) a heavy chain variable region comprising a HC-CDR1 set forth as SEQ ID NO:98, a HC-CDR2 set forth as SEQ ID NO:99, a HC-CDR3 set forth as SEQ ID NO:101; and a light chain variable region comprising a LC-CDR1 set forth as SEQ ID NO:169, a LC-CDR2 set forth as SEQ ID NO:171 and a LC-CDR3 set forth as SEQ ID NO:173; or (e) a heavy chain variable region comprising a HC-CDR1 set forth as SEQ ID NO:103, a HC-CDR2 set forth as SEQ ID NO:105, a HC-CDR3 set forth as SEQ ID NO:107; and a light chain variable region comprising a LC-CDR1 set forth as SEQ ID NO:176, a LC-CDR2 set forth as SEQ ID NO:178 and a LC-CDR3 set forth as SEQ ID NO:193; or (f) a heavy chain variable region comprising a HC-CDR1 set forth as SEQ ID NO:114, a HC-CDR2 set forth as SEQ ID NO:116, a HC-CDR3 set forth as SEQ ID NO:118; and a light chain variable region comprising a LC-CDR1 set forth as SEQ ID NO:188, a LC-CDR2 set forth as SEQ ID NO:178 and a LC-CDR3 set forth as SEQ ID NO:190; or (g) a heavy chain variable region comprising a HC-CDR1 set forth as SEQ ID NO:114, a HC-CDR2 set forth as SEQ ID NO:121, a HC-CDR3 set forth as SEQ ID NO:123; and a light chain variable region comprising a LC-CDR1 set forth as SEQ ID NO:191, a LC-CDR2 set forth as SEQ ID NO:178 and a LC-CDR3 set forth as SEQ ID NO:193; or (h) a heavy chain variable region comprising a HC-CDR1 set forth as SEQ ID NO:132, a HC-CDR2 set forth as SEQ ID NO:133, a HC-CDR3 set forth as SEQ ID NO:135; and a light chain variable region comprising a LC-CDR1 set forth as SEQ ID NO:203, a LC-CDR2 set forth as SEQ ID NO:165 and a LC-CDR3 set forth as SEQ ID NO:204.

Heavy Chain and Light Chain Variable Regions

In one embodiment, the invention provides a high affinity MASP-3 inhibitory antibody comprising a heavy chain variable region comprising or consisting of a sequence which is at least 80%, 85%, 90%, 95%, 98%, 99% identical to any of SEQ ID NO:s 24-39, 248-249, 251-252, 254-255 or wherein the antibody comprises a heavy chain variable region comprising SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:248, SEQ ID NO:249, SEQ ID NO:251, SEQ ID NO:252, SEQ ID NO:254 or SEQ ID NO:255.

In one embodiment, the invention provides a high affinity MASP-3 inhibitory antibody comprising a light chain variable region comprising or consisting of a sequence which is at least 80%, 85%, 90%, 95%, 98%, 99% identical to any of SEQ ID NO:s 40-54, 250, 253, 256, 278, 279, or 280 or wherein the antibody comprises a light chain variable region comprising SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:250, SEQ ID NO:253, SEQ ID NO:256, SEQ ID NO:278, SEQ ID NO:279 or SEQ ID NO:280.

In one embodiment, the MASP-3 monoclonal antibody comprises a heavy chain comprising at least 80%, 85%, 90%, 95%, 98%, 99% or 100% identical to SEQ ID NO:24, SEQ ID NO:248 or SEQ ID NO:249 and a light chain comprising at least 80%, 85%, 90%, 95%, 98%, 99% or 100% identical to SEQ ID NO:40, SEQ ID NO:250 or SEQ ID NO:278.

In one embodiment, the MASP-3 monoclonal antibody comprises a heavy chain comprising at least 80%, 85%, 90%, 95%, 98%, 99% or 100% identical to SEQ ID NO:25 and a light chain comprising at least 80%, 85%, 90%, 95%, 98%, 99% or 100% identical to SEQ ID NO:41.

In one embodiment, the MASP-3 monoclonal antibody comprises a heavy chain comprising at least 80%, 85%, 90%, 95%, 98%, 99% or 100% identical to SEQ ID NO:26 and a light chain comprising at least 80%, 85%, 90%, 95%, 98%, 99% or 100% identical to SEQ ID NO:42.

In one embodiment, the MASP-3 monoclonal antibody comprises a heavy chain comprising at least 80%, 85%, 90%, 95%, 98%, 99% or 100% identical to SEQ ID NO:27 and a light chain comprising at least 80%, 85%, 90%, 95%, 98%, 99% or 100% identical to SEQ ID NO:42.

In one embodiment, the MASP-3 monoclonal antibody comprises a heavy chain comprising at least 80%, 85%, 90%, 95%, 98%, 99% or 100% identical to SEQ ID NO:28, SEQ ID NO:251 or SEQ ID NO:252 and a light chain comprising at least 80%, 85%, 90%, 95%, 98%, 99% or 100% identical to SEQ ID NO:43, SEQ ID NO:253 or SEQ ID NO:279.

In one embodiment, the MASP-3 monoclonal antibody comprises a heavy chain comprising at least 80%, 85%, 90%, 95%, 98%, 99% or 100% identical to SEQ ID NO:29 and a light chain comprising at least 80%, 85%, 90%, 95%, 98%, 99% or 100% identical to SEQ ID NO:44.

In one embodiment, the MASP-3 monoclonal antibody comprises a heavy chain comprising at least 80%, 85%, 90%, 95%, 98%, 99% or 100% identical to SEQ ID NO:30, SEQ ID NO:254 or SEQ ID NO:255 and a light chain comprising at least 80%, 85%, 90%, 95%, 98%, 99% or 100% identical to SEQ ID NO:45, SEQ ID NO:256 or SEQ ID NO:280.

In one embodiment, the MASP-3 monoclonal antibody comprises a heavy chain comprising at least 80%, 85%, 90%, 95%, 98%, 99% or 100% identical to SEQ ID NO:31 and a light chain comprising at least 80%, 85%, 90%, 95%, 98%, 99% or 100% identical to SEQ ID NO:46.

In one embodiment, the MASP-3 monoclonal antibody comprises a heavy chain comprising at least 80%, 85%, 90%, 95%, 98%, 99% or 100% identical to SEQ ID NO:32 and a light chain comprising at least 80%, 85%, 90%, 95%, 98%, 99% or 100% identical to SEQ ID NO:47.

In one embodiment, the MASP-3 monoclonal antibody comprises a heavy chain comprising at least 80%, 85%, 90%, 95%, 98%, 99% or 100% identical to SEQ ID NO:33 and a light chain comprising at least 80%, 85%, 90%, 95%, 98%, 99% or 100% identical to SEQ ID NO:48.

In one embodiment, the MASP-3 monoclonal antibody comprises a heavy chain comprising at least 80%, 85%, 90%, 95%, 98%, 99% or 100% identical to SEQ ID NO:34 and a light chain comprising at least 80%, 85%, 90%, 95%, 98%, 99% or 100% identical to SEQ ID NO:49.

In one embodiment, the MASP-3 monoclonal antibody comprises a heavy chain comprising at least 80%, 85%, 90%, 95%, 98%, 99% or 100% identical to SEQ ID NO:35 and a light chain comprising at least 80%, 85%, 90%, 95%, 98%, 99% or 100% identical to SEQ ID NO:50.

In one embodiment, the MASP-3 monoclonal antibody comprises a heavy chain comprising at least 80%, 85%, 90%, 95%, 98%, 99% or 100% identical to SEQ ID NO:36 and a light chain comprising at least 80%, 85%, 90%, 95%, 98%, 99% or 100% identical to SEQ ID NO:51.

In one embodiment, the MASP-3 monoclonal antibody comprises a heavy chain comprising at least 80%, 85%, 90%, 95%, 98%, 99% or 100% identical to SEQ ID NO:37 and a light chain comprising at least 80%, 85%, 90%, 95%, 98%, 99% or 100% identical to SEQ ID NO:52.

In one embodiment, the MASP-3 monoclonal antibody comprises a heavy chain comprising at least 80%, 85%, 90%, 95%, 98%, 99% or 100% identical to SEQ ID NO:38 and a light chain comprising at least 80%, 85%, 90%, 95%, 98%, 99% or 100% identical to SEQ ID NO:53.

In one embodiment, the MASP-3 monoclonal antibody comprises a heavy chain comprising at least 80%, 85%, 90%, 95%, 98%, 99% or 100% identical to SEQ ID NO:39 and a light chain comprising at least 80%, 85%, 90%, 95%, 98%, 99% or 100% identical to SEQ ID NO:54.

Cross-Competition of High Affinity MASP-3 Antibodies

As described herein, the high affinity MASP-3 inhibitory antibodies disclosed herein recognize overlapping epitopes within the serine protease domain of MASP-3. As described in Example 18, shown in FIGS. 61A-E and 62-67, and summarized in TABLES 4 and 28, cross-competition analysis and pepscan binding analysis shows that the high affinity MASP-3 inhibitory antibodies cross-compete and bind to common epitopes located within the MASP-3 serine protease domain. Thus, in one embodiment, the invention provides high affinity MASP-3 inhibitory antibodies that specifically recognize an epitope or part thereof within the serine protease domain of human MASP-3 recognised by one or more selected from the group consisting of:

a monoclonal antibody comprising a heavy chain variable region set forth as SEQ ID NO:24 and a light chain variable region set forth as SEQ ID NO:40;

a monoclonal antibody comprising a heavy chain variable region set forth as SEQ ID NO:25 and a light chain variable region set forth as SEQ ID NO:41;

a monoclonal antibody comprising a heavy chain variable region set forth as SEQ ID NO:26 and a light chain variable region set forth as SEQ ID NO:42;

a monoclonal antibody comprising a heavy chain variable region set forth as SEQ ID NO:27 and a light chain variable region set forth as SEQ ID NO:42;

a monoclonal antibody comprising a heavy chain variable region set forth as SEQ ID NO:28 and a light chain variable region set forth as SEQ ID NO:43;

a monoclonal antibody comprising a heavy chain variable region set forth as SEQ ID NO:29 and a light chain variable region set forth as SEQ ID NO:44;

a monoclonal antibody comprising a heavy chain variable region set forth as SEQ ID NO:30 and a light chain variable region set forth as SEQ ID NO:45;

a monoclonal antibody comprising a heavy chain variable region set forth as SEQ ID NO:31 and a light chain variable region set forth as SEQ ID NO:46;

a monoclonal antibody comprising a heavy chain variable region set forth as SEQ ID NO:32 and a light chain variable region set forth as SEQ ID NO:47;

a monoclonal antibody comprising a heavy chain variable region set forth as SEQ ID NO:33 and a light chain variable region set forth as SEQ ID NO:48;

a monoclonal antibody comprising a heavy chain variable region set forth as SEQ ID NO:34 and a light chain variable region set forth as SEQ ID NO:49;

a monoclonal antibody comprising a heavy chain variable region set forth as SEQ ID NO:35 and a light chain variable region set forth as SEQ ID NO:50;

a monoclonal antibody comprising a heavy chain variable region set forth as SEQ ID NO:36 and a light chain variable region set forth as SEQ ID NO:51;

a monoclonal antibody comprising a heavy chain variable region set forth as SEQ ID NO:37 and a light chain variable region set forth as SEQ ID NO:52;

a monoclonal antibody comprising a heavy chain variable region set forth as SEQ ID NO:38 and a light chain variable region set forth as SEQ ID NO:53; and a monoclonal antibody comprising a heavy chain variable region set forth as SEQ ID NO:39 and a light chain variable region set forth as SEQ ID NO:54.

According to the present invention, when a given antibody recognises at least part of an epitope recognised by another given antibody, these two antibodies are said to recognise the same or overlapping epitopes.

Different assays available to the person skilled in the art may be used to determine whether an antibody (also designated test antibody) recognises the same or an overlapping epitope as a particular monoclonal antibody (also designated reference antibody). Preferably, the assay involves the steps of:

Providing MASP-3 or a fragment thereof comprising the epitope recognised by the reference antibody Add the test antibody and the reference antibody to the said MASP-3, wherein either the test antibody or the reference antibody is labelled with a detectable label. Alternatively, both antibodies may be labeled with different detectable labels Detecting the presence of the detectable label at MASP-3

Thereby detecting whether the test antibody may displace the reference antibody

If the reference antibody is displaced, the test antibody recognises the same or an overlapping epitope as the reference antibody. Thus, if the reference antibody is labeled with a detectable label, then a low detectable signal at MASP-3 is indicative of displacement of the reference antibody. If the test antibody is labelled with a detectable label, then a high detectable signal at MASP-3 is indicative of displacement of the reference antibody. The MASP-3 fragment may preferably be immobilised on a solid support enabling facile handling. The detectable label may be any directly or indirectly detectable label, such as an enzyme, a radioactive isotope, a heavy metal, a coloured compound or a fluorescent compound. In Example 18 in the section "Competition Binding Analysis" herein below describes an exemplary method of determining whether a test antibody recognises the same or an overlapping epitope as a reference antibody is described. The person skilled in the art may easily adapt said method to the particular antibodies in question.

The MASP-3 antibodies useful in this aspect of the invention include monoclonal or recombinant antibodies derived from any antibody producing mammal and may be multispecific (i.e., bispecific or trispecific), chimeric, humanized, fully human, anti-idiotype, and antibody fragments. Antibody fragments include Fab, Fab', F(ab)$_2$, F(ab')$_2$, Fv fragments, scFv fragments and single-chain antibodies as further described herein.

MASP-3 antibodies can be screened for the ability to inhibit alternative pathway complement activation system using the assays described herein. The inhibition of alternative pathway complement activation is characterized by at least one or more of the following changes in a component of the complement system that occurs as a result of administration of a high affinity MASP-3 inhibitory antibody in accordance with various embodiments of the invention: inhibition of hemolysis and/or opsonization; inhibition of lectin-independent conversion of factor B; inhibition of lectin-independent conversion of factor D, inhibition of MASP-3 serine protease substrate-specific cleavage; the reduction of hemolysis or the reduction of C3 cleavage and C3b surface deposition; the reduction of Factor B and Bb deposition on an activating surface; the reduction of resting levels (in circulation, and without the experimental addition of an activating surface) of active Factor D relative to pro-Factor D; the reduction of levels of active Factor D relative to pro-Factor D in response to an activating surface; and/or the production of resting and surface-induced levels of fluid-phase Ba, Bb, C3b, or C3a.

MASP-3 Antibodies with Reduced Effector Function

In some embodiments of this aspect of the invention, the high affinity MASP-3 inhibitory antibodies described herein have reduced effector function in order to reduce inflammation that may arise from the activation of the classical complement pathway. The ability of IgG molecules to trigger the classical complement pathway has been shown to reside within the Fc portion of the molecule (Duncan, A. R., et al., *Nature* 332:738-740 (1988)). IgG molecules in which the Fc portion of the molecule has been removed by enzymatic cleavage are devoid of this effector function (see Harlow, *Antibodies: A Laboratory Manual*, Cold Spring Harbor Laboratory, New York, 1988). Accordingly, antibodies with reduced effector function can be generated as the result of lacking the Fc portion of the molecule by having a genetically engineered Fc sequence that minimizes effector function, or being of either the human IgG$_2$ or IgG$_4$ isotype.

Antibodies with reduced effector function can be produced by standard molecular biological manipulation of the Fc portion of the IgG heavy chains as described in Jolliffe et al., *Int'l Rev. Immunol.* 10:241-250, (1993), and Rodrigues et al., *J. Immunol.* 151:6954-6961, (1998). Antibodies with reduced effector function also include human IgG2 and IgG4 isotypes that have a reduced ability to activate complement and/or interact with Fc receptors (Ravetch, J. V., et al., *Annu. Rev. Immunol.* 9:457-492, (1991); Isaacs, J. D., et al., *J. Immunol.* 148:3062-3071, 1992; van de Winkel, J. G., et al., *Immunol. Today* 14:215-221, (1993)). Humanized or fully human antibodies specific to human MASP-1, MASP-2 or MASP-3 (including dual, pan, bispecific or trispecific antibodies) comprised of IgG2 or IgG4 isotypes can be produced by one of several methods known to one of ordinary skilled in the art, as described in Vaughan, T. J., et al., *Nature Biotechnical* 16:535-539, (1998).

Production of High Affinity MASP-3 Inhibitory Antibodies

MASP-3 antibodies can be produced using MASP-3 polypeptides (e.g., full-length MASP-3) or using antigenic MASP-3 epitope-bearing peptides (e.g., a portion of the MASP-3 polypeptide), for example as described in Example 14 herein below. Immunogenic peptides may be as small as five amino acid residues. The MASP-3 peptides and polypeptides used to raise antibodies may be isolated as natural polypeptides, or recombinant or synthetic peptides and catalytically inactive recombinant polypeptides. Antigens useful for producing MASP-3 antibodies also include fusion polypeptides, such as fusions of a MASP-3 polypeptide or a portion thereof with an immunoglobulin polypeptide or with maltose-binding protein. The polypeptide immunogen may be a full-length molecule or a portion thereof. If the polypeptide portion is hapten-like, such portion may be advantageously joined or linked to a macromolecular carrier (such as keyhole limpet hemocyanin (KLH), bovine serum albumin (BSA) or tetanus toxoid) for immunization.

Monoclonal Antibodies

As used herein, the modifier "monoclonal" indicates the character of the antibody as being obtained from a substantially homogenous population of antibodies, and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, (1975), or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, (1991), and Marks, J. D., et al., *J. Mol. Biol.* 222:581-597, (1991). Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-3 polypeptide, or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-3. (See also *Current Protocols in Immunology*, Vol. 1, John Wiley & Sons, pages 2.5.1-2.6.7, 1991.)

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology. Methods for obtaining human antibodies from transgenic mice are described, for example, by Green, L. L., et al., *Nature Genet.* 7:13, 1994; Lonberg, N., et al., *Nature* 368:856, 1994; and Taylor, L. D., et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, The Humana Press, Inc., Vol. 10, pages 79-104, 1992).

Once produced, monoclonal antibodies are first tested for specific MASP-3 binding or, where desired, dual MASP-1/3, MASP-2/3 or MASP-1/2 binding. Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, plasmon surface resonance method (e.g., BIAcore system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," $2^{nd}$ Edition, Oxford University Press, NY, Oxford; Johne et al. (1993), *Immunol. Meth.* 160:191-198; Jonsson et al. (1993) *Ann. Biol. Clin.* 51: 19-26; and Jonsson et al. (1991) *Biotechniques* 11:620-627. See also, U.S. Pat. No. 6,355,245.

The affinity of MASP-3 monoclonal antibodies can be readily determined by one of ordinary skill in the art (see, e.g., Scatchard, A., *NY Acad. Sci.* 51:660-672, 1949). In one embodiment, the MASP-3 monoclonal antibodies useful for the methods of the invention bind to MASP-3 with a binding affinity of <100 nM, preferably <10 nM, preferably <2 nM, and most preferably with high affinity of <500 pM.

Once antibodies are identified that specifically bind to MASP-3, the MASP-3 antibodies are tested for the ability to function as an alternative pathway inhibitor in one of several functional assays, such as, for example, the inhibition of alternative pathway complement activation is characterized by at least one or more of the following changes in a component of the complement system that occurs as a result of administration of a high affinity MASP-3 inhibitory antibody in accordance with various embodiments of the invention: inhibition of hemolysis and/or opsonization; inhibition of lectin-independent conversion of factor B; inhibition of lectin-independent conversion of factor D, inhibition of MASP-3 serine protease substrate-specific cleavage; the reduction of hemolysis or the reduction of C3 cleavage and C3b surface deposition; the reduction of Factor B and Bb deposition on an activating surface; the reduction of resting levels (in circulation, and without the experimental addition of an activating surface) of active Factor D relative to pro-Factor D; the reduction of levels of active Factor D relative to pro-Factor D in response to an activating surface; the reduction in production of resting and surface-induced levels of fluid-phase Ba, Bb, C3b, or C3a; and/or the reduction in deposition of factor P.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567, to Cabilly; and Morrison, S. L., et al., Proc. Nat'l Acad. Sci. USA 81:6851-6855, (1984)).

One form of a chimeric antibody useful in the invention is a humanized monoclonal MASP-3 antibody. Humanized forms of non-human (e.g., murine) antibodies are chimeric antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to further refine antibody performance. In general, the humanized antibody will comprise substantially all of at least one, and typically two, variable domains in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fc), typically that of a human immunoglobulin. For further details, see Jones, P. T., et al., Nature 321:522-525, (1986); Reichmann, L., et al., Nature 332:323-329, (1988); and Presta, Curr. Op. Struct. Biol. 2:593-596, (1992).

The humanized antibodies useful in the invention include human monoclonal antibodies including at least a MASP-3 binding CDR3 region. In addition, the Fc portions may be replaced so as to produce IgA or IgM as well as human IgG antibodies. Such humanized antibodies will have particular clinical utility because they will specifically recognize human MASP-3 but will not evoke an immune response in humans against the antibody itself. Consequently, they are better suited for in vivo administration in humans, especially when repeated or long-term administration is necessary Techniques for producing humanized monoclonal antibodies are also described, for example, by Jones, P. T., et al., Nature 321:522, (1986); Carter, P., et al., Proc. Nat'l. Acad. Sci. USA 89:4285, (1992); Sandhu, J. S., Crit. Rev. Biotech. 12:437, (1992); Singer, et al., J. Immun. 150:2844, (1993); Sudhir (ed.), Antibody Engineering Protocols, Humana Press, Inc., (1995); Kelley, "Engineering Therapeutic Antibodies," in Protein Engineering: Principles and Practice, Cleland et al. (eds.), John Wiley & Sons, Inc., pages 399-434, (1996); and by U.S. Pat. No. 5,693,762, to Queen, 1997. In addition, there are commercial entities that will synthesize humanized antibodies from specific murine antibody regions, such as Protein Design Labs (Mountain View, Calif.).

Recombinant Antibodies

MASP-3 antibodies can also be made using recombinant methods. For example, human antibodies can be made using human immunoglobulin expression libraries (available for example, from Stratagene, Corp., La Jolla, Calif.) to produce fragments of human antibodies ($V_H$, $V_L$, Fv, Factor D, Fab or $F(ab')_2$). These fragments are then used to construct whole human antibodies using techniques similar to those for producing chimeric antibodies.

Immunoglobulin Fragments

The MASP-3 inhibitory agents useful in the method of the invention encompass not only intact immunoglobulin molecules but also the well-known fragments including Fab, Fab', $F(ab)_2$, $F(ab')_2$ and Fv fragments, scFv fragments, diabodies, linear antibodies, single-chain antibody molecules and multispecific (e.g., bispecific and trispecific) antibodies formed from antibody fragments.

It is well known in the art that only a small portion of an antibody molecule, the paratope, is involved in the binding of the antibody to its epitope (see, e.g., Clark, W. R., The Experimental Foundations of Modern Immunology, Wiley & Sons, Inc., NY, 1986). The pFc' and Fc regions of the antibody are effectors of the classical complement pathway but are not involved in antigen binding. An antibody from which the pFc' region has been enzymatically cleaved, or which has been produced without the pFc' region, is designated an $F(ab')_2$ fragment and retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331,647 to Goldenberg; Nisonoff, A., et al., Arch. Biochem. Biophys. 89:230, (1960); Porter, R. R., Biochem. J. 73:119, (1959); Edelman, et al., in Methods in Enzymology 1:422, Academic Press, (1967); and by Coligan at pages 2.8.1-2.8.10 and 2.10-2.10.4.

In some embodiments, the use of antibody fragments lacking the Fc region are preferred to avoid activation of the classical complement pathway which is initiated upon binding Fc to the Fcγ receptor. There are several methods by which one can produce a monoclonal antibody that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or $F(ab)_2$ fragments (Marian, M., et al., Mol. Immunol. 28:69-71, (1991)). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for MASP-3 in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as E. coli. The recombinant host cells synthesize a single polypeptide chain with a linker peptide bridging the two V domains. Methods for producing scFvs are described for example, by Whitlow, et al., "Methods: A Companion to Methods in Enzymology" 2:97, (1991); Bird, et al., Science 242:423, (1988); U.S. Pat. No. 4,946,778, to Ladner; Pack, P., et al., Bio/Technology 11:1271, (1993).

As an illustrative example, a MASP-3-specific scFv can be obtained by exposing lymphocytes to MASP-3 polypeptide in vitro and selecting antibody display libraries in phage or similar vectors (for example, through the use of immobilized or labeled MASP-3 protein or peptide). Genes encoding polypeptides having potential MASP-3 polypeptide binding domains can be obtained by screening random peptide libraries displayed on phage or on bacteria such as E. coli. These random peptide display libraries can be used to screen for peptides which interact with MASP-3. Techniques for creating and screening such random peptide display libraries are well known in the art (U.S. Pat. No. 5,223,409, to Lardner; U.S. Pat. No. 4,946,778, to Ladner; U.S. Pat. No. 5,403,484, to Lardner; U.S. Pat. No. 5,571, 698, to Lardner; and Kay et al., Phage Display of Peptides and Proteins Academic Press, Inc., 1996) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.).

Another form of a MASP-3 antibody fragment useful in this aspect of the invention is a peptide coding for a single complementarity-determining region (CDR) that binds to an epitope on a MASP-3 antigen and inhibits alternative complement pathway activation.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Methods in Enzymology 2:106, (1991); Courtenay-Luck, "Genetic Manipulation of Monoclonal Antibodies," in Monoclonal Antibodies: Production, Engineering and Clinical Application, Ritter et al. (eds.), page 166, Cambridge University Press, (1995); and Ward et al., "Genetic Manipulation and Expression of Antibodies," in Monoclonal Antibodies: Principles and Applications, Birch et al. (eds.), page 137, Wiley-Liss, Inc., 1995).

The high affinity MASP-3 inhibitory antibodies described herein are administered to a subject in need thereof to inhibit alternative pathway activation. In some embodiments, the high affinity MASP-3 inhibitory antibody is a humanized monoclonal MASP-3 antibody. optionally with reduced effector function.

Bispecific Antibodies

The high affinity MASP-3 inhibitory antibodies useful in the method of the invention encompass multispecific (i.e., bispecific and trispecific) antibodies. Bispecific antibodies are monoclonal, preferably human or humanized, antibodies that have binding specificities for at least two different antigens. In one embodiment, the compositions and methods comprise the use of a bispecific antibody comprising a binding specificity for the serine protease domain of MASP-3 and a binding specificity for MASP-2 (e.g., binding to at least one of CCP1-CCP2 or serine protease domain of MASP-2). In another embodiment, the method comprises the use of a bispecific antibody comprising a binding specificity for the serine protease domain of MASP-3 and a binding specificity for MASP-1 (e.g., binding to the serine protease domain of MASP-1). In another embodiment, the method comprises the use of a trispecific antibody comprising a binding specificity for MASP-3 (e.g., binding to the serine protease domain of MASP-3), a binding specificity for MASP-2 (e.g., binding to at least one of CCP1-CCP2 or serine protease domain of MASP-2) and a binding specificity for MASP-1 (e.g., binding to the serine protease domain of MASP-1).

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature 305:537-539 (1983)). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al., Methods in Enzymology 121:210 (1986); WO96/27011; Brennan et al., Science 229:81 (1985); Shalaby et al., J. Exp. Med. 175:217-225 (1992); Kostelny et al., J. Immunol. 148(5):1547-1553 (1992); Hollinger et al. Proc. Natl. Acad. Sci USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable crosslinking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. (See, e.g., Kostelny et al. J. Immunol. 148(5):1547-1553 (1992)). The "diabody" technology described by Hollinger et al. Proc. Natl. Acad. Sci USA 90:6444-6448 (1993), has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Another strategy for making bispecific antibody fragments by the use of single-chain Fv (scFv) dimers has also been reported. (See, e.g., Gruber et al. *J. Immunol.*, 152: 5368 (1994)). Alternatively, the antibodies can be "linear antibodies" as described in, e.g., Zapata et al., *Protein Eng.* 8(10):1057-1062 (1995). Briefly described, these antibodies comprise a pair of tandem Factor D segments ($V_H$-$C_H1$-$V_H$-$C_H1$) which form a pair of antigen binding regions. Linear antibodies can be bispecific or monospecific. The methods of the invention also embrace the use of variant forms of bispecific antibodies such as the tetravalent dual variable domain immunoglobulin (DVD-Ig) molecules described in Wu et al., *Nat Biotechnol* 25:1290-1297 (2007). The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., WO08/024188 and WO07/024715, the disclosures of each of which are incorporated herein by reference in their entirety.

III. Pharmaceutical Compositions and Delivery Methods Dosing

In another aspect, the invention provides compositions comprising high affinity MASP-3 inhibitory antibodies for inhibiting the adverse effects of alternative pathway complement activation in a subject in need thereof, such as, for example, a subject suffering from an alternative pathway-related disease or condition, such as, for example a hemolytic disease, such as PNH, or a disease or disorder selected from the group consisting of age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis (MS), Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

The methods of this aspect of the invention comprises administering to the subject a composition comprising an amount of a high affinity MASP-3 inhibitory antibody effective to inhibit alternative pathway complement activation and a pharmaceutically acceptable carrier. In some embodiments, the method further comprises administering a composition comprising a MASP-2 inhibitory agent. The high affinity MASP-3 inhibitory antibodies and MASP-2 inhibitory agents can be administered to a subject in need thereof, at therapeutically effective doses to treat or ameliorate conditions associated with alternative pathway complement activation, and optionally also MASP-2-dependent complement activation. A therapeutically effective dose refers to the amount of the MASP-3 inhibitory antibody, or a combination of a MASP-3 inhibitory antibody and a MASP-2 inhibitory agent sufficient to result in amelioration of symptoms of the condition. The inhibition of alternative pathway complement activation is characterized by at least one or more of the following changes in a component of the complement system that occurs as a result of administration of a high affinity MASP-3 inhibitory antibody in accordance with various embodiments of the invention: inhibition of hemolysis and/or opsonization; inhibition of lectin-independent conversion of factor B; inhibition of lectin-independent conversion of factor D, inhibition of MASP-3 serine protease substrate-specific cleavage; the reduction of hemolysis or the reduction of C3 cleavage and C3b surface deposition; the reduction of Factor B and Bb deposition on an activating surface; the reduction of resting levels (in circulation, and without the experimental addition of an activating surface) of active Factor D relative to pro-Factor D; the reduction of levels of active Factor D relative to pro-Factor D in response to an activating surface; and/or the reduction in the production of resting and surface-induced levels of fluid-phase Ba, Bb, C3b, or C3a.

Toxicity and therapeutic efficacy of MASP-3 and MASP-2 inhibitory agents can be determined by standard pharmaceutical procedures employing experimental animal models. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-3 inhibitory agents and MASP-2 inhibitory agents that exhibit large therapeutic ratios or indices are most preferred. The data obtained from the cell culture assays and animal studies can be used in formulating a range of dosages for use in humans. The dosage of the MASP-3 inhibitory agent and MASP-2 inhibitory agent preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration range that includes the MED Quantitative levels of the MASP-3 inhibitory agent or MASP-2 inhibitory agent in plasma may also be measured, for example, by high performance liquid chromatography.

In addition to toxicity studies, effective dosage may also be estimated based on the amount of target MASP protein present in a living subject and the binding affinity of the MASP-3 or MASP-2 inhibitory agent.

It has been reported that MASP-1 levels in normal human subjects is present in serum in levels in the range of from 1.48 to 12.83 µg/mL (Terai I. et al, *Clin Exp Immunol* 110:317-323 (1997); Theil et al., *Clin. Exp. Immunol.* 169: 38 (2012)). The mean serum MASP-3 concentrations in normal human subjects has been reported to be in the range of about 2.0 to 12.9 µg/mL (Skjoedt M et al., *Immunobiology* 215(11):921-31 (2010); Degn et al., *J. Immunol Methods,* 361-37 (2010); Csuka et al., *Mol. Immunol.* 54:271 (2013). It has been shown that MASP-2 levels in normal human subjects is present in serum in low levels in the range of 500 ng/mL, and MASP-2 levels in a particular subject can be determined using a quantitative assay for MASP-2 described in Moller-Kristensen M., et al., *J. Immunol. Methods* 282: 159-167 (2003) and Csuka et al., *Mol. Immunol.* 54:271 (2013).

Generally, the dosage of administered compositions comprising MASP-3 inhibitory agents or MASP-2 inhibitory agents varies depending on such factors as the subject's age, weight, height, sex, general medical condition, and previous medical history. As an illustration, MASP-3 inhibitory agents or MASP-2 inhibitory agents (such as MASP-3 antibodies, MASP-1 antibodies or MASP-2 antibodies), can be administered in dosage ranges from about 0.010 to 100.0 mg/kg, preferably 0.010 to 10 mg/kg, preferably 0.010 to 1.0 mg/kg, more preferably 0.010 to 0.1 mg/kg of the subject body weight. In some embodiments, MASP-2 inhibitory agents (such as MASP-2 antibodies) are administered in dosage ranges from about preferably 0.010 to 10 mg/kg, preferably 0.010 to 1.0 mg/kg, more preferably 0.010 to 0.1 mg/kg of the subject body weight. In some embodiments, MASP-1 inhibitory agents (such as MASP-1 antibodies) or MASP-3 inhibitory agents (such as MASP-3 antibodies) are administered in dosage ranges from about 0.010 to 100.0 mg/kg, preferably 0.010 to 10 mg/kg, such as form about 1 mg/kg to about 10 mg/kg, preferably 0.010 to 1.0 mg/kg, more preferably 0.010 to 0.1 mg/kg of the subject body weight.

Therapeutic efficacy of MASP-3 inhibitory compositions, optionally in combination with MASP-2 inhibitory compositions, or of MASP-1 inhibitory compositions, optionally in combination with MASP-2 inhibitory compositions, and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize monoclonal antibodies that react with new antigens (neoantigens) exposed on the fragment, but not on the native proteins from which they are formed, making these assays very simple and specific. Most rely on ELISA technology, although radio-immunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment and/or measurement of factor D activation. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of the alternative pathway in a mammalian subject is characterized by at least one or more of the following in the mammalian subject after treatment with a high affinity MASP-3 inhibitory antibody disclosed herein: inhibition of Factor D maturation; inhibition of the alternative pathway when administered to the subject at a molar ratio of from about 1:1 to about 2.5:1 (MASP-3 target to mAb); the classical pathway is not inhibited; inhibition of hemolysis and/or opsonization; a reduction of hemolysis or the reduction of C3 cleavage and C3b surface deposition; a reduction of Factor B and Bb deposition on an activating surface; a reduction of resting levels (in circulation, and without the experimental addition of an activating surface) of active Factor D relative to pro-Factor D; a reduction of levels of active Factor D relative to pro-Factor D in response to an activating surface; and/or a reduction of the production of resting and surface-induced levels of fluid-phase Ba, Bb, C3b, or C3a.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in measured, for example, as described in Example 2 of U.S. Pat. No. 7,919,094), the reduction of C4 cleavage and C4b deposition or the reduction of C3 cleavage and C3b deposition.

Pharmaceutical Carriers and Delivery Vehicles

In general, the MASP-3 inhibitory antibody compositions, or compositions comprising a combination of MASP-2 and MASP-3 inhibitory agents, may be combined with any other selected therapeutic agents, are suitably contained in a pharmaceutically acceptable carrier. The carrier is non-toxic, biocompatible and is selected so as not to detrimentally affect the biological activity of the MASP-3 inhibitory antibody or the MASP-2 inhibitory agent (and any other therapeutic agents combined therewith). Exemplary pharmaceutically acceptable carriers for peptides are described in U.S. Pat. No. 5,211,657 to Yamada. The MASP-3 antibodies useful in the invention, as described herein, may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO: PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

Compositions of the present invention may be formulated for delivery subcutaneously, intra-muscularly, intravenously, intra-arterially or as an inhalant.

For intra-articular delivery, the MASP-3 inhibitory antibody, optionally in combination with a MASP-2 inhibitory agent may be carried in above-described liquid or gel carriers that are injectable, above-described sustained-release delivery vehicles that are injectable, or a hyaluronic acid or hyaluronic acid derivative.

For oral administration of non-peptidergic agents, the MASP-3 inhibitory antibody, optionally in combination with a MASP-2 inhibitory agent may be carried in an inert filler or diluent such as sucrose, cornstarch, or cellulose.

For topical administration, the MASP-3 inhibitory antibody, optionally in combination with a MASP-2 inhibitory agent may be carried in ointment, lotion, cream, gel, drop, suppository, spray, liquid or powder, or in gel or microcapsular delivery systems via a transdermal patch.

Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavoring agents (for oral administration).

Pharmaceutical Carriers for Antibodies and Peptides

More specifically with respect to high affinity MASP-3 inhibitory antibodies, as described herein, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising MASP-3 antibodies. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The MASP-3 antibodies can also be administered in the form of a depot injection or implant preparation that can be formulated in such a manner as to permit a sustained or pulsatile release of the active agents.

IV. Modes of Administration

The pharmaceutical compositions comprising the MASP-3 inhibitory antibodies, optionally in combination with MASP-2 inhibitory agents may be administered in a number of ways depending on whether a local or systemic mode of administration is most appropriate for the condition being treated. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intraarterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous, intraarterial and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

The MASP-3 inhibitory antibodies, as described herein, can be delivered into a subject in need thereof by any suitable means. Methods of delivery of MASP-3 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-3 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, (1988); Lee, V. H. L., *J. Controlled Release* 13:213, (1990); Lee, V. H. L., Ed., *Peptide and Protein Drug Delivery*, Marcel Dekker, New York (1991); DeBoer, A. G., et al., *J. Controlled Release* 13:241, (1990). For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-3 inhibitory antibodies as described herein may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, (1990)). Many polymer systems have been reported for protein delivery (Bae, Y. H., et al., *J. Controlled Release* 9:271, (1989); Hori, R., et al., *Pharm. Res.* 6:813, (1989); Yamakawa, I., et al., *J. Pharm. Sci.* 79:505, (1990); Yoshihiro, I., et al., *J. Controlled Release* 10:195, (1989); Asano, M., et al., *J. Controlled Release* 9:111, (1989); Rosenblatt, J., et al., *J. Controlled Release* 9:195, (1989); Makino, K., *J. Controlled Release* 12:235, (1990); Takakura, Y., et al., *J. Pharm. Sci.* 78:117, (1989); Takakura, Y., et al., *J. Pharm. Sci.* 78:219, (1989)).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567, 434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-3 inhibitory antibodies, as described herein, may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-3 inhibitory antibodies may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-3 inhibitory antibody or the MASP-2 inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-3 inhibitory antibody or a MASP-2 inhibitory agent may be achieved in the context of surgical methods for treating a disease or condition, such as for example during procedures such as arterial bypass surgery, atherectomy, laser procedures, ultrasonic procedures, balloon angioplasty and stent placement. For example, a MASP-3 inhibitory antibody or a MASP-2 inhibitory agent can be administered to a subject in conjunction with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the vascular wall. As a result, the balloon surface is in contact with the layer of vascular endothelial cells on the surface of the blood vessel. The MASP-3 inhibitory antibody or MASP-2 inhibitory agent may be attached to the balloon angioplasty catheter in a manner that permits release of the agent at the site of the atherosclerotic plaque. The agent may be attached to the balloon catheter in accordance with standard procedures known in the art. For example, the agent may be stored in a compartment of the balloon catheter until the balloon is inflated, at which point it is released into the local environment. Alternatively, the agent may be impregnated on the balloon surface, such that it contacts the cells of the arterial wall as the balloon is inflated. The agent may also be delivered in a perforated balloon catheter such as those disclosed in Flugelman, M. Y., et al., *Circulation* 85:1110-1117, (1992). See also published PCT Application WO 95/23161 for an exemplary procedure for attaching a therapeutic protein to a balloon angioplasty catheter. Likewise, the MASP-3 inhibitory agent or MASP-2 inhibitory agent may be included in a gel or polymeric coating applied to a stent, or may be incorporated into the material of the stent, such that the stent elutes the MASP-3 inhibitory agent or MASP-2 inhibitory agent after vascular placement.

MASP-3 inhibitory antibodies used in the treatment of arthritides and other musculoskeletal disorders may be locally delivered by intra-articular injection. Such compositions may suitably include a sustained release delivery vehicle. As a further example of instances in which local delivery may be desired, MASP-3 inhibitory compositions used in the treatment of urogenital conditions may be suitably instilled intravesically or within another urogenital structure.

V. Treatment Regimens

In prophylactic applications, the pharmaceutical compositions are administered to a subject susceptible to, or otherwise at risk of, an alternative pathway associated disease or disorder, for example, an alternative pathway disease or disorder selected from the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) and thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis., in an amount sufficient to eliminate or reduce the risk of developing symptoms of the condition. In therapeutic applications, the pharmaceutical compositions are administered to a subject suspected of, or already suffering from, an alternative pathway-related disease or disorder, such as an alternative pathway disease or disorder selected from the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis, in a therapeutically effective amount sufficient to relieve, or at least partially reduce, the symptoms of the condition.

In one embodiment, the pharmaceutical composition comprising a high affinity MASP-3 inhibitory antibody is administered to a subject suffering from, or at risk for developing PNH. In accordance with this the subject's red blood cells are opsonized by fragments of C3 in the absence of the composition, and administration of the composition to the subject increases the survival of red blood cells in the subject. In one embodiment, the subject exhibits one or more symptoms in the absence of the composition selected from the group consisting of (i) below normal levels of hemoglobin, (ii) below normal levels of platelets; (iii) above normal levels of reticulocytes, and (iv) above normal levels of bilirubin, and administration of the composition to the subject improves at least one or more of the symptoms, resulting in (i) increased, normal, or nearly normal levels of hemoglobin (ii) increased, normal or nearly normal levels of platelets, (iii) decreased, normal or nearly normal levels of reticulocytes, and/or (iv) decreased, normal or nearly normal levels of bilirubin.

In both prophylactic and therapeutic regimens for the treatment, prevention or reduction in severity of a disease or condition selected from the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica and Behcet's disease, compositions comprising high affinity MASP-3 inhibitory antibodies and optionally MASP-2 inhibitory agents may be administered in several dosages until a sufficient therapeutic outcome has been achieved in the subject. In one embodiment of the invention, the high affinity MASP-3 inhibitory antibody and/or MASP-2 inhibitory agent may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg, or 10 to 200 mg. For pediatric patients, dosage can be adjusted in proportion to the patient's weight.

Application of the high affinity MASP-3 inhibitory antibodies and optional MASP-2 inhibitory compositions of the present invention may be carried out by a single administration of the composition (e.g., a single composition comprising MASP-3 and optionally MASP-2 inhibitory agents, or bispecific or dual inhibitory agents, or co-administration of separate compositions), or a limited sequence of administrations, for treatment of an alternative pathway-related disease or disorder, such as a disease or disorder selected form the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

Alternatively, the composition may be administered at periodic intervals such as daily, biweekly, weekly, every other week, monthly or bimonthly over an extended period of time for as determined by a physician for optimal therapeutic effect.

In some embodiments, a first composition comprising at least one high affinity MASP-3 inhibitory antibody and a second composition comprising at least one MASP-2 inhibitory agent are administered to a subject suffering from, or at risk for developing a disease or condition selected from the group consisting of paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

In one embodiment, the first composition comprising at least one high affinity MASP-3 inhibitory antibody and a second composition comprising at least one MASP-2 inhibitory agent are administered simultaneously (i.e., within a time separation of no more than about 15 minutes or less, such as no more than any of 10, 5 or 1 minute). In one embodiment, the first composition comprising at least one high affinity MASP-3 inhibitory antibody and a second composition comprising at least one MASP-2 inhibitory agent are administered sequentially (i.e., the first composition is administered either prior to or after the administration of the second composition, wherein the time separation of administration is more than 15 minutes). In some embodiments, the first composition comprising at least one high affinity MASP-3 inhibitory antibody and a second composition comprising at least one MASP-2 inhibitory agent are administered concurrently (i.e., the administration period of the first composition overlaps with the administration of the second composition). For example, in some embodiments, the first composition and/or the second composition are administered for a period of at least one, two, three or four weeks or longer. In one embodiment, at least one high affinity MASP-3 inhibitory antibody and at least one MASP-2 inhibitory agent are combined in a unit dosage form. In one embodiment, a first composition comprising at least one high affinity MASP-3 inhibitory antibody and a second composition comprising at least one MASP-2 inhibitory agent are packaged together in a kit for use in treatment of an alternative pathway-related disease or condition, such as paroxysmal nocturnal hemoglobinuria (PNH), age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy or Myasthenia Gravis.

In some embodiments, the subject suffering from PNH, age-related macular degeneration (AMD), ischemia-reperfusion injury, arthritis, disseminated intravascular coagulation, thrombotic microangiopathy (including hemolytic uremic syndrome (HUS), atypical hemolytic uremic syndrome (aHUS) or thrombotic thrombocytopenic purpura (TTP)), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis has previously undergone, or is currently undergoing treatment with a terminal complement inhibitor that inhibits cleavage of complement protein C5. In some embodiments, the method comprises administering to the subject a composition of the invention comprising a high affinity MASP-3 inhibitory antibody and optionally a MASP-2 inhibitor and further administering to the subject a terminal complement inhibitor that inhibits cleavage of complement protein C5. In some embodiments, the terminal complement inhibitor is a humanized anti-05 antibody or antigen-binding fragment thereof. In some embodiments, the terminal complement inhibitor is eculizumab.

VI. EXAMPLES

The following examples merely illustrate the best mode now contemplated for practicing the invention, but should not be construed to limit the invention. All literature citations herein are expressly incorporated by reference.

Example 1

This Example demonstrates that MASP-2 deficient mice are protected from *Neisseria meningitidis* induced mortality after infection with either *N. meningitidis* serogroup A or *N. meningitidis* serogroup B.

Methods:

MASP-2 knockout mice (MASP-2 KO mice) were generated as described in Example 1 of U.S. Pat. No. 7,919,094, hereby incorporated herein by reference. 10-week-old MASP-2 KO mice (n=10) and wild-type (WT) C57/BL6 mice (n=10) were inoculated by intraperitoneal (i.p.) injection with a dosage of $2.6 \times 10^7$ CFU of *N. meningitidis* serogroup A Z2491 in a volume of 100 µl. The infective dose was administered to mice in conjunction with iron dextran at a final concentration of 400 mg/kg. Survival of the mice after infection was monitored over a 72-hour time period.

In a separate experiment, 10-week-old MASP-2 KO mice (n=10) and WT C57/BL6 mice (n=10) were inoculated by i.p. injection with a dosage of $6 \times 10^6$ CFU of *N. meningitidis* serogroup B strain MC58 in a volume of 100 µL. The infective dose was administered to mice in conjunction with iron dextran at a final dose of 400 mg/kg. Survival of the mice after infection was monitored over a 72-hour time period. An illness score was also determined for the WT and MASP-2 KO mice during the 72-hour time period after infection, based on the illness scoring parameters described below in TABLE 5, which is based on the scheme of Fransen et al. (2010) with slight modifications.

TABLE 5

| Illness Scoring associated with clinical signs in infected mice | |
|---|---|
| Signs | Score |
| Normal | 0 |
| Slightly ruffled fur | 1 |
| Ruffled fur, slow and sticky eyes | 2 |
| Ruffled fur, lethargic and eyes shut | 3 |
| Very sick and no movement after stimulation | 4 |
| Dead | 5 |

Blood samples were taken from the mice at hourly intervals after infection and analyzed to determine the serum level (log cfu/mL) of *N. meningitidis* in order to verify infection and determine the rate of clearance of the bacteria from the serum.

Results:

FIG. 6 is a Kaplan-Meyer plot graphically illustrating the percent survival of MASP-2 KO and WT mice after administration of an infective dose of $2.6 \times 10^7$ cfu of *N. meningitidis* serogroup A Z2491. As shown in FIG. 6, 100% of the MASP-2 KO mice survived throughout the 72-hour period after infection. In contrast, only 80% of the WT mice (p=0.012) were still alive 24 hours after infection, and only 50% of the WT mice were still alive at 72 hours after infection. These results demonstrate that MASP-2-deficient mice are protected from *N. meningitidis* serogroup A Z2491-induced mortality.

FIG. 7 is a Kaplan-Meyer plot graphically illustrating the percent survival of MASP-2 KO and WT mice after administration of an infective dose of $6 \times 10^6$ cfu of *N. meningitidis* serogroup B strain MC58. As shown in FIG. 7, 90% of the MASP-2 KO mice survived throughout the 72-hour period after infection. In contrast, only 20% of the WT mice (p=0.0022) were still alive 24 hours after infection. These results demonstrate that MASP-2-deficient mice are protected from *N. meningitidis* serogroup B strain MC58-induced mortality.

FIG. 8 graphically illustrates the log cfu/mL of *N. meningitidis* serogroup B strain MC58 recovered at different time points in blood samples taken from the MASP-2 KO and WT mice after i.p. infection with $6\times10^6$ cfu of *N. meningitidis* serogroup B strain MC58 (n=3 at different time points for both groups of mice). The results are expressed as Means±SEM. As shown in FIG. 8, in WT mice the level of *N. meningitidis* in the blood reached a peak of about 6.0 log cfu/mL at 24 hours after infection and dropped to about 4.0 log cfu/mL by 36 hours after infection. In contrast, in the MASP-2 KO mice, the level of *N. meningitidis* reached a peak of about 4.0 log cfu/mL at 12 hours after infection and dropped to about 1.0 log cfu/mL by 36 hours after infection (the symbol "*" indicates p<0.05; the symbol "**" indicates p=0.0043). These results demonstrate that although the MASP-2 KO mice were infected with the same dose of *N. meningitidis* serogroup B strain MC58 as the WT mice, the MASP-2 KO mice have enhanced clearance of bacteremia as compared to WT.

Figure 9:
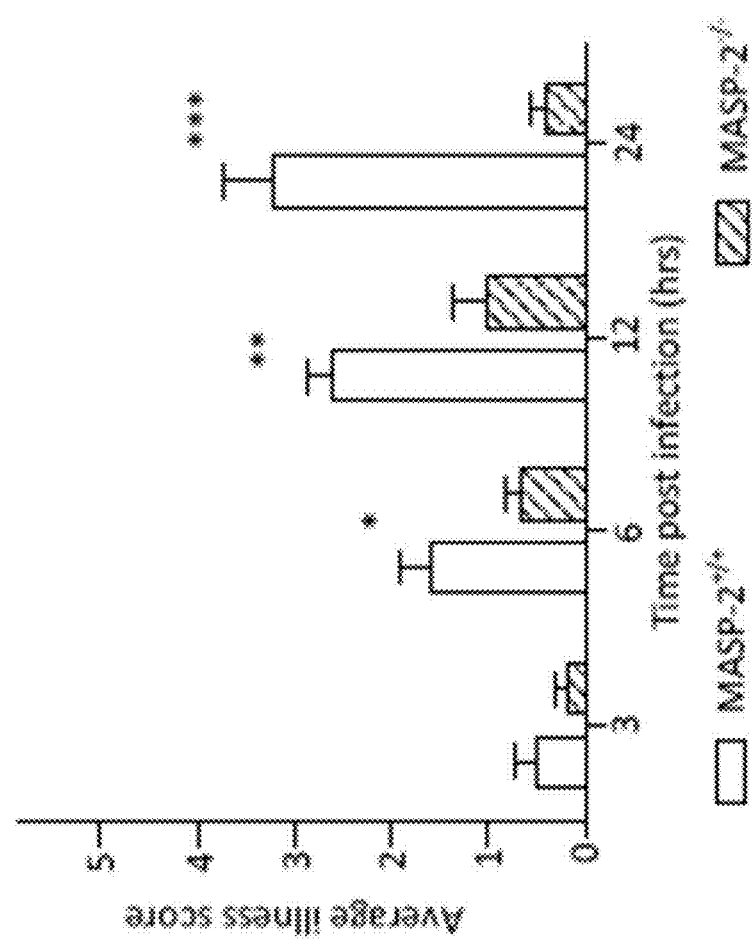
FIG. 9 graphically illustrates the average illness score of MASP-2 KO and WT mice at 3, 6, 12 and 24 hours after infection with $6 \times 10^6$ cfu of *N. meningitidis* serogroup B strain MC58, demonstrating that the MASP-2-deficient mice showed much lower illness scores at 6 hours, 12 hours, and 24 hours after infection, as compared to WT mice, as described in Example 1.

FIG. 9 graphically illustrates the average illness score of MASP-2 KO and WT mice at 3, 6, 12 and 24 hours after infection with $6\times10^6$ cfu of *N. meningitidis* serogroup B strain MC58. As shown in FIG. 9, the MASP-2-deficient mice showed high resistance to the infection, with much lower illness scores at 6 hours (symbol "*" indicates p=0.0411), 12 hours (symbol "" indicates p=0.0049) and 24 hours (symbol "*" indicates p=0.0049) after infection, as compared to WT mice. The results in FIG. 9 are expressed as means±SEM.

In summary, the results in this Example demonstrate that MASP-2-deficient mice are protected from *N. meningitides*-induced mortality after infection with either *N. meningitidis* serogroup A or *N. meningitidis* serogroup B.

Example 2

This Example demonstrates that the administration of MASP-2 antibody after infection with *N. meningitidis* increases the survival of mice infected with *N. meningitidis*.

Background/Rationale:

As described in Example 24 of U.S. Pat. No. 7,919,094, incorporated herein by reference, rat MASP-2 protein was utilized to pan a Fab phage display library, from which Fab2 #11 was identified as a functionally active antibody. Full-length antibodies of the rat IgG2c and mouse IgG2a isotypes were generated from Fab2 #11. The full-length MASP-2 antibody of the mouse IgG2a isotype was characterized for pharmacodynamic parameters (as described in Example 38 of U.S. Pat. No. 7,919,094).

In this Example, the mouse MASP-2 full-length antibody derived from Fab2 #11 was analyzed in the mouse model of *N. meningitidis* infection.

Methods:

The mouse IgG2a full-length MASP-2 antibody isotype derived from Fab2 #11, generated as described above, was tested in the mouse model of *N. meningitidis* infection as follows.

1. Administration of Mouse-MASP-2 Monoclonal Antibodies (MoAb) after Infection 9-week-old C57/BL6 Charles River mice were treated with inhibitory mouse MASP-2 antibody (1.0 mg/kg) (n=12) or control isotype antibody (n=10) at 3 hours after i.p. injection with a high dose ($4\times10^6$ cfu) of *N. meningitidis* serogroup B strain MC58.

Figure 10:
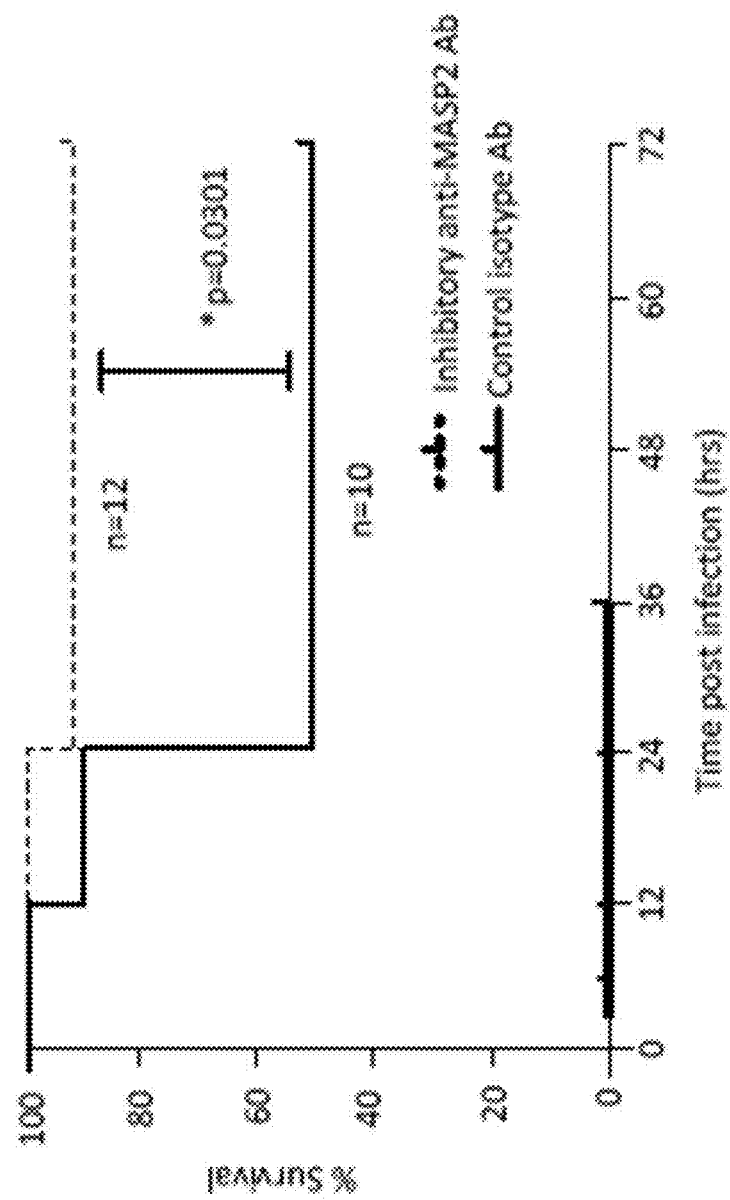
FIG. 10 is a Kaplan-Meyer plot graphically illustrating the percent survival of mice after administration of an infective dose of $4 \times 10^6$ cfu of *N. meningitidis* serogroup B strain MC58, followed by administration 3 hours post-infection of either inhibitory MASP-2 antibody (1 mg/kg) or control isotype antibody, demonstrating that MASP-2 antibody is effective to treat and improve survival in subjects infected with *N. meningitidis*, as described in Example 2.

Results:

FIG. 10 is a Kaplan-Meyer plot graphically illustrating the percent survival of mice after administration of an infective dose of $4\times10^6$ cfu of *N. meningitidis* serogroup B strain MC58, followed by administration 3 hours post-infection of either inhibitory MASP-2 antibody (1.0 mg/kg) or control isotype antibody. As shown in FIG. 10, 90% of the mice treated with MASP-2 antibody survived throughout the 72-hour period after infection. In contrast, only 50% of the mice treated with isotype control antibody survived throughout the 72-hour period after infection. The symbol "*" indicates p=0.0301, as determined by comparison of the two survival curves.

These results demonstrate that administration of a MASP-2 antibody is effective to treat and improve survival in subjects infected with *N. meningitidis*.

As demonstrated herein, the use of MASP-2 antibody in the treatment of a subject infected with *N. meningitidis* is effective when administered within 3 hours post-infection, and is expected to be effective within 24 hours to 48 hours after infection. Meningococcal disease (either meningococcemia or meningitis) is a medical emergency, and therapy will typically be initiated immediately if meningococcal disease is suspected (i.e., before *N. meningitidis* is positively identified as the etiological agent).

In view of the results in the MASP-2 KO mouse demonstrated in EXAMPLE 1, it is believed that administration of MASP-2 antibody prior to infection with *N. meningitidis* would also be effective to prevent or ameliorate the severity of infection.

Example 3

This Example demonstrates the complement-dependent killing of *N. meningitidis* in human sera is MASP-3-dependent.

Rationale:

Patients with decreased serum levels of functional MBL display increased susceptibility to recurrent bacterial and fungal infections (Kilpatrick et al., *Biochim Biophys Acta* 1572:401-413 (2002)). It is known that *N. meningitidis* is recognized by MBL, and it has been shown that MBL-deficient sera do not lyse *N. meningitidis*.

In view of the results described in Examples 1 and 2, a series of experiments were carried out to determine the efficacy of administration of MASP-2 antibody to treat *N. meningitidis* infection in complement-deficient and control human sera. Experiments were carried out in a high concentration of serum (20%) in order to preserve the complement pathway.

Methods:

1. Serum Bactericidal Activity in Various Complement-Deficient Human Sera and in Human Sera Treated with Human MASP-2 Antibody The following complement-deficient human sera and control human sera were used in this experiment:

TABLE 6

Human serum samples tested (as shown in FIG. 11)

| Sample | Serum type |
|---|---|
| A | Normal human sera (NHS) + human MASP-2 Ab |
| B | NHS + isotype control Ab |

TABLE 6-continued

| Human serum samples tested (as shown in FIG. 11) | |
|---|---|
| Sample | Serum type |
| C | MBL −/− human serum |
| D | NHS |
| E | Heat-Inactivated (HI) NHS |

A recombinant antibody against human MASP-2 was isolated from a combinatorial Antibody Library (Knappik, A., et al., *J. Mol. Biol.* 296:57-86 (2000)), using recombinant human MASP-2A as an antigen (Chen, C. B. and Wallis, *J. Biol. Chem.* 276:25894-25902 (2001)). An anti-human scFv fragment that potently inhibited lectin pathway-mediated activation of C4 and C3 in human plasma ($IC_{50}$~20 nM) was identified and converted to a full-length human IgG4 antibody.

*N. meningitidis* serogroup B-MC58 was incubated with the different sera show in TABLE 6, each at a serum concentration of 20%, with or without the addition of inhibitory human MASP-2 antibody (3 μg in 100 μl total volume) at 37° C. with shaking. Samples were taken at the following time points: 0-, 30-, 60- and 90-minute intervals, plated out and then viable counts were determined. Heat-inactivated human serum was used as a negative control.

Results:

FIG. 11 graphically illustrates the log cfu/mL of viable counts of *N. meningitidis* serogroup B-MC58 recovered at different time points in the human sera samples shown in TABLE 6. TABLE 7 provides the Student's t-test results for FIG. 11.

TABLE 7

| Student's t-test Results for FIG. 11 (time point 60 minutes) | | | |
|---|---|---|---|
| | Mean Diff. (Log) | Significant? P < 0.05? | P value summary |
| A vs B | −0.3678 | Yes | ***(0.0002) |
| A vs C | −1.1053 | Yes | ***(p < 0.0001) |
| A vs D | −0.2111 | Yes | **(0.0012) |
| C vs D | 1.9 | Yes | ***(p < 0.0001) |

As shown in FIG. 11 and TABLE 7, complement-dependent killing of *N. meningitidis* in human 20% serum was significantly enhanced by the addition of the human MASP-2 inhibitory antibody.

2. Serum Bactericidal Activity in Various Complement-Deficient Human Sera

The following complement-deficient human sera and control human sera were used in this experiment:

TABLE 8

| Human serum samples tested (as shown in FIG. 12) | |
|---|---|
| Sample | Serum Type |
| A | Normal human serum (NHS) |
| B | Heat-inactivated NHS |
| C | MBL−/− |
| D | MASP-3−/− (MASP-1+) |

Note: The MASP-3−/− (MASP-1+) serum in sample D was taken from a subject with 3MC syndrome, which is a unifying term for the overlapping Carnevale, Mingarelli, Malpuech and Michels syndromes. As further described in Example 4, the mutations in exon 12 of the MASP-1/3 gene render the serine protease domain of MASP-3, but not MASP-1 dysfunctional. As described in Example 10, pro-factor D is preferentially present in 3MC serum, whereas activated factor D is preferentially present in normal human serum.

*N. meningitidis* serogroup B-MC58 was incubated with different complement-deficient human sera, each at a serum concentration of 20%, at 37° C. with shaking. Samples were taken at the following time points: 0-, 15-, 30-, 45-, 60-, 90- and 120-minute intervals, plated out and then viable counts were determined. Heat-inactivated human serum was used as a negative control.

Results:

FIG. 12 graphically illustrates the log cfu/mL of viable counts of *N. meningitidis* serogroup B-MC58 recovered at different time points in the human sera samples shown in TABLE 8. As shown in FIG. 12, the WT (NHS) serum has the highest level of bactericidal activity for *N. meningitidis*. In contrast, the MBL−/− and MASP-3−/− (which is MASP-1-sufficient) human sera do not have any bactericidal activity. These results indicate that complement-dependent killing of *N. meningitidis* in human 20% (v/v) serum is MASP-3- and MBL-dependent. TABLE 9 provides the Student's t-test results for FIG. 12.

TABLE 9

| Student's t-test Results for FIG. 12 | | | | |
|---|---|---|---|---|
| Comparison | Time Point (min) | Mean Diff. (Log) | Significant? P < 0.05? | P value Summary |
| A vs B | 60 | −0.8325 | Yes | ***(p < 0.0001) |
| A vs B | 90 | −1.600 | Yes | ***(p < 0.0001) |
| A vs C | 60 | −1.1489 | Yes | ***(p < 0.0001) |
| A vs C | 90 | −1.822 | Yes | ***(p < 0.0001) |
| A vs D | 60 | −1.323 | Yes | ***(0.0005) |
| A vs D | 90 | −2.185 | Yes | ***(p < 0.0001) |

In summary, the results shown in FIG. 12 and TABLE 9 demonstrate that complement-dependent killing of *N. meningitidis* in 20% human serum is MASP-3- and MBL-dependent.

3. Complement-Dependent Killing of *N. meningitidis* in 20% (v/v) Mouse Sera Deficient of MASP-2, MASP-1/3 or MBL A/C.

The following complement-deficient mouse sera and control mouse sera were used in this experiment:

TABLE 10

| Mouse serum samples tested (as shown in FIG. 13) | |
|---|---|
| Sample | Serum Type |
| A | WT |
| B | MASP-2 −/− |
| C | MASP-1/3 −/− |
| D | MBL A/C −/− |
| E | WT heat-inactivated (HIS) |

*N. meningitidis* serogroup B-MC58 was incubated with different complement-deficient mouse sera, each at a serum concentration of 20%, at 37° C. with shaking. Samples were taken at the following time points: 0-, 15-, 30-, 60-, 90- and 120-minute intervals, plated out and then viable counts were determined. Heat-inactivated human serum was used as a negative control.

Results:
FIG. 13 graphically illustrates the log cfu/mL of viable counts of *N. meningitidis* serogroup B-MC58 recovered at different time points in the mouse serum samples shown in TABLE 10. As shown in FIG. 13, the MASP-2−/− mouse sera have a higher level of bactericidal activity for *N. meningitidis* than WT mouse sera. In contrast, the MASP-1/3−/− mouse sera do not have any bactericidal activity. The symbol "" indicates p=0.0058, the symbol "*" indicates p=0.001. TABLE 11 provides the Student's t-test results for FIG. 13.

TABLE 11

Student's t-test Results for FIG. 13

| Comparison | Time point | Mean Diff. (LOG) | Significant? (p < 0.05)? | P value summary |
|---|---|---|---|---|
| A vs. B | 60 min. | 0.39 | yes | ** (0.0058) |
| A vs. B | 90 min. | 0.6741 | yes | *** (0.001) |

In summary, the results in this Example demonstrate that MASP-2−/− serum has a higher level of bactericidal activity for *N. meningitidis* than WT serum and that complement-dependent killing of *N. meningitidis* in 20% serum is MASP-3- and MBL-dependent.

Example 4

This Example describes a series of experiments that were carried out to determine the mechanism of the MASP-3-dependent resistance to *N. meningitidis* infection observed in MASP-2 KO mice, as described in Examples 1-3.

Rationale:
In order to determine the mechanism of MASP-3-dependent resistance to *N. meningitidis* infection observed in MASP-2 KO mice (described in Examples 1-3 above), a series of experiments were carried out as follows.

1. MASP-1/3-Deficient Mice are not Deficient of Lectin Pathway Functional Activity (Also Referred to as "LEA-2")

Methods:
In order to determine whether MASP-1/3-deficient mice are deficient of lectin pathway functional activity (also referred to as LEA-2), an assay was carried out to measure the kinetics of C3 convertase activity in plasma from various complement-deficient mouse strains tested under lectin activation pathway-specific assay conditions (1% plasma), as described in Schwaeble W. et al., *PNAS* vol 108(18):7523-7528 (2011), hereby incorporated herein by reference.

Plasma was tested from WT, C4−/−, MASP-1/3−/−; Factor B−/−, and MASP-2−/− mice as follows.

To measure C3 activation, microtiter plates were coated with mannan (1 μg/well), zymosan (1 μg/well) in coating buffer (15 mM $Na_2Co_3$, 35 mM $NaHCO_3$), or immune complexes, generated in situ by coating with 1% human serum albumin (HSA) in coating buffer then adding sheep anti-HAS serum (2 μg/mL) in TBS (10 mM Tris, 140 mM NaCl, pH 7.4) with 0.05% Tween 20 and 5 mM $Ca^{++}$. Plates were blocked with 0.1% HSA in TBS and washed three times with TBS/Tween20/$Ca^{++}$. Plasma samples were diluted in 4 mM barbital, 145 mM NaCl, 2 mM $CaCl_2$, 1 mM $MgCl_2$, pH 7.4, added to the plates and incubated for 1.5 h at 37° C. After washing, bound C3b was detected using rabbit anti-human C3c (Dako), followed by alkaline phosphatase-conjugated goat anti-rabbit IgG and p-nitrophenyl phosphate.

Figure 14:
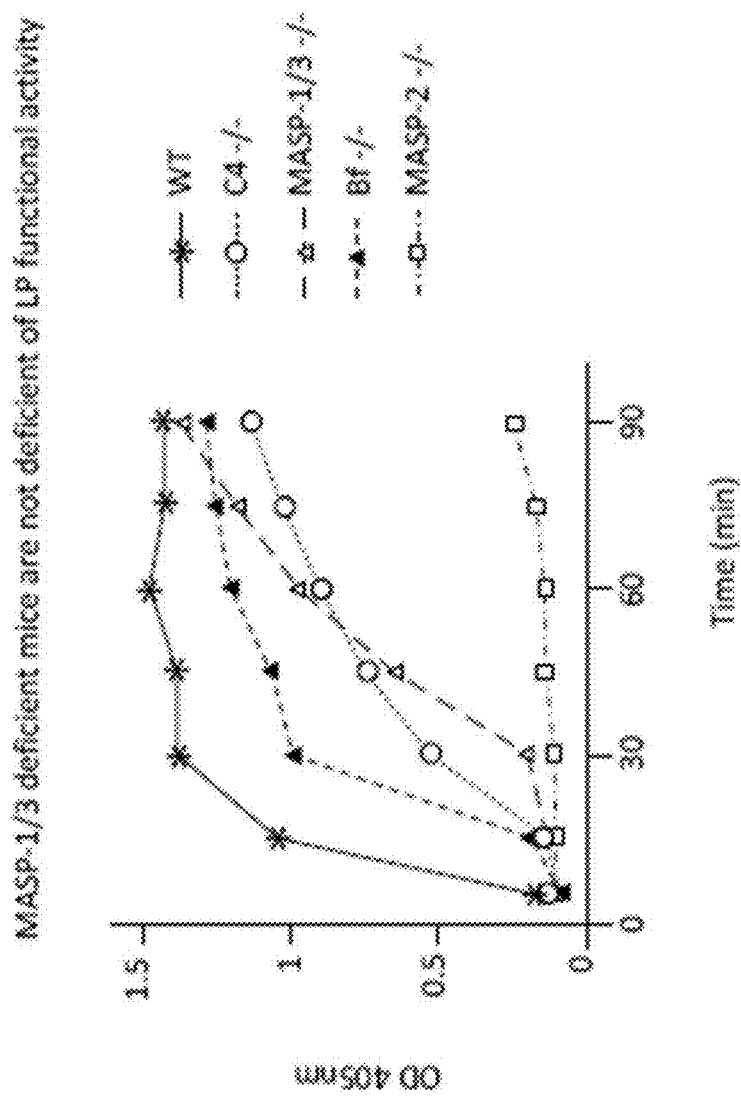
FIG. 14 graphically illustrates the kinetics of C3 activation under lectin pathway-specific conditions (1% plasma) in WT, C4-/-, MASP-1/3-/-, Factor B-/- and MASP-2-/- mouse sera, as described in Example 4.

Results:
The kinetics of C3 activation (as measured by C3b deposition on mannan-coated plates with 1% serum) under lectin pathway-specific conditions is shown in FIG. 14. No C3 cleavage was seen in MASP-2−/− plasma. Factor B−/− (Factor B−/−) plasma cleaved C3 at half the rate of WT plasma, likely due to the loss of the amplification loop. A significant delay in the lectin pathway-dependent conversion of C3 to C3b was seen in C4−/− ($T_{1/2}$=33 min) as well as in MASP-1/3−/− deficient plasma ($T_{1/2}$=49 min). This delay of C3 activation in MASP-1/3−/− plasma has been shown to be MASP-1- rather than MASP-3-dependent. (See Takahashi M. et al., *J Immunol* 180:6132-6138 (2008)). These results demonstrate that MASP-1/3-deficient mice are not deficient of lectin pathway functional activity (also referred to as "LEA-2").

2. Effect of Hereditary MASP-3 Deficiency on Alternative Pathway Activation.

Rationale:
The effect of hereditary MASP-3 deficiency on alternative pathway activation was determined by testing serum of a MASP-3-deficient patient with 3MC syndrome caused by a frame-shift mutation in the exon encoding the serine protease of MASP-3. The 3MC syndrome is a unifying term for the overlapping Carneavale, Mingarelli, Malpuech and Michels syndromes. These rare autosomal recessive disorders exhibit a spectrum of developmental features, including characteristic facial dysmorphism, cleft lip and/or palate, craniosynostosis, learning disability and genital, limb and vesicorenal abnormalities. Rooryck et al., *Nature Genetics* 43:197-203 (2011) studied 11 families with 3MC syndrome and identified two mutated genes, COLEC11 and MASP-1. The mutations in the MASP-1 gene render the exon encoding the serine protease domain of MASP-3, but not the exons encoding the serine protease of MASP-1, dysfunctional. Therefore, 3MC patients with mutations in the exon encoding the serine protease of MASP-3 are deficient of MASP-3 but sufficient in MASP-1.

Methods:
MASP-3-deficient serum was obtained from a 3MC patient, the mother and father of the 3MC patient (both heterozygous for the allele bearing a mutation that renders the exon encoding the MASP-3 serine protease domain dysfunctional), as well as from a C4-deficient patient (deficient in both human C4 genes) and an MBL-deficient subject. An alternative pathway assay was carried out under traditional AP-specific conditions (BBS/$Mg^{++}$/EGTA, without $Ca^{++}$, wherein BBS=barbital buffered saline containing sucrose), as described in Bitter-Suermann et al., *Eur. J. Immunol* 11:291-295 (1981)), on zymosan-coated microtiter plates at serum concentrations ranging from 0.5 to 25% and C3b deposition was measured over time.

Results:
FIG. 15 graphically illustrates the level of alternative pathway-driven C3b deposition on zymosan-coated microtiter plates as a function of serum concentration in serum samples obtained from MASP-3-deficient, C4-deficient and MBL-deficient subjects. As shown in FIG. 15, MASP-3-deficient patient serum has residual alternative pathway (AP) activity at high serum concentrations (25%, 12.5%, 6.25% serum concentrations), but a significantly higher $AP_{50}$ (i.e., 9.8% of serum needed to achieve 50% of maximum C3 deposition).

Figure 16:
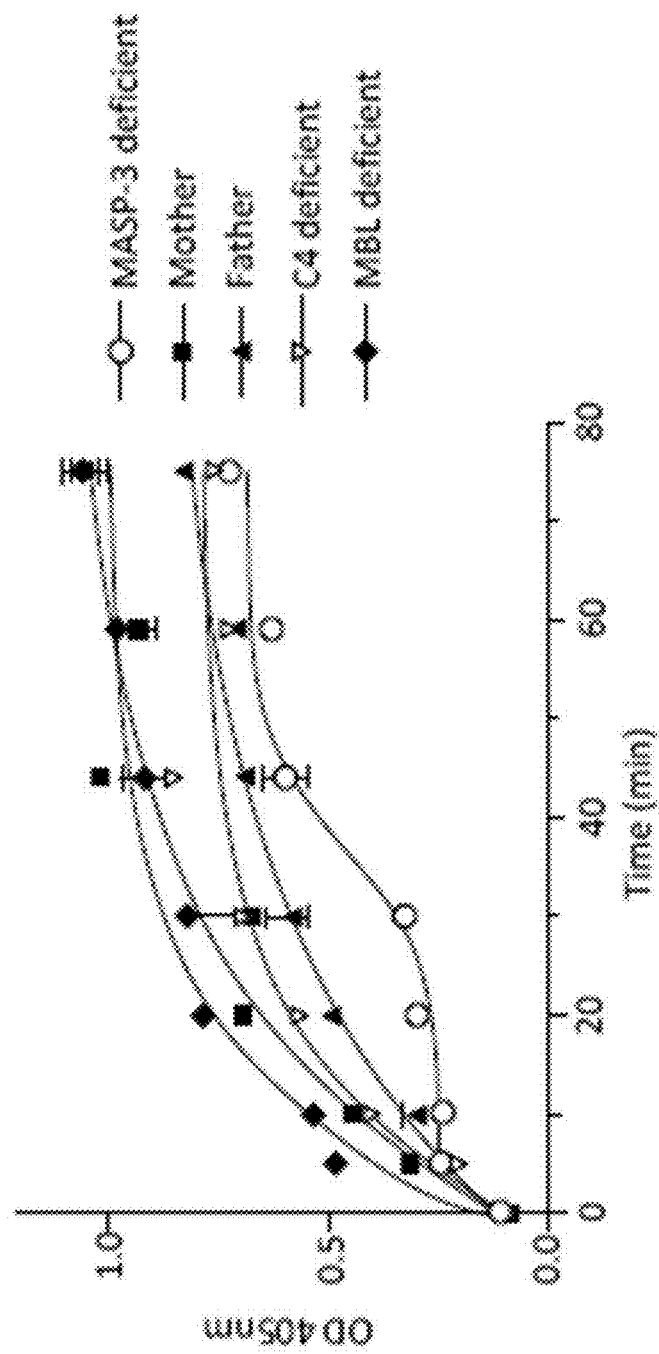
FIG. 16 graphically illustrates the level of AP-driven C3b deposition on zymosan-coated microtiter plates under "traditional" AP-specific conditions (i.e., BBS/EGTA/$Mg^{++}$ without $Ca^{++}$) as a function of time in 10% human serum samples obtained from MASP-3-deficient, C4-deficient and MBL-deficient human subjects, as described in Example 4.

FIG. 16 graphically illustrates the level of alternative pathway-driven C3b deposition on zymosan-coated microtiter plates under "traditional" alternative pathway-specific (AP-specific) conditions (i.e., BBS/EGTA/$Mg^{++}$ without $Ca^{++}$) as a function of time in 10% human serum samples obtained from MASP-3-deficient, C4-deficient and MBL-deficient human subjects.

TABLE 12 below summarizes the $AP_{50}$ results shown in FIG. 15 and the half-times for C3b deposition shown in FIG. 16.

TABLE 12

Summary of Results shown in FIGS. 15 and 16

| Serum type | $AP_{50}$ (%) | $T_{1/2}$ (min) |
|---|---|---|
| MASP-3-deficient (3MC patient) | 9.8 | 37.4 |
| Mother of 3MC patient (heterozygous) | 4.3 | 17.2 |
| Father of 3MC patient (heterozygous) | 4.3 | 20.9 |
| C4-deficient | 4.0 | 11.6 |
| MBL-deficient | 4.8 | 11.0 |

Note:
In $BBS/Mg^{++}/EGTA$ buffer, the lectin pathway-mediated effects are deficient due to absence of $Ca^{++}$ in this buffer.

In summary, under the conditions of these assays, the alternative pathway is significantly compromised in the 3MC patient.

3. Measurement of C3b Deposition on Mannan, Zymosan and S. pneumonia D39 in Mouse Sera Deficient of MASP-2 or MASP-1/3.

Methods:

C3b deposition was measured on mannan, zymosan and S. pneumonia D39-coated microtiter plates using mouse serum concentrations ranging from 0% to 20% obtained from MASP-2-/-, MASP-1/3-/- and WT mice. The C3b deposition assays were carried out under either "traditional" alternative pathway-specific conditions (i.e. $BBS/EGTA/Mg^{++}$ without $Ca^{++}$), or under physiological conditions allowing both the lectin pathway and the alternative pathway to function (i.e., $BBS/Mg^{++}/Ca^{++}$).

Figure 17A:
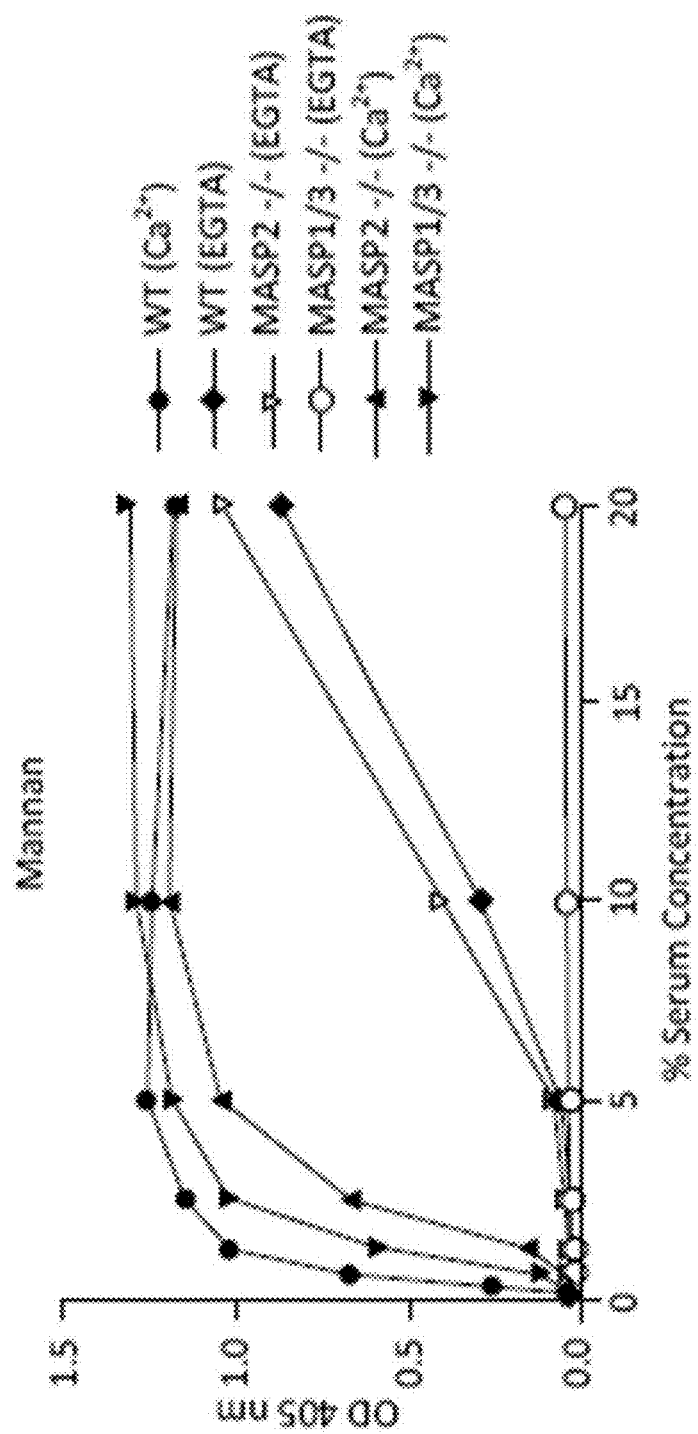
FIG. 17A graphically illustrates the level of C3b deposition on mannan-coated microtiter plates as a function of serum concentration in serum samples obtained from WT, MASP-2-deficient, and MASP-1/3-deficient mice under "traditional" AP-specific conditions (i.e. BBS/EGTA/$Mg^{++}$ without $Ca^{++}$) or under physiological conditions allowing both the lectin pathway and the alternative pathway (AP) to function (BBS/$Mg^{++}$/$Ca^{++}$), as described in Example 4.
Figure 17B:
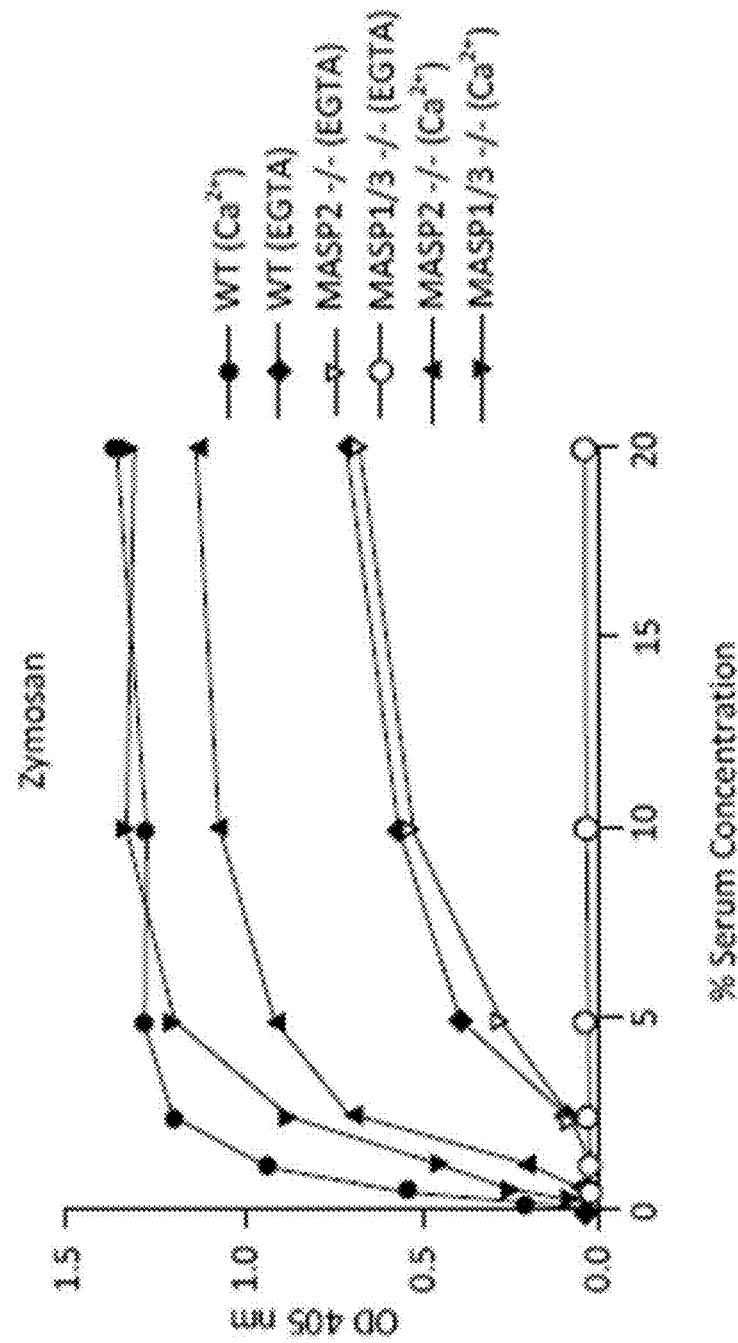
FIG. 17B graphically illustrates the level of C3b deposition on zymosan-coated microtiter plates as a function of serum concentration in serum samples obtained from WT, MASP-2-deficient, and MASP-1/3-deficient mice under traditional AP-specific conditions (i.e. BBS/EGTA/$Mg^{++}$ without $Ca^{++}$) or under physiological conditions allowing both the lectin pathway and the alternative pathway to function (BBS/$Mg^{++}$/$Ca^{++}$), as described in Example 4.
Figure 17C:
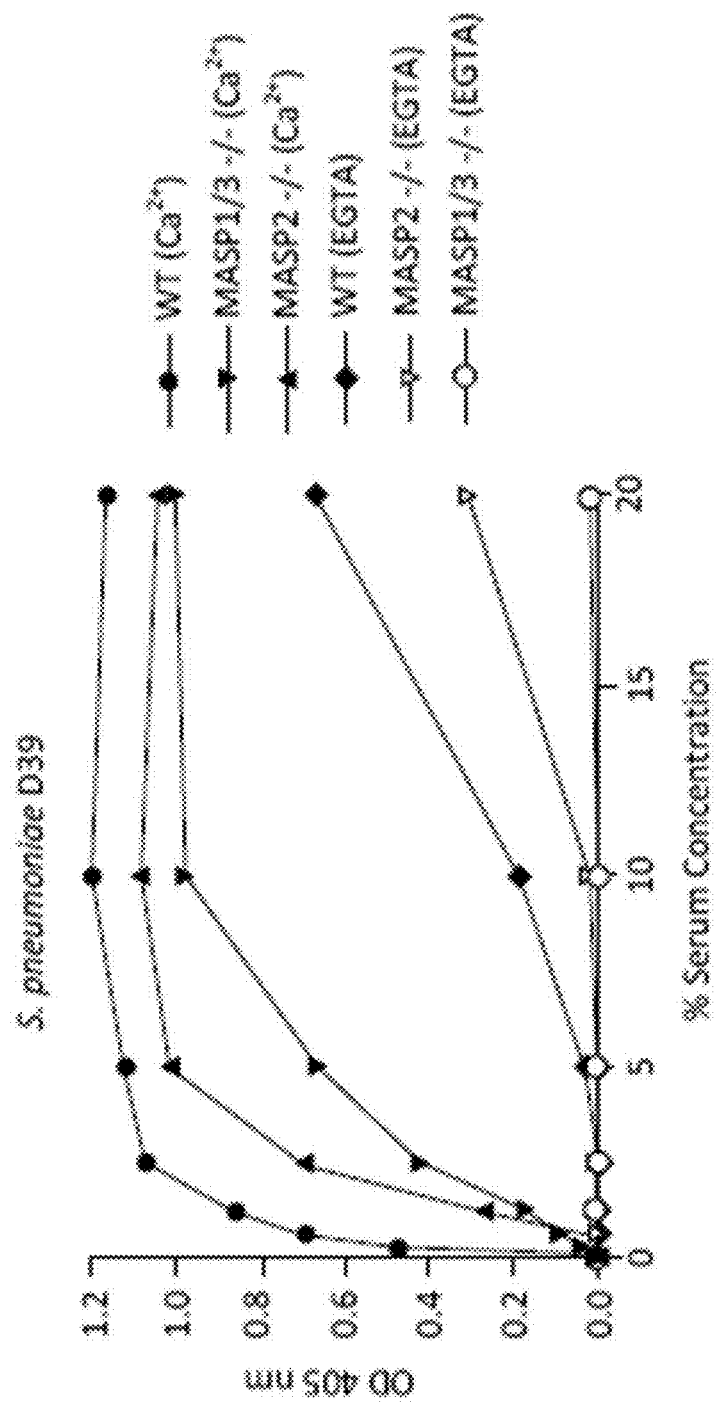
FIG. 17C graphically illustrates the level of C3b deposition on *S. pneumoniae* D39-coated microtiter plates as a function of serum concentration in serum samples obtained from WT, MASP-2-deficient, and MASP-1/3-deficient mice under traditional AP-specific conditions (i.e. BBS/EGTA/$Mg^{++}$ without $Ca^{++}$) or under physiological conditions allowing both the lectin pathway and the alternative pathway to function (BBS/$Mg^{++}$/$Ca^{++}$), as described in Example 4.

Results:

FIG. 17A graphically illustrates the level of C3b deposition on mannan-coated microtiter plates as a function of serum concentration in serum samples obtained from WT, MASP-2-deficient, and MASP-1/3-deficient mice under traditional alternative pathway-specific conditions (i.e., $BBS/EGTA/Mg^{++}$ without $Ca^{++}$), or under physiological conditions allowing both the lectin pathway and the alternative pathway to function ($BBS/Mg^{++}/Ca^{++}$). FIG. 17B graphically illustrates the level of C3b deposition on zymosan-coated microtiter plates as a function of serum concentration in serum samples from WT, MASP-2-deficient, and MASP-1/3-deficient mice under traditional AP-specific conditions (i.e., $BBS/EGTA/Mg^{++}$ without $Ca^{++}$), or under physiological conditions allowing both the lectin pathway and the alternative pathway to function ($BBS/Mg^{++}/Ca^{++}$). FIG. 17C graphically illustrates the level of C3b deposition on S. pneumoniae D39-coated microtiter plates as a function of serum concentration in serum samples from WT, MASP-2-deficient, and MASP-1/3-deficient mice under traditional AP-specific conditions (i.e., $BBS/EGTA/Mg^{++}$ without $Ca^{++}$), or under physiological conditions allowing both the lectin pathway and the alternative pathway to function ($BBS/Mg^{++}/Ca^{++}$).

Figure 18A:
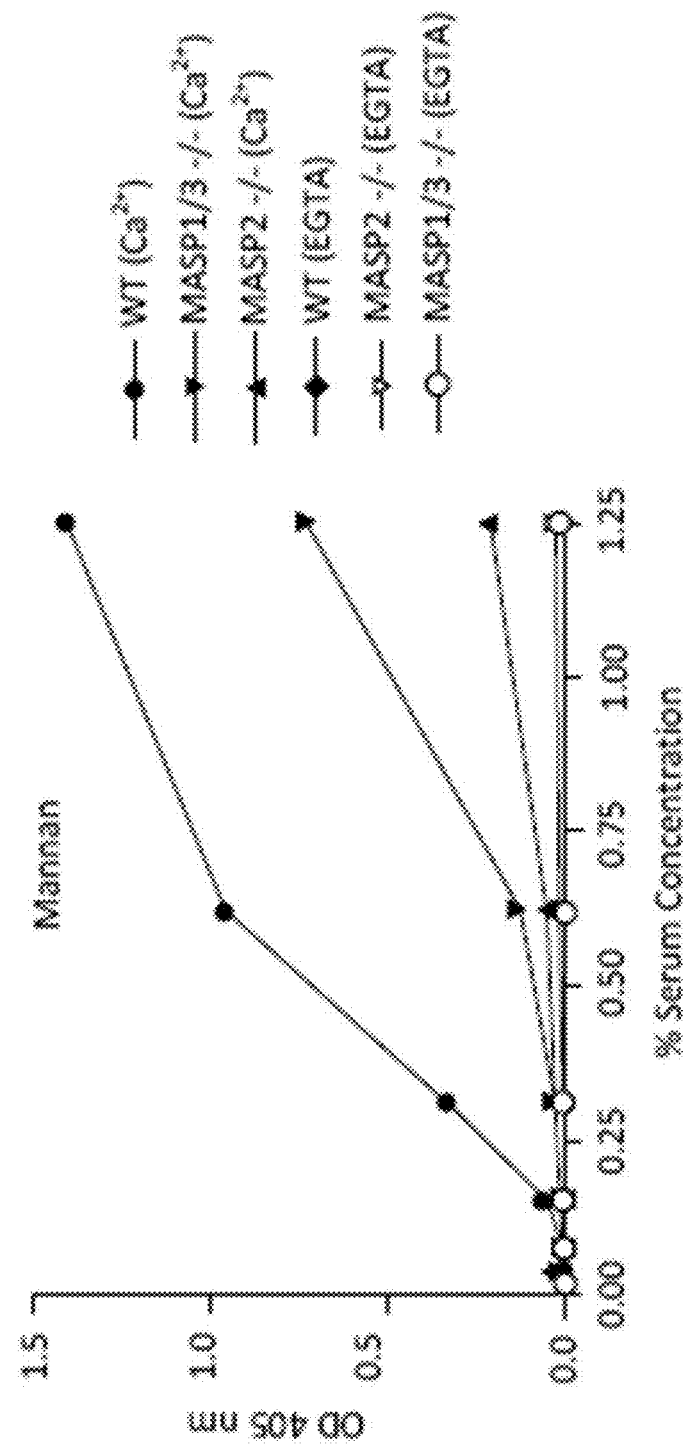
FIG. 18A graphically illustrates the results of a C3b deposition assay in highly diluted sera carried out on mannan-coated microtiter plates under traditional AP-specific conditions (i.e. BBS/EGTA/$Mg^{++}$ without $Ca^{++}$) or under physiological conditions allowing both the lectin pathway and the alternative pathway to function (BBS/$Mg^{++}$/$Ca^{++}$), using serum concentrations ranging from 0% up to 1.25%, as described in Example 4.
Figure 18B:
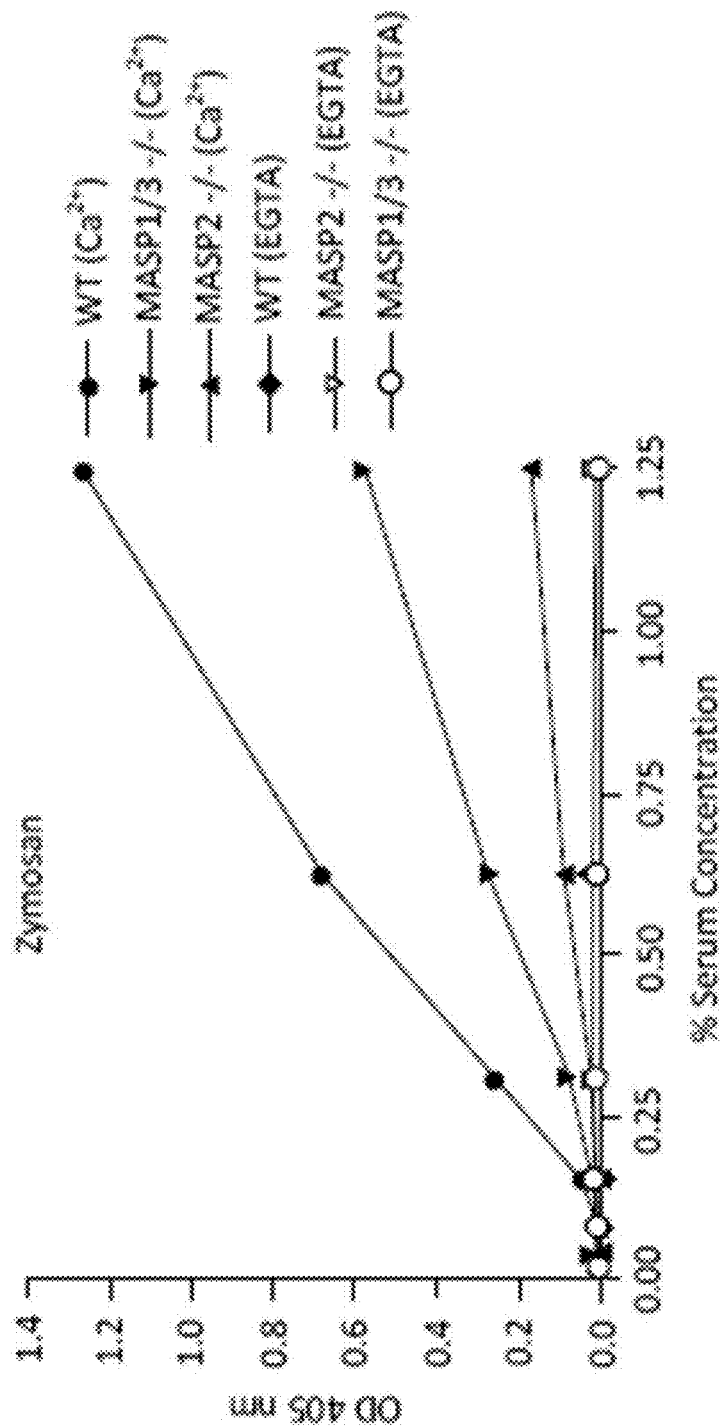
FIG. 18B graphically illustrates the results of a C3b deposition assay carried out on zymosan-coated microtiter plates under traditional AP-specific conditions (i.e. BBS/EGTA/$Mg^{++}$ without $Ca^{++}$) or under physiological conditions allowing both the lectin pathway and the alternative pathway to function (BB S/$Mg^{++}$/$Ca^{++}$), using serum concentrations ranging from 0% up to 1.25%, as described in Example 4.
Figure 18C:
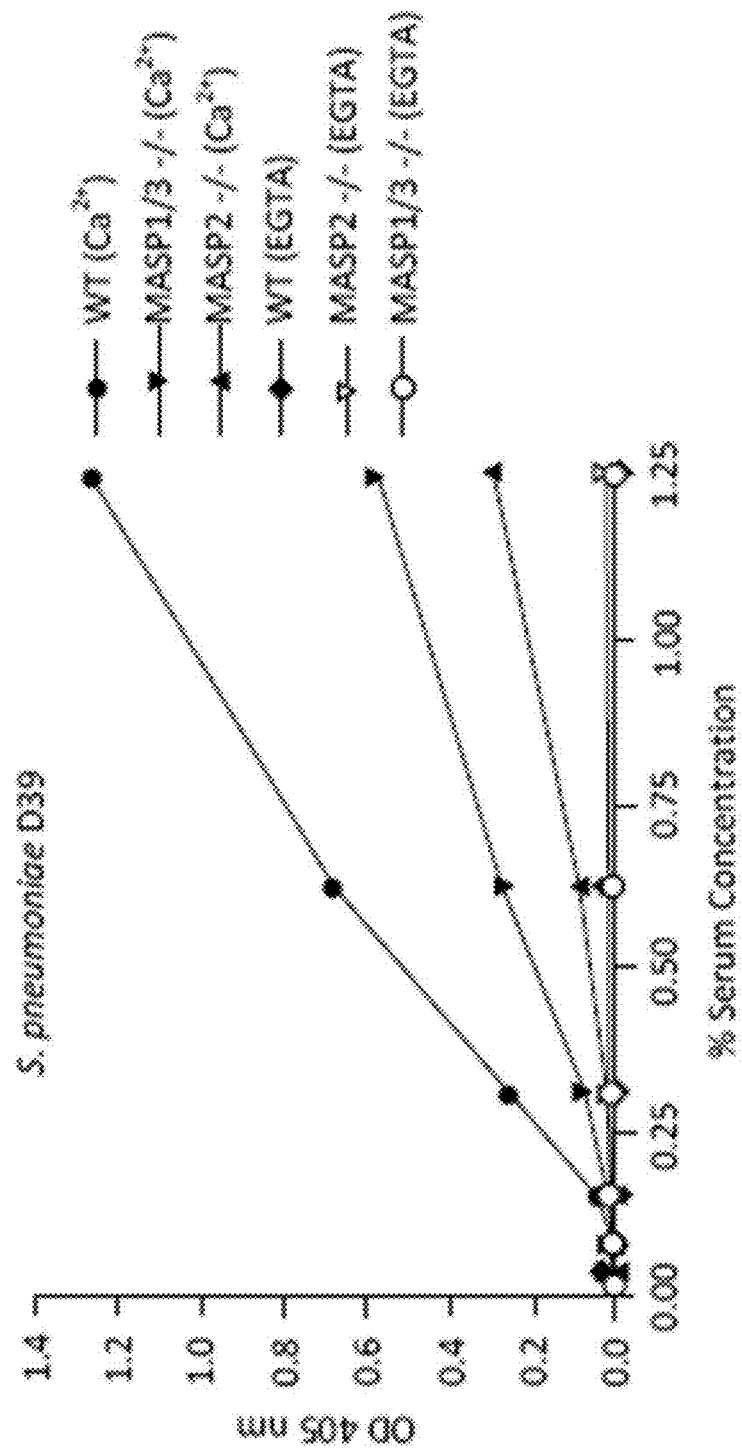
FIG. 18C graphically illustrates the results of a C3b deposition assay carried out on *S. pneumoniae* D39-coated microtiter plates under traditional AP-specific conditions (i.e. BBS/EGTA/$Mg^{++}$ without $Ca^{++}$) or under physiological conditions allowing both the lectin pathway and the alternative pathway to function (BB S/$Mg^{++}$/$Ca^{++}$), using serum concentrations ranging from 0% up to 1.25%, as described in Example 4.

FIG. 18A graphically illustrates the results of a C3b deposition assay in highly diluted sera carried out on mannan-coated microtiter plates under traditional AP-specific conditions (i.e. $BBS/EGTA/Mg^{++}$ without $Ca^{++}$) or physiological conditions allowing both the lectin pathway and the alternative pathway to function ($BBS/Mg^{++}/Ca^{++}$), using serum concentrations ranging from 0% up to 1.25%. FIG. 18B graphically illustrates the results of a C3b deposition assay carried out on zymosan-coated microtiter plates under traditional AP-specific conditions (i.e. $BBS/EGTA/Mg^{++}$ without $Ca^{++}$) or under physiological conditions allowing both the lectin pathway and the alternative pathway to function ($BBS/EGTA/Mg^{++}/Ca^{++}$), using serum concentrations ranging from 0% up to 1.25%. FIG. 18C graphically illustrates the results of a C3b deposition assay carried out on S. pneumoniae D39-coated microtiter plates under traditional AP-specific conditions (i.e. $BBS/EGTA/Mg^{++}$ without $Ca^{++}$) or under physiological conditions allowing both the lectin pathway and the alternative pathway to function ($BBS/EGTA/Mg^{++}/Ca^{++}$), using serum concentrations ranging from 0% up to 1.25%.

As shown in FIGS. 18A-C, C3b deposition assays were also carried out under traditional alternative pathway-specific conditions (i.e. $BBS/EGTA/Mg^{++}$ without $Ca^{++}$) or under physiological conditions allowing both the lectin pathway and the alternative pathway to function ($BBS/Mg^{++}/Ca^{++}$), using higher dilutions ranging from 0% up to 1.25% serum on mannan-coated plates (FIG. 18A); zymosan-coated plates (FIG. 18B) and S. pneumoniae D39-coated plates (FIG. 18C). The alternative pathway tails off under higher serum dilutions, so the activity observed in the MASP-1/3-deficient serum in the presence of $Ca^{++}$ is MASP-2-mediated LP activity, and the activity in MASP-2-deficient serum in the presence of $Ca^{++}$ is MASP-1/3-mediated residual activation of the AP.

Discussion:

The results described in this Example demonstrate that a MASP-2 inhibitor (or MASP-2 KO) provides significant protection from N. meningitidis infection by promoting MASP-3-driven alternative pathway activation. The results of the mouse serum bacteriolysis assays and the human serum bacteriolysis assays further show, by monitoring the serum bactericidal activity against N. meningitidis, that bactericidal activity against N. meningitidis is absent in MBL-deficient (mouse MBL A and MBL C double-deficient and human MBL-deficient sera).

FIG. 1 illustrates the new understanding of the lectin pathway and alternative pathway based on the results provided herein. FIG. 1 delineates the role of LEA-2 in both opsonization and lysis. While MASP-2 is the initiator of "downstream" C3b deposition (and resultant opsonization) in multiple lectin-dependent settings physiologically (FIG. 18A, 18B, 18C), it also plays a role in lysis of serum-sensitive bacteria. As illustrated in FIG. 1, the proposed molecular mechanism responsible for the increased bactericidal activity of MASP-2-deficient or MASP-2-depleted serum/plasma for serum-sensitive pathogens such as N. meningitidis is that, for the lysis of bacteria, lectin pathway recognition complexes associated with MASP-1 and MASP-3 have to bind in close proximity to each other on the bacterial surface, thereby allowing MASP-1 to cleave MASP-3. In contrast to MASP-1 and MASP-2, MASP-3 is not an auto-activating enzyme, but, in many instances, requires activation/cleavage by MASP-1 to be converted into its enzymatically active form.

As further shown in FIG. 1, activated MASP-3 can then cleave C3b-bound factor B on the pathogen surface to initiate the alternative pathway activation cascade by formation of the enzymatically active alternative pathway C3 and C5 convertase C3bBb and C3bBb(C3b)n, respectively. MASP-2-bearing lectin-pathway activation complexes have no part in the activation of MASP-3 and, in the absence or after depletion of MASP-2, all-lectin pathway activation complexes will either be loaded with MASP-1 or MASP-3. Therefore, in the absence of MASP-2, the likelihood is markedly increased that on the microbial surface MASP-1 and MASP-3-bearing lectin-pathway activation complexes will come to sit in close proximity to each other, leading to more MASP-3 being activated and thereby leading to a higher rate of MASP-3-mediated cleavage of C3b-bound factor B to form the alternative pathway C3 and C5 convertases C3bBb and C3bBb(C3b)n on the microbial surface. This leads to the activation of the terminal activation cascades C5b-C9 that forms the Membrane Attack Complex, composed of surface-bound C5b associated with C6, C5bC6 associated with C7, C5bC6C7 associated with C8, and C5bC6C7C8, leading to the polymerization of C9 that inserts into the bacterial surface structure and forms a pore in the bacterial wall, which will lead to osmolytic killing of the complement-targeted bacterium.

The core of this novel concept is that the data provided herein clearly show that the lectin-pathway activation complexes drive the two distinct activation routes, as illustrated in FIG. 1.

Example 5

This Example demonstrates the inhibitory effect of MASP-2 deficiency and/or MASP-3 deficiency on lysis of red blood cells from blood samples obtained from a mouse model of paroxysmal nocturnal hemoglobinuria (PNH).

Background/Rationale:

Paroxysmal nocturnal hemoglobinuria (PNH), also referred to as Marchiafava-Micheli syndrome, is an acquired, potentially life-threatening disease of the blood, characterized by complement-induced intravascular hemolytic anemia. The hallmark of PNH is the chronic complement-mediated intravascular hemolysis that is a consequence of unregulated activation of the alternative pathway of complement due to the absence of the complement regulators CD55 and CD59 on PNH erythrocytes, with subsequent hemoglobinuria and anemia. Lindorfer, M. A., et al., *Blood* 115(11) (2010), Risitano, A. M, *Mini-Reviews in Medicinal Chemistry,* 11:528-535 (2011). Anemia in PNH is due to destruction of red blood cells in the bloodstream. Symptoms of PNH include red urine, due to appearance of hemoglobin in the urine, back pain, fatigue, shortness of breath and thrombosis. PNH may develop on its own, referred to as "primary PNH" or in the context of other bone marrow disorders such as aplastic anemia, referred to as "secondary PNH". Treatment for PNH includes blood transfusion for anemia, anticoagulation for thrombosis and the use of the monoclonal antibody eculizumab (Soliris®), which protects blood cells against immune destruction by inhibiting the complement system (Hillmen P. et al., *N. Engl. J. Med.* 350(6):552-9 (2004)). Eculizumab (Soliris®) is a humanized monoclonal antibody that targets the complement component C5, blocking its cleavage by C5 convertases, thereby preventing the production of C5a and the assembly of MAC. Treatment of PNH patients with eculizumab has resulted in a reduction of intravascular hemolysis, as measured by lactate dehydrogenase (LDH), leading to hemoglobin stabilization and transfusion independence in about half of the patients (Hillmen P, et al., Mini-Reviews in Medicinal Chemistry, vol 11(6) (2011)). While nearly all patients undergoing therapy with eculizumab achieve normal or almost normal LDH levels (due to control of intravascular hemolysis), only about one third of the patients reach a hemoglobin value about 11 gr/dL, and the remaining patients on eculizumab continue to exhibit moderate to severe (i.e., transfusion-dependent) anemia, in about equal proportions (Risitano A. M. et al., *Blood* 113:4094-100 (2009)). As described in Risitano et al., Mini-Reviews in *Medicinal Chemistry* 11:528-535 (2011), it was demonstrated that PNH patients on eculizumab contained C3 fragments bound to a substantial portion of their PNH erythrocytes (while untreated patients did not), leading to the conclusion that membrane-bound C3 fragments work as opsonins on PNH erythrocytes, resulting in their entrapment in the reticuloendothelial cells through specific C3 receptors and subsequent extravascular hemolysis. Therefore, therapeutic strategies in addition to the use of eculizumab are needed for those patients developing C3 fragment-mediated extravascular hemolysis because they continue to require red cell transfusions.

This Example describes methods to assess the effect of MASP-2- and MASP-3-deficient serum on lysis of red blood cells from blood samples obtained from a mouse model of PNH and demonstrates the efficacy of MASP-2 inhibition and/or MASP-3 inhibition to treat subjects suffering from PNH, and also supports the use of inhibitors of MASP-2 and/or inhibitors of MASP-3 (including dual or bispecific MASP-2/MASP-3 inhibitors) to ameliorate the effects of C3 fragment-mediated extravascular hemolysis in PNH subjects undergoing therapy with a C5 inhibitor such as eculizumab.

Methods:

PNH Animal Model:

Blood samples were obtained from gene-targeted mice with deficiencies of Crry and C3 (Crry/C3−/−) and CD55/CD59-deficient mice. These mice are missing the respective surface complement regulators on their erythrocytes and these erythrocytes are, therefore, susceptible to spontaneous complement autolysis as are PNH human blood cells.

In order to sensitize these erythrocytes even more, these cells were used with and without coating by mannan and then tested for hemolysis in WT C56/BL6 plasma, MBL null plasma, MASP-2−/− plasma, MASP-1/3−/− plasma, human NHS, human MBL−/− plasma, and NHS treated with human MASP-2 antibody.

1. Hemolysis Assay of Crry/C3 and CD55/CD59 Double-Deficient Murine Erythrocytes in MASP-2-Deficient/Depleted Sera and Controls Day 1. Preparation of Murine RBC (±Mannan Coating).

Materials included: fresh mouse blood, BBS/Mg$^{++}$/Ca$^{++}$ (4.4 mM barbituric acid, 1.8 mM sodium barbitone, 145 mM NaCl, pH 7.4, 5 mM Mg$^{++}$, 5 mM Ca$^{++}$), chromium chloride, CrCl$_3$.6H$_2$0 (0.5 mg/mL in BB S/Mg$^{++}$/Ca$^{++}$) and mannan, 100 µg/mL in BB S/Mg$^{++}$/Ca$^{++}$.

Whole blood (2 mL) was spun down for 1-2 min at 2000×g in a refrigerated centrifuge at 4° C. The plasma and buffy coat were aspirated off. The sample was then washed 3× by re-suspending RBC pellet in 2 mL ice-cold BBS/gelatin/Mg$^{++}$/Ca$^{++}$ and repeating centrifugation step. After the third wash, the pellet was re-suspended in 4 mL BBS/Mg$^{++}$/Ca$^{++}$. A 2 mL aliquot of the RBC was set aside as an uncoated control. To the remaining 2 mL, 2 mL CrCl3 and 2 mL mannan were added and the sample was incubated with gentle mixing at RT for 5 minutes. The reaction was terminated by adding 7.5 mL BBS/gelatin/Mg$^{++}$/Ca$^{++}$. The sample was spun down as above, re-suspended in 2 mL BBS/gelatin/Mg$^{++}$/Ca$^{++}$ and washed a further two times as above, then stored at 4° C.

Day 2. Hemolysis Assay

Materials included BBS/gelatin/Mg$^{++}$/Ca$^{++}$ (as above), test sera, 96-well round-bottomed and flat-bottomed plates and a spectrophotometer that reads 96-well plates at 410-414 nm.

The concentration of the RBC was first determined and the cells were adjusted to $10^9$/mL, and stored at this concentration. Before use, the cells were diluted in assay buffer to $10^8$/mL, and then 100 μL per well was used. Hemolysis was measured at 410-414 nm (allowing for greater sensitivity than 541 nm). Dilutions of test sera were prepared in ice-cold BBS/gelatin/Mg$^{++}$/Ca$^{++}$. 100 μL of each serum dilution was pipetted into round-bottomed plate. 100 μL of appropriately diluted RBC preparation was added (i.e., $10^8$/mL), incubated at 37° C. for about 1 hour, and observed for lysis. (The plates may be photographed at this point.) The plate was then spun down at maximum speed for 5 minutes. 100 μL of the fluid phase was aspirated, transferred to flat-bottom plates, and the OD was recorded at 410-414 nm. The RBC pellets were retained (these can be subsequently lysed with water to obtain an inverse result).

Experiment #1

Fresh blood was obtained from CD55/CD59 double-deficient mice and blood of Crry/C3 double-deficient mice and erythrocytes were prepared as described in detail in the above protocol. The cells were split and half of the cells were coated with mannan and the other half were left untreated, adjusting the final concentration to $10^8$/mL, of which 100 μL was used in the hemolysis assay, which was carried out as described above.

Results of Experiment #1: The Lectin Pathway is Involved in Erythrocyte Lysis in the PNH Animal Model In an initial experiment, it was determined that non-coated WT mouse erythrocytes were not lysed in any mouse serum. It was further determined that mannan-coated Crry-/- mouse erythrocytes were slowly lysed (more than 3 hours at 37 degrees) in WT mouse serum, but they were not lysed in MBL null serum. (Data not shown).

It was determined that mannan-coated Crry-/- mouse erythrocytes were rapidly lysed in human serum but not in heat-inactivated NHS. Importantly, mannan-coated Crry-/- mouse erythrocytes were lysed in NHS diluted down to 1/640 (i.e., 1/40, 1/80, 1/160, 1/320 and 1/640 dilutions all lysed). (Data not shown). In this dilution, the alternative pathway does not work (AP functional activity is significantly reduced below 8% serum concentration).

Conclusions from Experiment #1

Mannan-coated Crry-/- mouse erythrocytes are very well lysed in highly diluted human serum with MBL but not in that without MBL. The efficient lysis in every serum concentration tested implies that the alternative pathway is not involved or needed for this lysis. The inability of MBL-deficient mouse serum and human serum to lyse the mannan-coated Crry-/- mouse erythrocytes indicates that the classical pathway also has nothing to do with the lysis observed. As lectin pathway recognition molecules are required (i.e., MBL), this lysis is mediated by the lectin pathway.

Experiment #2

Fresh blood was obtained from the Crry/C3 and CD55/CD59 double-deficient mice and mannan-coated Crry-/- mouse erythrocytes were analyzed in the haemolysis assay as described above in the presence of the following human serum: MASP-3-/-; MBL null; WT; NHS pretreated with human MASP-2 antibody; and heat-inactivated NHS as a control.

Results of Experiment #2: MASP-2 Inhibitors and MASP-3 Deficiency Prevents Erythrocyte Lysis in PNH Animal Model With the mannan-coated Crry-/- mouse erythrocytes, NHS was incubated in the dilutions diluted down to 1/640 (i.e., 1/40, 1/80, 1/160, 1/320 and 1/640), human MBL-/- serum, human MASP-3-deficient serum (from 3MC patient), and NHS pretreated with MASP-2 mAb, and heat-inactivated NHS as a control.

The ELISA microtiter plate was spun down and the non-lysed erythrocytes were collected on the bottom of the round-well plate. The supernatant of each well was collected and the amount of hemoglobin released from the lysed erythrocytes was measured by reading the OD415 nm in an ELISA reader.

It was observed that MASP-3-/- serum did not lyse mannan-coated mouse erythrocytes at all. In the control heat-inactivated NHS (negative control), as expected, no lysis was observed. MBL-/- human serum lysed mannan-coated mouse erythrocytes at ⅛ and 1/16 dilutions. MASP-2-antibody-pretreated NHS lysed mannan-coated mouse erythrocytes at ⅛ and 1/16 dilutions while WT human serum lysed mannan-coated mouse erythrocytes down to dilutions of 1/32.

Figure 19:
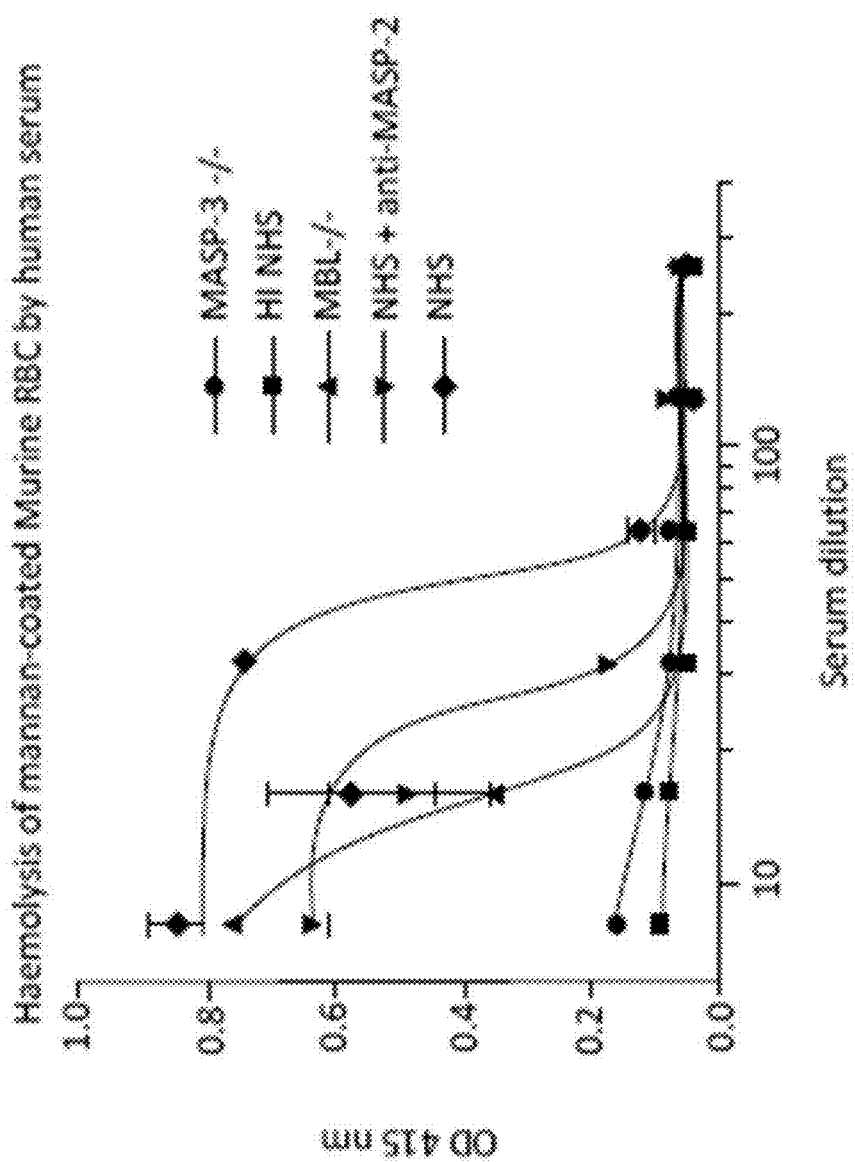
FIG. 19 graphically illustrates the level of hemolysis (as measured by hemoglobin release of lysed mouse erythrocytes (Crry/C3-/-) into the supernatant measured by photometry) of mannan-coated murine erythrocytes by human serum under physiological conditions (i.e., in the presence of $Ca^{++}$) over a range of serum dilutions in serum from MASP-3-/-, heat inactivated normal human serum (HI NHS), MBL-/-, NHS+MASP-2 monoclonal antibody and NHS control, as described in Example 5.

FIG. 19 graphically illustrates hemolysis (as measured by hemoglobin release of lysed mouse erythrocytes (Crry/C3-/-) into the supernatant measured by photometry) of mannan-coated murine erythrocytes by human serum over a range of serum dilutions in serum from MASP-3-/-, heat-inactivated (HI) NHS, MBL-/-, NHS pretreated with MASP-2 antibody, and NHS control.

FIG. 20 graphically illustrates hemolysis (as measured by hemoglobin release of lysed mouse erythrocytes (Crry/C3-/-) into the supernatant measured by photometry) of mannan-coated murine erythrocytes by human serum over a range of serum concentration in serum from MASP-3-/-, heat-inactivated (HI) NHS, MBL-/-, NHS pretreated with MASP-2 antibody, and NHS control.

From the results shown in FIGS. 19 and 20, it is demonstrated that inhibiting MASP-3 will prevent any complement-mediated lysis of sensitized erythrocytes with deficient protection from autologous complement activation. MASP-2 inhibition with MASP-2 antibody significantly shifted the CH$_{50}$ and was protective to some extent, but MASP-3 inhibition was more effective.

Experiment #3

Non-coated Crry-/- mouse erythrocytes obtained from fresh blood from the Crry/C3 and CD55/CD59 double-deficient mice were analyzed in the hemolysis assay as described above in the presence of the following sera: MASP-3-/-; MBL-/-; WT; NHS pretreated with human MASP-2 antibody, and heat-inactivated NHS as a control.

Results:

FIG. 21 graphically illustrates hemolysis (as measured by hemoglobin release of lysed WT mouse erythrocytes into the supernatant measured by photometry) of non-coated murine erythrocytes over a range of serum concentrations in human sera from a 3MC (MASP-3-/-) patient, heat inactivated (HI) NHS, MBL-/-, NHS pretreated with MASP-2 antibody, and NHS control. As shown in FIG. 21 and summarized in TABLE 13, it is demonstrated that inhibiting MASP-3 inhibits complement-mediated lysis of non-sensitized WT mouse erythrocytes.

FIG. 22 graphically illustrates hemolysis (as measured by hemoglobin release of lysed mouse erythrocytes (CD55/59-/-) into the supernatant measured by photometry) of non-coated murine erythrocytes by human serum over a range of serum concentrations in human sera from heat-inactivated (HI) NHS, MBL−/−, NHS pretreated with MASP-2 antibody, and NHS control. As shown in FIG. 22 and summarized in TABLE 13, it is demonstrated that inhibiting MASP-2 was protective to a limited extent.

TABLE 13

$CH_{50}$ values expressed as serum concentrations

| Serum | WT | CD55/59−/− |
|---|---|---|
| 3MC patient | No lysis | No lysis |
| Heat-inactivated NHS | No lysis | No lysis |
| MBL AO/XX donor (MBL deficient) | 7.2% | 2.1% |
| NHS + MASP-2 antibody | 5.4% | 1.5% |
| NHS | 3.1% | 0.73% |

Note:
"$CH_{50}$" is the point at which complement-mediated hemolysis reachs 50%.

In summary, the results in this Example demonstrate that inhibiting MASP-3 prevents any complement lysis of sensitized and non-sensitized erythrocytes with deficient protection from autologous complement activation. MASP-2 inhibition also is protective to some extent. Therefore, MASP-2 and MASP-3 inhibitors alone or in combination (i.e., co-administered, administered sequentially) or MASP-2/MASP-3 bispecific or dual inhibitors may be used to treat subjects suffering from PNH, and may also be used to ameliorate (i.e., inhibit, prevent or reduce the severity of) extravascular hemolysis in PNH patients undergoing treatment with a C5 inhibitor such as eculizumab (Soliris®).

Example 6

This Example describes a hemolysis assay testing mannan-coated rabbit erythrocytes for lysis in the presence of WT or MASP-1/3−/− mouse sera.

Methods:

1. Hemolysis Assay of Rabbit RBC (Mannan Coated) in Mouse MASP-1/3-Deficient Sera and WT Control Sera Day 1. Preparation of Rabbit RBC.

Materials included: fresh rabbit blood, BBS/Mg$^{++}$/Ca$^{++}$ (4.4 mM barbituric acid, 1.8 mM sodium barbitone, 145 mM NaCl, pH 7.4, 5 mM Mg$^{++}$, 5 mM Ca$^{++}$), BBS/Mg$^{++}$/Ca$^{++}$ with 0.1% gelatin, chromium chloride contained in buffer; i.e., CrCl$_3$.6 H$_2$O (0.5 mg/mL in BBS/Mg$^{++}$/Ca$^{++}$) and mannan, 100 μg/mL in BBS/Mg$^{++}$/Ca$^{++}$.

1. Rabbit whole blood (2 mL) was split into two 1.5 mL eppendorf tubes and centrifuged for 3 minutes at 8000 rpm (approximately 5.9 rcf) in a refrigerated eppendorf centrifuge at 4° C. The RBC pellet was washed three times after re-suspending in ice-cold BBS/Mg$^{++}$/Ca$^{++}$. After the third wash, the pellet was re-suspended in 4 mL BBS/Mg$^{++}$/Ca$^{++}$. Two mL of this aliquot were added to a 15-mL falcon tube to be used as the uncoated control. The remaining 2 mL of the RBCs aliquot were diluted in 2 mL of CrCl$_3$ buffer, 2 mL of the mannan solution were added and the suspension was incubated at room temperature for 5 minutes with gentle mixing. The reaction was terminated by adding 7.5 mL of BBS/0.1% gelatin/Mg$^{++}$/Ca$^{++}$ to the mixture. The erythrocytes were pelleted and the RBCs were washed twice with BBS/0.1% gelatin/Mg$^{++}$/Ca$^{++}$ as described above. The RBCs suspension was stored in BBS/0.1% gelatin/Mg$^{++}$/Ca$^{++}$ at 4° C.

2. 100 μL of suspended RBCs were diluted with 1.4 mL water and spun down at 8000 rpm (approximately 5.9 rcf) for 3 minutes and the OD of the supernatant was adjusted to 0.7 at 541 nm (an OD of 0.7 at 541 nm corresponds to approximately 10$^9$ erythrocytes/mL).

3. The re-suspended RBCs were diluted with BBS/0.1% gelatin/Mg$^{++}$/Ca$^{++}$ to a concentration of 10$^8$/mL.

4. Dilutions of the test sera were prepared in ice-cold BBS/gelatin/Mg$^{++}$/Ca$^{++}$ and 100 μL of each serum dilution were pipetted into the corresponding well of round-bottom plate. 100 μL of appropriately diluted RBC (108/mL) were added to each well. As a control for complete lysis, purified water (100 μL) was mixed with the diluted RBC (100 μL) to cause 100% lysis, while BBS/0.1% gelatin/Mg$^{++}$/Ca$^{++}$ without serum (100 μL) was used as a negative control. The plate was then incubated for 1 hour at 37° C.

5. The round-bottom plate was centrifuged at 3250 rpm for 5 minutes. The supernatant from each well (100 μL) was transferred into the corresponding wells of a flat-bottom plate and OD was read in an ELISA reader at 415-490 nm. Results are reported as the ratio of the OD at 415 nm to that at 49 0 nm.

Figure 23:
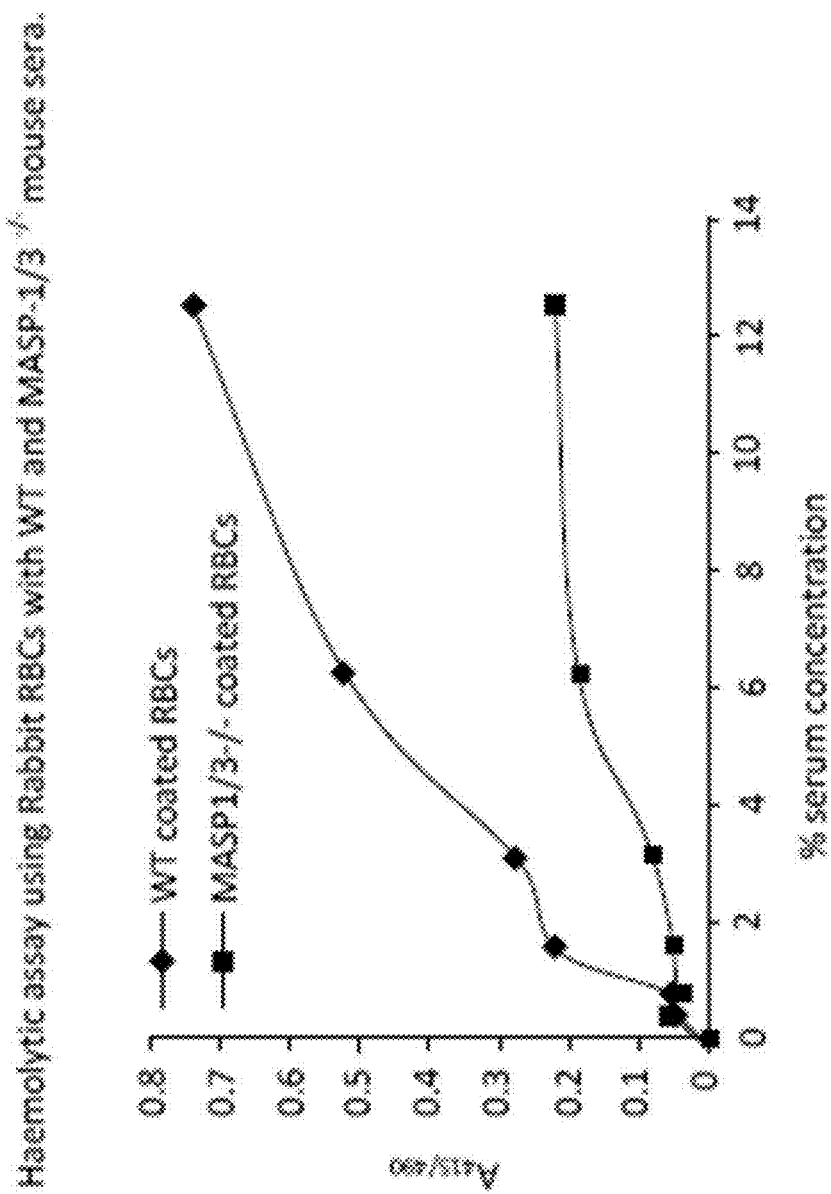
FIG. 23 graphically illustrates hemolysis (as measured by hemoglobin release of lysed rabbit erythrocytes into the supernatant measured by photometry) of mannan-coated rabbit erythrocytes by MASP-1/3-/- mouse serum and WT control mouse serum under physiological conditions (i.e., in the presence of $Ca^{++}$) over a range of serum concentrations, as described in Example 6.

Results:

FIG. 23 graphically illustrates hemolysis (as measured by hemoglobin release of lysed rabbit erythrocytes into the supernatant measured by photometry) of mannan-coated rabbit erythrocytes by mouse serum over a range of serum concentrations in serum from MASP-1/3−/− and WT control. As shown in FIG. 23, it is demonstrated that inhibiting MASP-3 prevents complement-mediated lysis of mannan-coated WT rabbit erythrocytes. These results further support the use of MASP-3 inhibitors for the treatment of one or more aspects of PNH as described in Example 5.

Example 7

This Example describes the generation of MASP-1 and MASP-3 monoclonal antibodies using an in vitro system comprising a modified DT40 cell line, DTLacO.

Background/Rationale:

Antibodies against human MASP-1 and MASP-3 were generated using an in vitro system comprising a modified DT40 cell line, DTLacO, that permits reversible induction of diversification of a particular polypeptide, as further described in WO2009029315 and US2010093033. DT40 is a chicken B cell line that is known to constitutively mutate its heavy and light chain immunoglobulin (Ig) genes in culture. Like other B cells, this constitutive mutagenesis targets mutations to the V region of Ig genes, and thus, the CDRs of the expressed antibody molecules. Constitutive mutagenesis in DT40 cells takes place by gene conversion using as donor sequences an array of non-functional V gene segments (pseudo-V genes; ψV) situated upstream of each functional V region. Deletion of the ψV region was previously shown to cause a switch in the mechanism of diversification from gene conversion to somatic hypermutation, the mechanism commonly observed in human B cells. The DT40 chicken B cell lymphoma line has been shown to be a promising starting point for antibody evolution ex vivo (Cumbers, S. J. et al. *Nat Biotechnol* 20, 1129-1134 (2002); Seo, H. et al. *Nat Biotechnol* 23, 731-735 (2005)). DT40 cells proliferate robustly in culture, with an 8-10 hour doubling time (compared to 20-24 hr for human B cell lines), and they support very efficient homologous gene targeting (Buerstedde, J. M. et al. *Embo J* 9, 921-927 (1990)). DT40 cells command enormous potential V region sequence diversity given that they can access two distinct physiological pathways for diversification, gene conversion and somatic hypermutation, which create templated and nontemplated mutations, respectively (Maizels, N. *Annu Rev*

Genet 39, 23-46 (2005)). Diversified heavy and light chain immunoglobulins (Igs) are expressed in the form of a cell-surface displayed IgM. Surface IgM has a bivalent form, structurally similar to an IgG molecule. Cells that display IgM with specificity for a particular antigen can be isolated by binding either immobilized soluble or membrane displayed versions of the antigen. However, utility of DT40 cells for antibody evolution has been limited in practice because—as in other transformed B cell lines—diversification occurs at less than 1% the physiological rate.

In the system used in this example, as described in WO2009029315 and US2010093033, the DT40 cells were engineered to accelerate the rate of Ig gene diversification without sacrificing the capacity for further genetic modification or the potential for both gene conversion and somatic hypermutation to contribute to mutagenesis. Two key modifications to DT40 were made to increase the rate of diversification and, consequently, the complexity of binding specificities in our library of cells. First, Ig gene diversification was put under the control of the potent *E. coli* lactose operator/repressor regulatory network. Multimers consisting of approximately 100 polymerized repeats of the potent *E. coli* lactose operator (PolyLacO) were inserted upstream of the rearranged and expressed Igλ, and IgH genes by homologous gene targeting. Regulatory factors fused to lactose repressor protein (LacI) can then be tethered to the LacO regulatory elements to regulate diversification, taking advantage of the high affinity ($k_D=10^{-14}$ M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was further elevated in cells engineered to carry PolyLacO targeted to both the Igλ and the IgH genes ("DTLacO"). DTLacO cells were demonstrated to have diversification rates 2.5- to 9.2-fold elevated relative to the 2.8% characteristic of the parental DT40 PolyLacO-$\lambda_R$ LacI-HP1 line. Thus, targeting PolyLacO elements to both the heavy and light chain genes accelerated diversification 21.7-fold relative to the DT40 parental cell line. Tethering regulatory factors to the Ig loci not only alters the frequency of mutagenesis, but also can change the pathway of mutagenesis creating a larger collection of unique sequence changes (Cummings et al. 2007; Cummings et al. 2008). Second, a diverse collection of sequence starting points for the tethered factor-accelerated Ig gene diversification was generated. These diverse sequence starting points were added to DTLacO by targeting rearranged Ig heavy-chain variable regions, isolated from a two month old chick, to the heavy chain locus. The addition of these heavy chain variable regions created a repertoire of $10^7$ new starting points for antibody diversification. Building these new starting points into the DTLacO cell line permits the identification of clones that bind a particular target, and then rapid affinity maturation by the tethered factors. Following affinity maturation, a full-length, recombinant chimeric IgG is made by cloning the matured, rearranged heavy- and light-chain variable sequences (VH and Vλ; consisting of chicken framework regions and the complementarity determining regions or CDRs) into expression vectors containing human IgG1 and lambda constant regions. These recombinant mAbs are suitable for in vitro and in vivo applications, and they serve as the starting point for humanization.

Methods:

Selection for MASP-1 and MASP-3 Antigen Binding.

Initial selections were performed by binding DTLacO populations diversified by gene targeting to beads complexed with human MASP-1 (SEQ ID NO:8) and MASP-3 antigen (SEQ ID NO:2); and subsequent selections by FACS, using fluorescence-labeled soluble antigen (Cumbers, S. J. et al. *Nat Biotechnol* 20, 1129-1134 (2002); Seo, H. et al. *Nat Biotechnol* 23, 731-735 (2005). Because of the conserved amino acid sequence in the alpha chain that is shared between MASP-1 and MASP-3 (shown in FIG. 2), and the distinct beta chain sequences (shown in FIG. 2), separate, parallel screens for binders to MASP-1 and MASP-3 were carried out to identify MASP-1 specific mAbs, MASP-3 specific mAbs and also mAbs capable of binding to both MASP-1 and MASP-3 (dual-specific). Two forms of antigen were used to select and screen for binders. First, recombinant MASP-1 or MASP-3, either full-length or a fragment, fused to an Fc domain were bound to Dynal magnetic Protein G beads or used in FACS-based selections using a PECy5-labeled anti-human IgG(Fc) secondary antibody. Alternatively, recombinant versions of MASP-1 or MASP-3 proteins were directly labeled with Dylight flours and used for selections and screening.

Binding and Affinity.

Recombinant antibodies were generated by cloning PCR-amplified V regions into a vector that supported expression of human IgG1 in 293F cells (Yabuki et al., *PLoS ONE*, 7(4):e36032 (2012)). Saturation binding kinetics were determined by staining DTLacO cells expressing antibody binding MASP-1 or MASP-3 with various concentrations of fluorescent-labeled soluble antigen. Functional assays for MASP-3 specific activity including MASP-3-dependent C3b deposition and MASP-3-dependent factor D cleavage were carried out as described in Examples 8 and 9, respectively. A functional assay for MASP-1-specific activity, namely the inhibition of MASP-1-dependent C3b deposition was carried out as described below.

Results:

Numerous MASP-1 and MASP-3 binding antibodies were generated using the methods described above. Binding, as demonstrated by FACS analysis, is described for the representative clones M3J5 and M3M1, which were isolated in screens for MASP-3 binders.

Figure 24B:
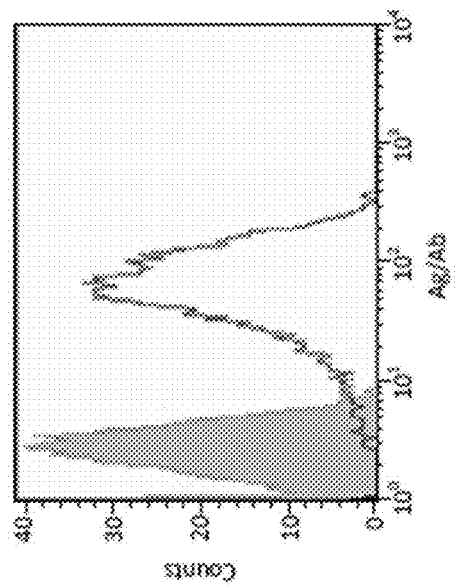
FIG. 24B is a FACS histogram of MASP-3 antigen/antibody binding for clone M3M1, as described in Example 7.
Figure 24A:
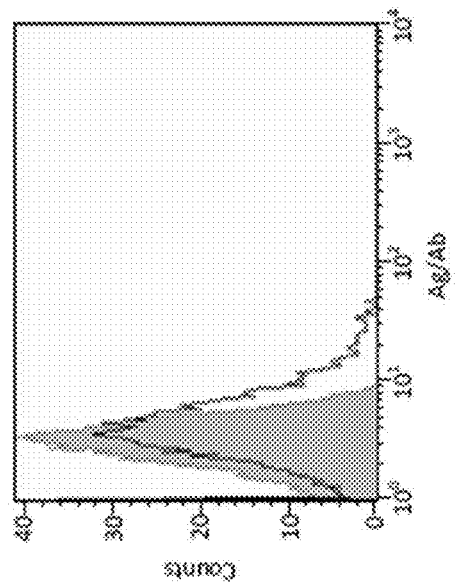
FIG. 24A is a FACS histogram of MASP-3 antigen/antibody binding for clone M3J5, as described in Example 7.

FIG. 24A is a FACS histogram of MASP-3 antigen/antibody binding for DTLacO clone M3J5. FIG. 24B is a FACS histogram of MASP-3 antigen/antibody binding for DTLacO clone M3M1. In FIGS. 24A and 24B the gray filled curves are IgG1-stained negative control, and thick black curves are MASP-3-staining.

Figure 25:
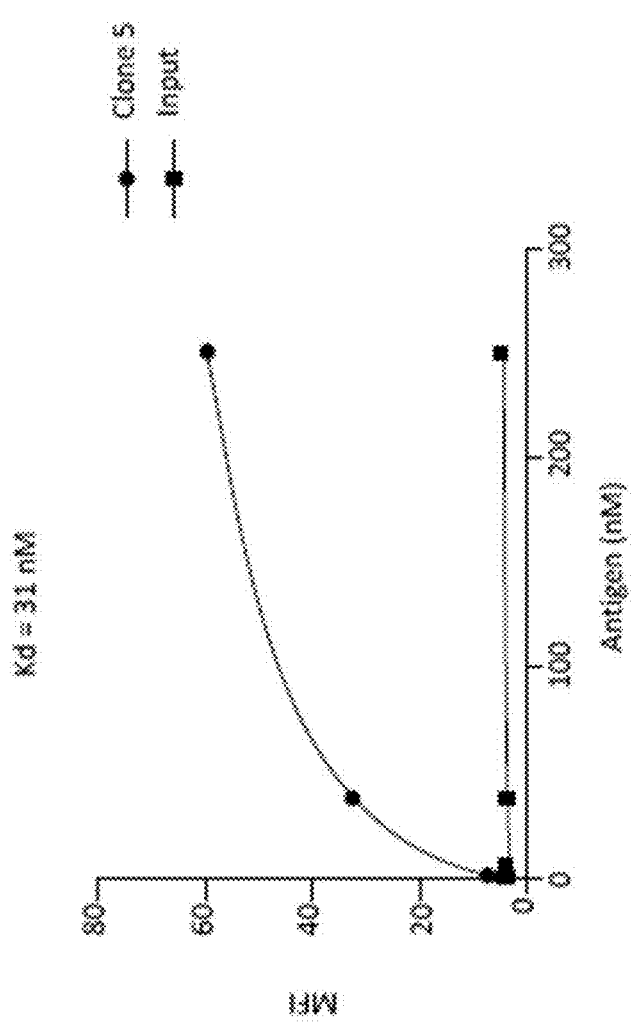
FIG. 25 graphically illustrates a saturation binding curve of clone M3J5 (Clone 5) for the MASP-3 antigen, as described in Example 7.

FIG. 25 graphically illustrates a saturation binding curve of clone M3J5 (Clone 5) for the MASP-3 antigen. As shown in FIG. 25, the apparent binding affinity of the M3J5 antibody for MASP-3 is about 31 nM.

Sequence analysis of identified clones was performed using standard methods. All clones were compared to the common (DT40) VH and VL sequences and to each other. Sequences for the two afore-mentioned clones, M3J5 and M3M1 are provided in an alignment with two additional representative clones, D14 and 1E10, which were identified in screens for CCP1-CCP2-SP fragments of MASP-1 and MASP-3, respectively. D14 and 1E10 bind regions common to both MASP-1 and MASP-3.

Figure 26A:
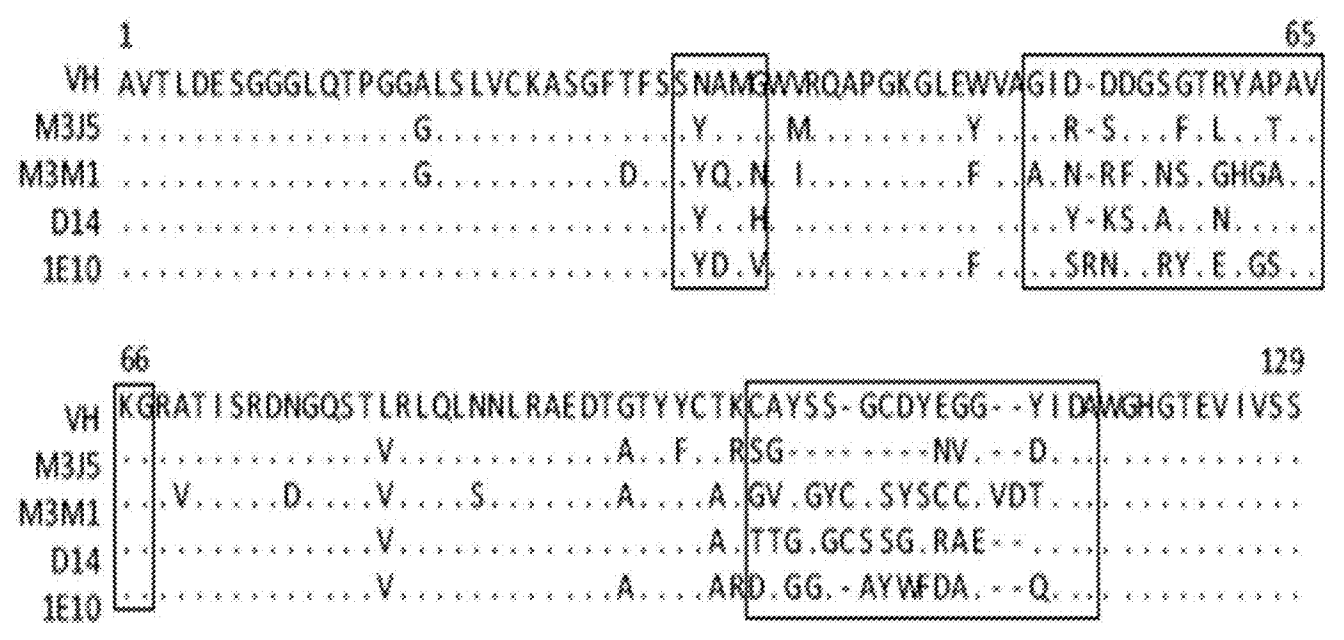

FIG. 26A is an amino acid sequence alignment of the VH regions of M3J5, M3M1, D14 and 1E10 to the chicken DT40 VH sequence.

Figure 26B:
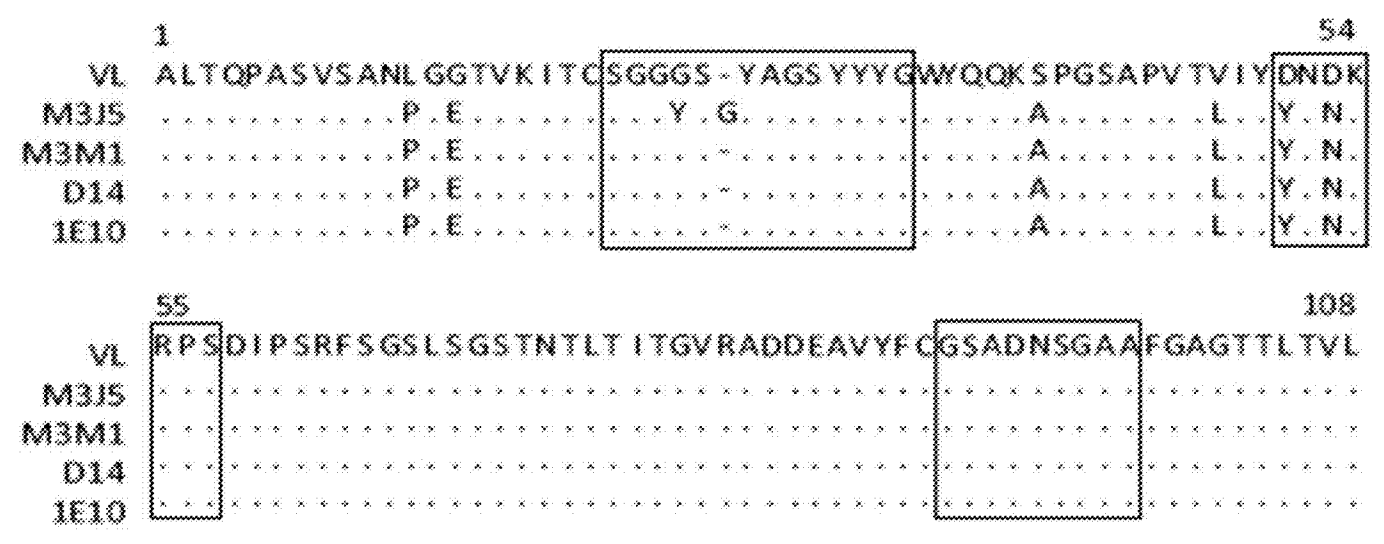

FIG. 26B is an amino acid sequence alignment of the VL regions of M3J5, M3M1, D14 and 1E10 to the chicken DT40 VL sequence.

The VH and VL amino acid sequence of each clone is provided below.

Heavy Chain Variable Region (VH) Sequences

FIG. 26A shows an amino acid alignment of the heavy-Chain Variable Region (VH) sequences for the parent DTLacO (SEQ ID NO:300), the MASP-3-binding clones M3J5 (SEQ ID NO:301), and M3M1 (SEQ ID NO:302), and the MASP-1/MASP-3 dual binding clones D14 (SEQ ID NO:306), and 1E10 (SEQ ID NO:308).

The Kabat CDRs in the VH sequences below are located at the following amino acid positions: H1:aa 31-35; H2:aa 50-62; and H3:aa 95-102.

The Chothia CDRs in the VH sequences below are located at the following amino acid positions: H1: aa 26-32; H2: aa 52-56; and H3: aa 95-101.

Parent DTLacO VH:
(SEQ ID NO: 300)
AVTLDESGGGLQTPGGALSLVCKASGFTFSSNAMGWVRQAPGKGLEWVAGI

DDDGSGTRYAPAVKGRATISRDNGQSTLRLQLNNLRAEDTGTYYCTKCAYS

SGCDYEGGYIDAWGHGTEVIVSS

Clone M3J5 VH:
(SEQ ID NO: 301)
AVTLDESGGGLQTPGGGLSLVCKASGFTFSSYAMGWMRQAPGKGLEYVAGI

RSDGSFTLYATAVKGRATISRDNGQSTVRLQLNNLRAEDTATYFCTRSGNV

GDIDAWGHGTEVIVSS

Clone M3M1 VH:
(SEQ ID NO: 302)
AVTLDESGGGLQTPGGGLSLVCKASGFDFSSYQMNWIRQAPGKGLEFVAAI

NRFGNSTGHGAAVKGRVTISRDDGQSTVRLQLSNLRAEDTATYYCAKGVYG

YCGSYSCCGVDTIDAWGHGTEVIVSS

Clone D14 VH:
(SEQ ID NO: 306)
AVTLDESGGGLQTPGGALSLVCKASGFTFSSYAMHWVRQAPGKGLEWVAGI

YKSGAGTNYAPAVKGRATISRDNGQSTVRLQLNNLRAEDTGTYYCAKTTGS

GCSSGYRAEYIDAWGHGTEVIVSS

Clone 1E10 VH:
(SEQ ID NO: 308)
AVTLDESGGGLQTPGGALSLVCKASGFTFSSYDMVWVRQAPGKGLEFVAGI

SRNDGRYTEYGSAVKGRATISRDNGQSTVRLQLNNLRAEDTATYYCARDAG

GSAYWFDAGQIDAWGHGTEVIVSS

Light Chain Variable Region (VL) Sequences

FIG. 26B shows an amino acid alignment of the light-Chain Variable Region (VL) sequences for the parent DTLacO (SEQ ID NO:303) and the MASP-3-binding clones M3J5 (SEQ ID NO:304), and M3M1 (SEQ ID NO:305), and the MASP-1/MASP-3 dual binding clones D14 (SEQ ID NO:307) and 1E10 (SEQ ID NO:309).

Parent DTLacO VL:
(SEQ ID NO: 303)
ALTQPASVSANLGGTVKITCSGGGSYAGSYYYGWYQQKSPGSAPVTIYDN

DKRPSDIPSRFSGSLSGSTNTLTITGVRADDEAVYFCGSADNSGAAFGAGT

TLTVL

Clone M3J5 VL:
(SEQ ID NO: 304)
ALTQPASVSANPGETVKITCSGGYSGYAGSYYYGWYQQKAPGSAPVTLIYY

NNKRPSDIPSRFSGSLSGSTNTLTITGVRADDEAVYFCGSADNSGAAFGAG

TTLTVL

Clone M3M1 VL:
(SEQ ID NO: 305)
ALTQPASVSANPGETVKITCSGGGSYAGSYYYGWYQQKAPGSAPVTLIYYN

NKRPSDIPSRFSGSLSGSTNTLTITGVRADDEAVYFCGSADNSGAAFGAGT

TLTVL

Clone D14 VL:
(SEQ ID NO: 307)
ALTQPASVSANPGETVKITCSGGGSYAGSYYYGWYQQKAPGSAPVTLIYYN

NKRPSDIPSRFSGSLSGSTNTLTITGVRADDEAVYFCGSADNSGAAFGAGT

TLTVL

Clone 1E10 VL:
(SEQ ID NO: 309)
ALTQPASVSANPGETVKITCSGGGSYAGSYYYGWYQQKAPGSAPVTLIYYN

NKRPSDIPSRFSGSLSGSTNTLTITGVRADDEAVYFCGSADNSGAAFGAGT

TLTVL

LEA-2 (MASP-2-Dependent) Functional Assay

MASP-1 contributes to LEA-2 via its ability to activate MASP-2 (see FIG. 1). The Wieslab® Complement System Screen MBL assay (Euro Diagnostica, Malmö, Sweden) measures C5b-C9 deposition under conditions that isolate LEA-2-dependent activation (i.e., traditional lectin pathway activity). The assay was carried out according to the manufacturer's instructions with representative clone 1E10 tested as a final concentration of 400 nM.

Figure 27:
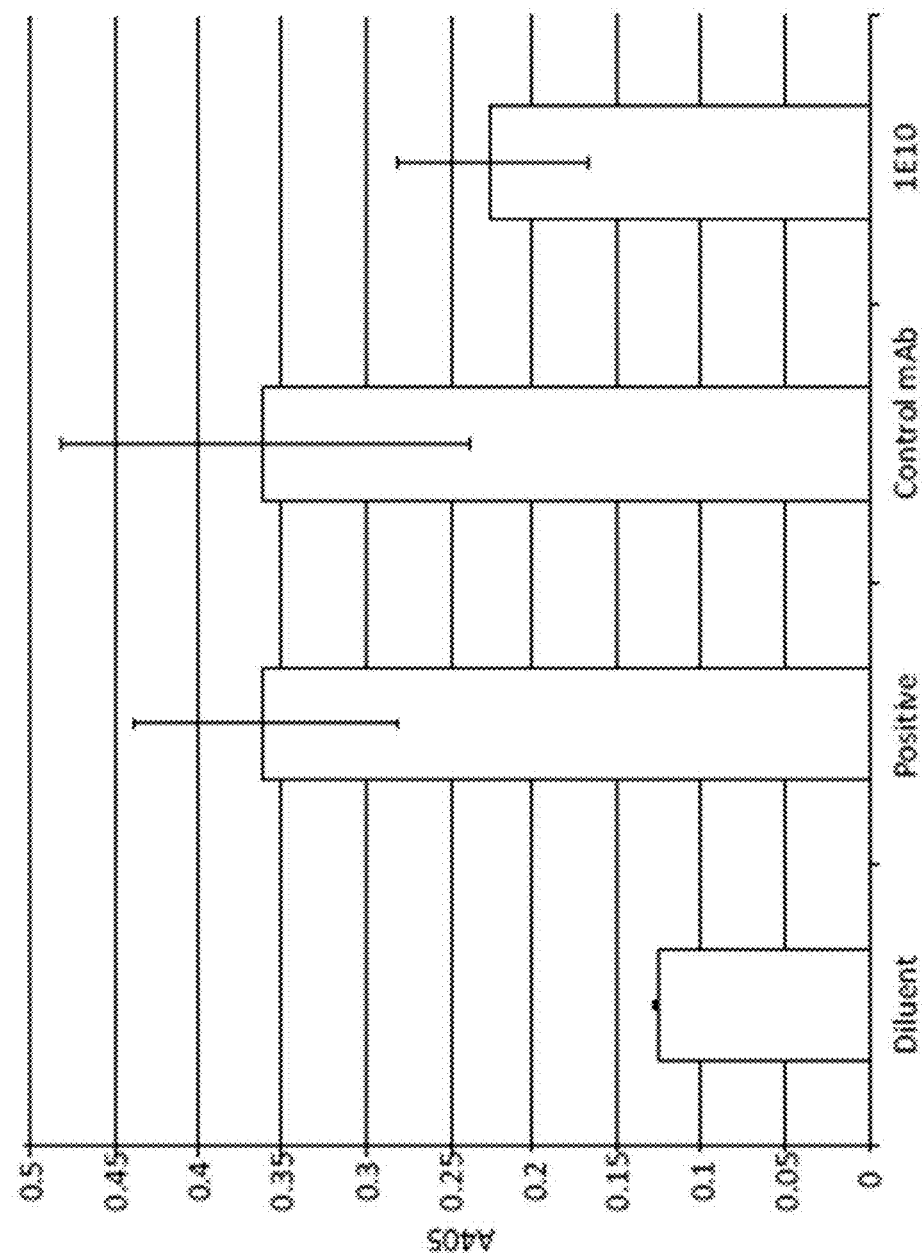
FIG. 27 is a bar graph showing the inhibitory activity of the monoclonal antibody (mAb) 1E10 in the Wieslab Complement System Screen, MBL Pathway in comparison to the positive serum provided with the assay kit, as well as an isotype control antibody, demonstrating that mAb1E10 partial inhibits LEA-2-dependent activation, (via inhibition of MASP-1-dependent activation of MASP-2), whereas the isotype control antibody does not, as described in Example 7.

FIG. 27 is a bar graph showing the inhibitory activity of the mAb 1E10 in comparison to the positive serum provided with the assay kit, as well as an isotype control antibody. As shown in FIG. 27, mAb 1E10 demonstrates partial inhibition of LEA-2-dependent activation (via inhibition of MASP-1-dependent activation of MASP-2), whereas the isotype control antibody does not. Stronger inhibition should be achieved by continued affinity maturation of this antibody for MASP-1 binding using the tethered factors in the DTLacO system.

LEA-1 (MASP-3-dependent) Function Assays for representative mAbs are described below in Examples 8 and 9.

Summary of Results:

The above results showed that the DTLacO platform permitted rapid ex vivo discovery of MASP-1 and MASP-3 monoclonal antibodies with inhibitory properties on LEA-1 (as shown below in Examples 8 and 9) and on LEA-2 (as shown in this Example).

Example 8

Analysis of the complement pathway in 3MC serum with *S. aureus*

Background/Rationale:

It was determined that MASP-3 is not activated through exposure to non-immobilized fluid-phase mannan, zymosan A or N-acetyl cysteine either in the presence or absence of normal human serum. However, it was determined that recombinant and native MASP-3 are activated on the surface of heat-inactivated *S. aureus* in the presence and absence of normal human serum (NHS) or heat-inactivated human serum (HIS) (data not shown). It was also determined that C3b deposition occurs on the surface of S. aureus in the presence of normal human serum, and that the deposition can be monitored using a flow cytometer. Therefore, the alternative pathway (AP) response to S. aureus was measured as described in this Example as a means of assessing the contribution of MASP-3 to LEA-1.

Methods:

Recombinant MASP-3: polynucleotide sequences encoding full length recombinant human MASP-3, a truncated serine protease (SP) active version of MASP-3 (CCP1-CCP2-SP), and a SP-inactivated form of MASP-3 (S679A) were cloned into the pTriEx7 mammalian expression vector (Invivogen). The resulting expression constructs encode the full length MASP-3 or the CCP1-CCP2-SP fragment with an amino-terminal Streptag and a carboxy-terminal $His_6$ tag. The expression constructs were transfected into Freestyle 293-F or Expi293F cells (Invitrogen) according to the protocols provided by the manufacturer. After three to four days of culture in 5% $CO_2$ at 37° C., recombinant proteins were purified utilizing Streptactin affinity chromatography.

Recombinant MASP-1: the full length or truncated CCP1-CCP2-SP forms of recombinant MASP-1 with or without the stabilizing R504Q (Dobo et al., *J. Immunol* 183:1207, 2009) or SP inactivating (S646A) mutations and bearing an amino-terminal Steptag and a carboxy-terminal His6 tag were generated as described for recombinant MASP-3 above.

1. C3b Deposition and Factor B Cleavage on S. aureus in 3MC (Human) Serum

An initial experiment was carried out to demonstrate that the flow cytometry assay is able to detect the presence or absence of AP-driven C3b deposition (AP-C3b) as follows. Five percent of the following sera: normal human serum, factor B (Factor B)-depleted human serum, factor D-depleted human serum and properdin-depleted human serum (obtained from Complement Technology, Tyler, Tex., USA) were mixed with test antibody in either $Mg^{++}$/EGTA buffer or EDTA at 4° C. overnight. Heat-killed S. aureus ($10^8$/ reaction) was added to each mixture to a total volume of 100 µL and rotated at 37° C. for 40 minutes. Bacteria were washed in washing buffer, the bacterial pellet was resuspended in washing buffer and a 80 µL aliquot of each sample was analyzed for C3b deposition on the bacterial surface, which was detected with anti-human C3c (Dako, UK) using flow cytometry.

The results of the flow cytometry detection of C3b are shown in FIG. 28A. As shown in FIG. 28A, panel 1, normal human serum in the presence of EDTA, which is known to inactivate the AP, no C3b deposition was observed (negative control). In normal human serum treated with $Mg^{++}$/EGTA, only lectin-independent complement pathways can function. In panel 2, $Mg^{++}$/EGTA buffer is used, therefore the AP is active, and AP-driven C3b deposition is observed (positive control). As shown in panel 3, 4 and 5, in factor B-depleted, factor D-depleted and properdin-depleted serum, respectively, no alternative pathway driven C3b deposition is observed, as expected. These results demonstrate that the assay is capable of detecting AP-dependent C3b deposition.

A C3b deposition on S. aureus assay was carried out as described above to assess the ability of recombinant MASP-3 to reconstitute the AP (LEA-1) in human 3MC serum, which is deficient in MASP-3 (Rooryck C, et al., *Nat Genet.* 43(3):197-203 (2011)). The following combinations of reagents were tested.

1. 5% normal human serum+EDTA
2. 5% normal human serum+Mg/EGTA
3. 5% human 3MC (MASP-3$^{-/-}$) serum+$Mg^{+/+}$ EGTA
4. 5% human 3MC (MASP-3$^{-/-}$) serum+$Mg^{++}$/EGTA plus active full-length rMASP-3
5. 5% human 3MC (MASP-3$^{-/-}$) serum+$Mg^{++}$/EGTA plus truncated active rMASP-3 (CCP1/CCP2/SP)
6. 5% human 3MC (MASP-3$^{-/-}$) serum+$Mg^{++}$/EGTA plus inactive rMASP-3 (S679A)
7. 5% human 3MC (MASP-3$^{-/-}$) serum+$Mg^{++}$/EGTA plus active full length rMASP-1

The various mixtures of 5% serum and recombinant proteins (5 µg of each) as shown above were incubated in the specified buffer conditions (either $Mg^{++}$/EGTA buffer or EDTA) at 4° C. overnight. After the incubation overnight, $10^8$ heat-killed S. aureus were added to each mixture in a total volume of 100 µL and rotated at 37° C. for 40 minutes. Bacteria were washed and re-suspended in washing buffer and an 80 µL aliquot of each sample was analyzed for C3b deposition by FACS. The remaining 20 µL aliquot of each sample was used to measure factor B cleavage by Western blot using anti-factor B antibody as described below.

The results of the flow cytometry detection of C3b are shown in FIG. 28B. Panel numbers correspond to the numbers designated for each of the reagent combination outlined above. The negative control (panel 1) and positive control (panel 2) show the absence and presence of C3b deposition, as expected. Panel 3 shows that AP-driven C3b deposition is absent in 3MC serum. Panels 4 and 5 show that active full length rMASP-3 (panel 4) and active rMASP-3 (CCP1-CCP2-SP) (panel 5) both restore AP-driven C3b deposition in 3MC serum. Panel 6 shows that inactive rMASP-3 (S679A) does not restore AP-driven C3b deposition in 3MC serum. Panel 7 shows that rMASP-1 does not restore AP-driven C3b deposition in 3MC serum.

Taken together, these results demonstrate that MASP-3 is required for AP-driven C3b deposition on S. aureus in human serum.

MASP-3-Dependent Activation of Factor B

In order to analyze MASP-3-dependent activation of Factor B, the various mixtures of 5% serum (either normal human serum or 3MC patient serum) and recombinant proteins as shown above were assayed as described above. From each reaction mixture, 20 µL were removed and added to protein sample loading buffer. The samples were heated at 70° C. for 10 minutes and loaded onto an SDS-PAGE gel. Western blot analysis was performed using a Factor B polyclonal antibody (R&D Systems). Activation of Factor B was apparent by the formation of two lower molecular weight cleavage products (Bb and Ba) derived from the higher molecular weight pro-Factor B protein.

Figure 29:
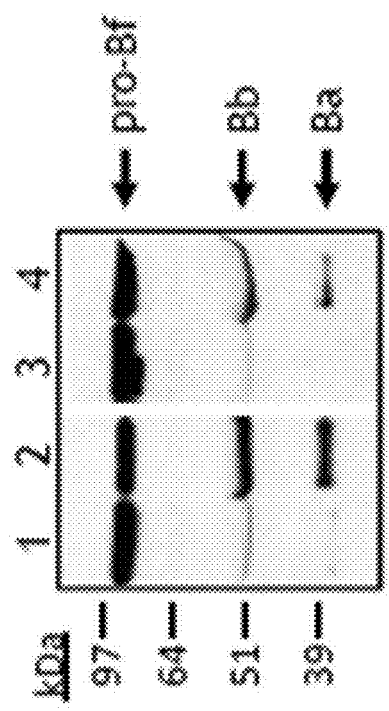
FIG. 29 shows the results of a Western blot analysis to determine factor B cleavage in response to *S. aureus* in 3MC serum in the presence or absence of rMASP-3, demonstrating that the normal human serum in the presence of EDTA (negative control, lane 1) demonstrates very little Factor B cleavage relative to normal human serum in the presence of $Mg^{++}$/EGTA, shown in lane 2 (positive control), as further shown in lane 3, 3MC serum demonstrates very little Factor B cleavage in the presence of $Mg^{++}$/EGTA. However, as shown in lane 4, Factor B cleavage is restored by the addition and pre-incubation of full-length, recombinant MASP-3 protein to the 3MC serum, as described in Example 8.

FIG. 29 shows the results of a Western blot analysis to determine factor B cleavage in response to S. aureus in 3MC serum in the presence or absence of rMASP-3. As shown in lane 1, the normal human serum in the presence of EDTA (negative control) demonstrates very little Factor B cleavage relative to normal human serum in the presence of $Mg^{++}$/ EGTA, shown in lane 2 (positive control). As shown in lane 3, 3MC serum demonstrates very little Factor B cleavage in the presence of $Mg^{++}$/EGTA. However, as shown in lane 4, Factor B cleavage is restored by the addition and pre-incubation of full-length, recombinant MASP-3 protein (5 µg) to the 3MC serum.

Assay to Determine the Effect of rMASP-3 on Pro-Factor D in Factor B/C3(H2O) Cleavage The following assay was carried out to determine the minimal requirement for MASP-3-dependent activation/ cleavage of factor B.

Figure 30:
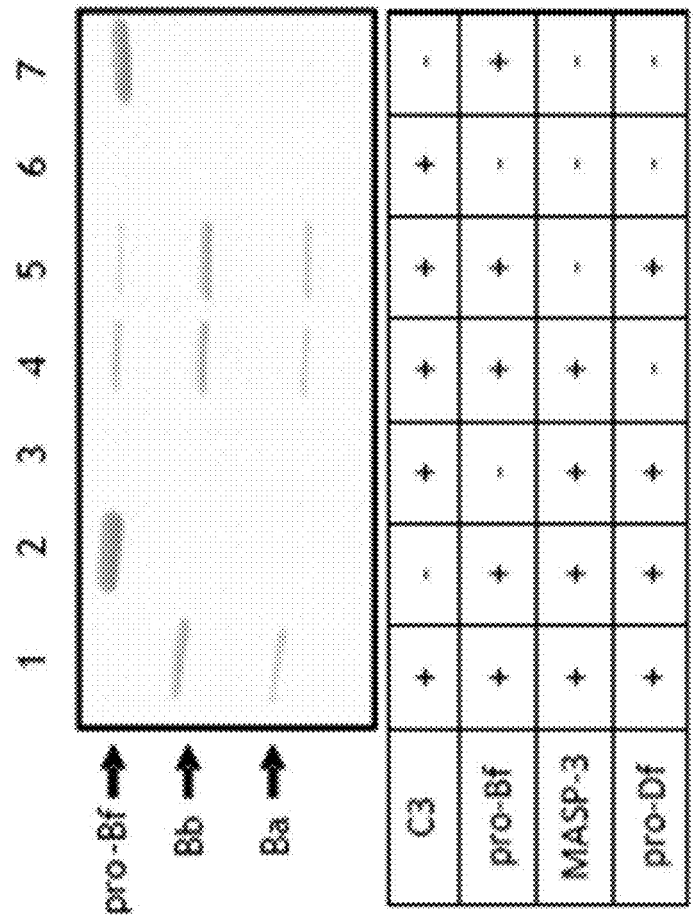
FIG. 30 shows Comassie staining of a protein gel in which Factor B cleavage is analyzed, demonstrating that Factor B cleavage is most optimal in the presence of C3, MASP-3 and pro-factor D (lane 1), and as shown in lanes 4 and 5, either MASP-3 or pro-factor D alone are able to mediate Factor B cleavage, as long as C3 is present, as described in Example 8.

C3(H₂O) (200 ng), purified plasma factor B (20 µg), recombinant pro-factor D (200 ng) and recombinant human MASP-3 (200 ng) were mixed together in various combinations (as shown in FIG. 30), in a total volume of 100 µL in BBS/Ca⁺⁺/Mg⁺⁺ and incubated at 30° C. for 30 minutes. The reaction was stopped by adding 25 uL of SDS loading dye containing 5% 2-mercaptoethanol. After boiling at 95° C. for 10 minutes under shaking (300 rpm), the mixture was spun down at 1400 rpm for 5 minutes and 20 uL of the supernatant was loaded and separated on a 10% SDS gel. The gel was stained with Coomassie brilliant blue.

Results:

FIG. 30 shows a Coomassie-stained SDS-PAGE gel in which factor B cleavage is analyzed. As shown in lane 1, factor B cleavage is most optimal in the presence of C3, MASP-3 and pro-factor D. As shown in lane 2, C3 is absolutely required; however, as shown in lanes 4 and 5, either MASP-3 or pro-factor D are able to mediate factor B cleavage, as long as C3 is present.

Analysis of the Ability of MASP-3 mAbs to Inhibit MASP-3-Dependent AP-Driven C3b Deposition As described in this Example it was demonstrated that MASP-3 is required for AP-driven C3b deposition on *S. aureus* in human serum. Therefore, the following assay was carried out to determine if a representative MASP-3 mAb identified as described in Example 7, could inhibit activity of MASP-3. Active, recombinant MASP-3 (CCP1-CCP2-SP) fragment protein (250 ng) was pre-incubated with an isotype control mAb, mAb1A5 (control obtained from the DTLacO platform that does not bind MASP-3 or MASP-1), or mAbD14 (binds MASP-3) at three different concentrations (0.5, 2 and 4 µM) for 1 hour on ice. The enzyme-mAb mixture was exposed to 5% 3MC serum (MASP-3 deficient) and 5×10⁷ heat-killed *S. aureus* in a final reaction volume of 50 µL. The reactions were incubated at 37° C. for 30 minutes, and then stained for the detection of C3b deposition. The stained bacterial cells were analyzed by a flow cytometer.

Figure 31:
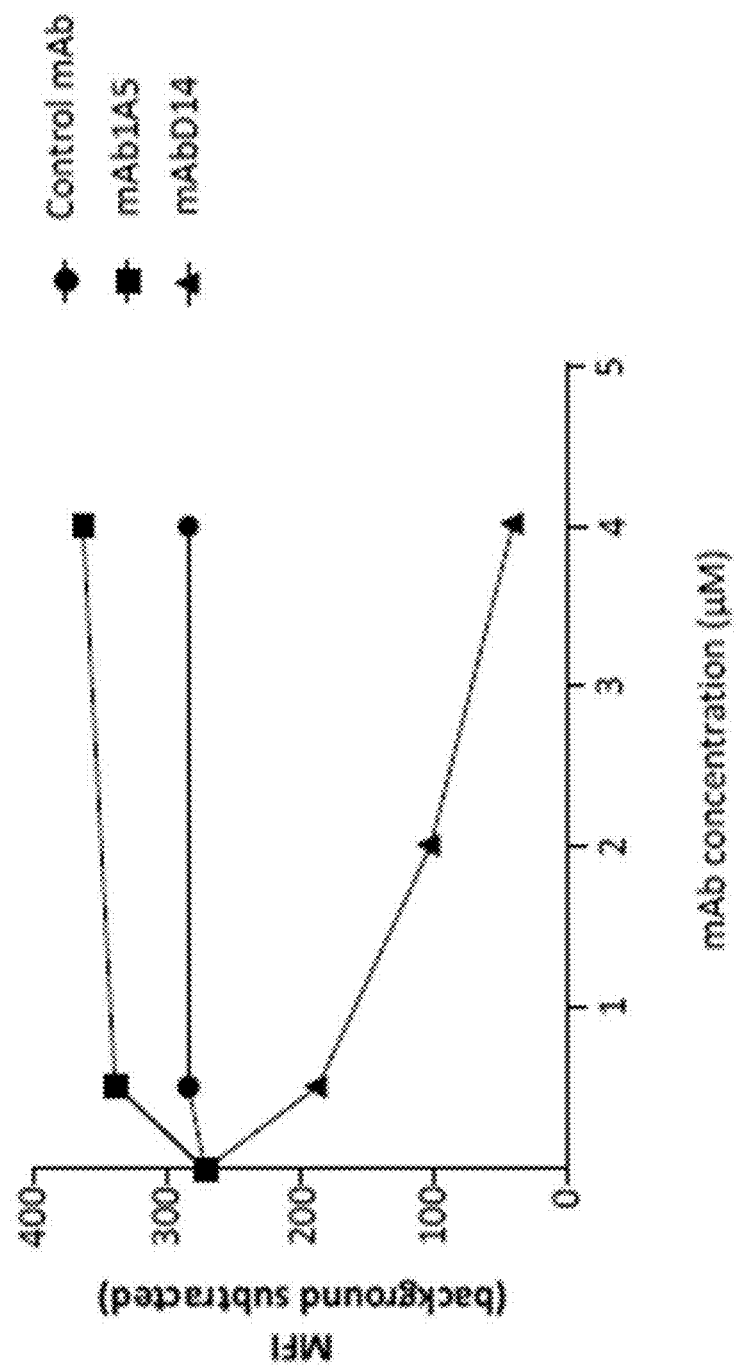
FIG. 31 graphically illustrates the mean fluorescent intensities (MFI) of C3b staining of *S. aureus* obtained from mAbD14 (which binds MASP-3), mAb1A5 (negative control antibody) and an isotype control antibody plotted as a function of mAb concentration in 3MC serum in the presence of rMASP-3, demonstrating that mAbD14 inhibits MASP-3-dependent C3b deposition in a concentration-dependent manner, as described in Example 8.

FIG. 31 graphically illustrates the mean fluorescent intensities (MFI) of C3b staining obtained from the three antibodies plotted as a function of mAb concentration in 3MC serum with the presence of rMASP-3. As shown in FIG. 31, mAbD14 demonstrates inhibition of C3b deposition in a concentration-dependent manner. In contrast, neither of the control mAbs inhibited C3b deposition. These results demonstrate that mAbD14 is able to inhibit MASP-3-dependent C3b deposition. Improved inhibitory activity for mAbD14 is expected following continued affinity maturation of this antibody for MASP-3 binding using the tethered factors in the DTLacO system.

Summary of Results:

In summary, the results in this Example demonstrate a clear defect of the AP in serum deficient for MASP-3. Thus, MASP-3 has been demonstrated to make a critical contribution to the AP, using factor B activation and C3b deposition as functional end-points. Furthermore, addition of functional, recombinant MASP-3, including the catalytically-active C-terminal portion of MASP-3 corrects the defect in factor B activation and C3b deposition in the serum from the 3MC patient. Conversely, as further demonstrated in this Example, addition of a MASP-3 antibody (e.g., mAbD14) in 3MC serum with rMASP-3 inhibits AP-driven C3b deposition. A direct role of MASP-3 in Factor B activation, and therefore the AP, is demonstrated by the observation that recombinant MASP-3, along with C3, is sufficient to activate recombinant factor B.

Example 9

This Example demonstrates that MASP-1 and MASP-3 activate factor D.

Methods:

Recombinant MASP-1 and MASP-3 were tested for their ability to cleave two different recombinant versions of pro-factor D. The first version (pro-factor D-His) lacks an N-terminal tag, but has a C-terminal His tag. Thus, this version of pro-factor D contains the 5 amino acid propeptide that is removed by cleavage during activation. The second version (ST-pro-factor D-His) has a Strep-TagII sequence on the N-terminus, thus increasing the cleaved N-terminal fragment to 15 amino acids. ST-pro-factor D also contains a His₆ tag at the C-terminus. The increased length of the propeptide of ST-pro-factor D-His improves the resolution between the cleaved and uncleaved forms by SDS-PAGE compared to the resolution possible with the pro-factor D-HIS form.

Recombinant MASP-1 or MASP-3 proteins (2 µg) was added to either pro-factor D-His or ST-pro-factor D-His substrates (100 ng) and incubated for 1 hour at 37° C. The reactions were electrophoresed on a 12% Bis-Tris gel to resolve pro-factor D and the active factor D cleavage product. The resolved proteins were transferred to a PVDF membrane and analyzed by Western blot by detection with a biotinylated factor D antibody (R&D Systems).

Figure 32:
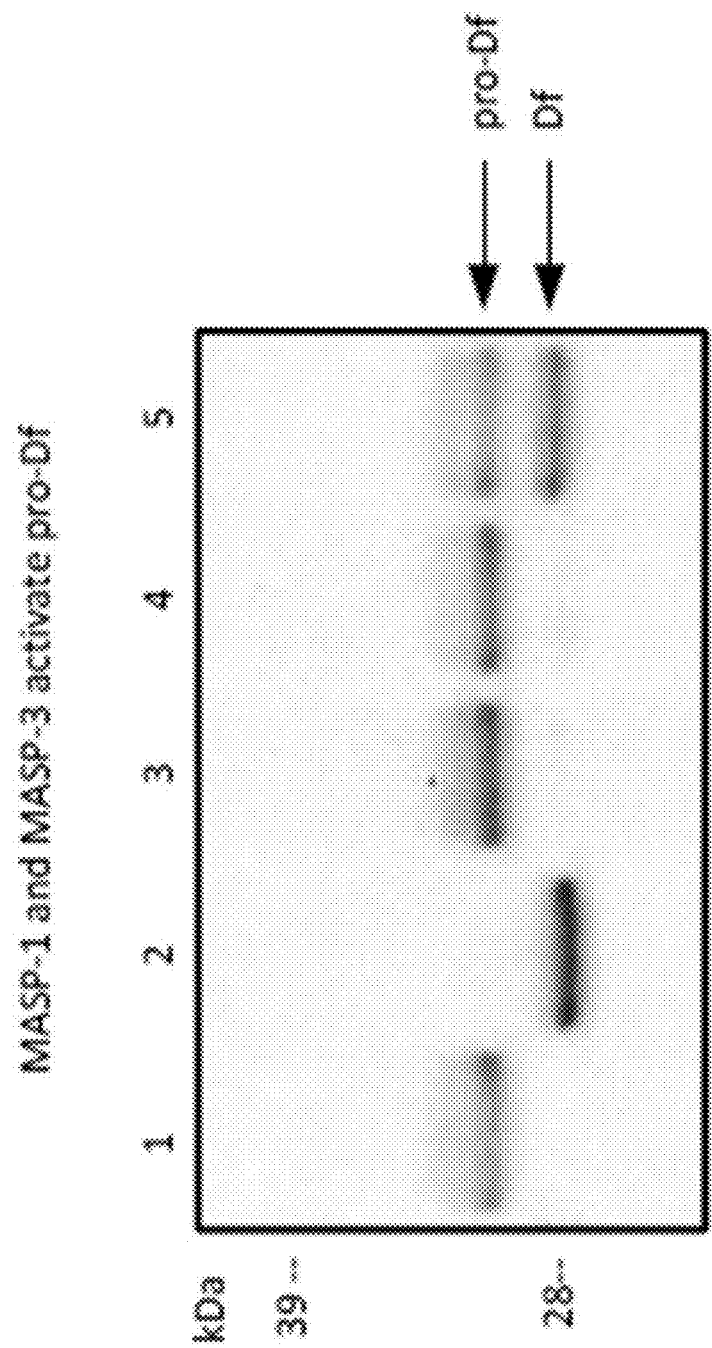
FIG. 32 shows Western blot analysis of pro-factor D substrate cleavage, wherein compared to pro-factor D alone (lane 1) or the inactive full length recombinant MASP-3 (S679A; lane 3) or MASP-1 (S646A; lane 4), full length wild type recombinant MASP-3 (lane 2) and MASP-1 (lane 5) either completely or partially cleave pro-factor D to generate mature factor D, as described in Example 9.

Results:

FIG. 32 shows the Western blot analysis of pro-factor D substrate cleavage.

TABLE 14

Lane Description for Western Blot shown in FIG. 32

| Experimental conditions | Lane 1 | Lane 2 | Lane 3 | Lane 4 | Lane 5 |
|---|---|---|---|---|---|
| Pro-Factor D | + | + | + | + | + |
| rMASP-3 (full-length) | − | + | − | − | − |
| rMASP-3a (S679A) | − | − | + | − | − |
| rMASP-1A (S646A) | − | − | − | + | − |
| rMASP-1 (CCP-1-CCP2-SP) | − | − | − | − | + |

As shown in FIG. 32, only full length MASP-3 (lane 2) and the MASP-1 CCP1-CCP2-SP) fragment (lane 5) cleaved ST-pro-factor D-His₆. The catalytically-inactive full length MASP-3 (S679A; lane 3) and MASP-1 (S646A; lane 3) failed to cleave either substrate. Identical results were obtained with the pro-factor D-His₆ polypeptide (not shown). The comparison of a molar excess of MASP-1 (CCP1-CCP2-SP) relative to MASP-3 suggests that MASP-3 is a more effective catalyst of pro-factor D cleavage than is MASP-1, as least under the conditions described herein.

Conclusions:

Both MASP-1 and MASP-3 are capable of cleaving and activating factor D. This activity directly connects LEA-1 with the activation of the AP. More specifically, activation of factor D by MASP-1 or MASP-3 will lead to factor B activation, C3b deposition, and likely opsonization and/or lysis.

Assay for Inhibition of MASP-3-Dependent Cleavage of Pro-Factor D with MASP-3 Antibodies An assay was carried out to determine the inhibitory effect of representative MASP-3 and MASP-1 mAbs, identified as described in Example 7, on MASP-3-dependent factor D cleavage as follows. Active, recombinant MASP-3 protein (80 ng) was pre-incubated with 1 µg of representative mAbs D14, M3M1 and a control antibody (which binds specifically to MASP-1, but not to MASP-3) at room temperature for 15 minutes. Pro-factor D with an N-terminal Strep-tag (ST-pro-factor D-His, 70 ng) was added and the mixture was incubated at 37° C. for 75 minutes. The reactions were then electrophoresed, blotted and stained with anti-factor D as described above.

Figure 33:
FIG. 33 is a Western blot showing the inhibitory activity of the MASP-3 binding mAbs D14 (lane 2) and M3M1 (lane 3) on MASP-3-dependent pro-factor D cleavage in comparison to a control reaction containing only MASP-3 and pro-factor D (no mAb, lane 1), as well as a control reaction containing a mAb obtained from the DTLacO library that binds MASP-1, but not MASP-3 (lane 4), as described in Example 9.

FIG. 33 is a Western blot showing the partial inhibitory activity of the mAbs D14 and M3M1 in comparison to a control reaction containing only MASP-3 and ST-pro-factor D-His (no mAb; lane 1), as well as a control reaction containing a mAb obtained from the DTLacO library that binds MASP-1, but not MASP-3 (lane 4). As shown in FIG. 33, in the absence of an inhibitory antibody, MASP-3 cleaves approximately 50% of pro-factor D into factor D (lane 1). The control MASP-1 specific antibody (lane 4) does not change the ratio of pro-factor D to factor D. In contrast, as shown in lanes 2 and 3, both mAb D14 and mAb M3M1 inhibit MASP-3-dependent cleavage of pro-factor D to factor D, resulting in a reduction in factor D generated.

Conclusions:

These results demonstrate that MASP-3 mAbs D14 and M3M1 are able to inhibit MASP-3-dependent factor D cleavage. Improved inhibitory activity for mAbD14 and mAb M3M1 is expected following continued affinity maturation of these antibodies for MASP-3 binding using the tethered factors in the DTLacO system.

Example 10

This Example demonstrates that MASP-3 deficiency prevents complement-mediated lysis of mannan-coated WT rabbit erythrocytes.

Background/Rationale:

As described in Examples 5 and 6 herein, the effect of MASP-2- and MASP-3-deficient serum on lysis of red blood cells from blood samples obtained from a mouse model of PNH demonstrated the efficacy of MASP-2 inhibition and/or MASP-3 inhibition to treat subjects suffering from PNH, and also supported the use of inhibitors of MASP-2 and/or inhibitors of MASP-3 (including dual or bi-specific MASP-2/MASP-3 inhibitors) to ameliorate the effects of C3 fragment-mediated extravascular hemolysis in PNH subjects undergoing therapy with a C5 inhibitor such as eculizumab.

As described in this Example, C3b deposition experiments and hemolysis experiments were carried out in MASP-3 deficient serum from additional 3MC patients, confirming the results obtained in Examples 5 and 6. In addition, experiments were carried out which demonstrated that addition of rMASP-3 to 3MC serum was able to reconstitute C3b deposition and hemolytic activity.

Methods:

MASP-3-deficient serum was obtained from three different 3MC patients as follows:

3MC Patient 1: contains an allele bearing a mutation that renders the exon encoding the MASP-3 serine protease domain dysfunctional, supplied along with the mother and father of the 3MC patient (both heterozygous for the allele bearing a mutation that renders the exon encoding the MASP-3 serine protease domain dysfunctional), 3MC Patient 2: Has C1489T (H497Y) mutation in exon 12 of MASP-1, the exon that encodes the serine protease domain of MASP-3, resulting in nonfunctional MASP-3, but functional MASP-1 proteins.

3MC Patient 3: Has a confirmed defect in the MASP-1 gene, resulting in nonfunctional MASP-3 and nonfunctional MASP-1 proteins.

Experiment #1: C3b Deposition Assay

An AP assay was carried out under traditional AP-specific conditions (BBS/Mg$^{++}$/EGTA, without Ca$^{++}$, wherein BBS=barbital buffered saline containing sucrose), as described in Bitter-Suermann et al., *Eur. J. Immunol* 11:291-295 (1981)), on zymosan-coated microtiter plates at serum concentrations ranging from 0.5 to 25% and C3b deposition was measured over time.

Figure 34:
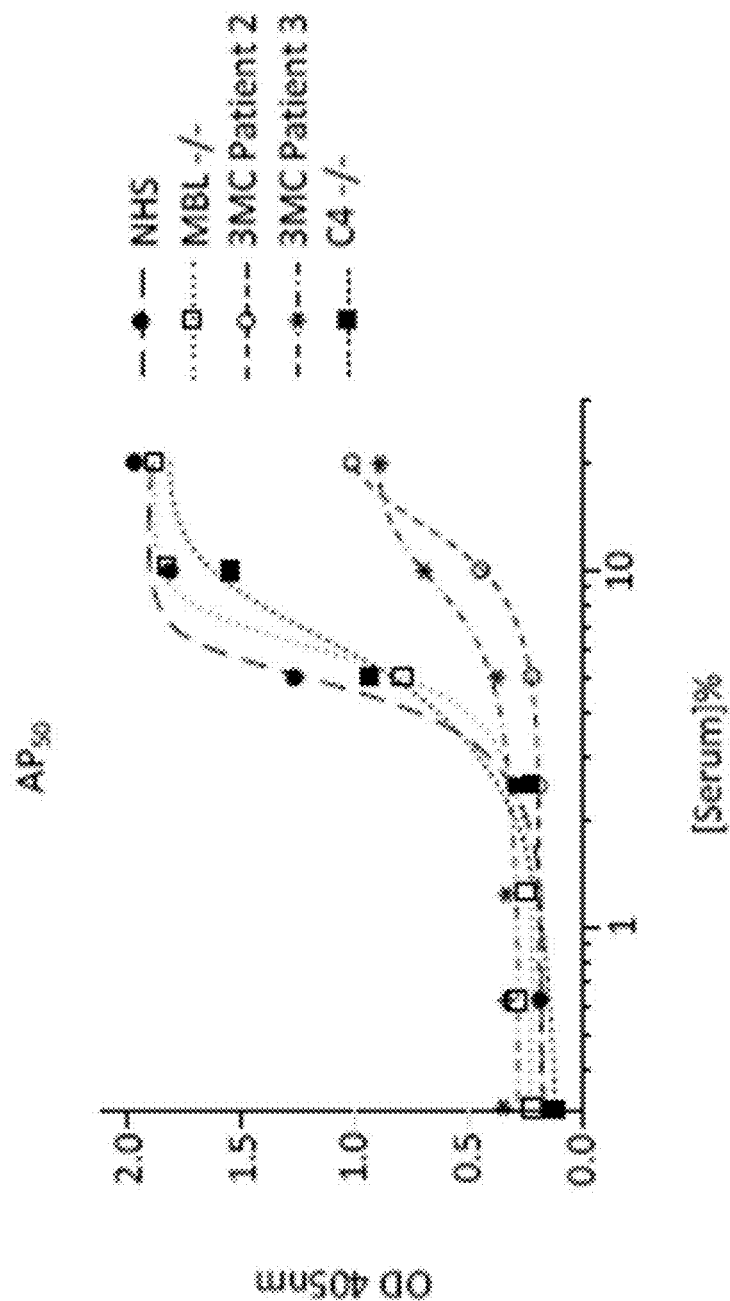
FIG. 34 graphically illustrates the level of AP-driven C3b deposition on zymosan-coated microtiter plates as a function of serum concentration in serum samples obtained from MASP-3-deficient (3MC), C4-deficient and MBL-deficient subjects, demonstrating that MASP-3-deficient sera from Patient 2 and Patient 3 have residual AP activity at high serum concentrations (25%, 12.5%, 6.25% serum concentrations), but a significantly higher $AP_{50}$ (i.e., 8.2% and 12.3% of serum needed to achieve 50% of maximum C3 deposition), as described in Example 10.

Results:

FIG. 34 graphically illustrates the level of AP-driven C3b deposition on zymosan-coated microtiter plates as a function of serum concentration in serum samples obtained from MASP-3-deficient (3MC), C4-deficient and MBL-deficient subjects. As shown in FIG. 34, and summarized below in TABLE 15, MASP-3-deficient patient sera from Patient 2 and Patient 3 have residual AP activity at high concentrations (25%, 12.5%, 6.25% serum concentrations), but a significantly higher AP$_{50}$ (i.e., 8.2% and 12.3% of serum needed to achieve 50% of maximum C3 deposition).

Figure 35A:
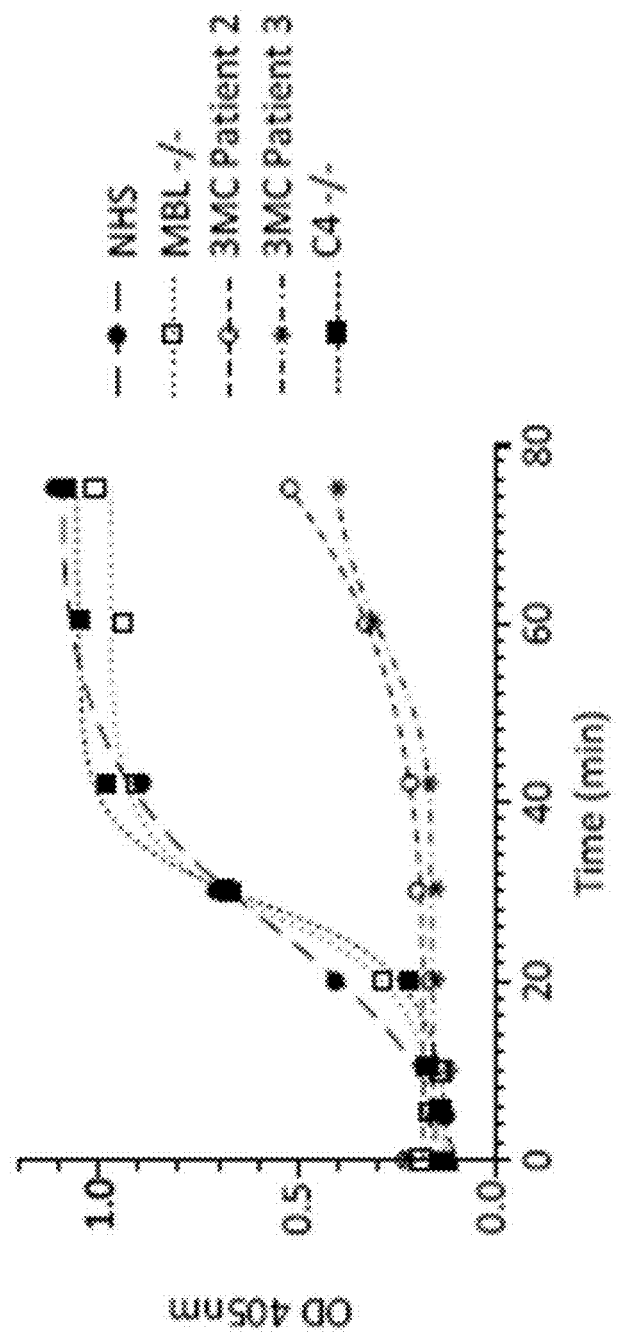
FIG. 35A graphically illustrates the level of AP-driven C3b deposition on zymosan-coated microtiter plates under "traditional" AP-specific conditions (i.e., BBS/EGTA/$Mg^{++}$ without $Ca^{++}$) as a function of time in 10% human serum samples obtained from MASP-3 deficient, C4-deficient and MBL-deficient human subjects, as described in Example 10.

FIG. 35A graphically illustrates the level of AP-driven C3b deposition on zymosan-coated microtiter plates under "traditional" AP-specific conditions (i.e., BBS/EGTA/Mg$^{++}$ without Ca$^{++}$) as a function of time in 10% human serum samples obtained from MASP-3 deficient, C4-deficient and MBL-deficient human subjects.

TABLE 15 below summarizes the AP$_{50}$ results shown in FIG. 34 and the half-times for C3b deposition shown in FIG. 35A.

TABLE 15

Summary of Results shown in FIGS. 34 and 35A

| Serum type | AP$_{50}$ (%) | T$_{1/2}$ (min) |
| --- | --- | --- |
| Normal | 4.5 | 26.3 |
| MBL-deficient (MBL−/−) | 5.7 | 27.5 |
| C4-deficient (C4−/−) | 5.1 | 28.6 |
| 3MC (Patient 3) | 8.2 | 58.2 |
| 3MC (Patient 2) | 12.3 | 72.4 |

Note:
In BBS/Mg$^{++}$/EGTA buffer, the lectin pathway-mediated effects are deficient due to absence of Ca$^{++}$ in this buffer.

Experiment #2: Analysis of Pro-Factor D Cleavage in 3MC Patient Sera by Western Blot Methods:

Serum was obtained from 3MC patient #2 (MASP-3(−/−), MASP-1(+/+)) and from 3MC patient #3 (MASP-3(−/−), MASP-1(−/−)). The patient sera, along with sera from normal donors (W), were separated by SDS-polyacrylamide gel and the resolved proteins were blotted to a polyvinylidine fluoride membrane. Human pro-factor D (25,040 Da) and/or mature factor D (24,405 Da) were detected with a human factor D-specific antibody.

Figure 35B:
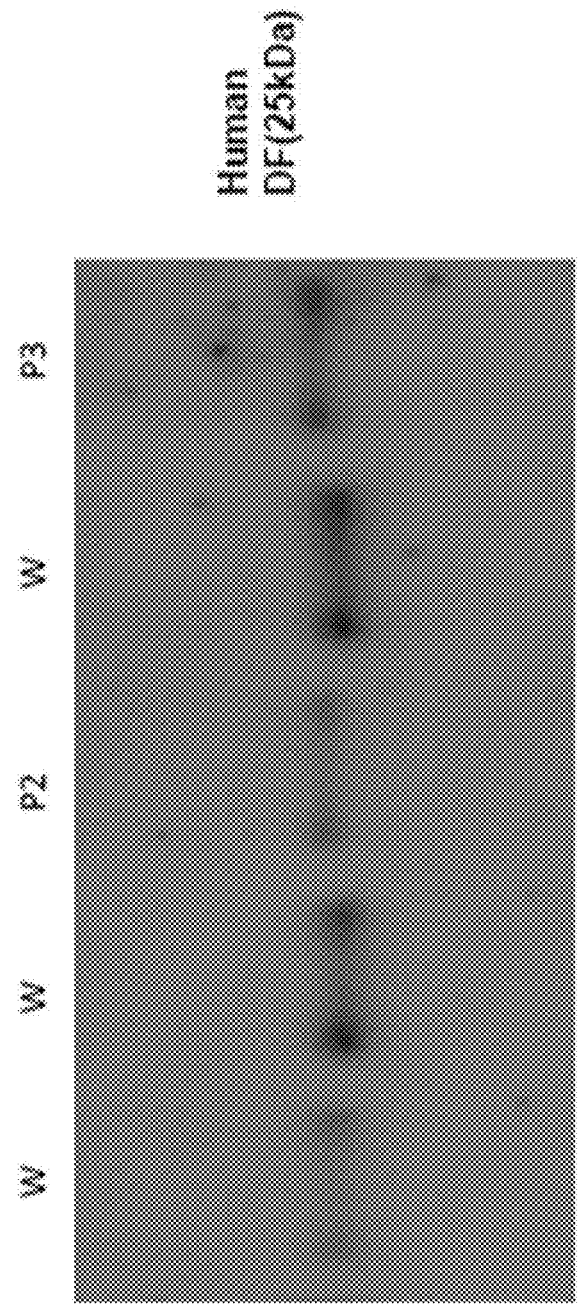
FIG. 35B shows a western blot with plasma obtained from 3MC patient #2 (MASP-3 (−/−), MASP-1 (+/+)), 3MC patient #3 (MASP-3 (−/−), MASP-1 (−/−)), and sera from normal donors (W), wherein human pro-factor D (25,040 Da) and/or mature factor D (24,405 Da) was detected with a human factor D-specific antibody, as described in Example 10.

Results:

The results of the Western blot are shown in FIG. 35B. As shown in FIG. 35B, in the sera from normal donors (W), the factor D antibody detected a protein of a size consistent with mature factor D (24,405 Da). As further shown in FIG. 35B, the factor D antibody detected a slightly larger protein in the sera from 3MC patient #2 (P2) and 3MC patient #3 (P3), consistent with the presence of pro-factor D (25,040 Da) in these 3MC patients.

Experiment #3: Wieslab Complement Assays with 3MC Patient Sera

Methods:

Sera obtained from 3MC patient #2 (MASP-3(−/−), MASP-1(+/+)) and from 3MC patient #3 (MASP-3(−/−), MASP-1(−/−)) were also tested for classical, lectin and alternative pathway activity using the Wieslab Complement System Screen (Euro-Diagnostica, Malmo, Sweden) according to the manufacturer's instructions. Normal human serum was tested in parallel as a control.

Figure 35C:
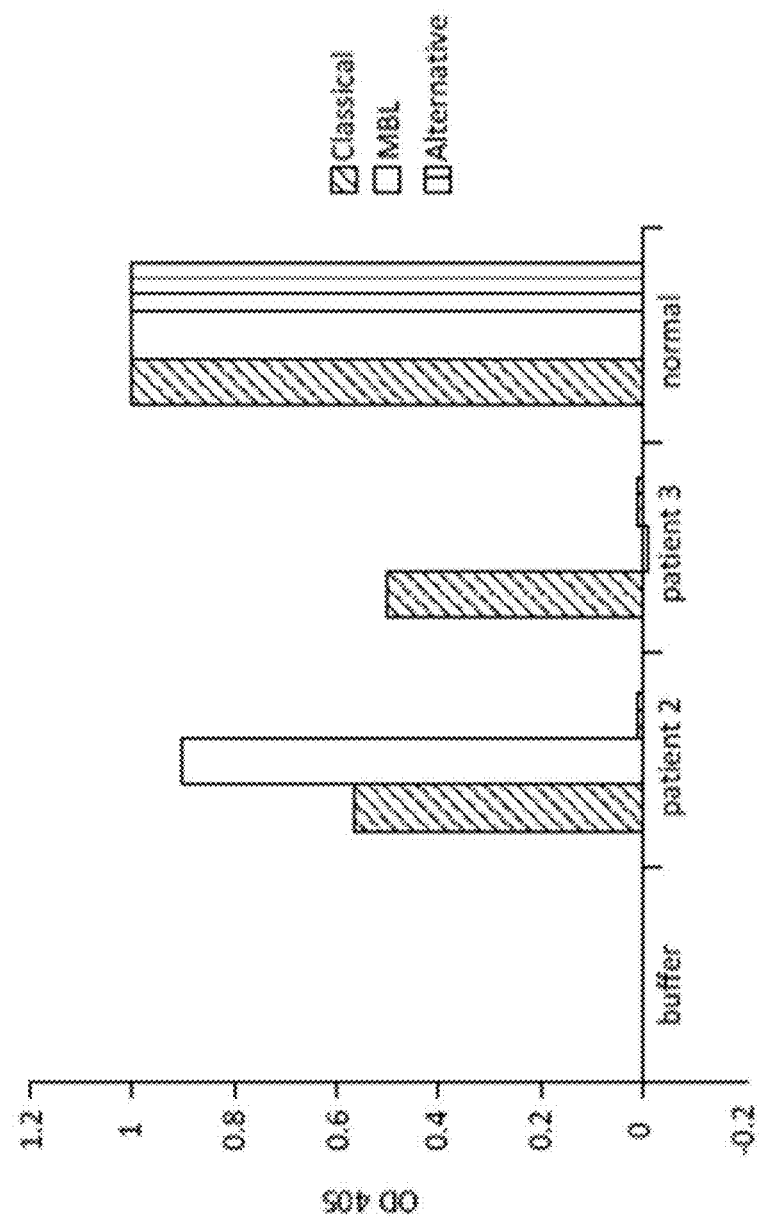
FIG. 35C graphically illustrates the results of the Weislab classical, lectin and alternative pathway assays with plasma obtained from 3MC patient #2, 3MC patient #3, and normal human serum, as described in Example 10.

Results:

FIG. 35C graphically illustrates the results of the Wieslab classical, lectin and alternative pathway assays with plasma obtained from 3MC patient #2, 3MC patient #3, and normal human serum. As shown in FIG. 35C, under conditions of the Wieslab assay, the classical, alternative, and MBL (lectin) pathways are all functional in the normal human serum. In serum from 3MC patient #2 (MASP-3(−/−), MASP-1(+/+)), the classical pathway and lectin pathway are functional, however there is no detectable alternative pathway activity. In serum from 3MC patient #3 (MASP-3(−/−), MASP-1(−/−)), the classical pathway is functional, however there is no detectable lectin pathway activity and no detectable alternative pathway activity.

The result in FIGS. 35B and 35C further support our understanding of the role of MASP-1 and MASP-3 in the LEA-1 and LEA-2 pathways. Specifically, the absence of the alternative pathway with a nearly fully functional lectin pathway in serum from Patient 2, who lacks only MASP-3, confirms that MASP-3 is essential for activation of the alternative pathway. Serum from Patient 3, who lacks both MASP-1 and MASP-3, has lost the ability to activate the lectin pathway as well as the alternative pathway. This result confirms the requirement of MASP-1 for a functional LEA-2 pathway, and is consistent with Example 7, and the literature demonstrating that MASP-1 activates MASP-2. The apparent inability of both sera to activate pro-factor D is also consistent with the data described in Example 9 demonstrating that MASP-3 cleaves pro-factor D. These observations are consistent with the LEA-1 and LEA-2 pathways as diagrammed in FIG. 1.

Experiment #4: Hemolysis Assay Testing Mannan-Coated Rabbit Erythrocytes for Lysis in the Presence of Human Normal or 3MC Serum (in the Absence of $Ca^{++}$)

Methods:

Preparation of Rabbit RBC in the Absence of $Ca^{++}$ (i.e., by Using EGTA)

Rabbit whole blood (2 mL) was split into two 1.5 mL eppendorf tubes and centrifuged for 3 minutes at 8000 rpm (approximately 5.9 rcf) in a refrigerated eppendorf centrifuge at 4° C. The RBC pellet was washed three times after re-suspending in ice-cold BBS/$Mg^{++}$/$Ca^{++}$ (4.4 mM barbituric acid, 1.8 mM sodium barbitone, 145 mM NaCl, pH 7.4, 5 mM 5 mM $Ca^{++}$). After the third wash, the pellet was re-suspended in 4 mL BBS/$Mg^{++}$/$Ca^{++}$. The erythrocytes were pelleted and the RBCs were washed with BBS/0.1% gelatin/$Mg^{++}$/$Ca^{++}$ as described above. The RBCs suspension was stored in BBS/0.1% gelatin/$Mg^{++}$/$Ca^{++}$ at 4° C. Then, 100 µL of suspended RBCs were diluted with 1.4 mL water and spun down at 8000 rpm (approximately 5.9 rcf) for 3 minutes and the OD of the supernatant was adjusted to 0.7 at 541 nm (an OD of 0.7 at 541 nm corresponds to approximately $10^9$ erythrocytes/nil). After that, 1 mL of the resuspended RBCs at OD 0.7 were added to 9 ml of BBS/$Mg^{++}$/EGTA in order to achieve a concentration of $10^8$ erythrocytes/ml. Dilutions of the test sera or plasma were prepared in ice-cold BBS, EGTA and 100 µL of each serum or plasma dilution was pipetted into the corresponding well of round-bottom plate. 100 µL of appropriately diluted RBC ($10^8$ erythrocytes/nil) were added to each well. Nano-water was used to produce the positive control (100% lysis), while a dilution with BBS/$Mg^{++}$/EGTA without serum or plasma was used as a negative control. The plate was then incubated for 1 hour at 37° C. The round bottom plate was spun down at 3750 rpm for 5 minutes. Then, 100 µL of the supernatant from each well was transferred into the corresponding wells of a flat-bottom plate and OD was read at 415-490 nm.

Figure 36:
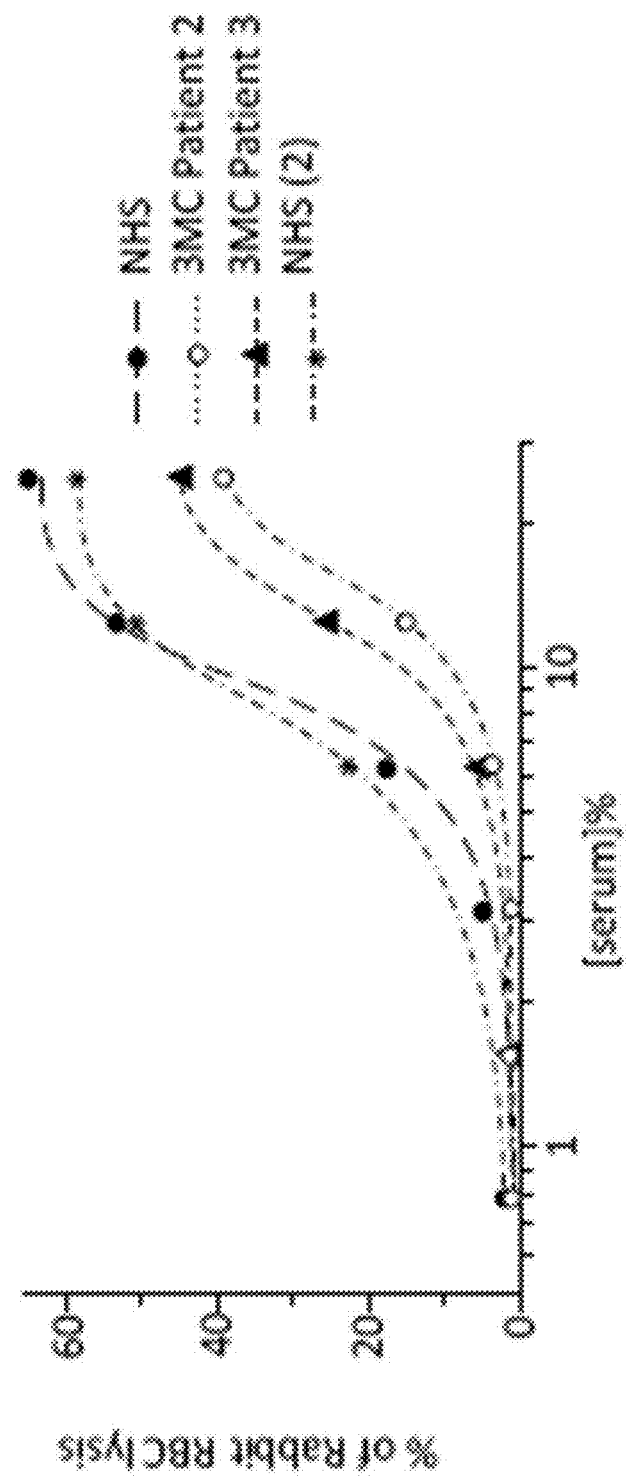
FIG. 36 graphically illustrates the percent hemolysis (as measured by hemoglobin release of lysed rabbit erythrocytes into the supernatant measured by photometry) of mannan-coated rabbit erythrocytes over a range of serum concentrations in serum from two normal human subjects (NHS) and from two 3MC patients (Patient 2 and Patient 3), measured in the absence of $Ca^{++}$, demonstrating that MASP-3 deficiency reduces the percentage of complement-mediated lysis of mannan-coated erythrocytes as compared to normal human serum, as described in Example 10.

Results:

FIG. 36 graphically illustrates the percent hemolysis (as measured by hemoglobin release of lysed rabbit erythrocytes into the supernatant measured by photometry) of mannan-coated rabbit erythrocytes over a range of serum concentrations in serum from normal subjects and from two 3MC patients (Patient 2 and Patient 3), measured in the absence of $Ca^{++}$. As shown in FIG. 36, it is demonstrated that MASP-3 deficiency reduces the percentage of complement-mediated lysis of mannan-coated erythrocytes as compared to normal human serum. The differences between the two curves from the normal human serum and the two curves from the 3MC patients is significant (p=0.013, Friedman test).

TABLE 16 below summarizes the $AP_{50}$ results shown in FIG. 36.

TABLE 16

Summary of Results shown in FIG. 36

| Serum type | $AP_{50}$ (%) |
|---|---|
| Normal human serum #1 | 7.1 |
| Normal human serum #2 | 8.6 |
| 3MC Patient #2 | 11.9 |
| 3MC Patient #3 | 14.3 |

It is noted that when the serum samples shown in TABLE 16 were pooled, the $AP_{50}$ value for normal human serum=7.9 and the $AP_{50}$ value for 3MC serum=12.8 (p=0.031, Wilcox matched-pairs signed rank test).

Experiment #5: Reconstitution of Human 3MC Serum by Recombinant MASP-3 Restores AP-Driven C3b Deposition on Zymosan Coated Plates Methods:

An AP assay was carried out under traditional AP-specific conditions (BBS/$Mg^{++}$/EGTA, without $Ca^{++}$, wherein BBS=barbital buffered saline containing sucrose), as described in Bitter-Suermann et al., *Eur. J. Immunol* 11:291-295 (1981)), on zymosan-coated microtiter plates in the following serum samples (1) 5% human serum from 3MC Patient #2 with full length active rMASP-3 added in at a range of 0 to 20 µg/mL; (2) 10% human serum from 3MC Patient #2 with full length active rMASP-3 added in at a range of 0 to 20 µg/mL; and (3) 5% human serum from 3MC Patient #2 with inactive rMASP-3A (S679A) added in at a range of 0 to 20 µg/mL.

Figure 37:
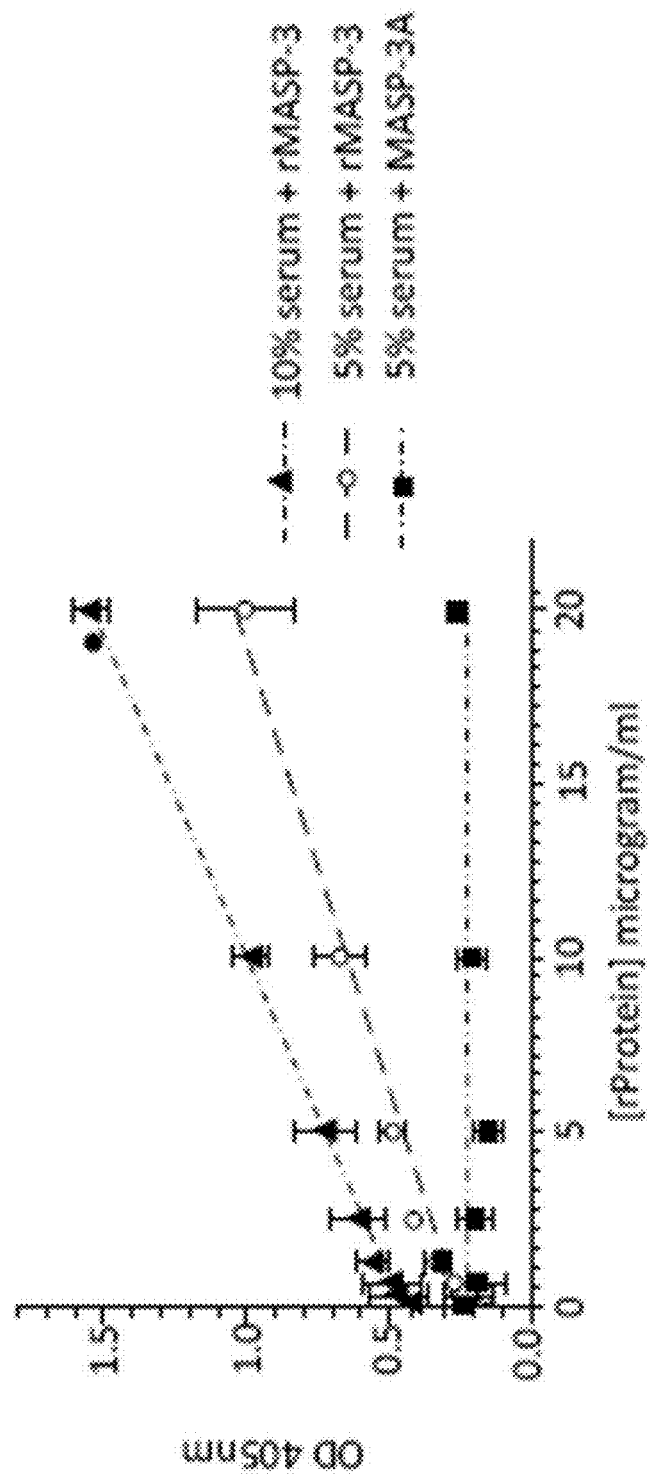
FIG. 37 graphically illustrates the level of AP-driven C3b deposition on zymosan-coated microtiter plates as a function of the concentration of recombinant full length MASP-3 protein added to serum samples obtained from human 3MC Patient 2 (MASP-3$^{−/−}$), demonstrating that, compared to the negative control inactive recombinant MASP-3 (MASP-3A; S679A), active recombinant MASP-3 protein reconstitutes AP-driven C3b deposition on zymosan-coated plates in a concentration-dependent manner, as described in Example 10.

Results:

FIG. 37 graphically illustrates the level of AP-driven C3b deposition on zymosan-coated microtiter plates as a function of the concentration of rMASP-3 protein added to serum samples obtained from human 3MC Patient #2 (MASP-3-deficient). As shown in FIG. 37, active recombinant MASP-3 protein reconstitutes AP-driven C3b deposition on zymosan-coated plates in a concentration-dependent manner. As further shown in FIG. 37, no C3b deposition was observed in the 3MC serum containing inactive rMASP-3 (S679A).

Experiment #6: Reconstitution of Human 3MC Serum by Recombinant MASP-3 Restores Hemolytic Activity in 3MC Patient Serum Methods:

A hemolytic assay was carried out using rabbit RBC using the methods described above in Experiment #2 with the following test sera at a range of 0 to 12% serum: (1) normal human serum; (2) 3MC patient serum; (3) 3MC patient serum plus active full length rMASP-3 (20 µg/ml); and (4) heat-inactivated human serum.

Figure 38:
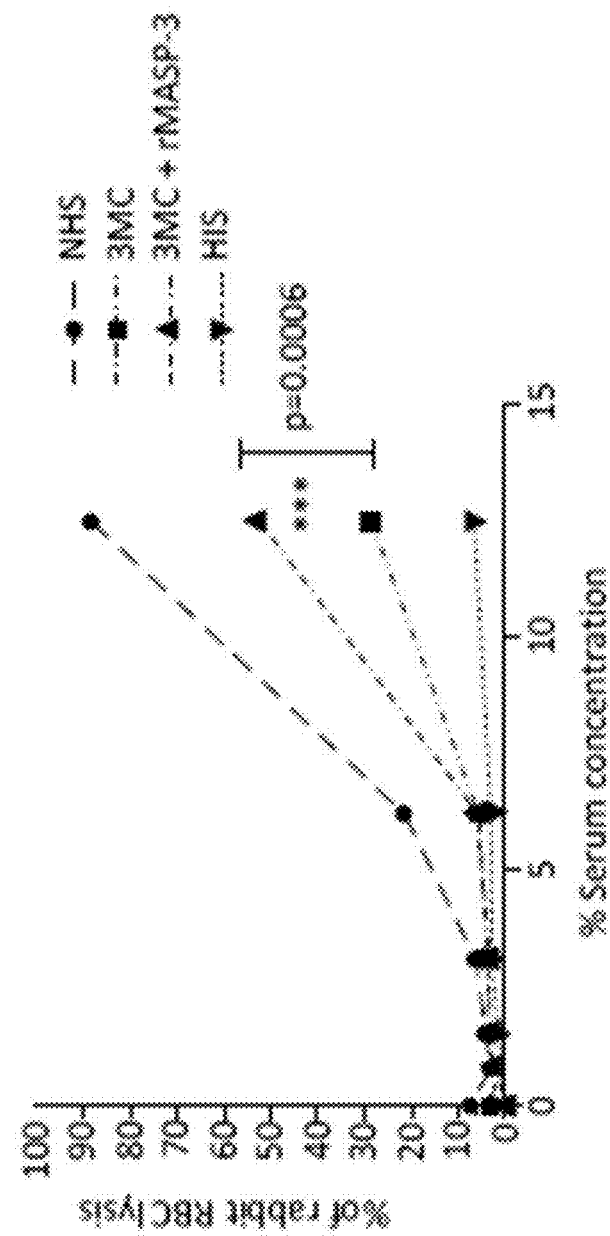
FIG. 38 graphically illustrates the percent hemolysis (as measured by hemoglobin release of lysed rabbit erythrocytes into the supernatant measured by photometry) of mannan-coated rabbit erythrocytes over a range of serum concentrations in (1) normal human serum (NHS); (2) 3MC patient serum; (3) 3MC patient serum plus active full length recombinant MASP-3 (20 μg/ml); and (4) heat-inactivated human serum (HIS), measured in the absence of $Ca^{++}$, demonstrating that the percent lysis of rabbit erythrocytes is significantly increased in 3MC serum containing rMASP-3 as compared to the percent lysis in 3MC serum without recombinant MASP-3 (p=0.0006), as described in Example 10.

Results:

FIG. 38 graphically illustrates the percent hemolysis (as measured by hemoglobin release of lysed rabbit erythrocytes into the supernatant measured by photometry) of mannan-coated rabbit erythrocytes over a range of serum concentrations in (1) normal human serum; (2) 3MC patient serum; (3) 3MC patient serum plus active full length rMASP-3 (20 µg/ml); and (4) heat-inactivated human serum, measured in the absence of $Ca^{++}$. As shown in FIG. 38, the percent lysis of rabbit RBC is significantly increased in 3MC serum including rMASP-3 as compared to the percent lysis in 3MC serum without rMASP-3 (p=0.0006).

Figure 39:
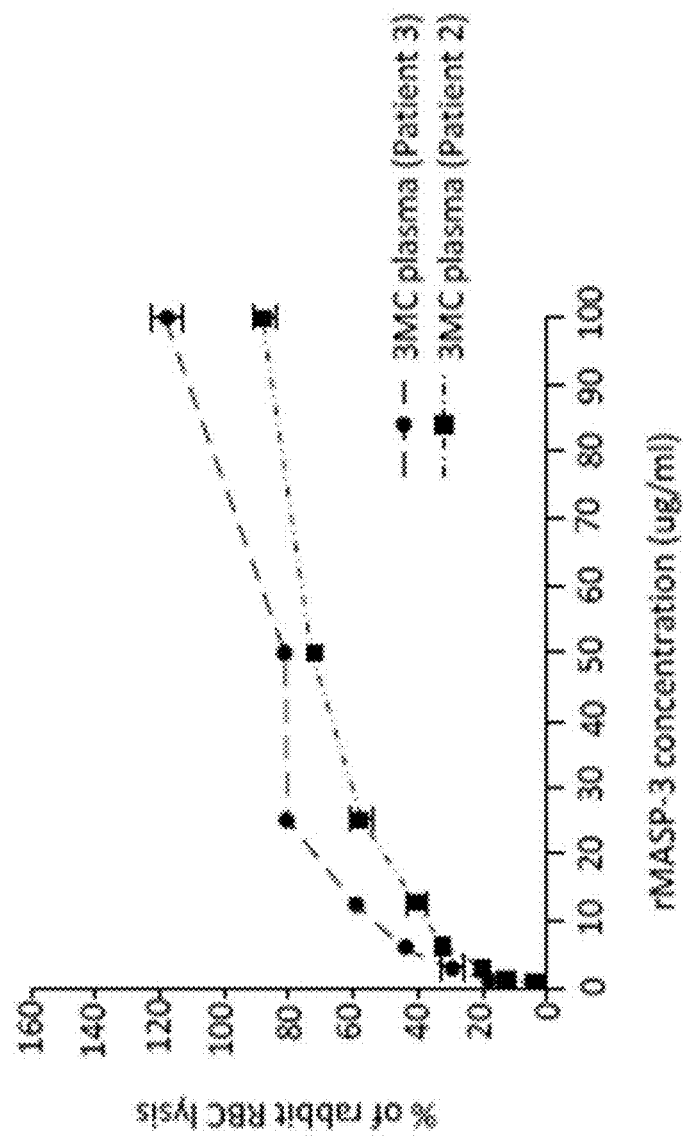
FIG. 39 graphically illustrates the percentage of rabbit erythrocyte lysis in 7% human serum from 3MC Patient 2 and from 3MC Patient 3 containing active recombinant MASP-3 at a concentration range of 0 to 110 μg/ml (in $BBS/Mg^{++}/EGTA$, demonstrating that the percentage of rabbit erythrocyte lysis increases with the amount of recombinant MASP-3 in a concentration-dependent manner, as described in Example 10.

FIG. 39 graphically illustrates the percentage of rabbit erythrocyte lysis in 7% human serum from 3MC Patient 2 and from 3MC Patient 3 containing active rMASP-3 at a concentration range of 0 to 110 µg/ml in BBS/Mg$^{++}$/EGTA. As shown in FIG. 39, the percentage of rabbit RBC lysis is restored with the amount of rMASP-3 in a concentration-dependent manner up to 100% activity.

Experiment #7: Serum of MASP-3 Deficient (3MC) Patient has Functional MASP-2 if MBL is Present Methods:

A C3b deposition assay was carried out using Mannan-coated ELISA plates under to examine whether 3MC serum is deficient in LEA-2. Citrate plasma was diluted in BBS buffer in serial dilutions (starting at 1:80, 1:160, 1:320, 1:640, 1:1280, 1:2560) and plated on Mannan-coated plates. Deposited C3b was detected using a chicken anti-human C3b assay. LEA-2 driven C3b deposition (the plasma dilutions are to high for the AP and LEA-1 to work) on Mannan-coated ELISA plates was evaluated as a function of human serum concentration in serum from a normal human subject (NHS), from two 3MC patients (Patient 2 and Patient 3), from the parents of Patient 3 and from a MBL-deficient subject.

Figure 40:
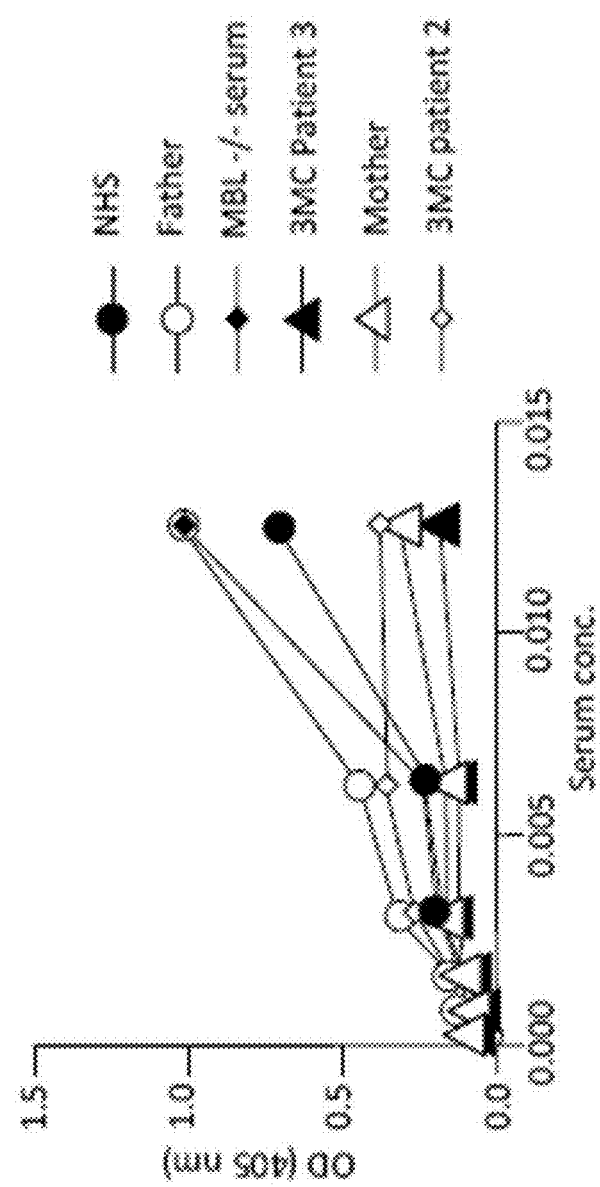
FIG. 40 graphically illustrates the level of LEA-2-driven C3b deposition on Mannan-coated ELISA plates as a function of the concentration of human serum diluted in BBS buffer, for serum from a normal human subject (NHS), from two 3MC patients (Patient 2 and Patient 3), from the parents of Patient 3 and from a MBL-deficient subject, as described in Example 10.

Results:

FIG. 40 graphically illustrates the level of LEA-2-driven (i.e., MASP-2-driven) C3b deposition on Mannan-coated ELISA plates as a function of the concentration of human serum diluted in BBS buffer, for serum from a normal human subject (NHS), from two 3MC patients (Patient 2 and Patient 3), from the parents of Patient 3 and from a MBL-deficient subject. These data indicate that Patient 2 is MBL sufficient. However, Patient 3 and the mother of Patient 3 are MBL deficient, and therefore their serum does not deposit C3b on Mannan via LEA-2. Replacement of MBL in these sera restores LEA-2 mediated C3b deposition in the serum of Patient 3 (who is homozygous for the SNP leading to MASP-3 deficiency) and his mother (who is heterozygous for the mutant MASP-3 allele) (data not shown). This finding demonstrates that 3MC serum is not deficient in LEA-2, but rather appears to have functional MASP-2.

Overall Summary and Conclusions:

These results demonstrate that MASP-3 deficiency in human serum results in loss of AP activity, as manifested in reduced C3b deposition on zymosan-coated wells and reduced rabbit erythrocyte lysis. The AP can be restored in both assays by supplementing the sera with functional, recombinant human MASP-3.

Example 11

This Example demonstrates that a chimeric mouse V region/human IgG4 constant region anti-human MASP-3 monoclonal antibody (mAb M3-1, also referred to as mAb 13B1) is a potent inhibitor of MASP-3-mediated Alternative Pathway Complement (APC) Activation.

Methods:

Generation of a Chimeric Mouse V Region/Human IgG Constant Region Anti-Human MASP-3 Monoclonal Antibody (mAb M3-1)

A murine anti-human MASP-3 inhibitory antibody (mAb M3-1) was generated by immunizing MASP-1/3 knockout mice with the human MASP-3 CCP1-CCP2-SP domain (aa 301-728 of SEQ ID NO:2) (see also Example 14). Briefly described, splenocytes from the immunized mice were fused with P3/NS1/1-Ag4-1 and supernatants from resulting hybridoma clones were screened for the production of antibodies that bind to human MASP-3 and for the ability to block MASP-3-mediated cleavage of complement pro-factor D (pro-CFD) to factor D (CFD). Monoclonal antibody (mAb) variable regions were isolated by RT-PCR, sequenced and cloned into human IgG4 expression vectors. Chimeric monoclonal antibodies were expressed in transiently transfected HEK293T cells, purified and tested for binding affinity to mouse and human MASP-3 and for the ability to inhibit MASP-3-mediated cleavage of pro-CFD to CFD.

The MASP-3 inhibitory monoclonal antibody M3-1 (13B1) comprises a heavy chain variable region (VH) set forth as SEQ ID NO:30 and a light chain variable region (VL) set forth as SEQ ID NO:45. The sequences of the variable regions of the M3-1 monoclonal antibody are provided below:

Heavy Chain Variable Region

Presented below is the heavy chain variable region (VH) sequence for mAb M3-1. The Kabat CDRs (31-35 (H1), 50-65 (H2) and 95-102 (H3) are underlined, which correspond to amino acid residues 31-35 (H1), 50-66 (H2) and 99-102 (H3) of SEQ ID NO:30.

mAb M3-1 heavy chain variable region (VH)
(SEQ ID NO: 30)
QVQLKQSGAELMKPGASVKLSCKATGYTFT<u>GKWIE</u>WVKQRPGHGLEWIG<u>EI LPGTGSTNYNEKFKG</u>KATFTADSSSNTAYMQLSSLTTEDSAMYYCLR<u>SEDV

WGTGTTVTSS

Light Chain Variable Region

Presented below is the light chain variable region (VL) sequence for mAb M3-1. The Kabat CDRs (24-34 (H1), 50-56 (H2) and 89-97 (H3) are underlined, which correspond to amino acid residues 24-40 (L1); 56-62 (L2) and 95-102 (L3) of SEQ ID NO:45. These regions are the same whether numbered by the Kabat or Chothia system.

```
mAb M3-1 light chain variable region (VL)
                                       (SEQ ID NO: 45)
DIVMTQSPSSLAVSAGEKVTMSCKSSQSLLNSRTRKNYLAWYQQKPGQSPK

LLIYWASTRESGVPDRFTGSGSGTDFTLTISSVQAEDLAVYYCKQSYNIPT

FGGGTKLEIKR mAb M3-1 VH CDRs
VHCDR1:
                                       (SEQ ID NO: 84)
GKWIE

VHCDR2:
                                       (SEQ ID NO: 86)
EILPGTGSTNYNEKFKG

VHCDR3:
                                       (SEQ ID NO: 88)
SEDV mAb M3-1 VL CDRs
VLCDR1:
                                       (SEQ ID NO: 142)
KSSQSLLNSRTRKNYLA

VLCDR2:
                                       (SEQ ID NO: 144)
WASTRES

VLCDR3:
                                       (SEQ ID NO: 161)
KQSYNIPT
```

As shown above, MASP-3 monoclonal antibody M3-1 comprises (a) a heavy chain variable region comprising (i) VHCDR1 comprising SEQ ID NO:84, (ii) VHCDR2 comprising SEQ ID NO:86 and (iii) VHCDR3 comprising SEQ ID NO:88; and (b) a light chain variable region comprising (i) VLCDR1 comprising SEQ ID NO:142, (ii) VLCDR2 comprising SEQ ID NO:144 and (iii) VLCDR3 comprising SEQ ID NO:161.

Binding of mAb M3-1 to Recombinant Forms of Human and Mouse MASP-3

A monovalent Fab version of M3-1 was tested for binding to recombinant, full-length human and mouse MASP-3 protein in an ELISA experiment. Binding affinity determinations were made by coating 96-well plates with an anti-MASP-3 capture antibody that binds the protein from multiple species. The capture antibody has been shown to bind the CCP1-CCP2 region of MASP-1 and MASP-3. Full-length versions of human and mouse protein were immobilized on ELISA plates coated with the capture antibody, and varying concentrations of M3-1 Fab were allowed to bind to the target protein in separate wells. Bound M3-1 was detected using an anti-kappa light chain antibody that is conjugated to HRP (Novus Biologicals NBP1-75064), and was visualized with the TMB substrate reagent set (BD Biosciences 555214).

Figure 41:
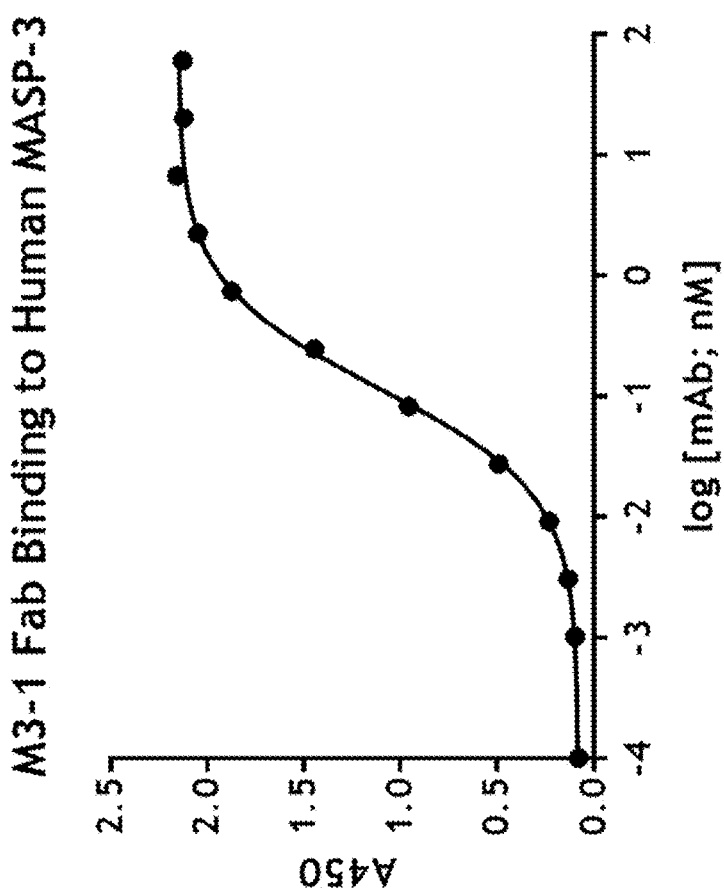
FIG. 41 graphically illustrates a representative example of a binding experiment that was performed with human MASP-3 in which the M3-1 Fab (also referred to as 13B1) shows an apparent binding affinity ($EC_{50}$) of about 0.117 nM to the human protein, as described in Example 11.

FIG. 41 graphically illustrates a representative example of a binding experiment that was performed with human MASP-3 in which the M3-1 Fab (also referred to as 13B1) shows an apparent binding affinity ($EC_{50}$) of about 0.117 nM to the human protein.

Figure 42:
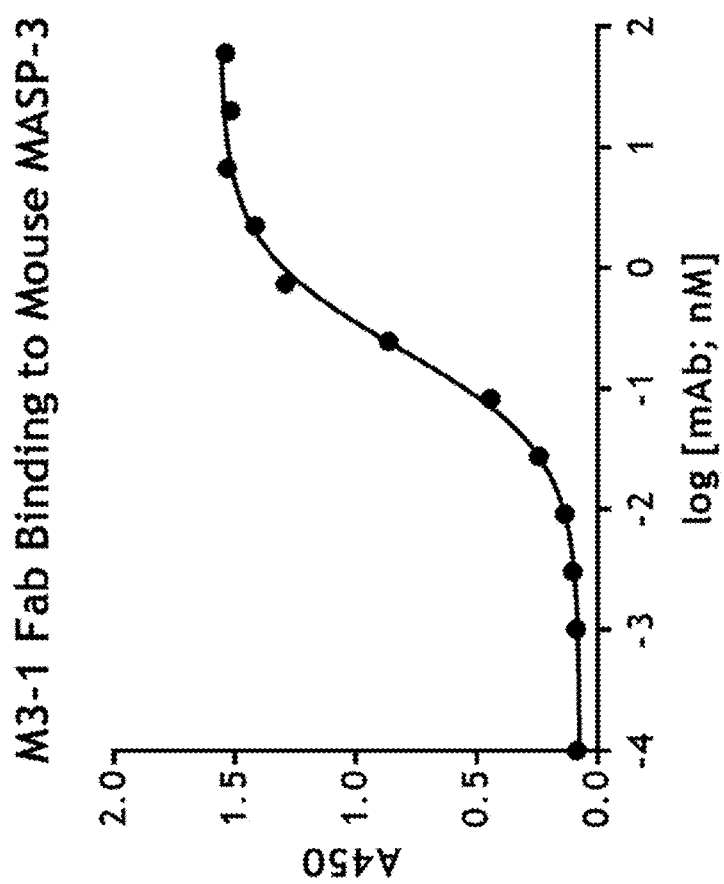
FIG. 42 graphically illustrates a representative example of a binding experiment that was performed with mouse MASP-3 in which the M3-1 Fab (also referred to as 13B1) shows an apparent binding affinity ($EC_{50}$) of about 0.214 nM to the mouse protein, as described in Example 11.

FIG. 42 graphically illustrates a representative example of a binding experiment that was performed with mouse MASP-3 in which the M3-1 Fab shows an apparent binding affinity ($EC_{50}$) of about 0.214 nM to the mouse protein.

These results demonstrate that mAb M3-1 (13B1) has a high binding affinity for both human and mouse MASP-3.

Demonstration that mAb M3-1 is Capable of Inhibiting Alternative Pathway Complement (APC) Activation and Measurement of the In Vitro Potency of mAb M3-1

As described in the present disclosure, it has been determined that MASP-3 is a key regulator of the APC, at least in part due to its requirement for the activation of CFD, a central APC enzyme. As also described in the present disclosure, MASP-3 circulates in the body at a relatively low concentration and has a slow catabolic rate, allowing for long-lasting inhibition of the pro-inflammatory pathway through intravenous, subcutaneous and oral routes of MASP-3 antibody administration. The following experiment was carried out to determine the efficacy of mAb M3-1 for inhibiting MASP-3-mediated CFD maturation and inhibition of APC in human serum. Normal human serum contains predominantly active or processed (i.e., mature) CFD, so we performed experiments in which CFD-depleted human serum (Complement Technology A336) was reconstituted with a recombinant, unprocessed form of CFD (pro-CFD). Thus, in this experimental system, APC activation requires the processing of pro-CFD into active CFD.

The APC was induced by the addition of zymosan particles, which function as an activating surface for complement deposition. Varying concentrations of mAb M3-1 were added to the serum prior to the addition of recombinant pro-CFD and zymosan. The mixtures were incubated at 37° C. for 75 minutes, and the APC activity was measured by the flow cytometric detection of complement factor Bb (Quidel A252) on the surface of the zymosan particles.

Figure 43:
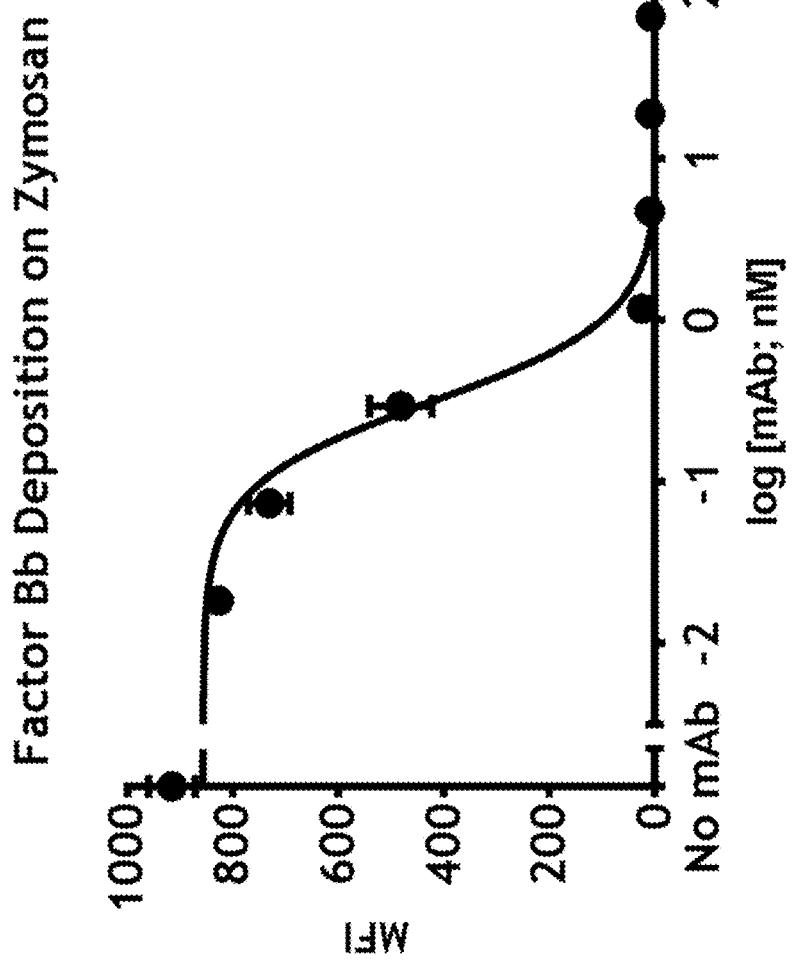
FIG. 43 graphically illustrates the level of complement factor Bb deposition on zymosan particles (determined by cytometric detection measured in MFI units) in the presence of varying concentrations of mAb M3-1 (also referred to as 13B1) in CFD-depleted human serum, as described in Example 11.

FIG. 43 graphically illustrates the level of complement factor Bb deposition on zymosan particles (determined by flow cytometric detection measured in MFI units) in the presence of varying concentrations of mAb M3-1 in CFD-depleted human serum. As shown in FIG. 43, mAb M3-1 shows potent inhibition of the APC in 10% human serum, with an $IC_{50}$ of 0.311 nM in this experimental example.

These results demonstrate that MASP-3 plays a key role in APC activation in an in vitro model in human serum, and further demonstrate that mAb M3-1 is a potent inhibitor of the APC.

Inhibition of the APC by mAb M3-1 In Vivo:

In order to determine the efficacy of mAb M3-1 for inhibiting the APC in vivo, a group of mice (n=4) received a single intravenous tail vein injection of 10 mg/kg mAb M3-1. Blood collected from the animals was used to prepare serum, providing a matrix for the flow cytometric assessment of APC activity in an ex vivo assay measuring the level of C3 (also C3b and iC3b) deposition on zymosan particles. Serum prepared from blood harvested at a pre-dose timepoint and multiple post-dose time points (96 hrs, 1 week, and 2 weeks) was diluted to 7.5% and zymosan particles were added to induce the APC. Antibody-treated mice were compared to a group of control mice (n=4) that were given a single intravenous dose of vehicle.

Figure 44:
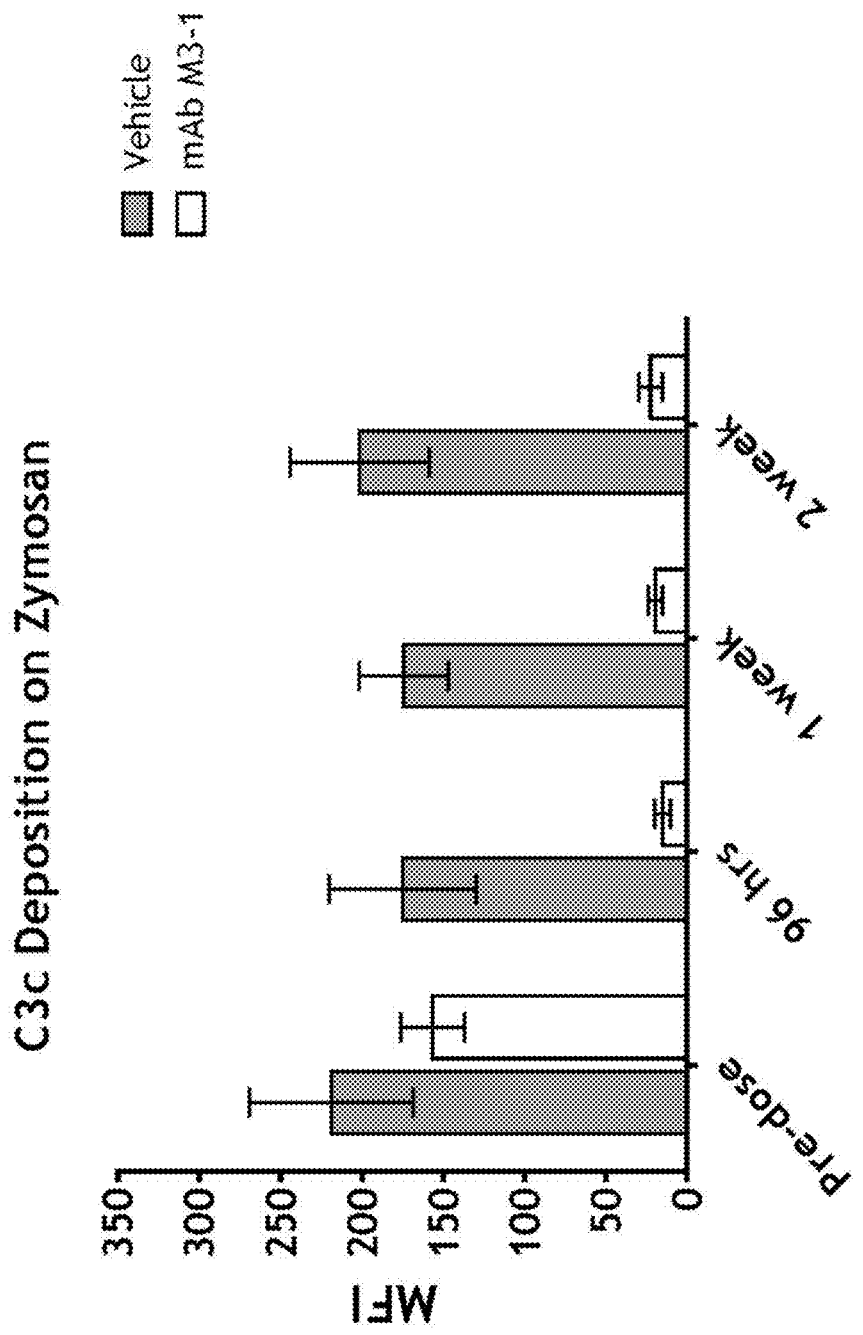
FIG. 44 graphically illustrates the level of C3 deposition on zymosan particles at various time points after a single dose of mAb M3-1 (13B1) (10 mg/kg i.v.) in wild-type mice, as described in Example 11.

FIG. 44 graphically illustrates the level of C3 deposition on zymosan particles at various time points after a single dose of mAb M3-1 (10 mg/kg i.v.) in wild-type mice. As shown in FIG. 44, in the pre-dose time point the two conditions show comparable levels of APC activity. At 96 hours and the two later time points, the mAb M3-1 treated group shows essentially complete APC inhibition, while the APC activity of the vehicle-treated group remains unabated. As shown in FIG. 44, a single dose of mAb M3-1 administered intravenously to mice led to near-complete ablation of systemic APC activity for at least 14 days.

These results demonstrate that mAb M3-1 is a potent inhibitor of the APC in vivo in a mouse model.

Example 12

This Example demonstrates that chimeric mouse V region/human IgG4 constant region anti-human MASP-3 monoclonal antibody (mAb M3-1, also referred to as mAb 13B1) provides a clear benefit to survival of red blood cells lacking Crry in a mouse model associated with paroxysmal nocturnal hemoglobinuria (PNH).

Methods:

The chimeric mouse V region/human IgG4 constant region anti-human MASP-3 monoclonal antibody (mAb M3-1) was generated as described in Example 11 and Example 14. As further described in Example 11, it was determined that mAb M3-1 is a potent inhibitor of the APC in a mouse model in vivo. This Example describes the analysis of mAb M3-1 for efficacy in a murine model associated with PNH.

Analysis of mAb M3-1 for Efficacy in a Murine Model Associated with PNH

In a mouse model associated with PNH, red blood cells (RBCs) from Crry-deficient mice lacking the major cell surface repressor of the APC in mouse were obtained for use as donor cells. RBCs obtained from a wild-type (WT) donor mouse were run in parallel. These donor RBCs were differentially labeled with fluorescent lipophilic dyes (Sigma): WT (red), and Crry– (green). In two different experiments, the labelled WT and Crry– donor cells were mixed 1:1 and injected intravenously into wild-type recipient mice and percent WT and Crry-deficient RBC survival (relative to the early time point) in the recipient mice were determined by flow cytometric assessment of 20,000 live cell events. In the first experiment, multiple pre-dose treatments of mAb M3-1 antibody were given, and the effect of the mAb M3-1 was compared to that of another inhibitory complement antibody mAb BB5.1 (available from Hycult Biotech), which is a C5 inhibitory antibody that has shown efficacy in multiple mouse studies (Wang et al., PNAS vol 92:8955-8959, 1995; Hugen et al., Kidney Int 71(7):646-54, 2007). Administration of a C5 inhibitor is the current standard of treatment for human patients with PNH. In the second experiment, a single pre-treatment dose of mAb M3-1 was evaluated.

In the first experiment, three different groups of mice (n=4 per condition) were assessed: vehicle-treated condition, mAb M3-1-treated condition, and mAb BB5.1 (mAb blocking mouse C5)-treated condition. Labeled cells were injected into mice on "day 0", and multiple doses of both M3-1 and BB5.1 were administered as follows: mAb M3-1 was administered intravenously (10 mg/kg) on days –11, –4, –1, and +6. The mAb BB5.1 was administered by intraperitoneal injection (40 mg/kg) on days –1, +3, +6, and +10. The vehicle treatment followed the same dosing schedule as mAb M3-1.

Figure 45:
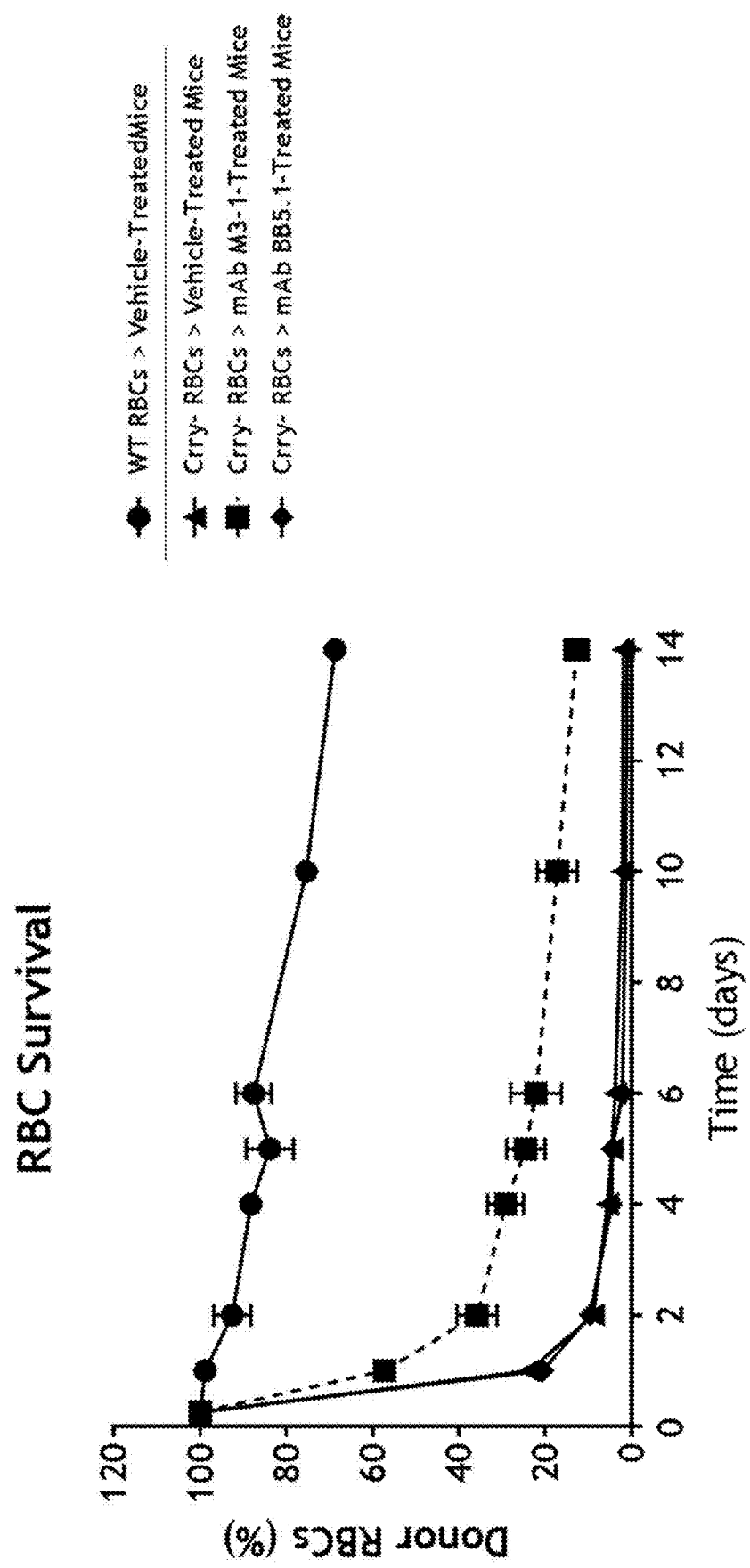
FIG. 45 graphically illustrates the percent survival of donor RBCs (WT or Crry−) over a period of 14 days in wild-type recipient mice treated with mAb M3-1 (13B1) (10 mg/kg on days −11, 04, −1 and +6), mAb BB5.1 treated, or vehicle treated mice, as described in Example 12.

FIG. 45 graphically illustrates the percent survival of donor RBCs (WT or Crry–) over a period of 14 days in WT recipient mice treated with mAb M3-1 (10 mg/kg on days –11, 04, –1 and +6), mAb BB5.1 treated, or vehicle treated mice. As shown in FIG. 45, compared to WT RBCs that showed survival typical of RBCs in mice in the vehicle-treated animals, Crry-deficient RBCs had rapid clearance (more than 75% cleared within 24 hours). Treatment of mice with mAb BB5.1 provided no improvement over vehicle treatment in Crry-deficient RBC survival. In contrast, mAb M3-1 treatment caused a dramatic improvement of Crry-deficient RBC survival over both mAb BB5.1 and vehicle-treated animals. The protective effect of mAb M3-1 was observed throughout the duration of the experiment.

In the second study, differentially labeled WT (red)– and Crry– (green) RBCs were evaluated in two different groups of WT mice (n=4 per condition): vehicle-treated and mAb M3-1-treated. A single dose of either vehicle or antibody (20 mg/kg) was given to the recipient mice by intravenous administration six days (day –6) before the labeled donor cells were injected into the recipient mice. The labeled donor RBCs were then analyzed for percent survival in the recipient mice at incremental time points after injection over a 16-day period.

Figure 46:
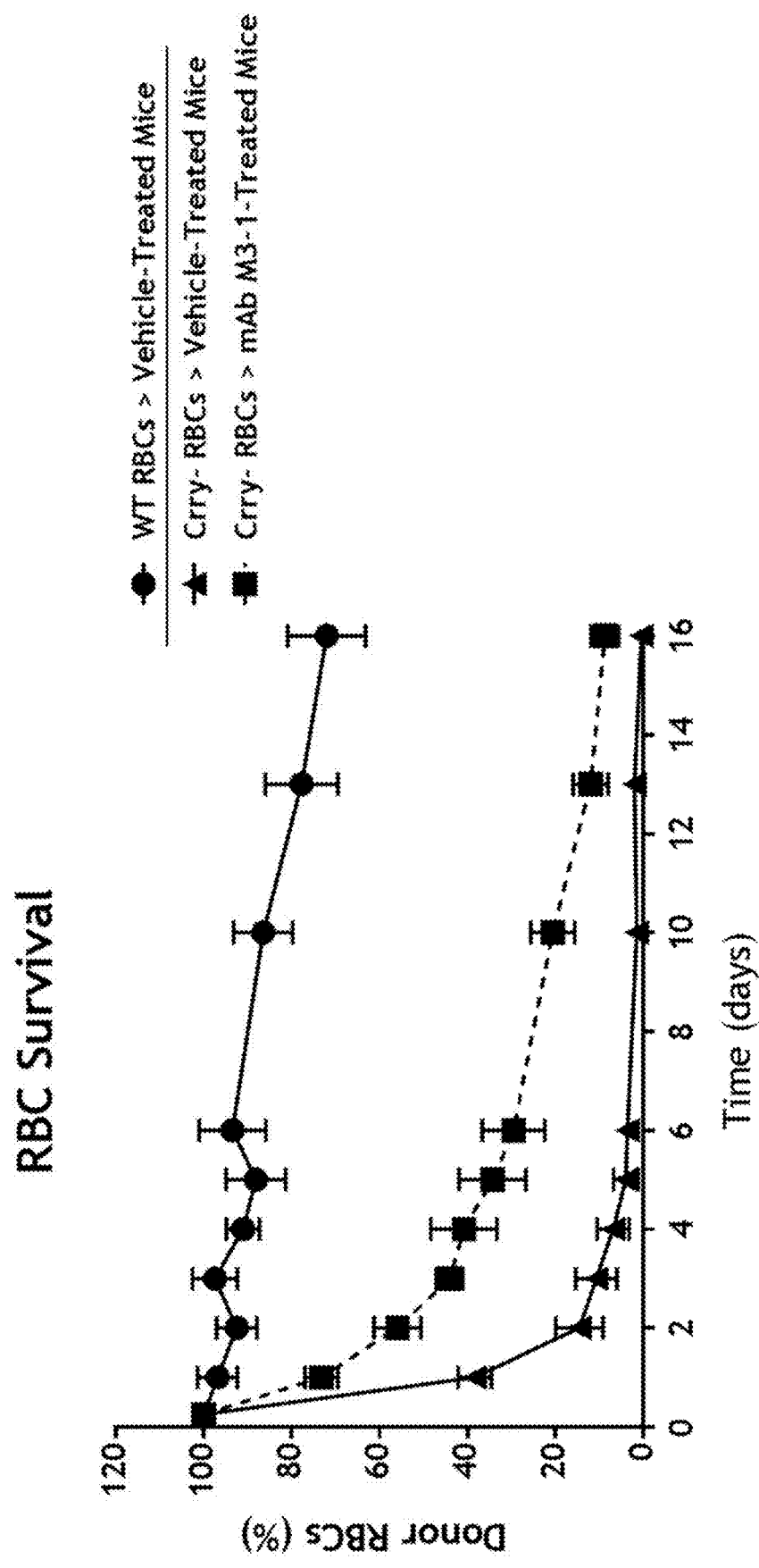
FIG. 46 graphically illustrates the percent survival of donor RBCs (WT or Crry−) over a period of 16 days in wild-type recipient mice treated with a single dose of mAb M3-1 (13B1) (20 mg/kg on day −6) or vehicle treated mice, as described in Example 12.

FIG. 46 graphically illustrates the percent survival of donor RBCs (WT or Crry–) over a period of 16 days in WT recipient mice treated with a single dose of mAb M3-1 (20 mg/kg on day –6) or vehicle-treated mice. As shown in FIG. 46, a single pre-treatment dose of mAb M3-1 demonstrated improved survival of Crry– RBCs as compared to the survival of Crry– RBCs in vehicle-treated mice. At 96 hours post injection, approximately 90% of the vehicle-treated WT RBCs survived under the control conditions, whereas only 5% of the Crry– RBCs survived in the vehicle-treated WT mice. In contrast to the vehicle-treated mice, 40% of the Crry– RBCs survived in the mice treated with mAb M3-1.

Taken together, these results demonstrate that the MASP-3 inhibitory antibody mAb M3-1 provides a clear benefit to survival of RBCs lacking Crry, a key surface complement inhibitor in a mouse model associated with PNH.

Example 13

This Example describes a study demonstrating that a chimeric MASP-3 inhibitory monoclonal antibody (mAb M3-1, also referred to as mAb 13B1) reduces clinical scores in collagen antibody-induced arthritis (CAIA), a murine model of rheumatoid arthritis (RA).

Background/Rationale:

CAIA is a well-established animal model of arthritis. In additional to providing insight into RA, the pathology of the CAIA model has an established connection with the APC. Banda and coworkers have demonstrated improved outcomes in the CAIA model in mice carrying deficiencies in components of the APC, such as factor B and factor D (Banda et al., J. Immunol vol 177:1904-1912, 2006 and Banda et al., Clinical & Exp Imunol vol 159:100-108, 2009). APC mouse knock-outs demonstrate lower arthritis (disease) scores, lower incidence, and less C3 and factor H deposition in synovium and surrounding tissues relative to WT controls. Additionally, disease activity scores, complement C3 tissue deposition in the joint, and histopathologic injury scores were markedly decreased in MASP1/3 knock-out mice (Banda et al., J Immunol vol 185:5598-5606, 2010). Therefore, the MASP-3 inhibitory antibody mAb M3-1 was analyzed for efficacy in the CAIA.

Methods:

The chimeric MASP-3 monoclonal antibody (mAb M3-1) was generated as described in Example 11 and Example 14. As further described in Example 11, it was determined that mAb M3-1 is a potent inhibitor of the APC in a mouse model in vivo.

mAb M3-1 was tested in the CAIA model as follows. Wild-type mice (n=7) were injected intravenously with 3 mg of a cocktail of anti-collagen antibodies on day 0. The mice were dosed intraperitoneally with E. coli lipopolysaccharide (LPS) (25 µg/mouse) on day +3. As described in Nandakumar et al. (Am J Pathol 163(5):1827-1837, 2003), arthritis typically occurs in this model on days +3 through +10. Terminal serum samples were collected on day +14. mAb M3-1 (5 mg/kg and 20 mg/kg) was dosed on days –12, –5, +1 and day +7. Vehicle (PBS) was injected as a negative control.

Clinical scores were evaluated for each mouse on all 4 paws on study days 0 through 14 using the following scoring standards:

0=normal

1=1 hind and/or fore paw joint affected or minimal diffuse erythema and swelling 2=2 hind and/or fore paw joints affected or mild diffuse erythema and swelling 3=3 hind and/or fore paw joints affected or moderate diffuse erythema and swelling 4=marked diffuse erythema and swelling, or 4 digit joints affected 5=severe diffuse erythema and severe swelling of entire paw, unable to flex digits.

The incidence=% mice within a treatment group showing arthritic symptoms was also determined.

Figure 47:
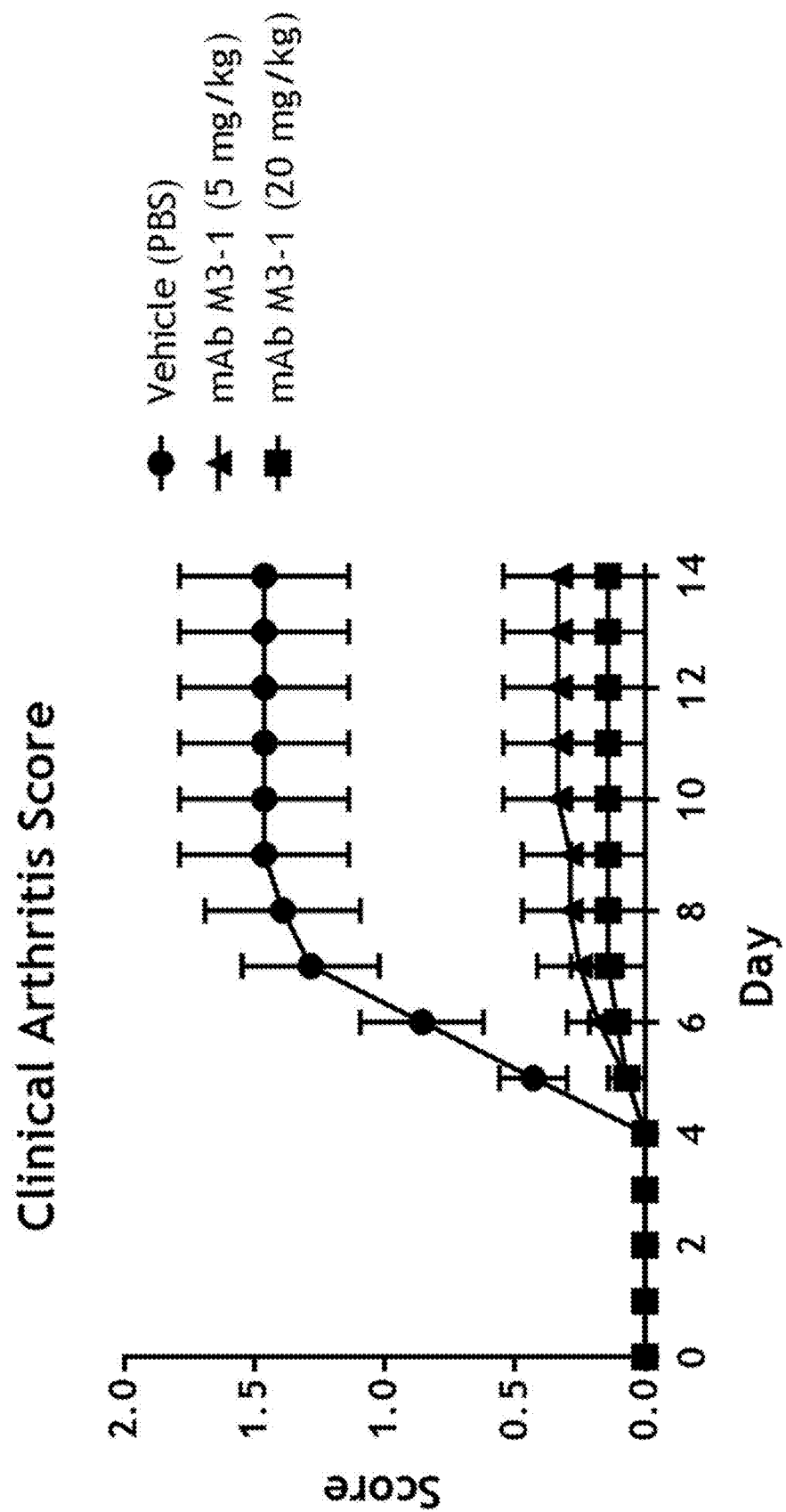
FIG. 47 graphically illustrates the clinical scores of the mice treated with mAb M3-1 (13B1) (5 mg/kg or 20 mg/kg) or vehicle treated mice over a 14 day time course in a collagen-antibody induced arthritis model, as described in Example 13.
Figure 48:
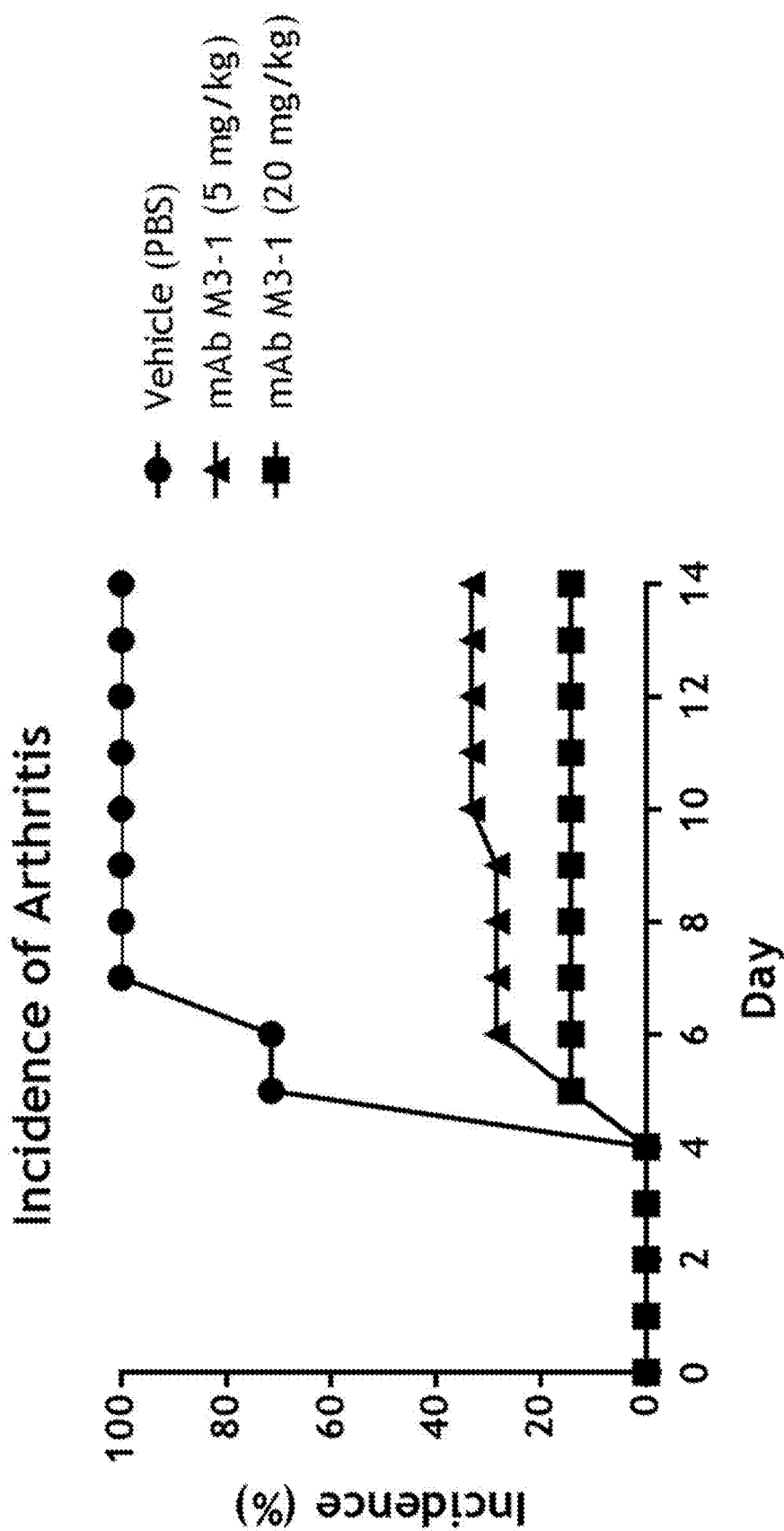
FIG. 48 graphically illustrates the percent incidence of arthritis of the mice treated with mAb M3-1 (13B1) (5 mg/kg or 20 mg/kg) or vehicle treated mice over a 14 day time course in a collagen-antibody induced arthritis model, as described in Example 13.

The results are shown in FIG. 47 (clinical scores) and FIG. 48 (incidence of arthritis). FIG. 47 graphically illustrates the clinical scores of the mice treated with mAb M3-1 (5 mg/kg or 20 mg/kg) or vehicle over a 14-day time course. FIG. 48 graphically illustrates the percent incidence of arthritis of the mice treated with mAb M3-1 (5 mg/kg or 20 mg/kg) or vehicle over a 14-day time course. As shown in FIG. 47, mAb M3-1 demonstrates a clear therapeutic benefit for both endpoints starting at day 5 and lasting throughout the duration of the study. As shown in FIG. 48, while the incidence of disease reached 100% in the vehicle-treated animals, two-thirds of the animals in the 5 mg/kg mAb M3-1 condition remained disease-free. Additionally, only one of the animals (i.e., only one in a total n=7) demonstrated any arthritic symptoms in the 20 mg/kg mAb M3-1 condition.

The results of this study demonstrate that the MASP-3 inhibitory antibody mAb M3-1 provides a clear therapeutic benefit in the CAIA model, a well-established murine model of rheumatoid arthritis (RA) and a model strongly linked to APC activation. As shown in Example 11, a single dose of mAb M3-1 administered intravenously to mice led to near-complete ablation of systemic APC activity for at least 14 days. As shown in this Example, in the animal model induced by administration of auto-antibodies against mouse connective tissue, mAb M3-1 reduced the incidence and severity of clinical arthritis scores in a dose-dependent fashion. Compared to control-treated animals, mAb M3-1 reduced the incidence and severity of the disease by approximately 80% at the highest dose tested. Therefore, it is expected that administration of a MASP-3 inhibitory antibody, such as mAb M3-1 will be an effective therapy in patients suffering from arthritis, such as rheumatoid arthritis, osteoarthritis, juvenile rheumatoid arthritis, infection-related arthritis, psoriatic arthritis, as well as ankylosing spondylitis and Bechcet's disease.

Example 14

This Example describes the generation of high affinity anti-human MASP-3 inhibitory antibodies.

Background/Rationale:

A limited number of antibodies specific for MASP-3 have been described (Thiel et al., *Mol. Immunol.* 43:122, 2006; Moller-Kristensen et al., *Int. Immunol.* 19:141, 2006; Skjoedt et al., *Immunobiol* 215:921, 2010). These antibodies were useful for detection assays such as Western blotting, immunoprecipitation, and as capture or detection reagents in ELISA assays. However, the antibodies described in Thiel et al., 2006, Moller-Kristensen et al., 2006 and Skjoedt et al., 2010 have not been found to inhibit MASP-3 catalytic activity.

MASP-3 antibodies were also generated previously, as described in Example 7 herein (also published as Example 15 in WO2013/192240) by screening a chicken antibody library in a modified DT40 cell line, DTLacO, for MASP-3 binding molecules. These antibodies bound to human MASP-3 in the nanomolar range with an $EC_{50}$ between 10 nM and 100 nM and partially inhibited cleavage of pro-CFD by MASP-3.

This Example describes the generation of anti-human MASP-3 inhibitory antibodies with unusually strong binding affinity (i.e., subnanomolar binding affinity, ranging from ≤500 pM to 20 pM). The antibodies described in this Example specifically bind to human MASP-3 with high affinity (e.g., ≤500 pM), inhibit Factor D maturation, and do not bind to human MASP-1 (SEQ ID NO:8).

Methods:

1. Generation of Chimeric Mouse V Region/Human IgG Constant Region Anti-Human MASP-3 Monoclonal Antibodies Seven to fourteen-week old C57BL/6, MASP-1/3 knock-out mice were immunized with either the human MASP-3 CCP1/CCP2/SP polypeptide (amino acid residues 299-728 of SEQ ID NO:2) including a StrepTag II epitope tag on the N-terminus; or were immunized with the human MASP-3 SP domain (amino acid residues 450-728 of SEQ ID NO:2), including StrepTagII on the N-terminus, using the Sigma Adjuvant System (Sigma-Aldrich, St Louis, Mo.). The mice were injected intraperitoneally with 50 µg of immunogen per mouse. The immunized mice were boosted 14 days later with additional immunogen in adjuvant. Thereafter, for several weeks, the mice were boosted every 14 to 21 days with immunogen in PBS. Serum samples from the mice were periodically prepared from tail bleeds and tested by ELISA for the presence of antigen-specific antibodies. Mice with a significant antibody titer received a pre-fusion immunogen boost in PBS four days prior to splenic fusion. Three days prior to the fusion, the mice were treated subcutaneously at the base of the tail with 50 µg of a anti-CD40 agonist mAb in PBS (R&D Systems, Minneapolis, Minn.) to increase B cells numbers (see Rycyzyn et al., *Hybridoma* 27:25-30, 2008). The mice were sacrificed and the spleen cells were harvested and fused to a selected murine myeloma cell line P3/NSI/1-AG4-1 (NS-1) (ATCC No. TIB18) using 50% polyethylene glycol or 50% polyethylene glycol plus 10% DMSO. The fusions generated hybridoma cells which were plated in 96 well tissue culture plates containing HAT (hypoxanthine, aminopterin and thymidine) medium to inhibit proliferation of non-fused cells, myeloma hybrids and spleen hybrids. After hybridoma selection, the culture supernatants were assayed for MASP-3 binding (ELISA) and inhibition of pro-Factor D activation. The positive hybridomas were identified and subcloned by serial dilution methods.

TABLE 17

Summary of Fusion Experiments

| Fusion | Immunogen: Human MASP-3 | Total hybridomas | MASP-3 Binding hybridomas | MASP-3 Functional hybridomas |
|---|---|---|---|---|
| 1 | SP | 434 | 38 | 10 |
| 2 | SP | 279 | 13 | 0 |
| 3 | CCP1/CCP2/SP | 348 | 40 | 2 |
| 4 | CCP1/CCP2/SP | 319 | 60 | 2 |

TABLE 17-continued

Summary of Fusion Experiments

| Fusion | Immunogen: Human MASP-3 | Total hybridomas | MASP-3 Binding hybridomas | MASP-3 Functional hybridomas |
|---|---|---|---|---|
| 5 | CCP1/CCP2/SP | 651 | 152 | 1 |
| 6 | CCP1/CCP2/SP | 1297 | ND | 1 |

Note:
"ND" means this fusion was only screened for functional inhibition of pro-CFD activation.

Results:
As shown in TABLE 17, a total of 3328 hybridomas from immunized MASP1/3 KO mice were screened, of which >303 were found to bind to MASP-3 and of which 16 were found to bind to MASP-3 and to inhibit pro-CFD activation. mAb M3-1 (13B1) described in Example 11 is one of the 16 functional MASP-3 inhibitory antibodies described in TABLE 17. As described in Example 15, it was determined that all 16 functional MASP-3 inhibitory antibodies bind to human MASP-3 with unusually strong binding affinity (≤500 pM).

Discussion:
This Example describes the generation of antibodies that inhibit human MASP-3 with unusually strong binding affinity (i.e., subnanomolar binding affinity, ranging from ≤500 pM to 20 pM) by immunizing MASP1/3 knockout mice. The antibodies described in this Example specifically bind to human MASP-3 with high affinity (e.g., ≤500 pM), inhibit Factor D maturation, and do not bind to human MASP-1. As described herein, the amino acid sequences of human, mouse and chicken MASP-3 revealed that the SP domain of MASP-3 is highly conserved, especially in the active site (see FIGS. 4 and 5). It is likely that the ability to generate MASP-3 inhibitory antibodies with unusually strong binding affinity in MASP1/3 KO mice, as described in this example, is due in part to avoidance of immunological tolerance that may hamper the generation of highly potent MASP-3 catalytic site-specific antibodies in wild-type animals.

Example 15

This Example describes the cloning and sequence analysis of high affinity anti-human MASP-3 inhibitory mAbs.

Methods:
Cloning and Purification of Recombinant Antibodies:
The heavy chain and light chain variable regions were cloned from the hybridomas described in Examples 11 and 14 using RT-PCR and were sequenced. Mouse-human chimeric mAbs consisting of the mouse mAb variable regions fused to the human IgG4 heavy chain (SEQ ID NO:311) and kappa light chain (SEQ ID NO:313) constant regions were produced as recombinant proteins in Expi293F cells. The IgG4 constant hinge region (SEQ ID NO:311) contains the stabilizing S228P amino acid substitution. In one embodiment, the chimeric mAbs were fused to the human IgG4 constant hinge region (SEQ ID NO:312) which contains the S228P amino acid substitution and also a mutation that promotes FcRn interations at low pH.
The sequences of the heavy chain variable regions and light chain variable regions are shown in FIGS. 49A and 49B, respectively ("SIN"="SEQ ID NO:" in FIG. 49A and FIG. 49B), and are included below. The complementarity regions (CDRs) and framework regions (FRs) of each are provided in TABLES 18-22 below.

Figure 50A:
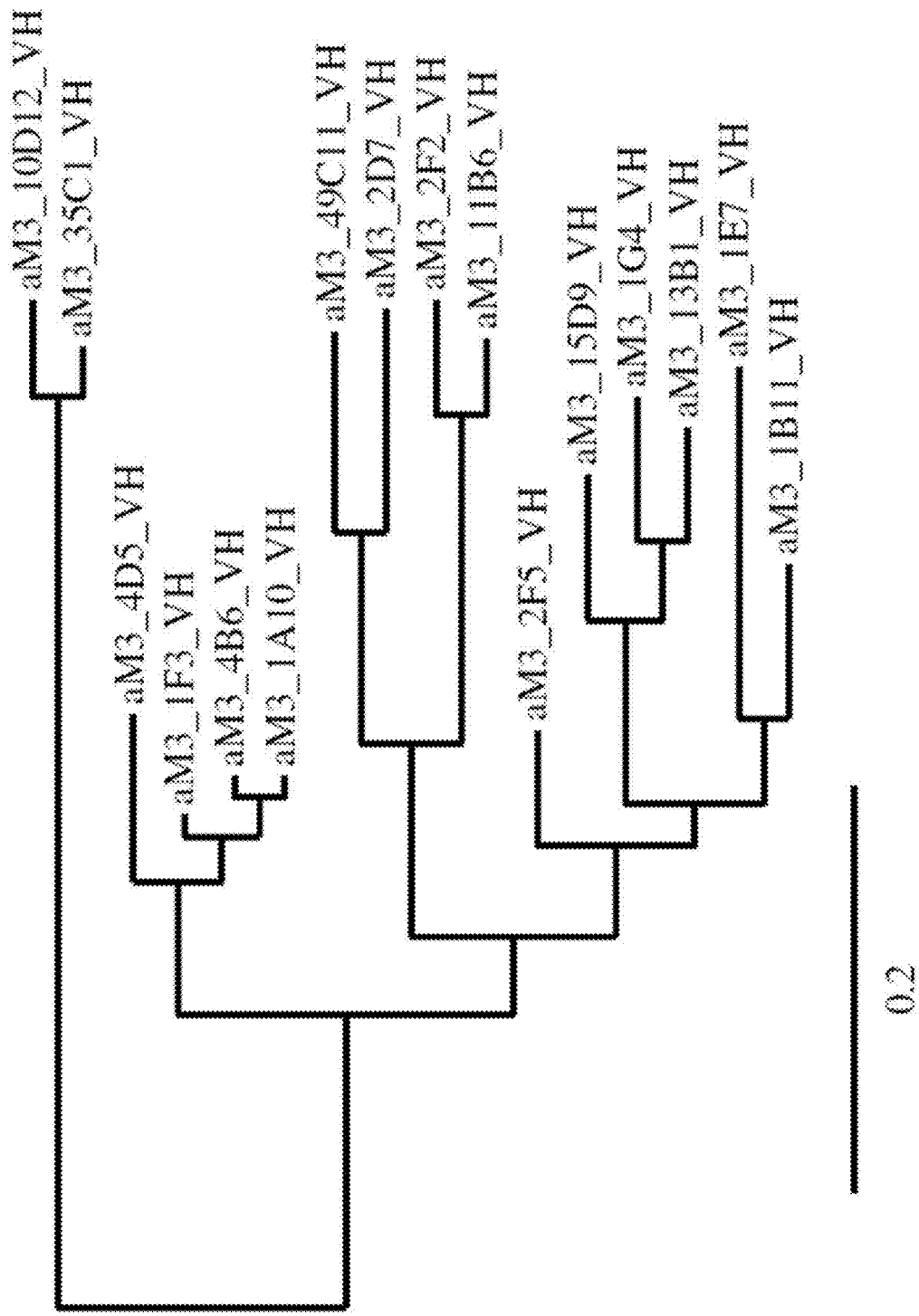
FIG. 50A is a dendrogram of the VH regions of high affinity anti-human MASP-3 inhibitory mAbs, as described in Example 15.
Figure 50B:
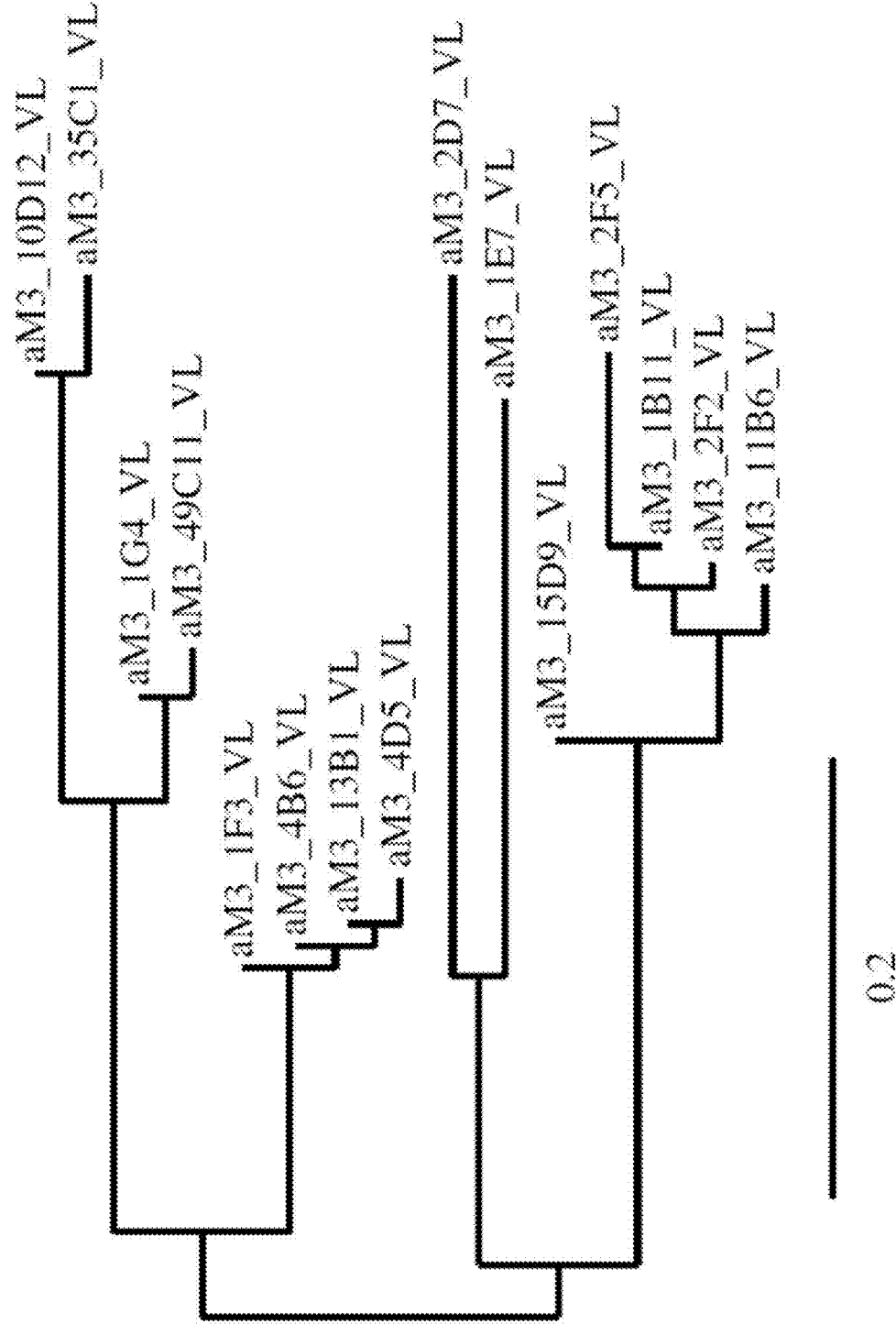
FIG. 50B is a dendrogram of the VL regions of high affinity anti-human MASP-3 inhibitory mAbs, as described in Example 15.

FIG. 50A is a dendrogram of the VH regions of high affinity anti-human MASP-3 inhibitory mAbs generated in MASP1/3 KO mice. FIG. 50B is a dendrogram of the VL regions of high affinity anti-human MASP-3 inhibitory mAbs generated in MASP1/3 KO mice. As shown in FIGS. 50A and 50B, several groups of related antibodies were identified.

Presented below is the heavy chain variable region (VH) sequence for each high affinity MASP-3 inhibitory antibody. The Kabat CDRs are underlined.

Heavy Chain Variable Regions:

4D5_VH:
SEQ ID NO: 24
QVQLKQSGPELVKPGASVKLSCKASGYTFT<u>TDDIN</u>WVKQRPGQGLEWIG<u>WI

YPRDDRTKYNDKFKD</u>KATLTVDTSSNTAYMDLHSLTSEDSAVYFCSS<u>LEDT

YW</u>GQGTLVAVSS

1F3_VH:
SEQ ID NO: 25
QVQLKQSGPELVKPGASVKLSCKASGYTFT<u>SNDIN</u>WVKQRPGQGLEWIG<u>WI

YPRDGSIKYNEKFTD</u>KATLTVDVSSSTAYMELHSLTSEDSAVYFCSG<u>VEDS

YW</u>GQGTLVTVSS

4B6_VH:
SEQ ID NO: 26
QVQLKQSGPELVKPGASVKLSCKASGYTFT<u>SNDIN</u>WVKQRPGQGLEWIG<u>WI

YPRDGTTKYNEEFTD</u>KATLTVDVSSSTAFMELHSLTSEDSAVYFCSS<u>VEDS

YW</u>GQGTLVTVSS

1A10_VH:
SEQ ID NO: 27
QVQLKQSGPELVKPGASVKLSCKASGYTFT<u>SNDIN</u>WVKQRPGQGLEWIG<u>WI

YPRDGTTKYNEKFTD</u>KATLTVDVSSSTAFMELHRLTSEDSAVYFCSS<u>VEDS

YW</u>GQGTLVTVSS

10D12_VH:
SEQ ID NO: 28
QIQLVQSGPELKKPGETVKISCKASGYIFT<u>SYGMS</u>WVRQAPGKGLKWMG<u>WI

NTYSGVPTYADDFKGR</u>FAFSLETSARTPYLQINNLKNEDTATYFCAR<u>GGEA

MDY</u>WGQGTSVTVSS

35C1_VH:
SEQ ID NO:29
QIQLVQSGPELKTPGETVKISCKASGYIFT<u>SYGIT</u>WVKQAPGKGLKWMG<u>WI

NTYSGVPTYADDFKGR</u>FAFSLETSASTAYLQINNLKNEDTTTYFCT<u>RGGDA

LDY</u>WGQGTSVTVSS

13B1_VH:
SEQ ID NO: 30
QVQLKQSGAELMKPGASVKLSCKATGYTFT<u>GKWIE</u>WVKQRPGHGLEWIG<u>EI

LPGTGSTNYNEKFKG</u>KATFTADSSSNTAYMQLSSLTTEDSAMYYCLR<u>SEDV

W</u>GTGTTVTVSS

1G4_VH:
SEQ ID NO: 31
QVQLKQSGAELMKPGASVKLACKATGYTFT<u>GYWIE</u>WIKQRPGQGLEWIG<u>EM

LPGSGSTHYNEKFKG</u>KATFTADTSSNTAYMQLSGLTTEDSAIYYCVR<u>SIDY

W</u>GQGTTLTVSS

-continued

1E7_VH:
SEQ ID NO: 32
QVQLKQSGPELARPWASVKISCQAFYTFSR RVHFAIRDTNYWMQ WVKQRPG

QGLEWIG AIYPNGDTSYNQKFKG KATLTADKSSTAYMQLSSLTSEDSAV

YYCAS GSHYFDY WGQGTTLTVSS

2D7_VH:
SEQ ID NO: 33
EVQLQQSGPELVKPGASVKVSCKASGYTLT DYYMN WVKQSHGKSLEWIG DV

NPNNDGTTYNQKFKG RATLTVDKSSNTASMELRSLTSEDSAVYYCAI CPFY

YLGKGTHFDY WGQGTSLTVSS

49C11_VH:
SEQ ID NO: 34
EVQLQQSGPVLVKPGASGKMSCKASGYKFT DYYMI WVKQSHGKSLEWIG VI

KIYNGGTSYNQKFKG KATLTVDKSSSTAYMELNSLTSEDSAVYYCAR GPSL

YDYDPYWYFDV WGTGTTVTVSS

15D9_VH:
SEQ ID NO: 35
QVQLKQSGTELMKPGASVNLSCKASGYTFT AYWIE WVKQRPGHGLEWIG EI

LPGSGTTNYNENFKD RATFTADTSSNTAYMQLSSLTSEDSAIYYCAR SYYY

ASRWFAF WGQGTLVTVSS

2F5_VH:
SEQ ID NO: 36
EVQLQQPGAELVKPGASVKMSCKASGYTFT SYWIT WVKQRPGQGLEWIG DI

YPGSGSTNYNEKFKS KATLTVDTSSSTAYMQLSSLTSEDSAVYYCAR RRYY

ATAWFAY WGQGTLVTVSS

1B11_VH:
SEQ ID NO: 37
QVQLKQSGAELVRPGASVKLSCKASGYTFT DYYIN WVKQRPGQGLEWIA RI

YPGSGNTYYNEKFKG KATLTAEKSSSTAYMQLSSLTSEDSAVYFCAR NYYI

SSPWFAY WGQGTLVTVSS

2F2_VH:
SEQ ID NO: 38
QVQLKQSGAELVTPGASVKMSCKASGYTFT TYPIE WMKQNHGKSLEWIG NF

HPYNDDTKYNEKFKG KATLTVEKSSNTVYLELSRLTSDDSAVYFCAR RVYY

SYFWFGY WGHGTLVTVSS

11B6_VH:
SEQ ID NO: 39
QVQLKQSGAELVKPGASVKMSCKASGYTFT TYPIE WMKQNHGKSLEWIG NF

HPYNGDSKYNEKFKG KATLTVEKSSSTVYLELSRLPSADSAIYYCAR RHYA

ASPWFAH WGQGTLVTVSS

TABLE 18

MASP-3 Antibody VH Sequences (CDRs and FR regions, Kabat)

| Antibody | HC FR1 | HC CDR1 |
|---|---|---|
| 4D5 | QVQLKQSGPELVKPGASVKLSCKASGYTFT (SEQ ID NO: 55) | TDDIN (SEQ ID NO: 56) |
| 1F3 | QVQLKQSGPELVKPGASVKLSCKASGYTFT (SEQ ID NO: 55) | SNDIN (SEQ ID NO: 62) |
| 4B6 | QVQLKQSGPELVKPGASVKLSCKASGYTFT (SEQ ID NO: 55) | SNDIN (SEQ ID NO: 62) |
| 1A10 | QVQLKQSGPELVKPGASVKLSCKASGYTFT (SEQ ID NO: 55) | SNDIN (SEQ ID NO: 62) |
| 10D12 | QIQLVQSGPELKKPGETVKISCKASGYIFT (SEQ ID NO: 71) | SYGMS (SEQ ID NO: 72) |
| 35C1 | QIQLVQSGPELKTPGETVKISCKASGYIFT (SEQ ID NO: 78) | SYGIT (SEQ ID NO: 79) |
| 13B1 | QVQLKQSGAELMKPGASVKLSCKATGYTFT (SEQ ID NO: 83) | GKWIE (SEQ ID NO: 84) |
| 1G4 | QVQLKQSGAELMKPGASVKLACKATGYTFT (SEQ ID NO: 90) | GYWIE (SEQ ID NO: 91) |
| 2F5 | EVQLQQPGAELVKPGASVKMSCKASGYTFT (SEQ ID NO: 97) | SYWIT (SEQ ID NO: 98) |
| 1B11 | QVQLKQSGAELVRPGASVKLSCKASGYTFT (SEQ ID NO: 102) | DYYIN (SEQ ID NO: 103) |
| 1E7 | QVQLKQSGPELARPWASVKISCQAFYTFSR (SEQ ID NO: 108) | RVHFAIRDTNYWMQ (SEQ ID NO: 109) |
| 2F2 | QVQLKQSGAELVTPGASVKMSCKASGYTFT (SEQ ID NO: 113) | TYPIE (SEQ ID NO: 114) |
| 11B6 | QVQLKQSGAELVKPGASVKMSCKASGYTFT (SEQ ID NO: 120) | TYPIE (SEQ ID NO: 114) |

TABLE 18-continued

MASP-3 Antibody VH Sequences (CDRs and FR regions, Kabat)

| Antibody | | |
|---|---|---|
| 2D7 | EVQLQQSGPELVKPGASVKVSCKASGYTLT (SEQ ID NO: 124) | DYYMN (SEQ ID NO: 125) |
| 49C11 | EVQLQQSGPVLVKPGASGKMSCKASGYKFT (SEQ ID NO: 131) | DYYMI (SEQ ID NO: 132) |
| 15D9 | QVQLKQSGIELMKPGASVNLSCKASGYTFT (SEQ ID NO: 136) | AYWIE (SEQ ID NO: 137) |
| | HC FR2 | HC CDR2 |
| 4D5 | WVKQRPGQGLEWIG (SEQ ID NO: 57) | WIYPRDDRTKYNDKFKD (SEQ ID NO: 58) |
| 1F3 | WVKQRPGQGLEWIG (SEQ ID NO: 57) | WIYPRDGSIKYNEKFTD (SEQ ID NO: 63) |
| 4B6 | WVKQRPGQGLEWIG (SEQ ID NO: 57) | WIYPRDGTTKYNEEFTD (SEQ ID NO: 67) |
| 1A10 | WVKQRPGQGLEWIG (SEQ ID NO: 57) | WIYPRDGTTKYNEKFTD (SEQ ID NO: 69) |
| 10D12 | WVRQAPGKGLKWMG (SEQ ID NO: 73) | WINTYSGVPTYADDFKG (SEQ ID NO: 74) |
| 35C1 | WVKQAPGKGLKWMG (SEQ ID NO: 80) | WINTYSGVPTYADDFKG (SEQ ID NO: 74) |
| 13B1 | WVKQRPGHGLEWIG (SEQ ID NO: 85) | EILPGTGSTNYNEKFKG (SEQ ID NO: 86) |
| 1G4 | WIKQRPGQGLEWIG (SEQ ID NO: 92) | EMLPGSGSTHYNEKFKG (SEQ ID NO: 93) |
| 2F5 | WVKQRPGQGLEWIG (SEQ ID NO: 57) | DIYPGSGSTNYNEKFKS (SEQ ID NO: 99) |
| 1B11 | WVKQRPGQGLEWIA (SEQ ID NO: 104) | RIYPGSGNTYYNEKFKG (SEQ ID NO: 105) |
| 1E7 | WVKQRPGQGLEWIG (SEQ ID NO: 57) | AIYPGNGDTSYNQKFKG (SEQ ID NO: 110) |
| 2F2 | WMKQNHGKSLEWIG (SEQ ID NO: 115) | NFHPYNDDTKYNEKFKG (SEQ ID NO: 116) |
| 11B6 | WMKQNHGKSLEWIG (SEQ ID NO: 115) | NFHPYNGDSKYNEKFKG (SEQ ID NO: 121) |
| 2D7 | WVKQSHGKSLEWIG (SEQ ID NO: 126) | DVNPNNDGTTYNQKFKG (SEQ ID NO: 127) |
| 49C11 | WVKQSHGKSLEWIG (SEQ ID NO: 126) | VIKIYNGGTSYNQKFKG (SEQ ID NO: 133) |
| 15D9 | WVKQRPGHGLEWIG (SEQ ID NO: 85) | EILPGSGTTNYNENFKD (SEQ ID NO: 138) |
| | HC FR3 | HC CDR3 |
| 4D5 | KATLTVDTSSNTAYMDLHSLTSEDSAVYFCSS (SEQ ID NO: 59) | LEDTY (SEQ ID NO: 60) |
| 1F3 | KATLTVDVSSSTAYMELHSLTSEDSAVYFCSG (SEQ ID NO: 64) | VEDSY (SEQ ID NO: 65) |
| 4B6 | KATLTVDVSSSTAFMELHSLTSEDSAVYFCSS (SEQ ID NO: 68) | VEDSY (SEQ ID NO: 65) |
| 1A10 | KATLTVDVSSSTAFMELHRLTSEDSAVYFCSS (SEQ ID NO: 70) | VEDSY (SEQ ID NO: 65) |
| 10D12 | RFAFSLETSARTPYLQINNLKNEDTATYFCAR (SEQ ID NO: 75) | GGEAMDY (SEQ ID NO: 76) |

TABLE 18-continued

MASP-3 Antibody VH Sequences (CDRs and FR regions, Kabat)

| Antibody | | |
|---|---|---|
| 35C1 | RFAFSLETSASTAYLQINNLKNEDTTTYFCTR (SEQ ID NO: 81) | GGDALDY (SEQ ID NO: 82) |
| 13B1 | KATFTADSSSNTAYMQLSSLTTEDSAMYYCLR (SEQ ID NO: 87) | SEDV (SEQ ID NO: 88) |
| 1G4 | KATFTADTSSNTAYMQLSGLTTEDSAIYYCVR (SEQ ID NO: 94) | SIDY (SEQ ID NO: 95) |
| 2F5 | KATLTVDTSSSTAYMQLSSLTSEDSAVYYCAR (SEQ ID NO: 100) | RRYYATAWFAY (SEQ ID NO: 101) |
| 1B11 | KATLTAEKSSSTAYMQLSSLTSEDSAVYFCAR (SEQ ID NO: 106) | NYYISSPWFAY (SEQ ID NO: 107) |
| 1E7 | KATLTADKSSSTAYMQLSSLTSEDSAVYYCAS (SEQ ID NO: 111) | GSHYFDY (SEQ ID NO: 112) |
| 2F2 | KATLTVEKSSNTVYLELSRLTSDDSAVYFCAR (SEQ ID NO: 117) | RVYYSYFWFGY (SEQ ID NO: 118) |
| 11B6 | KATLTVEKSSSTVYLELSRLPSADSAIYYCAR (SEQ ID NO: 122) | RHYAASPWFAH (SEQ ID NO: 123) |
| 2D7 | RATLTVDKSSNTASMELRSLTSEDSAVYYCAI (SEQ ID NO: 128 | CPFYYLGKGTHFDY (SEQ ID NO: 129) |
| 49C11 | KATLTVDKSSSTAYMELNSLTSEDSAVYYCAR (SEQ ID NO: 134) | GPSLYDYDPYWYFDV (SEQ ID NO: 135) |
| 15D9 | RATFTADTSSNTAYMQLSSLTSEDSAIYYCAR (SEQ ID NO: 139) | SYYYASRWFAF (SEQ ID NO: 140) |
| | HC FR4 | |
| 4D5 | WGQGTLVAVSS (SEQ ID NO: 61) | |
| 1F3 | WGQGTLVTVSS (SEQ ID NO: 66) | |
| 4B6 | WGQGTLVTVSS (SEQ ID NO: 66) | |
| 1A10 | WGQGTLVTVSS (SEQ ID NO: 66) | |
| 10D12 | WGQGTSVTVSS (SEQ ID NO: 77) | |
| 35C1 | WGQGTSVTVSS (SEQ ID NO: 77) | |
| 13B1 | WGTGTTVTVSS (SEQ ID NO: 89) | |
| 1G4 | WGQGTTLTVSS (SEQ ID NO: 96) | |
| 2F5 | WGQGTLVTVSS (SEQ ID NO: 66) | |
| 1B11 | WGQGTLVTVSS (SEQ ID NO: 66) | |
| 1E7 | WGQGTTLTVSS (SEQ ID NO: 96) | |
| 2F2 | WGHGTLVTVSS (SEQ ID NO: 119) | |
| 11B6 | WGQGTLVTVSS (SEQ ID NO: 66) | |

TABLE 18-continued

MASP-3 Antibody VH Sequences (CDRs and FR regions, Kabat)

| Antibody | |
|---|---|
| 2D7 | WGQGTSLTVSS (SEQ ID NO: 130) |
| 49C11 | WGTGTTVTVSS (SEQ ID NO: 89) |
| 15D9 | WGQGTLVTVSS (SEQ ID NO: 66) |

Presented below are the light chain variable region (VL) sequences for the high affinity MASP-3 inhibitory antibodies. The Kabat CDRs are underlined. These regions are the same whether numbered by the Kabat or Chothia system.

Light Chain Variable Regions:

4D5_VL:
SEQ ID NO: 40
DIVMTQSPSSLAVSAGEKVTMTC<u>KSSQSLLNSRTRKNYLA</u>WYQQKPGQSPK
LLIY<u>WASTRES</u>GVPDRFTGSGSGTDFSLTISSVQAEDLAVYYC<u>KQSYNLYT</u>
FGGGTKLEIKR

1F3_VL:
SEQ ID NO: 41
DIVMTQSPSSLAVSAGERVTMSC<u>KSSQSLLISRTRKNYLS</u>WYQQKPGQSPK
LLIY<u>WASTRES</u>GVPDRFTGSGSGTDFTLTISSVQAEDLAVYYC<u>KQSYNLYT</u>
FGGGTKLEIKR

4B6_VL: (SAME for 1A10_VL)
SEQ ID NO: 42
DIVMTQSPSSLAVSAGEKVTMSC<u>KSSQSLLISRTRKNYLS</u>WYQQKPGQSPK
LLIY<u>WASTRES</u>GVPDRFTGSGSGTDFTLTISSVQAEDLAVYYC<u>KQSYNLYT</u>
FGGGTKLEIKR 10D12_VL:
SEQ ID NO: 43
DVLMTQTPLTLSVTIGQPASISC<u>KSSQSLLDSDGKTYLN</u>WLLQRPGQSPKR
LIY<u>LVSKLDS</u>GVPDRFTGSGSGTDFTLKISRVEAEDLGVYYC<u>WQGTHFPWT</u>
FGGGTKLEIKR 35C1_VL:
SEQ ID NO: 44
DIVMTQAPLTLSVTIGQPASISC<u>KSSQSLLDSDGKTYLS</u>WLLQRPGQSPKR
LIY<u>LVSKLDS</u>GVPDRFTGSGSGTDFTLKISRVEAEDLGVYYC<u>WQGTHFPYT</u>
FGGGTKLEIKR 13B1_VL:
SEQ ID NO: 45
DIVMTQSPSSLAVSAGEKVTMSC<u>KSSQSLLNSRTRKNYLA</u>WYQQKPGQSPK
LLIY<u>WASTRES</u>GVPDRFTGSGSGTDFTLTISSVQAEDLAVYYC<u>KQSYNIPT</u>
FGGGTKLEIKR 1G4_VL:
SEQ ID NO: 46
DVLMTQTPLSLPVSLGEQASISC<u>RSSQSLVQSNGNTYLH</u>WYLQKPGQSPKL
LIY<u>KVSNRFS</u>GVPDRFSGSGSGTDFTLKISRVEAEDLGVYFC<u>SQSTHVPPT</u>
FGGGTKLEIKR 1E7_VL:
SEQ ID NO: 47
DIQLTQSPAILSVSPGERVSFSC<u>RASQSIGTSIH</u>WYQQRTNGSPRLLIK<u>YA
SESIS</u>GIPSRFSGSGSGTDFTLSINSVESEDIADYYC<u>QQSNSWPYT</u>FGGGT
KLEIKR 2D7_VL:
SEQ ID NO: 48
DIQMTQTPASLSASLGDRVTISC<u>RASQDISNFLN</u>WYQQKPNGTVKLLVF<u>YT
SRLHS</u>GVPSRFSGSGSGAEHSLTISNLEQEDVATYFC<u>QQGFTLPWT</u>FGGGT
KVEIKR 49C11_VL:
SEQ ID NO: 49
DVLMTQTPLSLPVSLGDQASFSC<u>RSSQSLIHSNGNTYLH</u>WYLQKPGQSPKL
LIY<u>KVSNRFS</u>GVPDRFSGSGSGTDFTLKISRVEAEDLGVYFC<u>SQSTHVPWT</u>
FGGGTKLEIKR 15D9_VL:
SEQ ID NO: 50
DIVMTQSQKFMSTSIGDRVSVTC<u>RASQNVGPNLA</u>WYQQKPGQSPKALIY<u>SA
SYRFS</u>GVPDRFTGSGSGTDFTLTISNVQSEDLAEYFC<u>QQYNRYPFT</u>FGSGT
KLEIKR 2F5_VL:
SEQ ID NO: 51
DIVMTQSQKFMSTVGDRVSITC<u>KASQNVGTAVA</u>WYQQKPGQSPKLLIS<u>SA
SNRYT</u>GVPDRFTGSGSGTDFTLTISNMQSEDVADYFC<u>QQYNSYPLT</u>FGAGT
KLELKR 1B11_VL:
SEQ ID NO: 52
DIVMTQSQKFMSTVGDRVSVTC<u>KASQNVGPNVA</u>WYQQKPGQSPKALIY<u>SA
SYRYS</u>GVPDRFTGSGSGTDFTLTISNVQSEDLADYFC<u>QQYNRYPLT</u>FGAGT
KLELKR 2F2_VL:
SEQ ID NO: 53
DIVMTQSQKFMSTVGDRVNVTC<u>KASQNVGTHVA</u>WYQQKPGQSPKALIY<u>SA
SYRYS</u>GVPDRFTGSGSGTDFTLTISNVQSEDLAEYFC<u>QQYNSYPRALT</u>FGA
GTKLELKR 11B6_VL:
SEQ ID NO: 54
DIVMTQSQKFMSTVGDRVNVTC<u>KASQNVGPTVA</u>WYQQKPGQSPKALIY<u>SA
SYRYS</u>GVPDRFTGSGSGTDFTLTISNVHSEDLAEYFC<u>QQYNSYPFT</u>FGSGT
KLEIKR

TABLE 19

MASP-3 Antibody VL Sequences (CDRs and FR regions, Kabat and Chothia)

| Antibody | LC FR1 | LC CDR1 |
|---|---|---|
| 4D5 | DIVMTQSPSSLAVSAGEKVTMTC (SEQ ID NO: 141) | KSSQSLLNSRTRKNYLA (SEQ ID NO: 142) |
| 1F3 | DIVMTQSPSSLAVSAGERVTMSC (SEQ ID NO: 148) | KSSQSLLISRTRKNYLS (SEQ ID NO: 149) |
| 4B6 | DIVMTQSPSSLAVSAGEKVTMSC (SEQ ID NO: 151) | KSSQSLLISRTRKNYLS (SEQ ID NO: 149) |
| 1A10* | [used 4B6 LC: SEQ ID NO: 151] | [used 4B6 LC: SEQ ID NO: 149] |
| 10D12 | DVLMTQTPLTLSVTIGQPASISC (SEQ ID NO: 152) | KSSQSLLDSDGKTYLN (SEQ ID NO: 153) |
| 35C1 | DIVMTQAPLTLSVTIGQPASISC (SEQ ID NO: 158) | KSSQSLLDSDGKTYLS (SEQ ID NO: 159) |
| 13B1 | DIVMTQSPSSLAVSAGEKVTMSC (SEQ ID NO: 151) | KSSQSLLNSRTRKNYLA (SEQ ID NO: 142) |
| 1G4 | DVLMTQTPLSLPVSLGEQASISC (SEQ ID NO: 162) | RSSQSLVQSNGNTYLH (SEQ ID NO: 163) |
| 2F5 | DIVMTQSQKFMSTSVGDRVSITC (SEQ ID NO: 168) | KASQNVGTAVA (SEQ ID NO: 169) |
| 1B11 | DIVMTQSQKFMSTSVGDRVSVTC (SEQ ID NO: 175) | KASQNVGPNVA (SEQ ID NO: 176) |
| 1E7 | DIQLTQSPAILSVSPGERVSFSC (SEQ ID NO: 181) | RASQSIGTSIH (SEQ ID NO: 182) |
| 2F2 | DIVMTQSQKFMSTSVGDRVNVTC (SEQ ID NO: 187) | KASQNVGTHVA (SEQ ID NO: 188) |
| 11B6 | DIVMTQSQKFMSTSVGDRVNVTC (SEQ ID NO: 187) | KASQNVGPTVA (SEQ ID NO: 191) |
| 2D7 | DIQMTQTPASLSASLGDRVTISC (SEQ ID NO: 195) | RASQDISNFLN (SEQ ID NO: 196) |
| 49C11 | DVLMTQTPLSLPVSLGDQASFSC (SEQ ID NO: 202) | RSSQSLIHSNGNTYLH (SEQ ID NO: 203) |
| 15D9 | DIVMTQSQKFMSTSIGDRVSVTC (SEQ ID NO: 205) | RASQNVGPNLA (SEQ ID NO: 206) |
| | LC FR2 | LC CDR2 |
| 4D5 | WYQQKPGQSPKLLIY (SEQ ID NO: 143) | WASTRES (SEQ ID NO: 144) |
| 1F3 | WYQQKPGQSPKLLIY (SEQ ID NO: 143) | WASTRES (SEQ ID NO: 144) |
| 4B6 | WYQQKPGQSPKLLIY (SEQ ID NO: 143) | WASTRES (SEQ ID NO: 144) |
| 1A10 | [used 4B6 LC: SEQ ID NO: 143] | [used 4B6 LC: SEQ ID NO: 144] |
| 10D12 | WLLQRPGQSPKRLIY (SEQ ID NO: 154) | LVSKLDS (SEQ ID NO: 155) |
| 35C1 | WLLQRPGQSPKRLIY (SEQ ID NO: 154) | LVSKLDS (SEQ ID NO: 155) |
| 13B1 | WYQQKPGQSPKLLIY (SEQ ID NO: 143) | WASTRES (SEQ ID NO: 144) |
| 1G4 | WYLQKPGQSPKLLIY (SEQ ID NO: 164) | KVSNRFS (SEQ ID NO: 165) |

TABLE 19-continued

MASP-3 Antibody VL Sequences (CDRs and FR regions, Kabat and Chothia)

| Antibody | | |
|---|---|---|
| 2F5 | WYQQKPGQSPKLLIS (SEQ ID NO: 170) | SASNRYT (SEQ ID NO: 171) |
| 1B11 | WYQQKPGQSPKALIY (SEQ ID NO: 177) | SASYRYS (SEQ ID NO: 178) |
| 1E7 | WYQQRTNGSPRLLIK (SEQ ID NO: 183) | YASESIS (SEQ ID NO: 184) |
| 2F2 | WYQQKPGQSPKALIY (SEQ ID NO: 177) | SASYRYS (SEQ ID NO: 178) |
| 11B6 | WYQQKPGQSPKALIY (SEQ ID NO: 177) | SASYRYS (SEQ ID NO: 178) |
| 2D7 | WYQQKPNGTVKLLVF (SEQ ID NO: 197) | YTSRLHS (SEQ ID NO: 198) |
| 49C11 | WYLQKPGQSPKLLIY (SEQ ID NO: 164) | KVSNRFS (SEQ ID NO: 165) |
| 15D9 | WYQQKPGQSPKALIY (SEQ ID NO: 177) | SASYRFS (SEQ ID NO: 207) |
| | LC FR3 | LC CDR3 |
| 4D5 | GVPDRFTGSGSGTDFSLTISSVQAEDLAVYYC (SEQ ID NO: 145) | KQSYNLYT (SEQ ID NO: 146) |
| 1F3 | GVPDRFTGSGSGTDFTLTISSVQAEDLAVYYC (SEQ ID NO: 150) | KQSYNLYT (SEQ ID NO: 146) |
| 4B6 | GVPDRFTGSGSGTDFTLTISSVQAEDLAVYYC (SEQ ID NO: 150) | KQSYNLYT (SEQ ID NO: 146) |
| 1A10 | [used 4B6 LC: SEQ ID NO: 150] | [used 4B6 LC: SEQ ID NO: 146] |
| 10D12 | GVPDRFTGSGSGTDFTLKISRVEAEDLGVYYC (SEQ ID NO: 156) | WQGTHFPWT (SEQ ID NO: 157) |
| 35C1 | GVPDRFTGSGSGTDFTLKISRVEAEDLGVYYC (SEQ ID NO: 156) | WQGTHFPYT (SEQ ID NO: 160) |
| 13B1 | GVPDRFTGSGSGTDFTLTISSVQAEDLAVYYC (SEQ ID NO: 150) | KQSYNIPT (SEQ ID NO: 161) |
| 1G4 | GVPDRFSGSGSGTDFTLKISRVEAEDLGVYFC (SEQ ID NO: 166) | SQSTHVPPT (SEQ ID NO: 167) |
| 2F5 | GVPDRFTGSGSGTDFTLTISNMQSEDVADYFC (SEQ ID NO: 172) | QQYNSYPLT (SEQ ID NO: 173) |
| 1B11 | GVPDRFTGSGSGTDFTLTISNVQSEDLADYFC (SEQ ID NO: 179) | QQYNRYPLT (SEQ ID NO: 180) |
| 1E7 | GIPSRFSGSGSGTDFTLSINSVESEDIADYYC (SEQ ID NO: 185) | QQSNSWPYT (SEQ ID NO: 186) |
| 2F2 | GVPDRFTGSGSGTDFTLTISNVQSEDLAEYFC (SEQ ID NO: 189) | QQYNSYPRALT (SEQ ID NO: 190) |
| 11B6 | GVPDRFTGSGSGTDFTLTISNVHSEDLAEYFC (SEQ ID NO: 192) | QQYNSYPFT (SEQ ID NO: 193) |
| 2D7 | GVPSRFSGSGSGAEHSLTISNLEQEDVATYFC (SEQ ID NO: 199) | QQGFTLPWT (SEQ ID NO: 200) |
| 49C11 | GVPDRFSGSGSGTDFTLKISRVEAEDLGVYFC (SEQ ID NO: 166) | SQSTHVPWT (SEQ ID NO: 204) |
| 15D9 | GVPDRFTGSGSGTDFTLTISNVQSEDLAEYFC (SEQ ID NO: 189) | QQYNRYPFT (SEQ ID NO: 208) |

TABLE 19-continued

MASP-3 Antibody VL Sequences (CDRs and FR regions, Kabat and Chothia)

| Antibody | LC FR4 |
|---|---|
| 4D5 | FGGGTKLEIKR (SEQ ID NO: 147) |
| 1F3 | FGGGTKLEIKR (SEQ ID NO: 147) |
| 4B6 | FGGGTKLEIKR (SEQ ID NO: 147) |
| 1A10 | [used 4B6 LC: SEQ ID NO: 147] |
| 10D12 | FGGGTKLEIKR (SEQ ID NO: 147) |
| 35C1 | FGGGTKLEIKR (SEQ ID NO: 147) |
| 13B1 | FGGGTKLEIKR (SEQ ID NO: 147) |
| 1G4 | FGGGTKLEIKR (SEQ ID NO: 147) |
| 2F5 | FGAGTKLELKR (SEQ ID NO: 174) |
| 1B11 | FGAGTKLELKR (SEQ ID NO: 174) |
| 1E7 | FGGGTKLEIKR (SEQ ID NO: 147) |
| 2F2 | FGAGTKLELKR (SEQ ID NO: 174) |
| 11B6 | FGSGTKLEIKR (SEQ ID NO: 194) |
| 2D7 | FGGGTKVEIKR (SEQ ID NO: 201) |
| 49C11 | FGGGTKLEIKR (SEQ ID NO: 147) |
| 15D9 | FGSGTKLEIKR (SEQ ID NO: 194) |

*Note:
the light chain for mAb 1A10 was not identified, so the light chain from 4B6 was used with the 1A10 HC.

TABLE 20

Consensus Sequences for Group IA HC CDRs:

| Antibody | Region | Sequence |
|---|---|---|
| 4D5 | HC-CDR1 | TDDIN (SEQ ID NO: 56) |
| 1F3 | HC-CDR1 | SNDIN (SEQ ID NO: 62) |
| 4B6 | HC-CDR1 | SNDIN (SEQ ID NO: 62) |
| 1A10 | HC-CDR1 | SNDIN (SEQ ID NO: 62) |
| Consensus | HC-CDR1 | XXDIN (SEQ ID NO: 209) wherein X at position 1 is S or T; and X at position 2 is N or D |
| 4D5 | HC-CDR2 | WIYPRDDRTKYNDKFKD (SEQ ID NO: 58) |
| 1F3 | HC-CDR2 | WIYPRDGSIKYNEKFTD (SEQ ID NO: 63) |
| 4B6 | HC-CDR2 | WIYPRDGTTKYNEEFTD (SEQ ID NO: 67) |
| 1A10 | HC-CDR2 | WIYPRDGTTKYNEKFTD (SEQ ID NO: 69) |
| Consensus | HC-CDR2 | WIYPRDXXXKYNXXFXD (SEQ ID NO: 210) wherein X at position 7 is G or D; X at position 8 is S, T or R; X at position 9 is I or T; X at position 13 is E or D; |

TABLE 20-continued

Consensus Sequences for Group IA HC CDRs:

| Antibody | Region | Sequence |
|---|---|---|
| | | X at position 14 is K or E; |
| | | X at position 16 is T or K |
| 4D5 | HC-CDR3 | LEDTY (SEQ ID NO: 60) |
| 1F3 | HC-CDR3 | VEDSY (SEQ ID NO: 65) |
| 4B6 | HC-CDR3 | VEDSY (SEQ ID NO: 65) |
| 1A10 | HC-CDR3 | VEDSY (SEQ ID NO: 65) |
| Consensus | HC-CDR3 | XEDXY (SEQ ID NO: 211) wherein X at position 1 is L or V, and wherein X at position 4 is T or S |

TABLE 21

Consensus Sequences for Group IA LC CDRs:

| Antibody | Region | Sequence |
|---|---|---|
| 4D5 | LC-CDR1 | KSSQSLLNSRTRKNYLA (SEQ ID NO: 142) |
| 4D5-NQ | LC-CDR1 | KSSQSLLQSRTRKNYLA (SEQ ID NO: 257) |
| 4D5-NA | LC-CDR1 | KSSQSLLASRTRKNYLA (SEQ ID NO: 258) |
| 4D5-ST | LC-CDR1 | KSSQSLLNTRTRKNYLA (SEQ ID NO: 259) |
| 1F3 | LC-CDR1 | KSSQSLLISRTRKNYLS (SEQ ID NO: 149) |
| 4B6 | LC-CDR1 | KSSQSLLISRTRKNYLS (SEQ ID NO: 149) |
| Consensus* | LC-CDR1 | KSSQSLLXXRTRKNYLX (SEQ ID NO: 212) wherein X at position 8 is N, I, Q or A; wherein X at position 9 is S or T; and wherein X at position 17 is A or S |
| 4D5 | LC-CDR2 | WASTRES (SEQ ID NO: 144) |
| 1F3 | LC-CDR2 | WASTRES (SEQ ID NO: 144) |
| 4B6 | LC-CDR2 | WASTRES (SEQ ID NO: 144) |
| Consensus | LC-CDR2 | WASTRES (SEQ ID NO: 144) |
| 4D5 | LC-CDR3 | KQSYNLYT (SEQ ID NO: 146) |
| 1F3 | LC-CDR3 | KQSYNLYT (SEQ ID NO: 146) |
| 4B6 | LC-CDR3 | KQSYNLYT (SEQ ID NO: 146) |
| Consensus | LC-CDR3 | KQSYNLYT (SEQ ID NO: 146) |

*Note:
CDR-L1 consensus includes variants generated as described in Example 19.

TABLE 22

Consensus Sequences for Group IB HC CDRs:

| Antibody | Region | Sequence |
|---|---|---|
| 10D12 | HC-CDR1 | SYGMS (SEQ ID NO: 72) |
| 35C1 | HC-CDR1 | SYGIT (SEQ ID NO: 79) |
| Consensus | HC-CDR1 | SYGXX (SEQ ID NO: 213) wherein X at position 4 is M or I; and wherein X at position 5 is S or T |
| 10D12 | HC-CDR2 | WINTYSGVPTYADDFKG (SEQ ID NO: 74) |
| 35C1 | HC-CDR2 | WINTYSGVPTYADDFKG (SEQ ID NO: 74) |
| Consensus | HC-CDR2 | WINTYSGVPTYADDFKG (SEQ ID NO: 74) |
| 10D12 | HC-CDR3 | GGEAMDY (SEQ ID NO: 76) |
| 35C1 | HC-CDR3 | GGDALDY (SEQ ID NO: 82) |
| Consensus | HC-CDR3 | GGXAXDY (SEQ ID NO: 214) wherein X at position 3 is E or D; and wherein X at position 5 is M or L |

TABLE 23

Consensus Sequences for Group IB LC CDRs:

| Antibody | Region | Sequence |
|---|---|---|
| 10D12 | LC-CDR1 | KSSQSLLDSDGKTYLN (SEQ ID NO: 153) |
| 10D12-DE | LC-CDR1 | KSSQSLLDSEGKTYLN (SEQ ID NO: 261) |
| 10D12-DA | LC-CDR1 | KSSQSLLDSAGKTYLN (SEQ ID NO: 262) |
| 10D12-GA | LC-CDR1 | KSSQSLLDSDAKTYLN (SEQ ID NO: 263) |
| 35C1 | LC-CDR1 | KSSQSLLDSDGKTYLS (SEQ ID NO: 159) |
| Consensus* | LC-CDR1 | KSSQSLLDSXXKTYLX (SEQ ID NO: 215) Wherein X at position 10 is D, E or A; Wherein X at position 11 is G or A; and wherein X at position 16 is N or S |
| 10D12 | LC-CDR2 | LVSKLDS (SEQ ID NO: 155) |
| 35C1 | LC-CDR2 | LVSKLDS (SEQ ID NO: 155) |
| Consensus | LC-CDR2 | LVSKLDS (SEQ ID NO: 155) |
| 10D12 | LC-CDR3 | WQGTHFPWT (SEQ ID NO: 157) |
| 35C1 | LC-CDR3 | WQGTHFPYT (SEQ ID NO: 160) |
| Consensus | LC-CDR3 | WQGTHFPXT (SEQ ID NO: 216) Wherein X at position 8 is W or Y |

*Note:
CDR-L1 consensus includes variants generated as described in Example 19.

DNA Encoding Mouse mAb Heavy and Light Chains:

SEQ ID NO: 217:
DNA encoding 4D5 heavy chain variable region (parental)
CAGGTGCAGCTGAAGCAGTCTGGACCTGAGCTGGTGAAGCCTGGGCTT

CAGTGAAGTTGTCCTGCAAGGCTTCTGGCTACACCTTCACAACCGACGA

TATAAACTGGGTGAAGCAGAGGCCTGGACAGGGACTTGAGTGGATTGGA

TGGATTTATCCTAGAGATGATAGAACTAAGTACAATGACAAGTTCAAGG

ACAAGGCCACATTGACTGTAGACACATCTTCCAACACAGCGTACATGGA

CCTCCACAGCCTGACATCTGAGGACTCTGCGGTCTATTTCTGTTCAAGC

CTCGAGGATACTTACTGGGGCCAAGGGACTCTGGTCGCTGTCTCTTCA

SEQ ID NO: 218:
DNA encoding 1F3 heavy chain variable region (parental)
CAGGTGCAGCTGAAGCAGTCTGGACCTGAGCTGGTGAAGCCTGGGCTT

CAGTGAAGTTGTCCTGCAAGGCTTCTGGCTACACCTTCACAAGTAACGA

TATAAACTGGGTGAAGCAGAGGCCTGGACAGGGACTTGAGTGGATTGGA

TGGATTTATCCTAGAGATGGGAGTATTAAATATAATGAGAAATTCACGG

ACAAGGCCACATTGACAGTTGACGTATCCTCCAGCACAGCGTACATGGA

GCTCCACAGCCTGACATCTGAGGACTCTGCGGTCTATTTCTGTTCAGGT

GTCGAGGATTCTTACTGGGGCCAAGGGACTCTGGTCACTGTCTCTTCA

SEQ ID NO: 219:
DNA encoding 4B6 heavy chain variable region (parental)
CAGGTGCAGCTGAAGCAGTCTGGACCTGAACTGGTGAAGCCTGGGCTT

CAGTGAAATTGTCCTGCAAGGCTTCTGGCTACACCTTCACAAGTAACGA

TATAAACTGGGTGAAACAGAGGCCTGGACAGGGACTTGAGTGGATTGGA

TGGATTTATCCTAGAGATGGTACTACTAAGTACAATGAGGAGTTCACGG

ACAAGGCCACATTGACTGTTGACGTATCCTCCAGCACAGCGTTCATGGA

GCTCCACAGCCTGACATCTGAGGACTCTGCTGTCTATTTCTGTTCAAGT

GTCGAGGATTCTTACTGGGGCCAAGGGACTCTGGTCACTGTCTCTTCA

SEQ ID NO: 220:
DNA encoding 1A10 heavy chain variable region (parental)
CAGGTGCAGCTGAAGCAGTCTGGACCTGAGCTGGTGAAGCCTGGGCTT

CAGTGAAGTTGTCCTGCAAGGCTTCTGGCTACACCTTCACAAGTAACGA

TATAAACTGGGTGAAGCAGAGGCCTGGACAGGGACTTGAGTGGATTGGA

TGGATTTATCCTAGAGATGGTACTACTAAGTACAATGAGAAGTTCACGG

ACAAGGCCACATTGACTGTTGACGTATCCTCCAGCACAGCGTTCATGGA

GCTCCACAGGCTGACATCTGAGGACTCTGCGGTCTATTTCTGTTCAAGT

GTCGAGGATTCTTACTGGGGCCAAGGGACTCTGGTCACTGTCTCTTCA

SEQ ID NO: 221:
DNA encoding 10D12 heavy chain variable region (parental)
CAGATCCAGTTGGTACAGTCTGGACCTGAGCTGAAGAAGCCTGGAGAGA

CAGTCAAGATCTCCTGCAAGGCTTCTGGGTATATTTTCACAAGCTATGG

AATGAGCTGGGTGAGACAGGCTCCAGGAAAGGGTTTAAAGTGGATGGGC

TGGATAAACACCTACTCTGGAGTGCCAACATATGCTGATGACTTCAAGG

GACGGTTTGCCTTCTCTTTGGAAACCTCTGCCAGAACTCCCTATTTGCA

GATCAACAACCTCAAAAATGAGGACACGGCTACATATTTCTGCGCAAGA

GGGGGCGAAGCTATGGACTACTGGGGTCAAGGAACCTCAGTCACCGTCT

CCTCA

SEQ ID NO: 222:
DNA encoding 35C1 heavy chain variable region (parental)
CAGATCCAGTTGGTACAGTCTGGACCTGAGCTGAAGACGCCAGGAGAGA

CAGTCAAGATCTCCTGCAAGGCTTCTGGGTATATCTTCACATCCTATGG

AATTACCTGGGTGAAACAGGCTCCAGGAAAGGGTTTAAAGTGGATGGGC

TGGATAAACACCTACTCTGGAGTGCCAACATATGCTGATGACTTCAAGG

GACGGTTTGCCTTCTCTTTGGAAACGTCTGCCAGCACTGCCTATTTGCA

GATCAACAACCTCAAAAATGAGGACACGACTACATATTTCTGTACAAGA

GGGGGTGATGCTTTGGACTACTGGGGTCAAGGAACCTCAGTCACCGTCT

CCTCA

SEQ ID NO: 223:
DNA encoding 13B1 heavy chain variable region (parental)
CAGGTGCAGCTGAAGCAGTCTGGAGCTGAGCTGATGAAGCCTGGGGCCT

CAGTGAAGCTTTCCTGCAAGGCTACTGGCTACACATTCACTGGCAAGTG

GATAGAGTGGGTAAAACAGAGGCCTGGACATGGCCTAGAGTGGATTGGA

GAGATTTTACCTGGAACTGGTAGTACTAACTACAATGAGAAGTTCAAGG

GCAAGGCCACATTCACTGCAGACTCATCCTCCAACACAGCCTACATGCA

ACTCAGCAGCCTGACAACTGAAGACTCTGCTATGTATTATTGTTTAAGA

TCCGAGGATGTCTGGGGCACAGGGACCACGGTCACCGTCTCCTCA

SEQ ID NO: 224:
DNA encoding 1G4 heavy chain variable region (parental)
CAGGTGCAGCTGAAGCAGTCTGGAGCTGAGCTGATGAAGCCTGGGGCCT

CAGTGAAGCTTGCCTGCAAGGCTACTGGCTACACATTCACTGGCTACTG

GATAGAGTGGATAAAGCAGAGGCCTGGACAAGGCCTTGAGTGGATTGGA

GAGATGTTACCTGGAAGTGGTAGTACTCACTACAATGAGAAGTTCAAGG

GTAAGGCCACATTCACTGCAGATACATCCTCCAACACAGCCTACATGCA

ACTCAGCGGCCTGACAACTGAGGACTCTGCCATCTATTACTGTGTAAGA

AGCATAGACTACTGGGGCCAAGGCACCACTCTCACAGTCTCCTCA

SEQ ID NO: 225:
DNA encoding 1E7 heavy chain variable region (parental)
CAGGTGCAGCTGAAGCAGTCTGGGCCTGAGCTGGCAAGGCCTTGGGCTT

CAGTGAAGATATCCTGCCAGGCTTTCTACACCTTTTCCAGAAGGGTGCA

CTTTGCCATTAGGGATACCAACTACTGGATGCAGTGGGTAAAACAGAGG

CCTGGACAGGGTCTGGAATGGATCGGGGCTATTTATCCTGGAAATGGTG

ATACTAGTTACAATCAGAAGTTCAAGGGCAAGGCACATTGACTGCAGA

CAAATCCTCCAGCACAGCCTACATGCAACTCAGCAGCCTGACATCTGAG

GACTCTGCGGTCTATTACTGTGCATCCGGTAGCCACTACTTTGACTACT

GGGGCCAAGGCACCACTCTCACAGTCTCCTCA

SEQ ID NO: 226:
DNA encoding 2D7 heavy chain variable region
(parental)
GAGGTCCAGCTGCAACAATCTGGGCCTGAGCTGGTGAAGCCTGGGCTT

CAGTGAAGGTATCCTGTAAGGCTTCTGGATACACGCTCACTGACTACTA

CATGAACTGGGTGAAGCAGAGCCATGGAAAGAGCCTTGAGTGGATTGGA

GATGTTAATCCTAACAATGATGGTACTACCTACAACCAGAAATTCAAGG

GCAGGGCCACATTGACTGTAGACAAGTCTTCCAACACAGCCTCCATGGA

GCTCCGCAGCCTGACATCTGAGGACTCTGCAGTCTACTACTGTGCAATA

TGCCCCTTTTATTACCTCGGTAAAGGGACCCACTTTGACTACTGGGGCC

AAGGCACCTCTCTCACAGTCTCCTCA

SEQ ID NO: 227:
DNA encoding 49C11 heavy chain variable region
(parental)
GAGGTCCAGCTGCAACAATCTGGACCTGTGCTGGTGAAGCCTGGGCTT

CAGGGAAGATGTCCTGTAAGGCTTCTGGATACAAATTCACTGACTACTA

TATGATCTGGGTGAAGCAGAGCCATGGAAAGAGCCTTGAGTGGATTGGA

GTTATTAAAATTTATAACGGTGGTACGAGCTACAACCAGAAGTTCAAGG

GCAAGGCCACATTGACTGTTGACAAGTCCTCCAGCACAGCCTACATGGA

GCTCAACAGCCTGACATCTGAGGACTCTGCAGTCTATTACTGTGCAAGA

GGGCCATCTCTCTATGATTACGACCCTTACTGGTACTTCGATGTCTGGG

GCACAGGGACCACGGTCACCGTCTCCTCA

SEQ ID NO: 228:
DNA encoding 15D9 heavy chain variable region
(parental)
CAGGTGCAGCTGAAGCAGTCTGGAACTGAGCTGATGAAGCCTGGGCCT

CAGTGAACCTTTCCTGCAAGGCTTCTGGCTACACATTCACTGCCTACTG

GATAGAGTGGGTAAAGCAGAGGCCTGGACATGGCCTTGAGTGGATTGGA

GAGATTTTACCTGGAAGTGGTACTACTAACTACAATGAGAACTTCAAGG

ACAGGGCCACATTCACTGCAGATACATCCTCCAACACAGCCTACATGCA

ACTCAGCAGCCTGACAAGTGAGGACTCTGCCATCTATTACTGTGCAAGA

TCCTATTACTACGCTAGTAGATGGTTTGCTTTCTGGGGCCAAGGGACTC

TGGTCACTGTCTCTTCA

SEQ ID NO: 229:
DNA encoding 2F5 heavy chain variable region
(parental)
GAGGTCCAGCTGCAGCAGCCTGGGGCTGAGCTTGTGAAGCCTGGGCTT

CAGTGAAGATGTCCTGTAAGGCTTCTGGCTACACCTTCACCAGCTACTG

GATAACCTGGGTGAAGCAGAGGCCTGGACAAGGCCTTGAGTGGATTGGA

GATATTTATCCTGGTAGTGGTAGTACTAACTACAATGAGAAGTTCAAGA

GCAAGGCCACACTGACTGTAGACACATCCTCCAGCACAGCCTACATGCA

GCTCAGCAGCCTGACATCTGAGGACTCTGCGGTCTATTACTGTGCAAGA

AGGAGATACTACGCTACGGCCTGGTTTGCTTACTGGGGCCAAGGGACTC

TGGTCACTGTCTCTTCA

SEQ ID NO: 230:
DNA encoding 1B11 heavy chain variable region
(parental)
CAGGTGCAGCTGAAGCAGTCTGGGGCTGAGCTGGTGAGGCCTGGGGCTT

CAGTGAAGCTGTCCTGCAAGGCTTCTGGCTACACTTTCACTGACTACTA

TATAAACTGGGTGAAGCAGAGGCCTGGACAGGGACTTGAGTGGATTGCA

AGGATTTATCCTGGAAGTGGTAATACTTACTACAATGAGAAGTTCAAGG

GCAAGGCCACACTGACTGCAGAAAAATCCTCCAGCACTGCCTACATGCA

GCTCAGCAGCCTGACATCTGAGGACTCTGCTGTCTATTTCTGTGCAAGA

AATTACTACATTAGTAGTCCCTGGTTTGCTTACTGGGGCCAAGGGACTC

TGGTCACTGTCTCTTCA

SEQ ID NO: 231:
DNA encoding 2F2 heavy chain variable region
(parental)
CAGGTGCAGCTGAAGCAGTCTGGGGCTGAGCTAGTGACGCCTGGAGCCT

CAGTGAAGATGTCCTGCAAGGCTTCTGGCTACACCTTCACTACCTATCC

TATAGAGTGGATGAAACAGAATCATGGAAAGAGCCTAGAGTGGATTGGA

AATTTTCATCCTTACAATGATGATACTAAGTACAATGAAAAGTTCAAGG

GCAAGGCCACATTGACTGTAGAAAAATCCTCTAACACAGTCTACTTGGA

GCTCAGCCGATTAACATCTGATGACTCTGCTGTTTATTTCTGTGCAAGG

AGGGTCTACTATAGTTACTTCTGGTTTGGTTACTGGGGCCACGGGACTC

TGGTCACTGTCTCTTCA

SEQ ID NO: 232:
DNA encoding 11B6 heavy chain variable region
(Parental)
CAGGTGCAGCTGAAGCAGTCTGGGGCTGAGCTAGTGAAACCTGGAGCCT

CAGTGAAGATGTCCTGCAAGGCTTCTGGCTACACCTTCACTACCTATCC

TATAGAGTGGATGAAGCAGAATCATGGGAAGAGCCTAGAGTGGATTGGA

AATTTTCATCCTTACAATGGTGATTCTAAGTACAATGAAAAGTTCAAGG

GCAAGGCCACCTTGACTGTAGAAAAATCCTCTAGCACAGTCTACTTAGA

ACTCAGCCGATTACCATCTGCTGACTCTGCTATTTATTACTGTGCAAGG

AGGCACTACGCTGCTAGTCCCTGGTTTGCTCACTGGGGCCAAGGGACTC

TGGTCACTGTCTCTTCA

DNA Encoding Light Chain Variable Region (Mouse mAbs):

SEQ ID NO: 233: DNA encoding 4D5 light chain
variable region (parental)
GACATTGTGATGACCCAGTCTCCATCCTCCCTGGCTGTGTCAGCAGGAG

AGAAGGTCACTATGACCTGCAAATCCAGTCAGAGTCTGCTCAACAGTAG

AACCCGAAAGAACTACTTGGCTTGGTACCAGCAGAAACCAGGGCAGTCT

CCTAAACTGCTGATCTACTGGGCATCCACTAGGGAATCTGGGGTCCCTG

ATCGCTTCACAGGCAGTGGATCTGGGACAGATTTCTCTCTCACCATCAG

CAGTGTGCAGGCTGAAGACCTGGCAGTTTATTACTGCAAGCAATCTTAT

AATCTGTACACGTTCGGAGGGGGGACCAAGCTGGAAATAAAACGG

SEQ ID NO: 234: DNA encoding 1F3 light chain
variable region (parental)
GACATTGTGATGACCCAGTCTCCATCCTCCCTGGCTGTGTCAGCAGGAG

AGAGGGTCACTATGAGCTGCAAATCCAGTCAGAGTCTGCTCATCAGTAG

AACCCGAAAGAACTATTTGTCTTGGTACCAGCAGAAACCAGGGCAGTCT

CCTAAACTGCTGATCTACTGGGCATCCACTAGGGAATCTGGGGTCCCTG

ATCGCTTCACAGGCAGTGGATCTGGGACAGATTTCACTCTCACCATCAG

CAGTGTACAGGCTGAAGACCTGGCAGTTTATTACTGCAAGCAATCTTAT

AATCTGTACACGTTCGGCGGGGGGACCAAGCTGGAAATAAAACGG

SEQ ID NO: 235: DNA encoding 4B6/1A10 light chain
variable region (parental)
GACATTGTGATGACCCAGTCTCCATCCTCCCTGGCTGTGTCAGCAGGAG

AGAAGGTCACTATGAGCTGCAAATCCAGTCAGAGTCTGCTCATCAGTAG

AACCCGAAAGAACTATTTGTCTTGGTACCAGCAGAAACCAGGGCAGTCT

CCTAAACTGCTGATCTATTGGGCATCCACTAGGGAATCTGGGGTCCCTG

ATCGCTTCACAGGCAGTGGATCTGGGACAGATTTCACTCTCACCATCAG

CAGTGTACAGGCTGAAGACCTGGCAGTTTATTACTGCAAACAATCTTAT

AATCTGTACACGTTCGGCGGGGGGACCAAGCTGGAAATCAAACGG

SEQ ID NO: 236: DNA encoding 10D12 light chain
variable region (parental)
GATGTTTTGATGACCCAAACTCCACTCACTTTGTCGGTTACCATTGGAC

AACCAGCCTCCATCTCTTGCAAGTCAAGTCAGAGCCTCTTAGATAGTGA

TGGAAAGACATATTTGAATTGGTTGTTACAGAGGCCAGGCCAGTCTCCA

AAGCGCCTAATCTATCTGGTGTCTAAACTGGACTCTGGAGTCCCTGACA

GGTTCACTGGCAGTGGATCAGGGACAGATTTCACACTGAAAATCAGCAG

AGTGGAGGCTGAGGATTTGGGAGTTTATTATTGCTGGCAAGGTACACAT

TTTCCGTGGACGTTCGGTGGAGGCACCAAGCTGGAAATCAAACGG

SEQ ID NO: 237: DNA encoding 35C1 light chain
variable region (parental)
GATATTGTGATGACGCAGGCTCCACTCACTTTGTCGGTTACCATTGGAC

AACCAGCCTCCATCTCTTGCAAGTCAAGTCAGAGCCTCTTAGATAGTGA

TGGAAAGACATATTTGAGTTGGTTGTTACAGAGGCCAGGCCAGTCTCCA

AAGCGCCTAATCTATCTGGTGTCTAAACTGGACTCTGGAGTCCCTGACA

GGTTCACTGGCAGTGGATCAGGGACAGATTTCACACTGAAAATCAGCAG

AGTGGAGGCTGAGGATTTGGGAGTTTATTATTGCTGGCAAGGTACACAT

TTTCCGTACACGTTCGGAGGGGGGACCAAGCTGGAAATAAAACGG

SEQ ID NO: 238: DNA encoding 13B1 light chain
variable region (parental)
GACATTGTGATGACCCAGTCTCCATCCTCCCTGGCTGTGTCAGCAGGAG

AGAAGGTCACTATGAGCTGCAAATCCAGTCAGAGTCTGCTCAACAGTAG

AACCCGAAAGAACTACTTGGCTTGGTACCAGCAGAAACCAGGGCAGTCT

CCTAAACTGCTGATCTACTGGGCATCCACTAGGGAATCTGGGGTCCCTG

ATCGCTTCACAGGCAGTGGATCTGGAACAGATTTCACTCTCACCATCAG

CAGTGTGCAGGCTGAAGACCTGGCAGTTTATTACTGCAAGCAATCTTAT

AATATTCCGACGTTCGGTGGAGGCACCAAGCTGGAAATCAAACGG

SEQ ID NO: 239: DNA encoding 1G4 light chain
variable region (parental)
GATGTTTTGATGACCCAAACTCCACTCTCCCTGCCTGTCAGTCTTGGAG

AACAAGCCTCCATCTCTTGCAGATCAAGTCAGAGCCTTGTACAAAGTAA

TGGAAACACCTATTTACATTGGTACCTGCAGAAGCCAGGCCAGTCTCCA

AAGCTCCTGATCTACAAAGTTTCCAACCGATTTTCTGGGGTCCCAGACA

GGTTCAGTGGCAGTGGATCAGGGACAGATTTCACACTCAAGATCAGCAG

AGTGGAGGCTGAGGATCTGGGAGTTTATTTCTGCTCTCAAAGTACACAT

GTTCCTCCGACGTTCGGTGGAGGCACCAAGCTGGAAATCAAACGG

SEQ ID NO: 240: DNA encoding 1E7 light chain
variable region (parental)
GACATCCAGCTGACTCAGTCTCCAGCCATCCTGTCTGTGAGTCCAGGAG

AAAGAGTCAGTTTCTCCTGCAGGGCCAGTCAGAGCATTGGCACAAGCAT

ACACTGGTATCAGCAAAGAACAAATGGTTCTCCAAGGCTTCTCATAAAG

TATGCTTCTGAGTCTATCTCTGGGATCCCTTCCAGGTTTAGTGGCAGTG

GATCAGGGACAGATTTTACTCTTAGCATCAACAGTGTGGAGTCTGAAGA

TATTGCAGATTATTACTGTCAACAAAGTAATAGCTGGCCGTACACGTTC

GGAGGGGGGACCAAGCTGGAAATAAAACGG

SEQ ID NO: 241: DNA encoding 2D7 light chain
variable region (parental)
GATATCCAGATGACACAGACTCCAGCCTCCCTGTCTGCCTCTCTGGGAG

ACAGAGTCACCATCAGTTGTAGGGCAAGTCAGGACATTAGCAATTTTTT

AAACTGGTATCAACAGAAACCGAATGGAACTGTTAAACTCCTAGTCTTC

TACACATCAAGATTACACTCAGGAGTCCCATCAAGGTTCAGTGGCAGTG

GGTCTGGAGCAGAGCATTCTCTCACCATTAGCAACCTGGAGCAGGAAGA

TGTTGCCACTTACTTTTGCCAACAGGGTTTTACGCTTCCGTGGACGTTC

GGTGGGGGCACCAAGGTGGAAATCAAACGG

SEQ ID NO: 242: DNA encoding 49C11 light chain
variable region (parental)
GATGTTTTGATGACCCAAACTCCACTCTCCCTGCCTGTCAGTCTTGGAG

ATCAAGCCTCCTTCTCTTGCAGATCTAGTCAGAGCCTTATACACAGTAA

TGGAAACACCTATTTACATTGGTACCTGCAGAAGCCAGGCCAGTCTCCA

AAGCTCCTGATCTACAAAGTTTCCAACCGATTTTCTGGGGTCCCAGACA

GGTTCAGTGGCAGTGGATCAGGGACAGATTTCACACTCAAGATCAGCAG

AGTGGAGGCTGAGGATCTGGGAGTTTATTTCTGCTCTCAAAGTACACAT

GTTCCGTGGACGTTCGGTGGAGGCACCAAGCTGGAAATCAAACGG

SEQ ID NO: 243: DNA encoding 15D9 light chain
variable region (parental)
GACATTGTGATGACCCAGTCTCAAAAATTCATGTCCACATCAATAGGAG

ACAGGGTCAGCGTCACCTGCAGGGCCAGTCAGAATGTGGGTCCCAATTT

AGCCTGGTATCAACAGAAACCAGGGCAATCTCCTAAAGCACTGATTTAC

TCGGCATCCTACCGATTCAGTGGAGTCCCTGATCGCTTCACAGGCAGTG

GATCTGGGACAGATTTCACTCTCACCATCAGCAATGTGCAGTCTGAAGA

CTTGGCAGAGTATTTCTGTCAGCAATATAACAGGTATCCATTCACGTTC

GGCTCGGGGACAAAGTTGGAAATAAAACGG

SEQ ID NO: 244: DNA encoding 2F5 light chain
variable region (parental)
GACATTGTGATGACCCAGTCTCAAAAATTCATGTCCACATCAGTAGGAG

ACAGGGTCAGCATCACCTGCAAGGCCAGTCAGAATGTGGGTACTGCTGT

AGCCTGGTATCAACAGAAACCAGGACAATCTCCTAAACTACTGATTTCC

TCGGCATCCAATCGGTACACTGGAGTCCCTGATCGCTTCACAGGCAGTG

GATCTGGGACAGATTTCACTCTCACCATCAGTAATATGCAGTCTGAAGA

CGTGGCAGATTATTTCTGCCAGCAATATAACAGCTATCCTCTCACGTTC

GGTGCTGGGACCAAGCTGGAGCTGAAACGG

SEQ ID NO: 245: DNA encoding 1B11 light chain
variable region (parental)
GACATTGTGATGACCCAGTCTCAAAAATTCATGTCCACTTCAGTAGGAG

ACAGGGTCAGCGTCACCTGCAAGGCCAGTCAGAATGTGGGTCCTAATGT

AGCCTGGTATCAACAGAAACCAGGGCAATCTCCTAAAGCACTGATTTAC

TCGGCATCCTACCGGTACAGTGGAGTCCCTGATCGCTTCACAGGCAGTG

GATCTGGGACAGATTTCACTCTCACCATCAGCAATGTGCAGTCTGAAGA

CTTGGCAGACTATTTCTGTCAGCAATATAACCGCTATCCTCTCACGTTC

GGTGCTGGGACCAAACTGGAGCTGAAACGG

SEQ ID NO: 246: DNA encoding 2F2 light chain
variable region (parental)
GACATTGTGATGACCCAGTCTCAAAAATTCATGTCCACATCAGTAGGAG

ACAGGGTCAACGTCACCTGCAAGGCCAGTCAGAATGTGGGTACTCATGT

AGCCTGGTATCAACAGAAACCAGGGCAATCTCCTAAAGCACTGATTTAC

TCGGCATCCTACCGGTACAGTGGCGTCCCTGATCGCTTCACAGGCAGTG

GATCTGGGACAGATTTCACTCTCACCATCAGCAATGTGCAGTCTGAAGA

CCTGGCAGAGTATTTCTGTCAGCAATATAACAGCTATCCTCGAGCGCTC

ACGTTCGGTGCTGGGACCAAGCTGGAGCTGAAACGG

SEQ ID NO: 247: DNA encoding 11B6 light chain
variable region (parental)
GACATTGTGATGACCCAGTCTCAAAAATTCATGTCCACATCAGTAGGAG

ACAGGGTCAACGTCACCTGCAAGGCCAGTCAGAATGTGGGTCCTACTGT

AGCCTGGTATCAACAGAAACCAGGGCAATCTCCTAAAGCACTAATTTAC

TCGGCATCCTACCGGTACAGTGGAGTCCCTGATCGCTTCACAGGCAGTG

GATCTGGGACAGATTTCACTCTCACCATCAGCAATGTGCACTCTGAAGA

CTTGGCAGAGTATTTCTGTCAGCAATATAACAGCTATCCATTCACGTTC

GGCTCGGGGACAAAGTTGGAAATAAAACGG

SEQ ID NO: 310: human IgG4 constant region
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

SEQ ID NO: 311: human IgG4 constant region with
S228P mutation
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

SEQ ID NO: 312: human IgG4 constant region with
S228P mutation and and also a mutation (Xtend)
that promotes FcRn interations at low pH
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVLHEALHSHYTQKSLSLSLGK

SEQ ID NO: 313: human IgK constant region
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC

Example 16

This Example describes functional characterization of recombinant purified high affinity MASP-3 inhibitory antibodies in several in vitro assays.

Methods:

The recombinant MASP-3 mAbs generated as described in Examples 11 and 14 were characterized for (i) binding to human MASP-3 and other species' MASP-3; (ii) the ability to inhibit cleavage of an artificial substrate; (iii) the capacity to inhibit pro-factor D to factor D cleavage; (iv) inhibition of complement deposition in human serum and (v) inhibition of rabbit erythrocyte lysis in human serum as follows:

1. Assays to Determine Binding to Human and Mouse MASP-3

ELISA Assays:

MASP-3 Binding Assay with Purified Recombinant MASP-3 mAbs:

Human MASP-3:

A sandwich ELISA assay was carried out to measure binding of 16 purified recombinant MASP-3 antibodies to human MASP-3 (CCP1-CCP2-SP fragment) as follows. An ELISA plate was coated in carbonate/bi-carbonate buffer overnight at 4° C. with capture antibody αM3-259 at 4 μg/mL. αM3-259 is a high avidity recombinant, chimeric chicken-human MASP-3 mAb from chickens immunized with the CCP1-CCP2-SP region of human MASP-3. Domain mapping studies revealed that αM3-259 binds the CCP1-CCP2 region of MASP-3 from multiple species, including human, cynomolgus monkey, mouse, rat and dog. As shown in FIG. 51C, αM3-259 also binds to MASP-1.

The plate was subsequently blocked with 1% BSA/PBS, washed in PBS and then incubated for one hour at room temperature with MASP-3 CCP1-CCP2-SP (2 µg/mL). The plate was then washed (PBS-T, 0.05%) and the candidate MASP-3 antibodies were added followed by incubation for one hour at room temperature. The plate was washed (PBS-T, 0.05%) and a detection antibody was added (mouse anti-human kappa-HRP, SouthernBiotech #9230-05) for one hour at room temperature. After another wash (PBS-T, 0.05%) the plate was developed (5 minutes) with OPT EIA TMB (BD Biosciences #555214). Absorbance reading at A450 was measured using the Spectramax M5e plate reader.

Figure 51A:
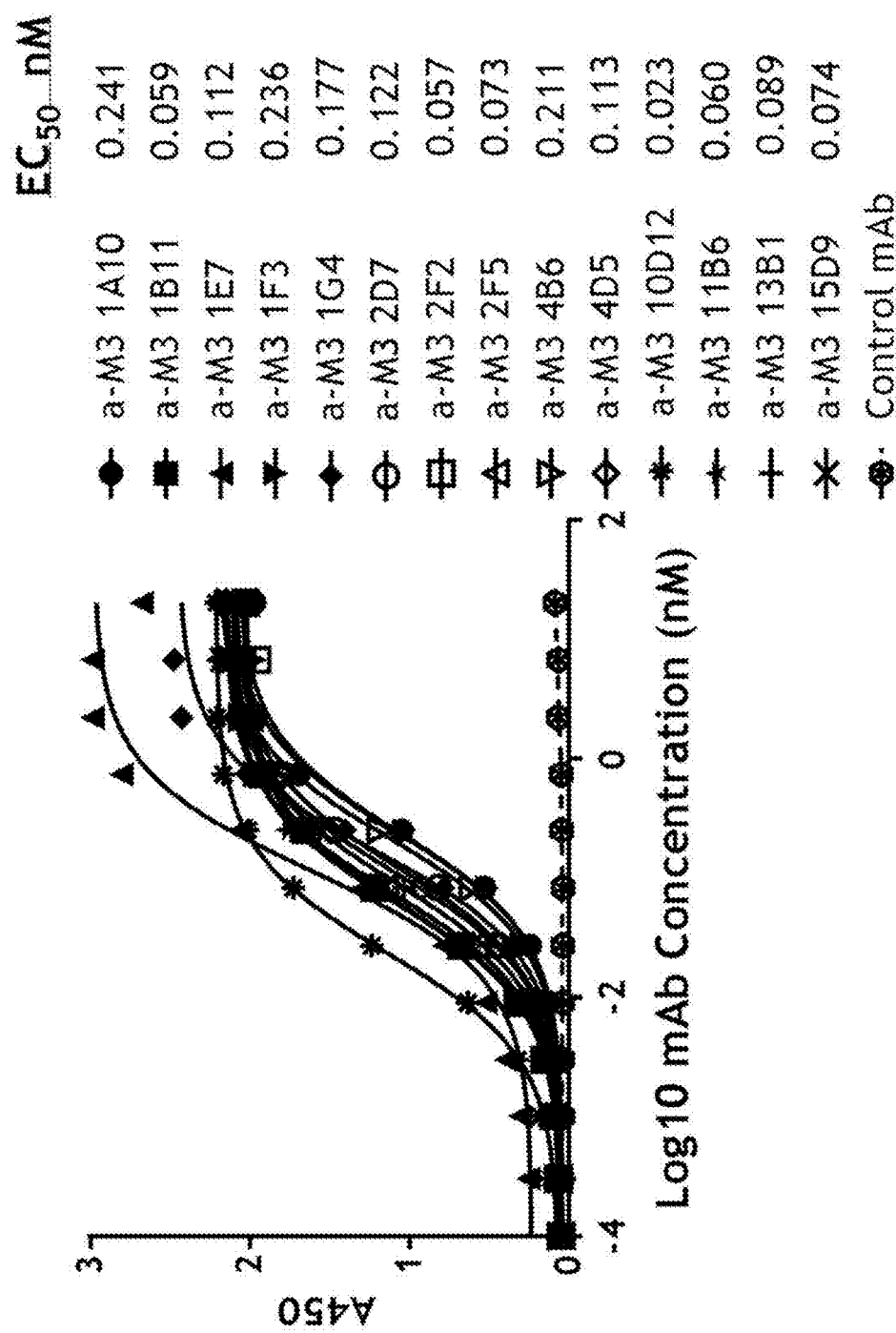
FIG. 51A graphically illustrates the results of a binding experiment in which representative purified recombinant anti-human MASP-3 inhibitory antibodies show an apparent binding avidity of less than 500 pM (e.g., from 240 pM to 23 pM) to the human MASP-3 protein, as described in Example 16.
Figure 51B:
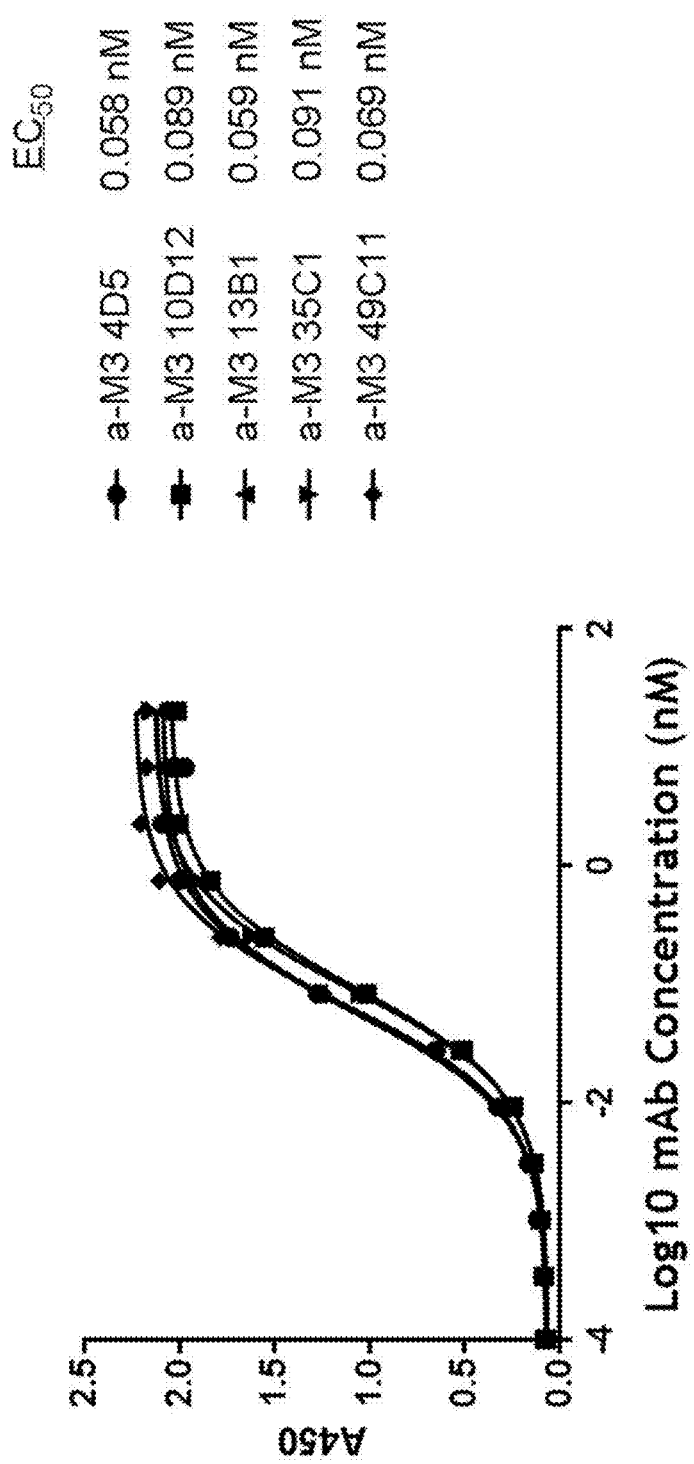
FIG. 51B graphically illustrates the results of a binding experiment in which representative purified recombinant anti-human MASP-3 inhibitory antibodies show an apparent binding avidity of less than 500 pM (e.g., from 91 pM to 58 pM) to the human MASP-3 protein, as described in Example 16.
Figure 51C:
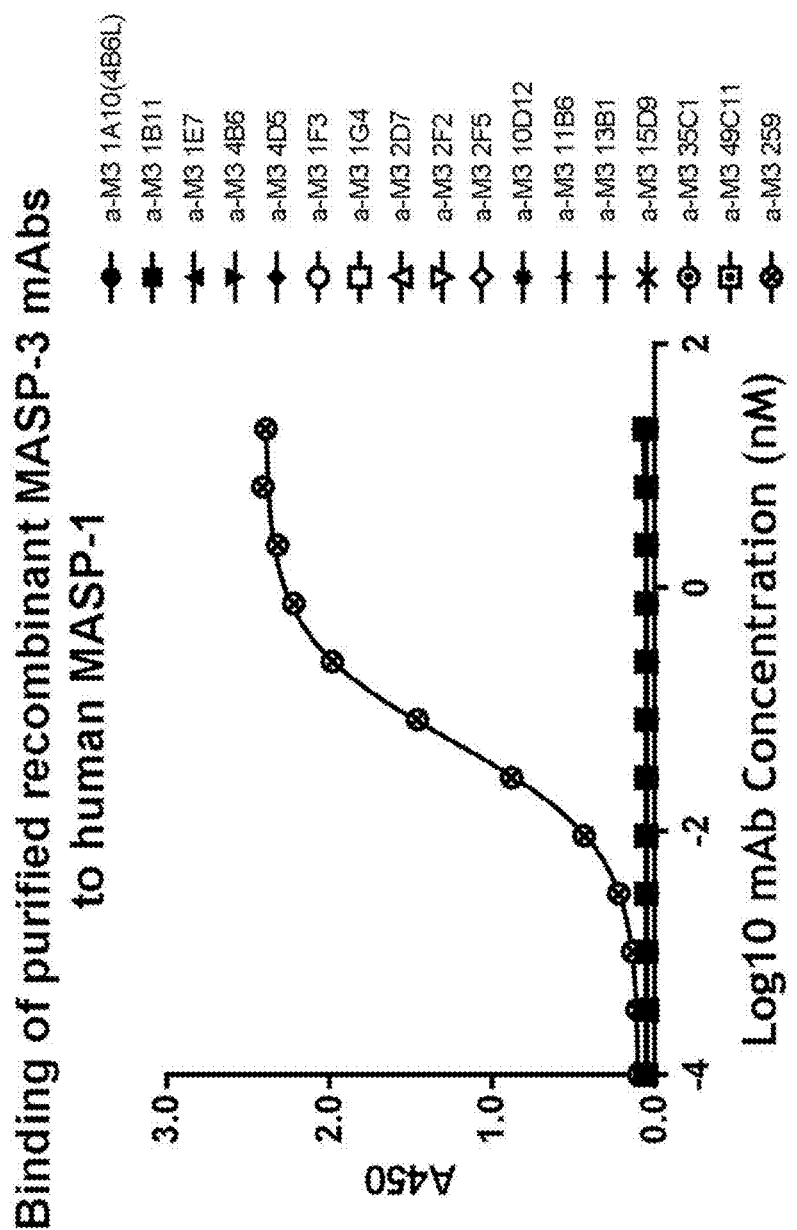
FIG. 51C graphically illustrates the results of a binding experiment in which representative purified recombinant high affinity anti-human MASP-3 inhibitory antibodies are shown to be selective for binding to MASP-3 and do not bind to human MASP-1, as described in Example 16.

Results:

FIG. 51A and FIG. 51B graphically illustrate the avidities of MASP-3 mAbs (purified recombinant) for human MASP-3 (CCP1-CCP2-SP). As shown in FIG. 51A, FIG. 51B, and Table 24, the MASP-3 mAbs have high avidity for human MASP-3, ranging from 0.241 nM to 0.023 nM. These values are 10 to 100-fold lower than those reported for the previously described MASP-3 mAbs (see Example 7 herein, also published as Example 15 in WO2013/192240).

MASP-3 mAb Binding Specificity:

To determine the specificity of the high affinity MASP-3 mabs for MASP-3, binding experiments were carried out to measure binding of 16 purified recombinant MASP-3 antibodies to human MASP-1 and to human MASP-2. Binding was determined as described for the MASP-3 binding ELISA, except that recombinant MASP-1A (S646A, CCP1-CCP2-SP fragment) and MASP-2 (CCP1-CCP2-SP fragment) were immobilized directly on the plate.

Results:

FIG. 51C graphically illustrates the results of a binding experiment in which representative purified recombinant high affinity human MASP-3 inhibitory antibodies are shown to be selective for binding to MASP-3 and do not bind to human MASP-1.

Figure 51D:
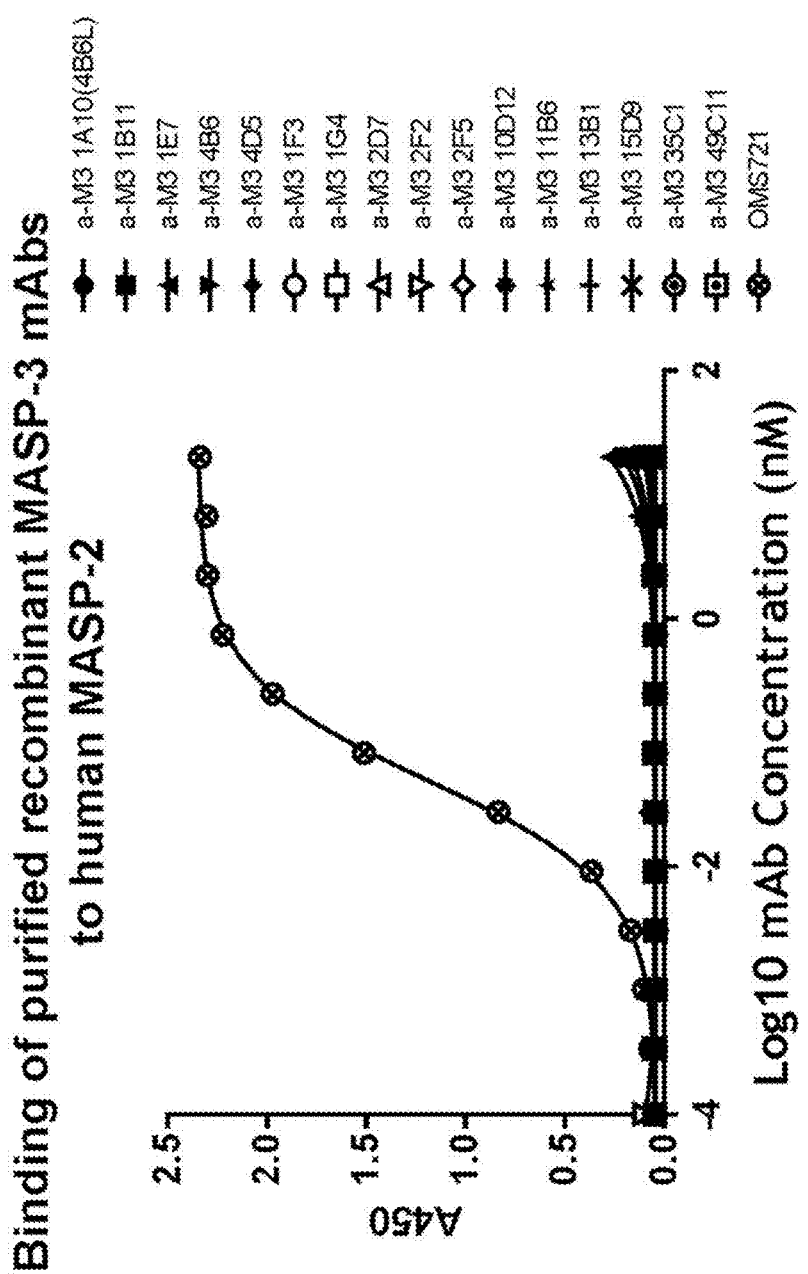
FIG. 51D graphically illustrates the results of a binding experiment in which representative purified recombinant high affinity anti-human MASP-3 inhibitory antibodies are shown to be selective for binding to MASP-3 and do not bind to human MASP-2, as described in Example 16.

FIG. 51D graphically illustrates the results of a binding experiment in which representative purified recombinant high affinity human MASP-3 inhibitory antibodies are shown to be selective for binding to MASP-3 and do not bind to human MASP-2.

Mouse MASP-3:

Binding of the MASP-3 mAbs to mouse MASP-3 was measured as described above for human MASP-3 except that recombinant, full-length mouse MASP-3 (SEQ ID NO:3) was captured on the plate with αM3-259. The negative control mAb used in both experiments was mAb77, a recombinant, chimeric chicken-human mAb obtained from the same immunized chickens as αM3-259, however, mAb 77 does not bind mouse MASP-3.

Figure 52:
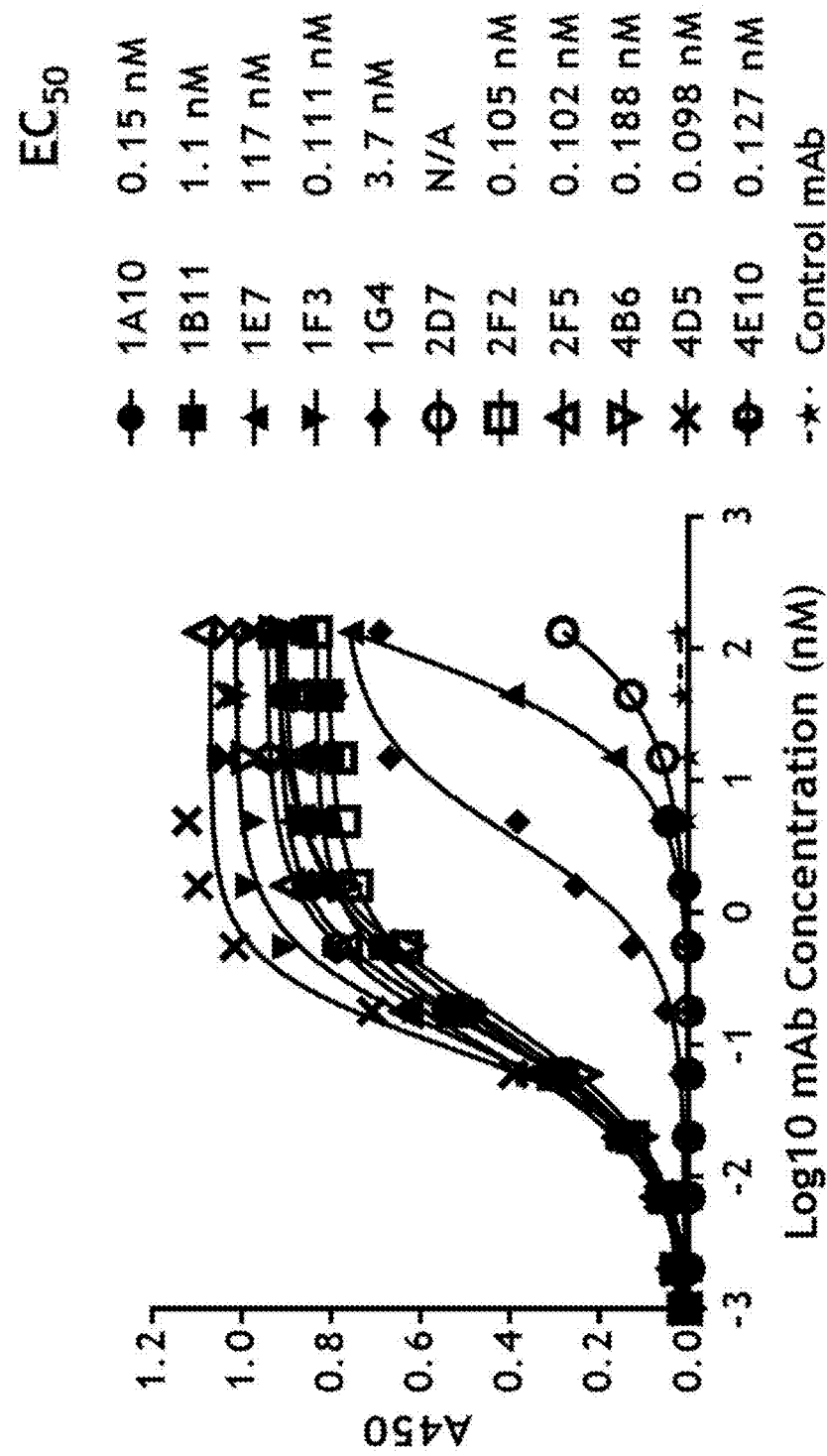
FIG. 52 graphically illustrates the results of a binding experiment in which representative purified recombinant anti-human MASP-3 inhibitory antibodies also show high binding avidity to the mouse MASP-3 protein, as described in Example 16.

Results:

FIG. 52 graphically illustrates the avidities of representative MASP-3 mAbs (purified recombinant) for mouse full length MASP-3. As shown in FIG. 52, most of the MASP-3 mAbs tested also have high avidity for mouse MASP-3.

The avidity values (EC$_{50}$) of the 16 recombinant chimeric MASP-3 mAbs for human and mouse MASP-3 are summarized in TABLE 24.

TABLE 24

Binding Avidity of MASP-3 mAbs for human and mouse MASP-3 (FIGS. 51A, 51B and 52)

| Antibody clone | Antigen used to generate mAb | Human MASP-3 (CCP1-CCP2-SP) Binding Avidity (EC$_{50}$ nM) | Mouse MASP-3 (full length) Binding Avidity (EC$_{50}$ nM) |
|---|---|---|---|
| 1A10* | SP | 0.241 | 0.15 |
| 1B11 | SP | 0.059 | 1.10 |
| 1E7 | SP | 0.112 | 117.00 |
| 1F3 | SP | 0.236 | 0.111 |
| 1G4 | SP | 0.177 | 3.70 |
| 2D7 | SP | 0.122 | NA |
| 2F2 | SP | 0.057 | 0.105 |
| 2F5 | SP | 0.073 | 0.102 |
| 4B6 | SP | 0.211 | 0.188 |
| 4D5 | SP | 0.058 | 0.098 |
| 10D12 | CCP1-CCP2-SP | 0.089 | 0.081 |
| 11B6 | CCP1-CCP2-SP | 0.060 | 0.066 |
| 13B1 | CCP1-CCP2-SP | 0.059 | 0.035 |
| 15D9 | CCP1-CCP2-SP | 0.074 | 0.092 |
| 35C1 | CCP1-CCP2-SP | 0.091 | 0.209 |
| 49C11 | CCP1-CCP2-SP | 0.069 | 0.064 |

Three of the MASP-3 mAbs—13B1, 10D12 and 4D5—were also tested for binding to recombinant cynomolgus monkey, dog, and rat MASP-3. These results are summarized below in Table 25.

TABLE 25

Summary of MASP-3 mAb Cross-Species Binding Experiments

| Species of MASP-3 | Ranking of Fab Binding |
|---|---|
| Human | 13B1 (pM) ≈ 10D12 (pM) ≈ 4D5 (pM) |
| Cynomolgus monkey | 13B1 (pM) ≈ 4D5 (pM) > 10D12 (pM) |
| Dog | 13B1 (pM) > 10D12 (pM) >> 4D5 (nM) |
| Rat | 13B1 (pM) ≈ 10D12 (pM) >> 4D5 (nM) |
| Mouse | 10D12 (pM) > 13B1 (pM) >> 4D5 (nM) |

As shown in TABLE 25, MASP-3 mAbs 13B1, 10D12 and 4D5 bind to all five species of MASP-3 tested (human, mouse, rat, dog and cynomolgus monkey). While these mAbs bind to human with high avidity (≤500 pM), they bind to other species of MASP-3 with varying avidities.

2. Fluorogenic Tripeptide Cleavage Assay

Background/Rationale:

In addition to its known natural substrates (Iwaki et al., *J. Immunol.* 187:3751, 2011; Cortesio and Jiang, *Arch. Biochem. Biophys.* 449:164-170, 2006), MASP-3 has been shown to hydrolyze various tripeptide substrates (Cortesio and Jiang, Ibid.). As very small substrates, these molecules can be used to map the catalytic site of the protease. Inhibition of tri-peptide cleavage is an indication that an inhibitory agent, such as an antibody, either directly blocks access of the small substrate to the catalytic site or causes a conformational shift in the SP domain that similarly denies access. As such, the antibody can also be expected to block catalysis of the large natural substrates by interfering with the active site of the enzyme. Functionally, this would most closely approximate the MASP-3 null mouse or 3MC patient (deficient in MASP-3).

Methods:

Titrations of the recombinant mAbs (3-fold dilution from 666 nM to 0.91 nM) were incubated with MASP-3 CCP1-CCP2-SP (197 nM) for 15 minutes at room temperature. Tri-peptide substrate BOC-V-P-R-AMC (t-Butyloxycarbonyl-Val-Pro-Arg-7-Amino-4-methylcoumarin) (R&D Systems, Cat. No. ES011) was added at a final concentration of 0.2 mM. Hydrolysis of the Arg-AMC amide bond releases AMC, a highly fluorescent group. Excitation 380 nm/emission 460 nm kinetic values were recorded every 5 minutes at 37° C. for 70 minutes using the Spectramax M5e fluorescence plate reader.

Figure 53:
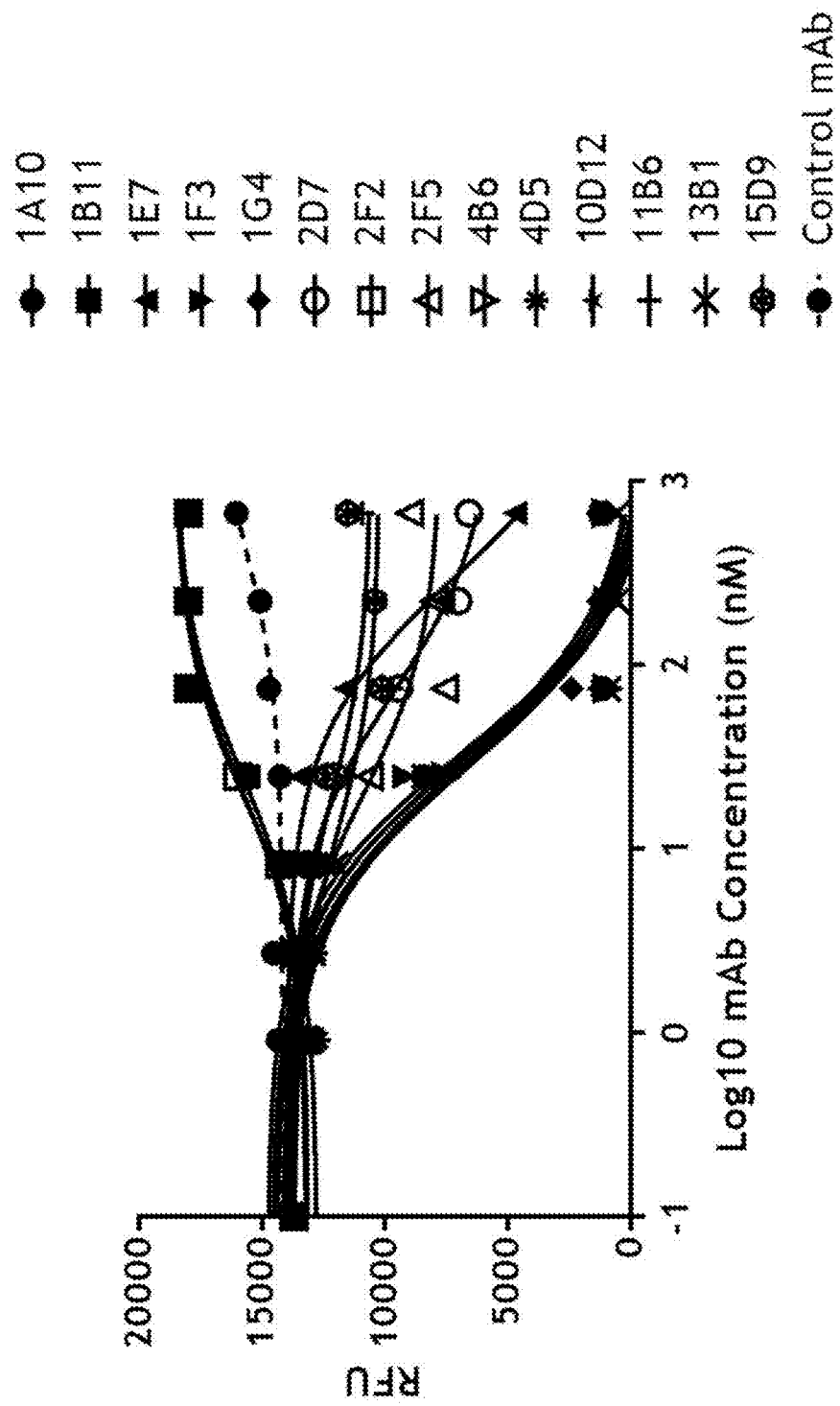
FIG. 53 graphically illustrates the results of an experiment measuring the ability of representative high affinity MASP-3 antibodies to inhibit fluorogenic tripeptide cleavage, as described in Example 16.

Results:

FIG. 53 graphically illustrates the results of the assay measuring inhibition of MASP-3-dependent fluorogenic tripeptide cleavage with the MASP-3 monoclonal antibodies. As shown in FIG. 53, the MASP-3 mAbs tested fall into three distinct groups:

1. MASP-3 mAbs that are strong inhibitors of peptide cleavage by MASP-3: 1A10 (29.77 nM), 1G4 (29.64 nM), 1F3 (32.99 nM), 4B6 (26.03 nM), 4D5 (27.54 nM), 10D12 (30.94 nM) and 13B1 (30.13 nM).
2. MASP-3 mAbs that are weak or very weak inhibitors of peptide cleavage by MASP-3: 15D9, 11B6, 2F5, 1E7 and 2D7
3. MASP-3 mAbs that are neutral or appear to stimulate peptide cleavage by MASP-3: 1B11; 2F2; 77 (control mAb)

3. Inhibition of Pro-Factor D to Factor D Cleavage

Methods:

Active, recombinant human MASP-3 protein (240 ng per reaction) was pre-incubated with representative MASP-3 mAbs and a control mAb (which binds to MASP-1 but not to MASP-3) in GVB++ buffer with a total volume of 9 µL at room temperature for 15 minutes. 70 ng of pro-factor D with an N-terminal Strep-tag II epitope tag (ST-pro-factor D-His) was then added to each tube to make the final volume per reaction to 10 µL. The reactions were incubated in a thermocycler at 37° C. for 6 hours. One tenth from each reaction was then electrophoresed on a 12% Bis-Tris gel to resolve pro-factor D and active factor D cleavage product. The resolved proteins were transferred to a PVDF membrane and analyzed using Western blot by detection with a biotinylated factor D antibody (R&D Systems).

Figure 54:
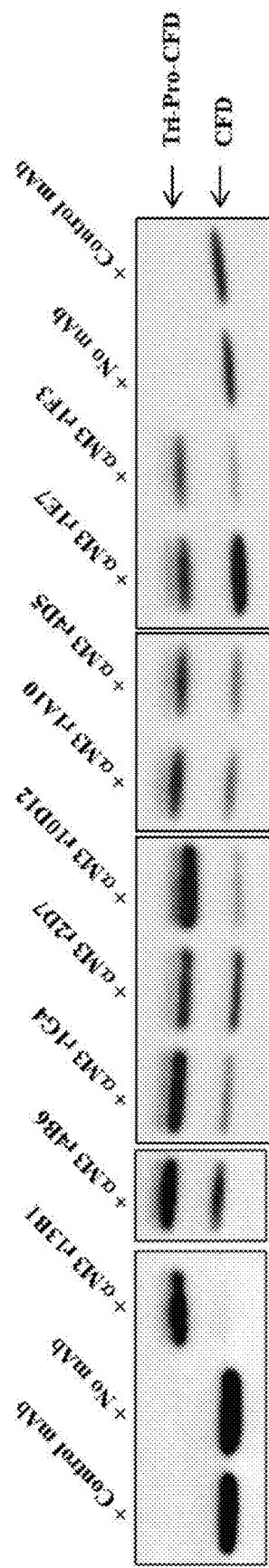
FIG. 54 shows a Western blot demonstrating the ability of representative high affinity MASP-3 inhibitory mAbs to block recombinant MASP-3-mediated cleavage of pro-factor D to factor D in an in vitro assay, as described in Example 16.

Results:

FIG. 54 shows a Western blot analysis demonstrating the ability of representative MASP-3 mAbs to block recombinant MASP-3-mediated cleavage of pro-CFD to CFD in an in vitro assay. As shown in FIG. 54, representative high affinity MASP-3 inhibitory mAbs 13B1, 4B6, 1G4, 2D7, 10D12, 1A10, 4D5, 1E7, and 1F3 mouse-human chimeric mAbs showed partial to full inhibition of the pro-CFD cleavage in this assay.

4. Factor Bb Deposition on Zymosan Assay

Methods:

Varying concentrations of MASP-3 mAbs were added to 10% CFD-depleted human serum (Complement Technology A336) and GVB+Mg/EGTA (20 nM) and incubated for 30 minutes on ice prior to the addition of recombinant ST-pro-factor D-His (2 µg/mL final) and zymosan (0.1 mg/mL final). The zymosan particles function as an activating surface for complement deposition. The mixtures were incubated at 37° C. and the APC activity was measured by the flow cytometric detection of complement factor Bb (Quidel antibody A252) on the surface of the zymosan particles.

Figure 55A:
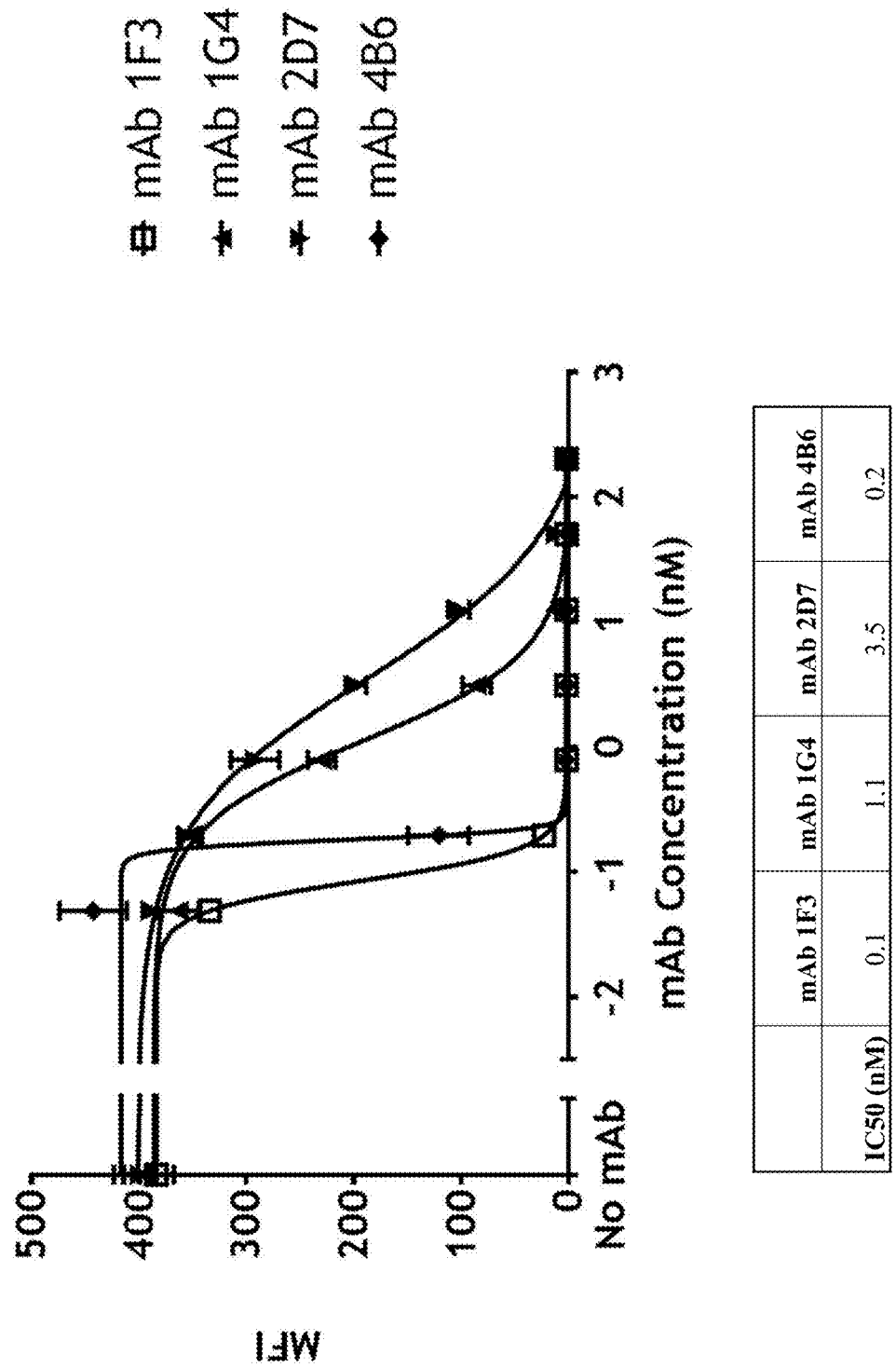
FIG. 55A graphically illustrates the level of complement factor Bb deposition on zymosan particles (determined by flow cytometric detection measured in MFI units) in the presence of varying concentrations of high affinity MASP-3 mAbs 1F3, 1G4, 2D7 and 4B6 in factor D-depleted human serum, as described in Example 16.

Results:

FIG. 55A graphically illustrates the level of factor Bb deposition on zymosan particles (determined by flow cytometric detection measured in MFI units) in the presence of varying concentrations of MASP-3 mAbs 1F3, 1G4, 2D7 and 4B6 in factor D-depleted human serum at 37° C. for 70 minutes.

FIG. 55B graphically illustrates the level of factor Bb deposition on zymosan particles (determined by flow cytometric detection measured in MFI units) in the presence of varying concentrations of MASP-3 mAbs 4D5, 10D12 and 13B1 in CFD-depleted human serum at 37° C. for 70 minutes.

The results shown in FIGS. 55A and 55B are summarized below in TABLE 26.

TABLE 26

Inhibition of Factor Bb deposition on zymosan by MASP-3 mAbs (FIG. 55A and FIG. 55B)

| Antibody | Inhibition of Factor Bb Deposition on Zymosan ($IC_{50}$ nM) |
|---|---|
| 1F3 | 0.1 |
| 1G4 | 1.1 |
| 2D7 | 3.5 |
| 4B6 | 0.2 |
| 4D5 | 0.4 |
| 10D12 | 0.5 |
| 13B1 | 0.3 |

As shown in FIG. 55A, FIG. 55B and TABLE 26, the MASP-3 mAbs show potent inhibition of the APC in human serum, with $IC_{50}$ values ranging from 0.1 nM to 3.5 nM. These results demonstrate that MASP-3 plays a key role in APC activation in an in vitro model in human serum, and further demonstrate that MASP-3 inhibitory antibodies are potent inhibitors of the APC.

5. Assay to Measure the Ability of Representative MASP-3 mAbs to Inhibit Rabbit Erythrocyte Lysis Methods:

To monitor the inhibition of the APC in another experimental context, we evaluated the ability of representative MASP-3 mAbs to block the lysis of rabbit erythrocytes in human serum. Varying concentrations of MASP-3 mAbs were added to 10% factor D-depleted human serum and GVB+Mg/EGTA (20 nM) and incubated for 30 minutes on ice prior to the addition of recombinant ST-pro-factor B-His (2 µg/mL final) and erythrocytes ($2.5 \times 10^8$ cells/mL final). The mixtures were incubated at 37° C. for 70 minutes and APC-mediated hemolysis was measured by diluting the reactions and measuring the absorbance (A405), which indicates levels of free hemoglobin.

Figure 56A:
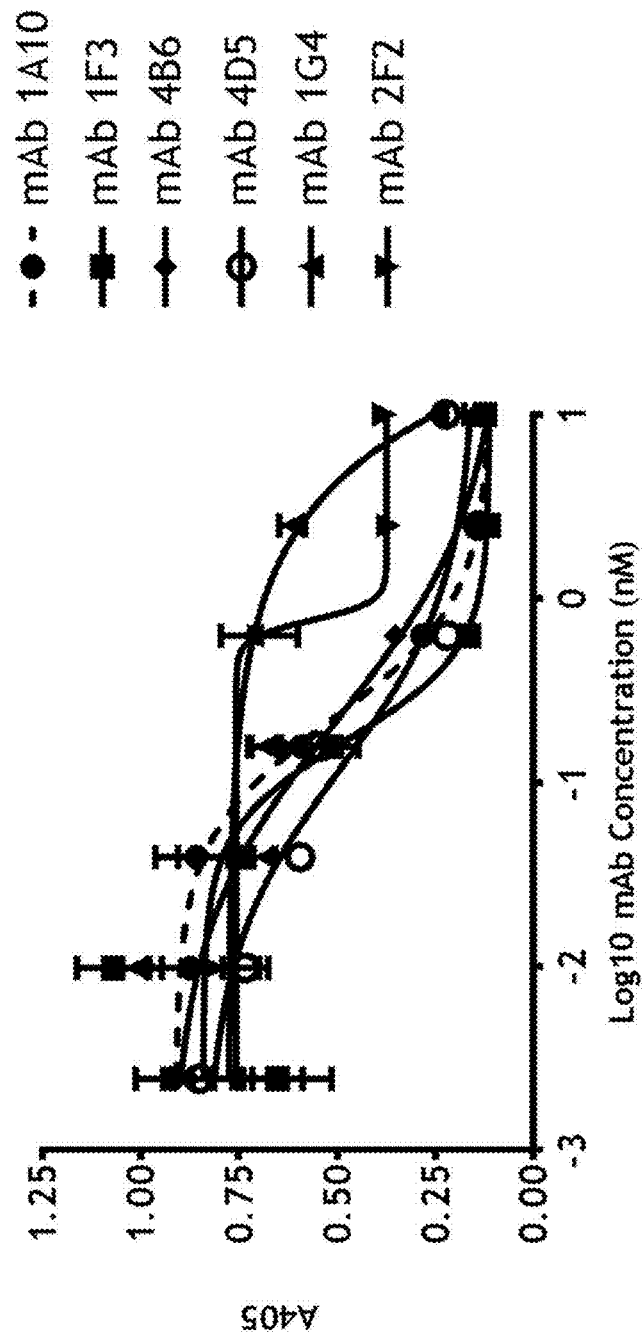
FIG. 56A graphically illustrates the level of inhibition of rabbit erythrocyte lysis in the presence of varying concentrations of high affinity MASP-3 mAbs 1A10, 1F3, 4B6, 4D5 and 2F2 as described in Example 16.
Figure 56B:
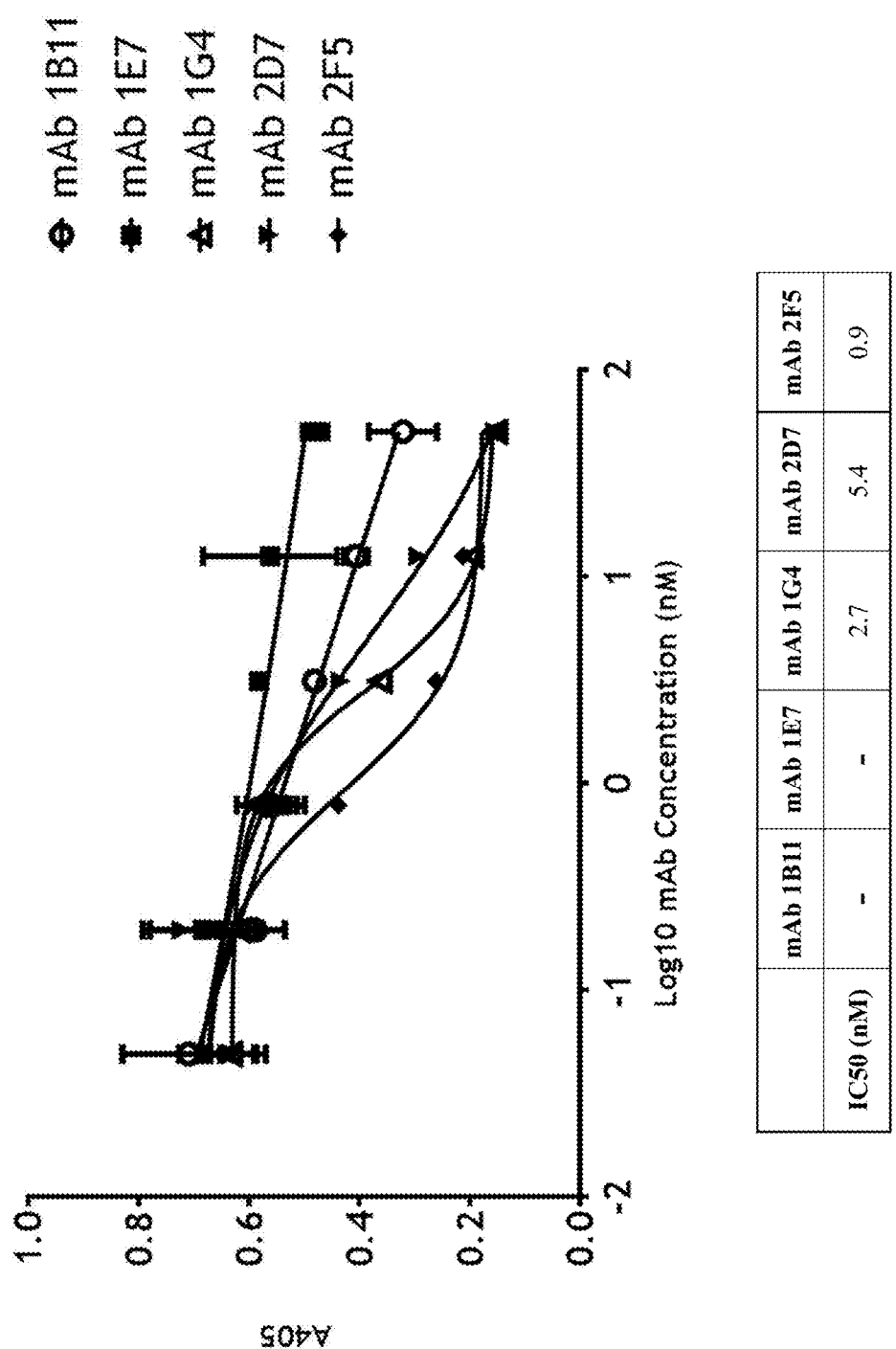
FIG. 56B graphically illustrates the level of inhibition of rabbit erythrocyte lysis in the presence of varying concentrations of high affinity MASP-3 mAbs 1B11, 1E7, 1G4, 2D7 and 2F5 as described in Example 16.

Results:

FIG. 56A graphically illustrates the level of inhibition of rabbit erythrocyte lysis in the presence of varying concentrations of MASP-3 mAbs 1A10, 1F3, 4B6, 4D5, 1G4 and 2F2 in CFD-depleted human serum. FIG. 56B graphically illustrates the level of inhibition of rabbit erythrocyte lysis in the presence of varying concentrations of MASP-3 mAbs 1B11, 1E7, 1G4, 2D7 and 2F5 in CFD-depleted human serum. The results are summarized in TABLE 27.

TABLE 27

Inhibition of Rabbit Erythrocyte Lysis by MASP-3 mAbs (FIG. 56A and FIG. 56B)

| Antibody | Inhibition of Rabbit Erythrocyte Lysis ($IC_{50}$ nM) |
|---|---|
| 1A10 | 0.2 |
| 1F3 | 0.2 |
| 4B6 | 0.2 |
| 4D5 | 0.1 |
| 1G4 | 2.7 |
| 2F2 | 0.8 |
| 1B11 | NA |
| 1E7 | NA |

TABLE 27-continued

Inhibition of Rabbit Erythrocyte Lysis
by MASP-3 mAbs (FIG. 56A and FIG. 56B)

| Antibody | Inhibition of Rabbit Erythrocyte Lysis (IC$_{50}$ nM) |
|---|---|
| 2D7 | 5.4 |
| 2F5 | 0.9 |

As shown in FIG. 56A, FIG. 56B and TABLE 27, the MASP-3 mAbs show inhibition of the APC-driven hemolysis of rabbit erythrocytes, with IC$_{50}$ values ranging from 0.1 nM to 5.4 nM. These results corroborate the observations of the MASP-3 antibodies in the zymosan assay, and further demonstrate that MASP-3 inhibitory antibodies are potent inhibitors of the APC.

6. Inhibition of Pro-Factor D Cleavage in 3MC Patient Serum

Methods:

A representative recombinant MASP-3 mAb (4D5) was tested for the ability to block recombinant MASP-3 cleavage (and activation) of pro-factor D originating from normal human serum and serum from 3MC Patient B ("Pat B"), an individual who has no detectable MASP-3 in the serum and manifests a deficiency in the APC.

Normal human serum and Patient B serum (10% final) and GVB+Mg/EGTA (30 nM) were incubated with no enzyme or with active recombinant MASP-3 (rMASP-3; 0.5 µg/mL), inactive rMASP-3, or active rMASP-3 plus MASP-3 mAb 4D5 (500 nM final) on ice for 1 hour. Zymosan (0.1 mg/mL final) was added, and the mixtures were incubated at 37° C. After 2 hours, the samples were centrifuged and the supernatants were collected. The samples were immunoprecipitated with goat antibody raised against human Factor D (R&D Systems AF1824), heat denatured and treated with Peptide-N-Glycosidase (New England Biolabs P0704L). The captured and deglycosylated proteins were resolved with SDS-PAGE and the gels were electroblotted for Western blot analysis with a biotinylated anti-CFD (R&D Systems BAF1824) and High Sensitivity Streptavidin-HRP (Thermo Fischer Scientific 21130).

Results:

FIG. 57 shows a Western blot analyzing the level of pro-factor D and factor D in 3MC Patient B serum in the presence active rMASP-3, inactive rMASP-3, and active rMASP-3 plus mAb 4D5. As shown in FIG. 57, normal human serum contains predominately the mature form, while Patient B serum principally contains the zymogen form of factor D. As further shown in FIG. 57, active rMASP-3 in the presence of zymosan causes cleavage of pro-factor D in Patient 3 serum, while the inactive (zymogen) form of MASP-3 does not. Finally, as shown in FIG. 57, the MASP-3 mAb 4D5 blocks cleavage of pro-factor D in Patient 3 serum in the presence of active rMASP-3. These results further demonstrate the role of MASP-3 in the cleavage of pro-factor D in the activation of the APC, and demonstrate that a MASP-3 inhibitory mAb is capable of blocking MASP-3 mediated pro-factor D cleavage and thereby blocking the APC.

Example 17

Analysis of representative MASP-3 inhibitory mAbs 10D12 and 13B1 for the ability to inhibit the APC in vivo.

1. Inhibition of the APC by mAb M3-1 (13B1) and 10D12 In Vivo:

Methods:

In order to determine the efficacy of MASP-3 mAb 13B1 (M3-1) and 10D12 for inhibiting the APC in vivo, a group of mice (n=4) received a single intravenous tail vein injection of 10 mg/kg mAb 13B1 and a second group of mice (n=4) received a single intravenous tail vein injection of 10 mg/kg mAb 10D12. Blood collected from the animals was used to prepare serum, providing a matrix for the flow cytometric assessment of APC activity in an ex vivo assay measuring the level of C3 (also C3b and iC3b, Dako F020102-2) deposition on zymosan particles. Serum prepared from blood harvested at a pre-dose timepoint and multiple post-dose time points (96 hrs, 1 week, and 2 weeks) was diluted to 7.5% and zymosan particles (0.1 mg/mL final) were added to induce the APC. Antibody-treated mice were compared to a group of control mice (n=4) that were given a single intravenous dose of vehicle.

Results:

FIG. 58 graphically illustrates the level of C3 deposition on zymosan particles at various time points after a single dose of mAb M3-1 (13B1), mAb 10D12, or vehicle in wild-type mice. As shown in FIG. 58, in the pre-dose time point the three conditions show comparable levels of APC activity. At 96 hours and the two later time points, both mAb-treated groups show near-complete ablation of systemic APC activity, while the APC activity of the vehicle-treated group remains unabated.

These results demonstrate that MASP-3 mAb M3-1 (13B1) and mAb 10D12 are potent inhibitors of the APC in vivo in mouse.

2. Status of Factor B in Mice Treated with MASP-3 mAb 10D12

Methods:

During the conversion of Factor B zymogen to an active proteolytic enzyme, Factor B is cleaved into the Ba (~30 kDa) and Bb (~60 kDa) fragments by Factor D. The status of the Ba fragment in mouse serum obtained from mice treated with the MASP-3 mAb 10D12 was determined as follows.

Mice (n=4) were given two intravenous tail vein injections of 10 mg/kg mAb 10D12. The treatments occurred seven days apart and blood was collected from the animals three days after the second injection. A second set of four mice received a single intravenous dose of vehicle (PBS). The blood collected from both groups was used to prepare serum, providing a matrix for complement activation. Zymosan particles (0.1 mg/mL final) were added to diluted serum (7.5% final) and incubated for 35 minutes at 37° C.

Figure 59:
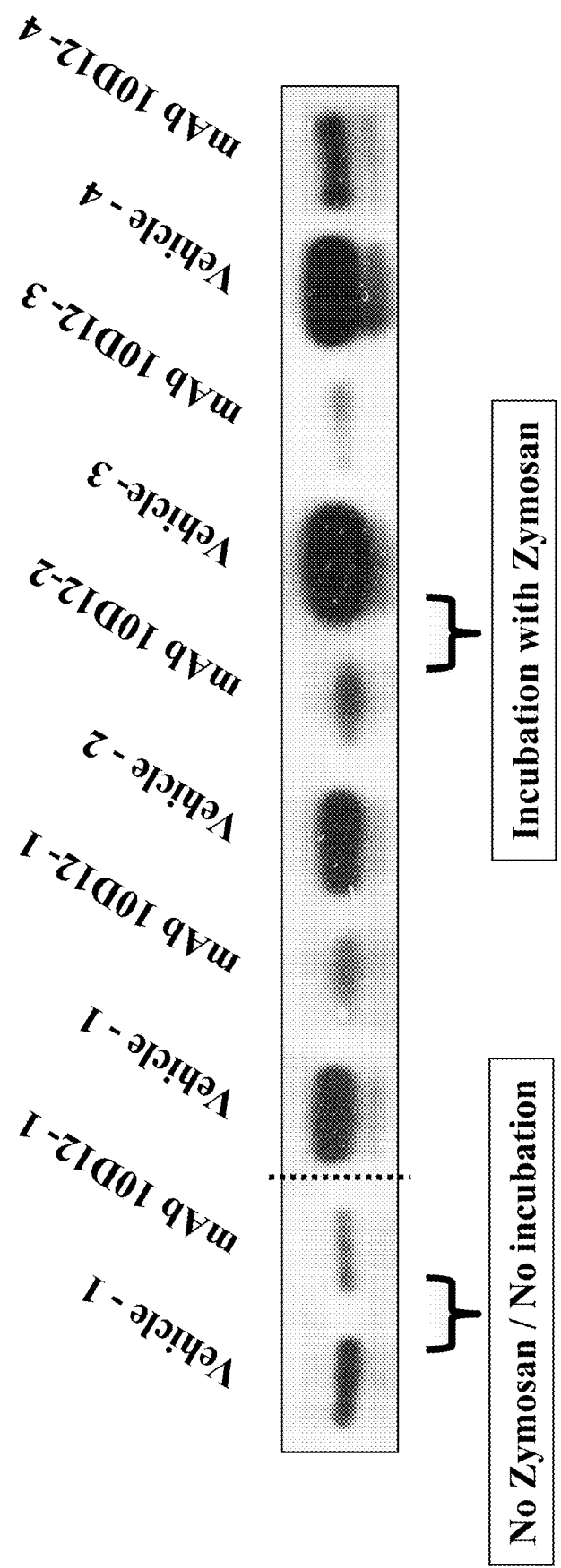
FIG. 59 shows a Western blot analyzing the status of the Factor Ba fragment of Factor B in mice treated with high affinity MASP-3 mAb 10D12 (10 mg/kg) or vehicle control treated mice, as described in Example 17.

Results:

As a measure of APC activation, FIG. 59 shows a Western blot analyzing the status of the Ba fragment in mouse serum obtained from mice treated with mAb 10D12 or PBS and stimulated with zymosan. Each lane in FIG. 59 represents a different mouse, and the lanes alternate to show serum from a representative vehicle mouse adjacent to a MASP-3 mAb-treated mouse for the purposes of comparison. Two control conditions, from mice treated with vehicle or mAb 10D12 are shown in lanes 1 and 2, respectively (starting from the left side of the blot) as representatives of the basal level of Ba present in the serum samples in the absence of zymosan. Lanes 3 to 10 all show the level of Ba fragment present after incubation with zymosan. In all cases, the MASP-3 mAb-treated mice demonstrate a reduced level of the Ba fragment in comparison to the vehicle-treated animals.

3. Serum from Mice Treated with mAb 10D12 Inhibits Hemolysis

Methods:

As another measure of APC inhibition by MASP-3 inhibitory antibodies, we evaluated the ability of the MASP-3 antibodies to block the lysis of rabbit erythrocytes in serum from mice treated with representative MASP-3 mAb 10D12 as compared to serum from vehicle control treated mice. Mice (n=4/group) were given three intravenous tail vein injections of vehicle control (PBS), 10 mg/kg MASP-3 mAb 10D12, or 25 mg/kg MASP-3 mAb 10D12. The treatments occurred seven days apart from one another and blood was collected from the animals three days after the third injection. The blood was used to prepare serum, providing a matrix for hemolysis reactions. Erythrocytes ($2.5 \times 10^8$ cells/mL final) were added to 20% pooled serum from four mice in GVB+Mg/EGTA (20 nM). The mixtures were incubated at 37° C. and APC-mediated hemolysis was measured by diluting the reactions and measuring the absorbance (A405).

Figure 60:
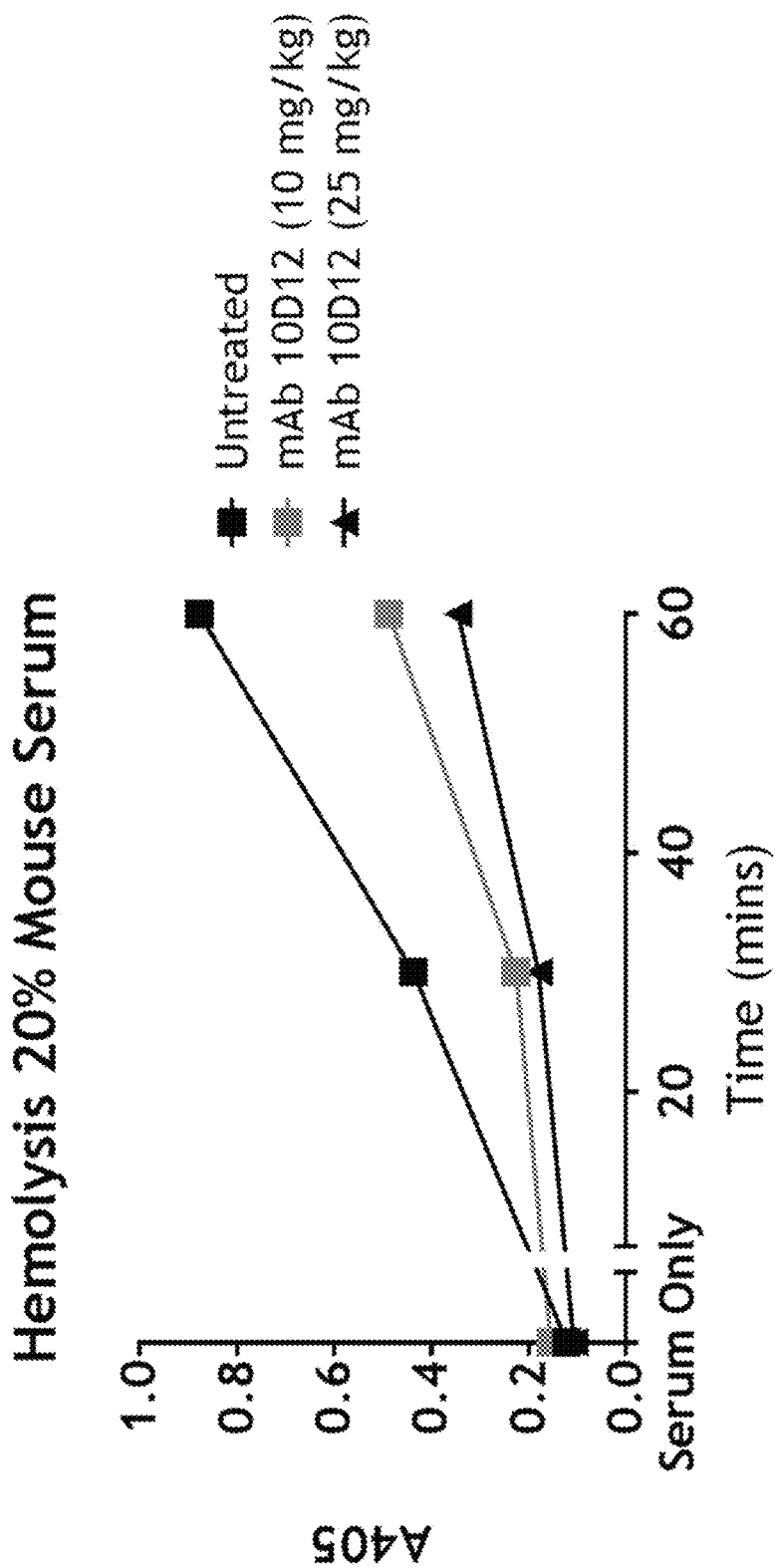
FIG. 60 graphically illustrates the level of inhibition of hemolysis by 20% serum from mice treated with high affinity MASP-3 mAb 10D12 (10 mg/kg or 25 mg/kg), as described in Example 17.

Results:

FIG. 60 graphically illustrates the level of inhibition of hemolysis by 20% serum from mice treated with MASP-3 mAb 10D12 (10 mg/kg or 25 mg/kg) or vehicle control treated mice. As shown in FIG. 60, serum from mice treated with MASP-3 mAb 10D12 at both 10 mg/kg and 25 mg/kg demonstrated less overall hemolysis during the 1 hour test period as compared to vehicle-treated mice.

Overall Summary of Results:

As described in this Example, representative high affinity MASP-3 inhibitory mAbs 13B1 and 10D12 inhibit the APC in vivo. As described in Example 12, it was determined that MASP-3 monoclonal antibody 13B1 (also referred to as mAb M3-1) provides a clear benefit to survival of red blood cells lacking Crry in a mouse model associated with paroxysmal nocturnal hemoglobinuria (PNH). As described in Example 13, it was determined that MASP-3 mAb M3-1 reduced the incidence and severity of clinical arthritis scores in a dose-dependent fashion.

Example 18

This Example describes the results of epitope binding analysis of high potency MASP-3 inhibitory mAbs.

1. Competition Binding Analysis

Methods:

96 well ELISA assay plates were coated with the capture antibody, αM3-259, an IgG4 isotype mAb which has been shown to bind the CCP1-CCP2 region of MASP-1 and MASP-3. The full-length human MASP-3 protein was immobilized on the plate via capture antibody αM3-259. In separate, non-coated wells, a 2-fold dilution series of one test MASP-3 mAb of an IgG4 isotype was mixed with a constant concentration of another test MASP-3 antibody of an IgG1 isotype. The mixture was added to the coated wells and allowed to bind to the captured MASP-3. Potential competition between the two antibodies was determined by the detection of the IgG1 isoform using an HRP-conjugated antibody against the human IgG1 hinge region (Southern Biotech 9052-05), and a TMB substrate reagent set (BD Biosciences 555214).

Results:

FIGS. 61A-61E graphically illustrate the results of the competition binding analysis.

Figure 61A:
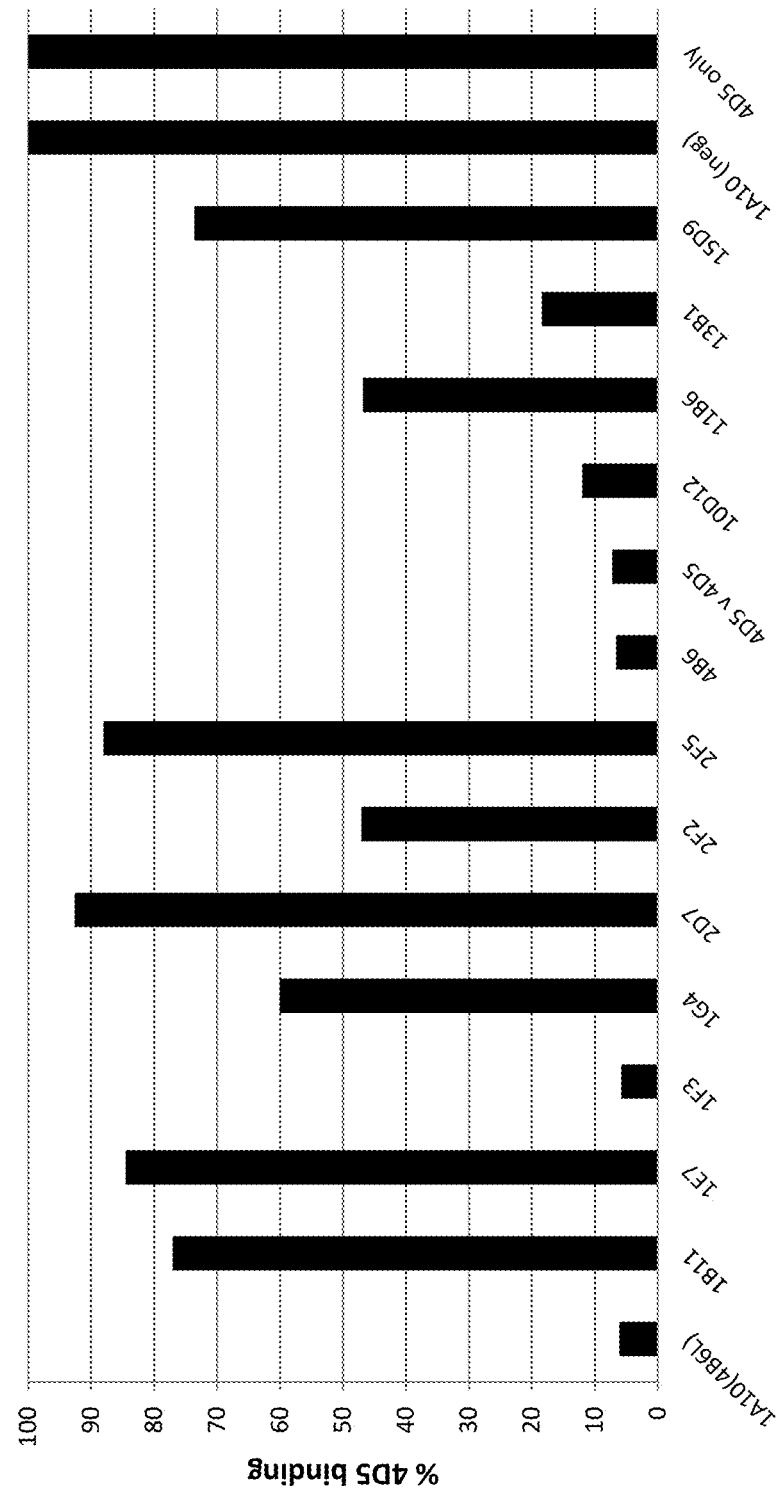
FIG. 61A graphically illustrates the results of competition binding analysis to identify high affinity MASP-3 mAbs that block the interaction between high affinity MASP-3 mAb 4D5 and human MASP-3, as described in Example 18.

FIG. 61A graphically illustrates the results of the competition binding analysis to identify MASP-3 mAbs (IgG4) that block the interaction between mAb 4D5 (IgG1) and human MASP-3.

Figure 61B:
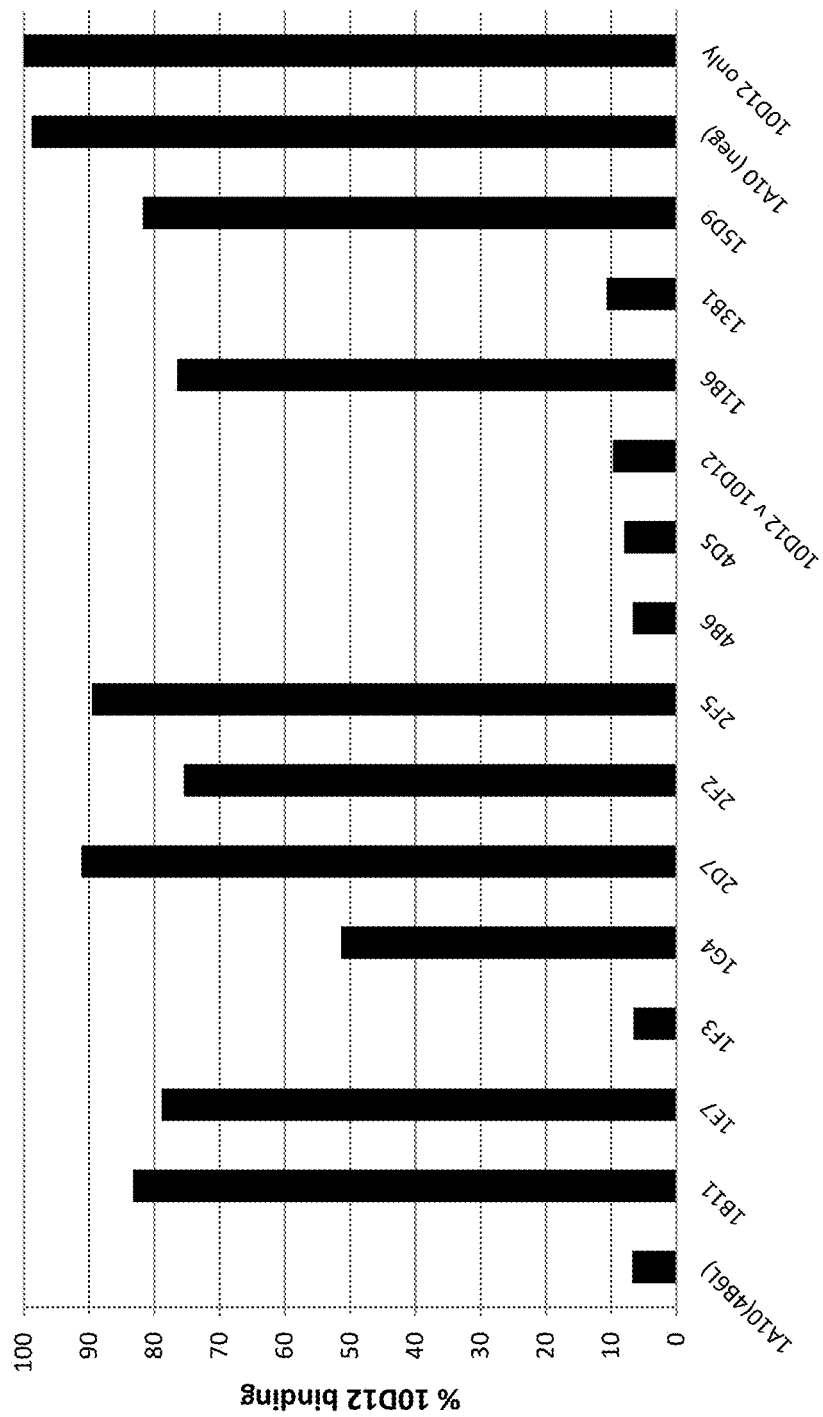
FIG. 61B graphically illustrates the results of competition binding analysis to identify high affinity MASP-3 mAbs that block the interaction between high affinity MASP-3 mAb 10D12 and human MASP-3, as described in Example 18.

FIG. 61B graphically illustrates the results of the competition binding analysis to identify MASP-3 mAbs (IgG4) that block the interaction between mAb 10D12 (IgG1) and human MASP-3.

Figure 61C:
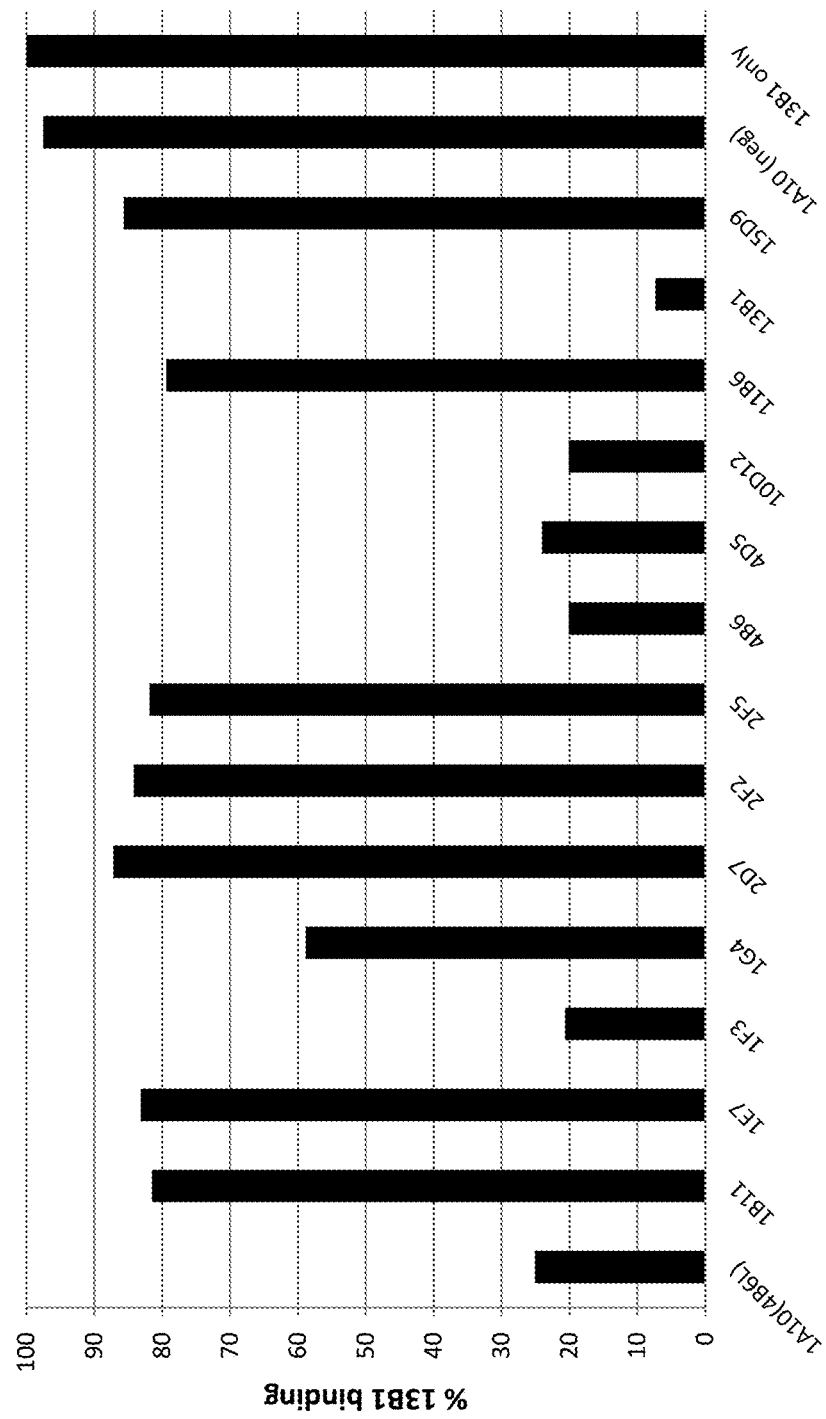
FIG. 61C graphically illustrates the results of competition binding analysis to identify high affinity MASP-3 mAbs that block the interaction between high affinity MASP-3 mAb 13B1 and human MASP-3, as described in Example 18.

FIG. 61C graphically illustrates the results of the competition binding analysis to identify MASP-3 mAbs (IgG4) that block the interaction between mAb 13B1 (IgG1) and human MASP-3.

FIG. 61D graphically illustrates the results of the competition binding analysis to identify MASP-3 mAbs (IgG4) that block the interaction between mAb 1F3 (IgG1) and human MASP-3.

Figure 61E:
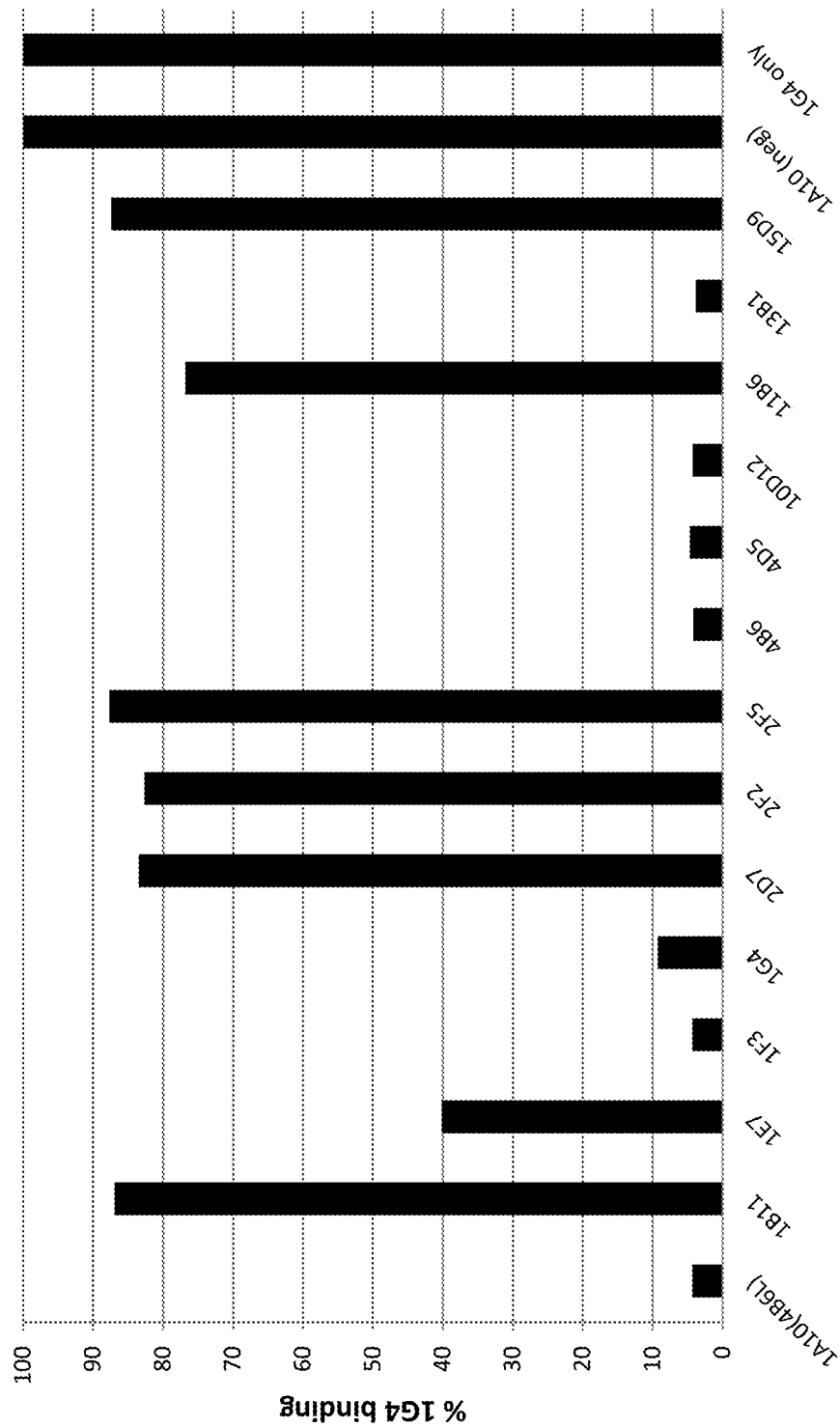
FIG. 61E graphically illustrates the results of competition binding analysis to identify high affinity MASP-3 mAbs that block the interaction between high affinity MASP-3 mAb 1G4 and human MASP-3, as described in Example 18.

FIG. 61E graphically illustrates the results of the competition binding analysis to identify MASP-3 mAbs (IgG4) that block the interaction between mAb 1G4 (IgG1) and human MASP-3.

The data from FIGS. 61A to 61E is summarized below in TABLE 28.

These data indicate that MASP-3 mAbs 4D5, 10D12, 13B1, 1A10, 1F3 and 1G4 share a common epitope or overlapping epitopes on human MASP-3. Surprisingly, 1G4 has a very limited capacity to block the binding of the other five mAbs to MASP-3, but those mAbs almost completely block the binding of 1G4 itself to MASP-3.

2. Analysis of mAb Binding to Peptides Representing Linear and Discontinuous MASP-3 Epitopes Methods:

Fourteen of the 16 MASP-3 mAbs were evaluated by Pepscan to identify the regions of MASP-3 to which they bind. To reconstruct both linear and potential discontinuous epitopes of the target molecule, a library of peptides was synthesized corresponding to amino acid residues 299 to 728 of SEQ ID NO:2 (human MASP-3). Amino acid residues 1-298 of MASP-3 were not present in the immunogen and were not included in this analysis.

Pepscan epitope analysis included use of the CLIPS technology, which structurally fixes peptides into defined three-dimensional structures (see Timmerman et al., *J Mol Recog.* 20:283-299, 2007 and Langedijk et al., *Analytical Biochemistry* 417:149-155, 2011). The binding of each antibody to each of the synthesized peptides was tested in a Pepscan-based ELISA.

Results:

The peptide binding results from Pepscan for each antibody analyzed is described below and summarized in TABLE 4, TABLE 28 and FIGS. 62-67.

Antibodies 1F3, 4B6, 4D5 and 1A10 (Group IA)

When tested under moderate stringency conditions, antibodies 1F3, 4B6, 4D5 and 1A10 bound discontinuous epitope mimics and also bound simple constrained and linear mimics. Data analysis demonstrates that antibodies 1F3, 4B6, 4D5 and 1A10 all dominantly recognize peptide stretch $_{498}$VLRSQRRDTTVI$_{509}$ (SEQ ID NO:9) of MASP-3. This peptide lies immediately adjacent to the active site histidine, H497. Data obtained for these antibodies with discontinuous mimics suggest that peptide stretches $_{544}$DFNIQNYNHDIALVQ$_{558}$ (SEQ ID NO:11), $_{639}$GNYSVTENMFC$_{649}$ (SEQ ID NO:13) and $_{704}$VSNYVDWVWE$_{713}$ (SEQ ID NO:14) of MASP-3 also contribute to the binding. Peptide $_{544}$DFNIQNYNHDIALVQ$_{558}$ (SEQ ID NO:11) contains the active site aspartate (D553).

Antibody 10D12 (Group IB)

When tested under moderate stringency conditions, antibody 10D12 bound peptides with core sequence $_{498}$VLRSQRRDTTVI$_{509}$ (SEQ ID NO:9) of MASP-3, the sequence adjacent to the active site histidine, H497.

Antibody 13B1 (Group IC)

When tested under moderate stringency conditions antibody 13B1 recognizes a discontinuous epitope comprising peptide stretches $_{494}$TAAHVLRSQRRDTTV$_{508}$ (SEQ ID NO:10) and $_{626}$PHAECKTSYESRS$_{638}$ (SEQ ID NO:12) of MASP-3, where peptide stretch $_{626}$PHAECKTSYESRS$_{638}$ (SEQ ID NO:12) appears to be the dominant part of the epitope as it can also be bound in simple constrained form. The peptide $_{494}$TAAHVLRSQRRDTTV$_{508}$ (SEQ ID NO:10) includes the active site histidine, H497.

Antibody 1G4 (Group II)

When tested under low stringency conditions antibody 1G4 recognizes a discontinuous epitope comprising peptide stretches $_{454}$RNAEPGLFPWQ$_{464}$ (SEQ ID NO:17), $_{514}$EHVTVYLGLH$_{523}$ (SEQ ID NO:19) and $_{667}$AFVIFDDLSQRW$_{678}$ (SEQ ID NO:23) of MASP-3, where peptide stretch $_{667}$AFVIFDDLSQRW$_{678}$ (SEQ ID NO:23) is the dominant part of the epitope. The dominant peptide lies within three amino acids of the active site serine, S664.

Antibodies 1E7 and 2D7 (Group IIIA)

When tested under high and low stringency conditions, respectively, antibodies 1E7 and 2D7 recognize a discontinuous epitope comprising peptide stretches $_{454}$RNAEPGLFPWQ$_{464}$ (SEQ ID NO:17), $_{514}$EHVTVYLGLH$_{523}$ (SEQ ID NO:19) and $_{667}$AFVIFDDLSQRW$_{678}$ (SEQ ID NO:23) of MASP-3, where peptide stretch $_{667}$AFVIFDDLSQRW$_{678}$ (SEQ ID NO:23) is the dominant part of the epitope and which lies within three amino acids of the active site serine, S664.

Antibodies 2F5 and 15D9 (Group IIIB)

When tested under low stringency conditions, antibodies 2F5 and 15D9 dominantly recognize a discontinuous epitope comprising peptide stretches $_{454}$RNAEPGLFPWQ$_{464}$ (SEQ ID NO:17), $_{479}$KWFGSGALLSASWIL$_{493}$ (SEQ ID NO:18), $_{562}$PVPLGPHVMP$_{571}$ (SEQ ID NO:20) and $_{667}$AFVIFDDLSQRW$_{678}$ (SEQ ID NO:23) of MASP-3. Peptides $_{479}$KWFGSGALLSASWIL$_{493}$ (SEQ ID NO:18) and $_{667}$AFVIFDDLSQRW$_{678}$ (SEQ ID NO:23) localize within four or three amino acids of the active site residues H497 and S664, respectively.

Antibody 1B11 (Group IIIC)

When tested under moderate stringency conditions, antibody 1B11 recognizes a discontinuous epitope comprising peptide stretches $_{435}$ECGQPSRSLPSLV$_{447}$ (SEQ ID NO:16), $_{454}$RNAEPGLFPWQ$_{464}$ (SEQ ID NO:17), $_{583}$APHMLGL$_{589}$ (SEQ ID NO:21) and $_{614}$SDVLQYVKLP$_{623}$ (SEQ ID NO:22) of MASP-3.

TABLE 28

Summary of Epitope Binding Analysis

| MASP-3 mAb Ref. No./Group | Peptide Binding Fragments (Epitopes) on human MASP-3 (w/leader) | Competes With | Peptide Cleavage Assay |
|---|---|---|---|
| 4D5 Group IA | $_{498}$VLRSQRRDTTVI$_{509}$ (SIN: 9)<br>$_{544}$DFNIQNYNHDIALVQ$_{558}$ (SIN: 11)<br>$_{639}$GNYSVTENMFC$_{649}$ (SIN: 13)<br>$_{704}$VSNYVDWVWE$_{713}$ (SIN: 14) | 1F3, 1G4, 4D5, 10D12, 13B1 | inhibits |
| 1F3 Group IA | $_{498}$VLRSQRRDTTVI$_{509}$ (SIN: 9)<br>$_{544}$DFNIQNYNHDIALVQ$_{558}$ (SIN: 11)<br>$_{639}$GNYSVTENMFC$_{649}$ (SIN: 13)<br>$_{704}$VSNYVDWVWE$_{713}$ (SIN: 14) | 1F3, 1G4, 4D5, 10D12, 13B1 | inhibits |
| 4B6 Group IA | $_{498}$VLRSQRRDTTVI$_{509}$ (SIN: 9)<br>$_{544}$DFNIQNYNHDIALVQ$_{558}$ (SIN: 11)<br>$_{639}$GNYSVTENMFC$_{649}$ (SIN: 13)<br>$_{704}$VSNYVDWVWE$_{713}$ (SIN: 14) | 1F3, 1G4, 4D5, 10D12, 13B1 | inhibits |
| 1A10 Group IA | $_{498}$VLRSQRRDTTVI$_{509}$ (SIN: 9)<br>$_{544}$DFNIQNYNHDIALVQ$_{558}$ (SIN: 11)<br>$_{639}$GNYSVTENMFC$_{649}$ (SIN: 13)<br>$_{704}$VSNYVDWVWE$_{713}$ (SIN: 14) | 1F3, 1G4, 4D5, 10D12, 13B1 | inhibits |
| 10D12 Group IB | $_{498}$VLRSQRRDTTVI$_{509}$ (SIN: 9) | 1F3, 1G4, 4D5, 10D12, 13B1 | inhibits |
| 13B1 Group IC | $_{494}$TAAHVLRSQRRDTTV$_{508}$ (SIN: 10)<br>$_{626}$PHAECKTSYESRS$_{638}$ (SIN: 12) | 1F3, 1G4, 4D5, 10D12, 13B1 | inhibits |
| Group I core sequence | $_{498}$VLRSQRRDTTV$_{508}$ (SIN: 15) | | |
| 1G4 Group II-cross competes with Group I and III | $_{454}$RNAEPGLFPWQ$_{464}$ (SIN: 17)<br>$_{514}$EHVTVYLGLH$_{523}$ (SIN: 19)<br>$_{667}$AFVIFDDLSQRW$_{678}$ (SIN: 23) | 1F3, 1G4, 4D5, 10D12, 13B1 | inhibits |
| 1E7 Group IIIA | $_{454}$RNAEPGLFPWQ$_{464}$ (SIN: 17)<br>$_{514}$EHVTVYLGLH$_{523}$ (SIN: 19)<br>$_{667}$AFVIFDDLSQRW$_{678}$ (SIN: 23) | 1G4 | Weakly inhibits |

TABLE 28-continued

Summary of Epitope Binding Analysis

| MASP-3 mAb Ref. No./Group | Peptide Binding Fragments (Epitopes) on human MASP-3 (w/leader) | Competes With | Peptide Cleavage Assay |
|---|---|---|---|
| 2D7 Group IIIA | $_{454}$RNAEPGLFPWQ$_{464}$ (SIN: 17) $_{514}$EHVTVYLGLH$_{523}$ (SIN: 19) $_{667}$AFVIFDDLSQRW$_{678}$ (SIN: 23) | | Weakly inhibits |
| 2F5 Group IIIB | $_{454}$RNAEPGLFPWQ$_{464}$ (SIN: 17) $_{479}$KWFGSGALLSASWIL$_{493}$ (SIN 18) $_{562}$PVPLGPHVMP$_{571}$ (SIN: 20) $_{667}$AFVIFDDLSQRW$_{678}$ (SIN: 23) | | No effect |
| 15D9 Group IIIB | $_{454}$RNAEPGLFPWQ$_{464}$ (SIN: 17) $_{479}$KWFGSGALLSASWIL$_{493}$ (SIN 18) $_{562}$PVPLGPHVMP$_{571}$ (SIN: 20) $_{667}$AFVIFDDLSQRW$_{678}$ (SIN: 23) | | No effect |
| 1B11 Group IIIC | $_{435}$ECGQPSRSLPSLV$_{447}$ (SIN: 16) $_{454}$RNAEPGLFPWQ$_{464}$ (SIN: 17) $_{583}$APHMLGL$_{589}$ (SIN: 21) $_{614}$SDVLQYVKLP$_{623}$ (SIN: 22) | | stimulates |
| Core sequence for Group II and Group III | $_{454}$RNAEPGLFPWQ$_{464}$ (SIN: 17) | | |
| 2F2 Group IV | Binding epitope not determined | 1F3, 4D5, 11B6, 2F2 | stimulates |
| 11B6 Group IV | Binding epitope not determined | 1F3, 4D5, 11B6, 2F2 | No effect |

Figure 62:
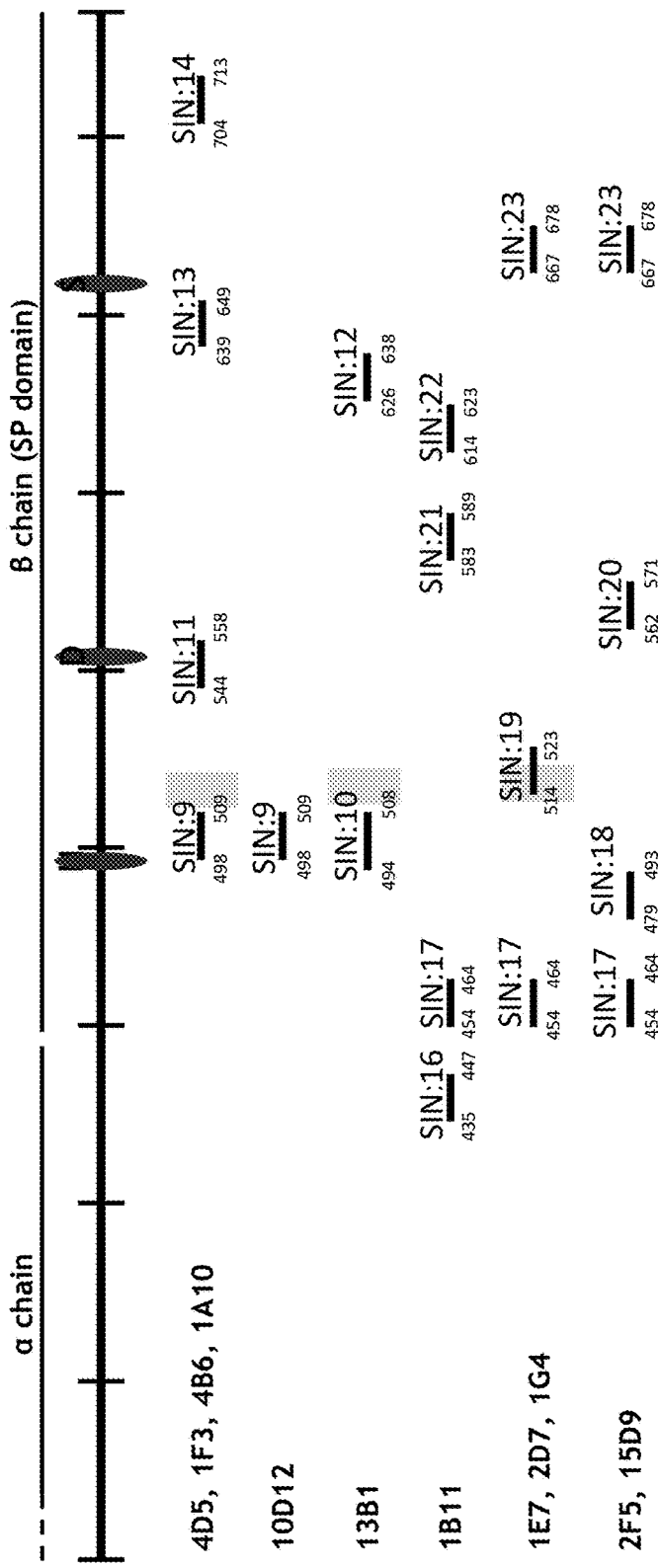
FIG. 62 provides a schematic diagram showing the regions of contact on human MASP-3 by the high affinity MASP-3 mAbs, as determined by Pepscan analysis, as described in Example 18.

FIG. 62 provides a schematic diagram showing the regions of contact on human MASP-3 by the MASP-3 mAbs, as determined by Pepscan Analysis. As shown in FIG. 62, all of the MASP-3 mAbs have regions of contact in the beta chain containing the SP domain of MASP-3. One mAb, 1B11, also has a region of contact between the CCP2 and SP domains in the alpha chain of MASP-3.

FIGS. 63A to 67 show 3-D models illustrating the regions of contact of the high affinity MASP-3 mAbs on the CCP1/2/SP domains of human MASP-3, wherein the SP domain active site of MASP-3 is facing towards the front and the catalytic triad is shown as side chains.

Figure 63A:
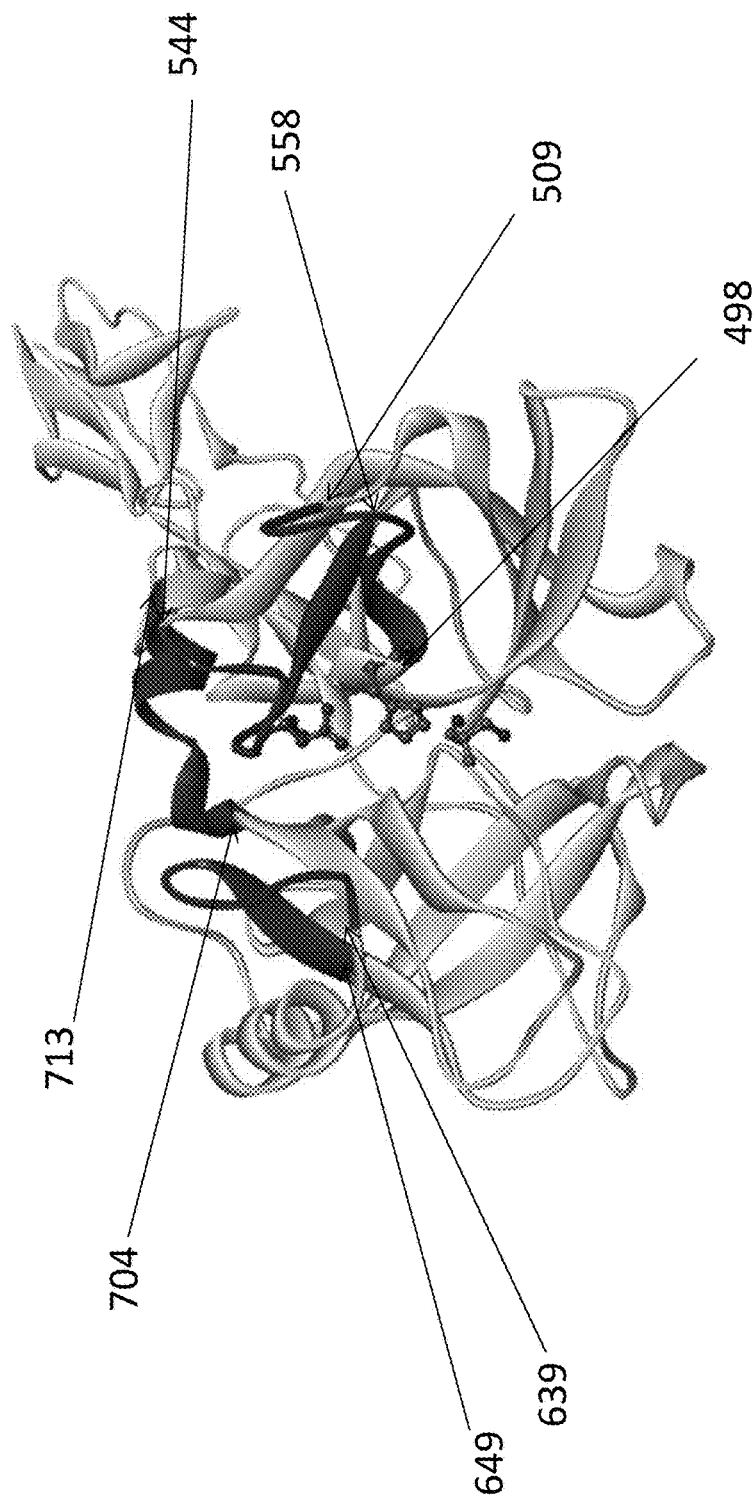
FIG. 63A shows the regions of contact between human MASP-3 and high affinity MASP-3 mAbs 1F3, 4D5 and 1A10, including amino acid residues 498-509 (SEQ ID NO:9), amino acid residues 544-558 (SEQ ID NO:11), amino acid residues 639 to 649 (SEQ ID NO:13) and amino acid residues 704 to 713 (SEQ ID NO:14) of MASP-3, as described in Example 18.

FIG. 63A shows the regions of contact between human MASP-3 and high affinity MASP-3 mAbs 1F3, 4D5 and 1A10, including aa residues 498-509 (SEQ ID NO:9), aa residues 544-558 (SEQ ID NO:11), aa residues 639 to 649 (SEQ ID NO:13) and aa residues 704 to 713 (SEQ ID NO:14).

Figure 63B:
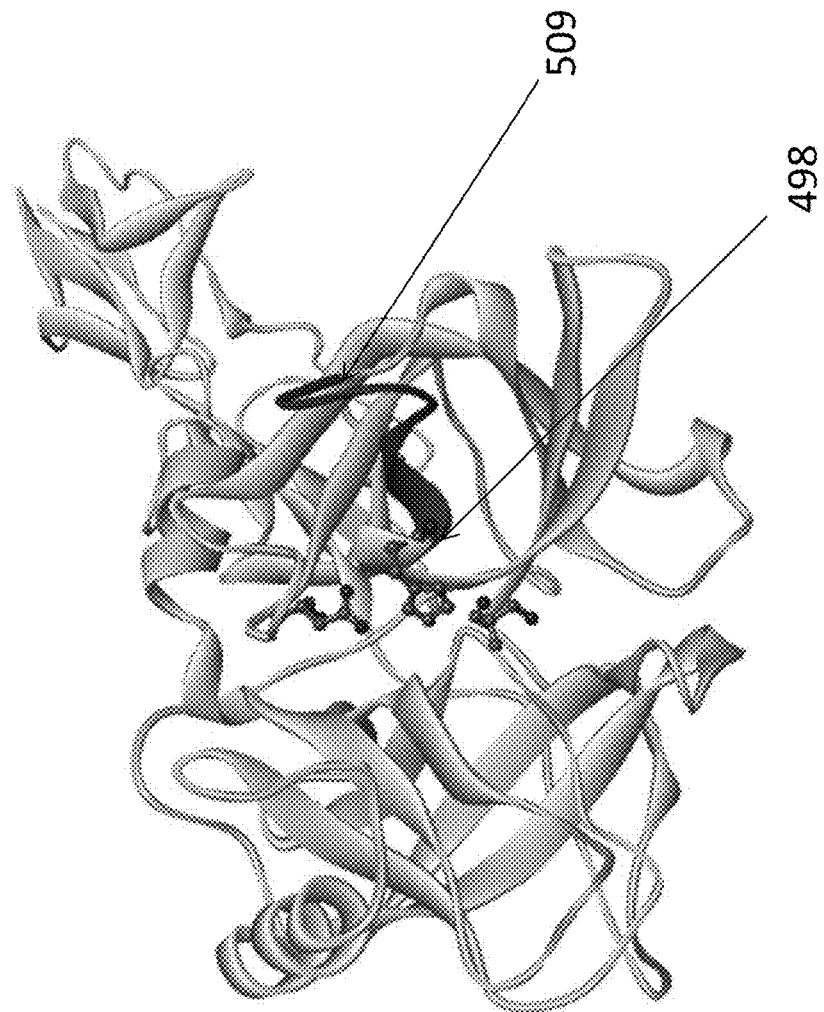
FIG. 63B shows the regions of contact between human MASP-3 and high affinity MASP-3 mAb 10D12, including amino acid residues 498 to 509 (SEQ ID NO:9) of MASP-3, as described in Example 18.

FIG. 63B shows the regions of contact between human MASP-3 and high affinity MASP-3 mAb 10D12, including aa residues 498 to 509 (SEQ ID NO:9).

Figure 64:
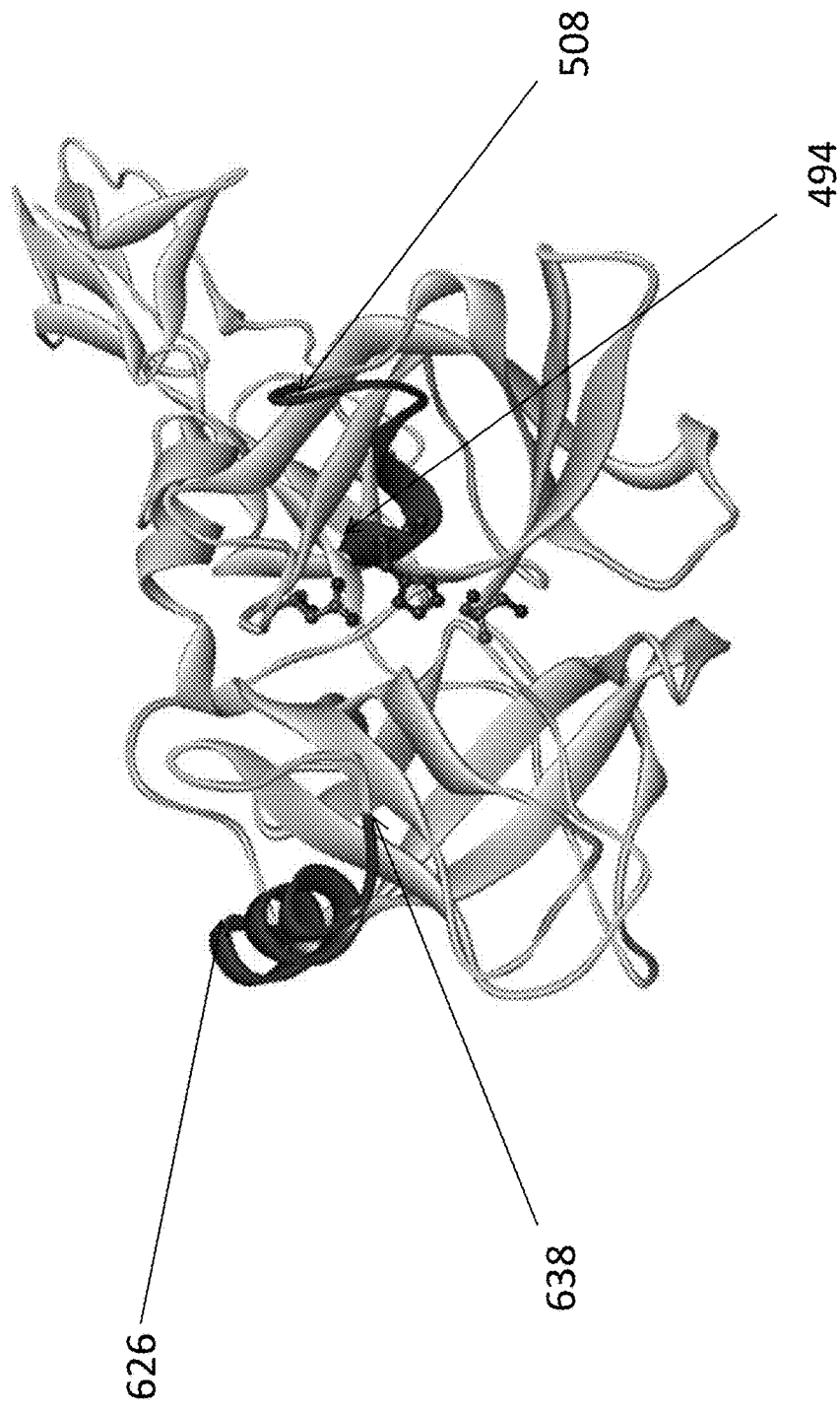
FIG. 64 shows the regions of contact between human MASP-3 and high affinity MASP-3 mAb 13B1, including amino acid residues 494 to 508 (SEQ ID NO:10) and amino acid residues 626 to 638 (SEQ ID NO: 12) of MASP-3, as described in Example 18.

FIG. 64 shows the regions of contact between human MASP-3 and high affinity MASP-3 mAb 13B1, including aa residues 494 to 508 (SEQ ID NO:10) and aa residues 626 to 638 (SEQ ID NO: 12).

Figure 65:
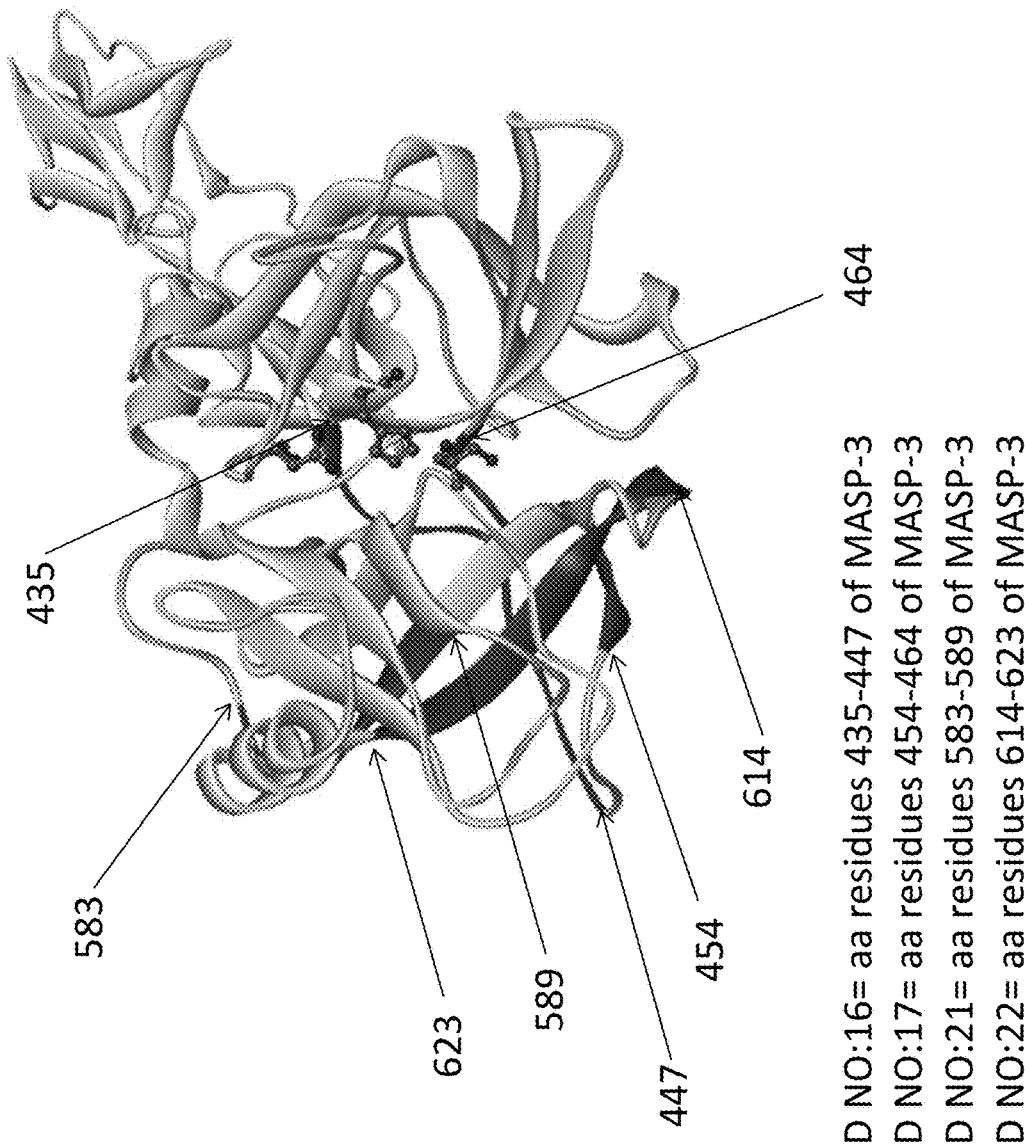
FIG. 65 shows the regions of contact between human MASP-3 and high affinity MASP-3 mAb 1B11, including amino acid residues 435 to 447 (SEQ ID NO:16), amino acid residues 454 to 464 (SEQ ID NO:17), amino acid residues 583 to 589 (SEQ ID NO:21) and amino acid residues 614 to 623 (SEQ ID NO:22) of MASP-3, as described in Example 18.

FIG. 65 shows the regions of contact between human MASP-3 and high affinity MASP-3 mAb 1B11, including aa residues 435 to 447 (SEQ ID NO:16), aa residues 454 to 464 (SEQ ID NO:17) and aa residues 583 to 589 (SEQ ID NO:21) and aa residues 614 to 623 (SEQ ID NO:22).

Figure 66:
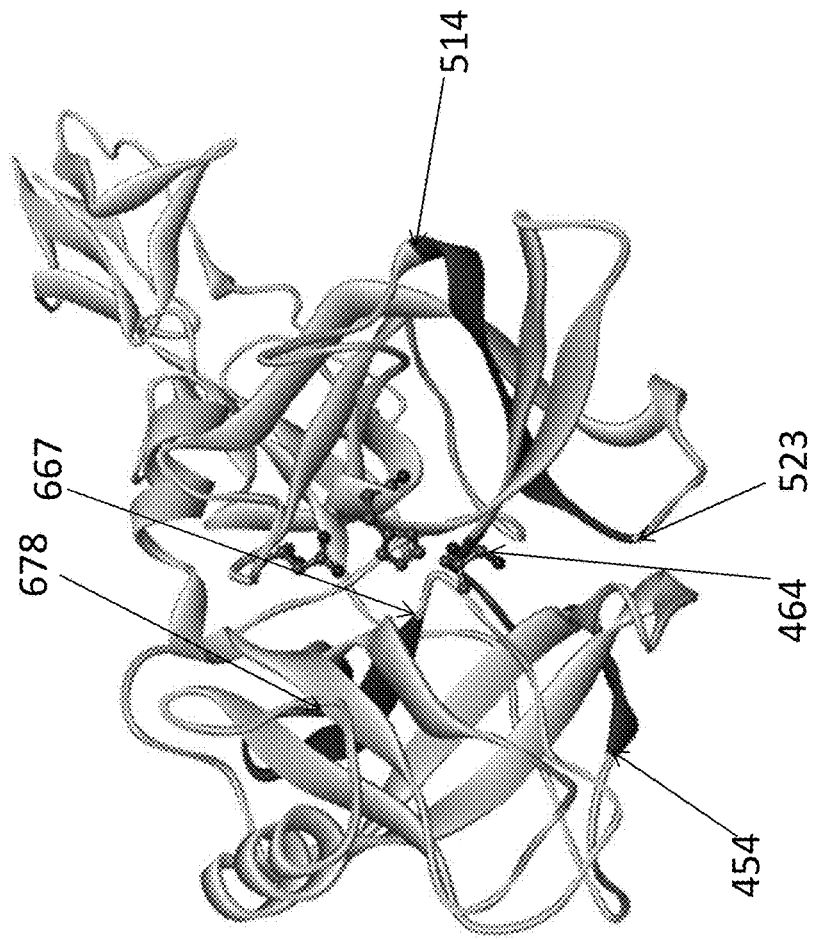
FIG. 66 shows the regions of contact between human MASP-3 and high affinity MASP-3 mAbs 1E7, 1G4 and 2D7, including amino acid residues 454 to 464 (SEQ ID NO:17), amino acid residues 514 to 523 (SEQ ID NO:19) and amino acid residues 667 to 678 (SEQ ID NO:23) of MASP-3, as described in Example 18.

FIG. 66 shows the regions of contact between human MASP-3 and high affinity MASP-3 mAbs 1E7, 1G4 and 2D7, including aa residues 454 to 464 (SEQ ID NO:17), aa residues 514 to 523 (SEQ ID NO:19) and aa residues 667 to 678 (SEQ ID NO:23).

Figure 67:
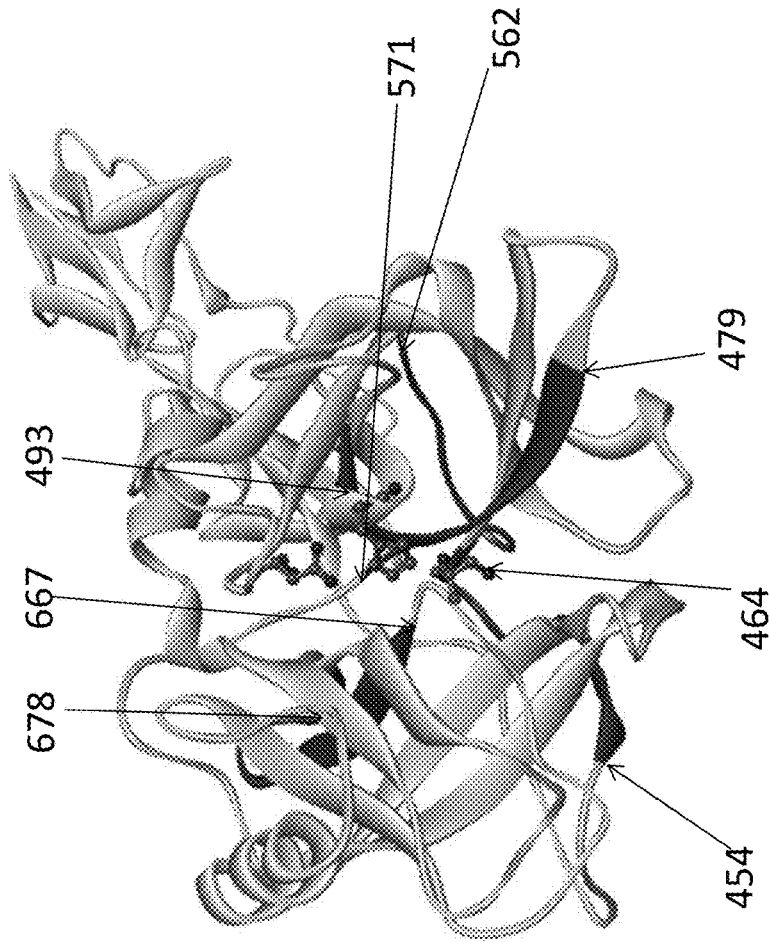
FIG. 67 shows the regions of contact between human MASP-3 and high affinity MASP-3 mAbs 15D9 and 2F5, including amino acid residues 454 to 464 (SEQ ID NO:17), amino acid residues 479 to 493 (SEQ ID NO:18), amino acid residues 562 to 571 (SEQ ID NO:20), and amino acid residues 667 to 678 (SEQ ID NO:23) of MASP-3, as described in Example 18.

FIG. 67 shows the regions of contact between human MASP-3 and high affinity MASP-3 mAbs 15D9 and 2F5, including aa residues 454 to 464 (SEQ ID NO:17), aa residues 479 to 493 (SEQ ID NO:18), aa residues 562 to 571 (SEQ ID NO:20), and aa residues 667 to 678 (SEQ ID NO:23).

In summary, conclusive binding profiles were obtained for 12 of the 14 antibodies. All 12 mapped antibodies recognized solvent exposed epitopes within the peptidase S1 domain. The close proximity of a number of the epitope determinants to residues for the active site catalytic triad (H497, D553, S664) is consistent with a model in which the high affinity inhibitory MASP-3 mAbs block enzymatic activity by interfering with the enzyme-substrate interaction.

Example 19

This Example describes the humanization of representative MASP-3 mAbs and engineering of potential post-translational modification sites.

Methods:

1. Humanization of Representative High Affinity MASP-3 mAbs

Methods:

To reduce immunogenicity risk, representative high affinity MASP-3 inhibitory antibodies 4D5, 10D12 and 13B1 were humanized by a CDR-grafting method. CDRS of each MASP-3 antibody were grafted into the closest consensus human framework sequences. Some of the Vernier zone residues were modified by Quickchange site-directed mutagenesis (Agilent Technologies). The resulting humanized VH and VL regions were transferred into pcDNA3.1-based human IgG1 or IgG4 and IgK expression contructs, and the recombinant antibodies were expressed and purified as described above. Affinity of the humanized antibodies was determined by ELISA using monovalent Fab fragments, and potency was assessed by C3 deposition assay using intact IgG4 formats.

Results:

Amino acid sequences of representative humanized versions of the heavy chain variable regions and light chain variable regions for mAbs 4D5, 10D12 and 13B1 are provided below. The CDRs (Kabat) are underlined.

4D5:
h4D5_VH-14
(SEQ ID NO: 248)
QVQLVQSGAEVKKPGASVKVSCKASGYTFT<u>TDDIN</u>WVRQAPGQGLEWI

<u>GWIYPRDDRTKYNDKFKD</u>KATLTVDTSSNTAYMELSSLRSEDTAVYYC

SS<u>LEDTY</u>WGQGTLVTVSS h4D5_VH-19
(SEQ ID NO: 249)
QVQLVQSGAEVKKPGASVKVSCKASGYTFT<u>TDDIN</u>WVRQAPGQGLEWI

<u>GWIYPRDDRTKYNDKFKD</u>RATLTVDTSSNTAYMELSSLRSEDTAVYYC

SS<u>LEDTY</u>WGQGTLVTVSS h4D5_VL-1
(SEQ ID NO: 250)
DIVMTQSPDSLAVSLGERATINC<u>KSSQSLLNSRTRKNYLA</u>WYQQKPGQ

PPKLLIY<u>WASTRES</u>GVPDRFSGSGSGTDFTLTISSLQAEDVAVYYC<u>KQ

SYNLYT</u>FGQGTKVEIKR

10D12:
h10D12_VH-45
(SEQ ID NO: 251)
QIQLVQSGSELKKPGASVKVSCKASGYIFT<u>SYGMS</u>WVRQAPGKGLKWM

<u>GWINTYSGVPTYADDFKG</u>RFVFSLDTSVRTPYLQISSLKAEDTAVYFC

AR<u>GGEAMDY</u>WGQGTLVTVSS h10D12_VH-49
(SEQ ID NO: 252)
QIQLVQSGSELKKPGASVKVSCKASGYIFT<u>SYGMS</u>WVRQAPGKGLKWM

<u>GWINTYSGVPTYADDFKG</u>RFVFSLDTSVRTPYLQISSLKAEDTATYFC

AR<u>GGEAMDY</u>WGQGTLVTVSS h10D12_VL-21
(SEQ ID NO: 253)
DVLMTQTPLSLSVTPGQPASISC<u>KSSQSLLDSDGKTYLN</u>WLLQRPGQS

PKRLIY<u>LVSKLDS</u>GVPDRFSGSGSGTDFTLKISRVEAEDVGVYYC<u>WQG

THFPWT</u>FGQGTKVEIKR

13B1
h13B1_VH-9
(SEQ ID NO: 254)
QVQLVQSGAEVKKPGASVKVSCKASGYTFT<u>GKWIE</u>WVRQAPGQGLEWI

<u>GEILPGTGSTNYAQKFQG</u>RATFTADSSTSTAYMELSSLRSEDTAVYYC

LR<u>SEDV</u>WGQGTLVTVSS h13B1_VH-10
(SEQ ID NO: 255)
QVQLVQSGAEVKKPGASVKVSCKASGYTFT<u>GKWIE</u>WVRQAPGQGLEWI

<u>GEILPGTGSTNYNEKFKG</u>RATFTADSSTSTAYMELSSLRSEDTAVYYC

LR<u>SEDV</u>WGQGTLVTVSS h13B1_VL-1
(SEQ ID NO: 256)
DIVMTQSPDSLAVSLGERATINC<u>KSSQSLLNSRTRKNYLA</u>WYQQKPGQ

PPKLLIY<u>WASTRES</u>GVPDRFSGSGSGTDFTLTISSLQAEDVAVYYC<u>KQ

SYNIPT</u>FGQGTKVEIKR

The affinity of representative humanized 4D5, 10D12 and 13B1 antibodies for human MASP-3 is shown below in TABLE 29.

TABLE 29

Binding of Representative humanized MASP-3 mAbs to MASP-3

| MASP-3 antibody clone (Fab format) | Binding to human MASP-3 $EC_{50}$ (nM) |
|---|---|
| 4D5 Parental Fab | 0.107 |
| h4D5_14-1 Fab (VH-14 and VL-1) | 0.085 |
| h4D5_19-1 Fab (VH-19 and VL-1) | 0.079 |
| 10D12 Parental Fab | 0.108 |
| h10D12_45-21 Fab (VH-45 and VL-21) | 0.108 |
| h10D12_49-21 Fab (VH-49 and VL-21) | 0.115 |
| 13B1 Parental Fab | 0.123 |
| h13B1_9-1 Fab (VH-9 and VL-1) | 0.101 |
| h13B1_10-1 Fab (VH-10 and VL-1) | 0.097 |

The percent identity of humanized framework sequences to those of human germline framework sequences:
h4D5_VH-14=90%; h4D5_VH-19=91%; h4D5_VL-1=100%;
h10D12_VH-45=92%; h10D12_VH-49=91%; h10D12_VL-21=93%;
h13B1_VH-9=95%; h13B1_VH-10=94%; h13B1_VL-1=100%

2. Mutagenesis of Representative MASP-3 mAbs to Remove Asn/Asp Modification Sites in CDR-1 of the Light Chain Variable Region of 4D5, 10D12 and 13B1

Representative high affinity MASP-3 inhibitory mAbs 4D5, 10D12 and 13B1 were analyzed for post-translational modification. Asparagine residues with a succeeding Glycine, Serine, Histidine, Alanine or Asparagine ("NG", "NS", "NH", "NA", or "NN" motif) are often susceptible to the hydrolysis of the amide group of Asparagine side-chain, or "deamidation." Aspartic acid residues with a succeeding Glycine or Proline ("DG" or "DP" motif) are often susceptible to the interconversion, or "isomerization." Such modifications result in charge heterogeneity and may affect antibody function if they occur in a binding interface. They also may increase risks of fragmentation, immunogenicity and aggregation.

Potential post-translational modification motifs were identified in CDR-1 of the light chain variable regions of 4D5, 10D12 and 13B1.

4D5 and 13B1 contained one possible Asn deamidation site in CDR1 of the light chain (shown as "NS" at positions 8 and 9 of SEQ ID NO:142 underlined in TABLE 30 below. As further shown below in Table 30, 10D12 contained one possible Asp isomerization site in CDR1 of the light chain. Variants of the humanized version of these MASP-3 mAbs were generated by site-directed mutagenesis as shown in TABLE 30. The variants were expressed and purified as described above. Affinity was determined by ELISA using monovalent Fab fragments, and potency was assessed by C3 deposition assay using intact IgG4 formats as described above.

TABLE 30

Variants of CDR-L1 for 4D5, 10D12 and 13B1

| Antibody | Region | Sequence |
|---|---|---|
| 4D5 parent | LC-CDR1 | KSSQSLLNSRTRKNYLA (SEQ ID NO: 142) |
| 4D5-NQ mutant | LC-CDR1 | KSSQSLLQSRTRKNYLA (SEQ ID NO: 257) |
| 4D5-NA mutant | LC-CDR1 | KSSQSLLASRTRKNYLA (SEQ ID NO: 258) |
| 4D5-ST mutant | LC-CDR1 | KSSQSLLNTRTRKNYLA (SEQ ID NO: 259) |
| 13B1 parent | LC-CDR1 | KSSQSLLNSRTRKNYLA (SEQ ID NO: 142) |
| 13B1-NQ | LC-CDR1 | KSSQSLLQSRTRKNYLA (SEQ ID NO: 257) |
| 13B1-NA | LC-CDR1 | KSSQSLLASRTRKNYLA (SEQ ID NO: 258) |
| 13B1-ST | LC-CDR1 | KSSQSLLNTRTRKNYLA (SEQ ID NO: 259) |
| Consensus for 4D5, 13B1 and variants | LC-CDR1 | KSSQSLLXXRTRKNYLA (SEQ ID NO: 260) Wherein X at position 8 is N, Q or A; and wherein X at position 9 is S or T |
| 10D12 parent | LC-CDR1 | KSSQSLLDSDGKTYLN (SEQ ID NO: 153) |
| 10D12-DE mutant | LC-CDR1 | KSSQSLLDSEGKTYLN (SEQ ID NO: 261) |
| 10D12-DA mutant | LC-CDR1 | KSSQSLLDSAGKTYLN (SEQ ID NO: 262) |
| 10D12-GA mutant | LC-CDR1 | KSSQSLLDSDAKTYLN (SEQ ID NO: 263) |
| 35C1 | LC-CDR1 | KSSQSLLDSDGKTYLS (SEQ ID NO: 159) |
| Consensus of 10D12, 35C1 and variants | LC-CDR1 | KSSQSLLDSXXKTYLX (SEQ ID NO: 215) Wherein X at position 10 is D, E or A; Wherein X at position 11 is G or A; and wherein X at position 16 is N or S |

TABLE 31

Binding of mutagenized candidates of humanized 4D5, 10D12 and 13B1 mAbs to human MASP-3

| MASP-3 antibody clone (Fab format) | Binding to human MASP-3 $EC_{50}$ (pM) |
|---|---|
| h4D5_19-1 parental Fab (VH-19 and VL-1) | 102 |
| h4D5-19-1-NQ Fab (VH-19 and VL-1-NQ) | 732 |
| h4D5-19-1-NA Fab (VH-19 and VL-1-NA) | 122 |
| h4D5-19-1-ST Fab (VH-19 and VL-1-ST) | 151 |
| h10D12_45-21 parental Fab (VH-45 and VL-21) | 108 |
| h10D12-45-21-DE Fab (VH-45 and VL-21-DE) | 326 |
| h10D12-45-21-DA Fab (VH-45 and VL-21-DA) | 294 |
| h10D12-45-21-GA Fab (VH-45 and VL-21-GA) | 181 |
| h13B1_10-1 parental Fab (VH-10 and VL-1) | 100 |
| h13B1_10-1-NQ Fab (VH-10 and VL-1-NQ) | 138 |
| H13B1_10-1-NA Fab (VH-10 and VL-1-NA) | 105 |
| h13B1_10-1-ST Fab (VH-10 and VL-1-ST) | 120 |

TABLE 32

MASP-3 Antibody humanized VH Sequences (CDRs and FR regions, Kabat)

| Antibody | HC FR1 | HC CDR1 |
|---|---|---|
| 4D5 parent (SIN: 24) | QVQLKQSGPELVKPGA SVKLSCKASGYTFT (SEQ ID NO: 55) | TDDIN (SEQ ID NO: 56) |
| h4D5_VH-14 (SIN: 248) | QVQLVQSGAEVKKPGA SVKVSCKASGYTFT (SEQ ID NO: 264) | TDDIN (SEQ ID NO: 56) |
| h4D5_VH-19 (SIN: 249) | QVQLVQSGAEVKKPGA SVKVSCKASGYTFT (SEQ ID NO: 264) | TDDIN (SEQ ID NO: 56) |
| 10D12 parent (SIN: 28) | QIQLVQSGPELKKPGE TVKISCKASGYIFT (SEQ ID NO: 71) | SYGMS (SEQ ID NO: 72) |
| h10D12_VH-45 (SIN: 251) | QIQLVQSGSELKKPGA SVKVSCKASGYIFT (SEQ ID NO: 269) | SYGMS (SEQ ID NO: 72) |
| h10D12-VH-49 (SIN: 252) | QIQLVQSGSELKKPGA SVKVSCKASGYIFT (SEQ ID NO: 269) | SYGMS (SEQ ID NO: 72) |
| 13B1 parent (SIN: 30) | QVQLKQSGAELMKPGA SVKLSCKATGYTFT (SEQ ID NO: 83) | GKWIE (SEQ ID NO: 84) |
| h13B1_VH-9 (SIN: 254) | QVQLVQSGAEVKKPGA SVKVSCKASGYTFT (SEQ ID NO: 273) | GKWIE (SEQ ID NO: 84) |

TABLE 32-continued

MASP-3 Antibody humanized VH Sequences
(CDRs and FR regions, Kabat)

| Antibody | | |
|---|---|---|
| h13B1_VH-10 (SIN: 255) | QVQLVQSGAEVKKPGA SVKVSCKASGYTFT (SEQ ID NO: 273) | GKWIE (SEQ ID NO: 84) |
| | HC FR2 | HC CDR2 |
| 4D5 parent | WVKQRPGQGLEWIG (SEQ ID NO: 57) | WIYPRDDRTKYNDKFKD (SEQ ID NO: 58) |
| h4D5_VH-14 | WVRQAPGQGLEWIG (SEQ ID NO: 265) | WIYPRDDRTKYNDKFKD (SEQ ID NO: 58) |
| h4D5_VH-19 | WVRQAPGQGLEWIG (SEQ ID NO: 265) | WIYPRDDRTKYNDKFKD (SEQ ID NO: 58) |
| 10D12 parent | WVRQAPGKGLKWMG (SEQ ID NO: 73) | WINTYSGVPTYADDFKG (SEQ ID NO: 74) |
| h10D12_VH-45 | WVRQAPGKGLKWMG (SEQ ID NO: 73) | WINTYSGVPTYADDFKG (SEQ ID NO: 74) |
| h10D12-VH-49 | WVRQAPGKGLKWMG (SEQ ID NO: 73) | WINTYSGVPTYADDFKG (SEQ ID NO: 74) |
| 13B1 parent | WVKQRPGHGLEWIG (SEQ ID NO: 85) | EILPGTGSTNYNEKFKG (SEQ ID NO: 86) |
| h13B1_VH-9 | WVRQAPGQGLEWIG (SEQ ID NO: 274) | EILPGTGSTNYAQKFQG (SEQ ID NO: 275) |
| h13B1_VH-10 | WVRQAPGQGLEWIG (SEQ ID NO: 274) | EILPGTGSTNYNEKFKG (SEQ ID NO: 86) |
| | HC FR3 | HC CDR3 |
| 4D5 parent | KATLTVDTSSNTAYMD LHSLTSEDSAVYFCSS (SEQ ID NO: 59) | LEDTY (SEQ ID NO: 60) |
| h4D5_VH-14 | KATLTVDTSSNTAYME LSSLRSEDTAVYYCSS (SEQ ID NO: 266) | LEDTY (SEQ ID NO: 60) |
| h4D5_VH-19 | RATLTVDTSSNTAYME LSSLRSEDTAVYYCSS (SEQ ID NO: 267) | LEDTY (SEQ ID NO: 60) |
| 10D12 parent | RFAFSLETSARTPYLQ INNLKNEDTATYFCAR (SEQ ID NO: 75) | GGEAMDY (SEQ ID NO: 76) |
| h10D12_VH-45 | RFVFSLDTSVRTPYLQ ISSLKAEDTAVYFCAR (SEQ ID NO: 270) | GGEAMDY (SEQ ID NO: 76) |
| h10D12-VH-49 | RFVFSLDTSVRTPYLQ ISSLKAEDTATYFCAR (SEQ ID NO: 271) | GGEAMDY (SEQ ID NO: 76) |
| 13B1 parent | KATFTADSSSNTAYMQ LSSLTTEDSAMYYCLR (SEQ ID NO: 87) | SEDV (SEQ ID NO: 88) |
| h13B1_VH-9 | RATFTADSSTSTAYME LSSLRSEDTAVYYCLR (SEQ ID NO: 276) | SEDV (SEQ ID NO: 88) |
| h13B1_VH-10 | RATFTADSSTSTAYME LSSLRSEDTAVYYCLR (SEQ ID NO: 276) | SEDV (SEQ ID NO: 88) |

TABLE 32-continued

MASP-3 Antibody humanized VH Sequences
(CDRs and FR regions, Kabat)

| Antibody | |
|---|---|
| | HC FR4 |
| 4D5 parent | WGQGTLVAVSS (SEQ ID NO: 61) |
| h4D5_VH-14 | WGQGTLVTVSS (SEQ ID NO: 268) |
| h4D5_VH-19 | WGQGTLVTVSS (SEQ ID NO: 268) |
| 10D12 parent | WGQGTSVTVSS (SEQ ID NO: 77) |
| h10D12_VH-45 | WGQGTLVTVSS (SEQ ID NO: 272) |
| h10D12-VH-49 | WGQGTLVTVSS (SEQ ID NO: 272) |
| 13B1 parent | WGTGTTVTVSS (SEQ ID NO: 89) |
| h13B1_VH-9 | WGQGTLVTVSS (SEQ ID NO: 277) |
| h13B1_VH-10 | WGQGTLVTVSS (SEQ ID NO: 277) |

Representative Humanized Light Chain Variable Regions with Variants:

h4D5_VL-1-NA
(SEQ ID NO: 278)
DIVMTQSPDSLAVSLGERATINCKSSQSLLASRTRKNYLAWYQQKP
GQPPKLLIYWASTRESGVPDRFSGSGSGTDFTLTISSLQAEDVAVY
YCKQSYNLYTFGQGTKVEIKR h10D12_VL-21-GA
(SEQ ID NO: 279)
DVLMTQTPLSLSVTPGQPASISCKSSQSLLDSDAKTYLNWLLQRPG
QSPKRLIYLVSKLDSGVPDRFSGSGSGTDFTLKISRVEAEDVGVYY
CWQGTHFPWTFGQGTKVEIKR h13B1_VL-1-NA
(SEQ ID NO: 280)
DIVMTQSPDSLAVSLGERATINCKSSQSLLASRTRKNYLAWYQQKP
GQPPKLLIYWASTRESGVPDRFSGSGSGTDFTLTISSLQAEDVAVY
YCKQSYNIPTFGQGTKVEIKR

TABLE 33

MASP-3 Antibody humanized VL Sequences
(CDRs and FR regions, Kabat)
[plus variants in LC-CDR1]

| Antibody | | |
|---|---|---|
| | LC FR1 | LC CDR1 |
| 4D5 parent (SIN: 40) | DIVMTQSPSSLAVSAG EKVTMTC (SEQ ID NO: 141) | KSSQSLLNSRTRKNYLA (SEQ ID NO: 142) |

TABLE 33-continued

MASP-3 Antibody humanized VL Sequences (CDRs and FR regions, Kabat) [plus variants in LC-CDR1]

| Antibody | | |
|---|---|---|
| h4D5_VL-1 (SIN: 250) | DIVMTQSPDSLAVSLG ERATINC (SEQ ID NO: 281) | KSSQSLLNSRTRKNYLA (SEQ ID NO: 142) |
| h4D5_VL-1-NA (SIN: 278) | DIVMTQSPDSLAVSLG ERATINC (SEQ ID NO: 281) | KSSQSLLASRTRKNYLA (SEQ ID NO: 258) |
| 10D12 parent (SIN: 43) | DVLMTQTPLTLSVTIG QPASISC (SEQ ID NO: 152) | KSSQSLLDSDGKTYLN (SEQ ID NO: 153) |
| h10D12_VL-21 (SIN: 253) | DVLMTQTPLSLSVTPG QPASISC (SEQ ID NO: 285) | KSSQSLLDSDGKTYLN (SEQ ID NO: 153) |
| h10D12_VL-21-GA (SIN: 279) | DVLMTQTPLSLSVTPG QPASISC (SEQ ID NO: 285) | KSSQSLLDSDAKTYLN (SEQ ID NO: 263) |
| 13B1 parent | DIVMTQSPSSLAVSAG EKVTMSC (SEQ ID NO: 151) | KSSQSLLNSRTRKNYLA (SEQ ID NO: 142) |
| h13B1_VL-1 | DIVMTQSPDSLAVSLG ERATINC (SEQ ID NO: 281) | KSSQSLLNSRTRKNYLA (SEQ ID NO: 142) |
| h13B1_VL-1-NA | DIVMTQSPDSLAVSLG ERATINC (SEQ ID NO: 281) | KSSQSLLASRTRKNYLA (SEQ ID NO: 258) |

| | LC FR2 | LC CDR2 |
|---|---|---|
| 4D5 parent | WYQQKPGQSPKLLIY (SEQ ID NO: 143) | WASTRES (SEQ ID NO: 144) |
| h4D5_VL-1 | WYQQKPGQPPKLLIY (SEQ ID NO: 282) | WASTRES (SEQ ID NO: 144) |
| h4D5_VL-1-NA | WYQQKPGQPPKLLIY (SEQ ID NO: 282) | WASTRES (SEQ ID NO: 144) |
| 10D12 parent | WLLQRPGQSPKRLIY (SEQ ID NO: 154) | LVSKLDS (SEQ ID NO: 155) |
| h10D12_VL-21 | WLLQRPGQSPKRLIY (SEQ ID NO: 154) | LVSKLDS (SEQ ID NO: 155) |
| h10D12_VL-21-GA | WLLQRPGQSPKRLIY (SEQ ID NO: 154) | LVSKLDS (SEQ ID NO: 155) |
| 13B1 parent | WYQQKPGQSPKLLIY (SEQ ID NO: 143) | WASTRES (SEQ ID NO: 144) |
| h13B1_VL-1 | WYQQKPGQPPKLLIY (SEQ ID NO: 282) | WASTRES (SEQ ID NO: 144) |
| h13B1_VL-1-NA | WYQQKPGQPPKLLIY (SEQ ID NO: 282) | WASTRES (SEQ ID NO: 144) |

| | LC FR3 | LC CDR3 |
|---|---|---|
| 4D5 parent | GVPDRFTGSGSGTDFS LTISSVQAEDLAVYYC (SEQ ID NO: 145) | KQSYNLYT (SEQ ID NO: 146) |
| h4D5_VL-1 | GVPDRFSGSGSGTDFT LTISSLQAEDVAVYYC (SEQ ID NO: 283) | KQSYNLYT (SEQ ID NO: 146) |
| h4D5_VL-1-NA | GVPDRFSGSGSGTDFT LTISSLQAEDVAVYYC (SEQ ID NO: 283) | KQSYNLYT (SEQ ID NO: 146) |
| 10D12 parent | GVPDRFTGSGSGTDFT LKISRVEAEDLGVYYC (SEQ ID NO: 156) | WQGTHFPWT (SEQ ID NO: 157) |
| h10D12_VL-21 | GVPDRFSGSGSGTDFT LKISRVEAEDVGVYYC (SEQ ID NO: 286) | WQGTHFPWT (SEQ ID NO: 157) |
| h10D12_VL-21-GA | GVPDRFSGSGSGTDFT LKISRVEAEDVGVYYC (SEQ ID NO: 286) | WQGTHFPWT (SEQ ID NO: 157) |
| 13B1 parent | GVPDRFTGSGSGTDFT LTISSVQAEDLAVYYC (SEQ ID NO: 150) | KQSYNIPT (SEQ ID NO: 161) |
| h13B1_VL-1 | GVPDRFSGSGSGTDFT LTISSLQAEDVAVYYC (SEQ ID NO: 283) | KQSYNIPT (SEQ ID NO: 161) |
| h13B1_VL-1-NA | GVPDRFSGSGSGTDFT LTISSLQAEDVAVYYC (SEQ ID NO: 283) | KQSYNIPT (SEQ ID NO: 161) |

| | LC FR4 |
|---|---|
| 4D5 parent | FGGGTKLEIKR (SEQ ID NO: 147) |
| h4D5_VL-1 | FGQGTKVEIKR (SEQ ID NO: 284) |
| h4D5_VL-1-NA | FGQGTKVEIKR (SEQ ID NO: 284) |
| 10D12 parent | FGGGTKLEIKR (SEQ ID NO: 147) |
| h10D12_VL-21 | FGQGTKVEIKR (SEQ ID NO: 287) |
| h10D12_VL-21-GA | FGQGTKVEIKR (SEQ ID NO: 287) |
| 13B1 parent | FGGGTKLEIKR (SEQ ID NO: 147) |
| h13B1_VL-1 | FGQGTKVEIKR (SEQ ID NO: 284) |
| h13B1_VL-1-NA | FGQGTKVEIKR (SEQ ID NO: 284) |

Example 20

Analysis of a representative MASP-3 inhibitory mAb 13B1 in a mouse model of multiple sclerosis.

Background/Rationale:

Experimental autoimmune encephalomyelitis (EAE), an acquired inflammatory and demyelinating autoimmune disorder, is an established animal model of multiple sclerosis (MS). Evidence suggesting that the APC plays a significant role in the development/progression of EAE was provided by reports that the disease is attenuated in mice treated with a Factor B-neutralizing antibody (Hu et al., *Mol. Immunol.*

54:302, 2013). This Example describes the analysis of a representative high affinity MASP-3 inhibitory antibody, 13B1, in the EAE model.

Methods:

EAE Induction:

A kit for inducing EAE, purchased from Hooke Laboratories (Lawrence, Mass.) was used to induce EAE in this study. This kit contained the neuroantigen $MOG_{35-55}$ in Complete Freund's Adjuvant (CFA) as well as pertussis toxin.

30 wild-type C57 Bl/6J female mice were used for this study and were acclimated to the facility for at least one week prior to EAE induction. The mice were approximately 10 weeks of age at the time of induction. As shown in TABLE 34 below, at the time of induction, each mouse received two 100 μL subcutaneous (sc) injections of MOG35-55 and one intraperitoneal (ip) injection of 100 μL (400 ng) pertussis toxin. A second injection of pertussis toxin was administered 24 hours after the first.

Treatment:

The 30 mice were divided into three groups of 10 and treated with an irrelevant isotype control mAb 10 mg/kg i.v.); mAb 13B1 (anti-MASP-3, 10 mg/kg i.v.) or mAb 1379 (anti-Factor B (Hu et al., *Mol. Immunol.* 54:302, 2013) 40 mg/kg i.p.). As shown in TABLE 34, dosing with the isotype control mAb and MASP-3 mAb 13B1 occurred weekly beginning at Day −16 and ending on Day +12. Dosing with mAb 1379 occurred every other day from Day +3 to Day +11, according to the dosing schedule described in Hu et al., *Mole Immunol* 54:302-308, (2013).

TABLE 34

Experimental Methods for EAE Experiment with MASP-3 mAb 13B1

| Day of Administration | Pertussis Toxin 400 ng i.p. | MOG peptide 35-55 250 μg | mAb 1379 (anti-Factor B) 40 mg i.p. | Isotype Control mAb 10 mg/kg i.v. | mAb 13B1 (anti-MASP-3) 10 mg/kg i.v. |
|---|---|---|---|---|---|
| −16 | | | | + | + |
| −9 | | | | + | + |
| −2 | | | | + | + |
| 0 | + | + | | | |
| +1 | + | | | | |
| +3 | | | + | | |
| +5 | | | + | + | + |
| +7 | | | + | | |
| +9 | | | + | | |
| +11 | | | + | | |
| +12 | | | | + | + |

Scoring:

The mice were checked every other day until the emergence of symptoms, after which they were checked daily. The first signs of disease appeared 7-12 days after immunization, as expected. The mice were scored according to the scale shown below in TABLE 35.

TABLE 35

EAE Model Scoring Criteria

| Score | Clinical Observations |
|---|---|
| 0.0 | No obvious changes in motor functions of the mouse in comparison to non-immunized mice. When picked up by the base of the tail, the tail has tension and is erect. Hind legs are usually spread apart. When the mouse is walking, there is no gait or head tilting. |
| 0.5 | Tip of tail is limp. When the mouse is picked up by the base of the tail, the tail has tension except for the tip. Muscle straining is felt in the tail, while the tail continues to move. |
| 1.0 | Limp tail. When mouse is picked up by the base of the tail, instead of being erect, the whole tail drapes over finger. Hind legs are usually spread apart. No signs of tail movement are observed. |
| 1.5 | Limp tail and hind leg inhibition. When picked up by the base of the tail, the whole tail drapes over finger. When the mouse is dropped on a wire rack, at least one hind leg falls through consistently. Walking is very slightly wobbly. |
| 2.0 | Limp tail and weakness of hind legs. When picked up by the base of the tail, the legs are not spread apart, but held close together. When the mouse is observed walking, it has a clearly apparent wobbly walk. One foot may have toes dragging, but the other leg has no apparent inhibitions of movement; OR, Mouse appears to be at score 0.0, but there are obvious signs of head tilting when the walk is observed. The balance is poor. |
| 2.5 | Limp tail and dragging of hind legs. Both hind legs have some movement, but both are dragging at the feet (mouse trips on hind feet). - OR- No movement in one leg/completely dragging one leg, but movement in the other leg.- OR - EAE severity appears mild when picked up (as score 0.0-1.5), but there is a strong head tilt that causes the mouse to occasionally fall over. |

TABLE 35-continued

EAE Model Scoring Criteria

| Score | Clinical Observations |
|---|---|
| 3.0 | Limp tail and complete paralysis of hind legs (most common). - OR - Limp tail and almost complete paralysis of hind legs. One or both hind legs are able to paddle, but neither hind leg is able to move forward of the hind hip. - OR - Limp tail with paralysis of one front and one hind leg. - OR - ALL of: Severe head tilting, walking only along the edges of the cage, pushing against the cage wall, spinning when picked up by base of tail. |
| 3.5 | Limp tail and complete paralysis of hind legs. In addition to: Mouse is moving around the cage, but when placed on its side, is unable to right itself. Hind legs are together on one side of body. - OR - Mouse is moving around the cage, but the hind quarters are flat like a pancake, giving the appearance of a hump in the front quarters of the mouse |
| 4.0 | Limp tail, complete hind leg and partial front leg paralysis. Mouse is minimally moving around the cage but appears alert and feeding. Often euthanasia is recommended after the mouse scores 4.0 for 2 days. However, with daily s.c. fluids some mice can recover to 3.5 or 3.0. When the mouse is euthanized because of severe paralysis, a score of 5.0 is entered for that mouse for the rest of the experiment. |
| 4.5 | Complete hind and partial front leg paralysis, no movement around the cage. Mouse is not alert. Mouse has minimal movement in the front legs. The mouse barely responds to contact. Euthanasia is recommended. When the mouse is euthanized because of severe paralysis, a score of 5.0 is entered for that mouse for the rest of the experiment. |
| 5.0 | Mouse is spontaneously rolling in the cage. |

Figure 68:
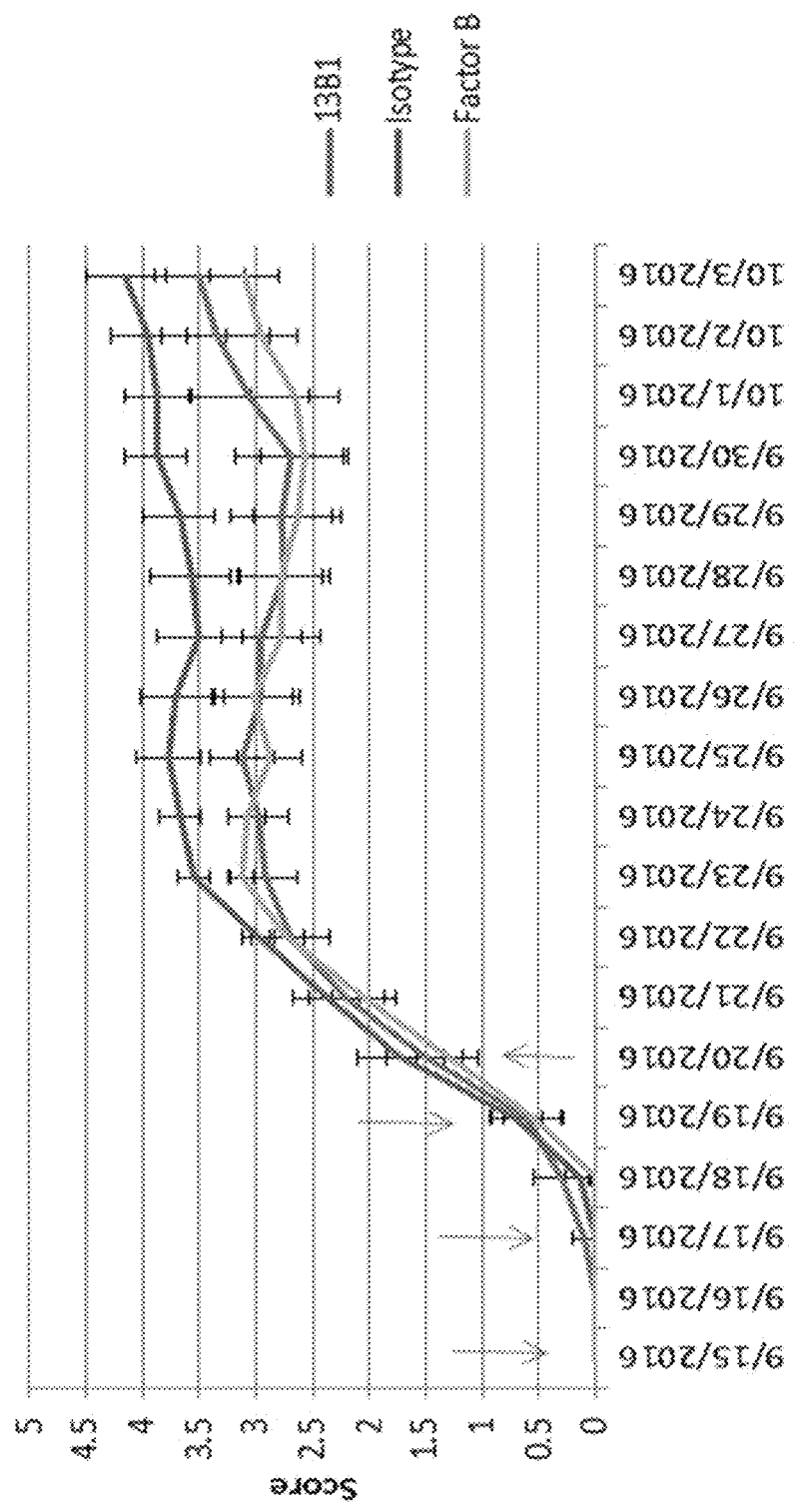
FIG. 68 graphically illustrates the results of the Experimental autoimmune encephalomyelitis (EAE) model in mice treated with either high affinity MASP-3 inhibitory mAb 13B1 (10 mg/kg), Factor B mAb 1379 (30 mg/kg) or isotype control mAb (10 mg/kg), as described in Example 20.

Results:

FIG. 68 graphically illustrates the results of the EAE model in mice treated with either MASP-3 inhibitory mAb 13B1 (10 mg/kg), Factor B mAb 1379 (40 mg/kg) or isotype control mAb (10 mg/kg), wherein downward pointing arrows indicate dosing of anti-Factor B antibody and upward pointing arrows indicates the last dose of mAb 13B1. As shown in FIG. 68, mice treated with MASP-3 inhibitory mAb 13B1 and Factor B mAb 1379 exhibited an improvement in clinical symptoms scored according to the parameters shown in TABLE 35, as compared to isotype control.

In accordance with the foregoing, MASP-3 inhibitory antibodies, such as the high affinity MASP-3 inhibitory antibodies disclosed herein, are expected to be beneficial (neuroprotective or neuroregenerative) in the treatment and/or rehabilitation of a subject suffering from multiple sclerosis, Balo concentric sclerosis, neuromyelitis optica, Marburg multiple sclerosis, Schilder's disease, Tumefactive multiple sclerosis and acute disseminated encephalomyelitis (ADM).

Example 21

Pharmacodynamic Study with Representative high affinity MASP-3 mAbs in Cynomolgus Monkeys.

Background/Rationale:

As was demonstrated in rodent studies (FIG. 44), a high affinity MASP-3 inhibitory antibody was capable of inhibiting steady-state (resting) pro-factor D maturation in vivo. This Example describes a study that was carried out in cynomolgus monkeys to determine if representative high affinity MASP-3 inhibitory mAbs are capable of inhibiting APC activity in a non-human primate.

Methods:

To confirm that MASP-3 functions in the APC in a non-human primate, and that the high affinity MASP-3 antibodies are capable of inhibiting the APC in a non-human primate, 9 cynomolgus monkeys (3 animals per mAb condition) were given a single 5 mg/kg intravenous dose with one of three representative high affinity MASP-3 inhibitory antibodies: h4D5X, h10D12X, or h13B1X. ("h" refers to humanized, "X" refers to the IgG4 constant hinge region (SEQ ID NO:312) containing the stabilizing S228P amino acid substitution and a mutation human IgG4 constant region with S228P mutation and also a mutation that promotes FcRn interations at low pH). Plasma (EDTA) and serum samples were collected at regular intervals over a period of three weeks or longer.

Two assays were employed to measure APC activity in the sera from treated monkeys. The first assay assessed levels of complement factor Bb deposited on zymosan beads added to diluted serum. The second assay measured the fluid phase products of the zymosan-activated APC, complement factors Ba and Bb, as well as C3a.

Flow cytometry using the factor Bb antibody A252 (Quidel) was used to detect factor Bb deposited on zymosan. As a means for determining the background signal in the assay following complete inhibition of the APC, an aliquot of serum (5% final, diluted in GVB+Mg/EGTA) prepared from MASP-3 mAb-treated cynomolgus monkeys was spiked with 300 nM of an inhibitory Factor D antibody. To determine the degree of APC inhibition by the MASP-3 mAb delivered intravenously to the monkey, another aliquot of diluted serum was spiked with 300 nM of a neutral isotype control antibody (that has no APC inhibitory activity) before testing factor Bb deposition on zymosan. The spiked antibody-serum mixtures were incubated for 30 minutes on ice prior to the addition of zymosan (0.1 mg/mL final). The mixtures were incubated at 37° C. for 65 minutes, and the APC activity was measured by the flow cytometric detection of complement factor Bb (Quidel antibody A252) on the surface of the zymosan particles.

For determining generation of the fluid phase markers Ba, Bb, and C3a, the APC was induced in ex vivo assays by incubating zymosan (1 mg/mL final) in serum (5% final, diluted in GVB+Mg/EGTA) prepared from anti-MASP-3 mAb-treated cynomolgus monkeys. The mixtures were incubated at 37° C. for 40 minutes, and the APC activity was measured by ELISA-based detection of the complement end-points. Ba, Bb, and C3a were detected in the reaction supernatants using commercially available ELISA kits (Quidel). Absorbance values of all tests were normalized by setting pre-treatment values as 100% activity, and a pre-treatment sample incubated, but not exposed to zymosan, to 0%.

In order to relate the degree of APC inhibition to the antibody to target ratio in MASP-3 mAb-treated monkeys, serum MASP-3 and inhibitory MASP-3 mAb levels were quantitated. Serum MASP-3 was measured by a sandwich ELISA assay. The MASP-3 protein was captured on a plate with αM3-259 (described in Example 16). Serum samples (diluted 1:40) were first incubated with unlabeled (non-biotinylated) MASP-3 mAb, corresponding to the treatment mAb, at 37° C. for 1 hour, then further diluted 1:250 (final 1:10,000) and added to the plate and incubated at 37° C. for another hour. The plate was washed and a biotinylated version of mAb 10D12 was used as a detection antibody. The large dilution of serum prior to the detection steps was used to uncouple target and treatment mAb, and to prevent competition between the treatment antibody and the detection antibody. After the plate was washed multiple times, streptavidin-HRP was used for the final detection step. Absorbance values were collected at A450 with a plate reader. MASP-3 serum concentrations were extrapolated from a standard curve created by assaying recombinant, full-length cyno MASP-3 protein. The amount of anti-MASP-3 antibody present in the serum was detected using the Human Therapeutic IgG4 ELISA Kit (Cayman Chemicals), following the manufacturer's instructions.

Western blot analysis was used to analyze the level of pro-Factor D and Factor D in serum from a cynomolgus monkey over time (hours) after treatment with a single 5 mg/kg intravenous dose of mAb h13B1X. Briefly described, the Western blot analysis was carried out by mixing 20 of cynomolgus plasma obtained at the different timepoints prior to treatment (−120 hr, −24 hr) and after treatment (72 hr, 168 hr, 336 hr, 504 hr, 672 hr and 840 hr) with PBS and 11.2 µL of anti-CFD antibody (0.5 µg/µL) in a total volume of 400 µL at 4° C. for 1 hour. 12 µL of Protein A/G Plus Agarose (Santa Cruz Biotech) was added and the mixture was incubated overnight at 4° C. Immunoprecipitates were collected by centrifugation at 1000×g for 5 minutes at 4° C. The pellets were washed five times with PBS. After the final wash, the pellets were resuspended in 30 µL of 1× Glycoprotein Denaturing Buffer and the glycoprotein was denatured by heating the reaction at 100° C. for 10 minutes. 10×G2 reaction buffer, 10% NP-40 and 2.5 µL Peptide-N-Glycosidase (New England Biolabs, P0704L) was added into each tube and the reaction was incubated at 37° C. for 2 hours. The agarose beads were pelleted by centrifugation at 1000×g for 5 minutes and 20 µL supernatant was collected into new tubes. The captured and deglycosylated proteins were resolved with SDS-PAGE (NuPAGE 12% Bis-Tris Mini Gel) and the gels were electroblotted for Western blot analysis with a biotinylated anti-CFD (R&D Systems BAF1824) and Pierce™ High Sensitivity Streptavidin-HRP (Thermo Fischer Scientific 21130).

Figure 69:
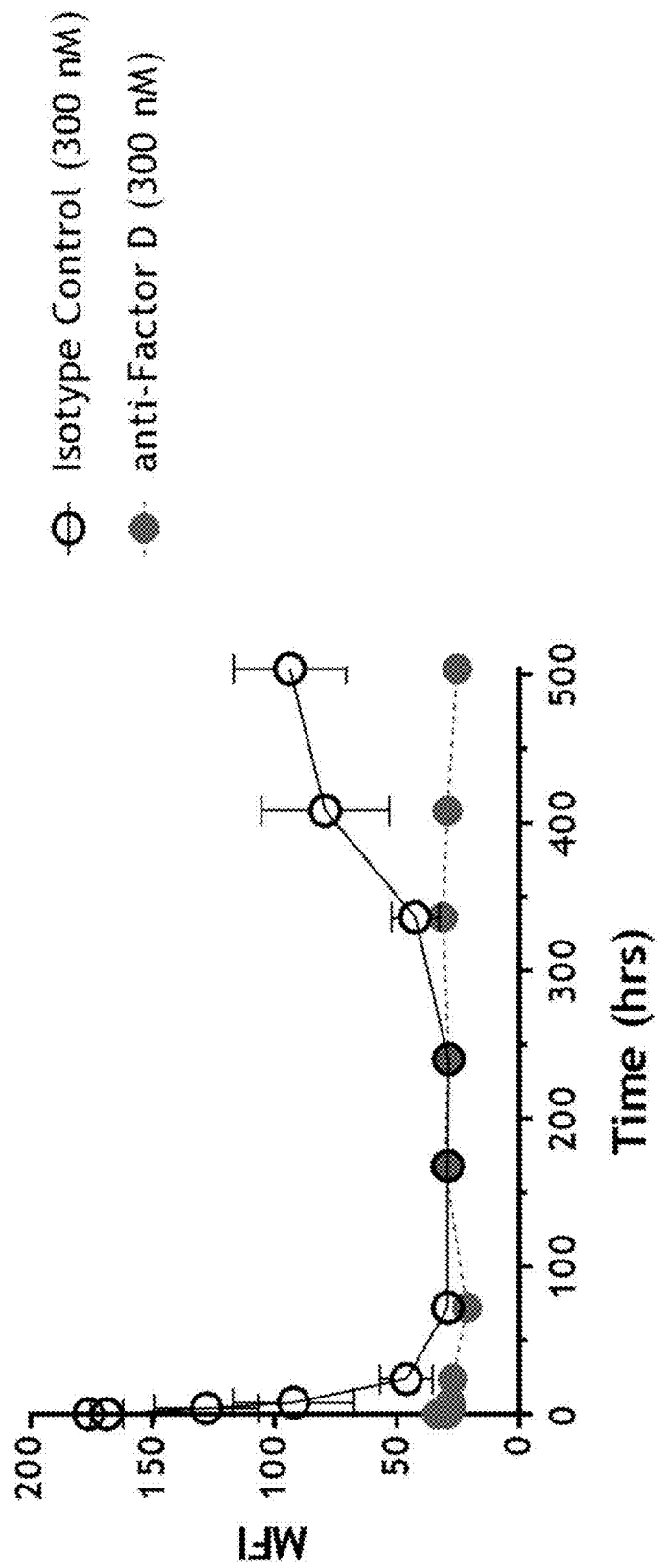
FIG. 69 graphically illustrates APC activity, as determined by the average MFI in a flow cytometric assay detecting complement factor Bb on the surface of zymosan particles, in serum samples obtained from a group of three cynomolgus monkeys over time after treatment with high affinity MASP-3 mAb h13B1X, either in the presence or absence of anti-factor D antibody spiked into the serum sample, as described in Example 21.

Results:

FIG. 69 graphically illustrates APC activity in serum samples obtained from a group of three cynomolgus monkeys over time after a single treatment at time=0 with high affinity MASP-3 mAb h13B1X. The figure shows the average MFI in a flow cytometric assay detecting complement factor Bb on the surface of zymosan particles in 5% serum spiked with either the APC-inhibiting fact D mAb or the neutral isotype control mAb. As shown in FIG. 69, the animals demonstrate diminished APC activity as early as 4 hrs. If MASP-3 antibody treatment blocks the APC as effectively as Factor D inhibition, the two spiked antibody conditions will demonstrate identical levels of inhibition of Bb deposition in post-dose samples, but not in the pre-dose (or time=0; FIG. 69) condition. As shown in FIG. 69, by 72 hrs post-treatment, the APC activity is decreased to approximately that achieved by adding the Factor D mAb to the serum samples. Nearly complete inhibition due to h13B1X treatment, as experimentally determined by comparison with the spiked Factor D antibody, persists until 336 hrs (14 days) post-dose. Thus, these results demonstrate that treatment with a high affinity MASP-3 inhibitory mAb provides a complete, sustained inhibition of the APC in a non-human primate.

Figure 70:
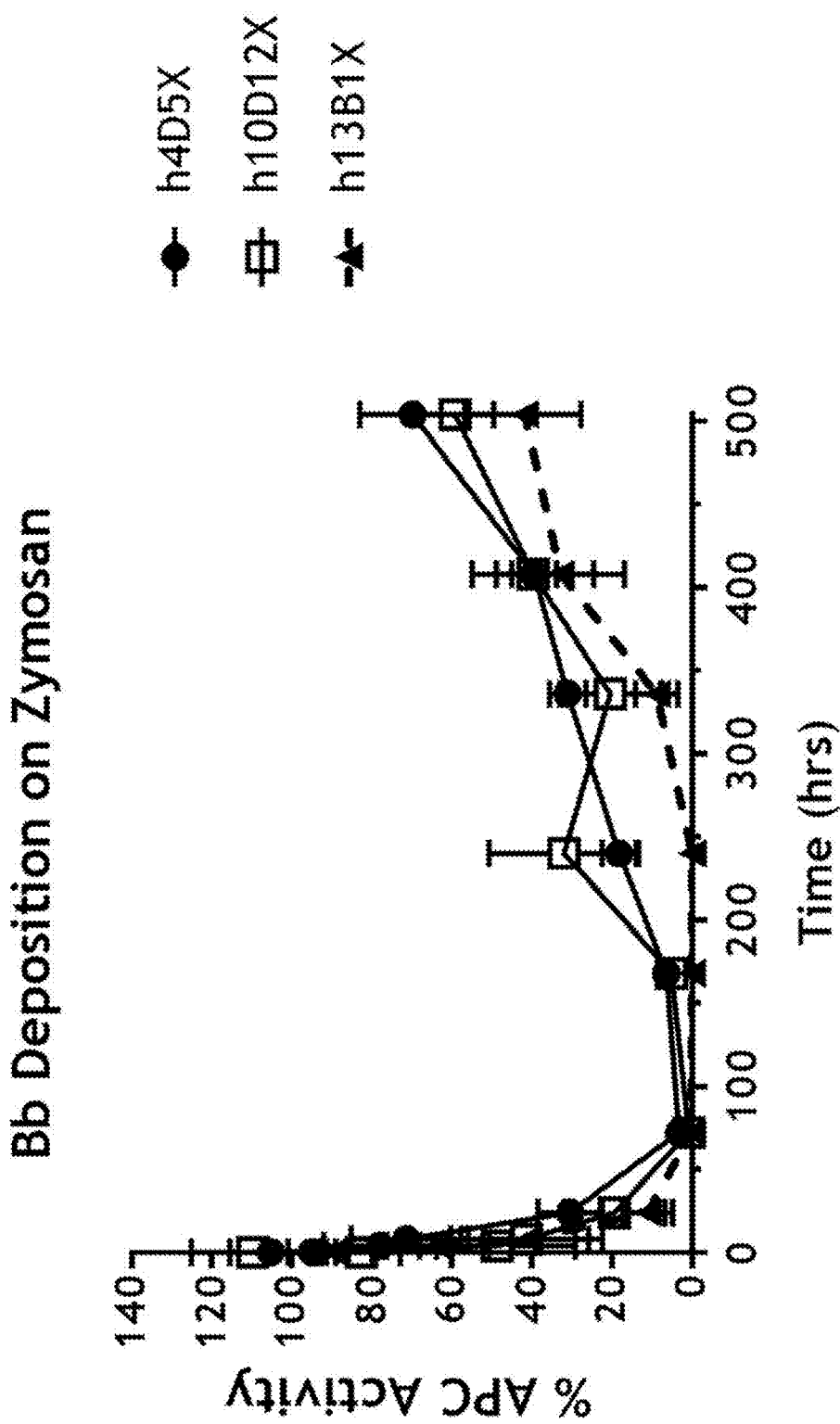
FIG. 70 graphically illustrates APC activity, as determined by Bb deposition on zymosan, in serum samples obtained from groups of cynomolgus monkeys (3 animals per group) treated with a single 5 mg/kg intravenous dose of high affinity MASP-3 inhibitory mAbs h4D5X, h10D12X or h13B1X, as described in Example 21.

FIG. 70 graphically illustrates APC activity, as determined by Bb deposition on zymosan, in serum samples obtained from groups of cynomolgus monkeys (3 animals per group) treated with a single 5 mg/kg intravenous dose of high affinity MASP-3 inhibitory mAbs h4D5X, h10D12X or h13B1X. Bb deposition data was collected as described above. APC activity for the treatment timepoints was normalized by setting pre-treatment MFIs of samples spiked with the non-inhibitory, isotype control antibody as 100% activity, and a pre-treatment sample incubated with 50 mM EDTA (to inhibit all complement activity) to 0%. The h13BX treatment data used for FIG. 70 are also reflected in FIG. 69. As shown in FIG. 70, treatment with all three high affinity MASP-3 inhibitory antibodies resulted in greater than 95% inhibition of the APC. The h4D5X-, h10D12X-, and h13B1X-treated animals maintained at least 90% inhibition of the APC for 6.7, 11.7, and 16 days, respectively. Thus, these results demonstrate that treatment with these representative high affinity MASP-3 inhibitory mAbs provides sustained inhibition of the APC in a nonhuman primate with a single 5 mg/kg dose.

Figure 71A:
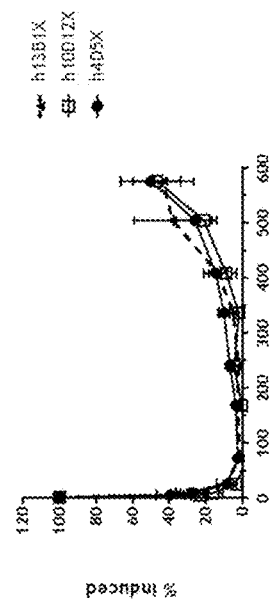
FIG. 71A graphically illustrates APC activity, as determined by fluid-phase Ba in serum samples obtained from groups of cynomolgus monkeys (3 animals per group) over time after treatment with a single 5 mg/kg intravenous dose of mAbs h4D5X, h10D12X, and h13B1X, as described in Example 21.
Figure 71B:
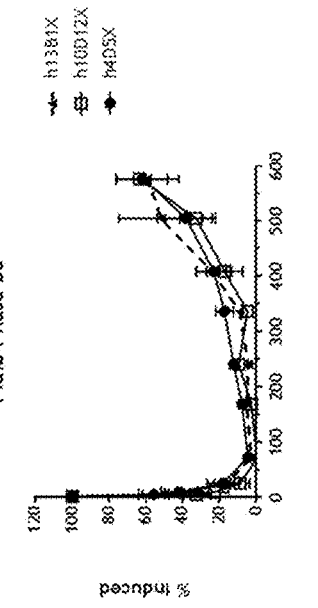
FIG. 71B graphically illustrates APC activity, as determined by fluid-phase Bb in serum samples obtained from groups of cynomolgus monkeys (3 animals per group) over time after treatment with a single 5 mg/kg intravenous dose of mAbs h4D5X, h10D12X, and h13B1X, as described in Example 21.
Figure 71C:
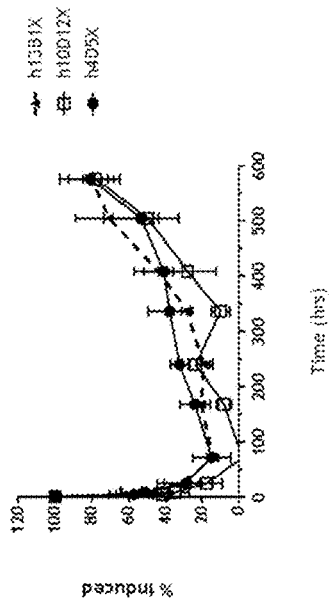
FIG. 71C graphically illustrates APC activity, as determined by fluid-phase C3a in serum samples obtained from groups of cynomolgus monkeys (3 animals per group) over time after treatment with a single 5 mg/kg intravenous dose of mAbs h4D5X, h10D12X, and h13B1X, as described in Example 21.

FIG. 71A-C graphically illustrates additional measures of APC activity. Fluid-phase Ba (FIG. 71A), Bb (FIG. 71B) and C3a (FIG. 71C) were measured in zymosan-treated, diluted serum samples obtained from groups of cynomolgus monkeys (3 animals per group) over time after treatment with a single 5 mg/kg intravenous dose of h4D5X, h10D12X, and h13B1X as described above.

As shown in FIG. 71A-C, single administrations of all three high affinity MASP-3 inhibitory antibodies resulted in inhibition of the APC, as defined by three different fluid-phase endpoints. These data are consistent with level of APC inhibition demonstrated in the Bb deposition study of FIG. 70, and further illustrate the efficacy of these mAbs to inhibit the pathway for multiple weeks.

Figure 72A:
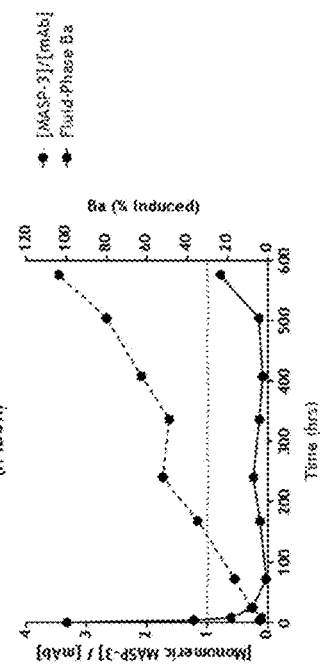
FIG. 72A graphically illustrates the molar ratio of target (MASP-3) to the high affinity MASP-3 inhibitory antibody h4D5X at the timepoints of complete APC inhibition, as measured by fluid-phase Ba, as described in Example 21.
Figure 72B:
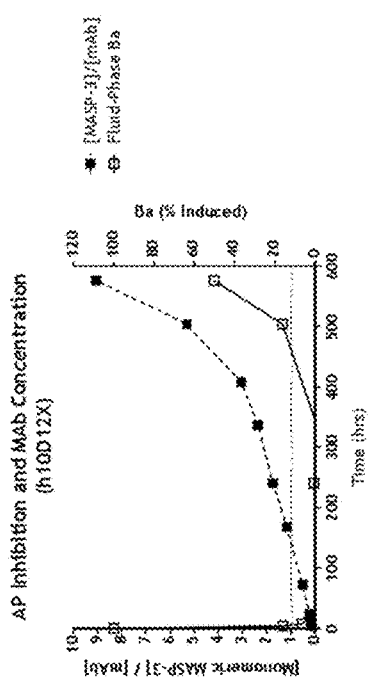
FIG. 72B graphically illustrates the molar ratio of target (MASP-3) to the high affinity MASP-3 inhibitory antibody h10D12X at the timepoints of complete APC inhibition, as measured by fluid-phase Ba, as described in Example 21.
Figure 72C:
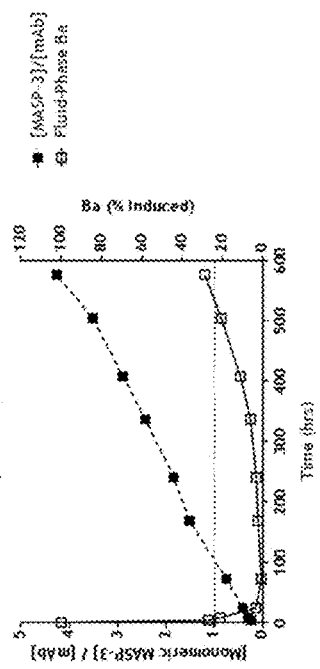
FIG. 72C graphically illustrates the molar ratio of target (MASP-3) to the high affinity MASP-3 inhibitory antibody h13B1X at the timepoints of complete APC inhibition, as measured by fluid-phase Ba, as described in Example 21.

FIG. 72A-C graphically illustrates the relationship of APC activity, as determined by fluid-phase Ba production, relative to the molar ratio of monomeric MASP-3 and MASP-3 mAb antibody detected in serum from monkeys treated with either h4D5X (FIG. 72A), h10D12X (FIG. 72B) or h13B1X (FIG. 72C). Each panel in FIG. 72A-C represents the data from one monkey. The monkey subjects used and serum (or plasma) obtained in this study are the same as those described above (FIGS. 69, 70, and 71).

FIGS. 72A-C graphically illustrates the molar ratio of target (MASP-3) to the high affinity MASP-3 inhibitory antibodies h4D5X (FIG. 72A), h10D12X (FIG. 72B) and h13B1X (FIG. 72C) at the timepoints of complete APC inhibition, as measured by fluid-phase Ba. For reference purposes, the molar ratio of 1:1 target to antibody is shown as a dotted line in each graph. As shown in FIGS. 72A-C, target (MASP-3) to the high affinity MASP-3 inhibitory mAbs h4D5X, h10D12X and h13B1X at a molar ratio in the range of about 2:1 to about 2.5:1 (target to antibody) are sufficient to completely inhibit the APC. These data demonstrate that these three representative MASP-3 inhibitory mAbs are potent, high-affinity MASP-3 inhibitory antibodies that are capable at inhibiting the APC when present at molar concentrations less than the concentration of target.

These levels of potency strongly indicate that the mAbs have the potential to be used clinically to treat diseases or indications caused by the APC.

Figure 73:
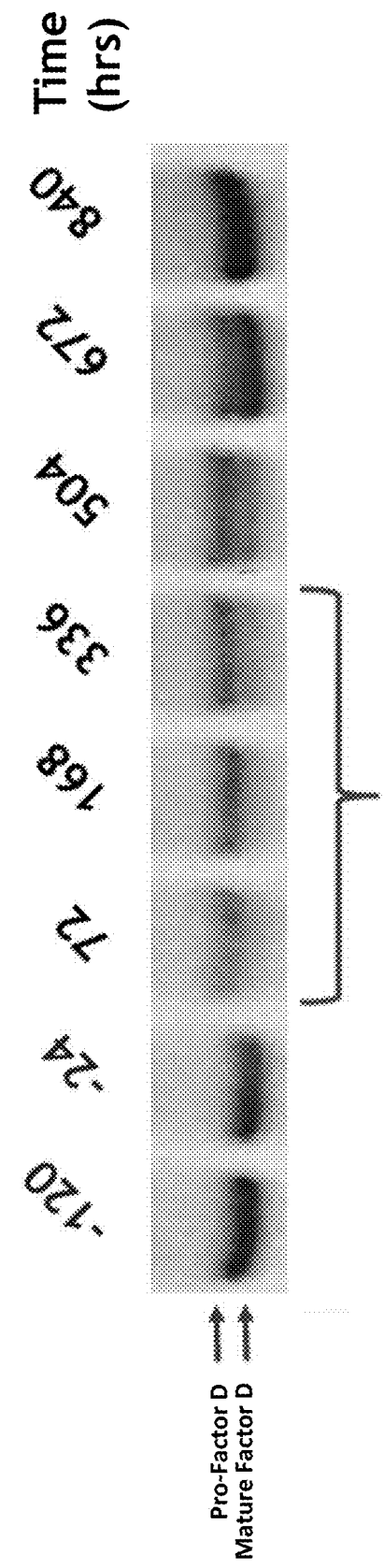
FIG. 73 shows a Western blot analyzing the level of pro-Factor D and Factor D in serum from a cynomolgus monkey over time (hours) after treatment with a single 5 mg/kg intravenous dose of mAb h13B1X, as described in Example 21.

FIG. 73 shows a Western blot analyzing the level of pro-Factor D and Factor D in serum from a cynomolgus monkey over time (hours) prior to and after treatment with a single 5 mg/kg intravenous dose of mAb h13B1X. As shown in FIG. 73, Factor D is present in plasma as pro-Factor D for at least 336 hours (14 days) following a single dose of mAb h13B1X.

Summary of Results

As described in Example 11, a single dose administration of a high affinity MASP-3 inhibitory antibody, mAb 13B1, to mice led to near-complete ablation of systemic alternative pathway complement activity for at least 14 days. As further described in Example 12, in a study conducted in a well-established animal model associated with PNH it was demonstrated that mAb 13B1 significantly improved the survival of PNH-like red blood cells and protected PNH-like red blood cells significantly better than did C5 inhibition. As described in Example 13, it was further demonstrated that mAb 13B1 reduced the incidence and severity of disease in a mouse model of arthritis. The results in this example demonstrate that representative high affinity MASP-3 inhibitory mAbs 13B1, 10D12 and 4D5 are highly effective at blocking the alternative pathway in primates. Single dose administration of mAb 13B1, 10D12 or 4D5 to cynomolgus monkeys resulted in sustained ablation of systemic alternative pathway activity lasting for approximately 16 days. The extent of alternative pathway ablation in cynomolgus monkeys treated with high affinity MASP-3 inhibitory antibodies was comparable to that achieved by factor D blockade in vitro, indicating complete blockade of factor D conversion by the MASP-3 inhibitory antibodies. Therefore, high affinity MASP-3 inhibitory mAbs have therapeutic utility in the treatment of patients suffering from diseases related to alternative pathway hyperactivity, such as, for example, paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenic purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

VII. Other Embodiments

All publications, patent applications, and patents mentioned in this specification are herein incorporated by reference.

Various modifications and variations of the described methods, compositions, and compounds, of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, oncology, or related fields are intended to be within the scope of the invention.

In accordance with the foregoing, the invention features the following embodiments.

High Affinity MASP-3 Inhibitory Antibodies that Bind One or More Epitopes within the SP Domain 1A. An isolated monoclonal antibody or antigen-binding fragment thereof that specifically binds to the serine protease domain of human MASP-3 (amino acid residues 450 to 728 of SEQ ID NO:2) with high affinity (having a $K_D$ of less than 500 pM), wherein the antibody or antigen-binding fragment thereof inhibits alternative pathway complement activation.

2A. The isolated antibody or antigen-binding fragment thereof of paragraph 1, wherein the antibody or antigen-binding fragment is characterized by at least one or more of the following properties:
 (a) inhibits pro-Factor D maturation;
 (b) does not bind to human MASP-1 (SEQ ID NO:8);
 (c) inhibits the alternative pathway at a molar ratio of from about 1:1 to about 2.5:1 (MASP-3 target to mAb) in a mammalian subject;
 (d) does not inhibit the classical pathway.
 (e) inhibition of hemolysis and/or opsonization;
 (f) inhibition of MASP-3 serine protease substrate-specific cleavage;
 (g) a reduction of hemolysis or the reduction of C3 cleavage and C3b surface deposition;
 (h) a reduction of Factor B and Bb deposition on an activating surface;
 (i) a reduction of resting levels (in circulation, and without the experimental addition of an activating surface) of active Factor D relative to pro-Factor D;
 (j) a reduction of levels of active Factor D relative to pro-Factor D in response to an activating surface;
 (k) a reduction of the production of resting and/or surface-induced levels of fluid-phase Ba, Bb, C3b, or C3a and/or
 (l) a reduction in factor P deposition.

3A. The isolated antibody or antigen-binding fragment thereof of paragraph 1 or 2, wherein said antibody or antigen-binding fragment thereof specifically binds to an epitope located within the serine protease domain of human MASP-3, wherein said epitope is located within at least one or more of: VLRSQRRDTTVI (SEQ ID NO:9), TAAHVLRSQRRDTTV (SEQ ID NO:10), DFNIQNYNHDIALVQ (SEQ ID NO:11), PHAECKTSYESRS (SEQ ID NO:12), GNYSVTENMFC (SEQ ID NO:13), VSNYVDWVWE (SEQ ID NO:14) and/or VLRSQRRDTTV (SEQ ID NO:15). [Group I]

4A. The antibody or antigen-binding fragment thereof of paragraph 3, wherein said antibody or antigen-binding fragment binds to an epitope within SEQ ID NO:15. [includes all group I abs]

5A. The antibody or antigen-binding fragment of paragraph 3, wherein said antibody or antigen-binding fragment binds to an epitope within SEQ ID NO:9. [10D12]

6A. The antibody or antigen-binding fragment of paragraph 3, wherein said antibody or antigen-binding fragment binds to an epitope within SEQ ID NO:10. [13B1]

7A. The antibody or antigen-binding fragment of paragraph 6, wherein said antibody or antigen binding fragment also binds to an epitope within SEQ ID NO:12. [13B1]

8A. The antibody or antigen-binding fragment of paragraph 3, wherein said antibody or antigen-binding fragment also binds to an epitope within SEQ ID NO:10 and/or SEQ ID NO:12. [13B1]

9A. The antibody or antigen-binding fragment of paragraph 3, wherein said antibody or antigen binding fragment binds to an epitope within SEQ ID NO:9. [1F3, 4B6, 4D5, 1A10]

10A. The antibody or antigen-binding fragment of paragraph 7, wherein said antibody or antigen binding fragment also binds to an epitope within at least one of SEQ ID NO:11, SEQ ID NO: 13 and/or SEQ ID NO:14. [1F3, 4B6, 4D5, 1A10]

11A. The antibody or antigen-binding fragment of paragraph 7, wherein the antibody or antigen-binding fragment also binds to an epitope within at least one of SEQ ID NO:10, SEQ ID NO:11, SEQ ID NO:13 and/or SEQ ID NO:14. [1F3, 4B6, 4D5, 1A10]

12A. The antibody or antigen-binding fragment of paragraph 1 or 2, wherein said antibody binds to an epitope within at least one of: ECGQPSRSLPSLV (SEQ ID NO:16), RNAEPGLFPWQ (SEQ ID NO:17); KWFGSGALLSAS-WIL (SEQ ID NO:18); EHVTVYLGLH (SEQ ID NO:19); PVPLGPHVMP (SEQ ID NO:20); APHMLGL (SEQ ID NO:21); SDVLQYVKLP (SEQ ID NO:22); and/or AFV-IFDDLSQRW (SEQ ID NO:23). [group II and III]

13A. The antibody or antigen-binding fragment of paragraph 12, wherein said antibody or antigen-binding fragment binds to an epitope within SEQ ID NO:17. [all group II and III abs]

14A. The antibody or antigen-binding fragment of paragraph 13, wherein said antibody or antigen binding fragment also binds to an epitope within EHVTVYLGLH (SEQ ID NO:19) and/or AFVIFDDLSQRW (SEQ ID NO:23). [1G4, 1E7, 2D7 15D9]

15A. The antibody or antigen-binding fragment of paragraph 14, wherein said antibody or antigen binding fragment also binds to an epitope within SEQ ID NO:23. [1G4, 1E7, 2D7, 15D9, 2F5]

16A. The antibody or antigen-binding fragment of paragraph 14, wherein said antibody or antigen binding fragment also binds to an epitope within SEQ ID NO:19 and/or SEQ ID NO:23. [Ig4, 1E7, 2D7]

17A. The antibody or antigen-binding fragment of paragraph 14, wherein said antibody or antigen-binding fragment also binds to an epitope within SEQ ID NO:18, SEQ ID NO:20 and/or SEQ ID NO:23. [15D9, 2F5]

18A. The antibody or antigen-binding fragment of paragraph 14, wherein said antibody or antigen-binding fragment also binds to an epitope within at least one of SEQ ID NO:18, SEQ ID NO:20 and/or SEQ ID NO:23 [15D9, 2F5].

19A. The antibody or antigen-binding fragment of paragraph 14, wherein said antibody or antigen-binding fragment also binds to an epitope within at least one of SEQ ID NO:16, SEQ ID NO: 21 and/or SEQ ID NO:22. [1B11]

20A. The antibody or antigen-binding fragment of paragraph 14, wherein said antibody or antigen-binding fragment also binds to an epitope within at least one of SEQ ID NO:16, SEQ ID NO: 21 and/or SEQ ID NO:22 [1B11].

21A. The antibody or antigen binding fragment thereof of any one of paragraphs 1-20, wherein the antibody or antigen-binding fragment is selected from the group consisting of a human antibody, a humanized antibody, a chimeric antibody, a murine antibody, and an antigen-binding fragment of any of the foregoing.

22A. The antibody or antigen-binding fragment thereof of any one of paragraphs 1-21, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

23A. The antibody or antigen-binding fragment thereof of any one of paragraphs 1-22, further comprising an immunoglobulin constant region.

24A. The antibody or antigen binding fragment thereof of any one of paragraphs 1-23, wherein the antibody or antigen-binding fragment is humanized.

25A. The antibody or antigen-binding fragment thereof of any one of paragraphs 1-24 wherein said antibody binds to the serine protease domain of human MASP-3 with an affinity of less than 500 pM.

26A. The antibody or antigen-binding fragment thereof of any of paragraphs 1-25, wherein said antibody inhibits alternative pathway activation in mammalian blood.

27A. A composition comprising the antibody or antigen-binding fragment of any of paragraphs 1A-26A and a pharmaceutically acceptable excipient.

A. Group IA High Affinity MASP-3 Inhibitory Antibodies that Bind One or More Epitopes within the SP Domain (4D5, 4B6, 1A10 Plus 4D5 Variants)

1B. An isolated antibody, or antigen-binding fragment thereof, that binds to MASP-3 comprising:
  (a) a heavy chain variable region comprising a HC-CDR1 set forth as SEQ ID NO:209 (XXDIN, wherein X at position 1 is S or T and wherein X at position 2 is N or D); a HC-CDR2 set forth as SEQ ID NO:210 (WIY-PRDXXXKYNXXFXD, wherein X at position 7 is G or D; X at position 8 is S, T or R; X at position 9 is I or T; X at position 13 is E or D; X at position 14 is K or E; and X at position 16 is T or K); and a HC-CDR3 set forth as SEQ ID NO:211 (XEDXY, wherein X at position 1 is L or V, and wherein X at position 4 is T or S); and
  (b) a light chain variable region comprising a LC-CDR1 set forth as SEQ ID NO:212 (KSSQSLLXXRTRK-NYLX, wherein X at position 8 is N, I, Q or A; wherein X at position 9 is S or T; and wherein X at position 17 is A or S); a LC-CDR2 set forth as SEQ ID NO:144 (WASTRES) and a LC-CDR3 set forth as SEQ ID NO:146 (KQSYNLYT).

2B. The isolated antibody or antigen-binding fragment thereof of paragraph 1, wherein the HC-CDR1 of the heavy chain variable region according to (a) comprises SEQ ID NO:56 (TDDIN). [4D5 and variants]

3B. The isolated antibody or antigen-binding fragment thereof of paragraph 1, wherein the HC-CDR1 of the heavy chain variable region according to (a) comprises SEQ ID NO:62 (SNDIN). [1F3, 4B6 and 1A10]

4B. The isolated antibody or antigen-binding fragment thereof of paragraph 1, wherein the HC-CDR2 of the heavy chain variable region according to (a) comprises SEQ ID NO:58 (WIYPRDDRTKYNDKFKD) [4D5 and variants].

5B. The isolated antibody or antigen-binding fragment thereof of paragraph 1, wherein the HC-CDR2 of the heavy chain variable region according to (a) comprises SEQ ID NO:63 (WIYPRDGSIKYNEKFTD). [1F3]

6B. The isolated antibody or antigen-binding fragment thereof of paragraph 1, wherein the HC-CDR2 of the heavy chain variable region according to (a) comprises SEQ ID NO:67 (WIYPRDGTTKYNEEFTD). [4B6]

7B. The isolated antibody or antigen-binding fragment thereof of paragraph 1, wherein the HC-CDR2 of the heavy chain variable region according to (a) comprises SEQ ID NO:69 (WIYPRDGTTKYNEKFTD). [1A10]

8B. The isolated antibody or antigen-binding fragment thereof of paragraph 1, wherein the HC-CDR3 of the heavy chain variable region according to (a) comprises SEQ ID NO:60 (LEDTY) [4D5 and variants]

9B. The isolated antibody or antigen-binding fragment thereof of paragraph 1, wherein the HC-CDR3 of the heavy chain variable region according to (a) comprises SEQ ID NO:65 (VEDSY). [1F3, 4B6 and 1A10]

10B. The isolated antibody or antigen-binding fragment thereof of paragraph 1, wherein the LC-CDR1 of the light chain variable region according to (b) comprises SEQ ID NO:142 (KSSQSLLNSRTRKNYLA); SEQ ID NO:257 (KSSQSLLQSRTRKNYLA), SEQ ID NO:258 (KSSQSLLASRTRKNYLA); or SEQ ID NO:259 (KSSQSLLNTRTRKNYLA). [4D5 and variants]

11B. The isolated antibody or antigen-binding fragment thereof of paragraph 10, wherein the LC-CDR1 of the light chain variable region according to (b) comprises SEQ ID NO:258 (KSSQSLLASRTRKNYLA). [4D5 NA mutant]

12B. The isolated antibody or antigen-binding fragment thereof of paragraph 1, wherein the LC-CDR1 of the light chain variable region according to (b) comprises SEQ ID NO:149 (KSSQSLLISRTRKNYLS). [1F3 and 4B6]

13B. The isolated antibody or antigen-binding fragment thereof of paragraph 1, wherein the HC-CDR1 comprises SEQ ID NO:56, the HC-CDR2 comprises SEQ ID NO:58, the HC-CDR3 comprises SEQ ID NO:60 and wherein the LC-CDR1 comprises SEQ ID NO:142, SEQ ID NO:257, SEQ ID NO:258 or SEQ ID NO:259; wherein the LC-CDR2 comprises SEQ ID NO:144 and wherein the LC-CDR3 comprises SEQ ID NO:146. [all 6 CDRs of 4D5 with variants at LC-CDR1].

14B. The isolated antibody or antigen-binding fragment thereof of paragraph 1, wherein the HC-CDR1 comprises SEQ ID NO:62, the HC-CDR2 comprises SEQ ID NO:63, SEQ ID NO:67 or SEQ ID NO:69, the HC-CDR3 comprises SEQ ID NO:65 and wherein the LC-CDR1 comprises SEQ ID NO:149, the LC-CDR2 comprises SEQ ID NO:144 and the LC-CDR3 comprises SEQ ID NO:146. [all 6 CDRS of 1F3, 4B6 and 1A10]

15B. The antibody or antigen binding fragment thereof of any one of paragraphs 1-14, wherein the antibody or antigen-binding fragment is selected from the group consisting of a human antibody, a humanized antibody, a chimeric antibody, a murine antibody, and an antigen-binding fragment of any of the foregoing.

16B. The antibody or antigen-binding fragment thereof of any one of paragraphs 1-15, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

17B. The antibody or antigen-binding fragment thereof of any one of paragraphs 1-16, further comprising an immunoglobulin constant region.

18B. The antibody or antigen binding fragment thereof of any one of paragraphs 1-17, wherein the antibody or antigen-binding fragment is humanized.

19B. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:24, SEQ ID NO:248 or SEQ ID NO:249 and a light chain comprising at least 80%, 85%, 90%, 95%, 98%, 99% or 100% identical to SEQ ID NO:40, SEQ ID NO:250 or SEQ ID NO:278 [4D5 parental, humanized and modified versions].

20B. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:25 and a light chain comprising at least 80%, 85%, 90%, 95%, 98%, 99% or 100% identical to SEQ ID NO:41 [1F3].

21B. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:26 and a light chain comprising at least 80%, 85%, 90%, 95%, 98%, 99% or 100% identical to SEQ ID NO:42 [4B6].

22B. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:27 and a light chain comprising at least 80%, 85%, 90%, 95%, 98%, 99% or 100% identical to SEQ ID NO:42 [1A10].

23B. The antibody or antigen-binding fragment thereof of any one of paragraphs 1-22 wherein said antibody binds to human MASP-3 with an affinity of less than 500 pM.

24B. The antibody or antigen-binding fragment thereof of any of paragraphs 1-23, wherein said antibody inhibits alternative pathway activation in mammalian blood.

25B. A composition comprising the antibody or antigen-binding fragment of any of paragraphs 1B-24B and a pharmaceutically acceptable excipient.

B. Group IB High Affinity MASP-3 Inhibitory Antibodies that Bind One or More Epitopes within the SP Domain (10D12, 35C1 and 10D12 Variants)

1C. An isolated antibody, or antigen-binding fragment thereof, that binds to MASP-3 comprising:
  (a) a heavy chain variable region comprising a HC-CDR1 set forth as SEQ ID NO:213 (SYGXX, wherein X at position 4 is M or I and wherein X at position 5 is S or T); a HC-CDR2 set forth as SEQ ID NO:74; and a HC-CDR3 set forth as SEQ ID NO:214 (GGXAXDY, wherein X at position 3 is E or D and wherein X at position 5 is M or L); and
  (b) a light chain variable region comprising a LC-CDR1 set forth as SEQ ID NO:215 (KSSQSLL-DSXXKTYLX, wherein X at position 10 is D, E or A; wherein X at position 11 is G or A; and wherein X at position 16 is N or S); a LC-CDR2 set forth as SEQ ID NO:155; and a LC-CDR3 set forth as SEQ ID NO:216 (WQGTHFPXT, wherein X at position 8 is W or Y).

2C. The isolated antibody or antigen-binding fragment thereof of paragraph 1, wherein the HC-CDR1 of the heavy chain variable region according to (a) comprises SEQ ID NO:72 (SYGMS). [10D12 and variants]

3C. The isolated antibody or antigen-binding fragment thereof of paragraph 1, wherein the HC-CDR1 of the heavy chain variable region according to (a) comprises SEQ ID NO:79 (SYGIT). [35C1]

4C. The isolated antibody or antigen-binding fragment thereof of paragraph 1, wherein the HC-CDR3 of the heavy chain variable region according to (a) comprises SEQ ID NO:76 (GGEAMDY). [10D12 and variants].

5C. The isolated antibody or antigen-binding fragment thereof of paragraph 1, wherein the HC-CDR3 of the heavy chain variable region according to (a) comprises SEQ ID NO:82 (GGDALDY). [35C1]

6C. The isolated antibody or antigen-binding fragment thereof of paragraph 1, wherein the LC-CDR1 of the light chain variable region according to (b) comprises SEQ ID NO:153 (KSSQSLLDSDGKTYLN); SEQ ID NO:261 (KSSQSLLDSEGKTYLN), SEQ ID NO:262 (KSSQSLLDSAGKTYLN) or SEQ ID NO:263 (KSSQSLLDSDAKTYLN). [10D12 and variants]

7C. The isolated antibody or antigen-binding fragment thereof of paragraph 6, wherein the LC-CDR1 of the light chain variable region comprises SEQ ID NO:263 (KSSQSLLDSDAKTYLN). [10D12 GA variant]

8C. The isolated antibody or antigen-binding fragment thereof of paragraph 1, wherein the LC-CDR1 of the light chain variable region comprises SEQ ID NO:152. [35C1]

9C. The isolated antibody or antigen-binding fragment thereof of paragraph 1, wherein the LC-CDR3 of the light chain variable region according to (b) comprises SEQ ID NO:159 (KSSQSLLDSDGKTYLS). [10D12]

10C. The isolated antibody or antigen-binding fragment thereof of paragraph 1, wherein the LC-CDR3 of the light chain variable region according to (b) comprises SEQ ID NO:160 (WQGTHFPYT). [35C1]

11C. The isolated antibody or antigen-binding fragment thereof of paragraph 1, wherein the HC-CDR1 comprises SEQ ID NO:72, the HC-CDR2 comprises SEQ ID NO:74, the HC-CDR3 comprises SEQ ID NO:76, the LC-CDR1 comprises SEQ ID NO:153, SEQ ID NO:261, SEQ ID NO:262 or SEQ ID NO:263; the LC-CDR2 comprises SEQ ID NO:155 and the LC-CDR3 comprises SEQ ID NO:157. [all 6 CDRs of 10D12 with variants at LC-CDR1]

12C. The isolated antibody or antigen-binding fragment thereof of paragraph 1, wherein the HC-CDR1 comprises SEQ ID NO:79, the HC-CDR2 comprises SEQ ID NO:74, the HC-CDR3 comprises SEQ ID NO:82, the LC-CDR1 comprises SEQ ID NO:159, the LC-CDR2 comprises SEQ ID NO:155 and the LC-CDR3 comprises SEQ ID NO:160. [all 6 CDRs of 35C1]

13C. The antibody or antigen binding fragment thereof of any one of paragraphs 1-12, wherein the antibody or antigen-binding fragment is selected from the group consisting of a human antibody, a humanized antibody, a chimeric antibody, a murine antibody, and an antigen-binding fragment of any of the foregoing.

14C. The antibody or antigen-binding fragment thereof of any one of paragraphs 1-13, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

15C. The antibody or antigen-binding fragment thereof of any one of paragraphs 1-14, further comprising an immunoglobulin constant region.

16C. The antibody or antigen binding fragment thereof of any one of paragraphs 1-15, wherein the antibody or antigen-binding fragment is humanized.

17C. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:28, SEQ ID NO:251 or SEQ ID NO:252 and a light chain comprising at least 80%, 85%, 90%, 95%, 98%, 99% or 100% identical to SEQ ID NO:43, SEQ ID NO:253 or SEQ ID NO:279 [10D12 parental, humanized and variants].

18C. The isolated antibody or antigen-binding fragment thereof of paragraph 1, wherein the antibody or antigen-binding fragment thereof comprises a heavy chain comprising at least 80%, 85%, 90%, 95%, 98%, 99% or 100% identical to SEQ ID NO:29 and a light chain comprising at least 80%, 85%, 90%, 95%, 98%, 99% or 100% identical to SEQ ID NO:44 [35C1].

19C. The antibody or antigen-binding fragment thereof of any one of paragraphs 1-18 wherein said antibody binds to human MASP-3 with an affinity of less than 500 pM.

20C. The antibody or antigen-binding fragment thereof of any of paragraphs 1-19, wherein said antibody inhibits alternative pathway activation in mammalian blood.

21C. A composition comprising the antibody or antigen-binding fragment of any of paragraphs 1C-20C and a pharmaceutically acceptable excipient.

C. Group IC High Affinity MASP-3 Inhibitory Antibodies that Bind One or More Epitopes within the SP Domain (13B1 and Variants)

1D. An isolated antibody, or antigen-binding fragment thereof, that binds to MASP-3 comprising:
  (a) a heavy chain variable region comprising a HC-CDR1 set forth as SEQ ID NO:84 (GKWIE); a HC-CDR2 set forth as SEQ ID NO:86 (EILPGTGSTNYNEKFKG) or SEQ ID NO:275 (EILPGTGSTNYAQKFQG); and a HC-CDR3 set forth as SEQ ID NO:88 (SEDV); and
  (b) a light chain variable region comprising a LC-CDR1 set forth as SEQ ID NO:142 (KSSQSLL NSRTRKNYLA), SEQ ID NO:257 (KSSQSLL QSRTRKNYLA); SEQ ID NO:258 (KSSQSLL ASRTRKNYLA); or SEQ ID NO:259 (KSSQSLL NTRTRKNYLA), a LC-CDR2 set forth as SEQ ID NO:144 (WASTRES); and a LC-CDR3 set forth as SEQ ID NO:161 (KQSYNIPT). [all 6 CDRs of 13B1 and variants in LC-CDR1]

2D. The isolated antibody or antigen-binding fragment thereof of paragraph 1, wherein the LC-CDR1 comprises SEQ ID NO:258. [13B1 LC-CDR1 NA variant]

3D. The antibody or antigen binding fragment thereof of any one of paragraphs 1-2, wherein the antibody or antigen-binding fragment is selected from the group consisting of a human antibody, a humanized antibody, a chimeric antibody, a murine antibody, and an antigen-binding fragment of any of the foregoing.

4D. The antibody or antigen-binding fragment thereof of any one of paragraphs 1-3, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

5D. The antibody or antigen-binding fragment thereof of any one of paragraphs 1-4, further comprising an immunoglobulin constant region.

6D. The antibody or antigen binding fragment thereof of any one of paragraphs 1-5, wherein the antibody or antigen-binding fragment is humanized.

7D. The isolated antibody or antigen-binding fragment of paragraph 1, wherein the antibody or antigen-binding fragment thereof comprises a heavy chain comprising at least 80%, 85%, 90%, 95%, 98%, 99% or 100% identical to SEQ ID NO:30, SEQ ID NO:254 or SEQ ID NO:255 and a light chain comprising at least 80%, 85%, 90%, 95%, 98%, 99% or 100% identical to SEQ ID NO:45, SEQ ID NO:256 or SEQ ID NO:280 [13B1 parental, humanized and variants].

8D. The antibody or antigen-binding fragment thereof of any one of paragraphs 1-7 wherein said antibody binds to human MASP-3 with an affinity of less than 500 pM.

9D. The antibody or antigen-binding fragment thereof of any of paragraphs 1-8, wherein said antibody inhibits alternative pathway activation in mammalian blood.

10D. A composition comprising the antibody or antigen-binding fragment of any of paragraphs 1D-9D and a pharmaceutically acceptable excipient.

D. Group II High Affinity MASP-3 Inhibitory Antibodies that Bind One or More Epitopes within the SP Domain (1G4)

1E. An isolated antibody, or antigen-binding fragment thereof, that binds to MASP-3 comprising:
  (a) a heavy chain variable region comprising a HC-CDR1 set forth as SEQ ID NO:91 (GYWIE); a HC-CDR2 set forth as SEQ ID NO:93 (EMLPGSGSTHYNEKFKG), and a HC-CDR3 set forth as SEQ ID NO:95 (SIDY); and
  (b) a light chain variable region comprising a LC-CDR1 set forth as SEQ ID NO:163 (RSSQSLVQSNGNTYLH), a LC-CDR2 set forth as SEQ ID NO:165 (KVSNRFS) and a LC-CDR3 set forth as SEQ ID NO:167 (SQSTHVPPT).

2E. The antibody or antigen binding fragment thereof of paragraph 1, wherein the antibody or antigen-binding fragment is selected from the group consisting of a human antibody, a humanized antibody, a chimeric antibody, a murine antibody, and an antigen-binding fragment of any of the foregoing.

3E. The antibody or antigen-binding fragment thereof of any one of paragraphs 1-2, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

4E. The antibody or antigen-binding fragment thereof of any one of paragraphs 1-3, further comprising an immunoglobulin constant region.

5E. The antibody or antigen binding fragment thereof of any one of paragraphs 1-4, wherein the antibody or antigen-binding fragment is humanized.

6E. The isolated antibody or antigen-binding fragment thereof of paragraph 1, wherein the antibody or antigen-binding fragment thereof comprise a heavy chain comprising at least 80%, 85%, 90%, 95%, 98%, 99% or 100% identical to SEQ ID NO:31 and a light chain comprising at least 80%, 85%, 90%, 95%, 98%, 99% or 100% identical to SEQ ID NO:46 [1G4].

7E. The antibody or antigen-binding fragment thereof of any one of paragraphs 1-6 wherein said antibody binds to human MASP-3 with an affinity of less than 500 pM.

8E. The antibody or antigen-binding fragment thereof of any of paragraphs 1-7, wherein said antibody inhibits alternative pathway activation in mammalian blood.

9E. A composition comprising the antibody or antigen-binding fragment of any of paragraphs 1E-8E and a pharmaceutically acceptable excipient.

E. Group III High Affinity MASP-3 Inhibitory Antibodies that Bind One or More Epitopes within the SP Domain (1E7, 2D7, 15D9, 2F5, 1B11, 2F2, 11B6)

1F. An isolated antibody, or antigen-binding fragment thereof, that binds to MASP-3 comprising:
  (a) a heavy chain variable region comprising a HC-CDR1 set forth as SEQ ID NO:109 (RVHFAIRDTNYWMQ), a HC-CDR2 set forth as SEQ ID NO:110 (AIYPGNGDTSYNQKFKG), a HC-CDR3 set forth as SEQ ID NO:112 (GSHYFDY); and a light chain variable region comprising a LC-CDR1 set forth as SEQ ID NO:182 (RASQSIGTSIH), a LC-CDR2 set forth as SEQ ID NO:184 (YASESIS) and a LC-CDR3 set forth as SEQ ID NO:186 (QQSNSWPYT) [1E7]; or
  (b) a heavy chain variable region comprising a HC-CDR1 set forth as SEQ ID NO:125 (DYYMN), a HC-CDR2 set forth as SEQ ID NO:127 (DVNPNNDGTTYNQKFKG), a HC-CDR3 set forth as SEQ ID NO:129 (CPFYYLGKGTHFDY); and a light chain variable region comprising a LC-CDR1 set forth as SEQ ID NO:196 (RASQDISNFLN), a LC-CDR2 set forth as SEQ ID NO:198 (YTSRLHS) and a LC-CDR3 set forth as SEQ ID NO:200 (QQGFTLPWT) [2D7]; or
  (c) a heavy chain variable region comprising a HC-CDR1 set forth as SEQ ID NO:132, a HC-CDR2 set forth as SEQ ID NO:133, a HC-CDR3 set forth as SEQ ID NO:135; and a light chain variable region comprising a LC-CDR1 set forth as SEQ ID NO:203, a LC-CDR2 set forth as SEQ ID NO:165 and a LC-CDR3 set forth as SEQ ID NO:204 [49C11]; or
  (d) a heavy chain variable region comprising a HC-CDR1 set forth as SEQ ID NO:137 a HC-CDR2 set forth as SEQ ID NO:138, a HC-CDR3 set forth as SEQ ID NO:140; and a light chain variable region comprising a LC-CDR1 set forth as SEQ ID NO:206, a LC-CDR2 set forth as SEQ ID NO:207 and a LC-CDR3 set forth as SEQ ID NO:208 [15D9]; or
  (e) a heavy chain variable region comprising a HC-CDR1 set forth as SEQ ID NO:98, a HC-CDR2 set forth as SEQ ID NO:99, a HC-CDR3 set forth as SEQ ID NO:101; and a light chain variable region comprising a LC-CDR1 set forth as SEQ ID NO:169, a LC-CDR2 set forth as SEQ ID NO:171 and a LC-CDR3 set forth as SEQ ID NO:173. [2F5]; or
  (f) a heavy chain variable region comprising a HC-CDR1 set forth as SEQ ID NO:103, a HC-CDR2 set forth as SEQ ID NO:105, a HC-CDR3 set forth as SEQ ID NO:107; and a light chain variable region comprising a LC-CDR1 set forth as SEQ ID NO:176, a LC-CDR2 set forth as SEQ ID NO:178 and a LC-CDR3 set forth as SEQ ID NO:193 [1B11]; or
  (g) a heavy chain variable region comprising a HC-CDR1 set forth as SEQ ID NO:114, a HC-CDR2 set forth as SEQ ID NO:116, a HC-CDR3 set forth as SEQ ID NO:118; and a light chain variable region comprising a LC-CDR1 set forth as SEQ ID NO:188, a LC-CDR2 set forth as SEQ ID NO:178 and a LC-CDR3 set forth as SEQ ID NO:190 [2F2]; or
  (h) a heavy chain variable region comprising a HC-CDR1 set forth as SEQ ID NO:114, a HC-CDR2 set forth as SEQ ID NO:121, a HC-CDR3 set forth as SEQ ID NO:123; and a light chain variable region comprising a LC-CDR1 set forth as SEQ ID NO:191, a LC-CDR2 set forth as SEQ ID NO:178 and a LC-CDR3 set forth as SEQ ID NO:193. [11B6]

2F. The antibody or antigen binding fragment thereof of paragraph 1(a)-(g), wherein the antibody or antigen-binding fragment is selected from the group consisting of a human antibody, a humanized antibody, a chimeric antibody, a murine antibody, and an antigen-binding fragment of any of the foregoing.

3F. The antibody or antigen-binding fragment thereof of any one of paragraphs 1-2, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

4F. The antibody or antigen-binding fragment thereof of any one of paragraphs 1-3, further comprising an immunoglobulin constant region.

5F. The antibody or antigen binding fragment thereof of any one of paragraphs 1-4, wherein the antibody or antigen-binding fragment is humanized.

6F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:32 and a light chain comprising at least 80%, 85%, 90%, 95%, 98%, 99% or 100% identical to SEQ ID NO:47 [1E7].

7F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:33 and a light chain comprising at least 80%, 85%, 90%, 95%, 98%, 99% or 100% identical to SEQ ID NO:48 [2D7].

8F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:34 and a light chain comprising at least 80%, 85%, 90%, 95%, 98%, 99% or 100% identical to SEQ ID NO:49 [49C11].

9F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:35 and a light chain comprising at least 80%, 85%, 90%, 95%, 98%, 99% or 100% identical to SEQ ID NO:50 [15D9]

10F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:36 and a light chain comprising at least 80%, 85%, 90%, 95%, 98%, 99% or 100% identical to SEQ ID NO:51 [2F5].

11F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:37 and a light chain comprising at least 80%, 85%, 90%, 95%, 98%, 99% or 100% identical to SEQ ID NO:52 [1B11].

12F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:38 and a light chain comprising at least 80%, 85%, 90%, 95%, 98%, 99% or 100% identical to SEQ ID NO:53 [2F2].

13F. The antibody or antigen-binding fragment thereof of paragraph 1, wherein the antibody or antigen binding fragment thereof comprises a heavy chain comprising at least 80%, 85%, 90%, 95%, 98%, 99% or 100% identical to SEQ ID NO:39 and a light chain comprising at least 80%, 85%, 90%, 95%, 98%, 99% or 100% identical to SEQ ID NO:54 [11B6].

14F. The antibody or antigen-binding fragment thereof of any one of paragraphs 1-13 wherein said antibody binds to human MASP-3 with an affinity of less than 500 pM.

15F. The antibody or antigen-binding fragment thereof of any of paragraphs 1-14, wherein said antibody inhibits alternative pathway activation in mammalian blood.

16F. A composition comprising the antibody or antigen-binding fragment of any of paragraphs 1F-15F and a pharmaceutically acceptable excipient.

F. Use of MASP-3 Inhibitory Antibodies for Treatment of AP Diseases

1. A method of inhibiting alternative pathway complement activation in a mammal, the method comprising administering to a mammal subject in need thereof an amount of a composition comprising a high affinity MASP-3 inhibitory antibody or antigen-binding fragment thereof sufficient to inhibit alternative pathway complement pathway activation in the mammal.

2. The method of claim 1, wherein the antibody, or antigen binding fragment thereof binds to MASP-3 with an affinity of less than 500 pM.

3. The method of paragraph 1, wherein as a result of administering the composition comprising the antibody or antigen-binding fragment one or more of the following is present in the mammalian subject:
   (a) inhibition of Factor D maturation;
   (b) inhibition of the alternative pathway when administered to the subject at a molar ratio of from about 1:1 to about 2.5:1 (MASP-3 target to mAb)
   (c) the classical pathway is not inhibited.
   (d) inhibition of hemolysis and/or opsonization;
   (e) a reduction of hemolysis or the reduction of C3 cleavage and C3b surface deposition;
   (f) a reduction of Factor B and Bb deposition on an activating surface;
   (g) a reduction of resting levels (in circulation, and without the experimental addition of an activating surface) of active Factor D relative to pro-Factor D;
   (h) a reduction of levels of active Factor D relative to pro-Factor D in response to an activating surface; and/or
   (i) a reduction of the production of resting and surface-induced levels of fluid-phase Ba, Bb, C3b, or C3a.

4. The method of paragraph 1, wherein the antibody inhibits the alternative pathway at a molar ratio of from about 1:1 to about 2.5:1 (MASP-3 target to mAb)

5. The method of any of paragraphs 1-3 wherein the high affinity MASP-3 antibody characterized according to any of claims 27A, 25B, 21C, 10D, 9E or 16F.

6. The method of any of paragraphs 1-4, wherein the antibody or antigen binding fragment thereof selectively inhibits the alternative pathway without affecting the classical pathway activation.

7. The method of any of paragraphs 1-6 wherein the mammal subject is suffering from, or at risk of developing an alternative-pathway disease or disorder selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenic purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated antibody, or antigen-binding fragment thereof, that binds to human MASP-3 comprising:
   a heavy chain variable region comprising a HC-CDR1 set forth as SEQ ID NO:72 (SYGMS) a HC-CDR2 set forth as SEQ ID NO:74 (WINTYSGVPTYADDFKG); and a HC-CDR3 set forth as SEQ ID NO:76 (GGEAMDY); and a light chain variable region comprising a LC-CDR1 selected from the group consisting of SEQ ID NO:153 (KSSQSLLDSDGKTYLN), SEQ ID NO:261 (KSSQSLLDSEGKTYLN), SEQ ID NO:262 (KSSQSLLDSAGKTYLN) and SEQ ID NO:263 (KSSQSLLDSDAKTYLN); a LC-CDR2 set forth as SEQ ID NO:155 (LVSKLDS); and a LC-CDR3 set forth as SEQ ID NO:157 (WQGTHFPWT).

2. The isolated antibody, or antigen-binding fragment thereof of claim 1, wherein the LC-CDR1 comprises SEQ ID NO:261 (KSSQSLLDSEGKTYLN).

3. The isolated antibody, or antigen-binding fragment thereof of claim 1, wherein the LC-CDR1 comprises SEQ ID NO:262 (KSSQSLLDSAGKTYLN).

4. The isolated antibody, or antigen-binding fragment thereof of claim 1, wherein the LC-CDR1 comprises SEQ ID NO:263 (KSSQSLLDSDAKTYLN).

5. The isolated antibody or antigen-binding fragment thereof of claim 1, wherein the HC-CDR1 comprises SEQ ID NO:72, the HC-CDR2 comprises SEQ ID NO:74, the HC-CDR3 comprises SEQ ID NO:76, the LC-CDR1 comprises SEQ ID NO:153, the LC-CDR2 comprises SEQ ID NO:155 and the LC-CDR3 comprises SEQ ID NO:157.

6. The isolated antibody or antigen-binding fragment thereof of claim 1, wherein the HC-CDR1 comprises SEQ ID NO:72, the HC-CDR2 comprises SEQ ID NO:74, the HC-CDR3 comprises SEQ ID NO:76, the LC-CDR1 comprises SEQ ID NO:263, the LC-CDR2 comprises SEQ ID NO:155 and the LC-CDR3 comprises SEQ ID NO:157.

7. The isolated antibody or antigen-binding fragment thereof of claim 1, wherein the heavy chain variable region comprises an amino acid sequence selected from the group consisting of SEQ ID NO:28, SEQ ID NO:251 and SEQ ID NO:252.

8. The isolated antibody or antigen-binding fragment thereof of claim 1, wherein the light chain variable region comprises an amino acid sequence selected from the group consisting of SEQ ID NO:43, SEQ ID NO:253 and SEQ ID NO:279.

9. The antibody or antigen binding fragment thereof of claim 1, wherein the antibody or antigen-binding fragment is selected from the group consisting of a humanized antibody, a chimeric antibody, a murine antibody, and an antigen-binding fragment of any of the foregoing.

10. The antibody or antigen-binding fragment thereof of claim 1, wherein said antibody or antigen binding fragment thereof is selected from the group consisting of a single chain antibody, an ScFv, a Fab fragment, an Fab' fragment, an F(ab')2 fragment, a univalent antibody lacking a hinge region and a whole antibody.

11. The antibody or antigen-binding fragment thereof of claim 1, wherein said antibody inhibits alternative pathway activation in mammalian blood.

12. A composition comprising the antibody or antigen-binding fragment of claim 1 and a pharmaceutically acceptable excipient.

13. An isolated antibody or antigen-binding fragment thereof that binds to human MASP-3, comprising a heavy chain variable region selected from the group consisting of SEQ ID NO:28, SEQ ID NO:251 and SEQ ID NO:252 and a light chain variable region selected from the group consisting of SEQ ID NO:43, SEQ ID NO:253 and SEQ ID NO:279.

14. The isolated antibody or antigen-binding fragment thereof of claim 13, wherein the heavy chain variable region comprises SEQ ID NO:28 and the light chain variable region comprises SEQ ID NO:43.

15. The isolated antibody or antigen-binding fragment thereof of claim 13, wherein the heavy chain variable region comprises SEQ ID NO:251 or SEQ ID NO:252 and the light chain variable region comprises SEQ ID NO:253.

16. The isolated antibody or antigen-binding fragment thereof of claim 13, wherein the heavy chain variable region comprises SEQ ID NO:251 or SEQ ID NO:252 and the light chain variable region comprises SEQ ID NO:279.

17. The isolated antibody of claim 13, wherein the antibody is selected from the group consisting of a single chain antibody, an ScFv, a Fab fragment, an Fab' fragment, an F(ab')2 fragment, a univalent antibody lacking a hinge region and a whole antibody.

18. The isolated antibody or antigen-binding fragment thereof of claim 13, wherein said antibody inhibits alternative pathway activation in mammalian blood.

19. A composition comprising the antibody or antigen-binding fragment of claim 13 and a pharmaceutically acceptable excipient.

* * * * *

UNITED STATES PATENT AND TRADEMARK OFFICE
CERTIFICATE OF CORRECTION

PATENT NO. : 11,027,015 B2
APPLICATION NO. : 16/909578
DATED : June 8, 2021
INVENTOR(S) : W. Jason Cummings It is certified that error appears in the above-identified patent and that said Letters Patent is hereby corrected as shown below:

On the Title Page

On page 2, in Column 1, Item (56), in OTHER PUBLICATIONS, Line 35, delete "Activatting" and insert -- Activating --, therefor.

On page 2, in Column 1, Item (56), in OTHER PUBLICATIONS, Line 41, delete "antbody" and insert -- antibody --, therefor.

On page 2, in Column 2, Item (56), in OTHER PUBLICATIONS, Line 52, delete "Serine Proteseases" and insert -- Serine Proteases --, therefor.

On page 6, in Column 2, Item (56), in OTHER PUBLICATIONS, Line 30, delete "MASP1" and insert -- MASP-1 --, therefor.

On page 7, in Column 1, Item (56), in OTHER PUBLICATIONS, Line 8, delete "Mannnan-Binding Lectin (MBL)" and insert -- Mannan-Binding Lectin (MBL) --, therefor.

On page 8, in Column 1, Item (56), in OTHER PUBLICATIONS, Line 41, delete "fumigatis,"" and insert -- fumigatus," --, therefor.

On page 8, in Column 1, Item (56), in OTHER PUBLICATIONS, Line 37, delete "degeration,"" and insert -- degeneration," --, therefor.

In the Specification

In Column 1, Line 9, delete "Apr. 1, 2020," and insert -- Apr.1, 2020, now patent no. 10,745,274 --, therefor.

In Column 4, Line 33, delete "bone morphogenic protein (CUB)" and insert -- bone morphogenetic protein (CUB) --, therefor.

Signed and Sealed this
Thirteenth Day of September, 2022

*Katherine Kelly Vidal*
Katherine Kelly Vidal
*Director of the United States Patent and Trademark Office*

CERTIFICATE OF CORRECTION (continued)
U.S. Pat. No. 11,027,015 B2

In Column 9, Line 10, delete "NO: 208: or" and insert -- NO: 208; or --, therefor.

In Column 9, Line 24, delete "NO: 193: or" and insert -- NO: 193; or --, therefor.

In Column 12, Line 6, delete "DESCRIPTION OF THE DRAWINGS" and insert -- BRIEF DESCRIPTION OF THE DRAWINGS --, therefor.

In Column 14, Line 9, delete "(BB S" and insert -- (BBS --, therefor.

In Column 14, Line 17, delete "(BB S" and insert -- (BBS --, therefor.

In Column 15, Line 61, delete "Comassie" and insert -- Coomassie --, therefor.

In Column 18, Lines 47-48, delete "Weislab classical" and insert -- Wieslab® classical --, therefor.

In Column 29, Line 48, delete "given value. Where ranges are stated, the endpoints" and insert -- given value. --, therefor.

In Column 33, Line 35, delete "osmolytic killing" and insert -- osmotic killing --, therefor.

In Column 35, Line 47, delete "bone morphogenic protein (or CUBI)" and insert -- bone morphogenetic protein (CUB) --, therefor.

In Column 36, Line 7, delete "disulphide-linked" and insert -- disulfide-linked --, therefor.

In Column 36, Lines 45-46, delete "bone morphogenic protein (CUBI)" and insert -- bone morphogenetic protein (CUBI) --, therefor.

In Column 36, Lines 63-64, delete "bone morphogenic protein (CUBI)" and insert -- bone morphogenetic protein (CUBI) --, therefor.

In Column 39, Line 50, delete "any the" and insert -- any of the --, therefor.

In Column 39, Line 66, delete "N. menigitidis" and insert -- N. meningitidis --, therefor.

In Column 42, Line 13, delete "(e.g" and insert -- e.g --, therefor.

In Column 42, Line 40, delete "hyperactivity" and insert -- hyperactivity. --, therefor.

In Column 42, Line 65, delete "Amylotrophic lateral sclerosis (ALS)," and insert -- Amyotrophic lateral sclerosis (ALS), --, therefor.

In Column 56, Line 52, delete "heterozygotus" and insert -- heterozygous --, therefor.

In Column 56, Line 56, delete "heterozygotus" and insert -- heterozygous --, therefor.

CERTIFICATE OF CORRECTION (continued)
U.S. Pat. No. 11,027,015 B2

In Column 57, Line 47, delete "FR injury," and insert -- I/R injury, --, therefor.

In Column 58, Line 53, delete "FR." and insert -- I/R. --, therefor.

In Column 59, Line 47, delete "ischemica-reperfusion" and insert -- ischemia-reperfusion --, therefor.

In Column 62, Line 36, delete "plays in important" and insert -- plays an important --, therefor.

In Column 62, Line 53, delete "(Chimenti at al.," and insert -- (Chimenti et al., --, therefor.

In Column 73, Line 24, delete "thomboses," and insert -- thrombosis, --, therefor.

In Column 74, Line 59, delete "mediated prothombin" and insert -- mediated prothrombin --, therefor.

In Column 77, Line 47, delete "(e.g.," and insert -- e.g., --, therefor.

In Column 77, Line 52, delete "(e.g.," and insert -- e.g., --, therefor.

In Column 82, Line 21, delete "eclizumab" and insert -- eculizumab --, therefor.

In Column 93, Line 42, delete "endogeneous" and insert -- endogenous --, therefor.

In Column 97, Line 32, delete "MASP-2" and insert -- MASP-2. --, therefor.

In Column 109, Line 43, delete "mAbs" and insert -- mAbs. --, therefor.

In Column 118, Lines 54-55, delete "(Mar-ian," and insert -- (Mariani, --, therefor.

In Column 123, Line 22, delete "form about" and insert -- from about --, therefor.

In Column 131, Line 59, delete "anti-05" and insert -- anti-C5 --, therefor.

In Column 135, Line 20, delete "show in" and insert -- shown in --, therefor.

In Column 138, Line 25, delete "Carneavale" and insert -- Carnevale --, therefor.

In Column 141, Line 17, delete "osmolytic killing" and insert -- osmotic killing --, therefor.

In Column 142, Line 52, delete "BB S" and insert -- BBS --, therefor.

In Column 142, Line 53, delete "BB S" and insert -- BBS --, therefor.

In Column 145, Line 18, delete "reachs" and insert -- reaches --, therefor.

In Column 146, Line 19, delete "49 0nm." and insert -- 490nm. --, therefor.

CERTIFICATE OF CORRECTION (continued)
U.S. Pat. No. 11,027,015 B2

In Column 147, Line 10, delete "1% the" and insert -- 1% of the --, therefor.

In Column 148, Line 24, delete "flours" and insert -- fluor --, therefor.

In Column 157, Line 15, delete "Weislab" and insert -- Wieslab® --, therefor.

In Column 157, Line 66, delete "erythrocytes/nil)." and insert -- erythrocytes/ml). --, therefor.

In Column 158, Line 3, delete "BBS, EGTA" and insert -- BBS, Mg++, EGTA --, therefor.

In Column 158, Line 6, delete "erythrocytes/nil)" and insert -- erythrocytes/ml) --, therefor.

In Column 164, Line 41, delete "Clinical & Exp Imunol" and insert -- Clinical & Exp Immunol --, therefor.

In Column 165, Line 51, delete "Bechcet's" and insert -- Behcet's --, therefor.

In Column 166, Line 39, delete "a anti –CD40" and insert -- an anti –CD40 --, therefor.

In Column 167, Line 61, delete "interations" and insert -- interactions --, therefor.

In Column 192, Line 18, delete "interations" and insert -- interactions --, therefor.

In Column 205, Line 3, delete "contructs," and insert -- constructs, --, therefor.

In Column 213, Line 15, delete "MOG35-55" and insert -- $MOG_{35-55}$ --, therefor.

In Column 216, Line 28, delete "interations" and insert -- interactions --, therefor.

In Column 217, Line 29, delete "20" and insert -- 20μL --, therefor.

In Column 220, Line 29, delete "pathway." and insert -- pathway; --, therefor.

In Column 220, Line 44, delete "C3a" and insert -- C3a; --, therefor.

In Column 228, Line 55, delete "[11B6]" and insert -- [11B6]. --, therefor.

In Column 229, Line 37, delete "[15D9]" and insert -- [15D9]. --, therefor.

In Column 230, Line 30, delete "mAb)" and insert -- mAb). --, therefor.

In Column 230, Line 31, delete "inhibited." and insert -- inhibited; --, therefor.

In Column 230, Line 49, delete "mAb)" and insert -- mAb); --, therefor.

SEQUENCE LISTING

```
<160> NUMBER OF SEQ ID NOS: 313

<210> SEQ ID NO 1
<211> LENGTH: 3895
<212> TYPE: DNA
<213> ORGANISM: Homo Sapiens

<400> SEQUENCE: 1
attccggcac agggacacaa acaagctcac ccaacaaagc caagctggga ggaccaaggc      60
cgggcagccg ggagcaccca aggcaggaaa atgaggtggc tgcttctcta ttatgctctg     120
tgcttctccc tgtcaaaggc ttcagccac accgtggagc taaacaatat gtttggccag      180
atccagtcgc ctggttatcc agactcctat cccagtgatt cagaggtgac ttggaatatc     240
actgtcccag atgggtttcg gatcaagctt tacttcatgc acttcaactt ggaatcctcc     300
tacctttgtg aatatgacta tgtgaaggta gaaactgagg accaggtgct ggcaaccttc     360
tgtggcaggg agaccacaga cacagagcag actcccggcc aggaggtggt cctctcccct     420
ggctccttca tgtccatcac tttccggtca gatttctcca atgaggagcg tttcacaggc     480
tttgatgccc actacatggc tgtggatgtg gacgagtgca aggagaggga ggacgaggag     540
ctgtcctgtg accactactg ccacaactac attggcggct actactgctc ctgccgcttc     600
ggctacatcc tccacacaga caacaggacc tgccgagtgg agtgcagtga caacctcttc     660
actcaaagga ctggggtgat caccagccct gacttcccaa acccttaccc caagagctct     720
gaatgcctgt ataccatcga gctggaggag ggtttcatgg tcaacctgca gtttgaggac     780
atatttgaca ttgaggacca tcctgaggtg ccctgcccct atgactacat caagatcaaa     840
gttggtccaa aagttttggg gccttctgt ggagagaaag cccagaacc catcagcacc     900 cagagccaca gtgtcctgat cctgttccat agtgacaact cgggagagaa ccggggctgg     960
aggctctcat acagggctgc aggaaatgag tgccagagc tacagcctcc tgtccatggg    1020
aaaatcgagc cctcccaagc caagtatttc ttcaaagacc aagtgctcgt cagctgtgac    1080
acaggctaca agtgctgaa ggataatgtg gagatggaca cattccagat tgagtgtctg    1140
aaggatggga cgtggagtaa caagattccc acctgtaaaa ttgtagactg tagagcccca    1200
ggagagctgg aacacgggct gatcaccttc tctacaagga caaacctcac cacatacaag    1260
tctgagatca aatactcctg tcaggagccc tattacaaga tgctcaacaa taacacaggt    1320
atatatacct gttctgccca aggagtctgg atgaataaag tattggggag aagcctaccc    1380
acctgccttc cagagtgtgg tcagccctcc cgctccctgc caagcctggt caagaggatc    1440 attggggcc gaaatgctga gcctggcctc ttcccgtggc aggccctgat agtggtggag    1500
gacacttcga gagtgccaaa tgacaagtgg tttgggagtg gggccctgct ctctgcgtcc    1560
tggatcctca cagcagctca tgtgctgcgc tcccagcgta gagacaccac ggtgatacca    1620
gtctccaagg agcatgtcac cgtctacctg ggcttgcatg atgtgcgaga caaatcgggg    1680
```

```
gcagtcaaca gctcagctgc ccgagtggtg ctccacccag acttcaacat ccaaaactac    1740
aaccacgata tagctctggt gcagctgcag gagcctgtgc ccctgggacc ccacgttatg    1800
cctgtctgcc tgccaaggct tgagcctgaa ggcccggccc ccacatgct gggcctggtg     1860 gccggctggg gcatctccaa tcccaatgtg acagtggatg agatcatcag cagtggcaca    1920
cggaccttgt cagatgtcct gcagtatgtc aagttacccg tggtgcctca cgctgagtgc    1980
aaaactagct atgagtcccg ctcgggcaat tacagcgtca cggagaacat gttctgtgct    2040
ggctactacg agggcggcaa agacacgtgc cttggagata gcggtggggc ctttgtcatc    2100
tttgatgact tgagccagcg ctgggtggtg caaggcctgg tgtcctgggg gggacctgaa    2160
gaatgcggca gcaagcaggt ctatggagtc tacacaaagg tctccaatta cgtggactgg    2220
gtgtgggagc agatgggctt accacaaagt gttgtggagc cccaggtgga acggtgagct    2280
gacttacttc ctcggggcct gcctcccctg agcgaagcta caccgcactt ccgacagcac    2340
actccacatt acttatcaga ccatatgaa tggaacacac tgacctagcg gtggcttctc     2400
ctaccgagac agcccccagg accctgagag gcagagtgtg gtatagggaa aaggctccag    2460
gcaggagacc tgtgttcctg agcttgtcca agtctctttc cctgtctggg cctcactcta    2520
ccgagtaata caatgcagga gctcaaccaa ggcctctgtg ccaatcccag cactcctttc    2580
caggccatgc ttcttacccc agtggccttt attcactcct gaccacttat caaacccatc    2640
ggtcctactg ttggtataac tgagcttgga cctgactatt agaaaatggt ttctaacatt    2700
gaactgaatg ccgcatctgt atattttcct gctctgcctt ctgggactag ccttggccta    2760
atccttcctc taggagaaga gcattcaggt tttgggagat ggctcatagc caagcccctc    2820
tctcttagtg tgatcccttg gagcaccttc atgcctgggg tttctctccc aaaagcttct    2880
tgcagtctaa gccttatccc ttatgttccc cattaaagga atttcaaaag acatggagaa    2940
agttgggaag gtttgtgctg actgctggga gcagaatagc cgtgggaggc ccaccaagcc    3000
cttaaattcc cattgtcaac tcagaacaca tttgggccca tatgccaccc tggaacacca    3060
gctgacacca tgggcgtcca cacctgctgc tccagacaag cacaaagcaa tctttcagcc    3120
ttgaaatgta ttatctgaaa ggctaccgga agcccaggcc cgaatatggg gacttagtcg    3180
attacctgga aaagaaaag acccacactg tgtcctgctg tgcttttggg caggaaaatg     3240
gaagaaagag tggggtgggc acattagaag tcacccaaat cctgccaggc tgcctggcat    3300
ccctggggca tgagctgggc ggagaatcca ccccgcagga tgttcagagg gacccactcc    3360 ttcattttc agagtcaaag gaatcagagg ctcacccatg gcaggcagtg aaaagagcca    3420
ggagtcctgg gttctagtcc ctgctctgcc cccaactggc tgtataacct ttgaaaaatc    3480
attttctttg tctgagtctc tggttctccg tcagcaacag gctggcataa ggtcccctgc    3540
aggttccttc tagctggagc actcagagct tccctgactg ctagcagcct ctctggccct    3600
cacagggctg attgttctcc ttctccctgg agctctctct cctgaaaatc tccatcagag    3660
caaggcagcc agagaagccc ctgagaggga atgattggga agtgtccact ttctcaaccg    3720
gctcatcaaa cacactcctt tgtctatgaa tggcacatgt aaatgatgtt atattttgta    3780
tcttttatat catatgcttc accattctgt aaagggcctc tgcattgttg ctcccatcag    3840
gggtctcaag tggaaataaa ccctcgtgga taaccaaaaa aaaaaaaaaa aaaaa         3895
```

<210> SEQ ID NO 2
<211> LENGTH: 728
<212> TYPE: PRT
<213> ORGANISM: Homo sapiens

<400> SEQUENCE: 2

```
Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
```

```
                405                 410                 415
Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
            435                 440                 445

Arg Ile Ile Gly Gly Arg Asn Ala Glu Pro Gly Leu Phe Pro Trp Gln
            450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
            515                 520                 525

Ser Gly Ala Val Asn Ser Ser Ala Ala Arg Val Val Leu His Pro Asp
            530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
            580                 585                 590

Trp Gly Ile Ser Asn Pro Asn Val Thr Val Asp Glu Ile Ile Ser Ser
            595                 600                 605

Gly Thr Arg Thr Leu Ser Asp Val Leu Gln Tyr Val Lys Leu Pro Val
            610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
            660                 665                 670

Asp Leu Ser Gln Arg Trp Val Val Gln Gly Leu Val Ser Trp Gly Gly
            675                 680                 685

Pro Glu Glu Cys Gly Ser Lys Gln Val Tyr Gly Val Tyr Thr Lys Val
            690                 695                 700

Ser Asn Tyr Val Asp Trp Val Trp Gln Met Gly Leu Pro Gln Ser
705                 710                 715                 720

Val Val Glu Pro Gln Val Glu Arg
                725

<210> SEQ ID NO 3
<211> LENGTH: 733
<212> TYPE: PRT
<213> ORGANISM: Mus musculus

<400> SEQUENCE: 3

Met Arg Phe Leu Ser Phe Trp Arg Leu Leu Leu Tyr His Ala Leu Cys
1               5                   10                  15

Leu Ala Leu Pro Glu Val Ser Ala His Thr Val Glu Leu Asn Glu Met
            20                  25                  30

Phe Gly Gln Ile Gln Ser Pro Gly Tyr Pro Asp Ser Tyr Pro Ser Asp
        35                  40                  45
```

```
Ser Glu Val Thr Trp Asn Ile Thr Val Pro Glu Gly Phe Arg Ile Lys
    50                  55                  60
Leu Tyr Phe Met His Phe Asn Leu Glu Ser Ser Tyr Leu Cys Glu Tyr
 65                  70                  75                  80
Asp Tyr Val Lys Val Glu Thr Glu Asp Gln Val Leu Ala Thr Phe Cys
                 85                  90                  95
Gly Arg Glu Thr Thr Asp Thr Glu Gln Thr Pro Gly Gln Glu Val Val
                100                 105                 110
Leu Ser Pro Gly Thr Phe Met Ser Val Thr Phe Arg Ser Asp Phe Ser
            115                 120                 125
Asn Glu Glu Arg Phe Thr Gly Phe Asp Ala His Tyr Met Ala Val Asp
130                 135                 140
Val Asp Glu Cys Lys Glu Arg Glu Asp Glu Glu Leu Ser Cys Asp His
145                 150                 155                 160
Tyr Cys His Asn Tyr Ile Gly Gly Tyr Tyr Cys Ser Cys Arg Phe Gly
                165                 170                 175
Tyr Ile Leu His Thr Asp Asn Arg Thr Cys Arg Val Glu Cys Ser Gly
            180                 185                 190
Asn Leu Phe Thr Gln Arg Thr Gly Thr Ile Thr Ser Pro Asp Tyr Pro
            195                 200                 205
Asn Pro Tyr Pro Lys Ser Ser Glu Cys Ser Tyr Thr Ile Asp Leu Glu
210                 215                 220
Glu Gly Phe Met Val Ser Leu Gln Phe Glu Asp Ile Phe Asp Ile Glu
225                 230                 235                 240
Asp His Pro Glu Val Pro Cys Pro Tyr Asp Tyr Ile Lys Ile Lys Ala
                245                 250                 255
Gly Ser Lys Val Trp Gly Pro Phe Cys Gly Glu Lys Ser Pro Glu Pro
            260                 265                 270
Ile Ser Thr Gln Thr His Ser Val Gln Ile Leu Phe Arg Ser Asp Asn
            275                 280                 285
Ser Gly Glu Asn Arg Gly Trp Arg Leu Ser Tyr Arg Ala Ala Gly Asn
290                 295                 300
Glu Cys Pro Lys Leu Gln Pro Pro Val Tyr Gly Lys Ile Glu Pro Ser
305                 310                 315                 320
Gln Ala Val Tyr Ser Phe Lys Asp Gln Val Leu Val Ser Cys Asp Thr
                325                 330                 335
Gly Tyr Lys Val Leu Lys Asp Asn Gly Val Met Asp Thr Phe Gln Ile
            340                 345                 350
Glu Cys Leu Lys Asp Gly Ala Trp Ser Asn Lys Ile Pro Thr Cys Lys
            355                 360                 365
Ile Val Asp Cys Gly Ala Pro Ala Gly Leu Lys His Gly Leu Val Thr
370                 375                 380
Phe Ser Thr Arg Asn Asn Leu Thr Thr Tyr Lys Ser Glu Ile Arg Tyr
385                 390                 395                 400
Ser Cys Gln Gln Pro Tyr Tyr Lys Met Leu His Asn Thr Thr Gly Val
                405                 410                 415
Tyr Thr Cys Ser Ala His Gly Thr Trp Thr Asn Glu Val Leu Lys Arg
            420                 425                 430
Ser Leu Pro Thr Cys Leu Pro Val Cys Gly Gln Pro Ser Arg Ala Leu
            435                 440                 445
Pro Asn Leu Val Lys Arg Ile Ile Gly Gly Arg Asn Ala Glu Leu Gly
450                 455                 460
Leu Phe Pro Trp Gln Ala Leu Ile Val Val Glu Asp Thr Ser Arg Val
```

465                 470                 475                 480

Pro Asn Asp Lys Trp Phe Gly Ser Gly Ala Leu Leu Ser Glu Ser Trp
                    485                 490                 495

Ile Leu Thr Ala Ala His Val Leu Arg Ser Gln Arg Arg Asp Asn Thr
                500                 505                 510

Val Ile Pro Val Ser Lys Glu His Val Thr Val Tyr Leu Gly Leu His
            515                 520                 525

Asp Val Arg Asp Lys Ser Gly Ala Val Asn Ser Ser Ala Ala Arg Val
530                 535                 540

Ile Leu His Pro Asp Phe Asn Ile Gln Asn Tyr Asn His Asp Ile Ala
545                 550                 555                 560

Leu Val Gln Leu Gln Lys Pro Val Pro Leu Gly Ala His Val Met Pro
                565                 570                 575

Ile Cys Leu Pro Arg Pro Glu Pro Gly Pro Ala Pro His Met Leu
                580                 585                 590

Gly Leu Val Ala Gly Trp Gly Ile Ser Asn Pro Asn Val Thr Val Asp
            595                 600                 605

Glu Ile Ile Leu Ser Gly Thr Arg Thr Leu Ser Asp Val Leu Gln Tyr
        610                 615                 620

Val Lys Leu Pro Val Val Ser His Ala Glu Cys Lys Ala Ser Tyr Glu
625                 630                 635                 640

Ser Arg Ser Gly Asn Tyr Ser Val Thr Glu Asn Met Phe Cys Ala Gly
                    645                 650                 655

Tyr Tyr Glu Gly Gly Lys Asp Thr Cys Leu Gly Asp Ser Gly Gly Ala
                660                 665                 670

Phe Val Ile Phe Asp Glu Met Ser Gln His Trp Val Ala Gln Gly Leu
            675                 680                 685

Val Ser Trp Gly Gly Pro Glu Glu Cys Gly Ser Lys Gln Val Tyr Gly
        690                 695                 700

Val Tyr Thr Lys Val Ser Asn Tyr Val Asp Trp Leu Trp Glu Met
705                 710                 715                 720

Asn Ser Pro Arg Ala Val Arg Asp Leu Gln Val Glu Arg
                725                 730

<210> SEQ ID NO 4
<211> LENGTH: 733
<212> TYPE: PRT
<213> ORGANISM: Rattus norvegicus

<400> SEQUENCE: 4

Met Arg Phe Leu Ser Phe Arg Arg Leu Leu Leu Tyr His Val Leu Cys
1               5                   10                  15

Leu Thr Leu Thr Glu Val Ser Ala His Thr Val Glu Leu Asn Glu Met
                20                  25                  30

Phe Gly Gln Ile Gln Ser Pro Gly Tyr Pro Asp Ser Tyr Pro Ser Asp
            35                  40                  45

Ser Glu Val Thr Trp Asn Ile Thr Val Pro Glu Gly Phe Arg Val Gln
        50                  55                  60

Leu Tyr Phe Met His Phe Asn Leu Glu Ser Ser Tyr Leu Cys Glu Tyr
65                  70                  75                  80

Asp Tyr Val Lys Val Glu Thr Glu Asp Gln Val Leu Ala Thr Phe Cys
                    85                  90                  95

Gly Arg Glu Thr Thr Asp Thr Glu Gln Thr Pro Gly Gln Glu Val Val
                100                 105                 110

-continued

```
Leu Ser Pro Gly Ser Phe Met Ser Val Thr Phe Arg Ser Asp Phe Ser
            115                 120                 125
Asn Glu Glu Arg Phe Thr Gly Phe Asp Ala His Tyr Met Ala Val Asp
130                 135                 140
Val Asp Glu Cys Lys Glu Arg Glu Asp Glu Leu Ser Cys Asp His
145                 150                 155                 160
Tyr Cys His Asn Tyr Ile Gly Gly Tyr Tyr Cys Ser Cys Arg Phe Gly
                165                 170                 175
Tyr Ile Leu His Thr Asp Asn Arg Thr Cys Arg Val Glu Cys Ser Gly
                180                 185                 190
Asn Leu Phe Thr Gln Arg Thr Gly Thr Ile Thr Ser Pro Asp Tyr Pro
                195                 200                 205
Asn Pro Tyr Pro Lys Ser Ser Glu Cys Ser Tyr Thr Ile Asp Leu Glu
210                 215                 220
Glu Gly Phe Met Val Thr Leu Gln Phe Glu Asp Ile Phe Asp Ile Glu
225                 230                 235                 240
Asp His Pro Glu Val Pro Cys Pro Tyr Asp Tyr Ile Lys Ile Lys Ala
                245                 250                 255
Gly Ser Lys Val Trp Gly Pro Phe Cys Gly Glu Lys Ser Pro Glu Pro
                260                 265                 270
Ile Ser Thr Gln Ser His Ser Ile Gln Ile Leu Phe Arg Ser Asp Asn
                275                 280                 285
Ser Gly Glu Asn Arg Gly Trp Arg Leu Ser Tyr Arg Ala Ala Gly Asn
                290                 295                 300
Glu Cys Pro Lys Leu Gln Pro Pro Val Tyr Gly Lys Ile Glu Pro Ser
305                 310                 315                 320
Gln Ala Val Tyr Ser Phe Lys Asp Gln Val Leu Ile Ser Cys Asp Thr
                325                 330                 335
Gly Tyr Lys Val Leu Lys Asp Asn Glu Val Met Asp Thr Phe Gln Ile
                340                 345                 350
Glu Cys Leu Lys Asp Gly Ala Trp Ser Asn Lys Ile Pro Thr Cys Lys
                355                 360                 365
Ile Val Asp Cys Gly Val Pro Ala Val Leu Lys His Gly Leu Val Thr
                370                 375                 380
Phe Ser Thr Arg Asn Asn Leu Thr Thr Tyr Lys Ser Glu Ile Arg Tyr
385                 390                 395                 400
Ser Cys Gln Gln Pro Tyr Tyr Lys Met Leu His Asn Thr Thr Gly Val
                405                 410                 415
Tyr Thr Cys Ser Ala His Gly Thr Trp Thr Asn Glu Val Leu Lys Arg
                420                 425                 430
Ser Leu Pro Thr Cys Leu Pro Val Cys Gly Gln Pro Ser Arg Ala Leu
                435                 440                 445
Pro Asn Leu Val Lys Arg Ile Ile Gly Gly Arg Asn Ala Glu Leu Gly
450                 455                 460
Leu Phe Pro Trp Gln Ala Leu Ile Val Val Glu Asp Thr Ser Arg Ile
465                 470                 475                 480
Pro Asn Asp Lys Trp Phe Gly Ser Gly Ala Leu Leu Ser Glu Ser Trp
                485                 490                 495
Ile Leu Thr Ala Ala His Val Leu Arg Ser Gln Arg Arg Asp Asn Thr
                500                 505                 510
Val Ile Pro Val Ser Lys Asp His Val Thr Val Tyr Leu Gly Leu His
                515                 520                 525
Asp Val Arg Asp Lys Ser Gly Ala Val Asn Ser Ser Ala Ala Arg Val
```

```
                530               535               540
Val Leu His Pro Asp Phe Asn Ile Gln Asn Tyr Asn His Asp Ile Ala
545                 550               555               560

Leu Val Gln Leu Gln Glu Pro Val Pro Leu Gly Ala His Val Met Pro
                565               570               575

Ile Cys Leu Pro Arg Pro Glu Pro Glu Gly Pro Ala Pro His Met Leu
                580               585               590

Gly Leu Val Ala Gly Trp Gly Ile Ser Asn Pro Asn Val Thr Val Asp
                595               600               605

Glu Ile Ile Ile Ser Gly Thr Arg Thr Leu Ser Asp Val Leu Gln Tyr
610                 615               620

Val Lys Leu Pro Val Val Ser His Ala Glu Cys Lys Ala Ser Tyr Glu
625                 630               635               640

Ser Arg Ser Gly Asn Tyr Ser Val Thr Glu Asn Met Phe Cys Ala Gly
                645               650               655

Tyr Tyr Glu Gly Gly Lys Asp Thr Cys Leu Gly Asp Ser Gly Gly Ala
                660               665               670

Phe Val Ile Phe Asp Glu Met Ser Gln Arg Trp Val Ala Gln Gly Leu
                675               680               685

Val Ser Trp Gly Gly Pro Glu Glu Cys Gly Ser Lys Gln Val Tyr Gly
                690               695               700

Val Tyr Thr Lys Val Ser Asn Tyr Val Asp Trp Leu Leu Glu Glu Met
705                 710               715               720

Asn Ser Pro Arg Gly Val Arg Glu Leu Gln Val Glu Arg
                725               730

<210> SEQ ID NO 5
<211> LENGTH: 730
<212> TYPE: PRT
<213> ORGANISM: Gallus gallus

<400> SEQUENCE: 5

Met Arg Tyr Pro Leu Ala Trp Ser Met Cys Ala Trp Leu Leu Gly Val
1                   5                   10                  15

Val Gly Ala Val Glu Leu Thr Asp Met Phe Gly Glu Ile Arg Ser Pro
                20                  25                  30

Asn Phe Pro Asp Ser Tyr Pro Ser Asp Ser Glu Val Thr Trp Asn Ile
                35                  40                  45

Ser Val Pro Glu Gly Phe Lys Ile Lys Leu Tyr Tyr Met His Phe Asp
50                  55                  60

Leu Glu Ser Ser Tyr Leu Cys Glu Tyr Asp Tyr Val Lys Ile Glu Ala
65                  70                  75                  80

Glu Asp Gln Glu Leu Ala Thr Phe Cys Gly Arg Glu Thr Thr Asp Thr
                85                  90                  95

Glu Gln Ala Pro Gly Gln Gln Val Ile Leu Ser Pro Gly Pro Tyr Met
                100                 105                 110

Gly Leu Thr Phe Arg Ser Asp Phe Ser Asn Glu Glu Arg Phe Thr Gly
                115                 120                 125

Phe Asp Ala His Tyr Thr Ala Val Asp Val Asp Glu Cys Leu Glu Lys
                130                 135                 140

Ser Asp Glu Glu Leu Ala Cys Asp His Tyr Cys His Asn Tyr Ile Gly
145                 150                 155                 160

Gly Tyr Tyr Cys Ser Cys Arg Phe Gly Tyr Ile Leu His Ser Asp Asn
                165                 170                 175
```

-continued

```
Arg Thr Cys Lys Val Glu Cys Ser Asp Asn Leu Tyr Thr Gln Arg Ser
            180                 185                 190

Gly Val Val Thr Ser Ala Asp Phe Pro Ser Pro Tyr Pro Lys Ser Ser
        195                 200                 205

Asp Cys Leu Tyr Arg Ile Glu Leu Glu Asp Gly Phe Phe Ile Thr Leu
        210                 215                 220

Ser Phe Glu Asp Ser Phe Asp Val Glu Asp His Pro Glu Val Thr Cys
225                 230                 235                 240

Pro Tyr Asp Tyr Ile Lys Ile Lys Ala Gly Gln Arg Glu Phe Gly Pro
                245                 250                 255

Phe Cys Gly Glu Lys Ser Pro Gly Arg Ile Glu Thr Gln Thr Asn Ser
            260                 265                 270

Val Gln Ile Leu Phe His Ser Asp Asn Ser Gly Glu Asn Arg Gly Trp
        275                 280                 285

Lys Leu Ser Tyr Thr Ala Ile Gly Asn Pro Cys Pro Leu Val Gln Pro
        290                 295                 300

Pro Ile Asn Gly Lys Ile Glu Pro Ser Gln Ala Lys Tyr Thr Phe Lys
305                 310                 315                 320

Asp Gln Val Val Ile Ser Cys Asn Thr Gly Tyr Lys Val Leu Lys Asp
                325                 330                 335

Asn Leu Glu Ser Asp Ser Phe Gln Ile Glu Cys Leu Lys Asp Gly Thr
            340                 345                 350

Trp Ser Asn Lys Ile Pro Ile Cys Lys Ile Ala Asp Cys Gln Ala Pro
        355                 360                 365

Pro Glu Leu Glu His Gly Phe Val Thr Phe Leu Ser Arg Asn Asn Leu
        370                 375                 380

Thr Thr Tyr Arg Ala Arg Ile Gln Tyr His Cys Gln His Pro Tyr Tyr
385                 390                 395                 400

His Met Ala Pro Asn Ser Thr Ala Thr Tyr Thr Cys Asp Ala Ser Gly
                405                 410                 415

Val Trp Arg Ser Glu Glu Leu Gly Thr Val Leu Pro Ser Cys Arg Pro
            420                 425                 430

Val Cys Gly Arg Pro Val Arg Ala Leu Pro Gly Ile Ile Lys Arg Ile
        435                 440                 445

Ile Gly Gly Arg Asn Ala Glu Pro Gly Phe Phe Pro Trp Gln Ala Leu
        450                 455                 460

Ile Val Val Glu Asp Met Ser Arg Val Pro Asn Asp Lys Trp Phe Gly
465                 470                 475                 480

Ser Gly Ala Leu Leu Ser Asp Ser Trp Val Leu Thr Ala Ala His Val
                485                 490                 495

Leu Arg Ser Gln Arg Arg Asp Lys Thr Val Ile Pro Val Ser Lys Glu
            500                 505                 510

His Val Thr Val Tyr Leu Ala Leu His Asp Val Arg Asn Lys Leu Glu
        515                 520                 525

Ala Val Asn Arg Thr Val Glu Arg Ile Ile Leu His Glu Asp Phe Asp
        530                 535                 540

Ile Gln Asn Tyr Asn His Asp Ile Ala Leu Val Lys Leu Lys Glu Lys
545                 550                 555                 560

Val Thr Met Gly Asn Tyr Val Met Pro Ile Cys Leu Pro Gln Phe Glu
                565                 570                 575

His Glu Leu Glu Gly Pro His Pro Asn Thr Leu Gly Leu Val Ala Gly
            580                 585                 590

Trp Gly Ile Ser Asn Pro Asn Ile Thr Val Asp Glu Ile Ile Ser Ser
```

```
            595                 600                 605
Gly Met Arg Thr Leu Ser Asp Ile Leu Gln Tyr Val Lys Leu Pro Val
610                 615                 620

Val Leu His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Gln Asp
                660                 665                 670

Pro Gly Thr Arg Arg Trp Val Ala Gln Gly Leu Val Ser Trp Gly Gly
                675                 680                 685

Pro Glu Glu Cys Gly Ser Lys Gln Val Tyr Gly Val Tyr Thr Lys Val
690                 695                 700

Ser Asn Tyr Val Asp Trp Val Glu Lys Asn Thr Gly Ser Ser Glu Arg
705                 710                 715                 720

Trp Thr Phe Leu Asp Pro Glu Leu Glu Arg
                725                 730

<210> SEQ ID NO 6
<211> LENGTH: 728
<212> TYPE: PRT
<213> ORGANISM: Oryctolagus cuniculus

<400> SEQUENCE: 6

Met Arg Trp Leu Leu Cys His Ala Leu Cys Phe Ser Leu Leu Lys
1               5                   10                  15

Ala Ser Ala His Thr Val Glu Leu Asn Asp Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Glu Gly Phe Arg Ile Lys Leu Tyr Phe Met His
50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
                100                 105                 110

Phe Met Ser Ile Thr Phe Arg Ser Asp Phe Ser Asn Glu Glu Arg Phe
            115                 120                 125

Thr Gly Phe Asp Ala His Tyr Met Ala Val Asp Val Asp Glu Cys Lys
130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
                180                 185                 190

Arg Thr Gly Val Ile Thr Ser Pro Asp Tyr Pro Asn Pro Tyr Pro Lys
            195                 200                 205

Ser Ser Glu Cys Phe Tyr Thr Ile Glu Leu Glu Gly Phe Met Ile
        210                 215                 220

Ser Leu Gln Phe Glu Asp Ile Phe Asp Ile Glu Asp His Pro Glu Val
225                 230                 235                 240
```

```
Pro Cys Pro Tyr Asp Tyr Ile Lys Ile Lys Val Gly Glu Asn Val Trp
            245                 250                 255

Gly Pro Tyr Cys Gly Glu Lys Ala Pro Glu Ala Ile Ser Thr Gln Ser
        260                 265                 270

His Ser Val Gln Ile Leu Phe Arg Ser Asp Asn Ser Gly Glu Asn Arg
    275                 280                 285

Gly Trp Arg Leu Ser Tyr Arg Ala Ala Gly Asn Glu Cys Ser Glu Leu
        290                 295                 300

Gln Pro Pro Asp Gln Gly Lys Ile Glu Pro Leu Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asp Val Glu Met Asp Thr Phe Gln Ile Glu Cys Leu Lys Asp
                340                 345                 350

Gly Thr Trp Ser Asn Lys Ile Pro Thr Cys Lys Met Val Asp Cys Gly
            355                 360                 365

Val Pro Ala Glu Leu Glu His Gly Leu Leu Thr Phe Ser Ser Arg Ser
        370                 375                 380

Asn Leu Thr Thr Tyr Ala Ser Glu Val Thr Tyr Ser Cys Gln Gln Pro
385                 390                 395                 400

Tyr Tyr Arg Leu Leu His Asn Val Ser Gly Val Tyr Thr Cys Ser Ala
                405                 410                 415

Gln Gly Ile Trp Thr Asn Glu Val Leu Gly Arg Ser Leu Pro Thr Cys
            420                 425                 430

Ile Pro Val Cys Gly Gln Pro Ser Arg Ser Leu Pro Ser Leu Ile Lys
        435                 440                 445

Arg Ile Ile Gly Gly Arg Asn Ala Glu Pro Gly Leu Phe Pro Trp Gln
    450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Glu Ser Trp Ile Leu Thr Ala Ala
                485                 490                 495

His Val Leu Arg Ser Gln Arg Arg Asp Asn Thr Val Ile Pro Val Ser
            500                 505                 510

Arg Glu His Val Thr Val Tyr Leu Gly Leu His Asp Val Arg Asp Lys
        515                 520                 525

Ser Gly Ala Val Asn Ser Ser Ala Ala Arg Val Leu Leu His Pro Asp
    530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Ile Cys Leu Pro Arg
                565                 570                 575

Pro Glu Pro Glu Gly Pro Ala Pro Tyr Met Leu Gly Leu Val Ala Gly
            580                 585                 590

Trp Gly Ile Ser Asn Pro Asn Val Thr Val Asp Glu Ile Ile Ser Ser
        595                 600                 605

Gly Thr Arg Thr Leu Ser Asp Ile Leu Gln Tyr Val Lys Leu Pro Val
    610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Leu Asp
```

```
                        660                 665                 670
Asp Leu Ser Arg Arg Trp Val Ala Gln Gly Leu Val Ser Trp Gly Gly
                675                 680                 685

Pro Glu Glu Cys Gly Ser Lys Gln Val Tyr Gly Val Tyr Thr Lys Val
            690                 695                 700

Ser Asn Tyr Val Asp Trp Val Trp Glu Gln Met Gly Ser Pro Gln Gly
705                 710                 715                 720

Leu Gly Glu Leu Gln Val Glu Arg
                725

<210> SEQ ID NO 7
<211> LENGTH: 728
<212> TYPE: PRT
<213> ORGANISM: Cynomologus monkey

<400> SEQUENCE: 7

Met Arg Trp Leu Leu Leu Tyr His Ala Leu Cys Phe Ser Leu Ser Lys
1               5                   10                  15

Ala Ser Ala His Thr Val Glu Leu Asn Asp Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Asp Gly Phe Arg Ile Lys Leu Tyr Phe Met His
        50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Asn Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
290                 295                 300
```

```
Gln Pro Pro Val His Gly Lys Ile Glu Pro Ser Gln Ala Lys Tyr Ser
305                 310                 315                 320

Phe Lys Asp Gln Val Leu Ile Ser Cys Asp Thr Gly Tyr Lys Val Leu
            325                 330                 335

Lys Asp Asn Val Glu Met Asp Thr Phe Gln Ile Glu Cys Leu Lys Asp
                340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Val Thr Phe Ser Thr Arg Asn
370                 375                 380

Asn Leu Thr Thr Tyr Lys Ser Glu Ile Arg Tyr Ser Cys Gln Glu Pro
385                 390                 395                 400

Tyr Tyr Lys Met Leu Asn Asn Ile Thr Gly Ile Tyr Thr Cys Ser Ala
            405                 410                 415

Gln Gly Val Trp Met Asn Lys Val Leu Gly Arg Ser Leu Pro Thr Cys
                420                 425                 430

Leu Pro Glu Cys Gly Gln Pro Ser Arg Ser Leu Pro Ser Leu Val Lys
        435                 440                 445

Arg Ile Ile Gly Gly Arg Asn Ala Glu Pro Gly Leu Phe Pro Trp Gln
450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Glu Ser Trp Ile Leu Thr Ala Ala
            485                 490                 495

His Val Leu Arg Ser Gln Arg Arg Asp Thr Thr Val Ile Pro Val Ser
                500                 505                 510

Lys Glu His Val Thr Val Tyr Leu Gly Leu His Asp Val Arg Asp Lys
        515                 520                 525

Ser Gly Ala Val Asn Ser Ser Ala Ala Arg Val Val Leu His Pro Asp
530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
            565                 570                 575

Leu Glu Pro Glu Gly Pro Ser Pro His Met Leu Gly Leu Val Ala Gly
                580                 585                 590

Trp Gly Ile Ser Asn Pro Asn Val Thr Val Asp Glu Ile Ile Ser Ser
        595                 600                 605

Gly Thr Arg Thr Leu Ser Asp Val Leu Gln Tyr Val Lys Leu Pro Val
610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
            645                 650                 655

Lys Asp Thr Cys Leu Gly Asp Ser Gly Gly Ala Phe Val Ile Leu Asp
                660                 665                 670

Asp Leu Ser Gln Arg Trp Val Val Gln Gly Leu Val Ser Trp Gly Gly
        675                 680                 685

Pro Glu Glu Cys Gly Ser Lys Gln Val Tyr Gly Val Tyr Thr Lys Val
690                 695                 700

Ser Asn Tyr Val Asp Trp Val Trp Glu Gln Met Gly Ser Pro Gln Gly
705                 710                 715                 720

Arg Ala Pro Gly Gly Thr Val Ser
```

<210> SEQ ID NO 8
<211> LENGTH: 699
<212> TYPE: PRT
<213> ORGANISM: Homo sapiens

<400> SEQUENCE: 8

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

```
Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
        435                 440                 445

Ile Phe Asn Gly Arg Pro Ala Gln Lys Gly Thr Thr Pro Trp Ile Ala
    450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Lys Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
        515                 520                 525

Asn Glu Gln His Leu Gly Val Lys His Thr Thr Leu His Pro Lys Tyr
    530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Ser Thr Cys Gln Lys Ala Tyr Ala Pro Leu Lys Lys Lys
    610                 615                 620

Val Thr Arg Asp Met Ile Cys Ala Gly Glu Lys Glu Gly Gly Lys Asp
625                 630                 635                 640

Ala Cys Ser Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Gly Val Arg Asn
    690                 695

<210> SEQ ID NO 9
<211> LENGTH: 12
<212> TYPE: PRT
<213> ORGANISM: Artificial sequence
<220> FEATURE:
<223> OTHER INFORMATION: Synthetic

<400> SEQUENCE: 9

Val Leu Arg Ser Gln Arg Arg Asp Thr Thr Val Ile
1               5                   10

<210> SEQ ID NO 10
<211> LENGTH: 15
```

```
<212> TYPE: PRT
<213> ORGANISM: Artificial sequence
<220> FEATURE:
<223> OTHER INFORMATION: Synthetic

<400> SEQUENCE: 10

Thr Ala Ala His Val Leu Arg Ser Gln Arg Arg Asp Thr Thr Val
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic

<400> SEQUENCE: 11

Asp Phe Asn Ile Gln Asn Tyr Asn His Asp Ile Ala Leu Val Gln
1               5                   10                  15

<210> SEQ ID NO 12
<211> LENGTH: 13
<212> TYPE: PRT
<213> ORGANISM: Artificial sequence
<220> FEATURE:
<223> OTHER INFORMATION: Synthetic

<400> SEQUENCE: 12

Pro His Ala Glu Cys Lys Thr Ser Tyr Glu Ser Arg Ser
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Gly Asn Tyr Ser Val Thr Glu Asn Met Phe Cys
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic

<400> SEQUENCE: 14

Val Ser Asn Tyr Val Asp Trp Val Trp Glu
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic

<400> SEQUENCE: 15

Val Leu Arg Ser Gln Arg Arg Asp Thr Thr Val
1               5                   10

<210> SEQ ID NO 16
<211> LENGTH: 13
<212> TYPE: PRT
```

```
<213> ORGANISM: Artificial sequence
<220> FEATURE:
<223> OTHER INFORMATION: Synthetic

<400> SEQUENCE: 16

Glu Cys Gly Gln Pro Ser Arg Ser Leu Pro Ser Leu Val
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic

<400> SEQUENCE: 17

Arg Asn Ala Glu Pro Gly Leu Phe Pro Trp Gln
1               5                   10

<210> SEQ ID NO 18
<211> LENGTH: 15
<212> TYPE: PRT
<213> ORGANISM: Artificial sequence
<220> FEATURE:
<223> OTHER INFORMATION: Synthetic

<400> SEQUENCE: 18

Lys Trp Phe Gly Ser Gly Ala Leu Leu Ser Ala Ser Trp Ile Leu
1               5                   10                  15

<210> SEQ ID NO 19
<211> LENGTH: 10
<212> TYPE: PRT
<213> ORGANISM: Artificial sequence
<220> FEATURE:
<223> OTHER INFORMATION: Synthetic

<400> SEQUENCE: 19

Glu His Val Thr Val Tyr Leu Gly Leu His
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic

<400> SEQUENCE: 20

Pro Val Pro Leu Gly Pro His Val Met Pro
1               5                   10

<210> SEQ ID NO 21
<211> LENGTH: 7
<212> TYPE: PRT
<213> ORGANISM: Artificial sequence
<220> FEATURE:
<223> OTHER INFORMATION: Synthetic

<400> SEQUENCE: 21

Ala Pro His Met Leu Gly Leu
1               5

<210> SEQ ID NO 22
<211> LENGTH: 10
<212> TYPE: PRT
<213> ORGANISM: Artificial sequence
```

```
<220> FEATURE:
<223> OTHER INFORMATION: Synthetic

<400> SEQUENCE: 22

Ser Asp Val Leu Gln Tyr Val Lys Leu Pro
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic

<400> SEQUENCE: 23

Ala Phe Val Ile Phe Asp Asp Leu Ser Gln Arg Trp
1               5                   10

<210> SEQ ID NO 24
<211> LENGTH: 114
<212> TYPE: PRT
<213> ORGANISM: Artificial sequence
<220> FEATURE:
<223> OTHER INFORMATION: Synthetic

<400> SEQUENCE: 24

Gln Val Gln Leu Lys Gln Ser Gly Pro Glu Leu Val Lys Pro Gly Ala
1               5                   10                  15

Ser Val Lys Leu Ser Cys Lys Ala Ser Gly Tyr Thr Phe Thr Thr Asp
                20                  25                  30

Asp Ile Asn Trp Val Lys Gln Arg Pro Gly Gln Gly Leu Glu Trp Ile
            35                  40                  45

Gly Trp Ile Tyr Pro Arg Asp Asp Arg Thr Lys Tyr Asn Asp Lys Phe
        50                  55                  60

Lys Asp Lys Ala Thr Leu Thr Val Asp Thr Ser Ser Asn Thr Ala Tyr
65                  70                  75                  80

Met Asp Leu His Ser Leu Thr Ser Glu Asp Ser Ala Val Tyr Phe Cys
                85                  90                  95

Ser Ser Leu Glu Asp Thr Tyr Trp Gly Gln Gly Thr Leu Val Ala Val
            100                 105                 110

Ser Ser

<210> SEQ ID NO 25
<211> LENGTH: 114
<212> TYPE: PRT
<213> ORGANISM: Artificial sequence
<220> FEATURE:
<223> OTHER INFORMATION: Synthetic

<400> SEQUENCE: 25

Gln Val Gln Leu Lys Gln Ser Gly Pro Glu Leu Val Lys Pro Gly Ala
1               5                   10                  15

Ser Val Lys Leu Ser Cys Lys Ala Ser Gly Tyr Thr Phe Thr Ser Asn
                20                  25                  30

Asp Ile Asn Trp Val Lys Gln Arg Pro Gly Gln Gly Leu Glu Trp Ile
            35                  40                  45

Gly Trp Ile Tyr Pro Arg Asp Gly Ser Ile Lys Tyr Asn Glu Lys Phe
        50                  55                  60

Thr Asp Lys Ala Thr Leu Thr Val Asp Val Ser Ser Ser Thr Ala Tyr
65                  70                  75                  80
```

```
Met Glu Leu His Ser Leu Thr Ser Glu Asp Ser Ala Val Tyr Phe Cys
                85                  90                  95

Ser Gly Val Glu Asp Ser Tyr Trp Gly Gln Gly Thr Leu Val Thr Val
            100                 105                 110

Ser Ser
```

<210> SEQ ID NO 26
<211> LENGTH: 114
<212> TYPE: PRT
<213> ORGANISM: Artificial sequence
<220> FEATURE:
<223> OTHER INFORMATION: Synthetic

<400> SEQUENCE: 26

```
Gln Val Gln Leu Lys Gln Ser Gly Pro Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Thr Thr Lys Tyr Asn Glu Glu Phe
50                  55                  60

Thr Asp Lys Ala Thr Leu Thr Val Asp Val Ser Ser Thr Ala Phe
65                  70                  75                  80

Met Glu Leu His Ser Leu Thr Ser Glu Asp Ser Ala Val Tyr Phe Cys
                85                  90                  95

Ser Ser Val Glu Asp Ser Tyr Trp Gly Gln Gly Thr Leu Val Thr Val
            100                 105                 110

Ser Ser
```

<210> SEQ ID NO 27
<211> LENGTH: 114
<212> TYPE: PRT
<213> ORGANISM: Artificial sequence
<220> FEATURE:
<223> OTHER INFORMATION: Synthetic

<400> SEQUENCE: 27

```
Gln Val Gln Leu Lys Gln Ser Gly Pro Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Thr Thr Lys Tyr Asn Glu Lys Phe
50                  55                  60

Thr Asp Lys Ala Thr Leu Thr Val Asp Val Ser Ser Thr Ala Phe
65                  70                  75                  80

Met Glu Leu His Arg Leu Thr Ser Glu Asp Ser Ala Val Tyr Phe Cys
                85                  90                  95

Ser Ser Val Glu Asp Ser Tyr Trp Gly Gln Gly Thr Leu Val Thr Val
            100                 105                 110

Ser Ser
```

<210> SEQ ID NO 28
<211> LENGTH: 116
<212> TYPE: PRT
<213> ORGANISM: Artificial sequence
<220> FEATURE:
<223> OTHER INFORMATION: Synthetic

<400> SEQUENCE: 28

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Ser Tyr
            20                  25                  30

Gly Met Ser Trp Val Arg Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Arg Thr Pro Tyr
65                  70                  75                  80

Leu Gln Ile Asn Asn Leu Lys Asn Glu Asp Thr Ala Thr Tyr Phe Cys
                85                  90                  95

Ala Arg Gly Gly Glu Ala Met Asp Tyr Trp Gly Gln Gly Thr Ser Val
            100                 105                 110

Thr Val Ser Ser
            115

<210> SEQ ID NO 29
<211> LENGTH: 116
<212> TYPE: PRT
<213> ORGANISM: Artificial sequence
<220> FEATURE:
<223> OTHER INFORMATION: Synthetic

<400> SEQUENCE: 29

Gln Ile Gln Leu Val Gln Ser Gly Pro Glu Leu Lys Thr Pro Gly Glu
1               5                   10                  15

Thr Val Lys Ile Ser Cys Lys Ala Ser Gly Tyr Ile Phe Thr Ser Tyr
            20                  25                  30

Gly Ile Thr Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Thr Thr Tyr Phe Cys
                85                  90                  95

Thr Arg Gly Gly Asp Ala Leu Asp Tyr Trp Gly Gln Gly Thr Ser Val
            100                 105                 110

Thr Val Ser Ser
            115

<210> SEQ ID NO 30
<211> LENGTH: 113
<212> TYPE: PRT
<213> ORGANISM: Artificial sequence
<220> FEATURE:
<223> OTHER INFORMATION: Synthetic

<400> SEQUENCE: 30

Gln Val Gln Leu Lys Gln Ser Gly Ala Glu Leu Met Lys Pro Gly Ala
1               5                   10                  15

Ser Val Lys Leu Ser Cys Lys Ala Thr Gly Tyr Thr Phe Thr Gly Lys
            20                  25                  30

Trp Ile Glu Trp Val Lys Gln Arg Pro Gly His Gly Leu Glu Trp Ile
            35                  40                  45

Gly Glu Ile Leu Pro Gly Thr Gly Ser Thr Asn Tyr Asn Glu Lys Phe
    50                  55                  60

Lys Gly Lys Ala Thr Phe Thr Ala Asp Ser Ser Asn Thr Ala Tyr
65                  70                  75                  80

Met Gln Leu Ser Ser Leu Thr Thr Glu Asp Ser Ala Met Tyr Tyr Cys
                85                  90                  95

Leu Arg Ser Glu Asp Val Trp Gly Thr Gly Thr Thr Val Thr Val Ser
            100                 105                 110

Ser

<210> SEQ ID NO 31
<211> LENGTH: 113
<212> TYPE: PRT
<213> ORGANISM: Artificial sequence
<220> FEATURE:
<223> OTHER INFORMATION: Synthetic

<400> SEQUENCE: 31

Gln Val Gln Leu Lys Gln Ser Gly Ala Glu Leu Met Lys Pro Gly Ala
1               5                   10                  15

Ser Val Lys Leu Ala Cys Lys Ala Thr Gly Tyr Thr Phe Thr Gly Tyr
            20                  25                  30

Trp Ile Glu Trp Ile Lys Gln Arg Pro Gly Gln Gly Leu Glu Trp Ile
            35                  40                  45

Gly Glu Met Leu Pro Gly Ser Gly Ser Thr His Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Gly Leu Thr Thr Glu Asp Ser Ala Ile Tyr Tyr Cys
                85                  90                  95

Val Arg Ser Ile Asp Tyr Trp Gly Gln Gly Thr Thr Leu Thr Val Ser
            100                 105                 110

Ser

<210> SEQ ID NO 32
<211> LENGTH: 125
<212> TYPE: PRT
<213> ORGANISM: Artificial sequence
<220> FEATURE:
<223> OTHER INFORMATION: Synthetic

<400> SEQUENCE: 32

Gln Val Gln Leu Lys Gln Ser Gly Pro Glu Leu Ala Arg Pro Trp Ala
1               5                   10                  15

Ser Val Lys Ile Ser Cys Gln Ala Phe Tyr Thr Phe Ser Arg Arg Val
            20                  25                  30

His Phe Ala Ile Arg Asp Thr Asn Tyr Trp Met Gln Trp Val Lys Gln
            35                  40                  45

Arg Pro Gly Gln Gly Leu Glu Trp Ile Gly Ala Ile Tyr Pro Gly Asn
    50                  55                  60

Gly Asp Thr Ser Tyr Asn Gln Lys Phe Lys Gly Lys Ala Thr Leu Thr
65                  70                  75                  80

Ala Asp Lys Ser Ser Ser Thr Ala Tyr Met Gln Leu Ser Ser Leu Thr
                85                  90                  95

Ser Glu Asp Ser Ala Val Tyr Tyr Cys Ala Ser Gly Ser His Tyr Phe

Asp Tyr Trp Gly Gln Gly Thr Thr Leu Thr Val Ser Ser
         115                 120                 125

<210> SEQ ID NO 33
<211> LENGTH: 123
<212> TYPE: PRT
<213> ORGANISM: Artificial sequence
<220> FEATURE:
<223> OTHER INFORMATION: Synthetic

<400> SEQUENCE: 33

Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Thr Leu Thr Asp Tyr
            20                  25                  30

Tyr Met Asn Trp Val Lys Gln Ser His Gly Lys Ser Leu Glu Trp Ile
        35                  40                  45

Gly Asp Val Asn Pro Asn Asn Asp Gly Thr Thr Tyr Asn Gln Lys Phe
    50                  55                  60

Lys Gly Arg Ala Thr Leu Thr Val Asp Lys Ser Ser Asn Thr Ala Ser
65                  70                  75                  80

Met Glu Leu Arg Ser Leu Thr Ser Glu Asp Ser Ala Val Tyr Tyr Cys
                85                  90                  95

Ala Ile Cys Pro Phe Tyr Tyr Leu Gly Lys Gly Thr His Phe Asp Tyr
            100                 105                 110

Trp Gly Gln Gly Thr Ser Leu Thr Val Ser Ser
        115                 120

<210> SEQ ID NO 34
<211> LENGTH: 124
<212> TYPE: PRT
<213> ORGANISM: Artificial sequence
<220> FEATURE:
<223> OTHER INFORMATION: Synthetic

<400> SEQUENCE: 34

Glu Val Gln Leu Gln Gln Ser Gly Pro Val Leu Val Lys Pro Gly Ala
1               5                   10                  15

Ser Gly Lys Met Ser Cys Lys Ala Ser Gly Tyr Lys Phe Thr Asp Tyr
            20                  25                  30

Tyr Met Ile Trp Val Lys Gln Ser His Gly Lys Ser Leu Glu Trp Ile
        35                  40                  45

Gly Val Ile Lys Ile Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Gly Pro Ser Leu Tyr Asp Tyr Asp Pro Tyr Trp Tyr Phe Asp
            100                 105                 110

Val Trp Gly Thr Gly Thr Thr Val Thr Val Ser Ser
        115                 120

<210> SEQ ID NO 35
<211> LENGTH: 120
<212> TYPE: PRT
<213> ORGANISM: Artificial sequence
<220> FEATURE:

<223> OTHER INFORMATION: Synthetic

<400> SEQUENCE: 35

```
Gln Val Gln Leu Lys Gln Ser Gly Thr Glu Leu Met Lys Pro Gly Ala
1               5                   10                  15
Ser Val Asn Leu Ser Cys Lys Ala Ser Gly Tyr Thr Phe Thr Ala Tyr
            20                  25                  30
Trp Ile Glu Trp Val Lys Gln Arg Pro Gly His Gly Leu Glu Trp Ile
        35                  40                  45
Gly Glu Ile Leu Pro Gly Ser Gly Thr Thr Asn Tyr Asn Glu Asn Phe
    50                  55                  60
Lys Asp Arg Ala Thr Phe Thr Ala Asp Thr Ser Ser Asn Thr Ala Tyr
65                  70                  75                  80
Met Gln Leu Ser Ser Leu Thr Ser Glu Asp Ser Ala Ile Tyr Tyr Cys
                85                  90                  95
Ala Arg Ser Tyr Tyr Tyr Ala Ser Arg Trp Phe Ala Phe Trp Gly Gln
            100                 105                 110
Gly Thr Leu Val Thr Val Ser Ser
        115                 120
```

<210> SEQ ID NO 36
<211> LENGTH: 120
<212> TYPE: PRT
<213> ORGANISM: Artificial sequence
<220> FEATURE:
<223> OTHER INFORMATION: Synthetic

<400> SEQUENCE: 36

```
Glu Val Gln Leu Gln Gln Pro Gly Ala Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Trp Ile Thr Trp Val Lys Gln Arg Pro Gly Gln Gly Leu Glu Trp Ile
        35                  40                  45
Gly Asp Ile Tyr Pro Gly Ser Gly Ser Thr Asn Tyr Asn Glu Lys Phe
    50                  55                  60
Lys Ser Lys Ala Thr Leu Thr Val Asp Thr Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Arg Arg Tyr Tyr Ala Thr Ala Trp Phe Ala Tyr Trp Gly Gln
            100                 105                 110
Gly Thr Leu Val Thr Val Ser Ser
        115                 120
```

<210> SEQ ID NO 37
<211> LENGTH: 120
<212> TYPE: PRT
<213> ORGANISM: Artificial sequence
<220> FEATURE:
<223> OTHER INFORMATION: Synthetic

<400> SEQUENCE: 37

```
Gln Val Gln Leu Lys Gln Ser Gly Ala Glu Leu Val Arg Pro Gly Ala
1               5                   10                  15
Ser Val Lys Leu Ser Cys Lys Ala Ser Gly Tyr Thr Phe Thr Asp Tyr
            20                  25                  30
Tyr Ile Asn Trp Val Lys Gln Arg Pro Gly Gln Gly Leu Glu Trp Ile
```

```
               35                  40                  45
Ala Arg Ile Tyr Pro Gly Ser Gly Asn Thr Tyr Tyr Asn Glu Lys Phe
 50                  55                  60

Lys Gly Lys Ala Thr Leu Thr Ala Glu Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asn Tyr Tyr Ile Ser Ser Pro Trp Phe Ala Tyr Trp Gly Gln
                100                 105                 110

Gly Thr Leu Val Thr Val Ser Ser
            115                 120

<210> SEQ ID NO 38
<211> LENGTH: 120
<212> TYPE: PRT
<213> ORGANISM: Artificial sequence
<220> FEATURE:
<223> OTHER INFORMATION: Synthetic

<400> SEQUENCE: 38

Gln Val Gln Leu Lys Gln Ser Gly Ala Glu Leu Val Thr Pro Gly Ala
 1               5                  10                  15

Ser Val Lys Met Ser Cys Lys Ala Ser Gly Tyr Thr Phe Thr Thr Tyr
                20                  25                  30

Pro Ile Glu Trp Met Lys Gln Asn His Gly Lys Ser Leu Glu Trp Ile
                35                  40                  45

Gly Asn Phe His Pro Tyr Asn Asp Asp Thr Lys Tyr Asn Glu Lys Phe
 50                  55                  60

Lys Gly Lys Ala Thr Leu Thr Val Glu Lys Ser Ser Asn Thr Val Tyr
 65                  70                  75                  80

Leu Glu Leu Ser Arg Leu Thr Ser Asp Asp Ser Ala Val Tyr Phe Cys
                 85                  90                  95

Ala Arg Arg Val Tyr Tyr Ser Tyr Phe Trp Phe Gly Tyr Trp Gly His
                100                 105                 110

Gly Thr Leu Val Thr Val Ser Ser
            115                 120

<210> SEQ ID NO 39
<211> LENGTH: 120
<212> TYPE: PRT
<213> ORGANISM: Artificial sequence
<220> FEATURE:
<223> OTHER INFORMATION: Synthetic

<400> SEQUENCE: 39

Gln Val Gln Leu Lys Gln Ser Gly Ala Glu Leu Val Lys Pro Gly Ala
 1               5                  10                  15

Ser Val Lys Met Ser Cys Lys Ala Ser Gly Tyr Thr Phe Thr Thr Tyr
                20                  25                  30

Pro Ile Glu Trp Met Lys Gln Asn His Gly Lys Ser Leu Glu Trp Ile
                35                  40                  45

Gly Asn Phe His Pro Tyr Asn Gly Asp Ser Lys Tyr Asn Glu Lys Phe
 50                  55                  60

Lys Gly Lys Ala Thr Leu Thr Val Glu Lys Ser Ser Ser Thr Val Tyr
 65                  70                  75                  80

Leu Glu Leu Ser Arg Leu Pro Ser Ala Asp Ser Ala Ile Tyr Tyr Cys
                 85                  90                  95
```

Ala Arg Arg His Tyr Ala Ala Ser Pro Trp Phe Ala His Trp Gly Gln
            100                 105                 110

Gly Thr Leu Val Thr Val Ser Ser
        115                 120

<210> SEQ ID NO 40
<211> LENGTH: 113
<212> TYPE: PRT
<213> ORGANISM: Artificial sequence
<220> FEATURE:
<223> OTHER INFORMATION: Synthetic

<400> SEQUENCE: 40

Asp Ile Val Met Thr Gln Ser Pro Ser Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

Arg

<210> SEQ ID NO 41
<211> LENGTH: 113
<212> TYPE: PRT
<213> ORGANISM: Artificial sequence
<220> FEATURE:
<223> OTHER INFORMATION: Synthetic

<400> SEQUENCE: 41

Asp Ile Val Met Thr Gln Ser Pro Ser Ser Leu Ala Val Ser Ala Gly
1               5                   10                  15

Glu Arg Val Thr Met Ser Cys Lys Ser Ser Gln Ser Leu Leu Ile Ser
            20                  25                  30

Arg Thr Arg Lys Asn Tyr Leu Ser Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

Arg

<210> SEQ ID NO 42
<211> LENGTH: 113
<212> TYPE: PRT
<213> ORGANISM: Artificial sequence
<220> FEATURE:
<223> OTHER INFORMATION: Synthetic

<400> SEQUENCE: 42

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Ile Ser
            20                  25                  30

Arg Thr Arg Lys Asn Tyr Leu Ser Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

Arg

<210> SEQ ID NO 43
<211> LENGTH: 113
<212> TYPE: PRT
<213> ORGANISM: Artificial sequence
<220> FEATURE:
<223> OTHER INFORMATION: Synthetic

<400> SEQUENCE: 43

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg

<210> SEQ ID NO 44
<211> LENGTH: 113
<212> TYPE: PRT
<213> ORGANISM: Artificial sequence
<220> FEATURE:
<223> OTHER INFORMATION: Synthetic

<400> SEQUENCE: 44

Asp Ile Val Met Thr Gln Ala Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Ser Trp Leu Leu Gln Arg Pro Gly Gln Ser
        35                  40                  45

Pro Lys Arg Leu Ile Tyr Leu Val Ser Lys Leu Asp Ser Gly Val Pro

```
                50                  55                  60
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Tyr Thr Phe Gly Gly Gly Thr Lys Leu Glu Ile Lys
                100                 105                 110

Arg

<210> SEQ ID NO 45
<211> LENGTH: 113
<212> TYPE: PRT
<213> ORGANISM: Artificial sequence
<220> FEATURE:
<223> OTHER INFORMATION: Synthetic

<400> SEQUENCE: 45

Asp Ile Val Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Ile Pro Thr Phe Gly Gly Gly Thr Lys Leu Glu Ile Lys
                100                 105                 110

Arg

<210> SEQ ID NO 46
<211> LENGTH: 113
<212> TYPE: PRT
<213> ORGANISM: Artificial sequence
<220> FEATURE:
<223> OTHER INFORMATION: Synthetic

<400> SEQUENCE: 46

Asp Val Leu Met Thr Gln Thr Pro Leu Ser Leu Pro Val Ser Leu Gly
 1               5                  10                  15

Glu Gln Ala Ser Ile Ser Cys Arg Ser Ser Gln Ser Leu Val Gln Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Gly Gly Thr Lys Leu Glu Ile Lys
                100                 105                 110

Arg
```

```
<210> SEQ ID NO 47
<211> LENGTH: 108
<212> TYPE: PRT
<213> ORGANISM: Artificial sequence
<220> FEATURE:
<223> OTHER INFORMATION: Synthetic

<400> SEQUENCE: 47

Asp Ile Gln Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Ile Lys Arg
            100                 105

<210> SEQ ID NO 48
<211> LENGTH: 108
<212> TYPE: PRT
<213> ORGANISM: Artificial sequence
<220> FEATURE:
<223> OTHER INFORMATION: Synthetic

<400> SEQUENCE: 48

Asp Ile Gln Met Thr Gln Thr Pro Ala Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asn Gly Thr Val Lys Leu Leu Val
        35                  40                  45

Phe Tyr Thr Ser Arg Leu His Ser Gly Val Pro Ser Arg Phe Ser Gly
50                  55                  60

Ser Gly Ser Gly Ala Glu His Ser Leu Thr Ile Ser Asn Leu Glu Gln
65                  70                  75                  80

Glu Asp Val Ala Thr Tyr Phe Cys Gln Gln Gly Phe Thr Leu Pro Trp
                85                  90                  95

Thr Phe Gly Gly Gly Thr Lys Val Glu Ile Lys Arg
            100                 105

<210> SEQ ID NO 49
<211> LENGTH: 113
<212> TYPE: PRT
<213> ORGANISM: Artificial sequence
<220> FEATURE:
<223> OTHER INFORMATION: Synthetic

<400> SEQUENCE: 49

Asp Val Leu Met Thr Gln Thr Pro Leu Ser Leu Pro Val Ser Leu Gly
1               5                   10                  15

Asp Gln Ala Ser Phe Ser Cys Arg Ser Ser Gln Ser Leu Ile His Ser
            20                  25                  30

Asn Gly Asn Thr Tyr Leu His Trp Tyr Leu Gln Lys Pro Gly Gln Ser
```

```
            35                  40                  45
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110

Arg
```

<210> SEQ ID NO 50
<211> LENGTH: 108
<212> TYPE: PRT
<213> ORGANISM: Artificial sequence
<220> FEATURE:
<223> OTHER INFORMATION: Synthetic

<400> SEQUENCE: 50

```
Asp Ile Val Met Thr Gln Ser Gln Lys Phe Met Ser Thr Ser Ile Gly
1               5                   10                  15

Asp Arg Val Ser Val Thr Cys Arg Ala Ser Gln Asn Val Gly Pro Asn
                20                  25                  30

Leu Ala Trp Tyr Gln Gln Lys Pro Gly Gln Ser Pro Lys Ala Leu Ile
            35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Arg Tyr Pro Phe
                85                  90                  95

Thr Phe Gly Ser Gly Thr Lys Leu Glu Ile Lys Arg
                100                 105
```

<210> SEQ ID NO 51
<211> LENGTH: 108
<212> TYPE: PRT
<213> ORGANISM: Artificial sequence
<220> FEATURE:
<223> OTHER INFORMATION: Synthetic

<400> SEQUENCE: 51

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Lys Leu Leu Ile
            35                  40                  45

Ser Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Val Ala Asp Tyr Phe Cys Gln Gln Tyr Asn Ser Tyr Pro Leu
                85                  90                  95

Thr Phe Gly Ala Gly Thr Lys Leu Glu Leu Lys Arg
                100                 105
```

```
<210> SEQ ID NO 52
<211> LENGTH: 108
<212> TYPE: PRT
<213> ORGANISM: Artificial sequence
<220> FEATURE:
<223> OTHER INFORMATION: Synthetic

<400> SEQUENCE: 52

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Pro Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Arg Tyr Pro Leu
                85                  90                  95

Thr Phe Gly Ala Gly Thr Lys Leu Glu Leu Lys Arg
            100                 105

<210> SEQ ID NO 53
<211> LENGTH: 110
<212> TYPE: PRT
<213> ORGANISM: Artificial sequence
<220> FEATURE:
<223> OTHER INFORMATION: Synthetic

<400> SEQUENCE: 53

Asp Ile Val Met Thr Gln Ser Gln Lys Phe Met Ser Thr Ser Val Gly
1               5                   10                  15

Asp Arg Val Asn Val Thr Cys Lys Ala Ser Gln Asn Val Gly Thr His
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Arg
                85                  90                  95

Ala Leu Thr Phe Gly Ala Gly Thr Lys Leu Glu Leu Lys Arg
            100                 105                 110

<210> SEQ ID NO 54
<211> LENGTH: 108
<212> TYPE: PRT
<213> ORGANISM: Artificial sequence
<220> FEATURE:
<223> OTHER INFORMATION: Synthetic

<400> SEQUENCE: 54

Asp Ile Val Met Thr Gln Ser Gln Lys Phe Met Ser Thr Ser Val Gly
1               5                   10                  15

Asp Arg Val Asn Val Thr Cys Lys Ala Ser Gln Asn Val Gly Pro Thr
            20                  25                  30

Val Ala Trp Tyr Gln Gln Lys Pro Gly Gln Ser Pro Lys Ala Leu Ile
        35                  40                  45
```

Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Asn Val His Ser
 65                  70                  75                  80

Glu Asp Leu Ala Glu Tyr Phe Cys Gln Gln Tyr Asn Ser Tyr Pro Phe
                 85                  90                  95

Thr Phe Gly Ser Gly Thr Lys Leu Glu Ile Lys Arg
            100                 105

<210> SEQ ID NO 55
<211> LENGTH: 30
<212> TYPE: PRT
<213> ORGANISM: Artificial sequence
<220> FEATURE:
<223> OTHER INFORMATION: Synthetic

<400> SEQUENCE: 55

Gln Val Gln Leu Lys Gln Ser Gly Pro Glu Leu Val Lys Pro Gly Ala
 1               5                   10                  15

Ser Val Lys Leu Ser Cys Lys Ala Ser Gly Tyr Thr Phe Thr
             20                  25                  30

<210> SEQ ID NO 56
<211> LENGTH: 5
<212> TYPE: PRT
<213> ORGANISM: Artificial sequence
<220> FEATURE:
<223> OTHER INFORMATION: Synthetic

<400> SEQUENCE: 56

Thr Asp Asp Ile Asn
 1               5

<210> SEQ ID NO 57
<211> LENGTH: 14
<212> TYPE: PRT
<213> ORGANISM: Artificial sequence
<220> FEATURE:
<223> OTHER INFORMATION: Synthetic

<400> SEQUENCE: 57

Trp Val Lys Gln Arg Pro Gly Gln Gly Leu Glu Trp Ile Gly
 1               5                   10

<210> SEQ ID NO 58
<211> LENGTH: 17
<212> TYPE: PRT
<213> ORGANISM: Artificial sequence
<220> FEATURE:
<223> OTHER INFORMATION: Synthetic

<400> SEQUENCE: 58

Trp Ile Tyr Pro Arg Asp Asp Arg Thr Lys Tyr Asn Asp Lys Phe Lys
 1               5                   10                  15

Asp

<210> SEQ ID NO 59
<211> LENGTH: 32
<212> TYPE: PRT
<213> ORGANISM: Artificial sequence
<220> FEATURE:
<223> OTHER INFORMATION: Synthetic

<400> SEQUENCE: 59

```
Lys Ala Thr Leu Thr Val Asp Thr Ser Ser Asn Thr Ala Tyr Met Asp
1               5                   10                  15

Leu His Ser Leu Thr Ser Glu Asp Ser Ala Val Tyr Phe Cys Ser Ser
                20                  25                  30
```

<210> SEQ ID NO 60
<211> LENGTH: 5
<212> TYPE: PRT
<213> ORGANISM: Artificial sequence
<220> FEATURE:
<223> OTHER INFORMATION: Synthetic

<400> SEQUENCE: 60

```
Leu Glu Asp Thr Tyr
1               5
```

<210> SEQ ID NO 61
<211> LENGTH: 11
<212> TYPE: PRT
<213> ORGANISM: Artificial sequence
<220> FEATURE:
<223> OTHER INFORMATION: Synthetic

<400> SEQUENCE: 61

```
Trp Gly Gln Gly Thr Leu Val Ala Val Ser Ser
1               5                   10
```

<210> SEQ ID NO 62
<211> LENGTH: 5
<212> TYPE: PRT
<213> ORGANISM: Artificial sequence
<220> FEATURE:
<223> OTHER INFORMATION: Synthetic

<400> SEQUENCE: 62

```
Ser Asn Asp Ile Asn
1               5
```

<210> SEQ ID NO 63
<211> LENGTH: 17
<212> TYPE: PRT
<213> ORGANISM: Artificial sequence
<220> FEATURE:
<223> OTHER INFORMATION: Synthetic

<400> SEQUENCE: 63

```
Trp Ile Tyr Pro Arg Asp Gly Ser Ile Lys Tyr Asn Glu Lys Phe Thr
1               5                   10                  15

Asp
```

<210> SEQ ID NO 64
<211> LENGTH: 32
<212> TYPE: PRT
<213> ORGANISM: Artificial sequence
<220> FEATURE:
<223> OTHER INFORMATION: Synthetic

<400> SEQUENCE: 64

```
Lys Ala Thr Leu Thr Val Asp Val Ser Ser Thr Ala Tyr Met Glu
1               5                   10                  15

Leu His Ser Leu Thr Ser Glu Asp Ser Ala Val Tyr Phe Cys Ser Gly
                20                  25                  30
```

<210> SEQ ID NO 65

```
<211> LENGTH: 5
<212> TYPE: PRT
<213> ORGANISM: Artificial sequence
<220> FEATURE:
<223> OTHER INFORMATION: Synthetic

<400> SEQUENCE: 65

Val Glu Asp Ser Tyr
1               5

<210> SEQ ID NO 66
<211> LENGTH: 11
<212> TYPE: PRT
<213> ORGANISM: Artificial sequence
<220> FEATURE:
<223> OTHER INFORMATION: Synthetic

<400> SEQUENCE: 66

Trp Gly Gln Gly Thr Leu Val Thr Val Ser Ser
1               5                   10

<210> SEQ ID NO 67
<211> LENGTH: 17
<212> TYPE: PRT
<213> ORGANISM: Artificial sequence
<220> FEATURE:
<223> OTHER INFORMATION: Synthetic

<400> SEQUENCE: 67

Trp Ile Tyr Pro Arg Asp Gly Thr Thr Lys Tyr Asn Glu Glu Phe Thr
1               5                   10                  15

Asp

<210> SEQ ID NO 68
<211> LENGTH: 32
<212> TYPE: PRT
<213> ORGANISM: Artificial sequence
<220> FEATURE:
<223> OTHER INFORMATION: Synthetic

<400> SEQUENCE: 68

Lys Ala Thr Leu Thr Val Asp Val Ser Ser Thr Ala Phe Met Glu
1               5                   10                  15

Leu His Ser Leu Thr Ser Glu Asp Ser Ala Val Tyr Phe Cys Ser Ser
                20                  25                  30

<210> SEQ ID NO 69
<211> LENGTH: 17
<212> TYPE: PRT
<213> ORGANISM: Artificial sequence
<220> FEATURE:
<223> OTHER INFORMATION: Synthetic

<400> SEQUENCE: 69

Trp Ile Tyr Pro Arg Asp Gly Thr Thr Lys Tyr Asn Glu Lys Phe Thr
1               5                   10                  15

Asp

<210> SEQ ID NO 70
<211> LENGTH: 32
<212> TYPE: PRT
<213> ORGANISM: Artificial sequence
<220> FEATURE:
<223> OTHER INFORMATION: Synthetic

<400> SEQUENCE: 70
```

-continued

Lys Ala Thr Leu Thr Val Asp Val Ser Ser Thr Ala Phe Met Glu
1               5                   10                  15

Leu His Arg Leu Thr Ser Glu Asp Ser Ala Val Tyr Phe Cys Ser Ser
            20                  25                  30

<210> SEQ ID NO 71
<211> LENGTH: 30
<212> TYPE: PRT
<213> ORGANISM: Artificial sequence
<220> FEATURE:
<223> OTHER INFORMATION: Synthetic

<400> SEQUENCE: 71

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr
            20                  25                  30

<210> SEQ ID NO 72
<211> LENGTH: 5
<212> TYPE: PRT
<213> ORGANISM: Artificial sequence
<220> FEATURE:
<223> OTHER INFORMATION: Synthetic

<400> SEQUENCE: 72

Ser Tyr Gly Met Ser
1               5

<210> SEQ ID NO 73
<211> LENGTH: 14
<212> TYPE: PRT
<213> ORGANISM: Artificial sequence
<220> FEATURE:
<223> OTHER INFORMATION: Synthetic

<400> SEQUENCE: 73

Trp Val Arg Gln Ala Pro Gly Lys Gly Leu Lys Trp Met Gly
1               5                   10

<210> SEQ ID NO 74
<211> LENGTH: 17
<212> TYPE: PRT
<213> ORGANISM: Artificial sequence
<220> FEATURE:
<223> OTHER INFORMATION: Synthetic

<400> SEQUENCE: 74

Trp Ile Asn Thr Tyr Ser Gly Val Pro Thr Tyr Ala Asp Asp Phe Lys
1               5                   10                  15

Gly

<210> SEQ ID NO 75
<211> LENGTH: 32
<212> TYPE: PRT
<213> ORGANISM: Artificial sequence
<220> FEATURE:
<223> OTHER INFORMATION: Synthetic

<400> SEQUENCE: 75

Arg Phe Ala Phe Ser Leu Glu Thr Ser Ala Arg Thr Pro Tyr Leu Gln
1               5                   10                  15

Ile Asn Asn Leu Lys Asn Glu Asp Thr Ala Thr Tyr Phe Cys Ala Arg
            20                  25                  30

<210> SEQ ID NO 76
<211> LENGTH: 7
<212> TYPE: PRT
<213> ORGANISM: Artificial sequence
<220> FEATURE:
<223> OTHER INFORMATION: Synthetic

<400> SEQUENCE: 76

Gly Gly Glu Ala Met Asp Tyr
1               5

<210> SEQ ID NO 77
<211> LENGTH: 11
<212> TYPE: PRT
<213> ORGANISM: Artificial sequence
<220> FEATURE:
<223> OTHER INFORMATION: Synthetic

<400> SEQUENCE: 77

Trp Gly Gln Gly Thr Ser Val Thr Val Ser Ser
1               5                   10

<210> SEQ ID NO 78
<211> LENGTH: 30
<212> TYPE: PRT
<213> ORGANISM: Artificial sequence
<220> FEATURE:
<223> OTHER INFORMATION: Synthetic

<400> SEQUENCE: 78

Gln Ile Gln Leu Val Gln Ser Gly Pro Glu Leu Lys Thr Pro Gly Glu
1               5                   10                  15

Thr Val Lys Ile Ser Cys Lys Ala Ser Gly Tyr Ile Phe Thr
            20                  25                  30

<210> SEQ ID NO 79
<211> LENGTH: 5
<212> TYPE: PRT
<213> ORGANISM: Artificial sequence
<220> FEATURE:
<223> OTHER INFORMATION: Synthetic

<400> SEQUENCE: 79

Ser Tyr Gly Ile Thr
1               5

<210> SEQ ID NO 80
<211> LENGTH: 14
<212> TYPE: PRT
<213> ORGANISM: Artificial sequence
<220> FEATURE:
<223> OTHER INFORMATION: Synthetic

<400> SEQUENCE: 80

Trp Val Lys Gln Ala Pro Gly Lys Gly Leu Lys Trp Met Gly
1               5                   10

<210> SEQ ID NO 81
<211> LENGTH: 32
<212> TYPE: PRT
<213> ORGANISM: Artificial sequence
<220> FEATURE:
<223> OTHER INFORMATION: Synthetic

<400> SEQUENCE: 81

```
Arg Phe Ala Phe Ser Leu Glu Thr Ser Ala Ser Thr Ala Tyr Leu Gln
1               5                   10                  15

Ile Asn Asn Leu Lys Asn Glu Asp Thr Thr Tyr Phe Cys Thr Arg
            20                  25                  30
```

<210> SEQ ID NO 82
<211> LENGTH: 7
<212> TYPE: PRT
<213> ORGANISM: Artificial sequence
<220> FEATURE:
<223> OTHER INFORMATION: Synthetic

<400> SEQUENCE: 82

```
Gly Gly Asp Ala Leu Asp Tyr
1               5
```

<210> SEQ ID NO 83
<211> LENGTH: 30
<212> TYPE: PRT
<213> ORGANISM: Artificial sequence
<220> FEATURE:
<223> OTHER INFORMATION: Synthetic

<400> SEQUENCE: 83

```
Gln Val Gln Leu Lys Gln Ser Gly Ala Glu Leu Met Lys Pro Gly Ala
1               5                   10                  15

Ser Val Lys Leu Ser Cys Lys Ala Thr Gly Tyr Thr Phe Thr
            20                  25                  30
```

<210> SEQ ID NO 84
<211> LENGTH: 5
<212> TYPE: PRT
<213> ORGANISM: Artificial sequence
<220> FEATURE:
<223> OTHER INFORMATION: Synthetic

<400> SEQUENCE: 84

```
Gly Lys Trp Ile Glu
1               5
```

<210> SEQ ID NO 85
<211> LENGTH: 14
<212> TYPE: PRT
<213> ORGANISM: Artificial sequence
<220> FEATURE:
<223> OTHER INFORMATION: Synthetic

<400> SEQUENCE: 85

```
Trp Val Lys Gln Arg Pro Gly His Gly Leu Glu Trp Ile Gly
1               5                   10
```

<210> SEQ ID NO 86
<211> LENGTH: 17
<212> TYPE: PRT
<213> ORGANISM: Artificial sequence
<220> FEATURE:
<223> OTHER INFORMATION: Synthetic

<400> SEQUENCE: 86

```
Glu Ile Leu Pro Gly Thr Gly Ser Thr Asn Tyr Asn Glu Lys Phe Lys
1               5                   10                  15

Gly
```

<210> SEQ ID NO 87
<211> LENGTH: 32

```
<212> TYPE: PRT
<213> ORGANISM: Artificial sequence
<220> FEATURE:
<223> OTHER INFORMATION: Synthetic

<400> SEQUENCE: 87

Lys Ala Thr Phe Thr Ala Asp Ser Ser Ser Asn Thr Ala Tyr Met Gln
1               5                   10                  15

Leu Ser Ser Leu Thr Thr Glu Asp Ser Ala Met Tyr Tyr Cys Leu Arg
            20                  25                  30

<210> SEQ ID NO 88
<211> LENGTH: 4
<212> TYPE: PRT
<213> ORGANISM: Artificial sequence
<220> FEATURE:
<223> OTHER INFORMATION: Synthetic

<400> SEQUENCE: 88

Ser Glu Asp Val
1

<210> SEQ ID NO 89
<211> LENGTH: 11
<212> TYPE: PRT
<213> ORGANISM: Artificial sequence
<220> FEATURE:
<223> OTHER INFORMATION: Synthetic

<400> SEQUENCE: 89

Trp Gly Thr Gly Thr Thr Val Thr Val Ser Ser
1               5                   10

<210> SEQ ID NO 90
<211> LENGTH: 30
<212> TYPE: PRT
<213> ORGANISM: Artificial sequence
<220> FEATURE:
<223> OTHER INFORMATION: Synthetic

<400> SEQUENCE: 90

Gln Val Gln Leu Lys Gln Ser Gly Ala Glu Leu Met Lys Pro Gly Ala
1               5                   10                  15

Ser Val Lys Leu Ala Cys Lys Ala Thr Gly Tyr Thr Phe Thr
            20                  25                  30

<210> SEQ ID NO 91
<211> LENGTH: 5
<212> TYPE: PRT
<213> ORGANISM: Artificial sequence
<220> FEATURE:
<223> OTHER INFORMATION: Synthetic

<400> SEQUENCE: 91

Gly Tyr Trp Ile Glu
1               5

<210> SEQ ID NO 92
<211> LENGTH: 14
<212> TYPE: PRT
<213> ORGANISM: Artificial sequence
<220> FEATURE:
<223> OTHER INFORMATION: Synthetic

<400> SEQUENCE: 92

Trp Ile Lys Gln Arg Pro Gly Gln Gly Leu Glu Trp Ile Gly
```

```
<210> SEQ ID NO 93
<211> LENGTH: 17
<212> TYPE: PRT
<213> ORGANISM: Artificial sequence
<220> FEATURE:
<223> OTHER INFORMATION: Synthetic

<400> SEQUENCE: 93

Glu Met Leu Pro Gly Ser Gly Ser Thr His Tyr Asn Glu Lys Phe Lys
1               5                   10                  15

Gly

<210> SEQ ID NO 94
<211> LENGTH: 32
<212> TYPE: PRT
<213> ORGANISM: Artificial sequence
<220> FEATURE:
<223> OTHER INFORMATION: Synthetic

<400> SEQUENCE: 94

Lys Ala Thr Phe Thr Ala Asp Thr Ser Ser Asn Thr Ala Tyr Met Gln
1               5                   10                  15

Leu Ser Gly Leu Thr Thr Glu Asp Ser Ala Ile Tyr Tyr Cys Val Arg
            20                  25                  30

<210> SEQ ID NO 95
<211> LENGTH: 4
<212> TYPE: PRT
<213> ORGANISM: Artificial sequence
<220> FEATURE:
<223> OTHER INFORMATION: Synthetic

<400> SEQUENCE: 95

Ser Ile Asp Tyr
1

<210> SEQ ID NO 96
<211> LENGTH: 11
<212> TYPE: PRT
<213> ORGANISM: Artificial sequence
<220> FEATURE:
<223> OTHER INFORMATION: Synthetic

<400> SEQUENCE: 96

Trp Gly Gln Gly Thr Thr Leu Thr Val Ser Ser
1               5                   10

<210> SEQ ID NO 97
<211> LENGTH: 30
<212> TYPE: PRT
<213> ORGANISM: Artificial sequence
<220> FEATURE:
<223> OTHER INFORMATION: Synthetic

<400> SEQUENCE: 97

Glu Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 98
<211> LENGTH: 5
<212> TYPE: PRT
```

```
<213> ORGANISM: Artificial sequence
<220> FEATURE:
<223> OTHER INFORMATION: Synthetic

<400> SEQUENCE: 98

Ser Tyr Trp Ile Thr
1               5

<210> SEQ ID NO 99
<211> LENGTH: 17
<212> TYPE: PRT
<213> ORGANISM: Artificial sequence
<220> FEATURE:
<223> OTHER INFORMATION: Synthetic

<400> SEQUENCE: 99

Asp Ile Tyr Pro Gly Ser Gly Ser Thr Asn Tyr Asn Glu Lys Phe Lys
1               5                   10                  15

Ser

<210> SEQ ID NO 100
<211> LENGTH: 32
<212> TYPE: PRT
<213> ORGANISM: Artificial sequence
<220> FEATURE:
<223> OTHER INFORMATION: Synthetic

<400> SEQUENCE: 100

Lys Ala Thr Leu Thr Val Asp Thr Ser Ser Thr Ala Tyr Met Gln
1               5                   10                  15

Leu Ser Ser Leu Thr Ser Glu Asp Ser Ala Val Tyr Tyr Cys Ala Arg
            20                  25                  30

<210> SEQ ID NO 101
<211> LENGTH: 11
<212> TYPE: PRT
<213> ORGANISM: Artificial sequence
<220> FEATURE:
<223> OTHER INFORMATION: Synthetic

<400> SEQUENCE: 101

Arg Arg Tyr Tyr Ala Thr Ala Trp Phe Ala Tyr
1               5                   10

<210> SEQ ID NO 102
<211> LENGTH: 30
<212> TYPE: PRT
<213> ORGANISM: Artificial sequence
<220> FEATURE:
<223> OTHER INFORMATION: Synthetic

<400> SEQUENCE: 102

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr
            20                  25                  30

<210> SEQ ID NO 103
<211> LENGTH: 5
<212> TYPE: PRT
<213> ORGANISM: Artificial sequence
<220> FEATURE:
<223> OTHER INFORMATION: Synthetic

<400> SEQUENCE: 103
```

```
Asp Tyr Tyr Ile Asn
1               5
```

```
<210> SEQ ID NO 104
<211> LENGTH: 14
<212> TYPE: PRT
<213> ORGANISM: Artificial sequence
<220> FEATURE:
<223> OTHER INFORMATION: Synthetic

<400> SEQUENCE: 104

Trp Val Lys Gln Arg Pro Gly Gln Gly Leu Glu Trp Ile Ala
1               5                   10
```

```
<210> SEQ ID NO 105
<211> LENGTH: 17
<212> TYPE: PRT
<213> ORGANISM: Artificial sequence
<220> FEATURE:
<223> OTHER INFORMATION: Synthetic

<400> SEQUENCE: 105

Arg Ile Tyr Pro Gly Ser Gly Asn Thr Tyr Tyr Asn Glu Lys Phe Lys
1               5                   10                  15

Gly
```

```
<210> SEQ ID NO 106
<211> LENGTH: 32
<212> TYPE: PRT
<213> ORGANISM: Artificial sequence
<220> FEATURE:
<223> OTHER INFORMATION: Synthetic

<400> SEQUENCE: 106

Lys Ala Thr Leu Thr Ala Glu Lys Ser Ser Ser Thr Ala Tyr Met Gln
1               5                   10                  15

Leu Ser Ser Leu Thr Ser Glu Asp Ser Ala Val Tyr Phe Cys Ala Arg
            20                  25                  30
```

```
<210> SEQ ID NO 107
<211> LENGTH: 11
<212> TYPE: PRT
<213> ORGANISM: Artificial sequence
<220> FEATURE:
<223> OTHER INFORMATION: Synthetic

<400> SEQUENCE: 107

Asn Tyr Tyr Ile Ser Ser Pro Trp Phe Ala Tyr
1               5                   10
```

```
<210> SEQ ID NO 108
<211> LENGTH: 30
<212> TYPE: PRT
<213> ORGANISM: Artificial sequence
<220> FEATURE:
<223> OTHER INFORMATION: Synthetic

<400> SEQUENCE: 108

Gln Val Gln Leu Lys Gln Ser Gly Pro Glu Leu Ala Arg Pro Trp Ala
1               5                   10                  15

Ser Val Lys Ile Ser Cys Gln Ala Phe Tyr Thr Phe Ser Arg
            20                  25                  30
```

```
<210> SEQ ID NO 109
<211> LENGTH: 14
```

```
<212> TYPE: PRT
<213> ORGANISM: Artificial sequence
<220> FEATURE:
<223> OTHER INFORMATION: Synthetic

<400> SEQUENCE: 109

Arg Val His Phe Ala Ile Arg Asp Thr Asn Tyr Trp Met Gln
1               5                   10

<210> SEQ ID NO 110
<211> LENGTH: 17
<212> TYPE: PRT
<213> ORGANISM: Artificial sequence
<220> FEATURE:
<223> OTHER INFORMATION: Synthetic

<400> SEQUENCE: 110

Ala Ile Tyr Pro Gly Asn Gly Asp Thr Ser Tyr Asn Gln Lys Phe Lys
1               5                   10                  15

Gly

<210> SEQ ID NO 111
<211> LENGTH: 32
<212> TYPE: PRT
<213> ORGANISM: Artificial sequence
<220> FEATURE:
<223> OTHER INFORMATION: Synthetic

<400> SEQUENCE: 111

Lys Ala Thr Leu Thr Ala Asp Lys Ser Ser Thr Ala Tyr Met Gln
1               5                   10                  15

Leu Ser Ser Leu Thr Ser Glu Asp Ser Ala Val Tyr Tyr Cys Ala Ser
            20                  25                  30

<210> SEQ ID NO 112
<211> LENGTH: 7
<212> TYPE: PRT
<213> ORGANISM: Artificial sequence
<220> FEATURE:
<223> OTHER INFORMATION: Synthetic

<400> SEQUENCE: 112

Gly Ser His Tyr Phe Asp Tyr
1               5

<210> SEQ ID NO 113
<211> LENGTH: 30
<212> TYPE: PRT
<213> ORGANISM: Artificial sequence
<220> FEATURE:
<223> OTHER INFORMATION: Synthetic

<400> SEQUENCE: 113

Gln Val Gln Leu Lys Gln Ser Gly Ala Glu Leu Val Thr Pro Gly Ala
1               5                   10                  15

Ser Val Lys Met Ser Cys Lys Ala Ser Gly Tyr Thr Phe Thr
            20                  25                  30

<210> SEQ ID NO 114
<211> LENGTH: 5
<212> TYPE: PRT
<213> ORGANISM: Artificial sequence
<220> FEATURE:
<223> OTHER INFORMATION: Synthetic

<400> SEQUENCE: 114
```

-continued

Thr Tyr Pro Ile Glu
1               5

<210> SEQ ID NO 115
<211> LENGTH: 14
<212> TYPE: PRT
<213> ORGANISM: Artificial sequence
<220> FEATURE:
<223> OTHER INFORMATION: Synthetic

<400> SEQUENCE: 115

Trp Met Lys Gln Asn His Gly Lys Ser Leu Glu Trp Ile Gly
1               5                   10

<210> SEQ ID NO 116
<211> LENGTH: 17
<212> TYPE: PRT
<213> ORGANISM: Artificial sequence
<220> FEATURE:
<223> OTHER INFORMATION: Synthetic

<400> SEQUENCE: 116

Asn Phe His Pro Tyr Asn Asp Asp Thr Lys Tyr Asn Glu Lys Phe Lys
1               5                   10                  15

Gly

<210> SEQ ID NO 117
<211> LENGTH: 32
<212> TYPE: PRT
<213> ORGANISM: Artificial sequence
<220> FEATURE:
<223> OTHER INFORMATION: Synthetic

<400> SEQUENCE: 117

Lys Ala Thr Leu Thr Val Glu Lys Ser Ser Asn Thr Val Tyr Leu Glu
1               5                   10                  15

Leu Ser Arg Leu Thr Ser Asp Asp Ser Ala Val Tyr Phe Cys Ala Arg
            20                  25                  30

<210> SEQ ID NO 118
<211> LENGTH: 11
<212> TYPE: PRT
<213> ORGANISM: Artificial sequence
<220> FEATURE:
<223> OTHER INFORMATION: Synthetic

<400> SEQUENCE: 118

Arg Val Tyr Tyr Ser Tyr Phe Trp Phe Gly Tyr
1               5                   10

<210> SEQ ID NO 119
<211> LENGTH: 11
<212> TYPE: PRT
<213> ORGANISM: Artificial sequence
<220> FEATURE:
<223> OTHER INFORMATION: Synthetic

<400> SEQUENCE: 119

Trp Gly His Gly Thr Leu Val Thr Val Ser Ser
1               5                   10

<210> SEQ ID NO 120
<211> LENGTH: 30
<212> TYPE: PRT
<213> ORGANISM: Artificial sequence

```
<220> FEATURE:
<223> OTHER INFORMATION: Synthetic

<400> SEQUENCE: 120

Gln Val Gln Leu Lys Gln Ser Gly Ala Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 121
<211> LENGTH: 17
<212> TYPE: PRT
<213> ORGANISM: Artificial sequence
<220> FEATURE:
<223> OTHER INFORMATION: Synthetic

<400> SEQUENCE: 121

Asn Phe His Pro Tyr Asn Gly Asp Ser Lys Tyr Asn Glu Lys Phe Lys
1               5                   10                  15

Gly

<210> SEQ ID NO 122
<211> LENGTH: 32
<212> TYPE: PRT
<213> ORGANISM: Artificial sequence
<220> FEATURE:
<223> OTHER INFORMATION: Synthetic

<400> SEQUENCE: 122

Lys Ala Thr Leu Thr Val Glu Lys Ser Ser Thr Val Tyr Leu Glu
1               5                   10                  15

Leu Ser Arg Leu Pro Ser Ala Asp Ser Ala Ile Tyr Tyr Cys Ala Arg
            20                  25                  30

<210> SEQ ID NO 123
<211> LENGTH: 11
<212> TYPE: PRT
<213> ORGANISM: Artificial sequence
<220> FEATURE:
<223> OTHER INFORMATION: Synthetic

<400> SEQUENCE: 123

Arg His Tyr Ala Ala Ser Pro Trp Phe Ala His
1               5                   10

<210> SEQ ID NO 124
<211> LENGTH: 30
<212> TYPE: PRT
<213> ORGANISM: Artificial sequence
<220> FEATURE:
<223> OTHER INFORMATION: Synthetic

<400> SEQUENCE: 124

Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Thr Leu Thr
            20                  25                  30

<210> SEQ ID NO 125
<211> LENGTH: 5
<212> TYPE: PRT
<213> ORGANISM: Artificial sequence
<220> FEATURE:
<223> OTHER INFORMATION: Synthetic
```

```
<400> SEQUENCE: 125

Asp Tyr Tyr Met Asn
1               5

<210> SEQ ID NO 126
<211> LENGTH: 14
<212> TYPE: PRT
<213> ORGANISM: Artificial sequence
<220> FEATURE:
<223> OTHER INFORMATION: Synthetic

<400> SEQUENCE: 126

Trp Val Lys Gln Ser His Gly Lys Ser Leu Glu Trp Ile Gly
1               5                   10

<210> SEQ ID NO 127
<211> LENGTH: 17
<212> TYPE: PRT
<213> ORGANISM: Artificial sequence
<220> FEATURE:
<223> OTHER INFORMATION: Synthetic

<400> SEQUENCE: 127

Asp Val Asn Pro Asn Asn Asp Gly Thr Thr Tyr Asn Gln Lys Phe Lys
1               5                   10                  15

Gly

<210> SEQ ID NO 128
<211> LENGTH: 32
<212> TYPE: PRT
<213> ORGANISM: Artificial sequence
<220> FEATURE:
<223> OTHER INFORMATION: Synthetic

<400> SEQUENCE: 128

Arg Ala Thr Leu Thr Val Asp Lys Ser Ser Asn Thr Ala Ser Met Glu
1               5                   10                  15

Leu Arg Ser Leu Thr Ser Glu Asp Ser Ala Val Tyr Tyr Cys Ala Ile
            20                  25                  30

<210> SEQ ID NO 129
<211> LENGTH: 14
<212> TYPE: PRT
<213> ORGANISM: Artificial sequence
<220> FEATURE:
<223> OTHER INFORMATION: Synthetic

<400> SEQUENCE: 129

Cys Pro Phe Tyr Tyr Leu Gly Lys Gly Thr His Phe Asp Tyr
1               5                   10

<210> SEQ ID NO 130
<211> LENGTH: 11
<212> TYPE: PRT
<213> ORGANISM: Artificial sequence
<220> FEATURE:
<223> OTHER INFORMATION: Synthetic

<400> SEQUENCE: 130

Trp Gly Gln Gly Thr Ser Leu Thr Val Ser Ser
1               5                   10

<210> SEQ ID NO 131
<211> LENGTH: 30
<212> TYPE: PRT
```

```
<213> ORGANISM: Artificial sequence
<220> FEATURE:
<223> OTHER INFORMATION: Synthetic

<400> SEQUENCE: 131

Glu Val Gln Leu Gln Gln Ser Gly Pro Val Leu Val Lys Pro Gly Ala
1               5                   10                  15

Ser Gly Lys Met Ser Cys Lys Ala Ser Gly Tyr Lys Phe Thr
            20                  25                  30

<210> SEQ ID NO 132
<211> LENGTH: 5
<212> TYPE: PRT
<213> ORGANISM: Artificial sequence
<220> FEATURE:
<223> OTHER INFORMATION: Synthetic

<400> SEQUENCE: 132

Asp Tyr Tyr Met Ile
1               5

<210> SEQ ID NO 133
<211> LENGTH: 17
<212> TYPE: PRT
<213> ORGANISM: Artificial sequence
<220> FEATURE:
<223> OTHER INFORMATION: Synthetic

<400> SEQUENCE: 133

Val Ile Lys Ile Tyr Asn Gly Gly Thr Ser Tyr Asn Gln Lys Phe Lys
1               5                   10                  15

Gly

<210> SEQ ID NO 134
<211> LENGTH: 32
<212> TYPE: PRT
<213> ORGANISM: Artificial sequence
<220> FEATURE:
<223> OTHER INFORMATION: Synthetic

<400> SEQUENCE: 134

Lys Ala Thr Leu Thr Val Asp Lys Ser Ser Ser Thr Ala Tyr Met Glu
1               5                   10                  15

Leu Asn Ser Leu Thr Ser Glu Asp Ser Ala Val Tyr Tyr Cys Ala Arg
            20                  25                  30

<210> SEQ ID NO 135
<211> LENGTH: 15
<212> TYPE: PRT
<213> ORGANISM: Artificial sequence
<220> FEATURE:
<223> OTHER INFORMATION: Synthetic

<400> SEQUENCE: 135

Gly Pro Ser Leu Tyr Asp Tyr Asp Pro Tyr Trp Tyr Phe Asp Val
1               5                   10                  15

<210> SEQ ID NO 136
<211> LENGTH: 30
<212> TYPE: PRT
<213> ORGANISM: Artificial sequence
<220> FEATURE:
<223> OTHER INFORMATION: Synthetic

<400> SEQUENCE: 136
```

Gln Val Gln Leu Lys Gln Ser Gly Thr Glu Leu Met Lys Pro Gly Ala
1               5                   10                  15
Ser Val Asn Leu Ser Cys Lys Ala Ser Gly Tyr Thr Phe Thr
            20                  25                  30

<210> SEQ ID NO 137
<211> LENGTH: 5
<212> TYPE: PRT
<213> ORGANISM: Artificial sequence
<220> FEATURE:
<223> OTHER INFORMATION: Synthetic

<400> SEQUENCE: 137

Ala Tyr Trp Ile Glu
1               5

<210> SEQ ID NO 138
<211> LENGTH: 17
<212> TYPE: PRT
<213> ORGANISM: Artificial sequence
<220> FEATURE:
<223> OTHER INFORMATION: Synthetic

<400> SEQUENCE: 138

Glu Ile Leu Pro Gly Ser Gly Thr Thr Asn Tyr Asn Glu Asn Phe Lys
1               5                   10                  15
Asp

<210> SEQ ID NO 139
<211> LENGTH: 32
<212> TYPE: PRT
<213> ORGANISM: Artificial sequence
<220> FEATURE:
<223> OTHER INFORMATION: Synthetic

<400> SEQUENCE: 139

Arg Ala Thr Phe Thr Ala Asp Thr Ser Ser Asn Thr Ala Tyr Met Gln
1               5                   10                  15
Leu Ser Ser Leu Thr Ser Glu Asp Ser Ala Ile Tyr Tyr Cys Ala Arg
            20                  25                  30

<210> SEQ ID NO 140
<211> LENGTH: 11
<212> TYPE: PRT
<213> ORGANISM: Artificial sequence
<220> FEATURE:
<223> OTHER INFORMATION: Synthetic

<400> SEQUENCE: 140

Ser Tyr Tyr Tyr Ala Ser Arg Trp Phe Ala Phe
1               5                   10

<210> SEQ ID NO 141
<211> LENGTH: 23
<212> TYPE: PRT
<213> ORGANISM: Artificial sequence
<220> FEATURE:
<223> OTHER INFORMATION: Synthetic

<400> SEQUENCE: 141

Asp Ile Val Met Thr Gln Ser Pro Ser Ser Leu Ala Val Ser Ala Gly
1               5                   10                  15
Glu Lys Val Thr Met Thr Cys
            20

<210> SEQ ID NO 142
<211> LENGTH: 17
<212> TYPE: PRT
<213> ORGANISM: Artificial sequence
<220> FEATURE:
<223> OTHER INFORMATION: Synthetic

<400> SEQUENCE: 142

Lys Ser Ser Gln Ser Leu Leu Asn Ser Arg Thr Arg Lys Asn Tyr Leu
1               5                   10                  15

Ala

<210> SEQ ID NO 143
<211> LENGTH: 15
<212> TYPE: PRT
<213> ORGANISM: Artificial sequence
<220> FEATURE:
<223> OTHER INFORMATION: Synthetic

<400> SEQUENCE: 143

Trp Tyr Gln Gln Lys Pro Gly Gln Ser Pro Lys Leu Leu Ile Tyr
1               5                   10                  15

<210> SEQ ID NO 144
<211> LENGTH: 7
<212> TYPE: PRT
<213> ORGANISM: Artificial sequence
<220> FEATURE:
<223> OTHER INFORMATION: Synthetic

<400> SEQUENCE: 144

Trp Ala Ser Thr Arg Glu Ser
1               5

<210> SEQ ID NO 145
<211> LENGTH: 32
<212> TYPE: PRT
<213> ORGANISM: Artificial sequence
<220> FEATURE:
<223> OTHER INFORMATION: Synthetic

<400> SEQUENCE: 145

Gly Val Pro Asp Arg Phe Thr Gly Ser Gly Ser Gly Thr Asp Phe Ser
1               5                   10                  15

Leu Thr Ile Ser Ser Val Gln Ala Glu Asp Leu Ala Val Tyr Tyr Cys
            20                  25                  30

<210> SEQ ID NO 146
<211> LENGTH: 8
<212> TYPE: PRT
<213> ORGANISM: Artificial sequence
<220> FEATURE:
<223> OTHER INFORMATION: Synthetic

<400> SEQUENCE: 146

Lys Gln Ser Tyr Asn Leu Tyr Thr
1               5

<210> SEQ ID NO 147
<211> LENGTH: 11
<212> TYPE: PRT
<213> ORGANISM: Artificial sequence
<220> FEATURE:
<223> OTHER INFORMATION: Synthetic

<400> SEQUENCE: 147

Phe Gly Gly Gly Thr Lys Leu Glu Ile Lys Arg
1               5                   10

<210> SEQ ID NO 148
<211> LENGTH: 23
<212> TYPE: PRT
<213> ORGANISM: Artificial sequence
<220> FEATURE:
<223> OTHER INFORMATION: Synthetic

<400> SEQUENCE: 148

Asp Ile Val Met Thr Gln Ser Pro Ser Ser Leu Ala Val Ser Ala Gly
1               5                   10                  15

Glu Arg Val Thr Met Ser Cys
            20

<210> SEQ ID NO 149
<211> LENGTH: 17
<212> TYPE: PRT
<213> ORGANISM: Artificial sequence
<220> FEATURE:
<223> OTHER INFORMATION: Synthetic

<400> SEQUENCE: 149

Lys Ser Ser Gln Ser Leu Leu Ile Ser Arg Thr Arg Lys Asn Tyr Leu
1               5                   10                  15

Ser

<210> SEQ ID NO 150
<211> LENGTH: 32
<212> TYPE: PRT
<213> ORGANISM: Artificial sequence
<220> FEATURE:
<223> OTHER INFORMATION: Synthetic

<400> SEQUENCE: 150

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 151
<211> LENGTH: 23
<212> TYPE: PRT
<213> ORGANISM: Artificial sequence
<220> FEATURE:
<223> OTHER INFORMATION: Synthetic

<400> SEQUENCE: 151

Asp Ile Val Met Thr Gln Ser Pro Ser Ser Leu Ala Val Ser Ala Gly
1               5                   10                  15

Glu Lys Val Thr Met Ser Cys
            20

<210> SEQ ID NO 152
<211> LENGTH: 23
<212> TYPE: PRT
<213> ORGANISM: Artificial sequence
<220> FEATURE:
<223> OTHER INFORMATION: Synthetic

<400> SEQUENCE: 152

Asp Val Leu Met Thr Gln Thr Pro Leu Thr Leu Ser Val Thr Ile Gly
1               5                   10                  15

```
Gln Pro Ala Ser Ile Ser Cys
            20

<210> SEQ ID NO 153
<211> LENGTH: 16
<212> TYPE: PRT
<213> ORGANISM: Artificial sequence
<220> FEATURE:
<223> OTHER INFORMATION: Synthetic

<400> SEQUENCE: 153

Lys Ser Ser Gln Ser Leu Leu Asp Ser Asp Gly Lys Thr Tyr Leu Asn
1               5                   10                  15

<210> SEQ ID NO 154
<211> LENGTH: 15
<212> TYPE: PRT
<213> ORGANISM: Artificial sequence
<220> FEATURE:
<223> OTHER INFORMATION: Synthetic

<400> SEQUENCE: 154

Trp Leu Leu Gln Arg Pro Gly Gln Ser Pro Lys Arg Leu Ile Tyr
1               5                   10                  15

<210> SEQ ID NO 155
<211> LENGTH: 7
<212> TYPE: PRT
<213> ORGANISM: Artificial sequence
<220> FEATURE:
<223> OTHER INFORMATION: Synthetic

<400> SEQUENCE: 155

Leu Val Ser Lys Leu Asp Ser
1               5

<210> SEQ ID NO 156
<211> LENGTH: 32
<212> TYPE: PRT
<213> ORGANISM: Artificial sequence
<220> FEATURE:
<223> OTHER INFORMATION: Synthetic

<400> SEQUENCE: 156

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 157
<211> LENGTH: 9
<212> TYPE: PRT
<213> ORGANISM: Artificial sequence
<220> FEATURE:
<223> OTHER INFORMATION: Synthetic

<400> SEQUENCE: 157

Trp Gln Gly Thr His Phe Pro Trp Thr
1               5

<210> SEQ ID NO 158
<211> LENGTH: 23
<212> TYPE: PRT
<213> ORGANISM: Artificial sequence
<220> FEATURE:
<223> OTHER INFORMATION: Synthetic
```

<400> SEQUENCE: 158

Asp Ile Val Met Thr Gln Ala Pro Leu Thr Leu Ser Val Thr Ile Gly
1               5                   10                  15

Gln Pro Ala Ser Ile Ser Cys
            20

<210> SEQ ID NO 159
<211> LENGTH: 16
<212> TYPE: PRT
<213> ORGANISM: Artificial sequence
<220> FEATURE:
<223> OTHER INFORMATION: Synthetic

<400> SEQUENCE: 159

Lys Ser Ser Gln Ser Leu Leu Asp Ser Asp Gly Lys Thr Tyr Leu Ser
1               5                   10                  15

<210> SEQ ID NO 160
<211> LENGTH: 9
<212> TYPE: PRT
<213> ORGANISM: Artificial sequence
<220> FEATURE:
<223> OTHER INFORMATION: Synthetic

<400> SEQUENCE: 160

Trp Gln Gly Thr His Phe Pro Tyr Thr
1               5

<210> SEQ ID NO 161
<211> LENGTH: 8
<212> TYPE: PRT
<213> ORGANISM: Artificial sequence
<220> FEATURE:
<223> OTHER INFORMATION: Synthetic

<400> SEQUENCE: 161

Lys Gln Ser Tyr Asn Ile Pro Thr
1               5

<210> SEQ ID NO 162
<211> LENGTH: 23
<212> TYPE: PRT
<213> ORGANISM: Artificial sequence
<220> FEATURE:
<223> OTHER INFORMATION: Synthetic

<400> SEQUENCE: 162

Asp Val Leu Met Thr Gln Thr Pro Leu Ser Leu Pro Val Ser Leu Gly
1               5                   10                  15

Glu Gln Ala Ser Ile Ser Cys
            20

<210> SEQ ID NO 163
<211> LENGTH: 16
<212> TYPE: PRT
<213> ORGANISM: Artificial sequence
<220> FEATURE:
<223> OTHER INFORMATION: Synthetic

<400> SEQUENCE: 163

Arg Ser Ser Gln Ser Leu Val Gln Ser Asn Gly Asn Thr Tyr Leu His
1               5                   10                  15

<210> SEQ ID NO 164

```
<211> LENGTH: 15
<212> TYPE: PRT
<213> ORGANISM: Artificial sequence
<220> FEATURE:
<223> OTHER INFORMATION: Synthetic

<400> SEQUENCE: 164

Trp Tyr Leu Gln Lys Pro Gly Gln Ser Pro Lys Leu Leu Ile Tyr
1               5                   10                  15

<210> SEQ ID NO 165
<211> LENGTH: 7
<212> TYPE: PRT
<213> ORGANISM: Artificial sequence
<220> FEATURE:
<223> OTHER INFORMATION: Synthetic

<400> SEQUENCE: 165

Lys Val Ser Asn Arg Phe Ser
1               5

<210> SEQ ID NO 166
<211> LENGTH: 32
<212> TYPE: PRT
<213> ORGANISM: Artificial sequence
<220> FEATURE:
<223> OTHER INFORMATION: Synthetic

<400> SEQUENCE: 166

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 167
<211> LENGTH: 9
<212> TYPE: PRT
<213> ORGANISM: Artificial sequence
<220> FEATURE:
<223> OTHER INFORMATION: Synthetic

<400> SEQUENCE: 167

Ser Gln Ser Thr His Val Pro Pro Thr
1               5

<210> SEQ ID NO 168
<211> LENGTH: 23
<212> TYPE: PRT
<213> ORGANISM: Artificial sequence
<220> FEATURE:
<223> OTHER INFORMATION: Synthetic

<400> SEQUENCE: 168

Asp Ile Val Met Thr Gln Ser Gln Lys Phe Met Ser Thr Ser Val Gly
1               5                   10                  15

Asp Arg Val Ser Ile Thr Cys
            20

<210> SEQ ID NO 169
<211> LENGTH: 11
<212> TYPE: PRT
<213> ORGANISM: Artificial sequence
<220> FEATURE:
<223> OTHER INFORMATION: Synthetic

<400> SEQUENCE: 169
```

Lys Ala Ser Gln Asn Val Gly Thr Ala Val Ala
1               5                   10

<210> SEQ ID NO 170
<211> LENGTH: 15
<212> TYPE: PRT
<213> ORGANISM: Artificial sequence
<220> FEATURE:
<223> OTHER INFORMATION: Synthetic

<400> SEQUENCE: 170

Trp Tyr Gln Gln Lys Pro Gly Gln Ser Pro Lys Leu Leu Ile Ser
1               5                   10                  15

<210> SEQ ID NO 171
<211> LENGTH: 7
<212> TYPE: PRT
<213> ORGANISM: Artificial sequence
<220> FEATURE:
<223> OTHER INFORMATION: Synthetic

<400> SEQUENCE: 171

Ser Ala Ser Asn Arg Tyr Thr
1               5

<210> SEQ ID NO 172
<211> LENGTH: 32
<212> TYPE: PRT
<213> ORGANISM: Artificial sequence
<220> FEATURE:
<223> OTHER INFORMATION: Synthetic

<400> SEQUENCE: 172

Gly Val Pro Asp Arg Phe Thr Gly Ser Gly Ser Gly Thr Asp Phe Thr
1               5                   10                  15

Leu Thr Ile Ser Asn Met Gln Ser Glu Asp Val Ala Asp Tyr Phe Cys
            20                  25                  30

<210> SEQ ID NO 173
<211> LENGTH: 9
<212> TYPE: PRT
<213> ORGANISM: Artificial sequence
<220> FEATURE:
<223> OTHER INFORMATION: Synthetic

<400> SEQUENCE: 173

Gln Gln Tyr Asn Ser Tyr Pro Leu Thr
1               5

<210> SEQ ID NO 174
<211> LENGTH: 11
<212> TYPE: PRT
<213> ORGANISM: Artificial sequence
<220> FEATURE:
<223> OTHER INFORMATION: Synthetic

<400> SEQUENCE: 174

Phe Gly Ala Gly Thr Lys Leu Glu Leu Lys Arg
1               5                   10

<210> SEQ ID NO 175
<211> LENGTH: 23
<212> TYPE: PRT
<213> ORGANISM: Artificial sequence
<220> FEATURE:
<223> OTHER INFORMATION: Synthetic

```
<400> SEQUENCE: 175

Asp Ile Val Met Thr Gln Ser Gln Lys Phe Met Ser Thr Ser Val Gly
1               5                   10                  15

Asp Arg Val Ser Val Thr Cys
            20

<210> SEQ ID NO 176
<211> LENGTH: 11
<212> TYPE: PRT
<213> ORGANISM: Artificial sequence
<220> FEATURE:
<223> OTHER INFORMATION: Synthetic

<400> SEQUENCE: 176

Lys Ala Ser Gln Asn Val Gly Pro Asn Val Ala
1               5                   10

<210> SEQ ID NO 177
<211> LENGTH: 15
<212> TYPE: PRT
<213> ORGANISM: Artificial sequence
<220> FEATURE:
<223> OTHER INFORMATION: Synthetic

<400> SEQUENCE: 177

Trp Tyr Gln Gln Lys Pro Gly Gln Ser Pro Lys Ala Leu Ile Tyr
1               5                   10                  15

<210> SEQ ID NO 178
<211> LENGTH: 7
<212> TYPE: PRT
<213> ORGANISM: Artificial sequence
<220> FEATURE:
<223> OTHER INFORMATION: Synthetic

<400> SEQUENCE: 178

Ser Ala Ser Tyr Arg Tyr Ser
1               5

<210> SEQ ID NO 179
<211> LENGTH: 32
<212> TYPE: PRT
<213> ORGANISM: Artificial sequence
<220> FEATURE:
<223> OTHER INFORMATION: Synthetic

<400> SEQUENCE: 179

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Asp Tyr Phe Cys
            20                  25                  30

<210> SEQ ID NO 180
<211> LENGTH: 9
<212> TYPE: PRT
<213> ORGANISM: Artificial sequence
<220> FEATURE:
<223> OTHER INFORMATION: Synthetic

<400> SEQUENCE: 180

Gln Gln Tyr Asn Arg Tyr Pro Leu Thr
1               5

<210> SEQ ID NO 181
<211> LENGTH: 23
```

```
<212> TYPE: PRT
<213> ORGANISM: Artificial sequence
<220> FEATURE:
<223> OTHER INFORMATION: Synthetic

<400> SEQUENCE: 181

Asp Ile Gln Leu Thr Gln Ser Pro Ala Ile Leu Ser Val Ser Pro Gly
1               5                   10                  15

Glu Arg Val Ser Phe Ser Cys
            20

<210> SEQ ID NO 182
<211> LENGTH: 11
<212> TYPE: PRT
<213> ORGANISM: Artificial sequence
<220> FEATURE:
<223> OTHER INFORMATION: Synthetic

<400> SEQUENCE: 182

Arg Ala Ser Gln Ser Ile Gly Thr Ser Ile His
1               5                   10

<210> SEQ ID NO 183
<211> LENGTH: 15
<212> TYPE: PRT
<213> ORGANISM: Artificial sequence
<220> FEATURE:
<223> OTHER INFORMATION: Synthetic

<400> SEQUENCE: 183

Trp Tyr Gln Gln Arg Thr Asn Gly Ser Pro Arg Leu Leu Ile Lys
1               5                   10                  15

<210> SEQ ID NO 184
<211> LENGTH: 7
<212> TYPE: PRT
<213> ORGANISM: Artificial sequence
<220> FEATURE:
<223> OTHER INFORMATION: Synthetic

<400> SEQUENCE: 184

Tyr Ala Ser Glu Ser Ile Ser
1               5

<210> SEQ ID NO 185
<211> LENGTH: 32
<212> TYPE: PRT
<213> ORGANISM: Artificial sequence
<220> FEATURE:
<223> OTHER INFORMATION: Synthetic

<400> SEQUENCE: 185

Gly Ile Pro Ser Arg Phe Ser Gly Ser Gly Ser Gly Thr Asp Phe Thr
1               5                   10                  15

Leu Ser Ile Asn Ser Val Glu Ser Glu Asp Ile Ala Asp Tyr Tyr Cys
            20                  25                  30

<210> SEQ ID NO 186
<211> LENGTH: 9
<212> TYPE: PRT
<213> ORGANISM: Artificial sequence
<220> FEATURE:
<223> OTHER INFORMATION: Synthetic

<400> SEQUENCE: 186

Gln Gln Ser Asn Ser Trp Pro Tyr Thr
```

<210> SEQ ID NO 187
<211> LENGTH: 23
<212> TYPE: PRT
<213> ORGANISM: Artificial sequence
<220> FEATURE:
<223> OTHER INFORMATION: Synthetic

<400> SEQUENCE: 187

Asp Ile Val Met Thr Gln Ser Gln Lys Phe Met Ser Thr Ser Val Gly
1               5                   10                  15

Asp Arg Val Asn Val Thr Cys
            20

<210> SEQ ID NO 188
<211> LENGTH: 11
<212> TYPE: PRT
<213> ORGANISM: Artificial sequence
<220> FEATURE:
<223> OTHER INFORMATION: Synthetic

<400> SEQUENCE: 188

Lys Ala Ser Gln Asn Val Gly Thr His Val Ala
1               5                   10

<210> SEQ ID NO 189
<211> LENGTH: 32
<212> TYPE: PRT
<213> ORGANISM: Artificial sequence
<220> FEATURE:
<223> OTHER INFORMATION: Synthetic

<400> SEQUENCE: 189

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30

<210> SEQ ID NO 190
<211> LENGTH: 11
<212> TYPE: PRT
<213> ORGANISM: Artificial sequence
<220> FEATURE:
<223> OTHER INFORMATION: Synthetic

<400> SEQUENCE: 190

Gln Gln Tyr Asn Ser Tyr Pro Arg Ala Leu Thr
1               5                   10

<210> SEQ ID NO 191
<211> LENGTH: 11
<212> TYPE: PRT
<213> ORGANISM: Artificial sequence
<220> FEATURE:
<223> OTHER INFORMATION: Synthetic

<400> SEQUENCE: 191

Lys Ala Ser Gln Asn Val Gly Pro Thr Val Ala
1               5                   10

<210> SEQ ID NO 192
<211> LENGTH: 32
<212> TYPE: PRT
<213> ORGANISM: Artificial sequence
<220> FEATURE:

<223> OTHER INFORMATION: Synthetic

<400> SEQUENCE: 192

```
Gly Val Pro Asp Arg Phe Thr Gly Ser Gly Ser Gly Thr Asp Phe Thr
1               5                   10                  15
Leu Thr Ile Ser Asn Val His Ser Glu Asp Leu Ala Glu Tyr Phe Cys
            20                  25                  30
```

<210> SEQ ID NO 193
<211> LENGTH: 9
<212> TYPE: PRT
<213> ORGANISM: Artificial sequence
<220> FEATURE:
<223> OTHER INFORMATION: Synthetic

<400> SEQUENCE: 193

```
Gln Gln Tyr Asn Ser Tyr Pro Phe Thr
1               5
```

<210> SEQ ID NO 194
<211> LENGTH: 11
<212> TYPE: PRT
<213> ORGANISM: Artificial sequence
<220> FEATURE:
<223> OTHER INFORMATION: Synthetic

<400> SEQUENCE: 194

```
Phe Gly Ser Gly Thr Lys Leu Glu Ile Lys Arg
1               5                   10
```

<210> SEQ ID NO 195
<211> LENGTH: 23
<212> TYPE: PRT
<213> ORGANISM: Artificial sequence
<220> FEATURE:
<223> OTHER INFORMATION: Synthetic

<400> SEQUENCE: 195

```
Asp Ile Gln Met Thr Gln Thr Pro Ala Ser Leu Ser Ala Ser Leu Gly
1               5                   10                  15
Asp Arg Val Thr Ile Ser Cys
            20
```

<210> SEQ ID NO 196
<211> LENGTH: 11
<212> TYPE: PRT
<213> ORGANISM: Artificial sequence
<220> FEATURE:
<223> OTHER INFORMATION: Synthetic

<400> SEQUENCE: 196

```
Arg Ala Ser Gln Asp Ile Ser Asn Phe Leu Asn
1               5                   10
```

<210> SEQ ID NO 197
<211> LENGTH: 15
<212> TYPE: PRT
<213> ORGANISM: Artificial sequence
<220> FEATURE:
<223> OTHER INFORMATION: Synthetic

<400> SEQUENCE: 197

```
Trp Tyr Gln Gln Lys Pro Asn Gly Thr Val Lys Leu Leu Val Phe
1               5                   10                  15
```

```
<210> SEQ ID NO 198
<211> LENGTH: 7
<212> TYPE: PRT
<213> ORGANISM: Artificial sequence
<220> FEATURE:
<223> OTHER INFORMATION: Synthetic

<400> SEQUENCE: 198

Tyr Thr Ser Arg Leu His Ser
1               5

<210> SEQ ID NO 199
<211> LENGTH: 32
<212> TYPE: PRT
<213> ORGANISM: Artificial sequence
<220> FEATURE:
<223> OTHER INFORMATION: Synthetic

<400> SEQUENCE: 199

Gly Val Pro Ser Arg Phe Ser Gly Ser Gly Ser Gly Ala Glu His Ser
1               5                   10                  15

Leu Thr Ile Ser Asn Leu Glu Gln Glu Asp Val Ala Thr Tyr Phe Cys
            20                  25                  30

<210> SEQ ID NO 200
<211> LENGTH: 9
<212> TYPE: PRT
<213> ORGANISM: Artificial sequence
<220> FEATURE:
<223> OTHER INFORMATION: Synthetic

<400> SEQUENCE: 200

Gln Gln Gly Phe Thr Leu Pro Trp Thr
1               5

<210> SEQ ID NO 201
<211> LENGTH: 11
<212> TYPE: PRT
<213> ORGANISM: Artificial sequence
<220> FEATURE:
<223> OTHER INFORMATION: Synthetic

<400> SEQUENCE: 201

Phe Gly Gly Gly Thr Lys Val Glu Ile Lys Arg
1               5                   10

<210> SEQ ID NO 202
<211> LENGTH: 23
<212> TYPE: PRT
<213> ORGANISM: Artificial sequence
<220> FEATURE:
<223> OTHER INFORMATION: Synthetic

<400> SEQUENCE: 202

Asp Val Leu Met Thr Gln Thr Pro Leu Ser Leu Pro Val Ser Leu Gly
1               5                   10                  15

Asp Gln Ala Ser Phe Ser Cys
            20

<210> SEQ ID NO 203
<211> LENGTH: 16
<212> TYPE: PRT
<213> ORGANISM: Artificial sequence
<220> FEATURE:
<223> OTHER INFORMATION: Synthetic

<400> SEQUENCE: 203
```

Arg Ser Ser Gln Ser Leu Ile His Ser Asn Gly Asn Thr Tyr Leu His
1               5                   10                  15

<210> SEQ ID NO 204
<211> LENGTH: 9
<212> TYPE: PRT
<213> ORGANISM: Artificial sequence
<220> FEATURE:
<223> OTHER INFORMATION: Synthetic

<400> SEQUENCE: 204

Ser Gln Ser Thr His Val Pro Trp Thr
1               5

<210> SEQ ID NO 205
<211> LENGTH: 23
<212> TYPE: PRT
<213> ORGANISM: Artificial sequence
<220> FEATURE:
<223> OTHER INFORMATION: Synthetic

<400> SEQUENCE: 205

Asp Ile Val Met Thr Gln Ser Gln Lys Phe Met Ser Thr Ser Ile Gly
1               5                   10                  15

Asp Arg Val Ser Val Thr Cys
            20

<210> SEQ ID NO 206
<211> LENGTH: 11
<212> TYPE: PRT
<213> ORGANISM: Artificial sequence
<220> FEATURE:
<223> OTHER INFORMATION: Synthetic

<400> SEQUENCE: 206

Arg Ala Ser Gln Asn Val Gly Pro Asn Leu Ala
1               5                   10

<210> SEQ ID NO 207
<211> LENGTH: 7
<212> TYPE: PRT
<213> ORGANISM: Artificial sequence
<220> FEATURE:
<223> OTHER INFORMATION: Synthetic

<400> SEQUENCE: 207

Ser Ala Ser Tyr Arg Phe Ser
1               5

<210> SEQ ID NO 208
<211> LENGTH: 9
<212> TYPE: PRT
<213> ORGANISM: Artificial sequence
<220> FEATURE:
<223> OTHER INFORMATION: Synthetic

<400> SEQUENCE: 208

Gln Gln Tyr Asn Arg Tyr Pro Phe Thr
1               5

<210> SEQ ID NO 209
<211> LENGTH: 5
<212> TYPE: PRT
<213> ORGANISM: Artificial sequence
<220> FEATURE:
<223> OTHER INFORMATION: Synthetic

```
<220> FEATURE:
<221> NAME/KEY: VARIANT
<222> LOCATION: (1)..(1)
<223> OTHER INFORMATION: where Xaa at position 1 is S or T
<220> FEATURE:
<221> NAME/KEY: VARIANT
<222> LOCATION: (2)..(2)
<223> OTHER INFORMATION: where Xaa at position 2 is N or D

<400> SEQUENCE: 209

Xaa Xaa Asp Ile Asn
1               5

<210> SEQ ID NO 210
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (7)..(7)
<223> OTHER INFORMATION: where Xaa at position 7 is G or D
<220> FEATURE:
<221> NAME/KEY: VARIANT
<222> LOCATION: (8)..(8)
<223> OTHER INFORMATION: where Xaa at position 8 is S or T or R
<220> FEATURE:
<221> NAME/KEY: VARIANT
<222> LOCATION: (9)..(9)
<223> OTHER INFORMATION: where Xaa at position 9 is I or T
<220> FEATURE:
<221> NAME/KEY: VARIANT
<222> LOCATION: (13)..(13)
<223> OTHER INFORMATION: where Xaa at position 13 is E or D
<220> FEATURE:
<221> NAME/KEY: VARIANT
<222> LOCATION: (14)..(14)
<223> OTHER INFORMATION: where Xaa at position 14 is K or E
<220> FEATURE:
<221> NAME/KEY: VARIANT
<222> LOCATION: (16)..(16)
<223> OTHER INFORMATION: where Xaa at position 16 is T or K

<400> SEQUENCE: 210

Trp Ile Tyr Pro Arg Asp Xaa Xaa Xaa Lys Tyr Asn Xaa Xaa Phe Xaa
1               5                   10                  15
Asp

<210> SEQ ID NO 211
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: where Xaa at position 1 is L or V
<220> FEATURE:
<221> NAME/KEY: VARIANT
<222> LOCATION: (4)..(4)
<223> OTHER INFORMATION: where Xaa at position 4 is T or S

<400> SEQUENCE: 211

Xaa Glu Asp Xaa Tyr
1               5

<210> SEQ ID NO 212
<211> LENGTH: 17
<212> TYPE: PRT
<213> ORGANISM: Artificial sequence
```

<220> FEATURE:
<223> OTHER INFORMATION: Synthetic
<220> FEATURE:
<221> NAME/KEY: VARIANT
<222> LOCATION: (8)..(8)
<223> OTHER INFORMATION: where Xaa at position 8 is N or I or Q or A
<220> FEATURE:
<221> NAME/KEY: VARIANT
<222> LOCATION: (9)..(9)
<223> OTHER INFORMATION: where Xaa at position 9 is S or T
<220> FEATURE:
<221> NAME/KEY: VARIANT
<222> LOCATION: (17)..(17)
<223> OTHER INFORMATION: where Xaa at position 17 is A or S

<400> SEQUENCE: 212

Lys Ser Ser Gln Ser Leu Leu Xaa Xaa Arg Thr Arg Lys Asn Tyr Leu
1               5                   10                  15

Xaa

<210> SEQ ID NO 213
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (4)..(4)
<223> OTHER INFORMATION: where Xaa at position 4 is M or I
<220> FEATURE:
<221> NAME/KEY: VARIANT
<222> LOCATION: (5)..(5)
<223> OTHER INFORMATION: where Xaa at position 5 is S or T

<400> SEQUENCE: 213

Ser Tyr Gly Xaa Xaa
1               5

<210> SEQ ID NO 214
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: where Xaa at position 3 is E or D
<220> FEATURE:
<221> NAME/KEY: VARIANT
<222> LOCATION: (5)..(5)
<223> OTHER INFORMATION: where Xaa at position 5 is M or L

<400> SEQUENCE: 214

Gly Gly Xaa Ala Xaa Asp Tyr
1               5

<210> SEQ ID NO 215
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (10)..(10)
<223> OTHER INFORMATION: where Xaa at position 10 is D or E or A
<220> FEATURE:
<221> NAME/KEY: VARIANT
<222> LOCATION: (11)..(11)
<223> OTHER INFORMATION: where Xaa at position 11 is G or A

```
<220> FEATURE:
<221> NAME/KEY: VARIANT
<222> LOCATION: (16)..(16)
<223> OTHER INFORMATION: where Xaa at position 16 is N or S

<400> SEQUENCE: 215

Lys Ser Ser Gln Ser Leu Leu Asp Ser Xaa Xaa Lys Thr Tyr Leu Xaa
1               5                   10                  15

<210> SEQ ID NO 216
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (8)..(8)
<223> OTHER INFORMATION: where Xaa at position 8 is W or Y

<400> SEQUENCE: 216

Trp Gln Gly Thr His Phe Pro Xaa Thr
1               5

<210> SEQ ID NO 217
<211> LENGTH: 342
<212> TYPE: DNA
<213> ORGANISM: Artificial sequence
<220> FEATURE:
<223> OTHER INFORMATION: Synthetic

<400> SEQUENCE: 217
caggtgcagc tgaagcagtc tggacctgag ctggtgaagc ctggggcttc agtgaagttg      60
tcctgcaagg cttctggcta caccttcaca accgacgata taaactgggt gaagcagagg     120
cctggacagg gacttgagtg gattggatgg atttatccta gagatgatag aactaagtac     180
aatgacaagt tcaaggacaa ggccacattg actgtagaca catcttccaa cacagcgtac     240
atggacctcc acagcctgac atctgaggac tctgcggtct atttctgttc aagcctcgag     300
gatacttact ggggccaagg gactctggtc gctgtctctt ca                        342

<210> SEQ ID NO 218
<211> LENGTH: 342
<212> TYPE: DNA
<213> ORGANISM: Artificial sequence
<220> FEATURE:
<223> OTHER INFORMATION: Synthetic

<400> SEQUENCE: 218
caggtgcagc tgaagcagtc tggacctgag ctggtgaagc ctggggcttc agtgaagttg      60
tcctgcaagg cttctggcta caccttcaca agtaacgata taaactgggt gaagcagagg     120
cctggacagg gacttgagtg gattggatgg atttatccta gagatgggag tattaaatat     180
aatgagaaat tcacggacaa ggccacattg acagttgacg tatcctccag cacagcgtac     240
atggagctcc acagcctgac atctgaggac tctgcggtct atttctgttc aggtgtcgag     300
gattcttact ggggccaagg gactctggtc actgtctctt ca                        342

<210> SEQ ID NO 219
<211> LENGTH: 342
<212> TYPE: DNA
<213> ORGANISM: Artificial sequence
<220> FEATURE:
<223> OTHER INFORMATION: Synthetic
```

<400> SEQUENCE: 219

```
caggtgcagc tgaagcagtc tggacctgaa ctggtgaagc ctggggcttc agtgaaattg      60
tcctgcaagg cttctggcta caccttcaca agtaacgata taaactgggt gaaacagagg     120
cctggacagg gacttgagtg gattggatgg atttatccta gagatggtac tactaagtac     180
aatgaggagt tcacggacaa ggccacattg actgttgacg tatcctccag cacagcgttc     240
atggagctcc acagcctgac atctgaggac tctgctgtct atttctgttc aagtgtcgag     300
gattcttact ggggccaagg gactctggtc actgtctctt ca                        342
```

<210> SEQ ID NO 220
<211> LENGTH: 342
<212> TYPE: DNA
<213> ORGANISM: Artificial sequence
<220> FEATURE:
<223> OTHER INFORMATION: Synthetic

<400> SEQUENCE: 220

```
caggtgcagc tgaagcagtc tggacctgag ctggtgaagc ctggggcttc agtgaagttg      60
tcctgcaagg cttctggcta caccttcaca agtaacgata taaactgggt gaagcagagg     120
cctggacagg gacttgagtg gattggatgg atttatccta gagatggtac tactaagtac     180
aatgagaagt tcacggacaa ggccacattg actgttgacg tatcctccag cacagcgttc     240
atggagctcc acaggctgac atctgaggac tctgcggtct atttctgttc aagtgtcgag     300
gattcttact ggggccaagg gactctggtc actgtctctt ca                        342
```

<210> SEQ ID NO 221
<211> LENGTH: 348
<212> TYPE: DNA
<213> ORGANISM: Artificial sequence
<220> FEATURE:
<223> OTHER INFORMATION: Synthetic

<400> SEQUENCE: 221

```
cagatccagt tggtacagtc tggacctgag ctgaagaagc ctggagagac agtcaagatc      60
tcctgcaagg cttctgggta tattttcaca agctatggaa tgagctgggt gagacaggct     120
ccaggaaagg gtttaaagtg gatgggctgg ataaacacct actctggagt gccaacatat     180
gctgatgact caagggacg tttgccttc tctttggaaa cctctgccag aactccctat      240
ttgcagatca acaacctcaa aaatgaggac acggctacat atttctgcgc aagagggggc     300
gaagctatgg actactgggg tcaaggaacc tcagtcaccg tctcctca                  348
```

<210> SEQ ID NO 222
<211> LENGTH: 348
<212> TYPE: DNA
<213> ORGANISM: Artificial sequence
<220> FEATURE:
<223> OTHER INFORMATION: Synthetic

<400> SEQUENCE: 222

```
cagatccagt tggtacagtc tggacctgag ctgaagacgc aggagagac agtcaagatc      60
tcctgcaagg cttctgggta tatcttcaca tcctatggaa ttacctgggt gaaacaggct     120
ccaggaaagg gtttaaagtg gatgggctgg ataaacacct actctggagt gccaacatat     180
gctgatgact caagggacg tttgccttc tctttggaaa cgtctgccag cactgcctat      240
ttgcagatca acaacctcaa aaatgaggac acgactacat atttctgtac aagagggggt     300
gatgctttgg actactgggg tcaaggaacc tcagtcaccg tctcctca                  348
```

<210> SEQ ID NO 223
<211> LENGTH: 339
<212> TYPE: DNA
<213> ORGANISM: Artificial sequence
<220> FEATURE:
<223> OTHER INFORMATION: Synthetic

<400> SEQUENCE: 223

| | |
|---|---|
| caggtgcagc tgaagcagtc tggagctgag ctgatgaagc ctggggcctc agtgaagctt | 60 |
| tcctgcaagg ctactggcta cacattcact ggcaagtgga tagagtgggt aaaacagagg | 120 |
| cctggacatg gcctagagtg gattggagag attttacctg gaactggtag tactaactac | 180 |
| aatgagaagt tcaagggcaa ggccacattc actgcagact catcctccaa cacagcctac | 240 |
| atgcaactca gcagcctgac aactgaagac tctgctatgt attattgttt aagatccgag | 300 |
| gatgtctggg gcacagggac cacggtcacc gtctcctca | 339 |

<210> SEQ ID NO 224
<211> LENGTH: 339
<212> TYPE: DNA
<213> ORGANISM: Artificial sequence
<220> FEATURE:
<223> OTHER INFORMATION: Synthetic

<400> SEQUENCE: 224

| | |
|---|---|
| caggtgcagc tgaagcagtc tggagctgag ctgatgaagc ctggggcctc agtgaagctt | 60 |
| gcctgcaagg ctactggcta cacattcact ggctactgga tagagtggat aaagcagagg | 120 |
| cctggacaag gccttgagtg gattggagag atgttacctg gaagtggtag tactcactac | 180 |
| aatgagaagt tcaagggtaa ggccacattc actgcagata catcctccaa cacagcctac | 240 |
| atgcaactca gcggcctgac aactgaggac tctgccatct attactgtgt aagaagcata | 300 |
| gactactggg gccaaggcac cactctcaca gtctcctca | 339 |

<210> SEQ ID NO 225
<211> LENGTH: 375
<212> TYPE: DNA
<213> ORGANISM: Artificial sequence
<220> FEATURE:
<223> OTHER INFORMATION: Synthetic

<400> SEQUENCE: 225

| | |
|---|---|
| caggtgcagc tgaagcagtc tgggcctgag ctggcaaggc cttgggcttc agtgaagata | 60 |
| tcctgccagg ctttctacac cttttccaga agggtgcact tgccattag ggataccaac | 120 |
| tactggatgc agtgggtaaa acagaggcct ggacagggtc tggaatggat cggggctatt | 180 |
| tatcctggaa atggtgatac tagttacaat cagaagttca agggcaaggc acattgact | 240 |
| gcagacaaat cctccagcac agcctacatg caactcagca gcctgacatc tgaggactct | 300 |
| gcggtctatt actgtgcatc cggtagccac tactttgact actggggcca aggcaccact | 360 |
| ctcacagtct cctca | 375 |

<210> SEQ ID NO 226
<211> LENGTH: 369
<212> TYPE: DNA
<213> ORGANISM: Artificial sequence
<220> FEATURE:
<223> OTHER INFORMATION: Synthetic

<400> SEQUENCE: 226

```
gaggtccagc tgcaacaatc tgggcctgag ctggtgaagc ctggggcttc agtgaaggta      60
tcctgtaagg cttctggata cacgctcact gactactaca tgaactgggt gaagcagagc     120
catggaaaga gccttgagtg gattggagat gttaatccta caatgatggg tactacctac     180
aaccagaaat tcaagggcag ggccacattg actgtagaca gtcttccaa cacagcctcc      240 atggagctcc gcagcctgac atctgaggac tctgcagtct actactgtgc aatatgcccc     300
ttttattacc tcggtaaagg gacccacttt gactactggg gccaaggcac ctctctcaca     360
gtctcctca                                                             369
```

<210> SEQ ID NO 227
<211> LENGTH: 372
<212> TYPE: DNA
<213> ORGANISM: Artificial sequence
<220> FEATURE:
<223> OTHER INFORMATION: Synthetic

<400> SEQUENCE: 227

```
gaggtccagc tgcaacaatc tggacctgtg ctggtgaagc ctggggcttc agggaagatg      60
tcctgtaagg cttctggata caaattcact gactactata tgatctgggt gaagcagagc     120
catggaaaga gccttgagtg gattggagtt attaaaattt ataacggtgg tacgagctac     180
aaccagaagt tcaagggcaa ggccacattg actgttgaca gtcctccag cacagcctac       240 atggagctca cagcctgac atctgaggac tctgcagtct attactgtgc aagagggcca      300
tctctctatg attacgaccc ttactggtac ttcgatgtct ggggcacagg gaccacggtc     360
accgtctcct ca                                                         372
```

<210> SEQ ID NO 228
<211> LENGTH: 360
<212> TYPE: DNA
<213> ORGANISM: Artificial sequence
<220> FEATURE:
<223> OTHER INFORMATION: Synthetic

<400> SEQUENCE: 228

```
caggtgcagc tgaagcagtc tggaactgag ctgatgaagc ctggggcctc agtgaacctt      60
tcctgcaagg cttctggcta cacattcact gcctactgga tagagtgggt aaagcagagg     120
cctggacatg gccttgagtg gattggagag attttacctg aagtggtac tactaactac      180 aatgagaact tcaaggacag gccacattc actgcagata catcctccaa cacagcctac      240
atgcaactca gcagcctgac aagtgaggac tctgccatct attactgtgc aagatcctat     300
tactacgcta gtagatggtt tgctttctgg ggccaaggga ctctggtcac tgtctcttca     360
```

<210> SEQ ID NO 229
<211> LENGTH: 360
<212> TYPE: DNA
<213> ORGANISM: Artificial sequence
<220> FEATURE:
<223> OTHER INFORMATION: Synthetic

<400> SEQUENCE: 229

```
gaggtccagc tgcagcagcc tggggctgag cttgtgaagc ctggggcttc agtgaagatg      60
tcctgtaagg cttctggcta caccttcacc agctactgga taacctgggt gaagcagagg     120
cctggacaag gccttgagtg gattggagat atttatcctg gtagtggtag tactaactac     180
aatgagaagt tcaagagcaa ggccacactg actgtagaca catcctccag cacagcctac     240
atgcagctca gcagcctgac atctgaggac tctgcggtct attactgtgc aagaaggaga     300
```

```
tactacgcta cggcctggtt tgcttactgg ggccaaggga ctctggtcac tgtctcttca    360
```

<210> SEQ ID NO 230
<211> LENGTH: 360
<212> TYPE: DNA
<213> ORGANISM: Artificial sequence
<220> FEATURE:
<223> OTHER INFORMATION: Synthetic

<400> SEQUENCE: 230

```
caggtgcagc tgaagcagtc tggggctgag ctggtgaggc ctggggcttc agtgaagctg     60
tcctgcaagg cttctggcta cactttcact gactactata aaactgggt gaagcagagg    120
cctggacagg gacttgagtg gattgcaagg atttatcctg gaagtggtaa tacttactac    180
aatgagaagt tcaagggcaa ggccacactg actgcagaaa aatcctccag cactgcctac    240
atgcagctca gcagcctgac atctgaggac tctgctgtct atttctgtgc aagaaattac    300
tacattagta gtccctggtt tgcttactgg ggccaaggga ctctggtcac tgtctcttca    360
```

<210> SEQ ID NO 231
<211> LENGTH: 360
<212> TYPE: DNA
<213> ORGANISM: Artificial sequence
<220> FEATURE:
<223> OTHER INFORMATION: Synthetic

<400> SEQUENCE: 231

```
caggtgcagc tgaagcagtc tggggctgag ctagtgacgc ctggagcctc agtgaagatg     60
tcctgcaagg cttctggcta caccttcact acctatccta tagagtggat gaaacagaat    120
catggaaaga gcctagagtg gattggaaat tttcatcctt acaatgatga tactaagtac    180
aatgaaaagt tcaagggcaa ggccacattg actgtagaaa aatcctctaa cacagtctac    240
ttggagctca gccgattaac atctgatgac tctgctgttt atttctgtgc aaggagggtc    300
tactatagtt acttctggtt tggttactgg ggccacggga ctctggtcac tgtctcttca    360
```

<210> SEQ ID NO 232
<211> LENGTH: 360
<212> TYPE: DNA
<213> ORGANISM: Artificial sequence
<220> FEATURE:
<223> OTHER INFORMATION: Synthetic

<400> SEQUENCE: 232

```
caggtgcagc tgaagcagtc tggggctgag ctagtgaaac ctggagcctc agtgaagatg     60
tcctgcaagg cttctggcta caccttcact acctatccta tagagtggat gaagcagaat    120
catgggaaga gcctagagtg gattggaaat tttcatcctt acaatggtga ttctaagtac    180
aatgaaaagt tcaagggcaa ggccaccttg actgtagaaa aatcctctag cacagtctac    240
ttagaactca gccgattacc atctgctgac tctgctattt attactgtgc aaggaggcac    300
tacgctgcta gtccctggtt tgctcactgg ggccaaggga ctctggtcac tgtctcttca    360
```

<210> SEQ ID NO 233
<211> LENGTH: 339
<212> TYPE: DNA
<213> ORGANISM: Artificial sequence
<220> FEATURE:
<223> OTHER INFORMATION: Synthetic

<400> SEQUENCE: 233

```
gacattgtga tgacccagtc tccatcctcc ctggctgtgt cagcaggaga gaaggtcact      60
atgacctgca atccagtca gagtctgctc aacagtagaa cccgaaagaa ctacttggct     120
tggtaccagc agaaaccagg gcagtctcct aaactgctga tctactgggc atccactagg    180
gaatctgggg tccctgatcg cttcacaggc agtggatctg ggacagattt ctctctcacc    240
atcagcagtg tgcaggctga agacctggca gtttattact gcaagcaatc ttataatctg    300
tacacgttcg agggggggac caagctggaa ataaaacgg                           339
```

<210> SEQ ID NO 234
<211> LENGTH: 339
<212> TYPE: DNA
<213> ORGANISM: Artificial sequence
<220> FEATURE:
<223> OTHER INFORMATION: Synthetic
<400> SEQUENCE: 234

```
gacattgtga tgacccagtc tccatcctcc ctggctgtgt cagcaggaga gagggtcact     60
atgagctgca atccagtca gagtctgctc atcagtagaa cccgaaagaa ctatttgtct    120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tacaggctga agacctggca gtttattact gcaagcaatc ttataatctg   300
tacacgttcg gcggggggac caagctggaa ataaaacgg                          339
```

<210> SEQ ID NO 235
<211> LENGTH: 339
<212> TYPE: DNA
<213> ORGANISM: Artificial sequence
<220> FEATURE:
<223> OTHER INFORMATION: Synthetic
<400> SEQUENCE: 235

```
gacattgtga tgacccagtc tccatcctcc ctggctgtgt cagcaggaga gaaggtcact     60
atgagctgca atccagtca gagtctgctc atcagtagaa cccgaaagaa ctatttgtct    120
tggtaccagc agaaaccagg gcagtctcct aaactgctga tctattgggc atccactagg   180
gaatctgggg tccctgatcg cttcacaggc agtggatctg ggacagattt cactctcacc   240
atcagcagtg tacaggctga agacctggca gtttattact gcaaacaatc ttataatctg   300
tacacgttcg gcggggggac caagctggaa atcaaacgg                          339
```

<210> SEQ ID NO 236
<211> LENGTH: 339
<212> TYPE: DNA
<213> ORGANISM: Artificial sequence
<220> FEATURE:
<223> OTHER INFORMATION: Synthetic
<400> SEQUENCE: 236

```
gatgttttga tgacccaaac tccactcact ttgtcggtta ccattggaca accagcctcc     60
atctcttgca gtcaagtca gagcctctta gatagtgatg aaagacata tttgaattgg    120 ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttccg   300
tggacgttcg gtggaggcac caagctggaa atcaaacgg                          339
```

<210> SEQ ID NO 237
<211> LENGTH: 339
<212> TYPE: DNA
<213> ORGANISM: Artificial sequence
<220> FEATURE:
<223> OTHER INFORMATION: Synthetic

<400> SEQUENCE: 237

| gatattgtga tgacgcaggc tccactcact ttgtcggtta ccattggaca accagcctcc | 60 |
| atctcttgca agtcaagtca gagcctctta gatagtgatg aaagacata tttgagttgg | 120 |
| ttgttacaga ggccaggcca gtctccaaag cgcctaatct atctggtgtc taaactggac | 180 |
| tctggagtcc ctgacaggtt cactggcagt ggatcaggga cagatttcac actgaaaatc | 240 |
| agcagagtgg aggctgagga tttgggagtt tattattgct ggcaaggtac acattttccg | 300 |
| tacacgttcg gagggggggac caagctggaa ataaaacgg | 339 |

<210> SEQ ID NO 238
<211> LENGTH: 339
<212> TYPE: DNA
<213> ORGANISM: Artificial sequence
<220> FEATURE:
<223> OTHER INFORMATION: Synthetic

<400> SEQUENCE: 238

| gacattgtga tgacccagtc tccatcctcc ctggctgtgt cagcaggaga gaaggtcact | 60 |
| atgagctgca atccagtca gagtctgctc aacagtagaa cccgaaagaa ctacttggct | 120 |
| tggtaccagc agaaaccagg gcagtctcct aaactgctga tctactgggc atccactagg | 180 |
| gaatctgggg tccctgatcg cttcacaggc agtggatctg gaacagattt cactctcacc | 240 |
| atcagcagtg tgcaggctga agacctggca gtttattact gcaagcaatc ttataatatt | 300 |
| ccgacgttcg gtggaggcac caagctggaa atcaaacgg | 339 |

<210> SEQ ID NO 239
<211> LENGTH: 339
<212> TYPE: DNA
<213> ORGANISM: Artificial sequence
<220> FEATURE:
<223> OTHER INFORMATION: Synthetic

<400> SEQUENCE: 239

| gatgttttga tgacccaaac tccactctcc ctgcctgtca gtcttggaga caagcctcc | 60 |
| atctcttgca gatcaagtca gagccttgta caaagtaatg gaaacaccta tttacattgg | 120 |
| tacctgcaga agccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tctgggagtt tatttctgct ctcaaagtac acatgttcct | 300 |
| ccgacgttcg gtggaggcac caagctggaa atcaaacgg | 339 |

<210> SEQ ID NO 240
<211> LENGTH: 324
<212> TYPE: DNA
<213> ORGANISM: Artificial sequence
<220> FEATURE:
<223> OTHER INFORMATION: Synthetic

<400> SEQUENCE: 240

| gacatccagc tgactcagtc tccagccatc ctgtctgtga gtccaggaga aagagtcagt | 60 |
| ttctcctgca gggccagtca gagcattggc acaagcatac actggtatca gcaaagaaca | 120 |

| | |
|---|---|
| aatggttctc caaggcttct cataaagtat gcttctgagt ctatctctgg gatcccttcc | 180 |
| aggtttagtg gcagtggatc agggacagat tttactctta gcatcaacag tgtggagtct | 240 |
| gaagatattg cagattatta ctgtcaacaa agtaatagct ggccgtacac gttcggaggg | 300 |
| gggaccaagc tggaaataaa acgg | 324 |

<210> SEQ ID NO 241
<211> LENGTH: 324
<212> TYPE: DNA
<213> ORGANISM: Artificial sequence
<220> FEATURE:
<223> OTHER INFORMATION: Synthetic

<400> SEQUENCE: 241

| | |
|---|---|
| gatatccaga tgacacagac tccagcctcc ctgtctgcct ctctgggaga cagagtcacc | 60 |
| atcagttgta gggcaagtca ggacattagc aattttttaa actggtatca acagaaaccg | 120 |
| aatggaactg ttaaactcct agtcttctac acatcaagat tacactcagg agtcccatca | 180 |
| aggttcagtg gcagtgggtc tggagcagag cattctctca ccattagcaa cctggagcag | 240 |
| gaagatgttg ccacttactt ttgccaacag ggttttacgc ttccgtggac gttcggtggg | 300 |
| ggcaccaagg tggaaatcaa acgg | 324 |

<210> SEQ ID NO 242
<211> LENGTH: 339
<212> TYPE: DNA
<213> ORGANISM: Artificial sequence
<220> FEATURE:
<223> OTHER INFORMATION: Synthetic

<400> SEQUENCE: 242

| | |
|---|---|
| gatgttttga tgacccaaac tccactctcc ctgcctgtca gtcttggaga tcaagcctcc | 60 |
| ttctcttgca gatctagtca gagccttata cacagtaatg gaaacaccta tttacattgg | 120 |
| tacctgcaga agccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tctgggagtt tatttctgct ctcaaagtac acatgttccg | 300 |
| tggacgttcg gtggaggcac caagctggaa atcaaacgg | 339 |

<210> SEQ ID NO 243
<211> LENGTH: 324
<212> TYPE: DNA
<213> ORGANISM: Artificial sequence
<220> FEATURE:
<223> OTHER INFORMATION: Synthetic

<400> SEQUENCE: 243

| | |
|---|---|
| gacattgtga tgacccagtc tcaaaaattc atgtccacat caataggaga cagggtcagc | 60 |
| gtcacctgca gggccagtca gaatgtgggt cccaatttag cctggtatca acagaaacca | 120 |
| gggcaatctc ctaaagcact gatttactcg gcatcctacc gattcagtgg agtccctgat | 180 |
| cgcttcacag gcagtggatc tgggacagat ttcactctca ccatcagcaa tgtgcagtct | 240 |
| gaagacttgg cagagtattt ctgtcagcaa tataacaggt atccattcac gttcggctcg | 300 |
| gggacaaagt tggaaataaa acgg | 324 |

<210> SEQ ID NO 244
<211> LENGTH: 324
<212> TYPE: DNA
<213> ORGANISM: Artificial sequence

```
<220> FEATURE:
<223> OTHER INFORMATION: Synthetic

<400> SEQUENCE: 244
gacattgtga tgacccagtc tcaaaaattc atgtccacat cagtaggaga cagggtcagc    60
atcacctgca aggccagtca gaatgtgggt actgctgtag cctggtatca acagaaacca   120
ggacaatctc ctaaactact gatttcctcg gcatccaatc ggtacactgg agtccctgat   180
cgcttcacag gcagtggatc tgggacagat ttcactctca ccatcagtaa tatgcagtct   240
gaagacgtgg cagattattt ctgccagcaa tataacagct atcctctcac gttcggtgct   300
gggaccaagc tggagctgaa acgg                                          324

<210> SEQ ID NO 245
<211> LENGTH: 324
<212> TYPE: DNA
<213> ORGANISM: Artificial sequence
<220> FEATURE:
<223> OTHER INFORMATION: Synthetic

<400> SEQUENCE: 245
gacattgtga tgacccagtc tcaaaaattc atgtccactt cagtaggaga cagggtcagc    60
gtcacctgca aggccagtca gaatgtgggt cctaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagactattt ctgtcagcaa tataaccgct atcctctcac gttcggtgct   300
gggaccaaac tggagctgaa acgg                                          324

<210> SEQ ID NO 246
<211> LENGTH: 330
<212> TYPE: DNA
<213> ORGANISM: Artificial sequence
<220> FEATURE:
<223> OTHER INFORMATION: Synthetic

<400> SEQUENCE: 246
gacattgtga tgacccagtc tcaaaaattc atgtccacat cagtaggaga cagggtcaac    60
gtcacctgca aggccagtca gaatgtgggt actcatgtag cctggtatca acagaaacca   120
gggcaatctc ctaaagcact gatttactcg gcatcctacc ggtacagtgg cgtccctgat   180
cgcttcacag gcagtggatc tgggacagat ttcactctca ccatcagcaa tgtgcagtct   240
gaagacctgg cagagtattt ctgtcagcaa tataacagct atcctcgagc gctcacgttc   300
ggtgctggga ccaagctgga gctgaaacgg                                    330

<210> SEQ ID NO 247
<211> LENGTH: 324
<212> TYPE: DNA
<213> ORGANISM: Artificial sequence
<220> FEATURE:
<223> OTHER INFORMATION: Synthetic

<400> SEQUENCE: 247
gacattgtga tgacccagtc tcaaaaattc atgtccacat cagtaggaga cagggtcaac    60
gtcacctgca aggccagtca gaatgtgggt cctactgtag cctggtatca acagaaacca   120
gggcaatctc ctaaagcact aatttactcg gcatcctacc ggtacagtgg agtccctgat   180
cgcttcacag gcagtggatc tgggacagat ttcactctca ccatcagcaa tgtgcactct   240
```
gaagacttgg cagagtattt ctgtcagcaa tataacagct atccattcac gttcggctcg    300
gggacaaagt tggaaataaa acgg    324

<210> SEQ ID NO 248
<211> LENGTH: 114
<212> TYPE: PRT
<213> ORGANISM: Artificial sequence
<220> FEATURE:
<223> OTHER INFORMATION: Synthetic

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Asp
            20                  25                  30

Asp Ile Asn Trp Val Arg Gln Ala Pro Gly Gln Gly Leu Glu Trp Ile
        35                  40                  45

Gly Trp Ile Tyr Pro Arg Asp Asp Arg Thr Lys Tyr Asn Asp Lys Phe
    50                  55                  60

Lys Asp Lys Ala Thr Leu Thr Val Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ser Ser Leu Glu Asp Thr Tyr Trp Gly Gln Gly Thr Leu Val Thr Val
            100                 105                 110

Ser Ser

<210> SEQ ID NO 249
<211> LENGTH: 114
<212> TYPE: PRT
<213> ORGANISM: Artificial sequence
<220> FEATURE:
<223> OTHER INFORMATION: Synthetic

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Asp
            20                  25                  30

Asp Ile Asn Trp Val Arg Gln Ala Pro Gly Gln Gly Leu Glu Trp Ile
        35                  40                  45

Gly Trp Ile Tyr Pro Arg Asp Asp Arg Thr Lys Tyr Asn Asp Lys Phe
    50                  55                  60

Lys Asp Arg Ala Thr Leu Thr Val Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ser Ser Leu Glu Asp Thr Tyr Trp Gly Gln Gly Thr Leu Val Thr Val
            100                 105                 110

Ser Ser

<210> SEQ ID NO 250
<211> LENGTH: 113
<212> TYPE: PRT
<213> ORGANISM: Artificial sequence
<220> FEATURE:
<223> OTHER INFORMATION: Synthetic

<400> SEQUENCE: 250

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Val Glu Ile Lys
                100                 105                 110

Arg

<210> SEQ ID NO 251
<211> LENGTH: 116
<212> TYPE: PRT
<213> ORGANISM: Artificial sequence
<220> FEATURE:
<223> OTHER INFORMATION: Synthetic

<400> SEQUENCE: 251

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Met Ser Trp Val Arg Gln Ala Pro Gly Lys Gly Leu Lys Trp Met
        35                  40                  45

Gly Trp Ile Asn Thr Tyr Ser Gly Val Pro Thr Tyr Ala Asp Asp Phe
50                  55                  60

Lys Gly Arg Phe Val Phe Ser Leu Asp Thr Ser Val Arg Thr Pro Tyr
65                  70                  75                  80

Leu Gln Ile Ser Ser Leu Lys Ala Glu Asp Thr Ala Val Tyr Phe Cys
                85                  90                  95

Ala Arg Gly Gly Glu Ala Met Asp Tyr Trp Gly Gln Gly Thr Leu Val
                100                 105                 110

Thr Val Ser Ser
            115

<210> SEQ ID NO 252
<211> LENGTH: 116
<212> TYPE: PRT
<213> ORGANISM: Artificial sequence
<220> FEATURE:
<223> OTHER INFORMATION: Synthetic

<400> SEQUENCE: 252

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Met Ser Trp Val Arg Gln Ala Pro Gly Lys Gly Leu Lys Trp Met
        35                  40                  45

Gly Trp Ile Asn Thr Tyr Ser Gly Val Pro Thr Tyr Ala Asp Asp Phe
50                  55                  60
```

```
Lys Gly Arg Phe Val Phe Ser Leu Asp Thr Ser Val Arg Thr Pro Tyr
 65                  70                  75                  80

Leu Gln Ile Ser Ser Leu Lys Ala Glu Asp Thr Ala Thr Tyr Phe Cys
                 85                  90                  95

Ala Arg Gly Gly Glu Ala Met Asp Tyr Trp Gly Gln Gly Thr Leu Val
            100                 105                 110

Thr Val Ser Ser
        115

<210> SEQ ID NO 253
<211> LENGTH: 113
<212> TYPE: PRT
<213> ORGANISM: Artificial sequence
<220> FEATURE:
<223> OTHER INFORMATION: Synthetic

<400> SEQUENCE: 253

Asp Val Leu Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Trp Thr Phe Gly Gln Gly Thr Lys Val Glu Ile Lys
            100                 105                 110

Arg

<210> SEQ ID NO 254
<211> LENGTH: 113
<212> TYPE: PRT
<213> ORGANISM: Artificial sequence
<220> FEATURE:
<223> OTHER INFORMATION: Synthetic

<400> SEQUENCE: 254

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Lys
             20                  25                  30

Trp Ile Glu Trp Val Arg Gln Ala Pro Gly Gln Gly Leu Glu Trp Ile
         35                  40                  45

Gly Glu Ile Leu Pro Gly Thr Gly Ser Thr Asn Tyr Ala Gln Lys Phe
     50                  55                  60

Gln Gly Arg Ala Thr Phe Thr Ala Asp Ser Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Leu Arg Ser Glu Asp Val Trp Gly Gln Gly Thr Leu Val Thr Val Ser
            100                 105                 110

Ser
```

<210> SEQ ID NO 255
<211> LENGTH: 113
<212> TYPE: PRT
<213> ORGANISM: Artificial sequence
<220> FEATURE:
<223> OTHER INFORMATION: Synthetic

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Lys
            20                  25                  30

Trp Ile Glu Trp Val Arg Gln Ala Pro Gly Gln Gly Leu Glu Trp Ile
        35                  40                  45

Gly Glu Ile Leu Pro Gly Thr Gly Ser Thr Asn Tyr Asn Glu Lys Phe
    50                  55                  60

Lys Gly Arg Ala Thr Phe Thr Ala Asp Ser Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Arg Ser Glu Asp Val Trp Gly Gln Gly Thr Leu Val Thr Val Ser
            100                 105                 110

Ser

<210> SEQ ID NO 256
<211> LENGTH: 113
<212> TYPE: PRT
<213> ORGANISM: Artificial sequence
<220> FEATURE:
<223> OTHER INFORMATION: Synthetic

<400> SEQUENCE: 256

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Ile Pro Thr Phe Gly Gln Gly Thr Lys Val Glu Ile Lys
            100                 105                 110

Arg

<210> SEQ ID NO 257
<211> LENGTH: 17
<212> TYPE: PRT
<213> ORGANISM: Artificial sequence
<220> FEATURE:
<223> OTHER INFORMATION: Synthetic

<400> SEQUENCE: 257

Lys Ser Ser Gln Ser Leu Leu Gln Ser Arg Thr Arg Lys Asn Tyr Leu
1               5                   10                  15

Ala

<210> SEQ ID NO 258
<211> LENGTH: 17
<212> TYPE: PRT
<213> ORGANISM: Artificial sequence
<220> FEATURE:
<223> OTHER INFORMATION: Synthetic

<400> SEQUENCE: 258

Lys Ser Ser Gln Ser Leu Leu Ala Ser Arg Thr Arg Lys Asn Tyr Leu
1               5                   10                  15

Ala

<210> SEQ ID NO 259
<211> LENGTH: 17
<212> TYPE: PRT
<213> ORGANISM: Artificial sequence
<220> FEATURE:
<223> OTHER INFORMATION: Synthetic

<400> SEQUENCE: 259

Lys Ser Ser Gln Ser Leu Leu Asn Thr Arg Thr Arg Lys Asn Tyr Leu
1               5                   10                  15

Ala

<210> SEQ ID NO 260
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (8)..(8)
<223> OTHER INFORMATION: wherein Xaa at position 8 is N or Q or A
<220> FEATURE:
<221> NAME/KEY: VARIANT
<222> LOCATION: (9)..(9)
<223> OTHER INFORMATION: where Xaa at position 9 is S or T

<400> SEQUENCE: 260

Lys Ser Ser Gln Ser Leu Leu Xaa Xaa Arg Thr Arg Lys Asn Tyr Leu
1               5                   10                  15

Ala

<210> SEQ ID NO 261
<211> LENGTH: 16
<212> TYPE: PRT
<213> ORGANISM: Artificial sequence
<220> FEATURE:
<223> OTHER INFORMATION: Synthetic

<400> SEQUENCE: 261

Lys Ser Ser Gln Ser Leu Leu Asp Ser Glu Gly Lys Thr Tyr Leu Asn
1               5                   10                  15

<210> SEQ ID NO 262
<211> LENGTH: 16
<212> TYPE: PRT
<213> ORGANISM: Artificial sequence
<220> FEATURE:
<223> OTHER INFORMATION: Synthetic

<400> SEQUENCE: 262

Lys Ser Ser Gln Ser Leu Leu Asp Ser Ala Gly Lys Thr Tyr Leu Asn

<210> SEQ ID NO 263
<211> LENGTH: 16
<212> TYPE: PRT
<213> ORGANISM: Artificial sequence
<220> FEATURE:
<223> OTHER INFORMATION: Synthetic

<400> SEQUENCE: 263

Lys Ser Ser Gln Ser Leu Leu Asp Ser Asp Ala Lys Thr Tyr Leu Asn
1               5                   10                  15

<210> SEQ ID NO 264
<211> LENGTH: 30
<212> TYPE: PRT
<213> ORGANISM: Artificial sequence
<220> FEATURE:
<223> OTHER INFORMATION: Synthetic

<400> SEQUENCE: 264

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 265
<211> LENGTH: 14
<212> TYPE: PRT
<213> ORGANISM: Artificial sequence
<220> FEATURE:
<223> OTHER INFORMATION: Synthetic

<400> SEQUENCE: 265

Trp Val Arg Gln Ala Pro Gly Gln Gly Leu Glu Trp Ile Gly
1               5                   10

<210> SEQ ID NO 266
<211> LENGTH: 32
<212> TYPE: PRT
<213> ORGANISM: Artificial sequence
<220> FEATURE:
<223> OTHER INFORMATION: Synthetic

<400> SEQUENCE: 266

Lys Ala Thr Leu Thr Val Asp Thr Ser Ser Asn Thr Ala Tyr Met Glu
1               5                   10                  15

Leu Ser Ser Leu Arg Ser Glu Asp Thr Ala Val Tyr Tyr Cys Ser Ser
            20                  25                  30

<210> SEQ ID NO 267
<211> LENGTH: 32
<212> TYPE: PRT
<213> ORGANISM: Artificial sequence
<220> FEATURE:
<223> OTHER INFORMATION: Synthetic

<400> SEQUENCE: 267

Arg Ala Thr Leu Thr Val Asp Thr Ser Ser Asn Thr Ala Tyr Met Glu
1               5                   10                  15

Leu Ser Ser Leu Arg Ser Glu Asp Thr Ala Val Tyr Tyr Cys Ser Ser
            20                  25                  30

<210> SEQ ID NO 268
<211> LENGTH: 11

```
<212> TYPE: PRT
<213> ORGANISM: Artificial sequence
<220> FEATURE:
<223> OTHER INFORMATION: Synthetic

<400> SEQUENCE: 268

Trp Gly Gln Gly Thr Leu Val Thr Val Ser Ser
1               5                   10

<210> SEQ ID NO 269
<211> LENGTH: 30
<212> TYPE: PRT
<213> ORGANISM: Artificial sequence
<220> FEATURE:
<223> OTHER INFORMATION: Synthetic

<400> SEQUENCE: 269

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr
            20                  25                  30

<210> SEQ ID NO 270
<211> LENGTH: 32
<212> TYPE: PRT
<213> ORGANISM: Artificial sequence
<220> FEATURE:
<223> OTHER INFORMATION: Synthetic

<400> SEQUENCE: 270

Arg Phe Val Phe Ser Leu Asp Thr Ser Val Arg Thr Pro Tyr Leu Gln
1               5                   10                  15

Ile Ser Ser Leu Lys Ala Glu Asp Thr Ala Val Tyr Phe Cys Ala Arg
            20                  25                  30

<210> SEQ ID NO 271
<211> LENGTH: 32
<212> TYPE: PRT
<213> ORGANISM: Artificial sequence
<220> FEATURE:
<223> OTHER INFORMATION: Synthetic

<400> SEQUENCE: 271

Arg Phe Val Phe Ser Leu Asp Thr Ser Val Arg Thr Pro Tyr Leu Gln
1               5                   10                  15

Ile Ser Ser Leu Lys Ala Glu Asp Thr Ala Thr Tyr Phe Cys Ala Arg
            20                  25                  30

<210> SEQ ID NO 272
<211> LENGTH: 11
<212> TYPE: PRT
<213> ORGANISM: Artificial sequence
<220> FEATURE:
<223> OTHER INFORMATION: Synthetic

<400> SEQUENCE: 272

Trp Gly Gln Gly Thr Leu Val Thr Val Ser Ser
1               5                   10

<210> SEQ ID NO 273
<211> LENGTH: 30
<212> TYPE: PRT
<213> ORGANISM: Artificial sequence
<220> FEATURE:
<223> OTHER INFORMATION: Synthetic
```

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 274
<211> LENGTH: 14
<212> TYPE: PRT
<213> ORGANISM: Artificial sequence
<220> FEATURE:
<223> OTHER INFORMATION: Synthetic

<400> SEQUENCE: 274

Trp Val Arg Gln Ala Pro Gly Gln Gly Leu Glu Trp Ile Gly
1               5                   10

<210> SEQ ID NO 275
<211> LENGTH: 17
<212> TYPE: PRT
<213> ORGANISM: Artificial sequence
<220> FEATURE:
<223> OTHER INFORMATION: Synthetic

<400> SEQUENCE: 275

Glu Ile Leu Pro Gly Thr Gly Ser Thr Asn Tyr Ala Gln Lys Phe Gln
1               5                   10                  15

Gly

<210> SEQ ID NO 276
<211> LENGTH: 32
<212> TYPE: PRT
<213> ORGANISM: Artificial sequence
<220> FEATURE:
<223> OTHER INFORMATION: Synthetic

<400> SEQUENCE: 276

Arg Ala Thr Phe Thr Ala Asp Ser Ser Thr Ser Thr Ala Tyr Met Glu
1               5                   10                  15

Leu Ser Ser Leu Arg Ser Glu Asp Thr Ala Val Tyr Tyr Cys Leu Arg
            20                  25                  30

<210> SEQ ID NO 277
<211> LENGTH: 11
<212> TYPE: PRT
<213> ORGANISM: Artificial sequence
<220> FEATURE:
<223> OTHER INFORMATION: Synthetic

<400> SEQUENCE: 277

Trp Gly Gln Gly Thr Leu Val Thr Val Ser Ser
1               5                   10

<210> SEQ ID NO 278
<211> LENGTH: 113
<212> TYPE: PRT
<213> ORGANISM: Artificial sequence
<220> FEATURE:
<223> OTHER INFORMATION: Synthetic

<400> SEQUENCE: 278

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser

```
                    20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Val Glu Ile Lys
            100                 105                 110

Arg

<210> SEQ ID NO 279
<211> LENGTH: 113
<212> TYPE: PRT
<213> ORGANISM: Artificial sequence
<220> FEATURE:
<223> OTHER INFORMATION: Synthetic

<400> SEQUENCE: 279

Asp Val Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Ala Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110

Arg

<210> SEQ ID NO 280
<211> LENGTH: 113
<212> TYPE: PRT
<213> ORGANISM: Artificial sequence
<220> FEATURE:
<223> OTHER INFORMATION: Synthetic

<400> SEQUENCE: 280

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95
```

Ser Tyr Asn Ile Pro Thr Phe Gly Gln Gly Thr Lys Val Glu Ile Lys
            100                 105                 110
Arg

<210> SEQ ID NO 281
<211> LENGTH: 23
<212> TYPE: PRT
<213> ORGANISM: Artificial sequence
<220> FEATURE:
<223> OTHER INFORMATION: Synthetic

<400> SEQUENCE: 281

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 282
<211> LENGTH: 15
<212> TYPE: PRT
<213> ORGANISM: Artificial sequence
<220> FEATURE:
<223> OTHER INFORMATION: Synthetic

<400> SEQUENCE: 282

Trp Tyr Gln Gln Lys Pro Gly Gln Pro Pro Lys Leu Leu Ile Tyr
1               5                   10                  15

<210> SEQ ID NO 283
<211> LENGTH: 32
<212> TYPE: PRT
<213> ORGANISM: Artificial sequence
<220> FEATURE:
<223> OTHER INFORMATION: Synthetic

<400> SEQUENCE: 283

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 284
<211> LENGTH: 11
<212> TYPE: PRT
<213> ORGANISM: Artificial sequence
<220> FEATURE:
<223> OTHER INFORMATION: Synthetic

<400> SEQUENCE: 284

Phe Gly Gln Gly Thr Lys Val Glu Ile Lys Arg
1               5                   10

<210> SEQ ID NO 285
<211> LENGTH: 23
<212> TYPE: PRT
<213> ORGANISM: Artificial sequence
<220> FEATURE:
<223> OTHER INFORMATION: Synthetic

<400> SEQUENCE: 285

Asp Val Leu Met Thr Gln Thr Pro Leu Ser Leu Ser Val Thr Pro Gly
1               5                   10                  15

Gln Pro Ala Ser Ile Ser Cys
            20

<210> SEQ ID NO 286
<211> LENGTH: 32
<212> TYPE: PRT
<213> ORGANISM: Artificial sequence
<220> FEATURE:
<223> OTHER INFORMATION: Synthetic

<400> SEQUENCE: 286

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 287
<211> LENGTH: 11
<212> TYPE: PRT
<213> ORGANISM: Artificial sequence
<220> FEATURE:
<223> OTHER INFORMATION: Synthetic

<400> SEQUENCE: 287

Phe Gly Gln Gly Thr Lys Val Glu Ile Lys Arg
1               5                   10

<210> SEQ ID NO 288
<211> LENGTH: 342
<212> TYPE: DNA
<213> ORGANISM: Artificial sequence
<220> FEATURE:
<223> OTHER INFORMATION: Synthetic

<400> SEQUENCE: 288
caagtccaac tcgtccagtc cggggccgaa gtcaagaagc cgggagcctc agtgaaagtg      60
tcgtgcaaag cttccggcta caccttcacc accgatgaca ttaactgggt cagacaggcg     120
cccggacagg ggctggaatg gatcggttgg atctaccctc gggacgaccg gactaagtac     180
aacgacaagt tcaaggacaa agcgacgctc accgtcgaca ccagcagcaa cactgcctac     240
atggaactgt catccctgag gagcgaggac actgccgtgt attactgttc gagcctggag     300 gataccctact ggggacaggg cactcttgtg accgtgtcct cc                       342

<210> SEQ ID NO 289
<211> LENGTH: 342
<212> TYPE: DNA
<213> ORGANISM: Artificial sequence
<220> FEATURE:
<223> OTHER INFORMATION: Synthetic

<400> SEQUENCE: 289
caagtccaac tcgtccagtc cggggccgaa gtcaagaagc cgggagcctc agtgaaagtg      60
tcgtgcaaag cttccggcta caccttcacc accgatgaca ttaactgggt cagacaggcg     120
cccggacagg ggctggaatg gatcggttgg atctaccctc gggacgaccg gactaagtac     180
aacgacaagt tcaaggacag agcgacgctc accgtcgaca ccagcagcaa cactgcctac     240
atggaactgt catccctgag gagcgaggac actgccgtgt attactgttc gagcctggag     300 gataccctact ggggacaggg cactcttgtg accgtgtcct cc                       342

<210> SEQ ID NO 290
<211> LENGTH: 348
<212> TYPE: DNA
<213> ORGANISM: Artificial sequence

```
<220> FEATURE:
<223> OTHER INFORMATION: Synthetic

<400> SEQUENCE: 290
caaatccagc tggtccagtc cggttccgag ctcaagaagc cgggagcctc agtgaaagtg    60
tcgtgcaagg cctccggtta catcttcacc tcctacggaa tgtcgtgggt ccgccaagca   120
cctggaaagg gccttaagtg gatggggtgg atcaacacct atagcggcgt gcccacttac   180
gccgacgact ttaagggccg gttcgtgttc tccctggata cgtccgtgcg cactccgtac   240
ctccaaatta gcagcctgaa ggccgaagat actgcggtgt acttctgcgc tagaggaggg   300
gaagccatgg actactgggg acagggcacc ctggtcaccg tgtcgtcc               348

<210> SEQ ID NO 291
<211> LENGTH: 348
<212> TYPE: DNA
<213> ORGANISM: Artificial sequence
<220> FEATURE:
<223> OTHER INFORMATION: Synthetic

<400> SEQUENCE: 291
caaatccagc tggtccagtc cggttccgag ctcaagaagc cgggagcctc agtgaaagtg    60
tcgtgcaagg cctccggtta catcttcacc tcctacggaa tgtcgtgggt ccgccaagca   120
cctggaaagg gccttaagtg gatggggtgg atcaacacct atagcggcgt gcccacttac   180
gccgacgact ttaagggccg gttcgtgttc tccctggata cgtccgtgcg cactccgtac   240
ctccaaatta gcagcctgaa ggccgaagat actgcgacgt acttctgcgc tagaggaggg   300
gaagccatgg actactgggg acagggcacc ctggtcaccg tgtcgtcc               348

<210> SEQ ID NO 292
<211> LENGTH: 339
<212> TYPE: DNA
<213> ORGANISM: Artificial sequence
<220> FEATURE:
<223> OTHER INFORMATION: Synthetic

<400> SEQUENCE: 292
caagtccaac tcgtgcagtc aggagcagaa gtcaagaagc cgggagcctc cgtgaaagtg    60
tcgtgcaagg cctccggata cactttcacc gggaagtgga ttgaatgggt ccgccaggcg   120
cccggccagg gctggagtg gatcggagag atcctgcctg gtaccggtag cactaactac   180
gctcagaagt tccagggcag agcgaccttc accgccgact cgagcacctc cactgcgtac   240
atggaactga gctccctgag gtcggaggac accgccgtgt attactgcct ccggtccgaa   300
gatgtctggg gccaggggac cctcgtgact gtgtcatcc                          339

<210> SEQ ID NO 293
<211> LENGTH: 339
<212> TYPE: DNA
<213> ORGANISM: Artificial sequence
<220> FEATURE:
<223> OTHER INFORMATION: Synthetic

<400> SEQUENCE: 293
caagtccaac tcgtgcagtc aggagcagaa gtcaagaagc cgggagcctc cgtgaaagtg    60
tcgtgcaagg cctccggata cactttcacc gggaagtgga ttgaatgggt ccgccaggcg   120
cccggccagg gctggagtg gatcggagag atcctgcctg gtaccggtag cactaactac   180
aacgagaagt tcaagggcag agcgaccttc accgccgact cgagcacctc cactgcgtac   240
```

```
atggaactga gctccctgag gtcggaggac accgccgtgt attactgcct ccggtccgaa    300
gatgtctggg gccaggggac cctcgtgact gtgtcatcc                            339
```

<210> SEQ ID NO 294
<211> LENGTH: 339
<212> TYPE: DNA
<213> ORGANISM: Artificial sequence
<220> FEATURE:
<223> OTHER INFORMATION: Synthetic

<400> SEQUENCE: 294

```
gatattgtca tgacccagtc ccccgattcc cttgctgtct ccctgggcga acgcgcgact    60
attaactgca agagctcaca gtcgctgctg aattcccgga ctcggaagaa ctacctggcc   120
tggtaccagc agaagcctgg gcaaccgccg aagctcttga tctactgggc ctcgactaga   180
gagagcggag tgccagaccg cttctccggt tccggatcag gaaccgactt taccctgacc   240
atctcgagcc tgcaagcaga ggacgtggcc gtgtattact gcaagcagtc ctacaacctc   300
tacacgttcg gccagggcac caaagtggaa atcaagagg                          339
```

<210> SEQ ID NO 295
<211> LENGTH: 339
<212> TYPE: DNA
<213> ORGANISM: Artificial sequence
<220> FEATURE:
<223> OTHER INFORMATION: Synthetic

<400> SEQUENCE: 295

```
gatatcgtca tgacccaatc ccccgattcc cttgctgtct cactgggaga aagagccacc    60
atcaactgca agagctcgca gtccctgctg gctagcagga ctcgcaagaa ctacctggcc   120
tggtatcagc agaagcccgg acagcctcca aagctcttga tctactgggc ctccactcgg   180
gagtccggcg tgccggaccg gttcagcgga tcaggctccg gtactgactt caccctcacc   240
atttcgtcgc tgcaagcaga ggacgtggcg gtgtactact gcaagcagtc ctacaacatt   300
ccgacgtttg ggcagggcac caaagtggaa atcaagcgc                          339
```

<210> SEQ ID NO 296
<211> LENGTH: 339
<212> TYPE: DNA
<213> ORGANISM: Artificial sequence
<220> FEATURE:
<223> OTHER INFORMATION: Synthetic

<400> SEQUENCE: 296

```
gacgtgctga tgacccaaac ccccctttcc ctgtccgtga ctcctggaca accgcgtca    60 atctcctgca agagctcgca gtccctcctc gactccgacg gaaaaaccta cctgaactgg   120
cttttgcaga ggccagggca gagcccgaag cggctgatct acctcgtgtc caagctggac   180
tccggagtgc cggatcgctt ctcgggatca ggctcgggta ccgatttcac gctgaagatc   240
tccagagtgg aagccgagga cgtgggcgtc tactactgtt ggcagggcac tcactttccg   300
tggaccttcg gtcaagggac caaggtcgag attaagagg                          339
```

<210> SEQ ID NO 297
<211> LENGTH: 339
<212> TYPE: DNA
<213> ORGANISM: Artificial sequence
<220> FEATURE:
<223> OTHER INFORMATION: Synthetic

<400> SEQUENCE: 297
```

```
gacgtgctga tgacccaaac ccccctttcc ctgtccgtga ctcctggaca acccgcgtca    60
atctcctgca agagctcgca gtccctcctc gactccgacg caaaaaccta cctgaactgg   120
cttttgcaga ggccagggca gagcccgaag cggctgatct acctcgtgtc caagctggac   180
tccggagtgc cggatcgctt ctcgggatca ggctcgggta ccgatttcac gctgaagatc   240
tccagagtgg aagccgagga cgtgggcgtc tactactgtt ggcagggcac tcactttccg   300
tggaccttcg gtcaagggac caaggtcgag attaagagg                          339
```

<210> SEQ ID NO 298
<211> LENGTH: 339
<212> TYPE: DNA
<213> ORGANISM: Artificial sequence
<220> FEATURE:
<223> OTHER INFORMATION: Synthetic

<400> SEQUENCE: 298

```
gatatcgtca tgacccaatc ccccgattcc cttgctgtct cactgggaga aagagccacc    60
atcaactgca agagctcgca gtccctgctg aatagcagga ctcgcaagaa ctacctggcc   120
tggtatcagc agaagcccgg acagcctcca aagctcttga tctactgggc ctccactcgg   180
gagtccggcg tgccggaccg gttcagcgga tcaggctccg gtactgactt caccctcacc   240
atttcgtcgc tgcaagcaga ggacgtggcg gtgtactact gcaagcagtc ctacaacatt   300
ccgacgtttg ggcagggcac caaagtggaa atcaagcgc                          339
```

<210> SEQ ID NO 299
<211> LENGTH: 339
<212> TYPE: DNA
<213> ORGANISM: Artificial sequence
<220> FEATURE:
<223> OTHER INFORMATION: Synthetic

<400> SEQUENCE: 299

```
gatattgtca tgacccagtc ccccgattcc cttgctgtct ccctgggcga acgcgcgact    60
attaactgca agagctcaca gtcgctgctg gcttcccgga ctcggaagaa ctacctggcc   120
tggtaccagc agaagcctgg caaccgccg aagctcttga tctactgggc ctcgactaga   180
gagagcggag tgccagaccg cttctccggt tccggatcag gaaccgactt accctgacc   240 atctcgagcc tgcaagcaga ggacgtggcc gtgtattact gcaagcagtc ctacaacctc   300
tacacgttcg gccagggcac caaagtggaa atcaagagg                          339
```

<210> SEQ ID NO 300
<211> LENGTH: 125
<212> TYPE: PRT
<213> ORGANISM: Artificial sequence
<220> FEATURE:
<223> OTHER INFORMATION: Synthetic

<400> SEQUENCE: 300

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60
```

```
Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                 85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser
        115                 120                 125
```

<210> SEQ ID NO 301
<211> LENGTH: 118
<212> TYPE: PRT
<213> ORGANISM: Artificial sequence
<220> FEATURE:
<223> OTHER INFORMATION: Synthetic

<400> SEQUENCE: 301

```
Ala Val Thr Leu Asp Glu Ser Gly Gly Gly Leu Gln Thr Pro Gly Gly
  1               5                  10                  15

Gly Leu Ser Leu Val Cys Lys Ala Ser Gly Phe Thr Phe Ser Ser Tyr
                 20                  25                  30

Ala Met Gly Trp Met Arg Gln Ala Pro Gly Lys Gly Leu Glu Tyr Val
             35                  40                  45

Ala Gly Ile Arg Ser Asp Gly Ser Phe Thr Leu Tyr Ala Thr Ala Val
         50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Thr Tyr Phe Cys
                 85                  90                  95

Thr Arg Ser Gly Asn Val Gly Asp Ile Asp Ala Trp Gly His Gly Thr
            100                 105                 110

Glu Val Ile Val Ser Ser
        115
```

<210> SEQ ID NO 302
<211> LENGTH: 128
<212> TYPE: PRT
<213> ORGANISM: Artificial sequence
<220> FEATURE:
<223> OTHER INFORMATION: Synthetic

<400> SEQUENCE: 302

```
Ala Val Thr Leu Asp Glu Ser Gly Gly Gly Leu Gln Thr Pro Gly Gly
  1               5                  10                  15

Gly Leu Ser Leu Val Cys Lys Ala Ser Gly Phe Asp Phe Ser Ser Tyr
                 20                  25                  30

Gln Met Asn Trp Ile Arg Gln Ala Pro Gly Lys Gly Leu Glu Phe Val
             35                  40                  45

Ala Ala Ile Asn Arg Phe Gly Asn Ser Thr Gly His Gly Ala Ala Val
         50                  55                  60

Lys Gly Arg Val Thr Ile Ser Arg Asp Asp Gly Gln Ser Thr Val Arg
 65                  70                  75                  80

Leu Gln Leu Ser Asn Leu Arg Ala Glu Asp Thr Ala Thr Tyr Tyr Cys
                 85                  90                  95

Ala Lys Gly Val Tyr Gly Tyr Cys Gly Ser Tyr Ser Cys Cys Gly Val
            100                 105                 110

Asp Thr Ile Asp Ala Trp Gly His Gly Thr Glu Val Ile Val Ser Ser
        115                 120                 125
```

<210> SEQ ID NO 303
<211> LENGTH: 107
<212> TYPE: PRT
<213> ORGANISM: Artificial sequence
<220> FEATURE:
<223> OTHER INFORMATION: Synthetic

<400> SEQUENCE: 303

```
Ala Leu Thr Gln Pro Ala Ser Val Ser Ala Asn Leu Gly Gly Thr Val
1               5                   10                  15
Lys Ile Thr Cys Ser Gly Gly Gly Ser Tyr Ala Gly Ser Tyr Tyr Tyr
            20                  25                  30
Gly Trp Tyr Gln Gln Lys Ser Pro Gly Ser Ala Pro Val Thr Val Ile
        35                  40                  45
Tyr Asp Asn Asp Lys Arg Pro Ser Asp Ile Pro Ser Arg Phe Ser Gly
    50                  55                  60
Ser Leu Ser Gly Ser Thr Asn Thr Leu Thr Ile Thr Gly Val Arg Ala
65                  70                  75                  80
Asp Asp Glu Ala Val Tyr Phe Cys Gly Ser Ala Asp Asn Ser Gly Ala
                85                  90                  95
Ala Phe Gly Ala Gly Thr Thr Leu Thr Val Leu
            100                 105
```

<210> SEQ ID NO 304
<211> LENGTH: 108
<212> TYPE: PRT
<213> ORGANISM: Artificial sequence
<220> FEATURE:
<223> OTHER INFORMATION: Synthetic

<400> SEQUENCE: 304

```
Ala Leu Thr Gln Pro Ala Ser Val Ser Ala Asn Pro Gly Glu Thr Val
1               5                   10                  15
Lys Ile Thr Cys Ser Gly Gly Tyr Ser Gly Tyr Ala Gly Ser Tyr Tyr
            20                  25                  30
Tyr Gly Trp Tyr Gln Gln Lys Ala Pro Gly Ser Ala Pro Val Thr Leu
        35                  40                  45
Ile Tyr Tyr Asn Asn Lys Arg Pro Ser Asp Ile Pro Ser Arg Phe Ser
    50                  55                  60
Gly Ser Leu Ser Gly Ser Thr Asn Thr Leu Thr Ile Thr Gly Val Arg
65                  70                  75                  80
Ala Asp Asp Glu Ala Val Tyr Phe Cys Gly Ser Ala Asp Asn Ser Gly
                85                  90                  95
Ala Ala Phe Gly Ala Gly Thr Thr Leu Thr Val Leu
            100                 105
```

<210> SEQ ID NO 305
<211> LENGTH: 107
<212> TYPE: PRT
<213> ORGANISM: Artificial sequence
<220> FEATURE:
<223> OTHER INFORMATION: Synthetic

<400> SEQUENCE: 305

```
Ala Leu Thr Gln Pro Ala Ser Val Ser Ala Asn Pro Gly Glu Thr Val
1               5                   10                  15
Lys Ile Thr Cys Ser Gly Gly Gly Ser Tyr Ala Gly Ser Tyr Tyr Tyr
            20                  25                  30
```

Gly Trp Tyr Gln Gln Lys Ala Pro Gly Ser Ala Pro Val Thr Leu Ile
            35                  40                  45

Tyr Tyr Asn Asn Lys Arg Pro Ser Asp Ile Pro Ser Arg Phe Ser Gly
 50                  55                  60

Ser Leu Ser Gly Ser Thr Asn Thr Leu Thr Ile Thr Gly Val Arg Ala
 65                  70                  75                  80

Asp Asp Glu Ala Val Tyr Phe Cys Gly Ser Ala Asp Asn Ser Gly Ala
                 85                  90                  95

Ala Phe Gly Ala Gly Thr Thr Leu Thr Val Leu
            100                 105

<210> SEQ ID NO 306
<211> LENGTH: 126
<212> TYPE: PRT
<213> ORGANISM: Artificial sequence
<220> FEATURE:
<223> OTHER INFORMATION: Synthetic

<400> SEQUENCE: 306

Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Gly Ile Tyr Lys Ser Gly Ala Gly Thr Asn Tyr Ala Pro Ala Val
 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                 85                  90                  95

Ala Lys Thr Thr Gly Ser Gly Cys Ser Ser Gly Tyr Arg Ala Glu Tyr
            100                 105                 110

Ile Asp Ala Trp Gly His Gly Thr Glu Val Ile Val Ser Ser
        115                 120                 125

<210> SEQ ID NO 307
<211> LENGTH: 107
<212> TYPE: PRT
<213> ORGANISM: Artificial sequence
<220> FEATURE:
<223> OTHER INFORMATION: Synthetic

<400> SEQUENCE: 307

Ala Leu Thr Gln Pro Ala Ser Val Ser Ala Asn Pro Gly Glu Thr Val
 1               5                  10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
            35                  40                  45

Tyr Tyr Asn Asn Lys Arg Pro Ser Asp Ile Pro Ser Arg Phe Ser Gly
 50                  55                  60

Ser Leu Ser Gly Ser Thr Asn Thr Leu Thr Ile Thr Gly Val Arg Ala
 65                  70                  75                  80

Asp Asp Glu Ala Val Tyr Phe Cys Gly Ser Ala Asp Asn Ser Gly Ala
                 85                  90                  95

Ala Phe Gly Ala Gly Thr Thr Leu Thr Val Leu
            100                 105

<210> SEQ ID NO 308
<211> LENGTH: 126
<212> TYPE: PRT
<213> ORGANISM: Artificial sequence
<220> FEATURE:
<223> OTHER INFORMATION: Synthetic

<400> SEQUENCE: 308

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asp Met Val Trp Val Arg Gln Ala Pro Gly Lys Gly Leu Glu Phe Val
        35                  40                  45

Ala Gly Ile Ser Arg Asn Asp Gly Arg Tyr Thr Glu Tyr Gly Ser Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Ala Thr Tyr Tyr
                85                  90                  95

Cys Ala Arg Asp Ala Gly Gly Ser Ala Tyr Trp Phe Asp Ala Gly Gln
            100                 105                 110

Ile Asp Ala Trp Gly His Gly Thr Glu Val Ile Val Ser Ser
        115                 120                 125

<210> SEQ ID NO 309
<211> LENGTH: 107
<212> TYPE: PRT
<213> ORGANISM: Artificial sequence
<220> FEATURE:
<223> OTHER INFORMATION: Synthetic

<400> SEQUENCE: 309

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Tyr Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu
            100                 105

<210> SEQ ID NO 310
<211> LENGTH: 327
<212> TYPE: PRT
<213> ORGANISM: Artificial sequence
<220> FEATURE:
<223> OTHER INFORMATION: Synthetic

<400> SEQUENCE: 310

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 311
<211> LENGTH: 327
<212> TYPE: PRT
<213> ORGANISM: Artificial sequence
<220> FEATURE:
<223> OTHER INFORMATION: Synthetic

<400> SEQUENCE: 311

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 312
<211> LENGTH: 327
<212> TYPE: PRT
<213> ORGANISM: Artificial sequence
<220> FEATURE:
<223> OTHER INFORMATION: Synthetic

<400> SEQUENCE: 312

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ser His Tyr Thr Gln Lys Ser
305                 310                 315                 320

Leu Ser Leu Ser Leu Gly Lys
                325

<210> SEQ ID NO 313
<211> LENGTH: 106
<212> TYPE: PRT
<213> ORGANISM: Artificial sequence
<220> FEATURE:
<223> OTHER INFORMATION: Synthetic

<400> SEQUENCE: 313

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```